(12) United States Patent
Ma et al.

(10) Patent No.: US 11,963,444 B2
(45) Date of Patent: Apr. 16, 2024

(54) ORGANIC COMPOUND, ORGANIC ELECTROLUMINESCENT DEVICE AND ELECTRONIC APPARATUS INCLUDING SAME

(71) Applicant: Shaanxi Lighte Optoelectronics Material Co., Ltd., Xi'an (CN)

(72) Inventors: Tiantian Ma, Xi'an (CN); Min Yang, Xi'an (CN); Lei Yang, Xi'an (CN); Yan Zang, Xi'an (CN); Kongyan Zhang, Xi'an (CN)

(73) Assignee: Shaanxi Lighte Optoelectronics Material Co., Ltd., Xi'an (CN)

( * ) Notice: Subject to any disclaimer, the term of this patent is extended or adjusted under 35 U.S.C. 154(b) by 0 days.

(21) Appl. No.: 18/024,148

(22) PCT Filed: Feb. 9, 2022

(86) PCT No.: PCT/CN2022/075730
§ 371 (c)(1),
(2) Date: Mar. 1, 2023

(87) PCT Pub. No.: WO2023/070987
PCT Pub. Date: May 4, 2023

(65) Prior Publication Data
US 2023/0247903 A1     Aug. 3, 2023

(51) Int. Cl.
*C07D 209/86*     (2006.01)
*C07D 405/14*     (2006.01)
(Continued)

(52) U.S. Cl.
CPC ....... *H10K 85/6572* (2023.02); *C07D 209/86* (2013.01); *C07D 405/14* (2013.01);
(Continued)

(58) Field of Classification Search
CPC .............. C07D 209/86; C07B 2200/05; H10K 85/6572
See application file for complete search history.

(56) References Cited

U.S. PATENT DOCUMENTS

2013/0264558 A1* 10/2013 Matsuki .................. C09B 57/00
548/440
2015/0171346 A1*  6/2015 Ahn ...................... C07D 403/14
257/40

FOREIGN PATENT DOCUMENTS

CN         103250264 A      8/2013
CN         103467450 A     12/2013
(Continued)

OTHER PUBLICATIONS

Office Action from Korean Application No. KR10-2023-7009043, dated Aug. 11, 2023, 14 pages with translation.
(Continued)

*Primary Examiner* — Vu A Nguyen
(74) *Attorney, Agent, or Firm* — TUCKER ELLIS LLP

(57) ABSTRACT

The present disclosure provides an organic compound, an organic electroluminescent device and an electronic apparatus including the same, and belongs to the field of organic electroluminescence. The organic compound of the present disclosure has a structure represented by a formula 1, and
(Continued)

when the organic compound is applied to an organic electroluminescent device, the performance of the organic electroluminescent device can be significantly improved.

Formula 1

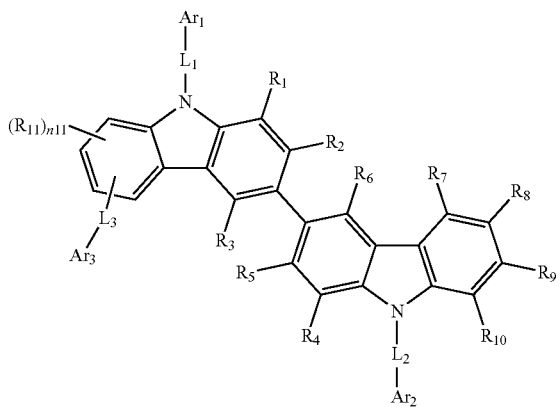

17 Claims, 1 Drawing Sheet

(51) Int. Cl.
C07D 409/14 (2006.01)
H01L 51/00 (2006.01)
H01L 51/50 (2006.01)
H10K 85/60 (2023.01)
H10K 50/11 (2023.01)
H10K 101/10 (2023.01)

(52) U.S. Cl.
CPC ....... C07D 409/14 (2013.01); H10K 85/6574 (2023.02); H10K 85/6576 (2023.02); C07B 2200/05 (2013.01); H10K 50/11 (2023.02); H10K 2101/10 (2023.02)

(56) References Cited

FOREIGN PATENT DOCUMENTS

| CN | 103502243 A | 1/2014 |
|---|---|---|
| CN | 108948008 A | 12/2018 |
| CN | 110088926 A | 8/2019 |
| CN | 113260608 A | 8/2021 |
| KR | 1020130102673 A | 9/2013 |
| KR | 20150116776 A | 10/2015 |
| KR | 20210018128 A | 2/2021 |
| KR | 102283849 B1 | 8/2021 |
| KR | 20230007931 A | 1/2023 |
| KR | 20230007960 A | 1/2023 |
| KR | 20230007961 A | 1/2023 |

OTHER PUBLICATIONS

Notice of Allowance from corresponding Korean Application No. KR10-2023-7009043, dated Oct. 14, 2023; 6 pages with translation.

* cited by examiner

ORGANIC COMPOUND, ORGANIC ELECTROLUMINESCENT DEVICE AND ELECTRONIC APPARATUS INCLUDING SAME

CROSS REFERENCE TO RELATED APPLICATIONS

This disclosure claims the priority of Chinese patent application No. 202111260690.0, filed on Oct. 28, 2021, and Chinese patent application No. 202111488233.7, filed on Dec. 7, 2021, the contents of which are incorporated herein by reference in their entirety as part of this application.

FIELD

The present disclosure belongs to the technical field of organic electroluminescence, in particular to an organic compound, an organic electroluminescent device and an electronic apparatus including the same.

BACKGROUND

Organic electroluminescent materials (OLED) have the advantages of ultra-thinness, self-illumination, wide viewing angle, fast response, high luminous efficiency, good temperature adaptability, simple production process, low driving voltage, low energy consumption, and the like as a new generation display technology, and have been widely used in industries such as flat panel display, flexible display, solid state lighting, and vehicle display.

Currently, for green organic electroluminescent devices, a phosphorescent organic electroluminescent device is a main development direction, and is mainly used in display devices such as mobile phones, vehicles, and the like. However, with respect to the green organic electroluminescent devices, problems such as lower luminous efficiency and shorter service life still exist, resulting in decreased device performance. Thus, there is a constant need to develop new materials usable in organic electroluminescent devices which are highly efficient, long in service life and suitable for mass production for the problem of the efficiency or service life of phosphorescent host materials.

It should be noted that the information disclosed in the above Background section is merely used to enhance an understanding of the background of the present disclosure, and thus may include information that does not constitute the prior art known to those of ordinary skill in the art.

SUMMARY

The present disclosure provides an organic compound, an organic electroluminescent device and an electronic apparatus including the same to solve the problems of lower luminous efficiency and shorter service life of an organic electroluminescent device in the prior art.

In order to achieve the above object, the present disclosure employs the following technical solutions:

according to a first aspect of the present disclosure, provided is an organic compound, having a structure represented by a formula 1:

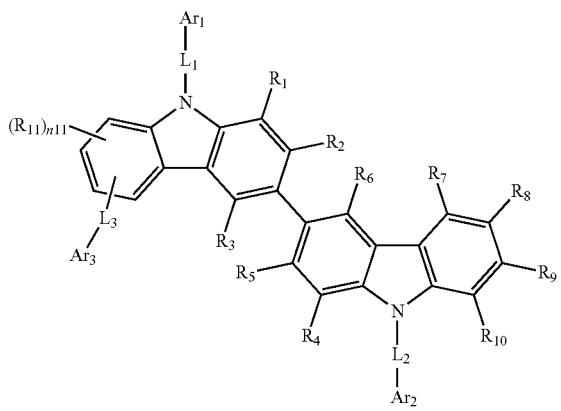

Formula 1 wherein $L_1$ and $L_2$ are respectively and independently selected from a single bond, substituted or unsubstituted arylene with 6 to 30 carbon atoms, and substituted or unsubstituted heteroarylene with 3 to 30 carbon atoms;

$L_3$ is selected from a single bond, and substituted or unsubstituted arylene with 6 to 30 carbon atoms;

$Ar_1$ and $Ar_2$ are respectively and independently selected from substituted or unsubstituted aryl with 6 to 30 carbon atoms, and substituted or unsubstituted heteroaryl with 3 to 30 carbon atoms;

$Ar_3$ is selected from substituted or unsubstituted aryl with 6 to 30 carbon atoms;

$R_1$, $R_2$, $R_3$, $R_4$, $R_5$, $R_6$, $R_7$, $R_8$, $R_9$ and $R_{10}$ are respectively and independently selected from hydrogen or deuterium, and at least two of $R_2$, $R_3$, $R_5$ and $R_6$ are deuterium;

$R_{11}$ is selected from hydrogen or deuterium;

$n_{11}$ is the number of $R_{11}$, and is selected from 1, 2 or 3, and when $n_{11}$ is greater than 1, any two $R_{11}$ are the same or different;

substituents in $L_1$, $L_2$, $L_3$, $Ar_1$, $Ar_2$ and $Ar_3$ are respectively and independently selected from deuterium, a halogen group, cyano, heteroaryl with 3 to 12 carbon atoms, aryl with 6 to 12 carbon atoms, trialkylsilyl with 3 to 12 carbon atoms, alkyl with 1 to 10 carbon atoms, haloalkyl with 1 to 10 carbon atoms, cycloalkyl with 3 to 10 carbon atoms, heterocycloalkyl with 2 to 10 carbon atoms, and alkoxy with 1 to 10 carbon atoms; and optionally, in $Ar_1$, $Ar_2$, and $Ar_3$, any two adjacent substituents form a ring.

According to the organic compound provided by the present disclosure, specific 3,3-bicarbazole is used as a parent core, deuteration is performed in at least two ortho positions of a connecting bond of bicarbazole, and aryl is connected to one carbazole ring, so that the twist angle between two carbazole rings is reduced, and the conjugation is increased, thus improving the hole mobility and charge transport balance of a host material. The organic compound is applied to a host material for a light-emitting layer of a phosphorescent organic electroluminescent device, in particular a green organic electroluminescent device, so that the light-emitting layer has good hole transport properties, and the efficiency of recombination of electrons and holes to form excitons is increased, thus making the device have a reduced voltage, and improving the luminous efficiency and service life characteristics of the device.

A second aspect of the present disclosure provides an organic electroluminescent device, including an anode and a cathode which are oppositely disposed, and a functional layer disposed between the anode and the cathode, wherein the functional layer includes the organic compound according to the first aspect.

A third aspect of the present disclosure provides an electronic apparatus, including the organic electroluminescent device according to the second aspect.

BRIEF DESCRIPTION OF THE DRAWINGS

The drawings here are incorporated into and constitute part of the description, illustrating the examples conforming to the present disclosure, and used together with the description to interpret the principles of the present disclosure.

DESCRIPTION OF REFERENCE SIGNS

Figure 1:
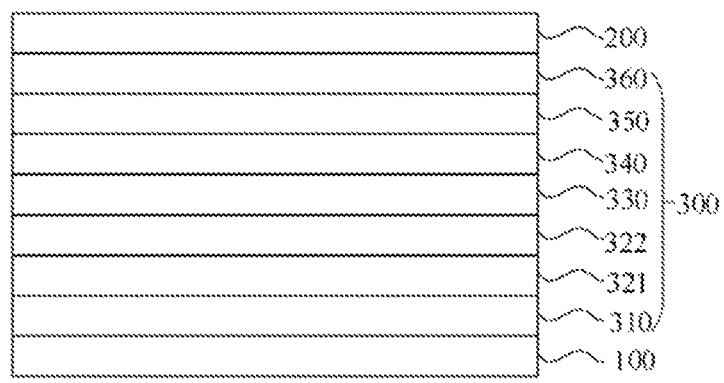
FIG. 1 is a structural schematic diagram of an organic electroluminescent device according to an embodiment of the present disclosure.

100, anode; 200, cathode; 300, functional layer; 310, hole injection layer; 321, hole transport layer; 322, hole auxiliary layer; 330, organic light-emitting layer; 340, hole blocking layer; 350, electron transport layer; 360, electron injection layer; and 400, electronic apparatus.

DETAILED DESCRIPTION

Exemplary embodiments will now be described more fully with reference to the accompanying drawings. However, the exemplary embodiments can be implemented in a variety of forms, and should not be understood as a limitation to the instances set forth here; and on the contrary, these embodiments are provided such that the present disclosure will be more comprehensive and complete, and the concepts of the exemplary embodiments are comprehensively conveyed to those skilled in the art. The described features, structures, or characteristics may be incorporated in one or more embodiments in any suitable manner. In the following description, many specific details are provided to give a sufficient understanding of the embodiments of the present disclosure.

The described features, structures, or characteristics may be incorporated in one or more embodiments in any suitable manner. In the following description, many specific details are provided to give a sufficient understanding of the embodiments of the present disclosure. However, those skilled in the art will realize that the technical solution of the present disclosure may be practiced without one or more of the specific details, or other methods, components, materials, etc. may be employed. In other cases, well-known structures, materials, or operations are not shown or described in detail to avoid obscuring the primary technical ideas of the present disclosure.

The present disclosure provides an organic compound, having a structure represented by a formula 1:

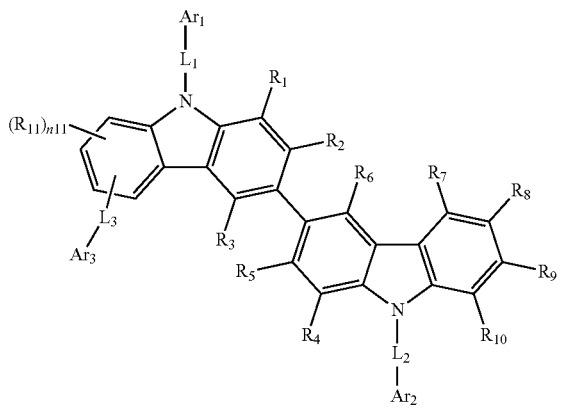

Formula 1 wherein $L_1$ and $L_2$ are respectively and independently selected from a single bond, substituted or unsubstituted arylene with 6 to 30 carbon atoms, and substituted or unsubstituted heteroarylene with 3 to 30 carbon atoms;

$L_3$ is selected from a single bond, and substituted or unsubstituted arylene with 6 to 30 carbon atoms;

$Ar_1$ and $Ar_2$ are respectively and independently selected from substituted or unsubstituted aryl with 6 to 30 carbon atoms, and substituted or unsubstituted heteroaryl with 3 to 30 carbon atoms;

$Ar_3$ is selected from substituted or unsubstituted aryl with 6 to 30 carbon atoms;

$R_1$, $R_2$, $R_3$, $R_4$, $R_5$, $R_6$, $R_7$, $R_8$, $R_9$ and $R_{10}$ are respectively and independently selected from hydrogen or deuterium, and at least two of $R_2$, $R_3$, $R_5$ and $R_6$ are deuterium;

$R_{11}$ is selected from hydrogen or deuterium;

$n_{11}$ is the number of $R_{11}$, and is selected from 1, 2 or 3, and when $n_{11}$ is greater than 1, any two $R_{11}$ are the same or different;

substituents in $L_1$, $L_2$, $L_3$, $Ar_1$, $Ar_2$ and $Ar_3$ are respectively and independently selected from deuterium, a halogen group, cyano, heteroaryl with 3 to 12 carbon atoms, aryl with 6 to 12 carbon atoms, trialkylsilyl with 3 to 12 carbon atoms, alkyl with 1 to 10 carbon atoms, haloalkyl with 1 to 10 carbon atoms, cycloalkyl with 3 to 10 carbon atoms, heterocycloalkyl with 2 to 10 carbon atoms, and alkoxy with 1 to 10 carbon atoms; and optionally, in $Ar_1$, $Ar_2$, and $Ar_3$, any two adjacent substituents form a ring.

In the present disclosure, the adopted description modes " . . . are each independently selected from", and " . . . are respectively and independently selected from" can be interchanged, and should be understood in a broad sense, which means that in different groups, specific options expressed between the same symbols do not influence each other, or in a same group, specific options expressed between the same symbols do not influence each other. For example, the meaning of

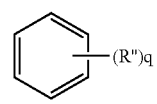

Q-1

-continued

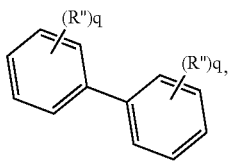
Q-2 wherein each q is independently 0, 1, 2 or 3, and each R" is independently selected from hydrogen, deuterium, fluorine and chlorine" is as follows: a formula Q-1 represents that q substituents R" exist on a benzene ring, each R" can be the same or different, and options of each R" do not influence each other; and a formula Q-2 represents that each benzene ring of biphenyl has q substituents R", the number q of the substituents R" on the two benzene rings can be the same or different, each R" can be the same or different, and options of each R" do not influence each other.

In the present disclosure, the term such as "substituted or unsubstituted" means that a functional group described behind the term may have or does not have a substituent (in the following, the substituent is collectively referred to as Rc in order to facilitate description). For example, the "substituted or unsubstituted aryl" refers to aryl having the substituent Rc or unsubstituted aryl. The above substituent, i.e., Rc, may be, for example, deuterium, a halogen group, cyano, heteroaryl with 3 to 12 carbon atoms, aryl with 6 to 12 carbon atoms, trialkylsilyl with 3 to 12 carbon atoms, alkyl with 1 to 10 carbon atoms, haloalkyl with 1 to 10 carbon atoms, cycloalkyl with 3 to 10 carbon atoms, heterocycloalkyl with 2 to 10 carbon atoms, or alkoxy with 1 to 10 carbon atoms.

In the present disclosure, a "substituted" functional group can be substituted by one or two or more substituents in the Rc; when two substituents Rc are connected to a same atom, the two substituents Rc may independently exist or are connected to each other to form a spirocyclic ring with the atom; and when one substituent Rc is present on each of two adjacent carbon atoms in the functional group, two adjacent substituents Rc may independently exist or are fused with the functional group to which they are connected to form a ring.

In the present disclosure, the terms "optional" and "optionally" mean that the subsequently described event may but need not occur, and that the description includes instances where the event occurs or does not occur. For example, "optionally, two adjacent substituents xx form a ring", which means that the two substituents can, but need not, form a ring, including scenarios in which two adjacent substituents form a ring and scenarios in which two adjacent substituents do not form a ring.

In the present disclosure, "any two adjacent" in the condition that "any two adjacent substituents form a ring" can include the condition that a same atom has two substituents, and the condition that two adjacent atoms each have one substituent; when the same atom has two substituents, the two substituents may form a saturated or unsaturated ring with the atom to which they are connected; and when two adjacent atoms each have one substituent, the two substituents may be fused to form a ring.

In the present disclosure, "optionally, in $Ar_1$, $Ar_2$ and $Ar_3$, any two adjacent substituents form a ring", which means that in $Ar_1$, $Ar_2$ or $Ar_3$, any two adjacent substituents may or may not form a ring. For example, when two adjacent substituents in $Ar_1$ form a ring, the number of carbon atoms in the ring may be 5 to 13, and the ring may be saturated or unsaturated; and the ring is, for example, cyclohexane, cyclopentane, adamantane, a benzene ring, a naphthalene ring, a fluorene ring or the like, but is not limited to this.

In the present disclosure, the number of carbon atoms in the substituted or unsubstituted functional group refers to the number of all carbon atoms. For example, if L is selected from substituted arylene with 12 carbon atoms, the number of all carbon atoms of the arylene and substituents on the arylene is 12. For example: if $Ar_1$ is

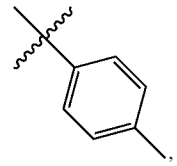

then the number of carbon atoms is 7; and if L is

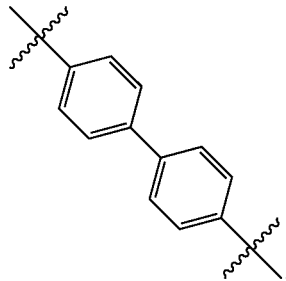

the number of carbon atoms is 12.

In the present disclosure, the "alkyl" may include linear alkyl or branched alkyl. The alkyl may have 1 to 10 carbon atoms, and in the present disclosure, the range of values such as "1 to 10" refers to each integer in a given range; for example, "alkyl with 1 to 10 carbon atoms" refers to alkyl that may include 1, 2, 3, 4, 5, 6, 7, 8, 9 or 10 carbon atoms. In addition, the alkyl may be substituted or unsubstituted.

Optionally, the alkyl is selected from alkyl with 1 to 5 carbon atoms, and specific examples include, but are not limited to, methyl, ethyl, propyl, isopropyl, n-butyl, isobutyl, sec-butyl, tert-butyl, and pentyl.

In the present disclosure, cycloalkyl refers to saturated hydrocarbon containing an alicyclic structure, including monocyclic and fused structures. The cycloalkyl can have 3 to 10 carbon atoms, and the range of values such as "3 to 10" refers to each integer in a given range; for example, "cycloalkyl with 3 to 10 carbon atoms" refers to cycloalkyl that may include 3, 4, 5, 6, 7, 8, 9, or 10 carbon atoms. The cycloalkyl may be substituted or unsubstituted. Examples of the cycloalkyl, such as cyclopentyl, cyclohexyl, and adamantyl.

In the present disclosure, aryl refers to an optional functional group or substituent derived from an aromatic carbon ring. The aryl may be monocyclic aryl (e.g., phenyl) or polycyclic aryl, in other words, the aryl can be monocyclic aryl, fused aryl, two or more monocyclic aryl conjugatedly connected by carbon-carbon bond, monocyclic aryl and fused aryl which are conjugatedly connected by a carbon-carbon bond, or two or more fused aryl conjugatedly connected by carbon-carbon bond. That is, unless otherwise noted, two or more aromatic groups conjugatedly connected by carbon-carbon bond can also be regarded as the aryl of the present disclosure. Wherein the fused aryl may, for example, include bicyclic fused aryl (e.g., naphthyl), tricyclic fused aryl (e.g., phenanthryl, fluorenyl, and anthryl), and the like. The aryl does not contain heteroatoms such as B, N, O, S, P, Se and Si. For example, in the present disclosure, biphenyl, terphenyl, etc. are aryl. Examples of the aryl can include, but are not limited to, phenyl, naphthyl, fluorenyl, anthryl, phenanthryl, biphenyl, terphenyl, quaterphenyl, triphenylene, pyrenyl, benzofluoranthenyl, chrysenyl, and the like.

In the present disclosure, "substituted or unsubstituted aryl" can contain 6 to 30 carbon atoms, in some embodiments, the number of carbon atoms in the substituted or unsubstituted aryl is 6 to 25, in other embodiments, the number of carbon atoms in the substituted or unsubstituted aryl is 6 to 20, in other embodiments, the number of carbon atoms in the substituted or unsubstituted aryl is 6 to 18, and in still other embodiments, the number of carbon atoms in the substituted or unsubstituted aryl is 6 to 12. For example, in the present disclosure, the number of carbon atoms in the substituted or unsubstituted aryl can be 6, 12, 13, 14, 15, 18, 20, 24, 25, 28, 29 or 30, and of course, the number of carbon atoms can also be other numbers, which will not be listed here. In the present disclosure, biphenyl can be understood as phenyl-substituted aryl or unsubstituted aryl.

In the present disclosure, the arylene involved is a divalent group formed by further loss of one hydrogen atom from aryl.

In the present disclosure, substituted aryl can be that one or two or more hydrogen atoms in the aryl are substituted with groups such as a deuterium atom, a halogen group, cyano, aryl, heteroaryl, trialkylsilyl, alkyl, haloalkyl, cycloalkyl, heterocycloalkyl, alkoxy, and the like. It should be understood that the number of carbon atoms in the substituted aryl refers to the total number of carbon atoms of the aryl and substituents on the aryl, for example, the substituted aryl with 18 carbon atoms means that the total number of carbon atoms of the aryl and its substituents is 18.

In the present disclosure, specific examples of aryl as a substituent in $L_1$, $L_2$, $L_3$, $Ar_1$, $Ar_2$, and $Ar_3$ include, but are not limited to, phenyl, naphthyl, anthryl, phenanthryl, dimethylfluorenyl, biphenyl, and the like.

In the present disclosure, heteroaryl refers to a monovalent aromatic ring containing 1, 2, 3, 4, 5, or 6 heteroatoms in the ring or its derivative, and the heteroatom may be at least one of B, O, N, P, Si, Se, and S. The heteroaryl may be monocyclic heteroaryl or polycyclic heteroaryl, in other words, the heteroaryl may be a single aromatic ring system or a multiple of aromatic ring systems conjugatedly connected by carbon-carbon bond, where any one aromatic ring system is one aromatic monocyclic ring or one aromatic fused ring. For example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridinopyrimidyl, pyridinopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuryl, phenanthrolinyl, isoxazolyl, thiadiazolyl, benzothiazolyl, phenothiazinyl, silafluorenyl, dibenzofuryl and N-arylcarbazolyl (e.g., N-phenylcarbazolyl), N-heteroarylcarbazolyl (e.g., N-pyridylcarbazolyl), N-alkylcarbazolyl (e.g., N-methylcarbazolyl), and the like, but is not limited to thereto. Wherein, thienyl, furyl, phenanthrolinyl and the like are heteroaryl of the single aromatic ring system, and N-phenylcarbazolyl and N-pyridylcarbazolyl are heteroaryl of the plurality of aromatic ring systems conjugatedly connected by carbon-carbon bonds. For example, in the present disclosure, the number of carbon atoms in the substituted or unsubstituted heteroaryl can be 3, 4, 5, 6, 10, 12, 18, 20, 24, 25, 28, 29 or 30, and of course, the number of carbon atoms can also be other numbers, which will not be listed here.

In the present disclosure, the heteroarylene involved refers to a divalent group formed by further loss of one hydrogen atom from heteroaryl.

In the present disclosure, substituted heteroaryl can be that one or two or more hydrogen atoms in the heteroaryl are substituted with groups such as a deuterium atom, a halogen group, cyano, aryl, heteroaryl, trialkylsilyl, alkyl, haloalkyl, cycloalkyl, heterocycloalkyl, alkoxy, and the like. It should be understood that the number of carbon atoms of the substituted heteroaryl refers to the total number of carbon atoms of heteroaryl and substituents on the heteroaryl.

In the present disclosure, specific examples of heteroaryl as a substituent in $L_1$, $L_2$, $L_3$, $Ar_1$, $Ar_2$, and $Ar_3$ include, but are not limited to, pyridyl, carbazolyl, dibenzofuranyl, and dibenzothienyl.

In the present disclosure, the halogen group may include fluorine, iodine, bromine, chlorine, and the like.

In the present disclosure, specific examples of the trialkylsilyl with 3 to 12 carbon atoms include, but are not limited to, trimethylsilyl, triethylsilyl, and the like.

In the present disclosure, specific examples of haloalkyl with 1 to 10 carbon atoms include, but are not limited to, trifluoromethyl.

In the present disclosure, an unpositioned connecting bond is a single bond "$\frac{1}{\ast}$" extending from a ring system, which means that one end of the connecting bond can be connected with any position in the ring system through which the bond penetrates, and the other end of the connecting bond is connected with the remaining part of a compound molecule.

For example, as shown in the following formula (f), naphthyl represented by the formula (f) is connected to other positions of a molecule through two unpositioned connecting bonds penetrating a dicyclic ring, and its meaning includes any one possible connecting mode represented by formulae (f-1)-(f-10):

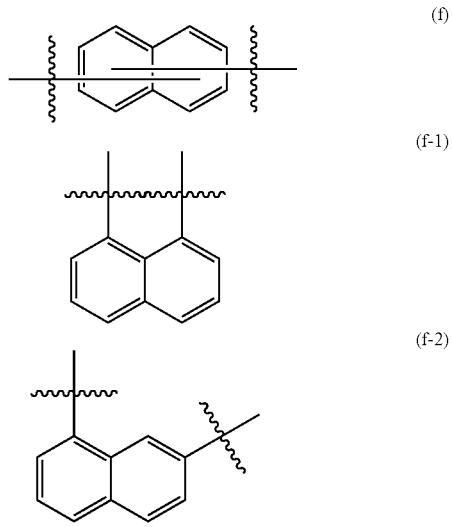

-continued (f-3)
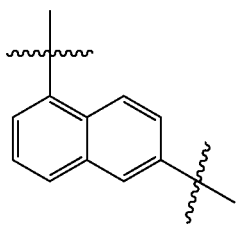

(f-4)
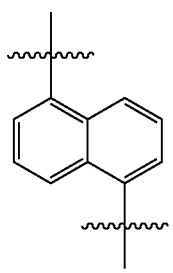

(f-5)
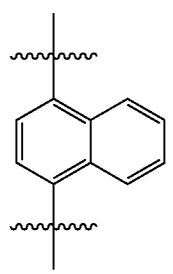

(f-6)
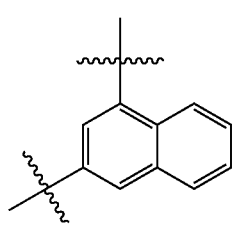

(f-7)
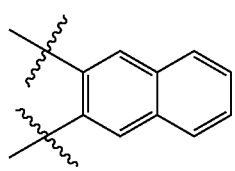

(f-8)

(f-9)
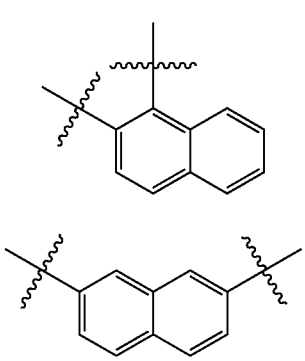

-continued (f-10)
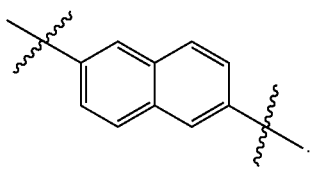

For another example, as shown in the following formula (X'), dibenzofuranyl represented by the formula (X') is connected with other positions of a molecule through one unpositioned connecting bond extending from the middle of a benzene ring on one side, and its meaning includes any one possible connecting mode represented by formulae (X'-1)-(X'-4):

(X')
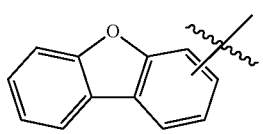

(X'-1)
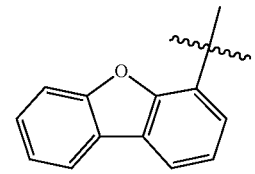

(X'-2)
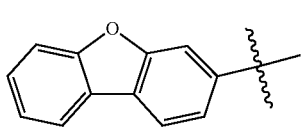

(X'-3)
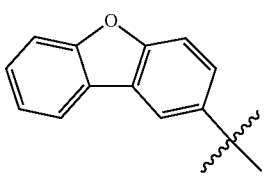

(X'-4)
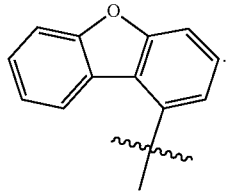

In the following, the meaning for unpositioned connection or unpositioned substitution is the same as here, which will not be repeated later.

In some embodiments, the organic compound is selected from compounds represented by a formula 2:

Formula 2

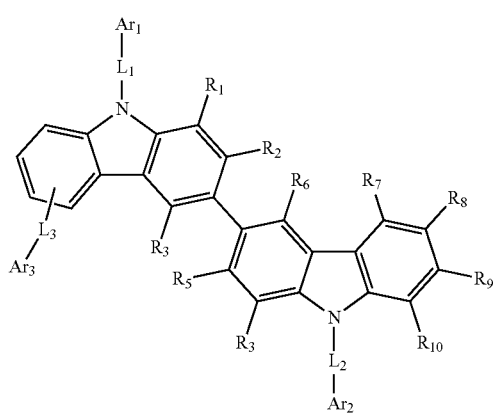

wherein L₁ and L₂ are respectively and independently selected from a single bond, substituted or unsubstituted arylene with 6 to 30 carbon atoms, and substituted or unsubstituted heteroarylene with 3 to 30 carbon atoms;

L₃ is selected from a single bond, and substituted or unsubstituted arylene with 6 to 30 carbon atoms;

Ar₁ and Ar₂ are respectively and independently selected from substituted or unsubstituted aryl with 6 to 30 carbon atoms, and substituted or unsubstituted heteroaryl with 3 to 30 carbon atoms;

Ar₃ is selected from substituted or unsubstituted aryl with 6 to 30 carbon atoms;

R₁, R₂, R₃, R₄, R₅, R₆, R₇, R₈, R₉ and R₁₀ are respectively and independently selected from hydrogen or deuterium, and at least two of R₂, R₃, R₅ and R₆ are deuterium;

substituents in L₁, L₂, L₃, Ar₁, Ar₂ and Ar₃ are respectively and independently selected from deuterium, a halogen group, cyano, heteroaryl with 3 to 12 carbon atoms, aryl with 6 to 12 carbon atoms, trialkylsilyl with 3 to 12 carbon atoms, alkyl with 1 to 10 carbon atoms, haloalkyl with 1 to 10 carbon atoms, cycloalkyl with 3 to 10 carbon atoms, heterocycloalkyl with 2 to 10 carbon atoms, and alkoxy with 1 to 10 carbon atoms; and optionally, in Ar₁, Ar₂, and Ar₃, any two adjacent substituents form a ring.

In some embodiments of the present disclosure, the organic compound is selected from compounds represented by formulae 2-1 to 2-6 below:

Formula 2-1

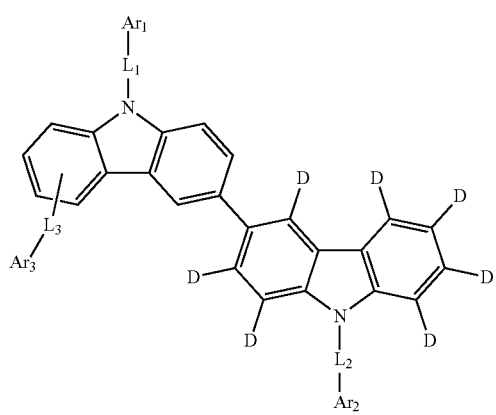

Formula 2-2

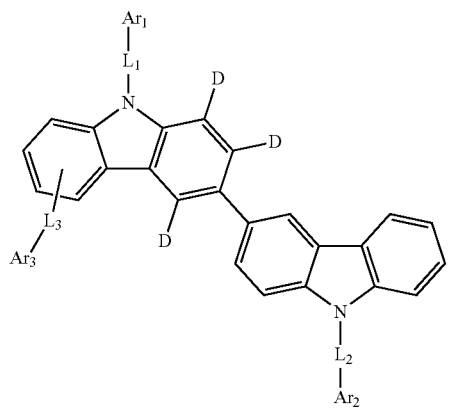

Formula 2-3

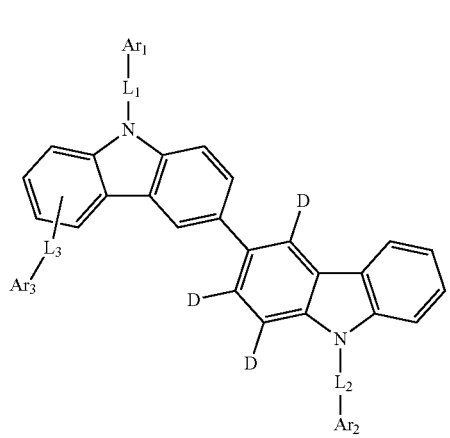

Formula 2-4

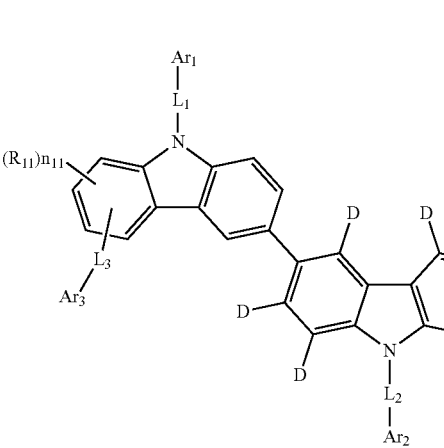

Formula 2-5

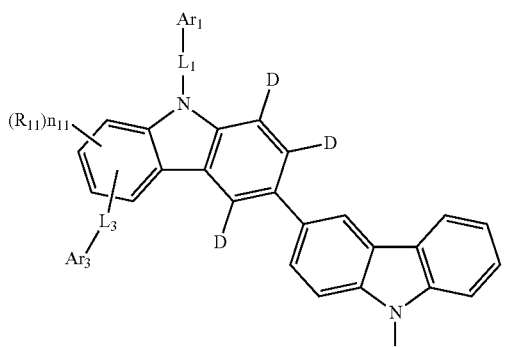

Formula 2-6

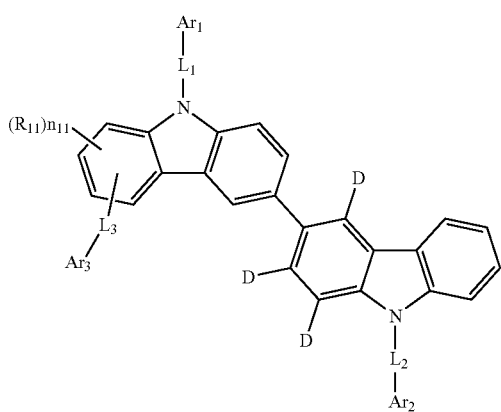

wherein, in the formulas 2-4 to 2-6, $R_{11}$ is deuterium and $n_{11}$ is selected from 1, 2, or 3.

Preferably, in the formulas 2-4 to 2-6, $R_{11}$ is deuterium and $n_{11}$ is selected from 3.

In some embodiments of the present disclosure, $L_1$ and $L_2$ are respectively and independently selected from a single bond, substituted or unsubstituted arylene with 6 to 12 carbon atoms, and substituted or unsubstituted heteroarylene with 12 to 18 carbon atoms.

Optionally, substituents in $L_1$ and $L_2$ are the same or different, and are respectively and independently selected from deuterium, a halogen group, cyano, alkyl with 1 to 5 carbon atoms, and phenyl.

Specifically, specific examples of the substituents in $L_1$ and $L_2$ include, but are not limited to, deuterium, fluorine, cyano, methyl, ethyl, n-propyl, isopropyl, tert-butyl, and phenyl.

In other embodiments of the present disclosure, $L_1$ and $L_2$ are respectively and independently selected from a single bond, substituted or unsubstituted phenylene, substituted or unsubstituted naphthylene, substituted or unsubstituted biphenylene, substituted or unsubstituted carbazolylene, substituted or unsubstituted dibenzofurylene, and substituted or unsubstituted dibenzothienylene.

Optionally, substituents in $L_1$ and $L_2$ are the same or different, and are respectively and independently selected from deuterium, fluorine, cyano, methyl, ethyl, n-propyl, isopropyl, tert-butyl, and phenyl.

In some embodiments of the present disclosure, $L_1$ and $L_2$ are respectively and independently selected from a single bond and a substituted or unsubstituted group V, wherein the unsubstituted group V is selected from the group consisting of:

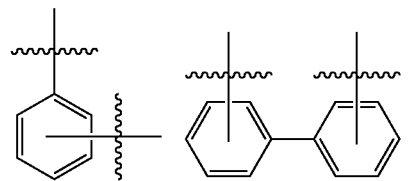

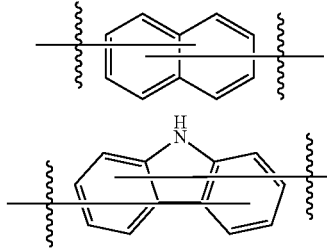

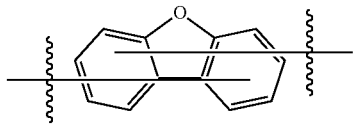

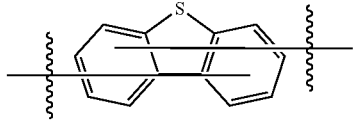

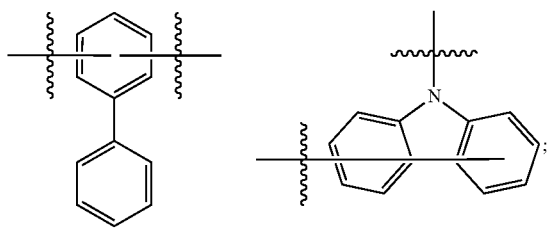

wherein, ⸺ represents a chemical bond; the substituted group V contains one or more substituents selected from deuterium, fluorine, cyano, methyl, ethyl, n-propyl, isopropyl, tert-butyl, and phenyl; and when the substituted group V contains a plurality of substituents, the substituents are the same or different.

Optionally, $L_1$ and $L_2$ are respectively and independently selected from a single bond or the group consisting of:

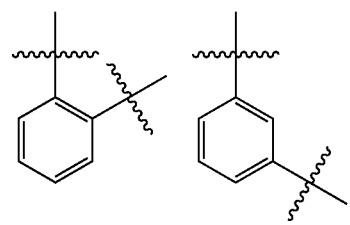

-continued
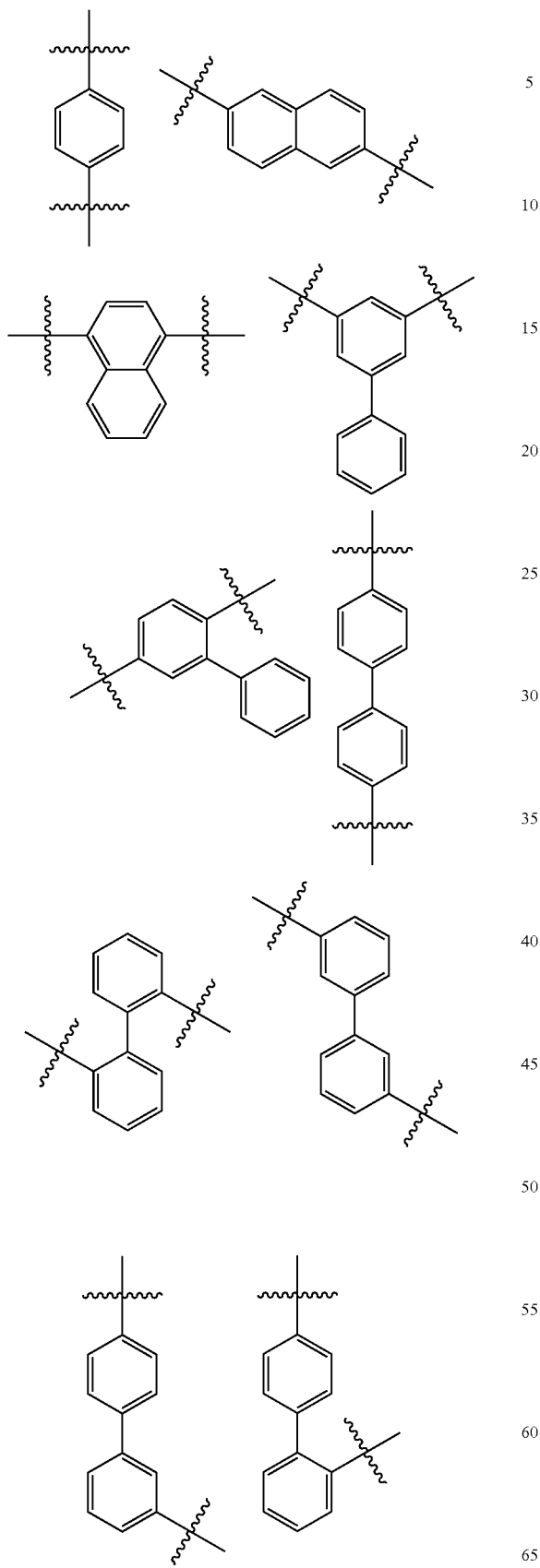
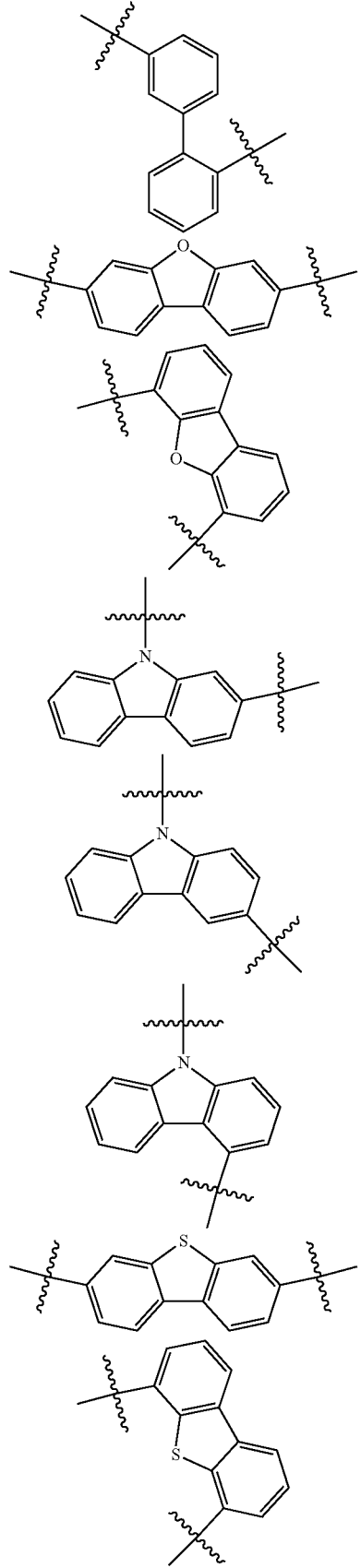

In some embodiments of the present disclosure, $L_3$ is selected from a single bond or phenylene.

In some embodiments of the present disclosure, $L_3$ is selected from a single bond or the group consisting of:

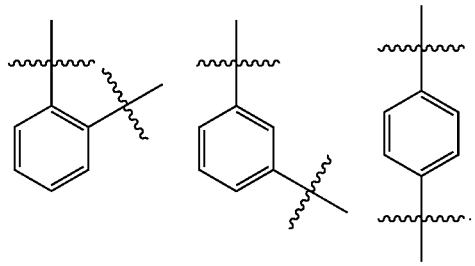 [SMILES: *c1ccccc1* ; *c1cccc(*)c1 ; *c1ccc(*)cc1]

In some embodiments of the present disclosure, $Ar_1$ and $Ar_2$ are respectively and independently selected from substituted or unsubstituted aryl with 6 to 25 carbon atoms and substituted or unsubstituted heteroarylene with 12 to 20 carbon atoms.

Optionally, substituents in $Ar_1$ and $Ar_2$ are the same or different, and are respectively and independently selected from deuterium, a halogen group, cyano, alkyl with 1 to 5 carbon atoms, and aryl with 6 to 12 carbon atoms.

Optionally, in $Ar_1$ and $Ar_2$, any two adjacent substituents form a saturated or unsaturated ring with 5 to 13 carbon atoms.

Optionally, in $Ar_1$ and $Ar_2$, any two adjacent substituents may form cyclohexane

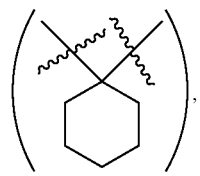

cyclopentane

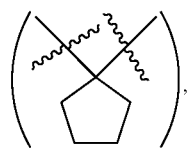

a benzene ring, a naphthalene ring, or a fluorene ring

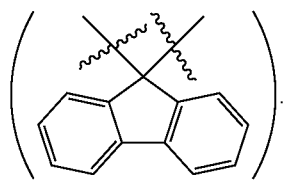

Specifically, specific examples of the substituents in $Ar_1$ and $Ar_2$ include, but are not limited to, deuterium, fluorine, cyano, methyl, ethyl, n-propyl, isopropyl, tert-butyl, phenyl, naphthyl, and biphenyl.

In other embodiments of the present disclosure, $Ar_1$ and $Ar_2$ are respectively and independently selected from substituted or unsubstituted phenyl, substituted or unsubstituted naphthyl, substituted or unsubstituted biphenyl, substituted or unsubstituted terphenyl, substituted or unsubstituted phenanthryl, substituted or unsubstituted fluorenyl, substituted or unsubstituted dibenzofuranyl, substituted or unsubstituted carbazolyl, and substituted or unsubstituted dibenzothienyl.

Optionally, substituents in $Ar_1$ and $Ar_2$ are the same or different, and are respectively and independently selected from deuterium, fluorine, cyano, methyl, ethyl, n-propyl, isopropyl, tert-butyl, phenyl, and naphthyl.

Optionally, in $Ar_1$ and $Ar_2$, any two adjacent substituents form a fluorene ring.

In some embodiments of the present disclosure, $Ar_1$ and $Ar_2$ are respectively and independently selected from a substituted or unsubstituted group W, wherein the unsubstituted group W is selected from the group consisting of:

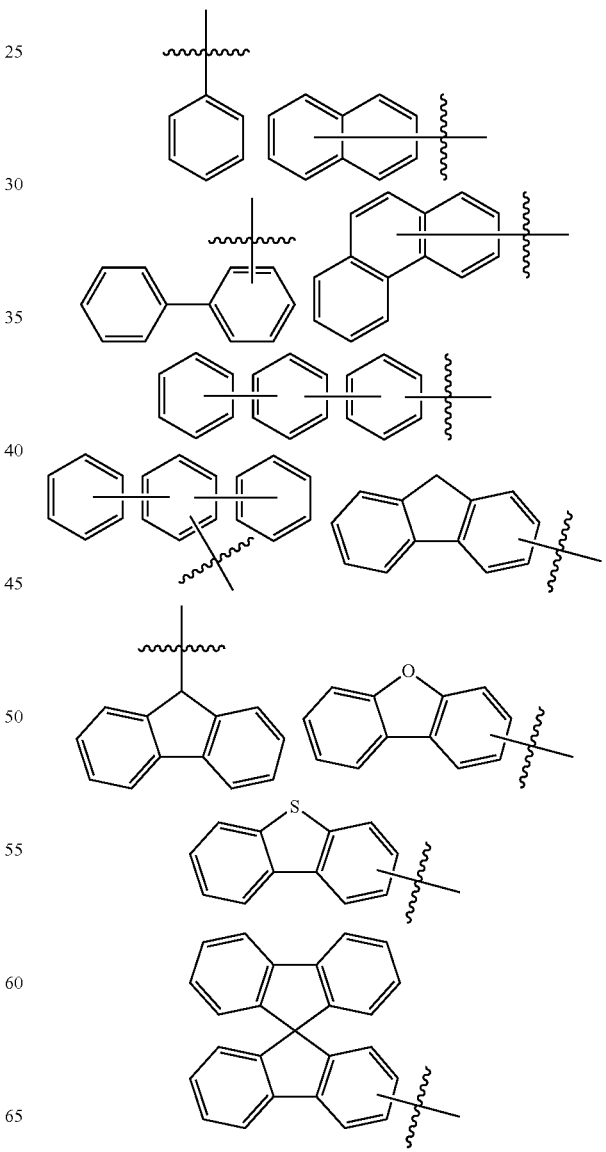

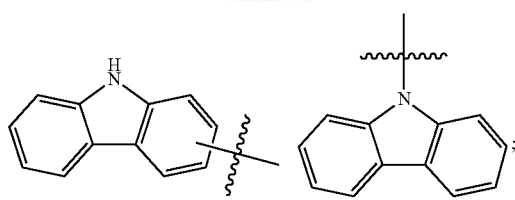

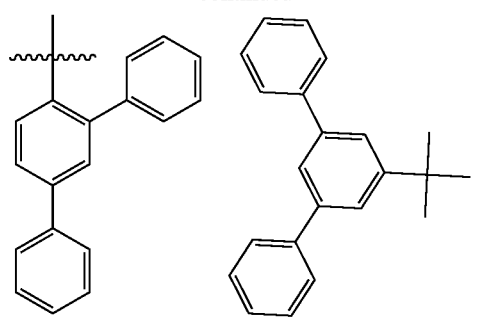

wherein ⚡ represents a chemical bond; the substituted group W contains one or more substituents selected from deuterium, fluorine, cyano, methyl, ethyl, n-propyl, isopropyl, tert-butyl, phenyl, and naphthyl; and when the substituted group W contains a plurality of substituents, the substituents are the same or different.

Optionally, $Ar_1$ and $Ar_2$ are respectively and independently selected from the group consisting of:

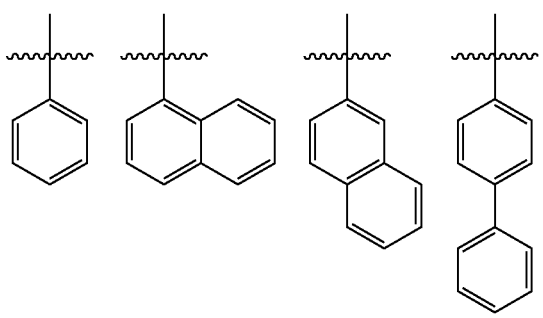

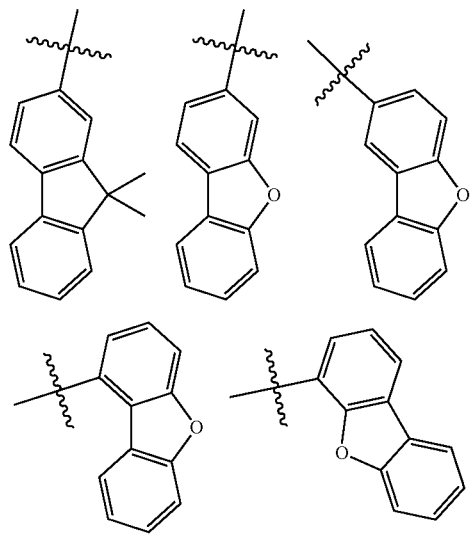

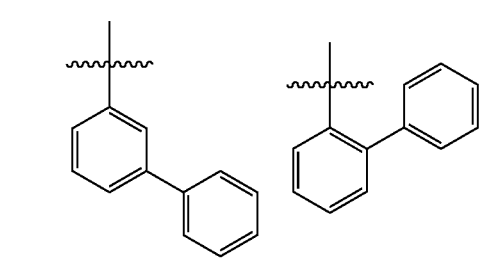

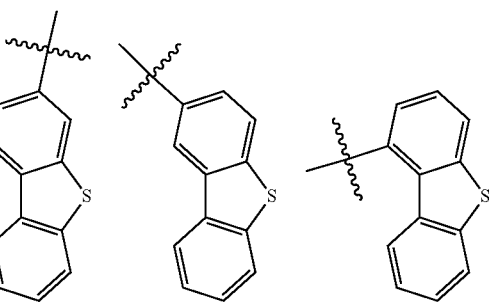

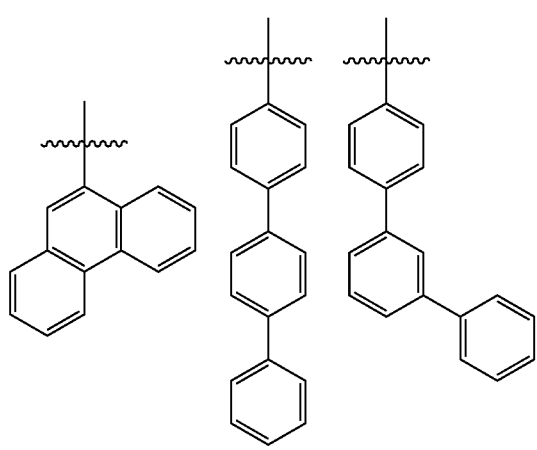

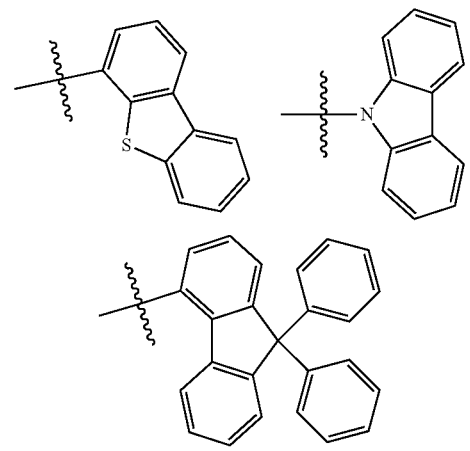

-continued

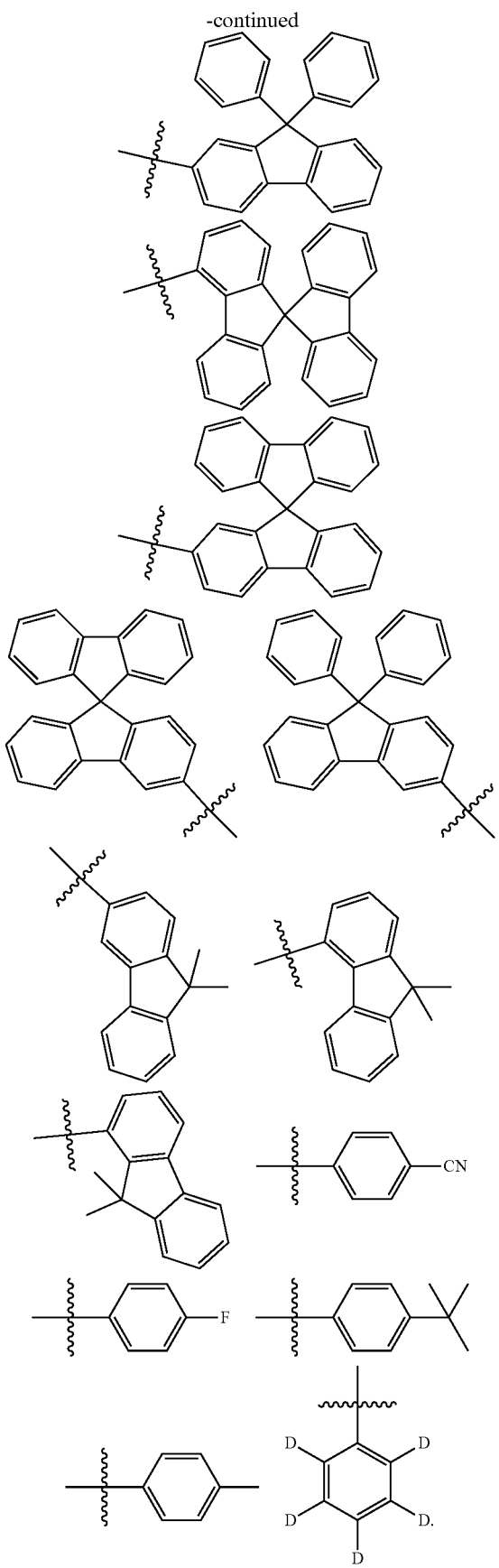

In some embodiments of the present disclosure, Ar₃ is substituted or unsubstituted aryl with 6 to 20 carbon atoms.

Optionally, Ar₃ is substituted or unsubstituted aryl with 6 to 15 carbon atoms.

Optionally, Ar₃ is substituted or unsubstituted aryl with 6 to 12 carbon atoms.

Optionally, substituents in Ar₃ are the same or different, and are respectively and independently selected from deuterium, a halogen group, cyano, alkyl with 1 to 5 carbon atoms, and phenyl.

Specifically, specific examples of the substituents in Ar₃ include, but are not limited to: deuterium, fluorine, cyano, methyl, ethyl, n-propyl, isopropyl, tert-butyl, and phenyl.

In other embodiments of the present disclosure, Ar₃ is selected from substituted or unsubstituted phenyl, substituted or unsubstituted naphthyl, and substituted or unsubstituted biphenyl.

Optionally, substituents in Ar₃ are the same or different, and are respectively and independently selected from deuterium, fluorine, cyano, methyl, ethyl, n-propyl, isopropyl, tert-butyl, and phenyl.

In some embodiments of the present disclosure, Ar₃ is selected from the group consisting of:

In some embodiments of the present disclosure, R₁, R₂ and R₃ are all deuterium, or R₄, R₅ and R₆ are all deuterium.

When $R_1$, $R_2$ and $R_3$, or $R_4$, $R_5$ and $R_6$ in the organic compound of the present disclosure are all deuterium, the device performance is significantly improved when the organic compound is used in a host material for an organic electroluminescent device.

In some embodiments of the present disclosure, $R_4$, $R_5$, $R_6$, $R_7$, $R_8$, $R_9$ and $R_{10}$ are all deuterium.

In some specific embodiments of the present disclosure, when $R_4$, $R_5$, $R_6$, $R_7$, $R_8$, $R_9$, and $R_{10}$ in the organic compound of the present disclosure are all deuterium, the device has lower operating voltage, higher luminous efficiency, and longer service life.

Optionally, the organic compound is selected from the group consisting of:

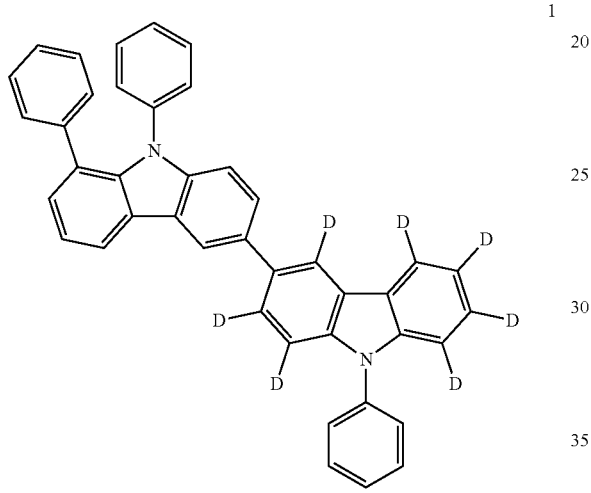

1

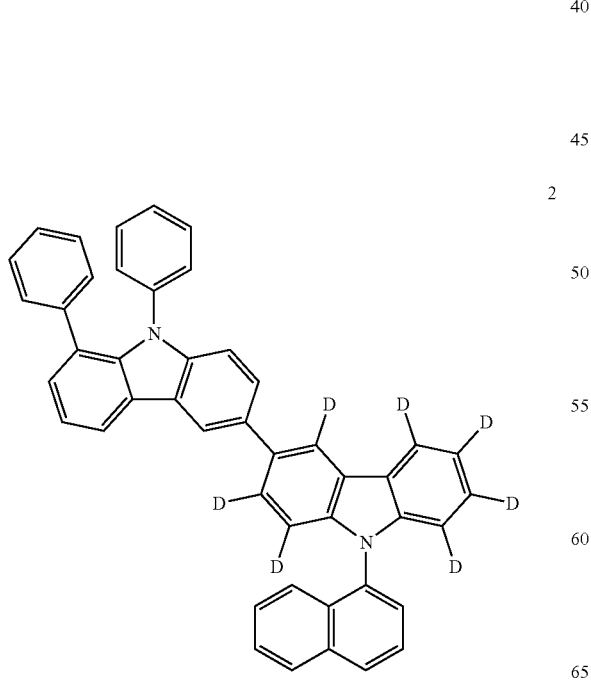

2

-continued

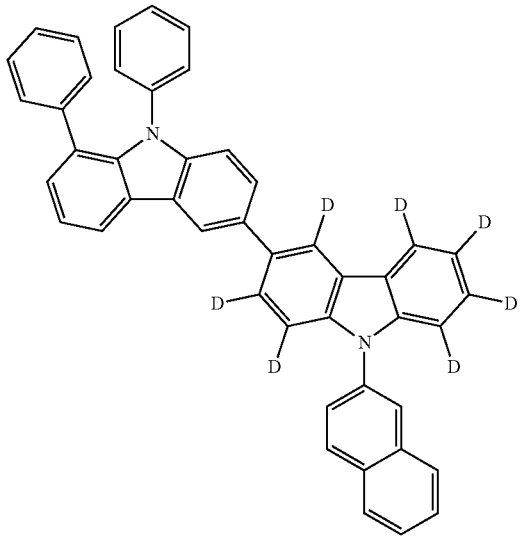

3

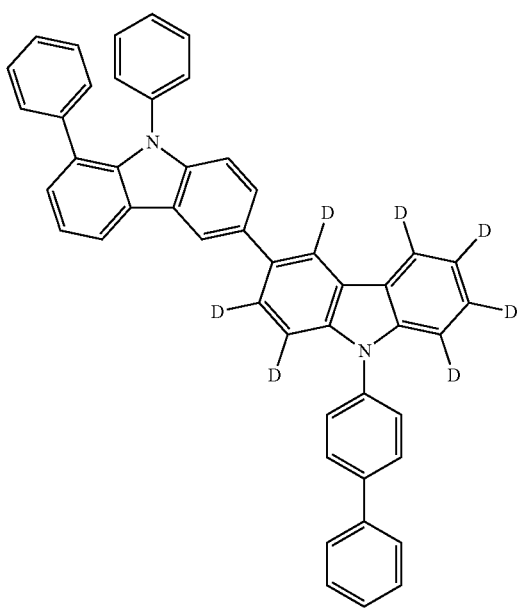

4

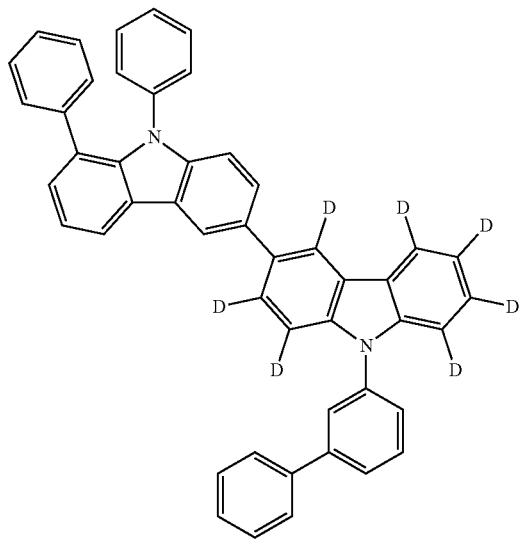
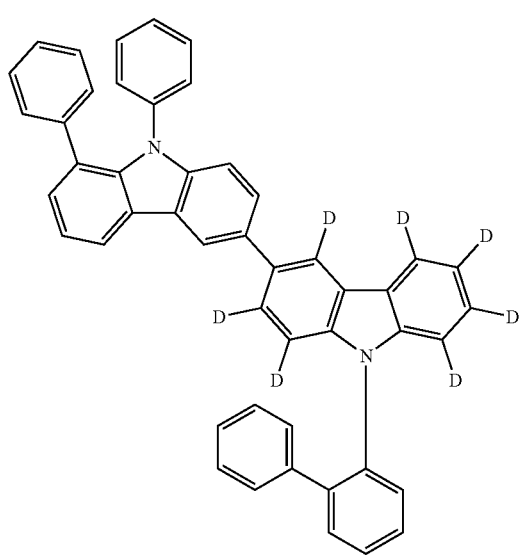
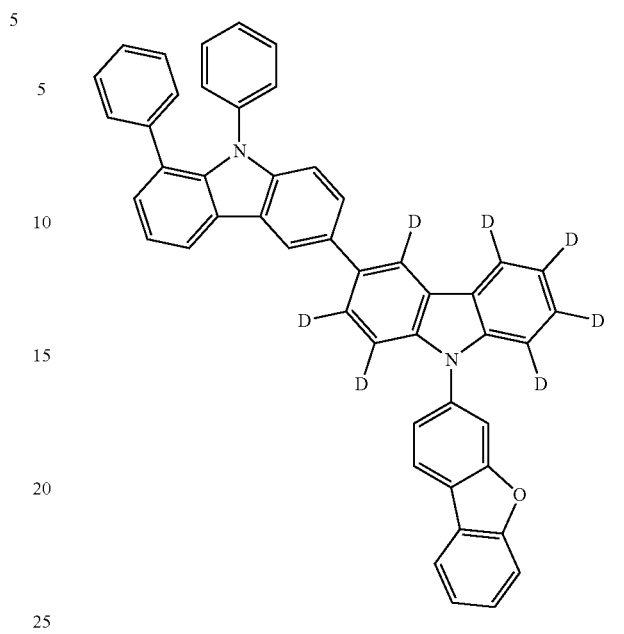
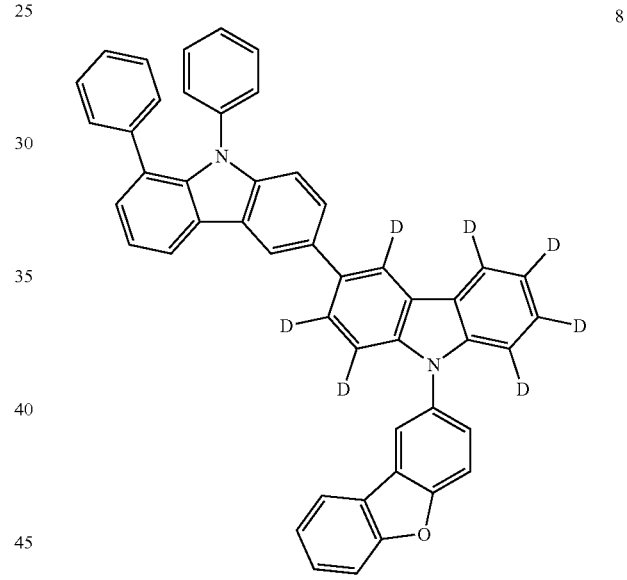
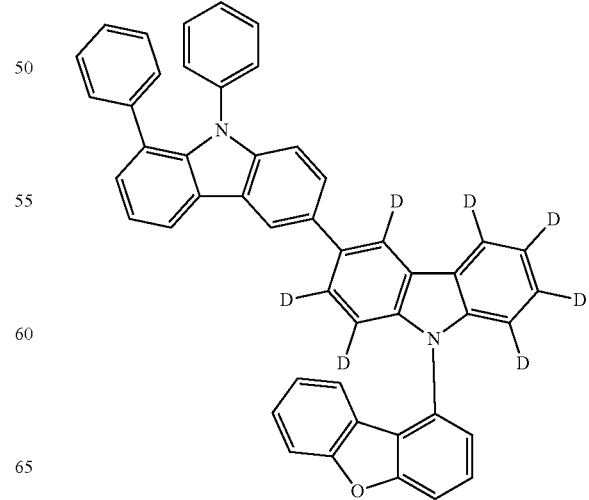

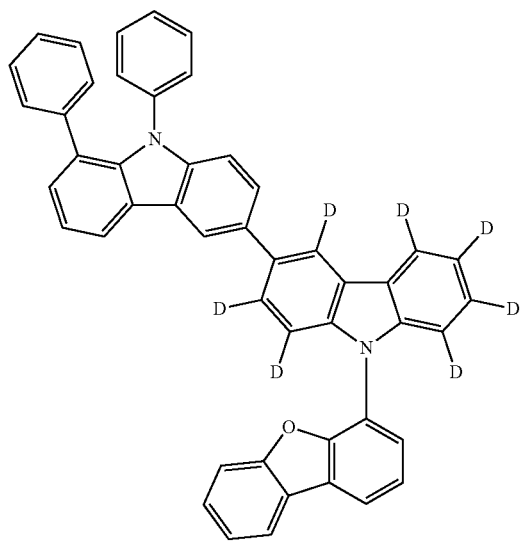
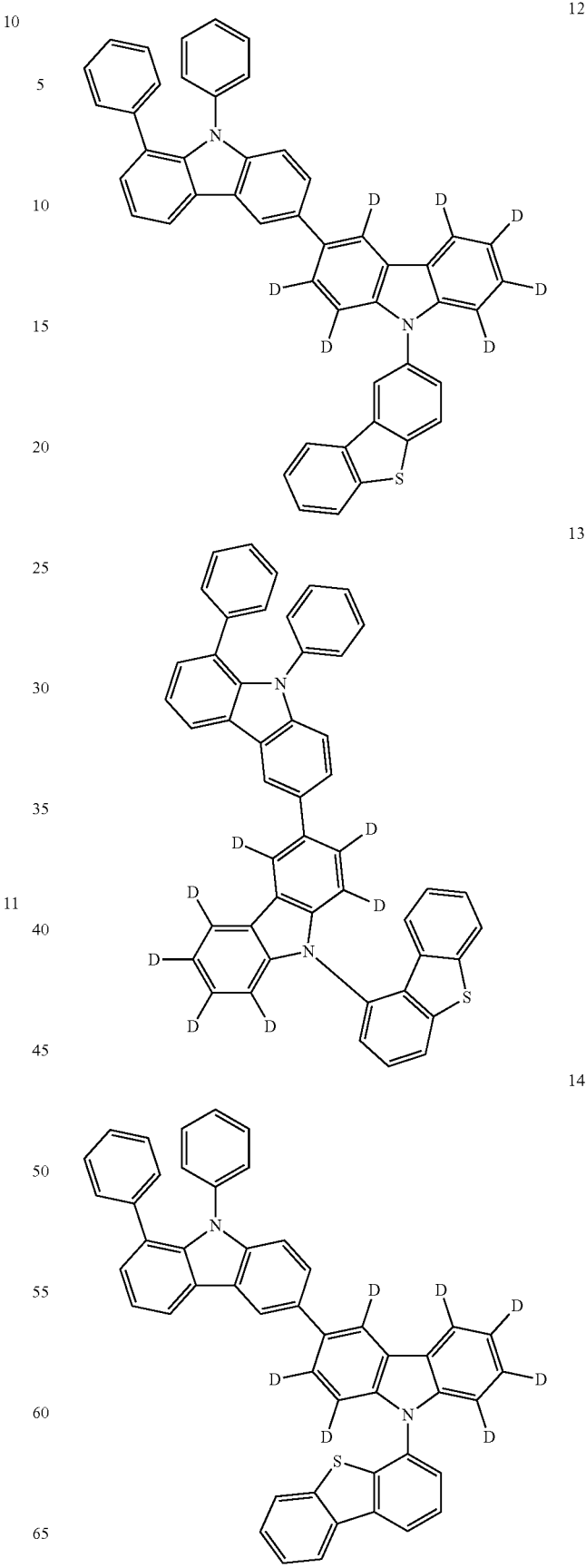

15
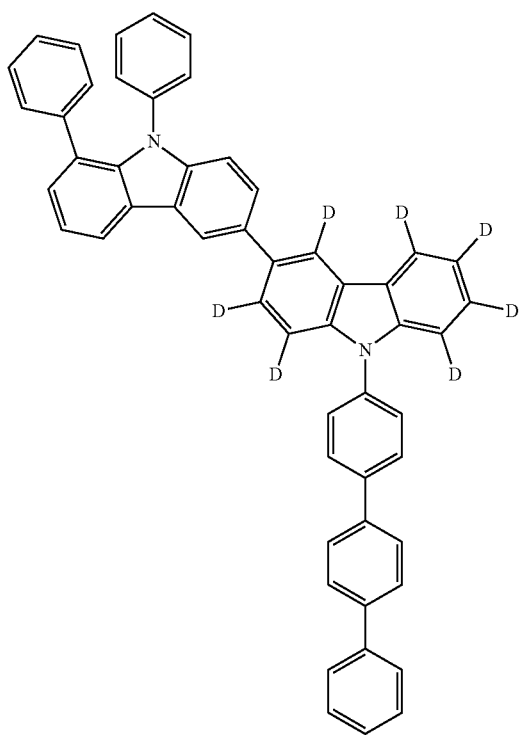
17
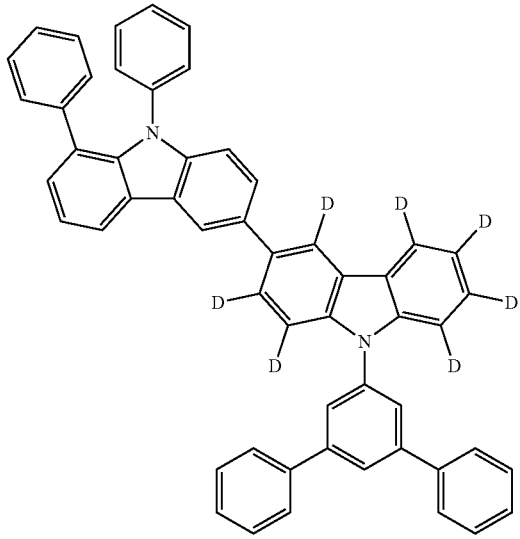
16
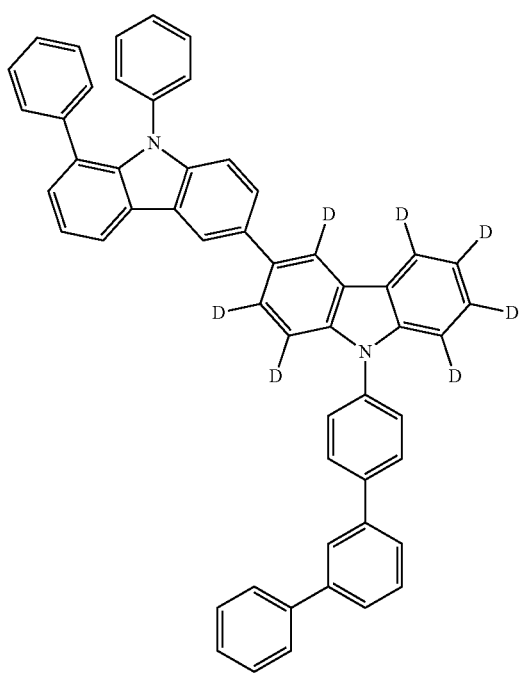
18
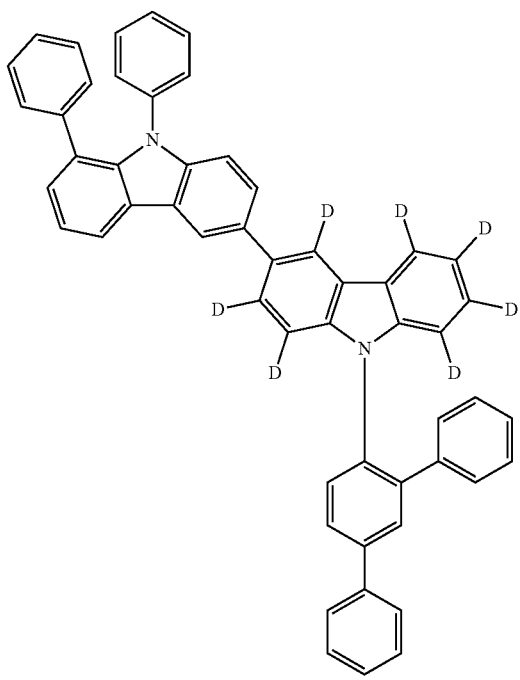

19
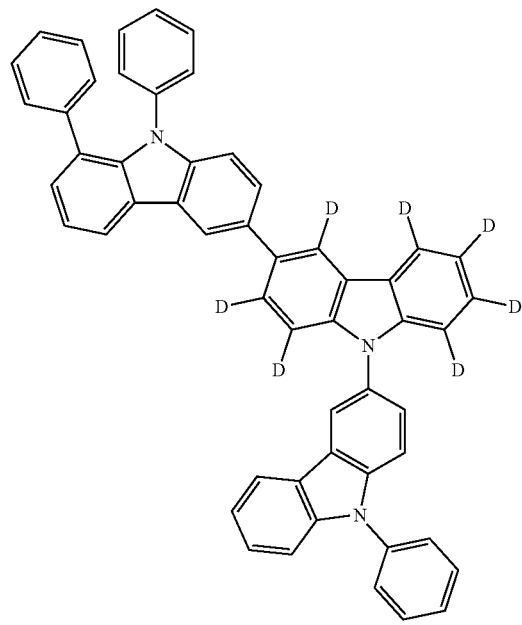
20
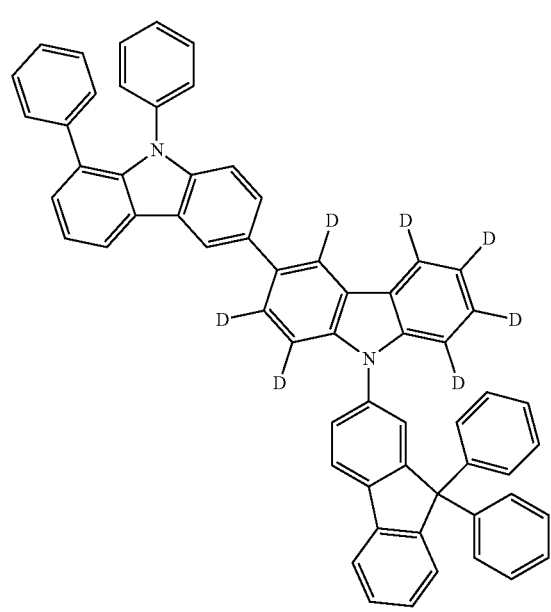
21
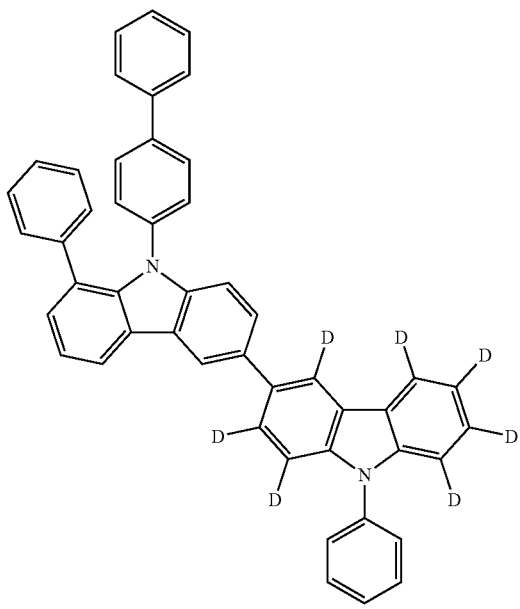
22
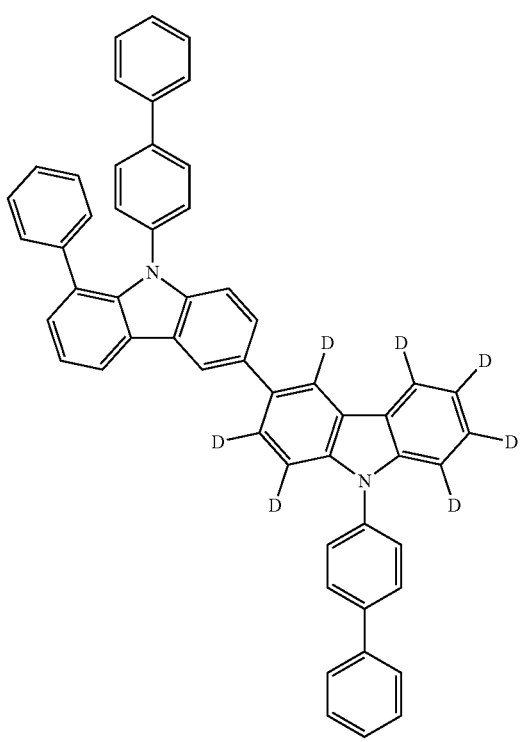

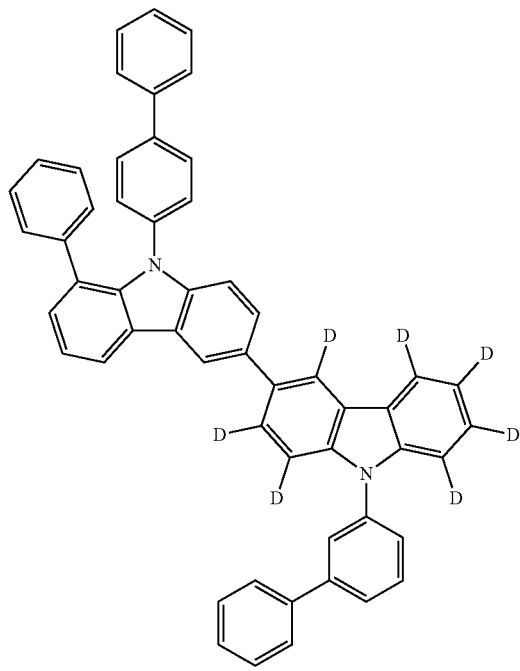
23
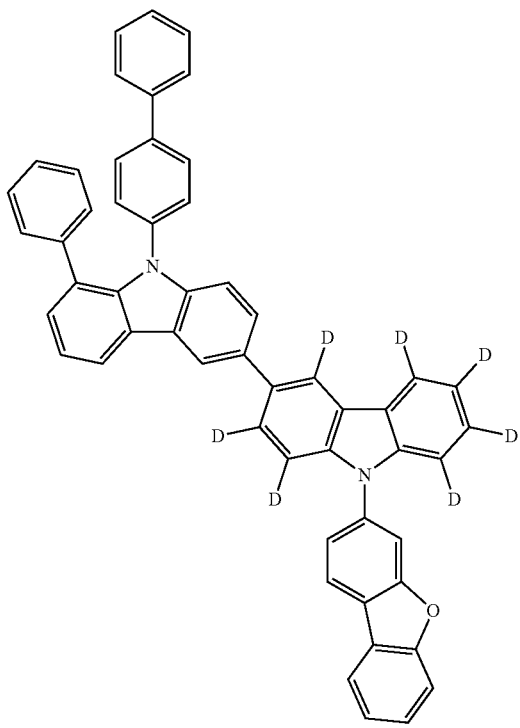
25
24
26
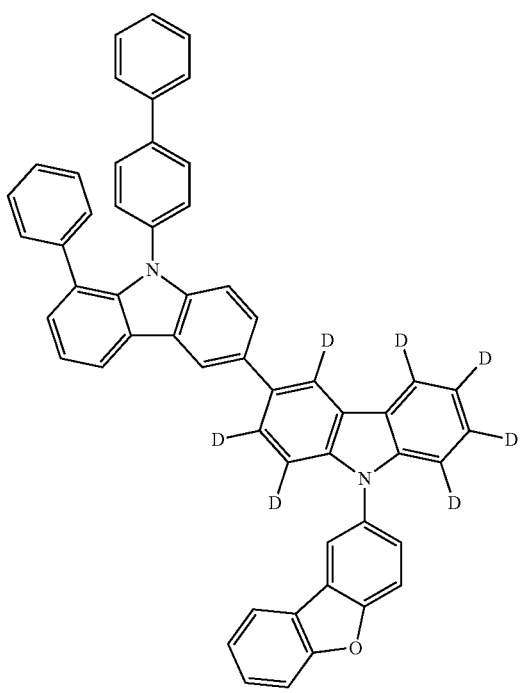

27
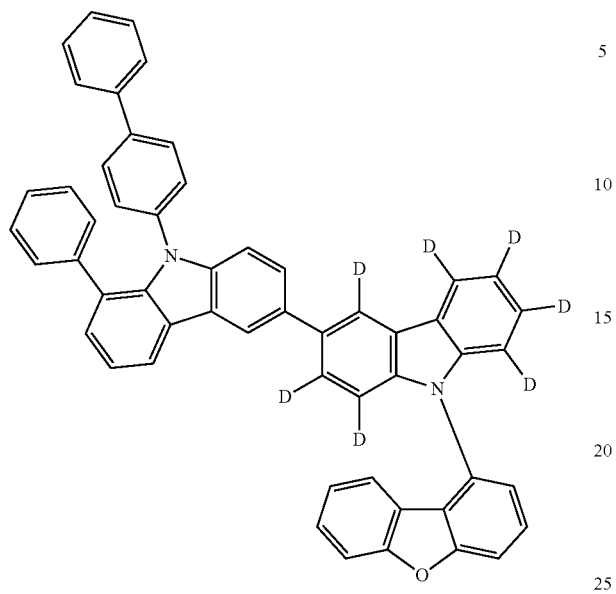
28
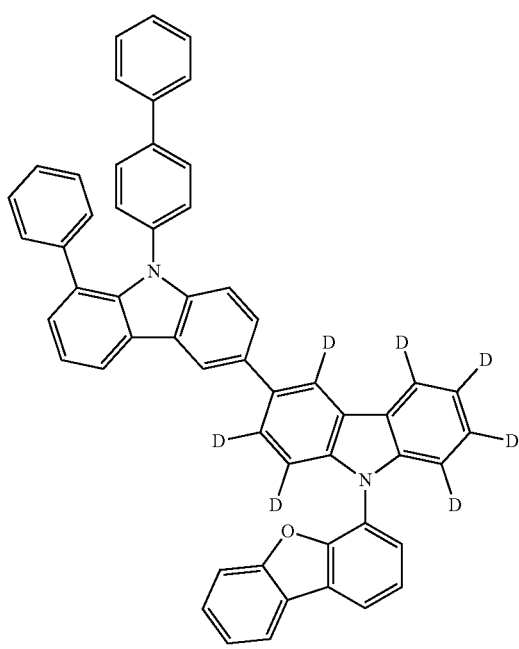
29
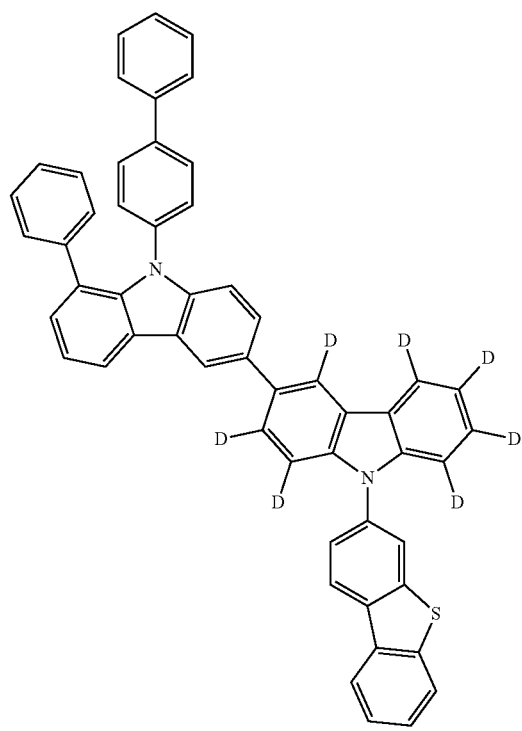
30
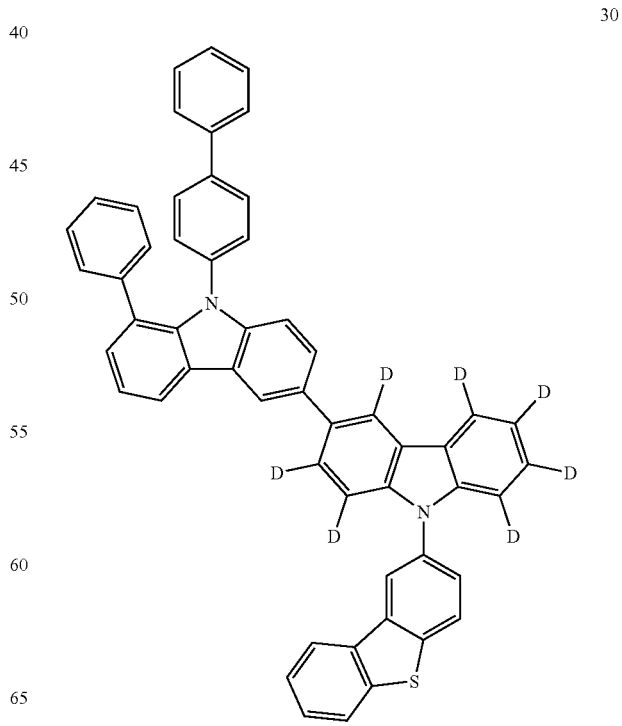

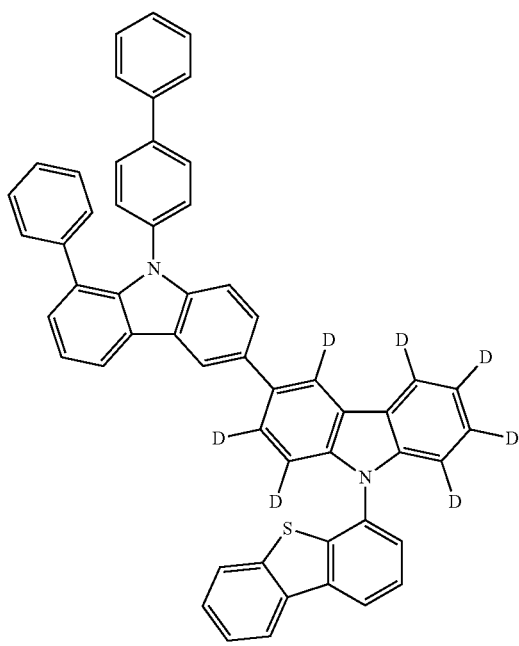

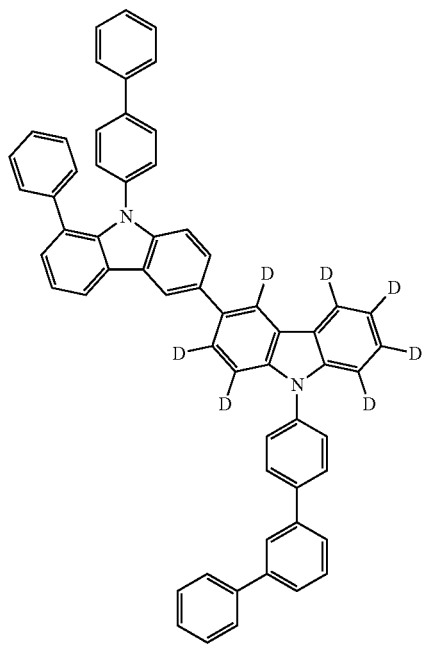
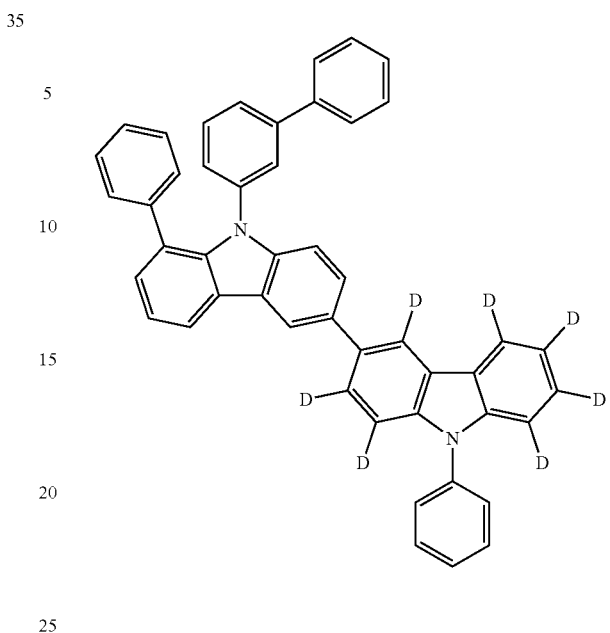

39
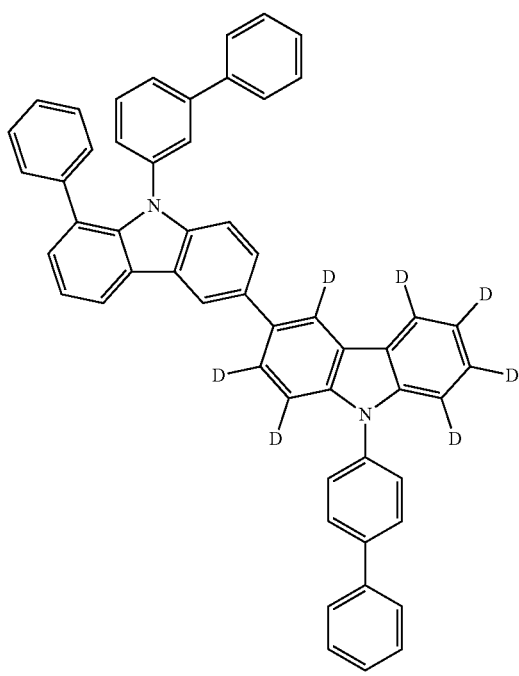
41
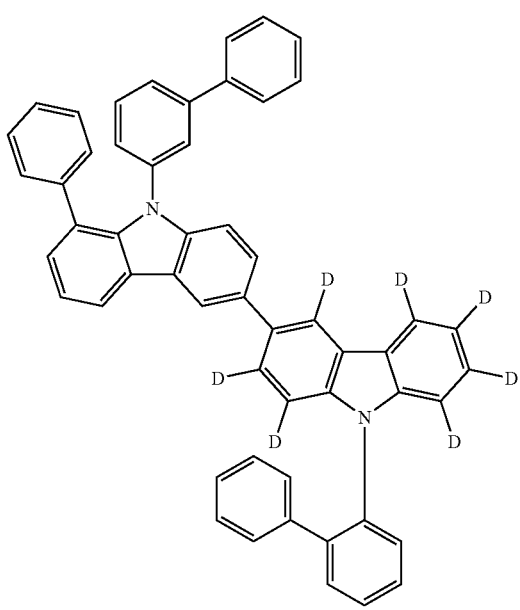
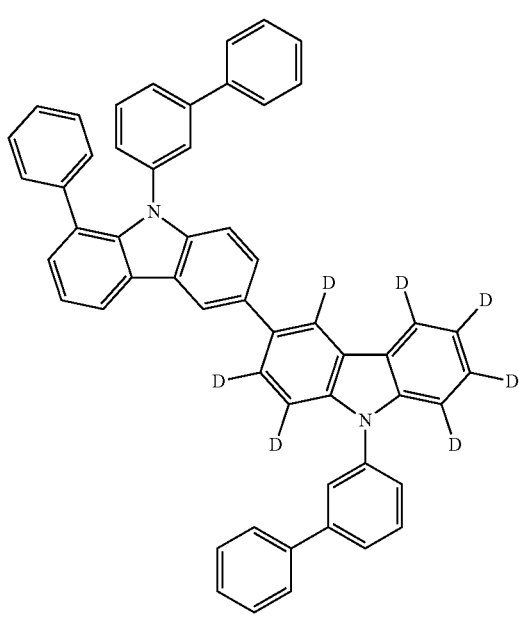
42
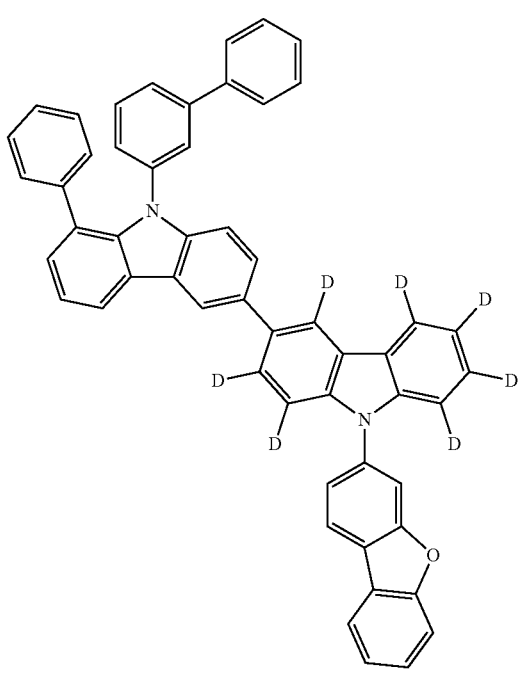

43
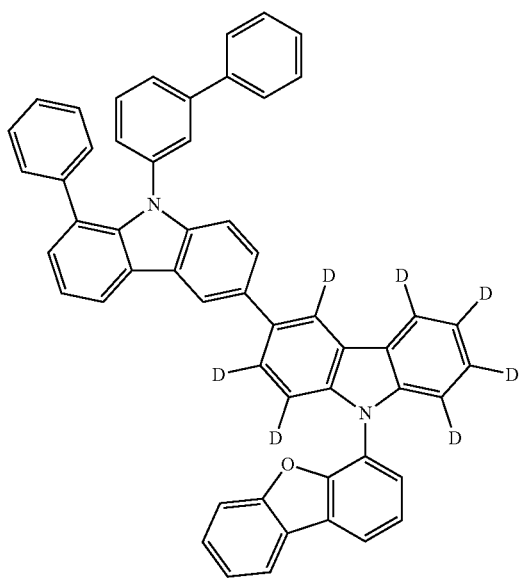
44
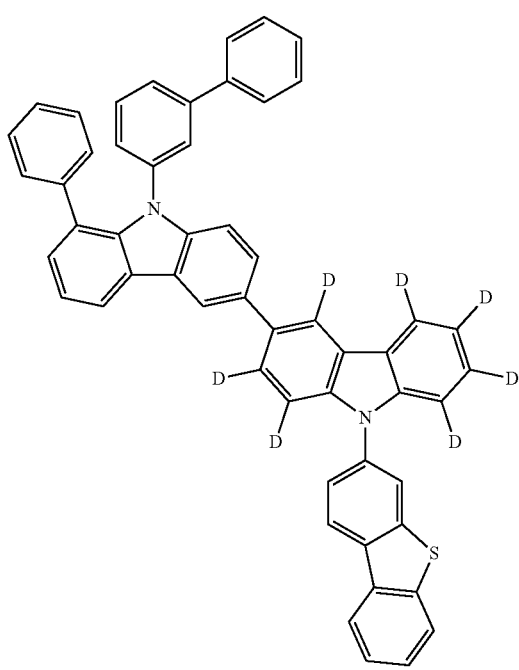
45
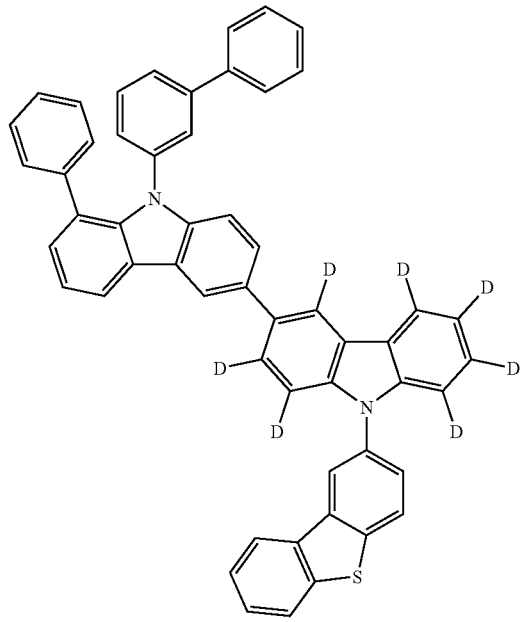
46
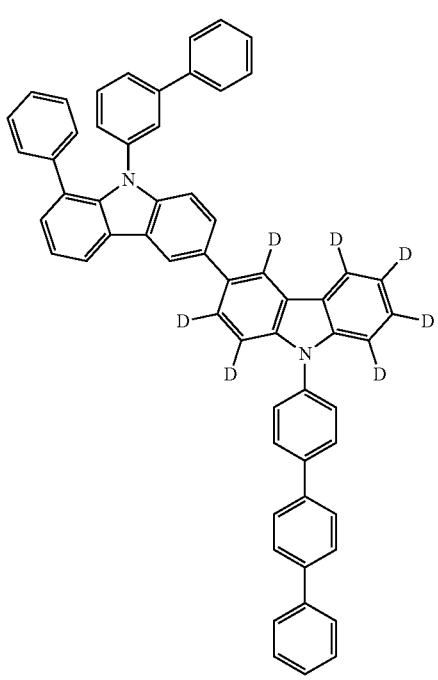

47
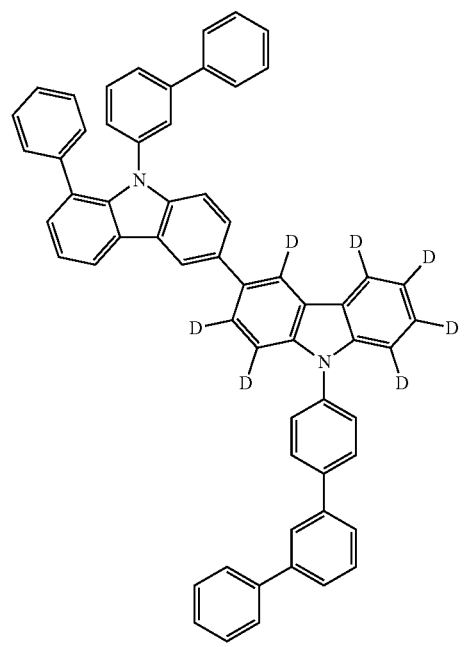
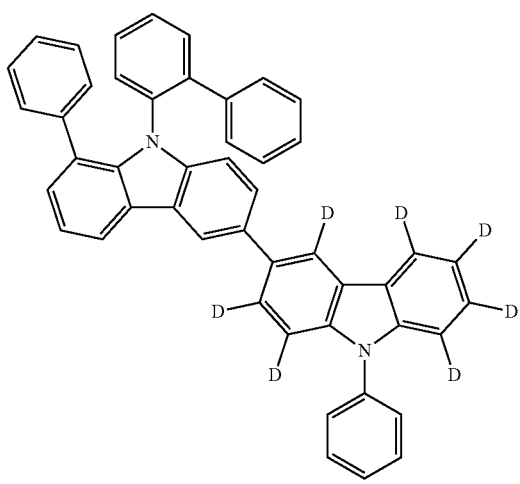
48
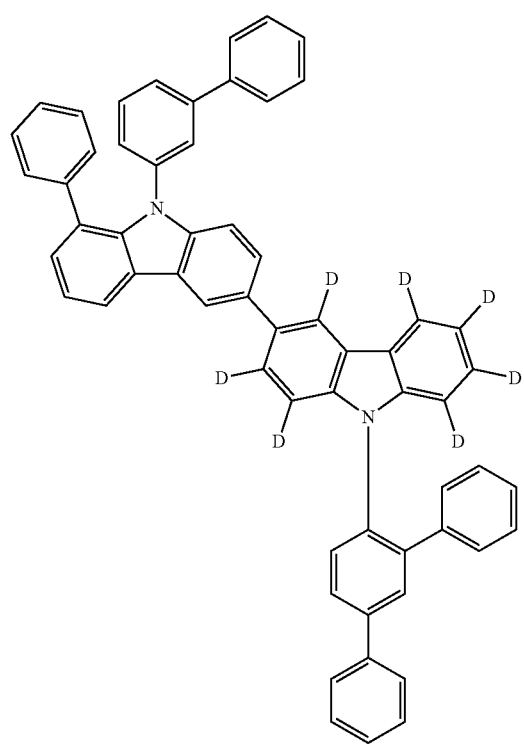
49
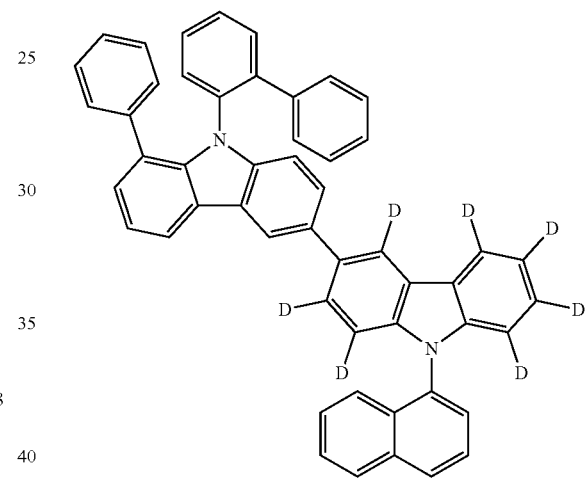
50
51
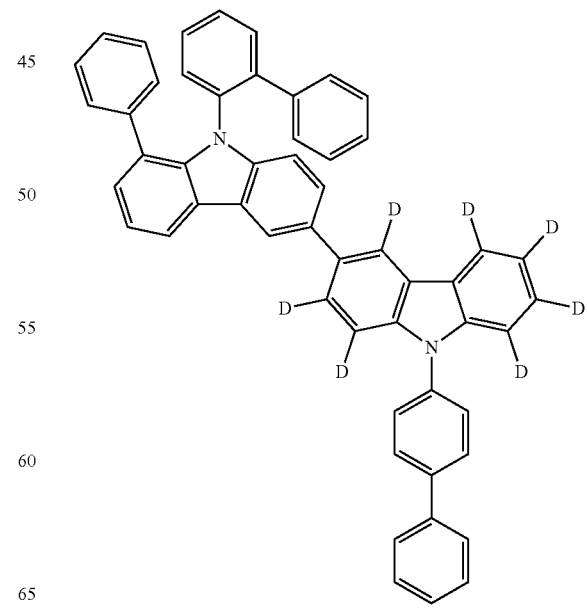

52
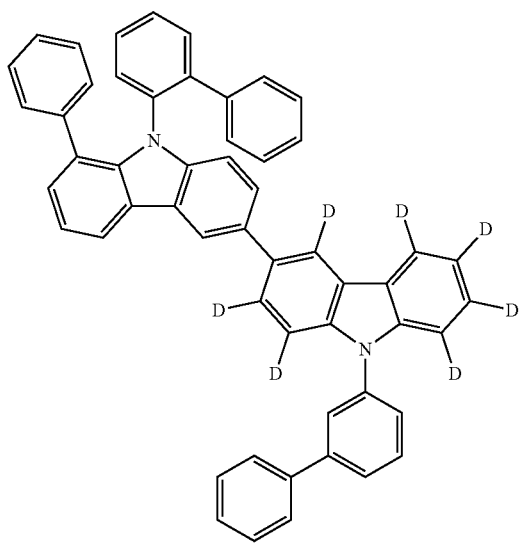
53
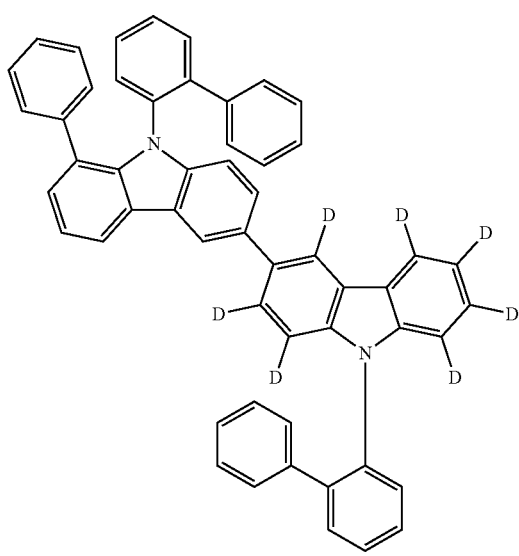
54
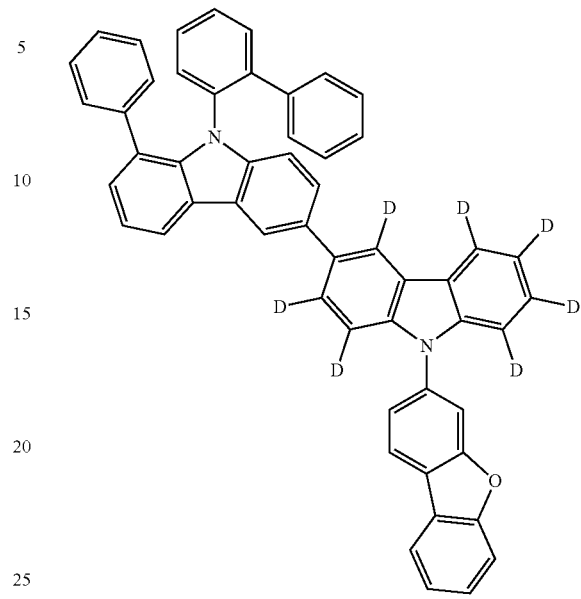
55
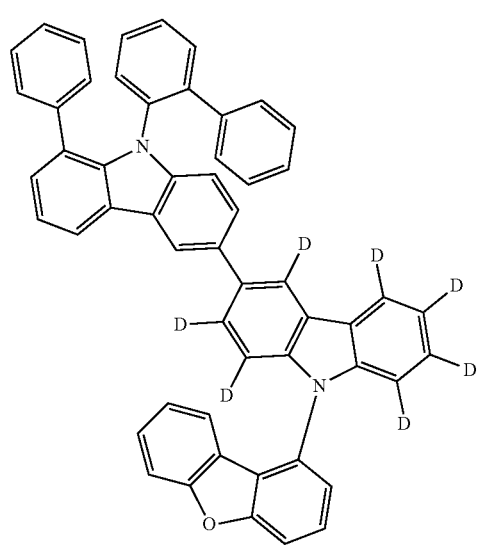

56
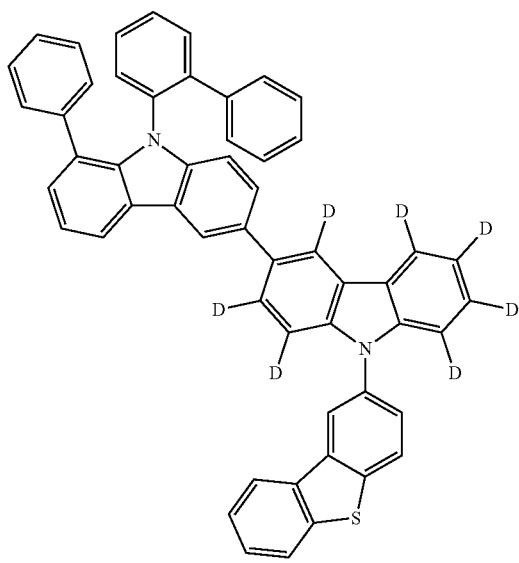
57
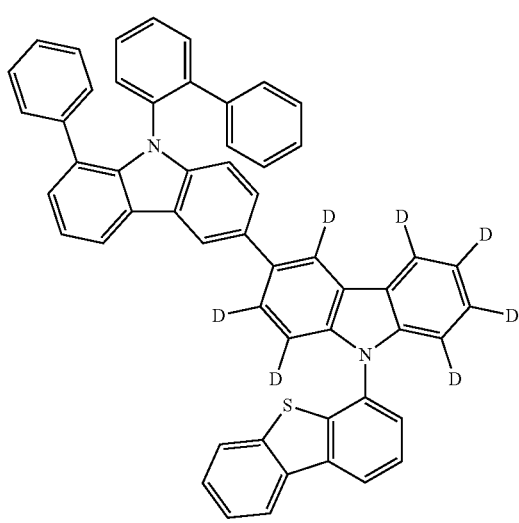
58
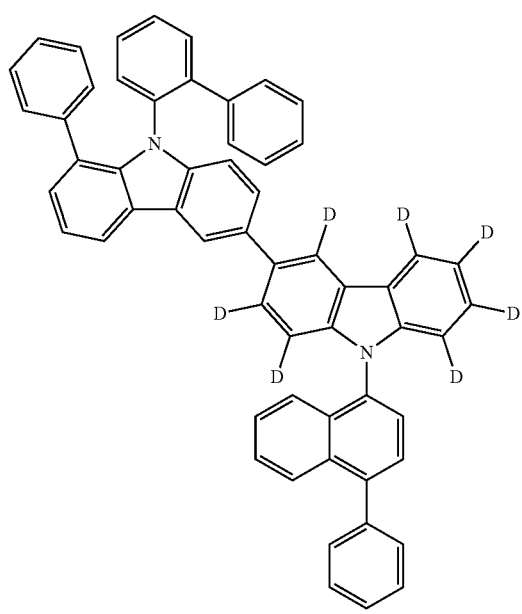
59
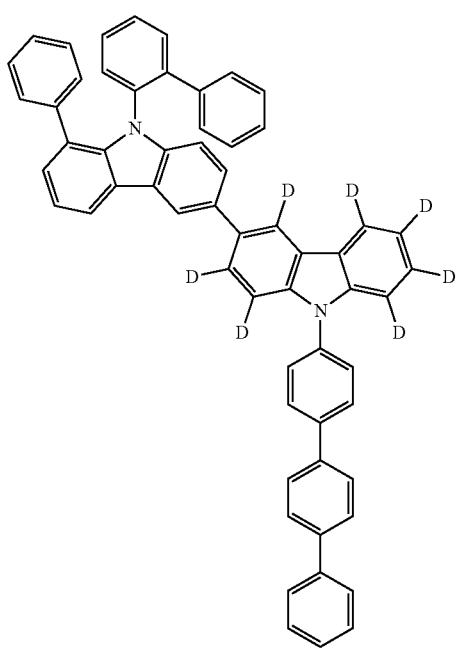

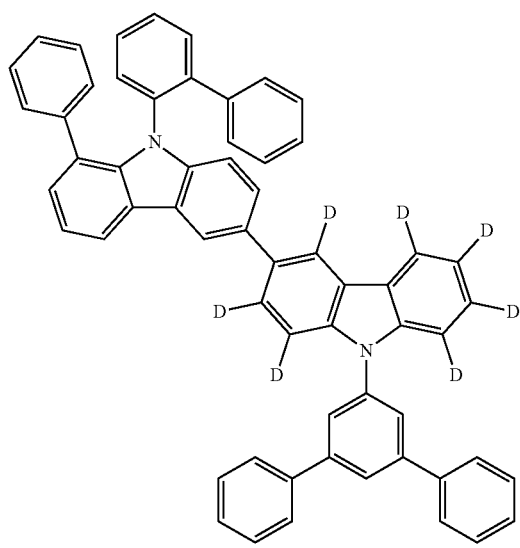
60
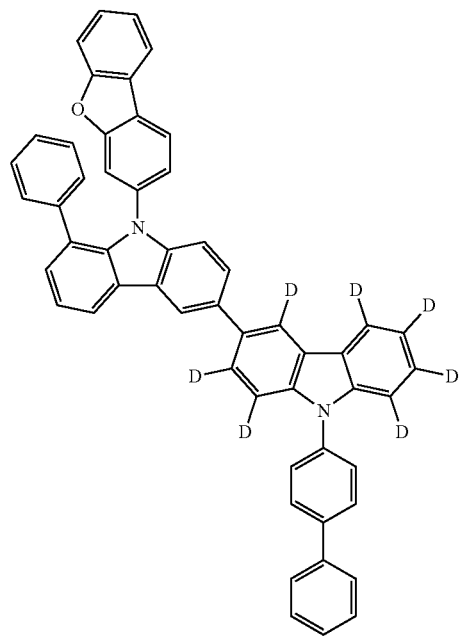
62
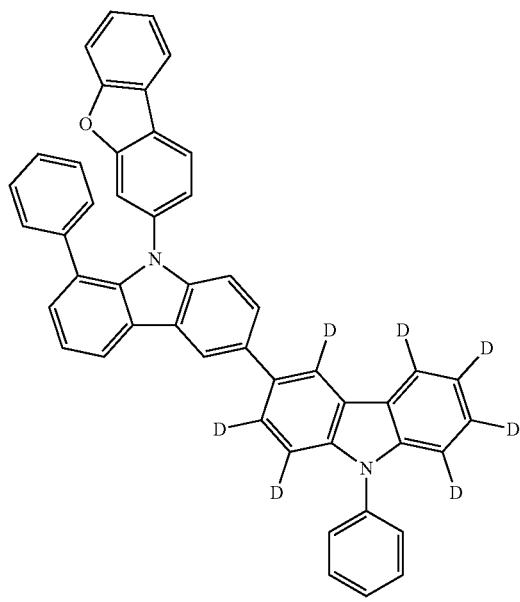
61
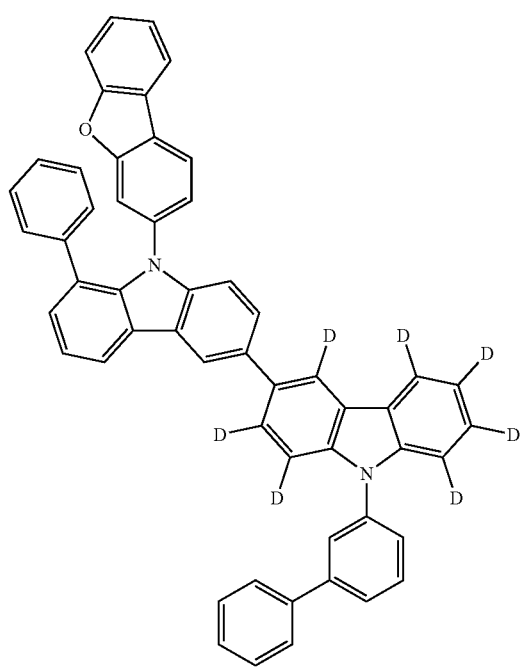
63

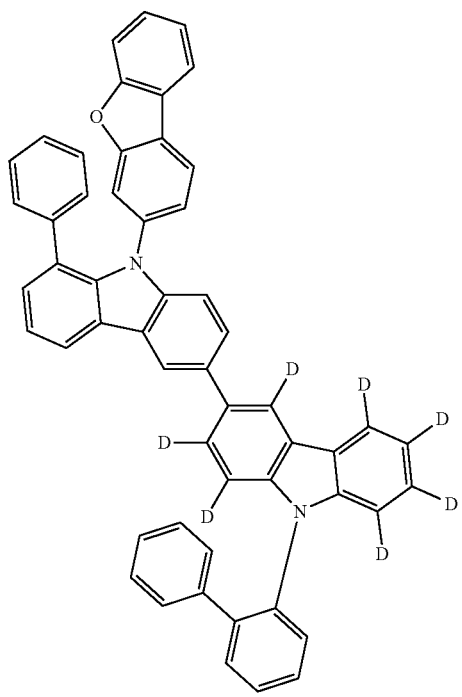
64
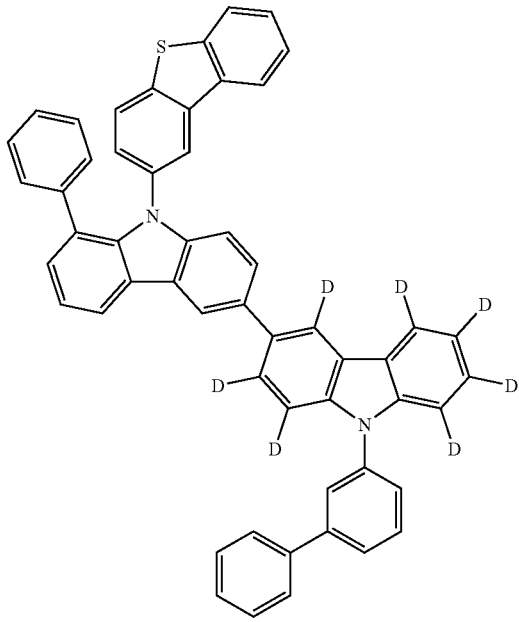
66
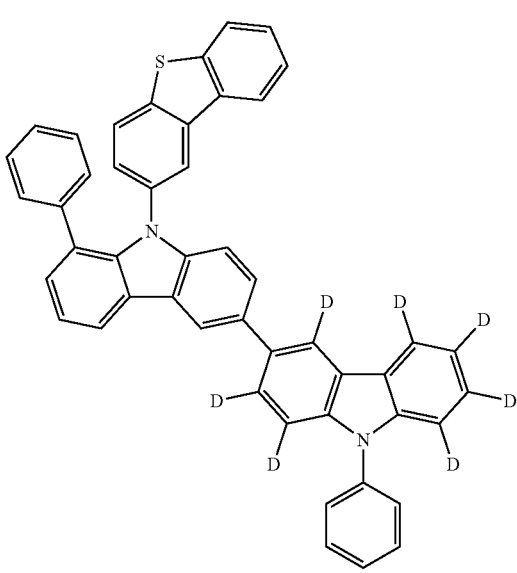
65
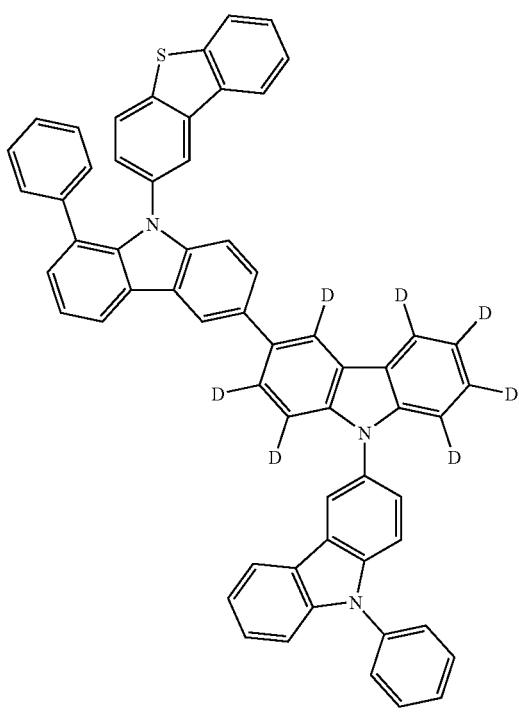
67

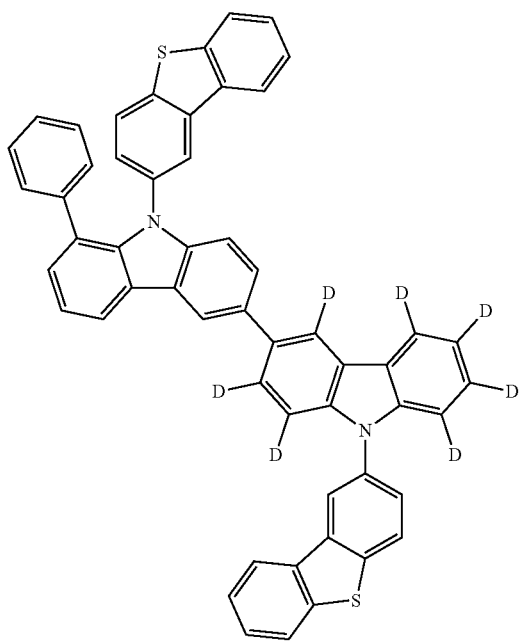
68
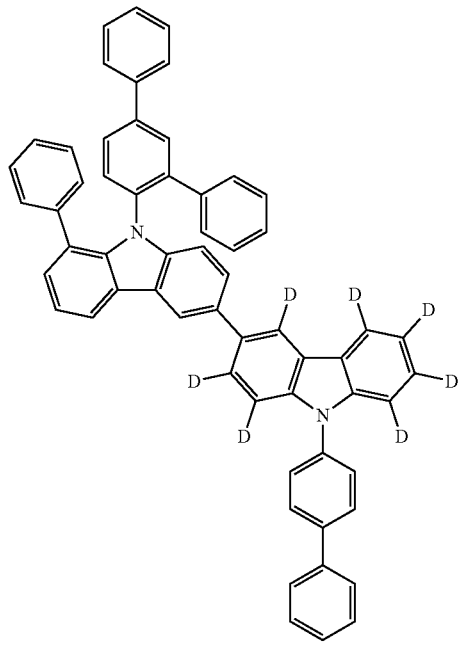
70
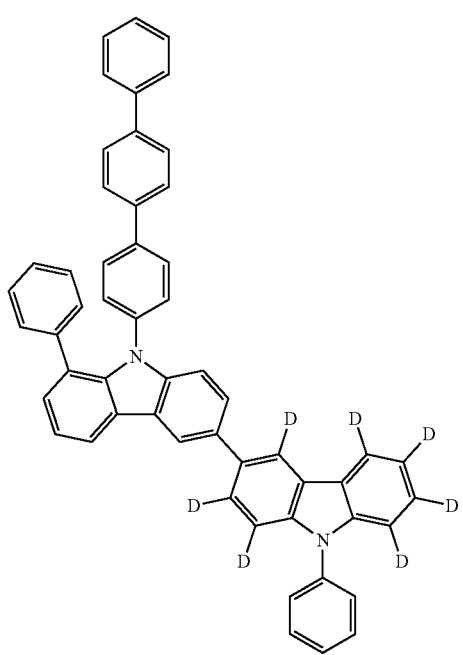
69
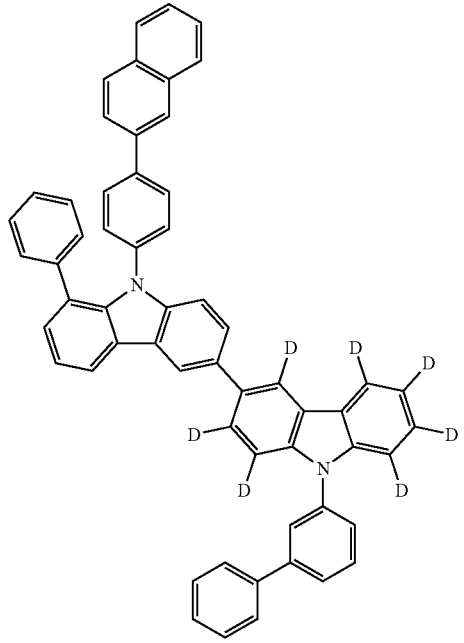
71

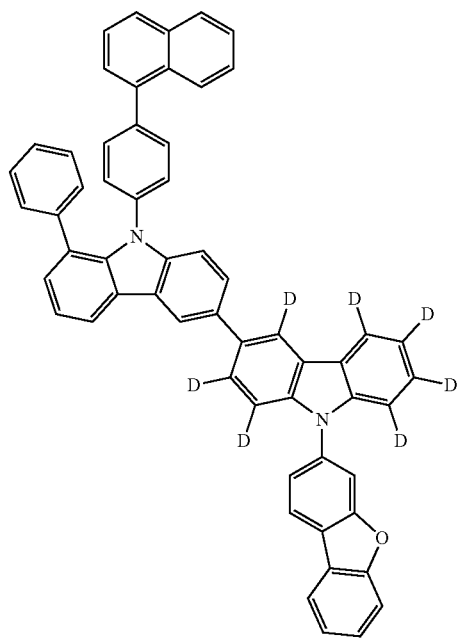
72
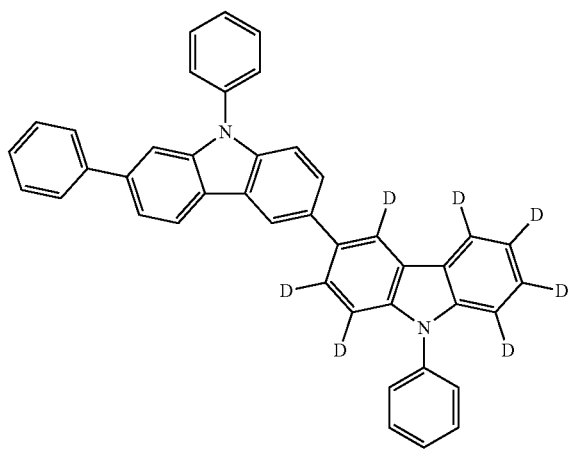
73
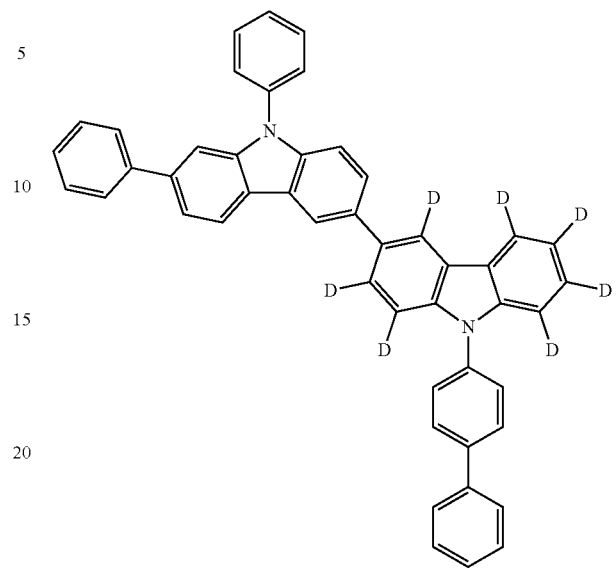
74
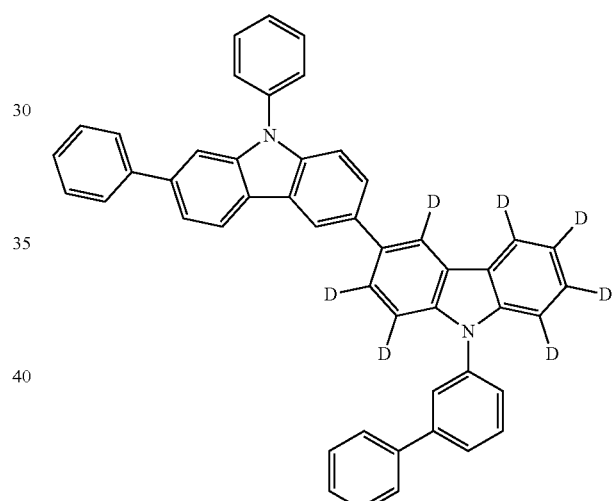
75
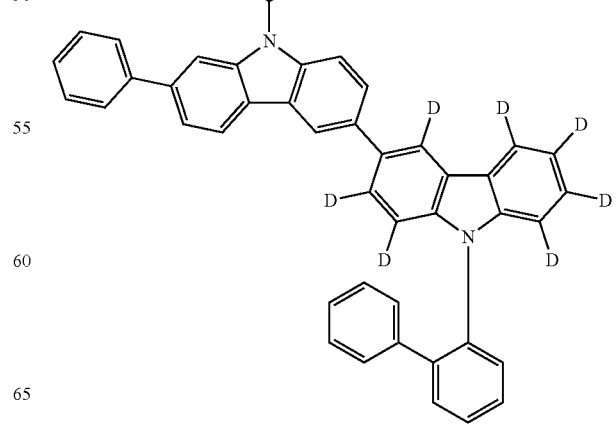
76

77
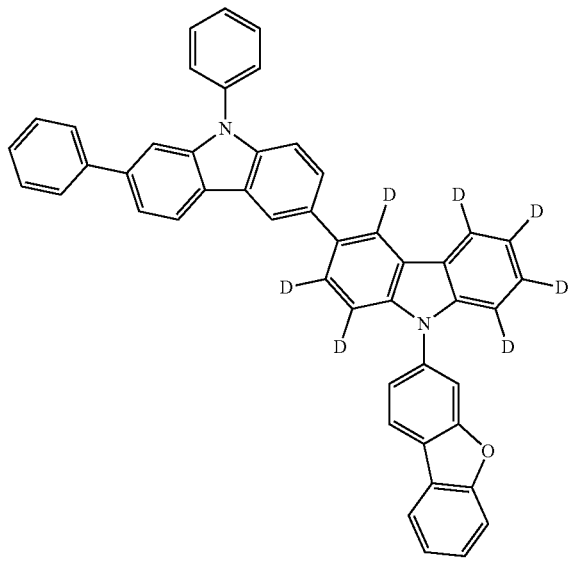
78
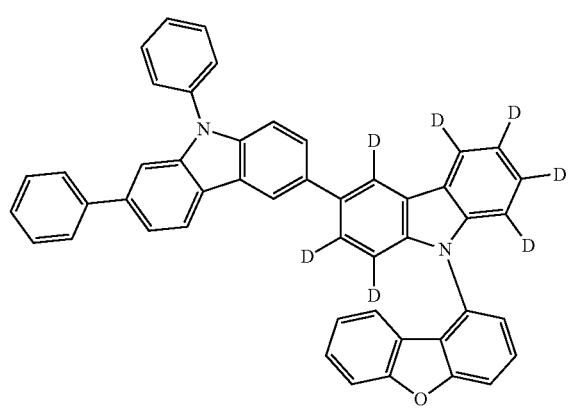
79
80
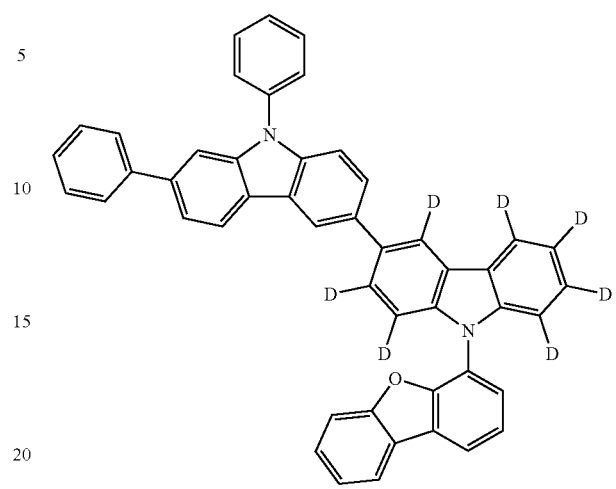
81
82
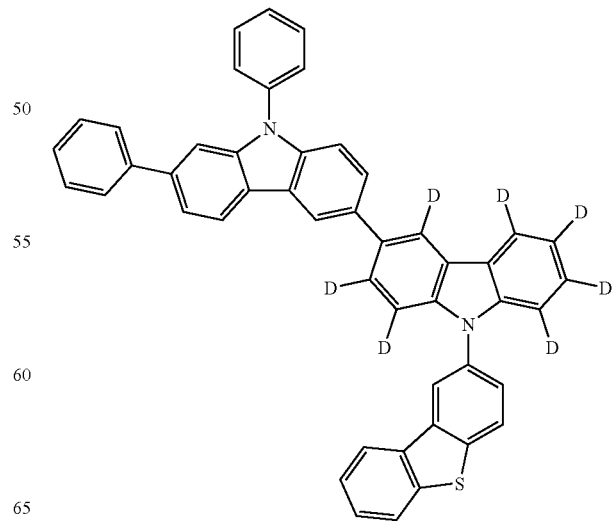

83
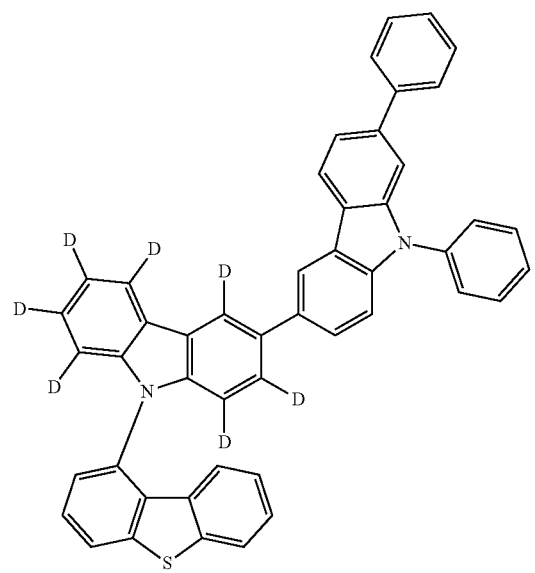
84
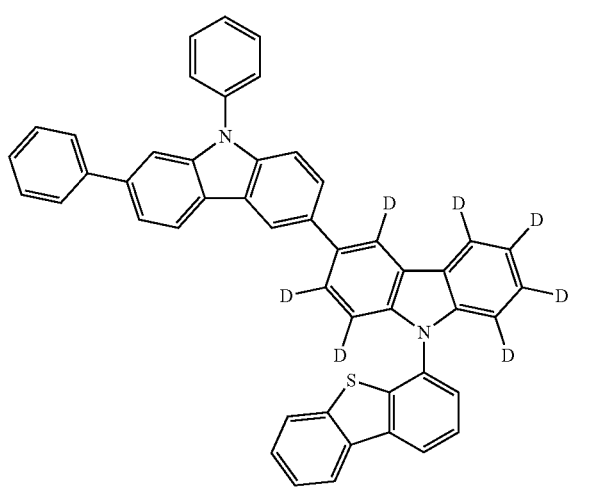
85
86
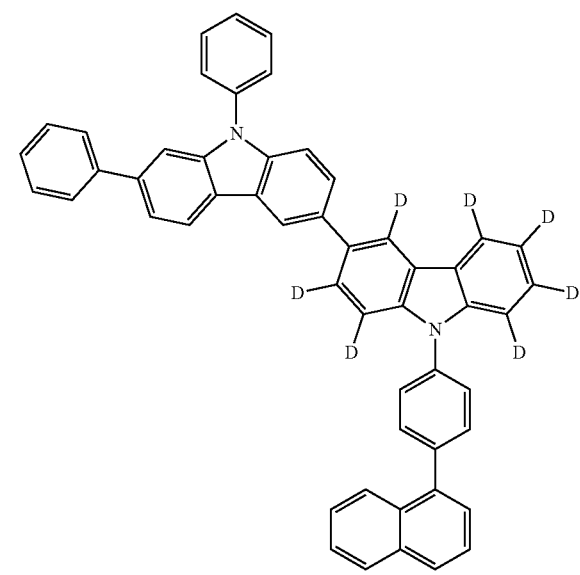
87
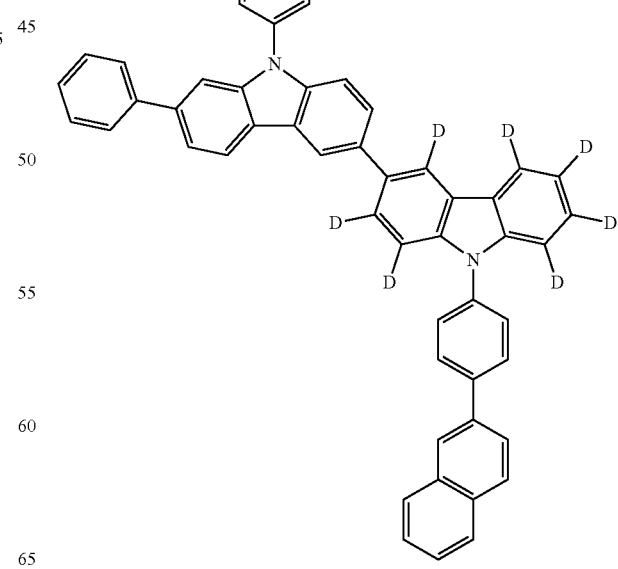

88
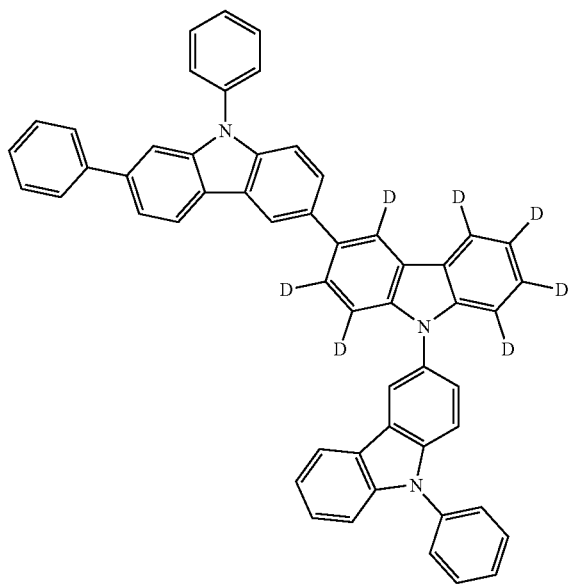
89
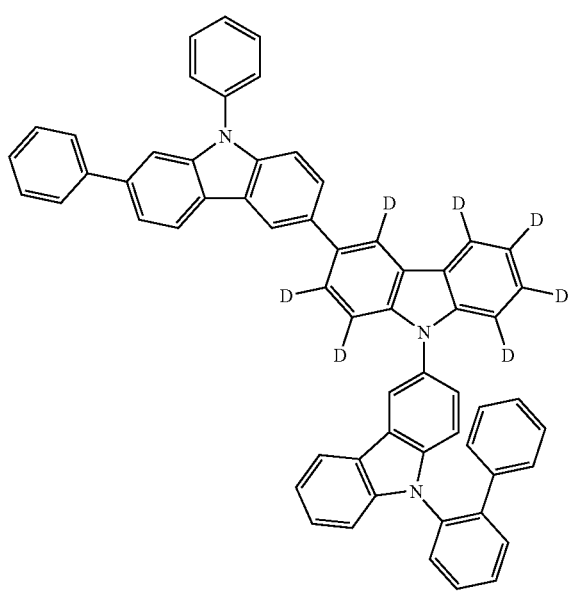
90
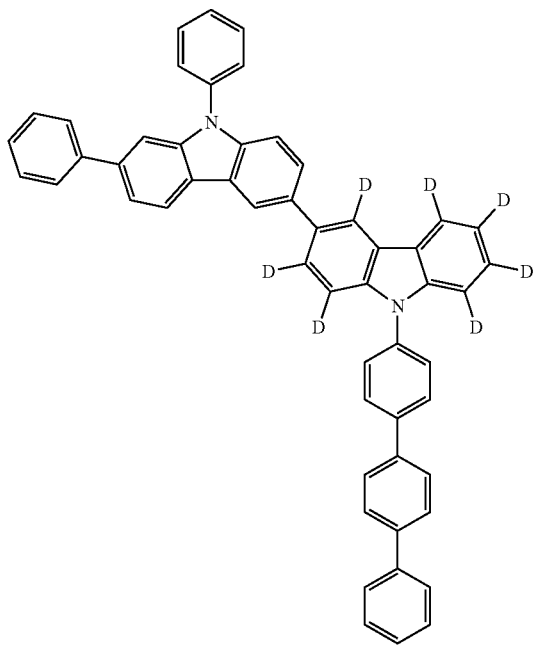
91
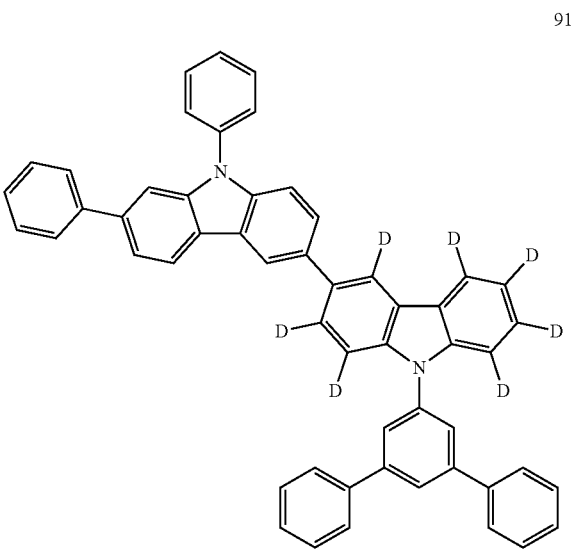

92
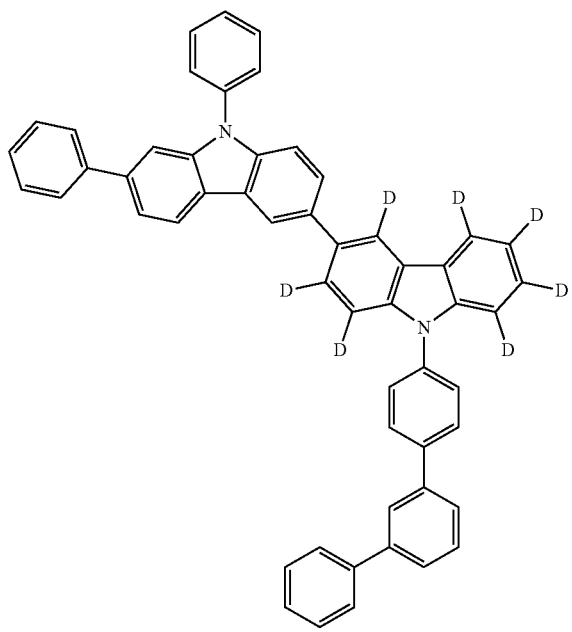
93
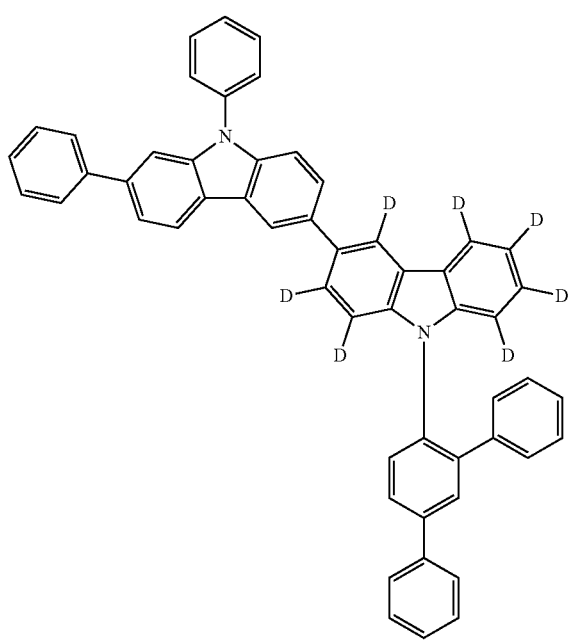
94
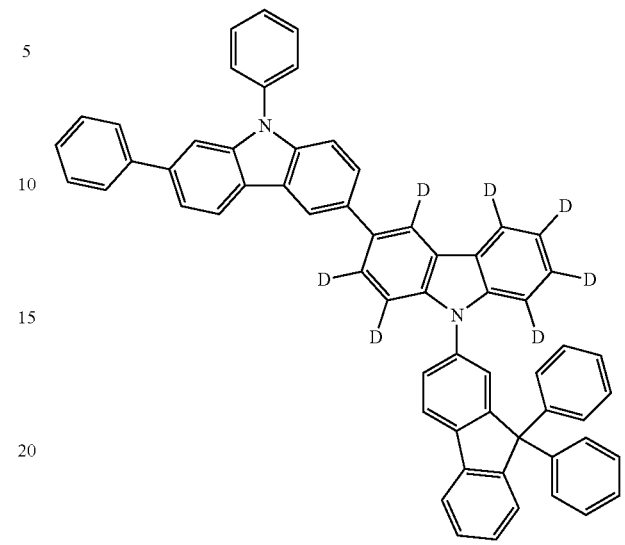
95
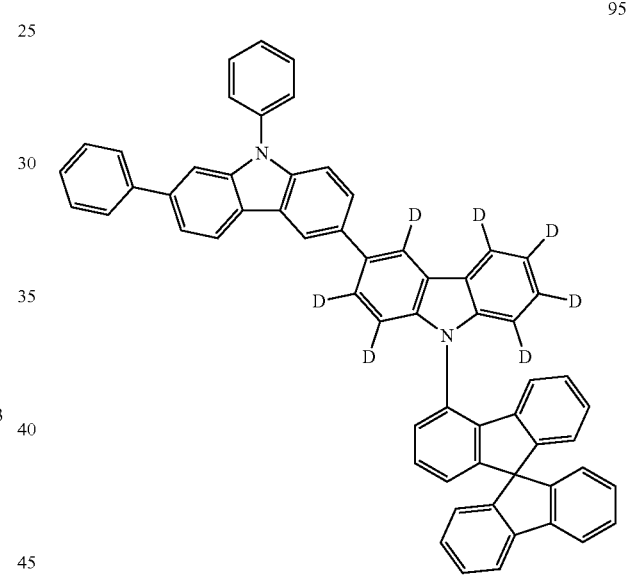
96
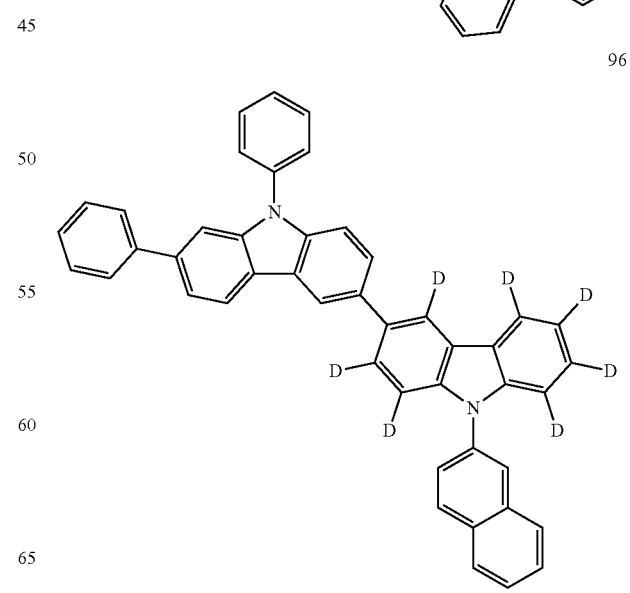

97
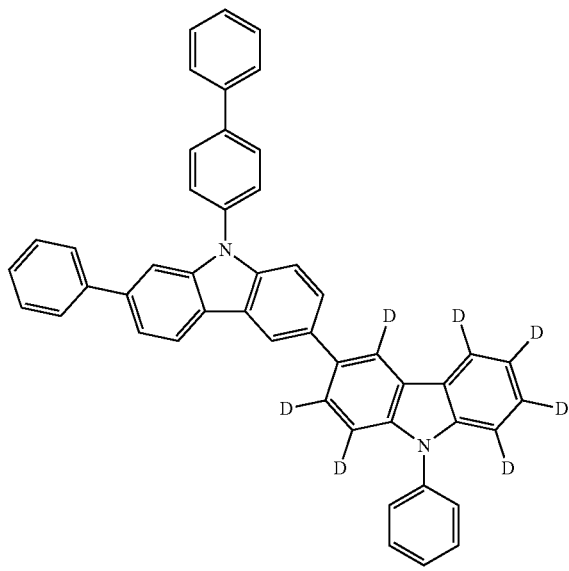
98
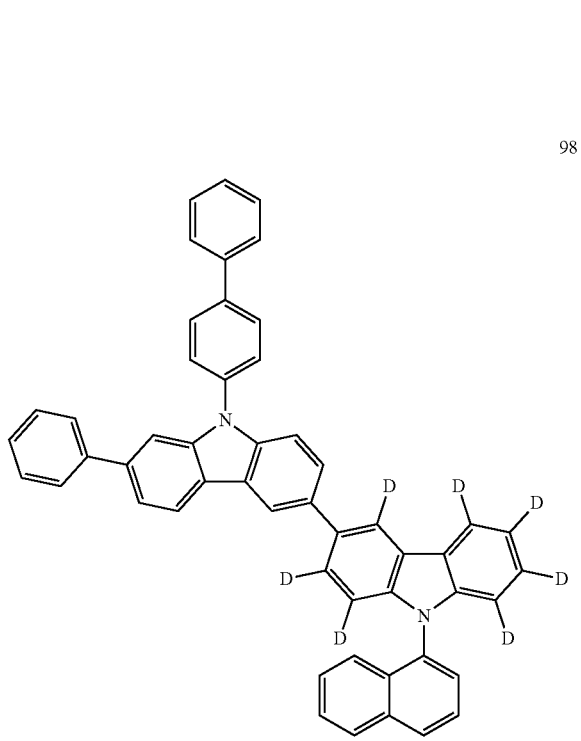
99
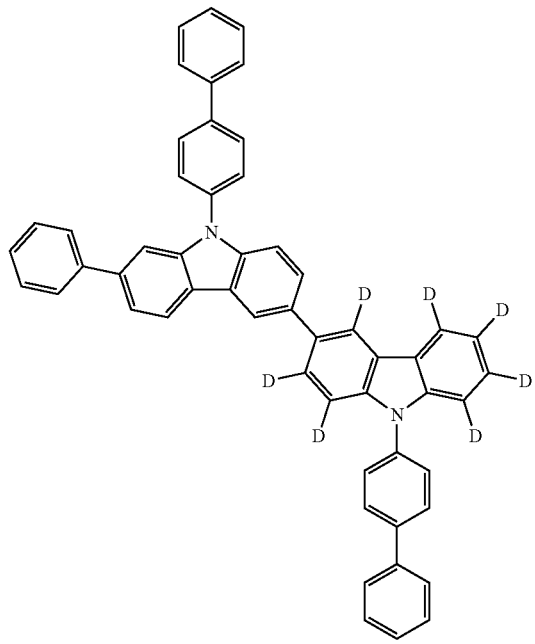
100
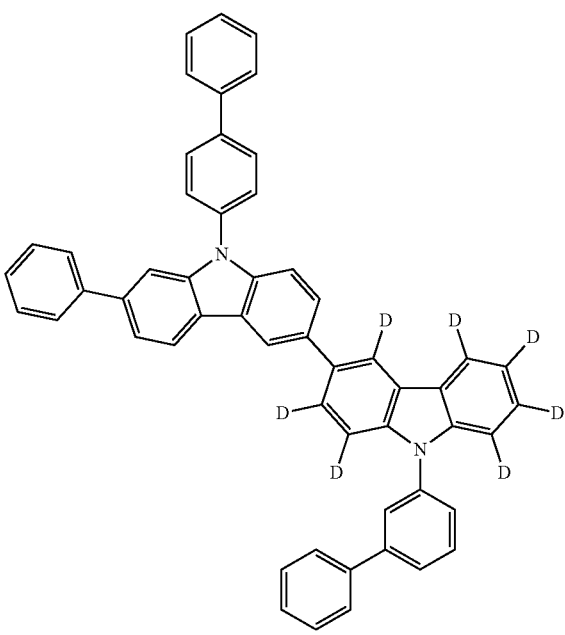

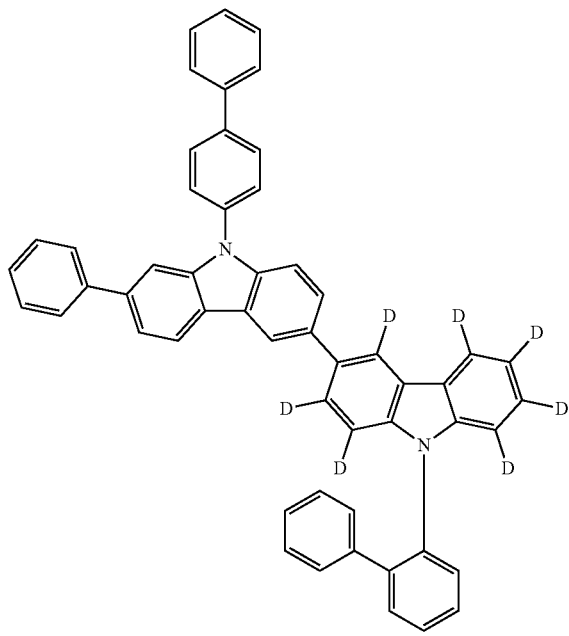
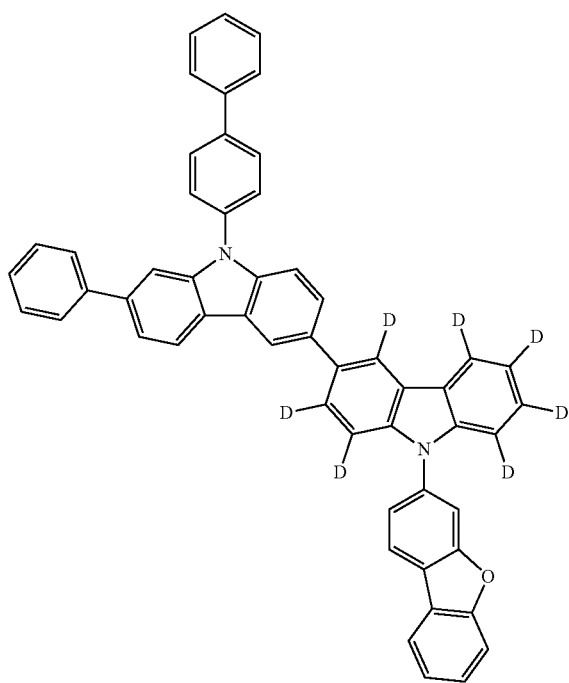

105
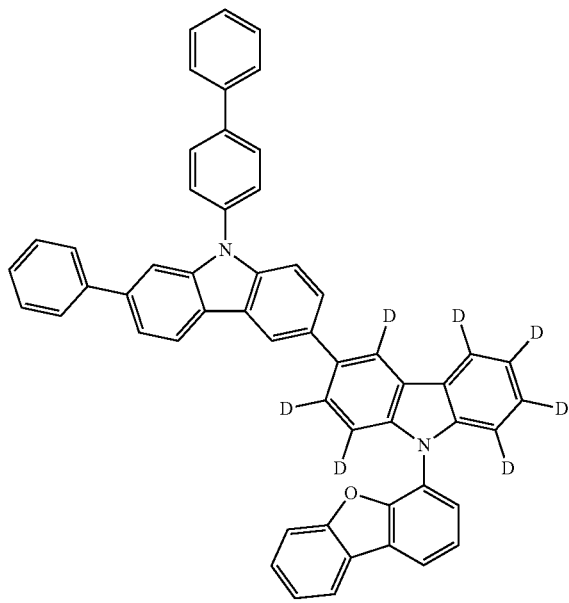
106
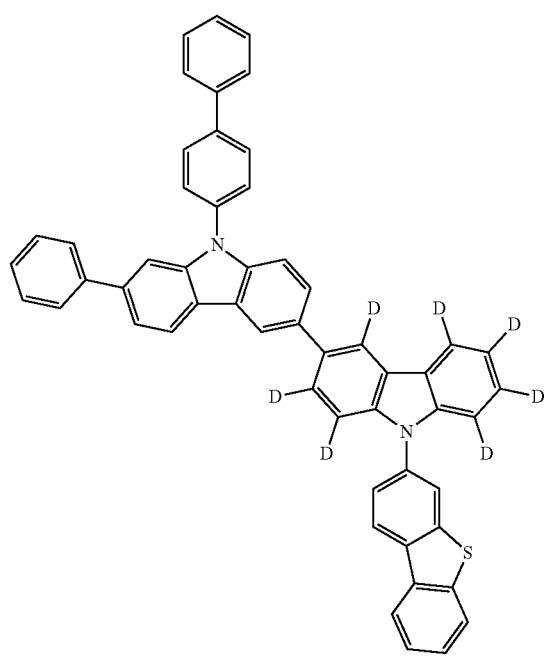
107
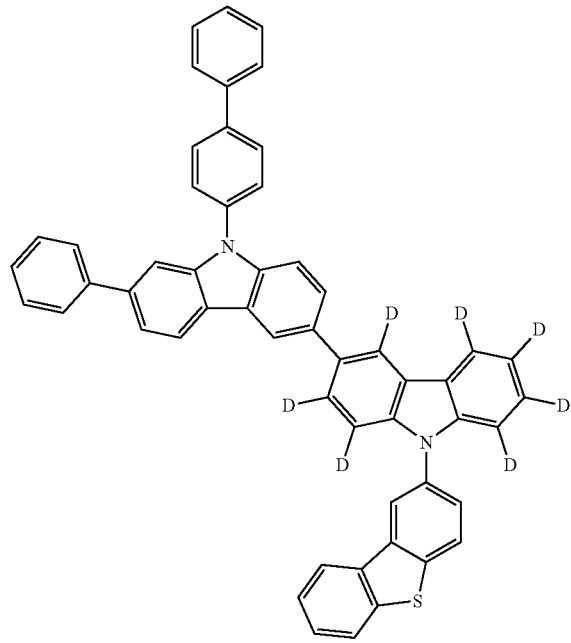
108

109
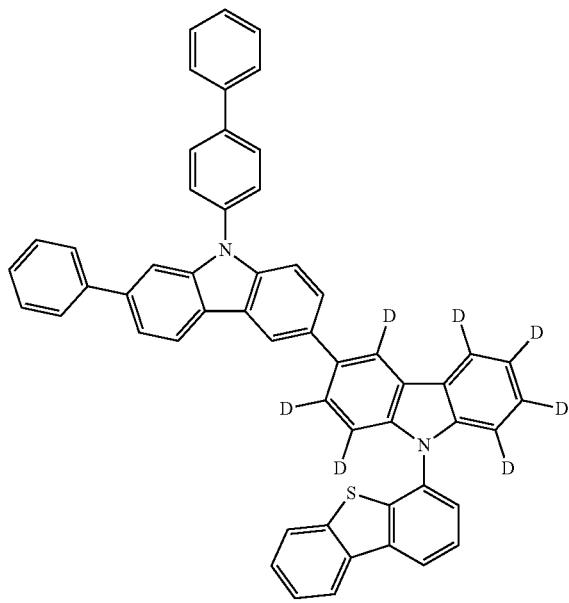
110
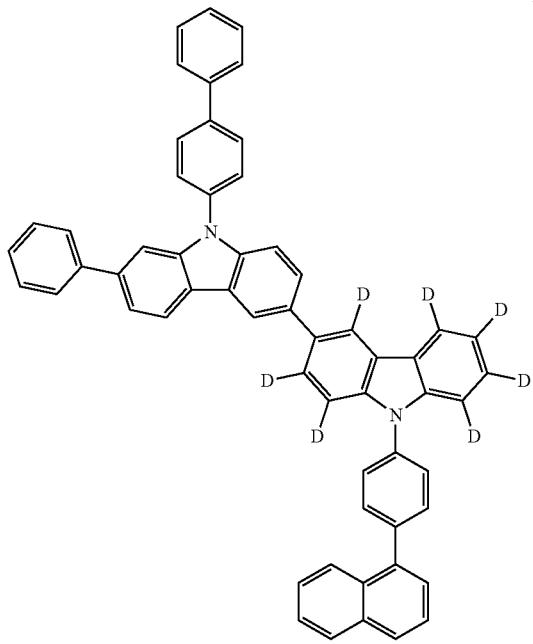
111
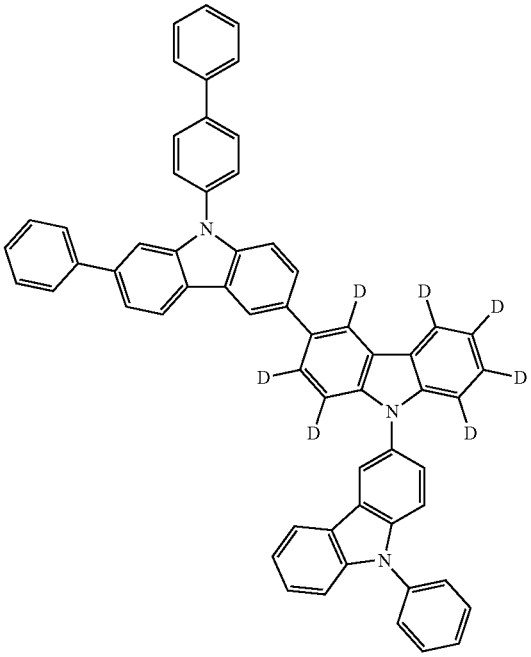
112
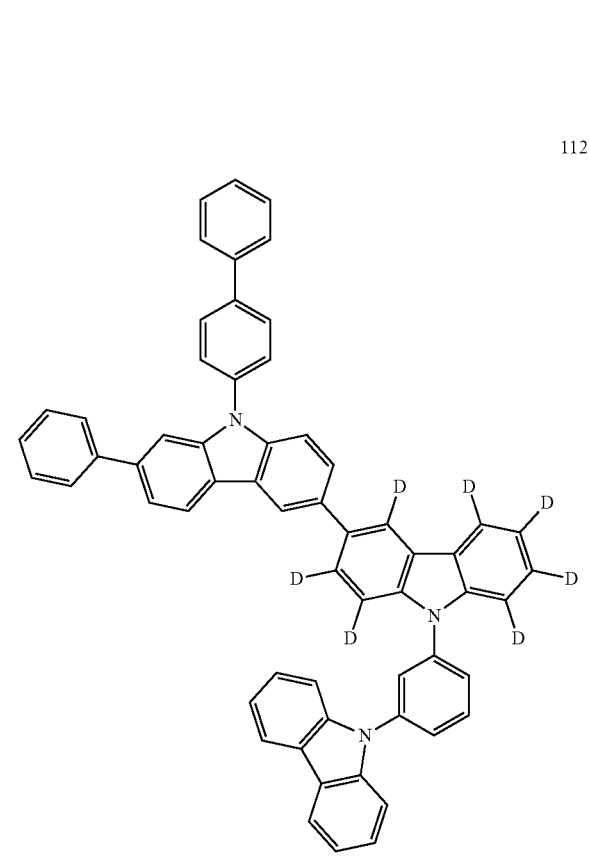

113
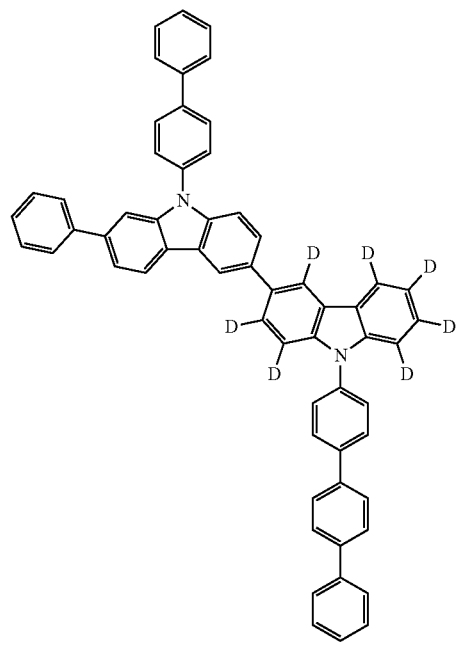
114
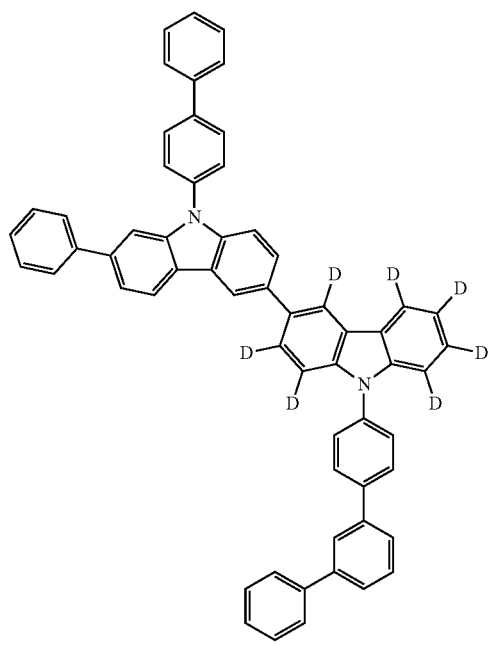
115
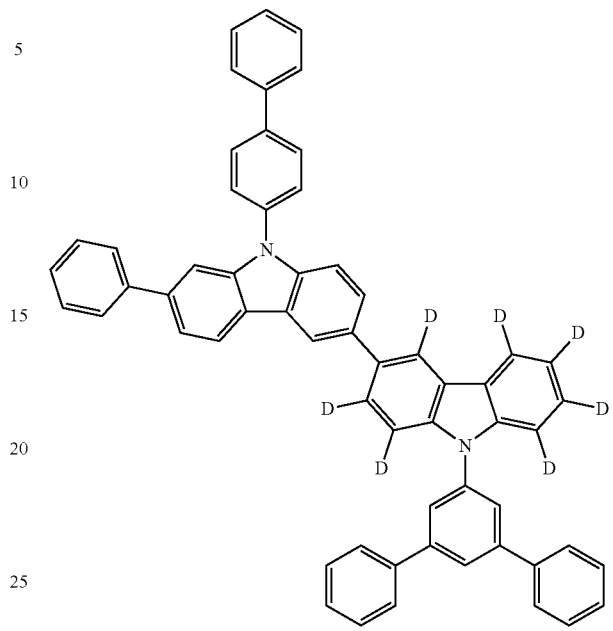
116
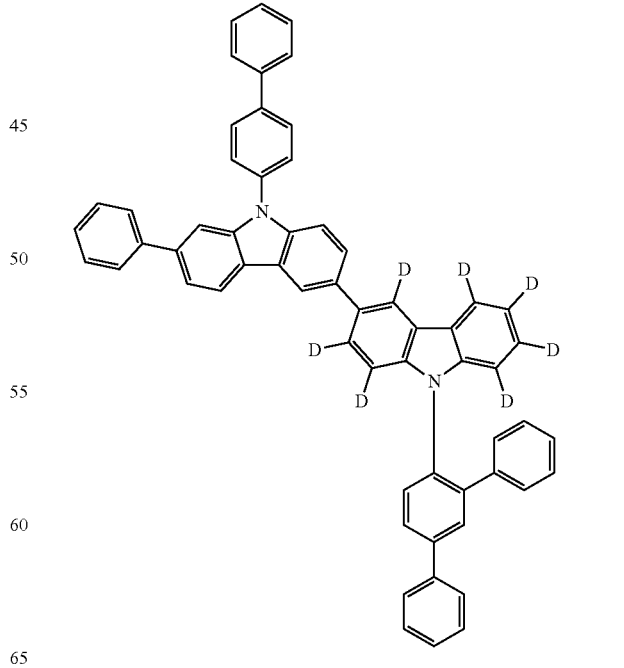

117
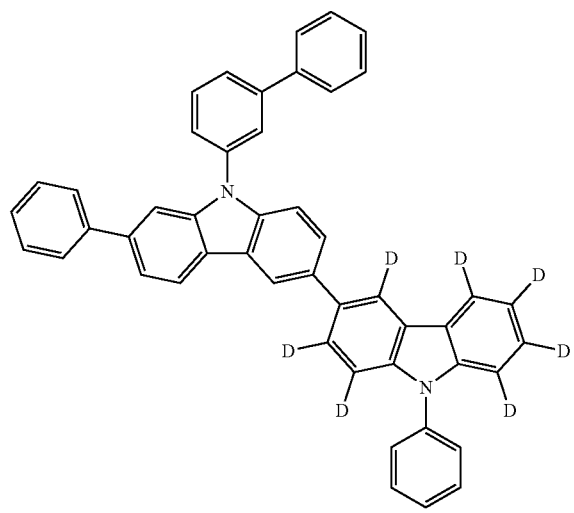
118
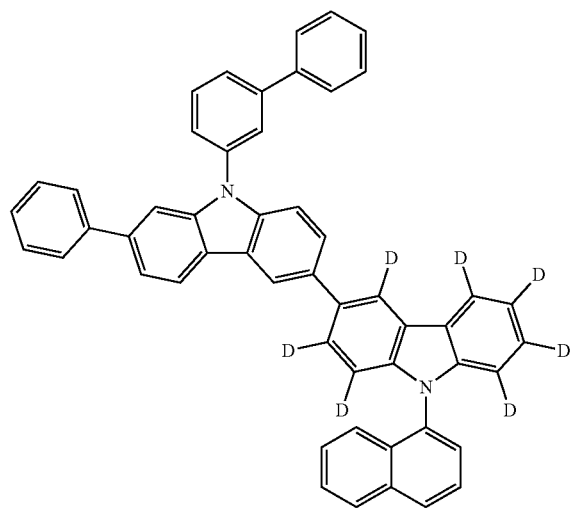
119
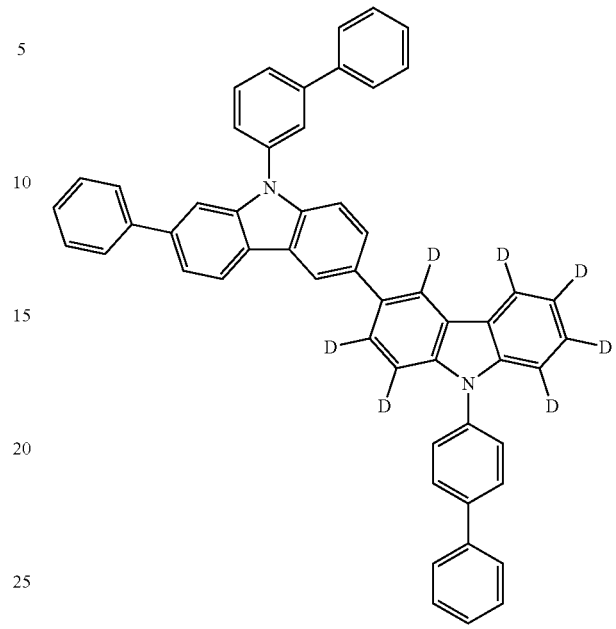
120
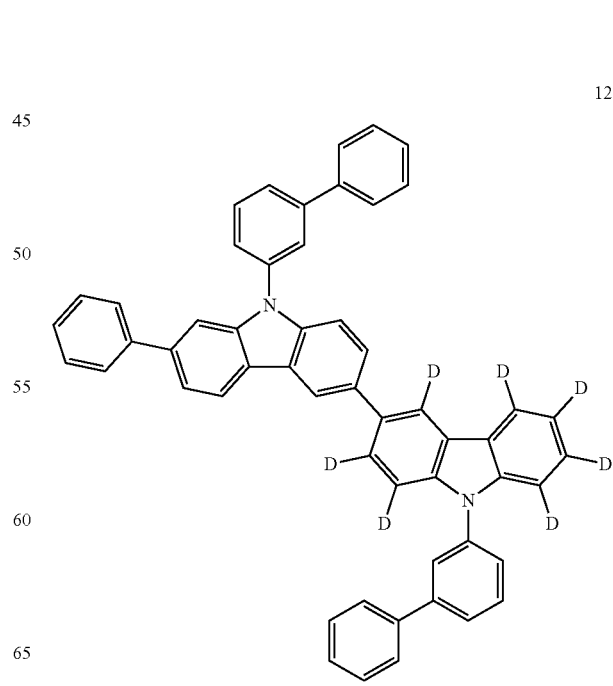

121
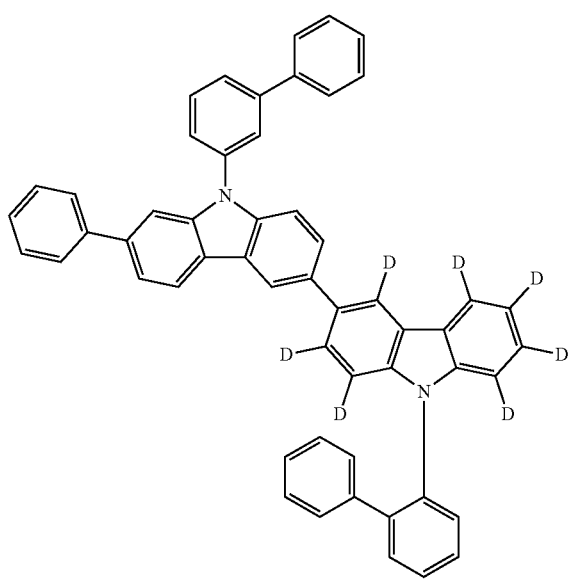
122
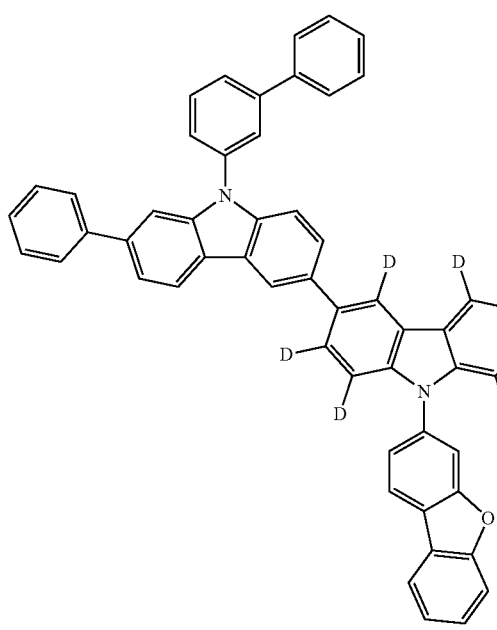
123
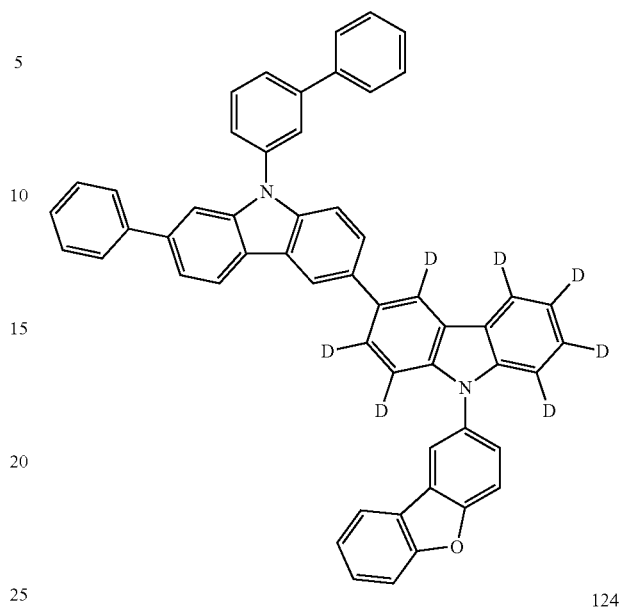
124
125
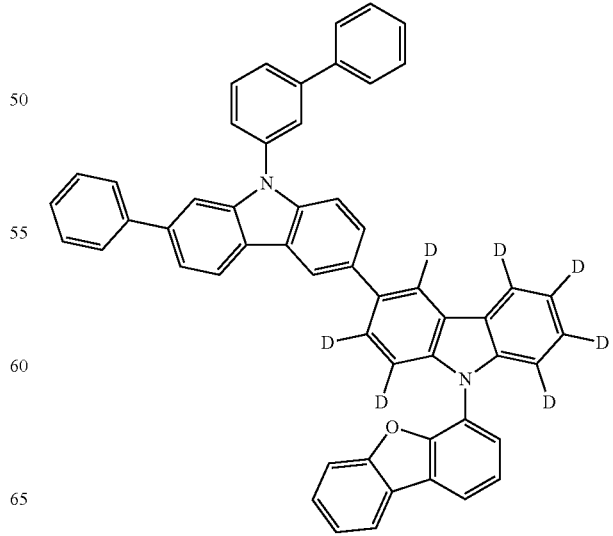

126
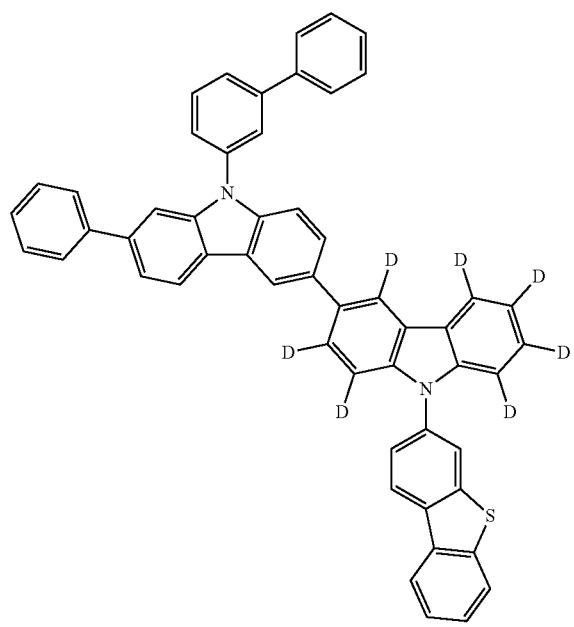
127
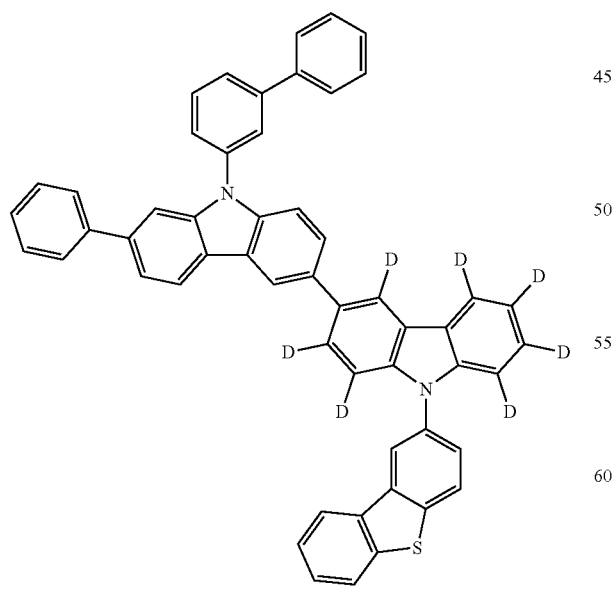
128
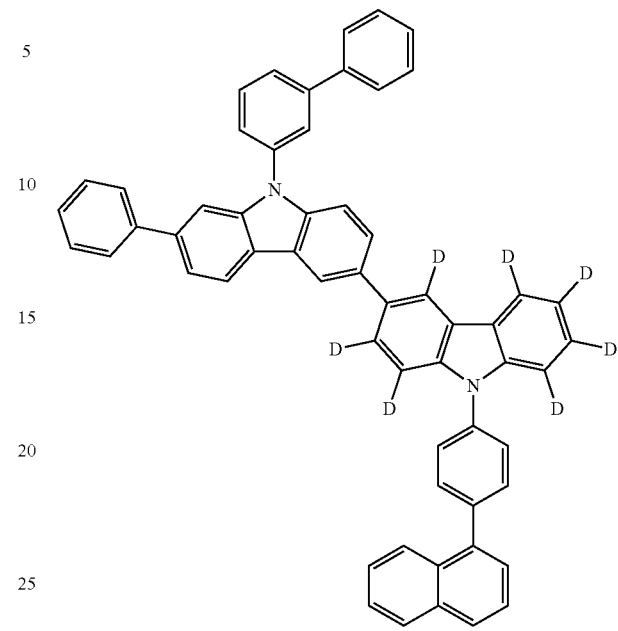
129
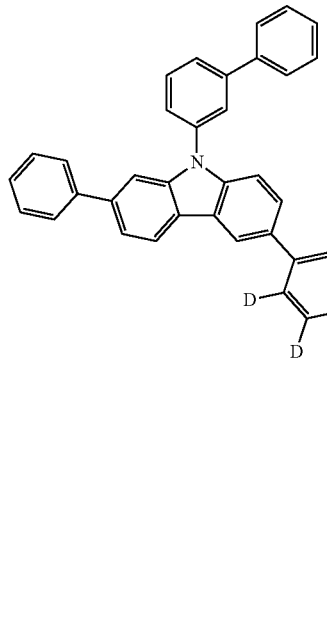

130
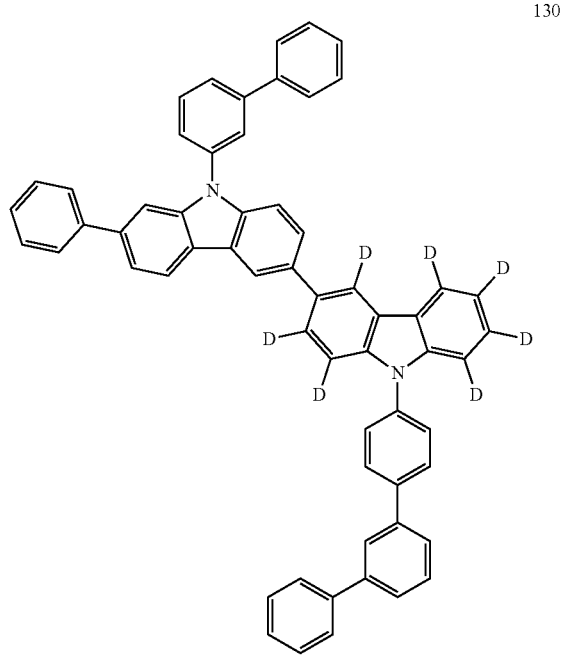
131
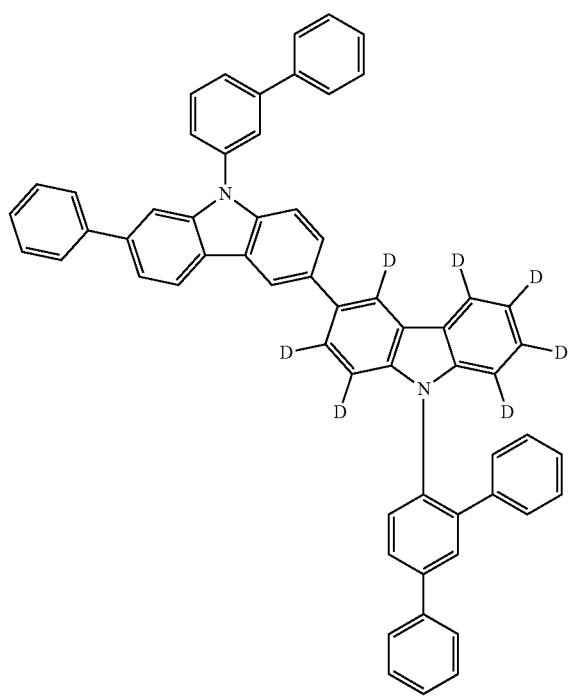
132
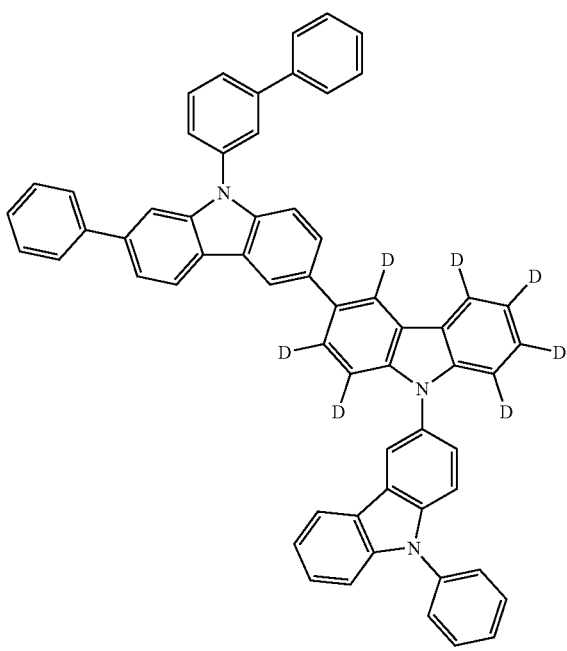
133
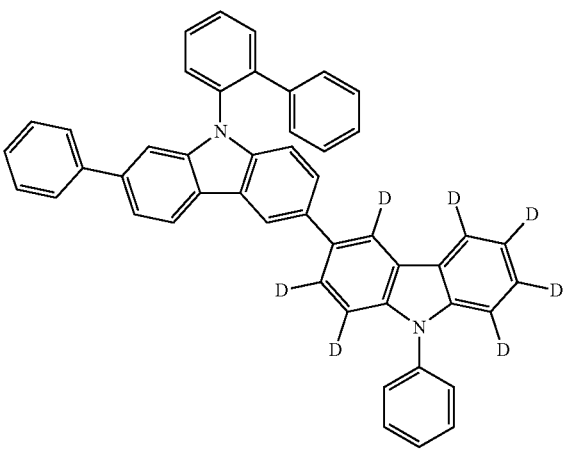

134
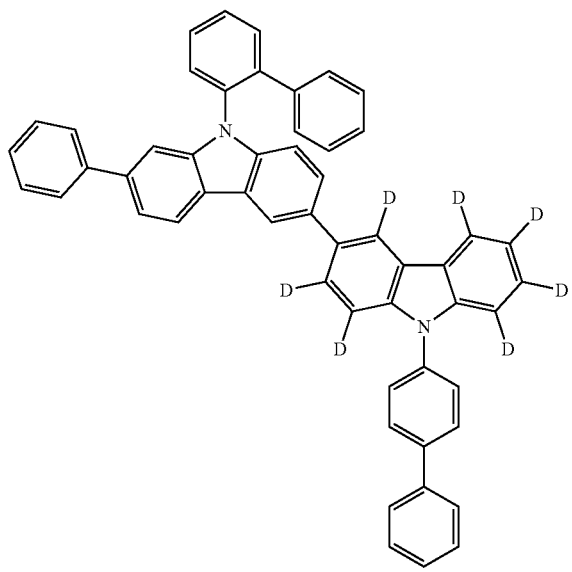
135
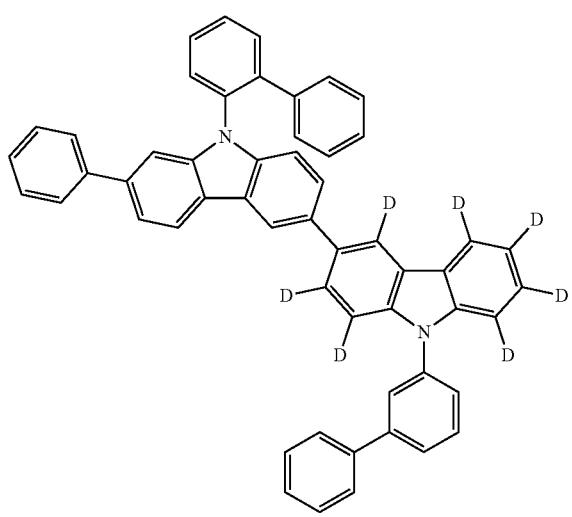
136
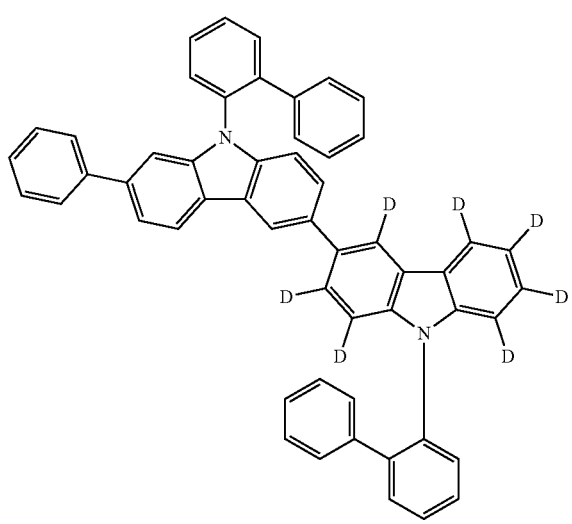
137
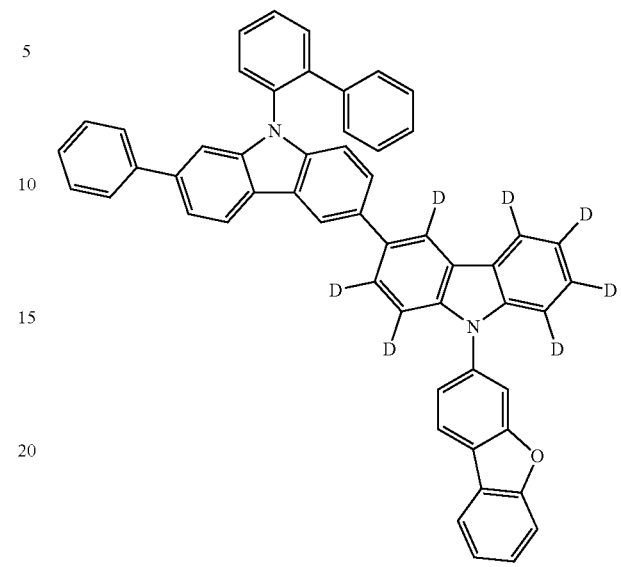
138
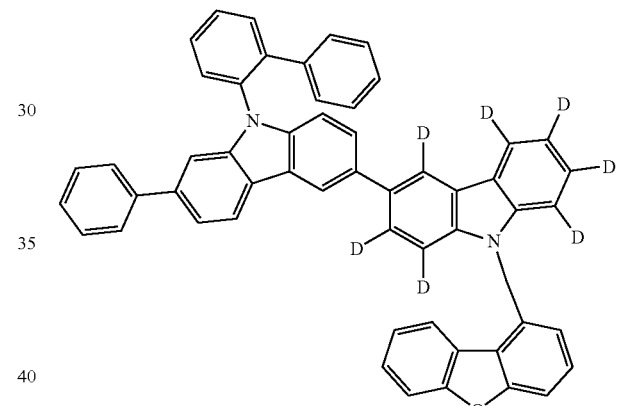
139
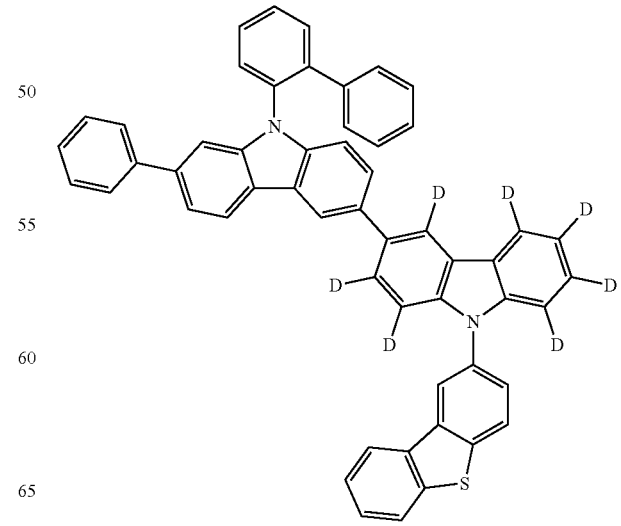

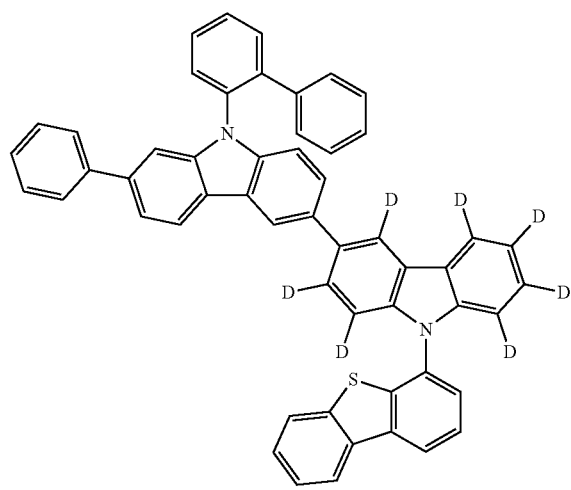
140
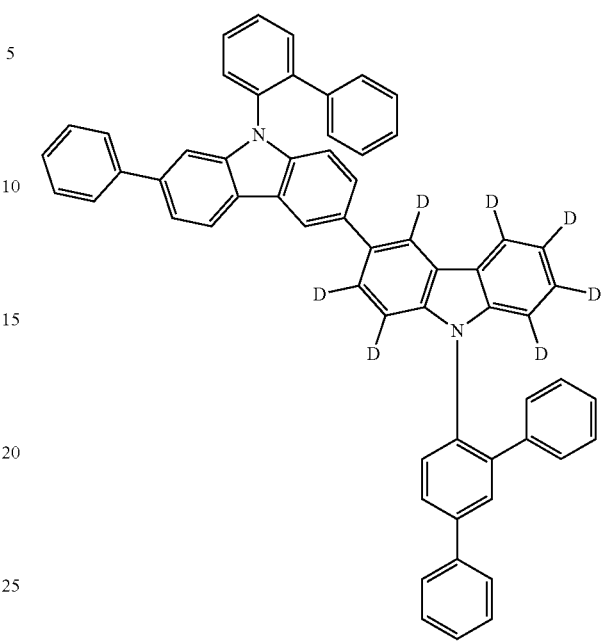
142
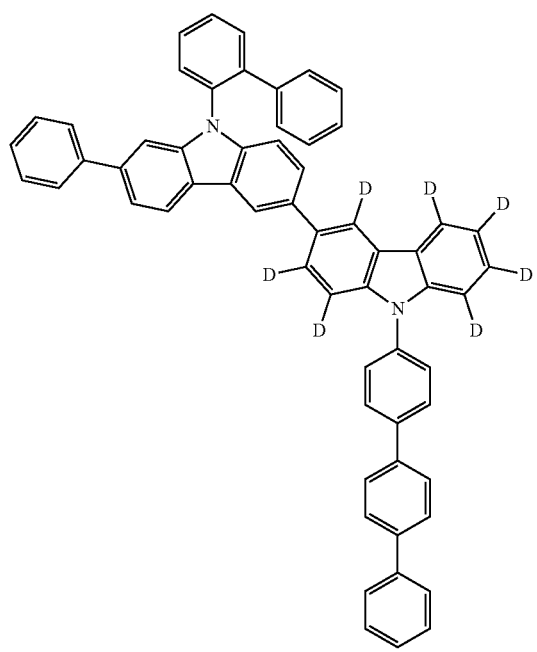
141
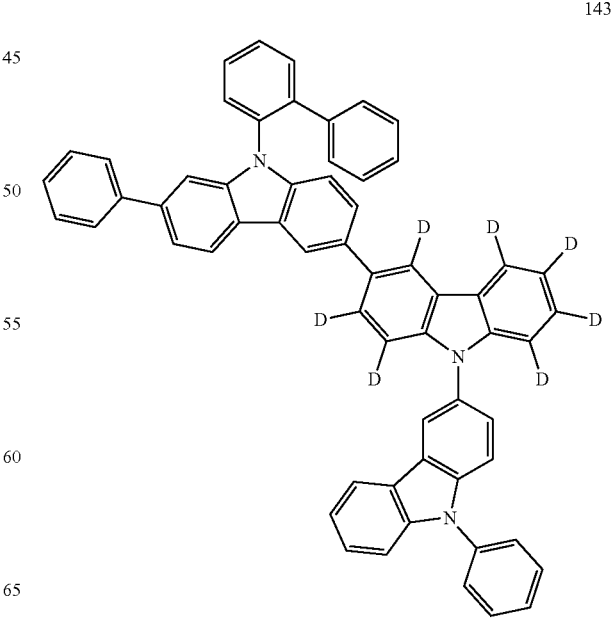
143

144
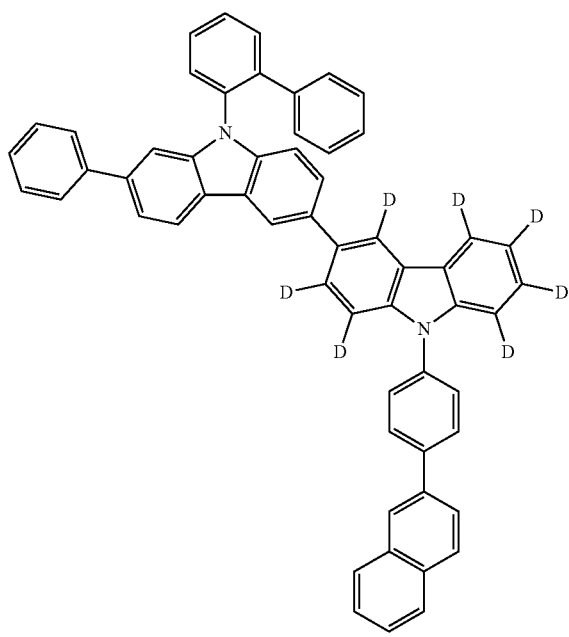
145
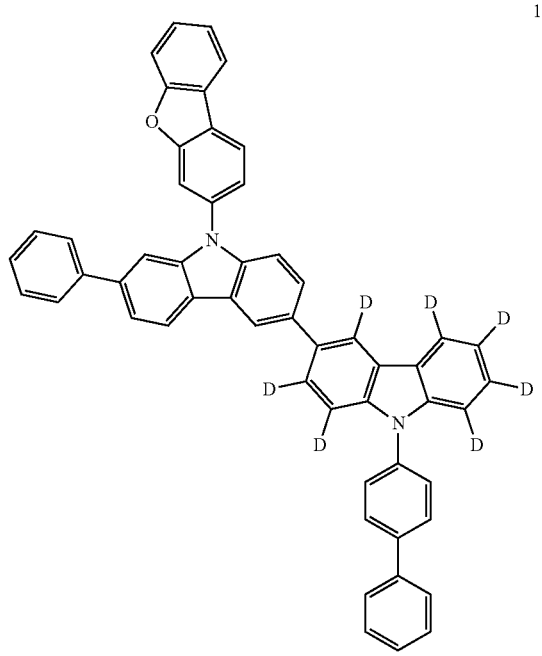
146
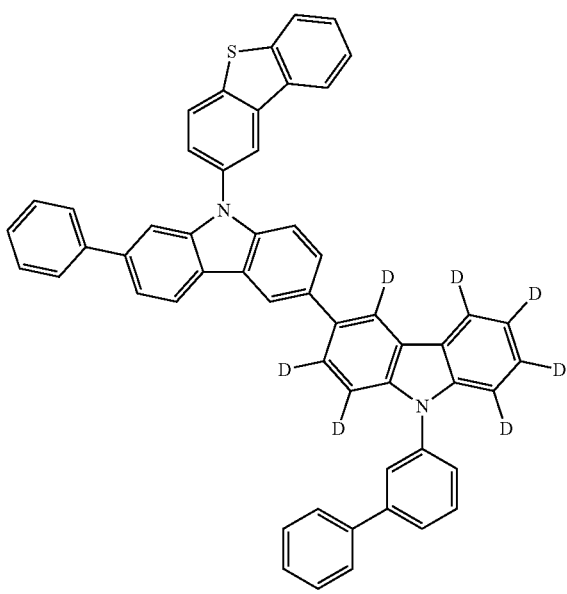
147
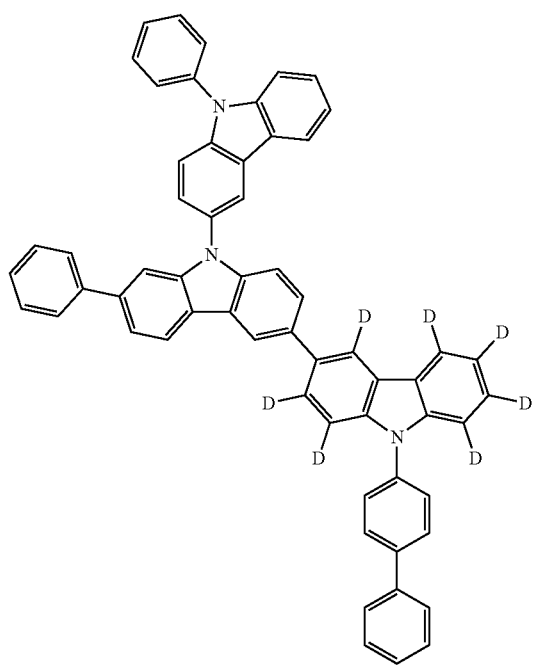

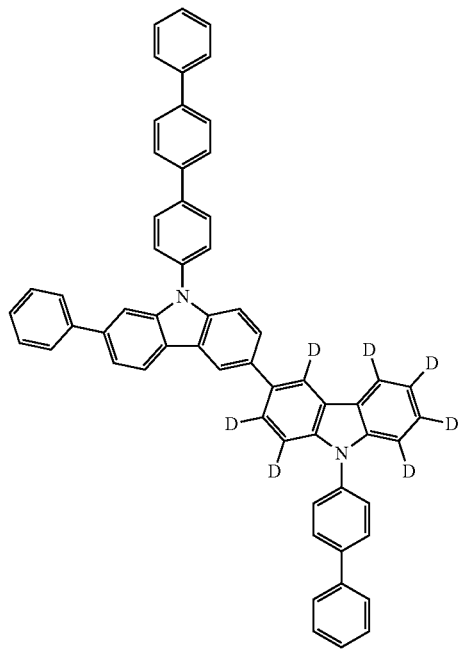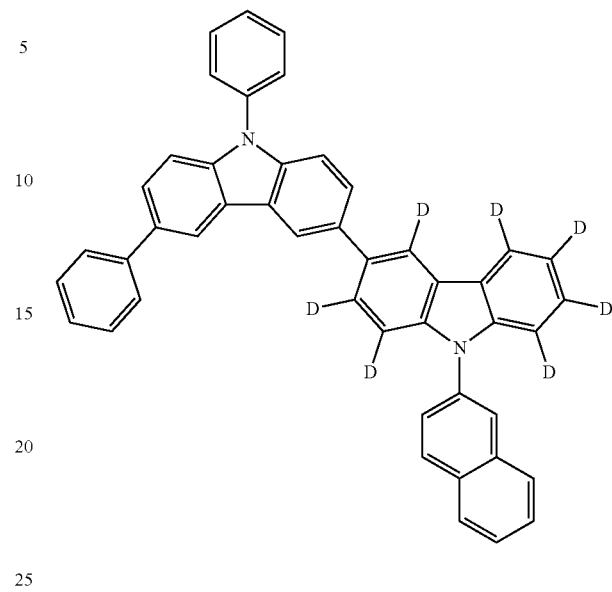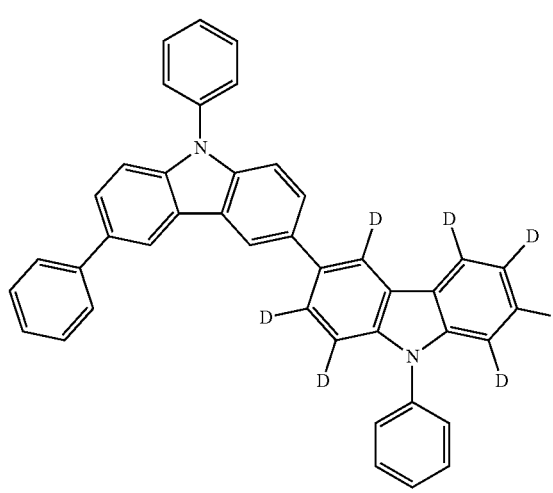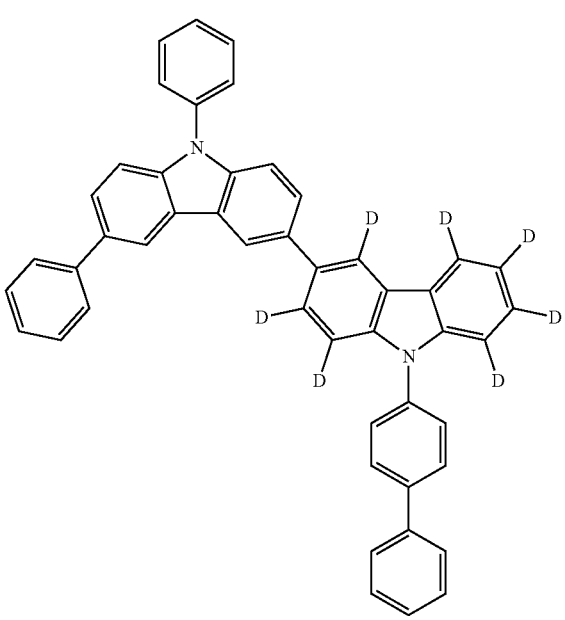

152
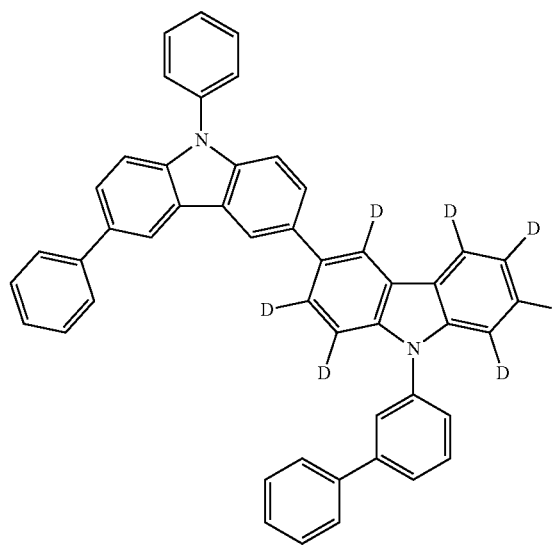
153
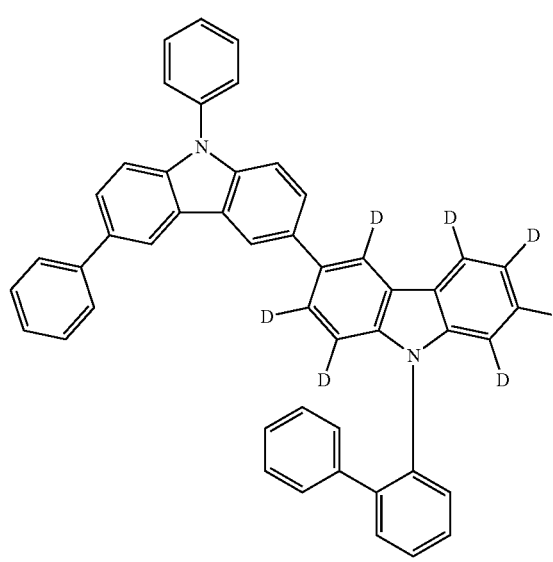
154
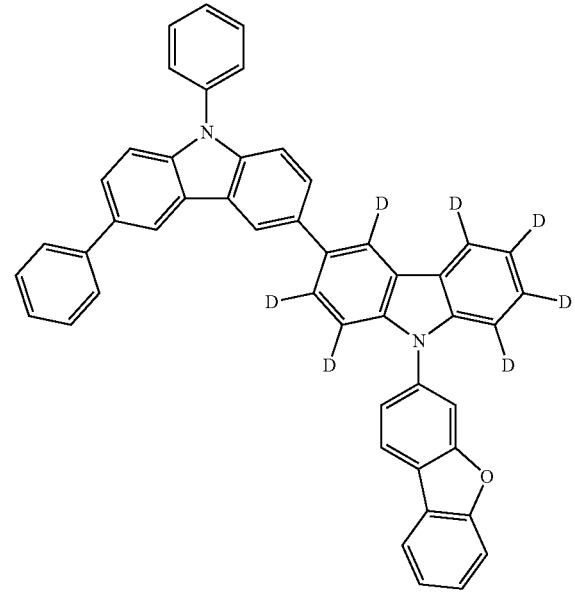
155
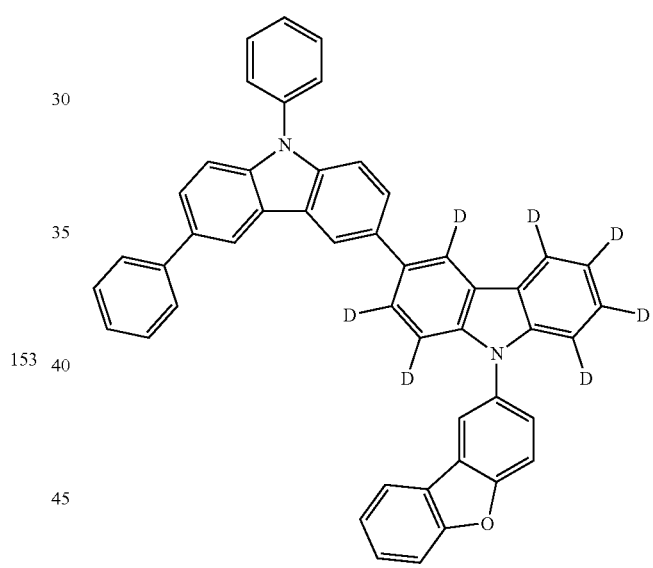
156
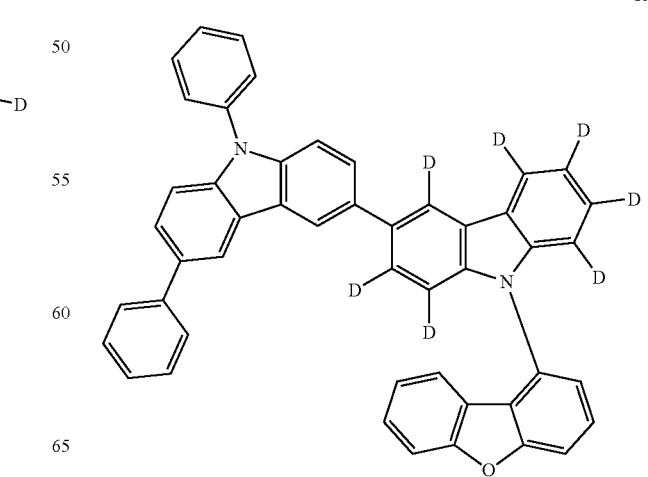

157
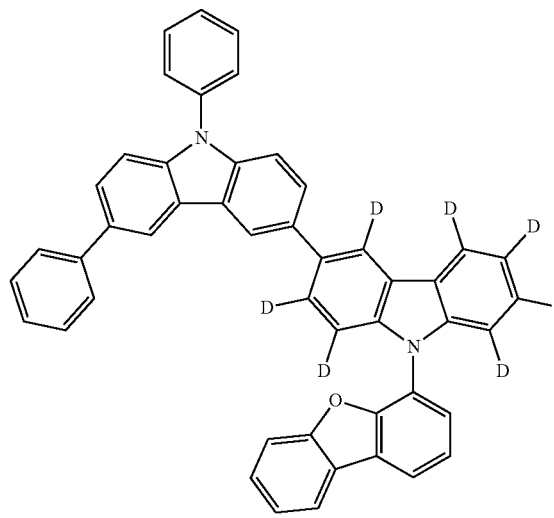
158
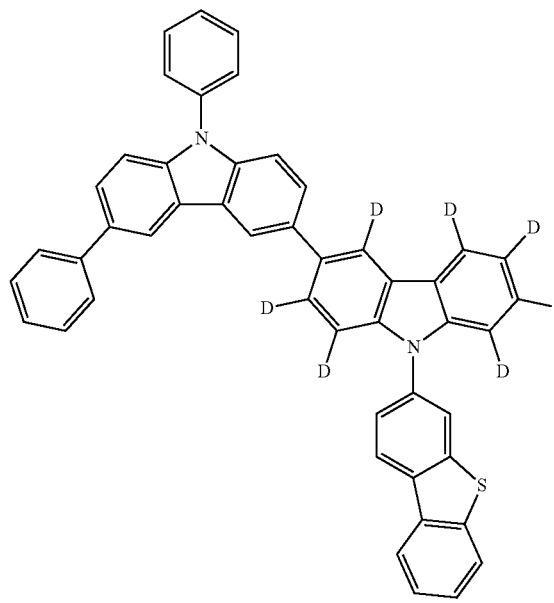
159
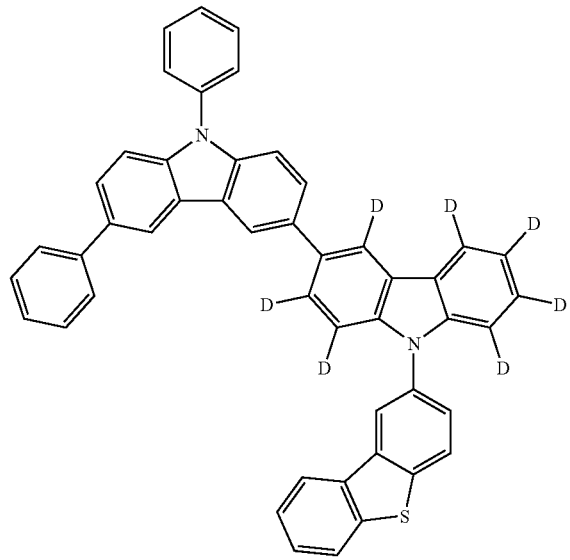
160
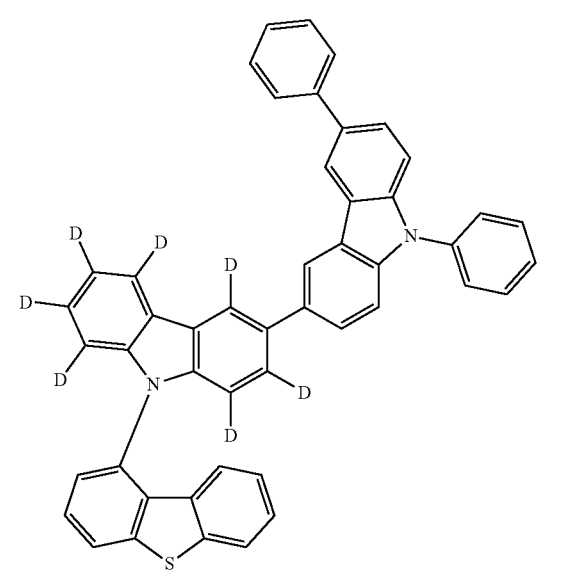

161
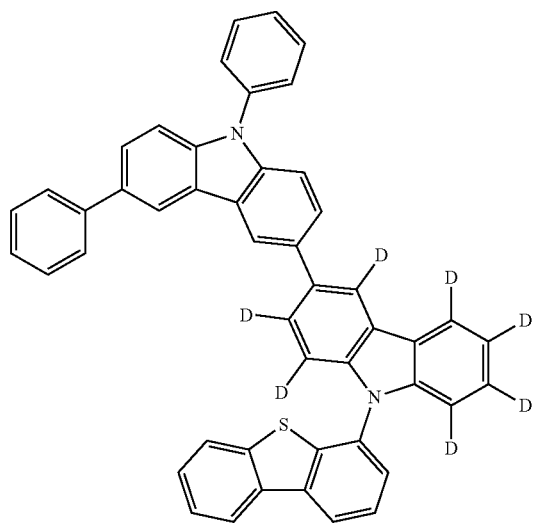
162
163
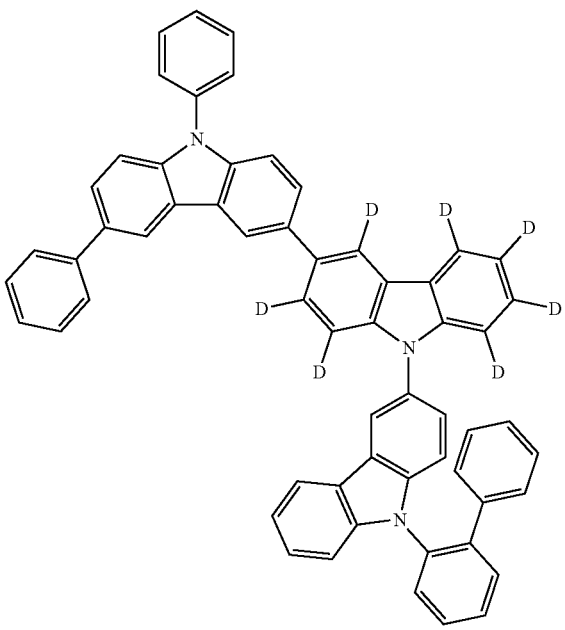
164
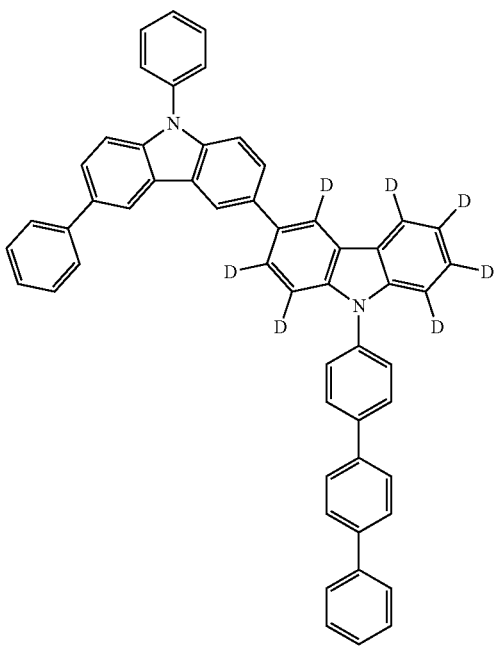

165
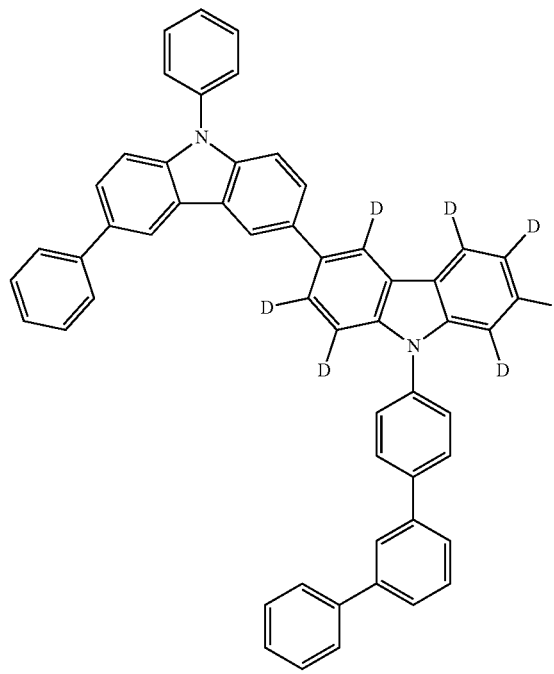
166
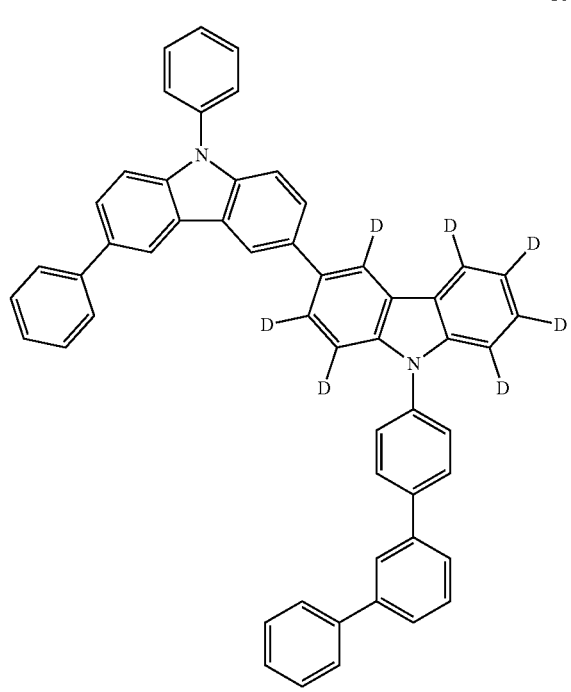
167
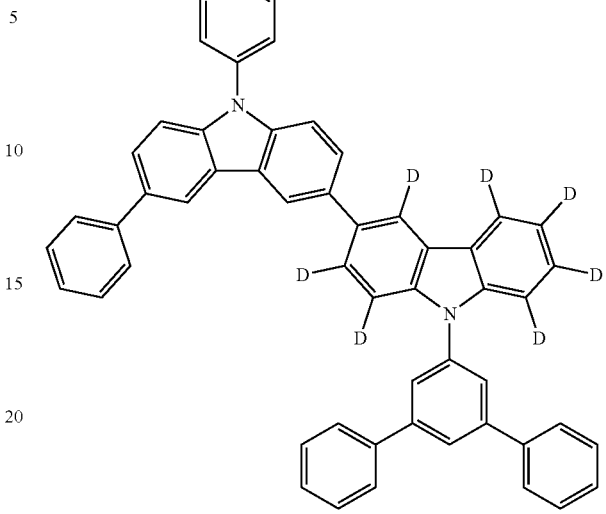
167'
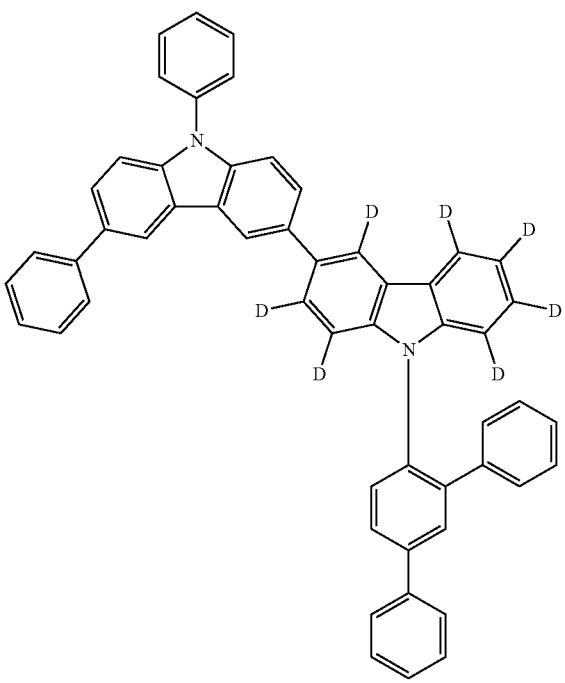

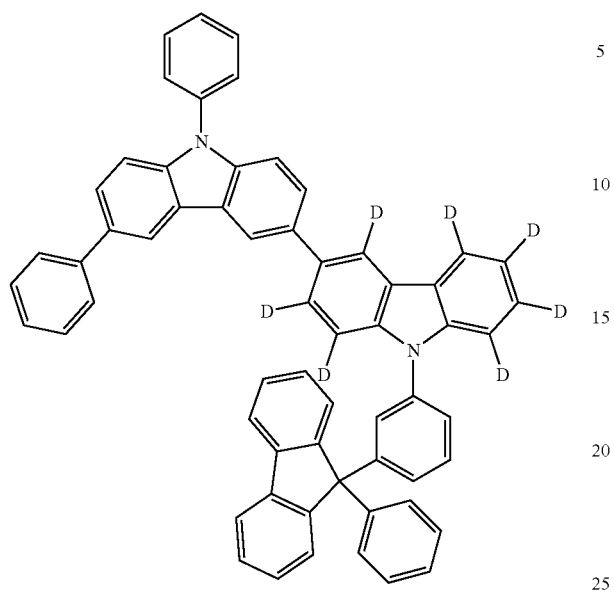
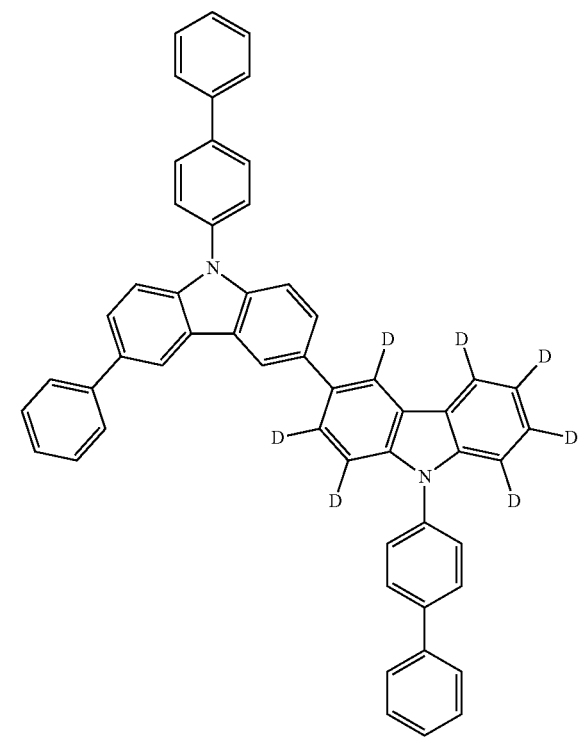

172
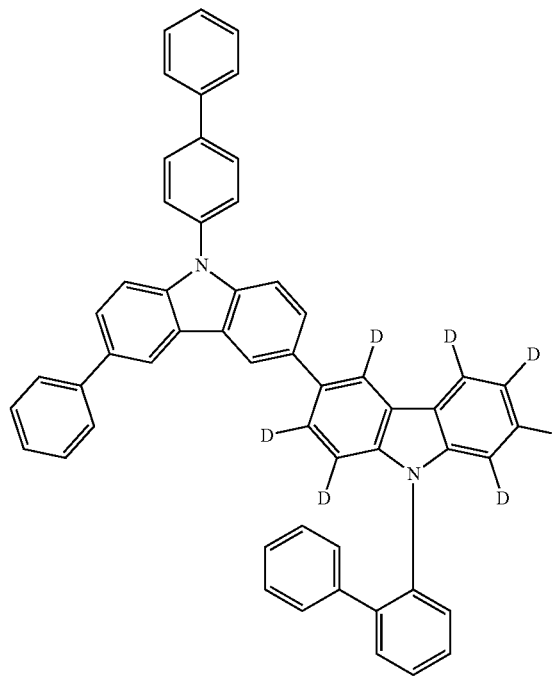
173
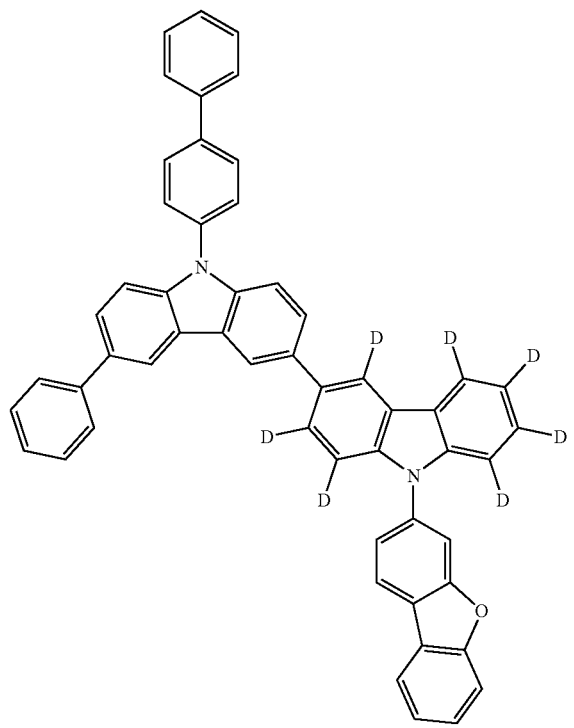
174
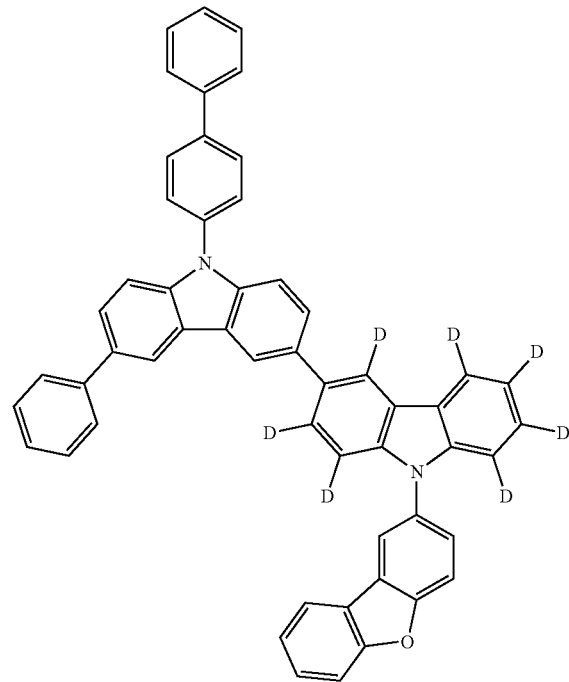
175
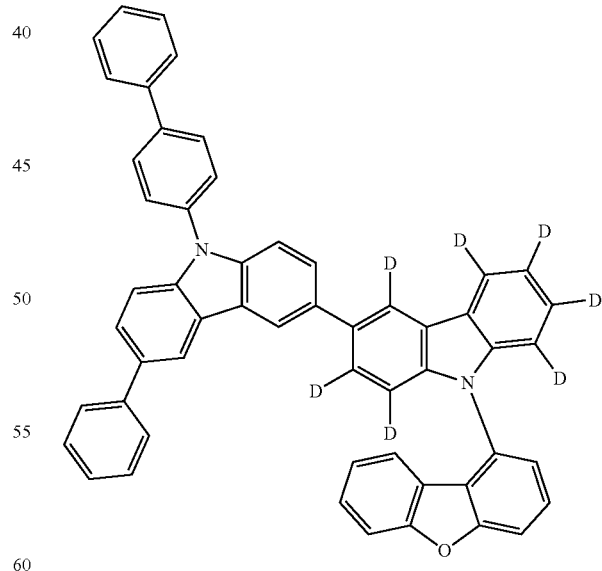

176
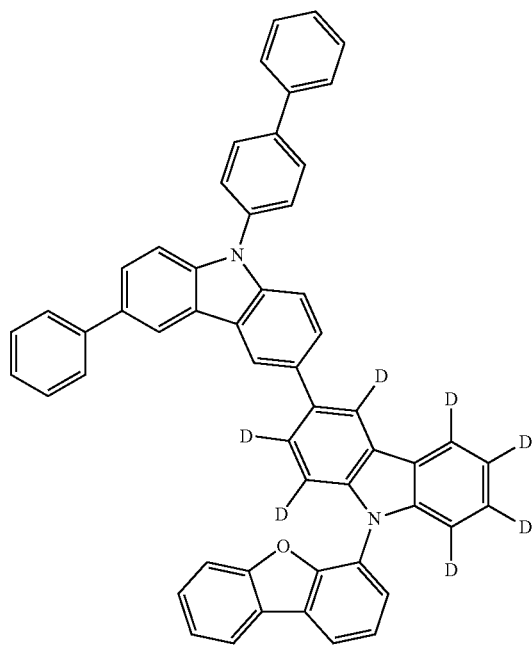
177
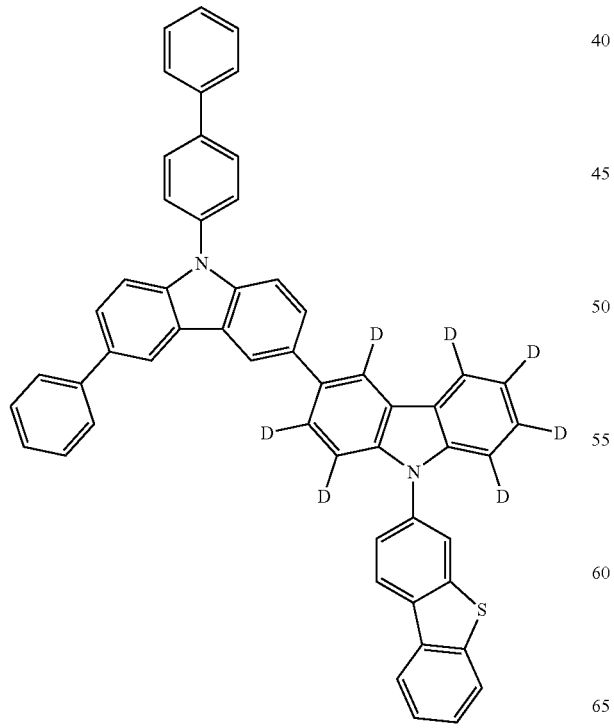
178
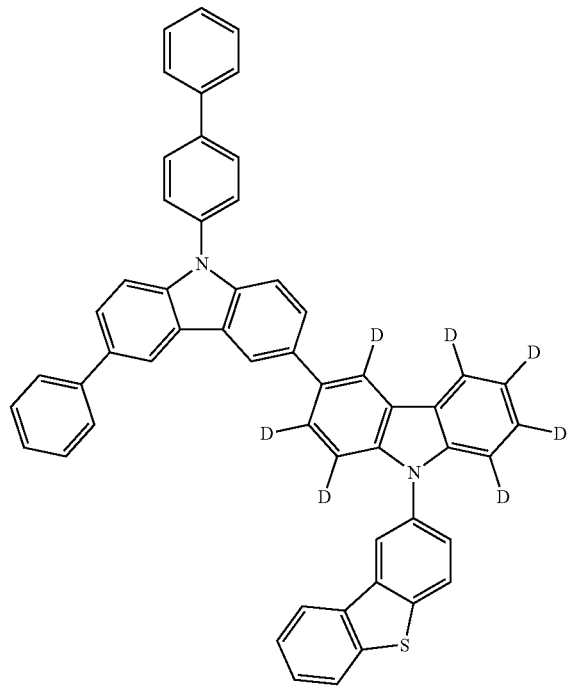
179
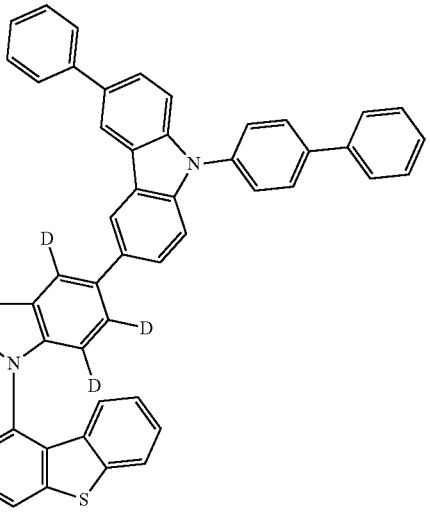

-continued
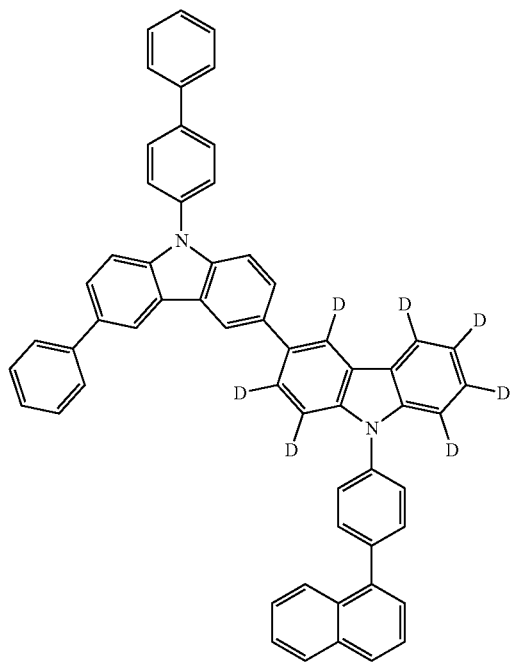
180
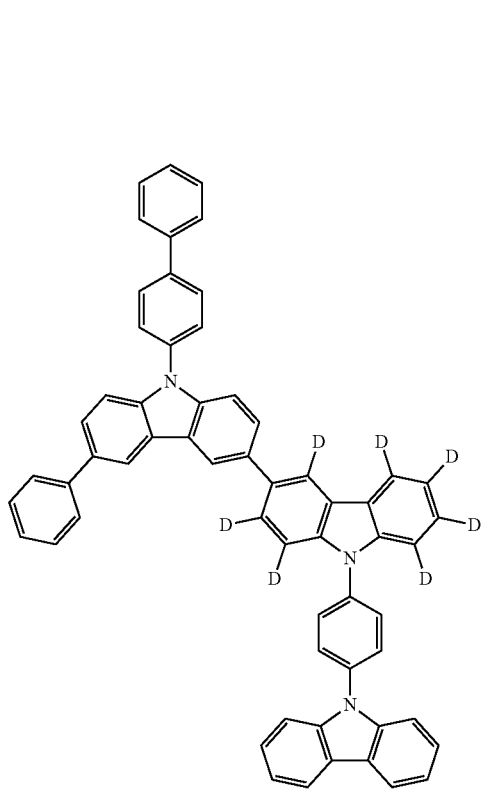
181
-continued
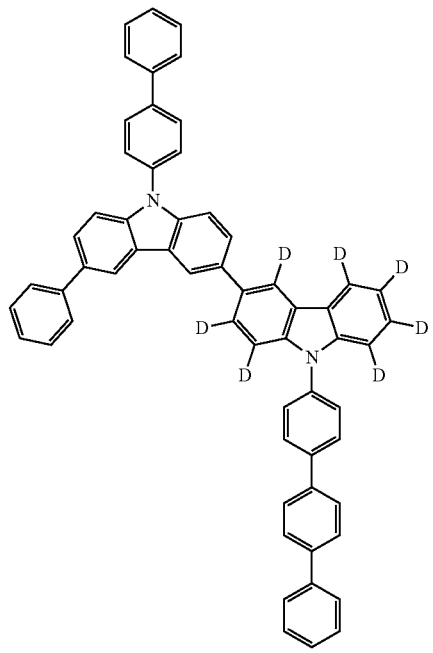
182
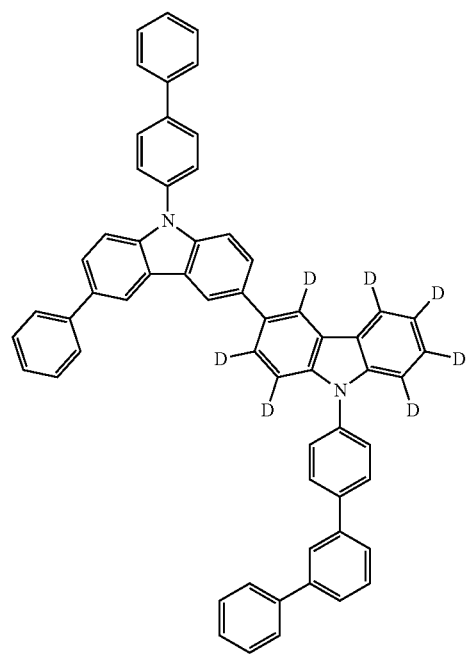
183

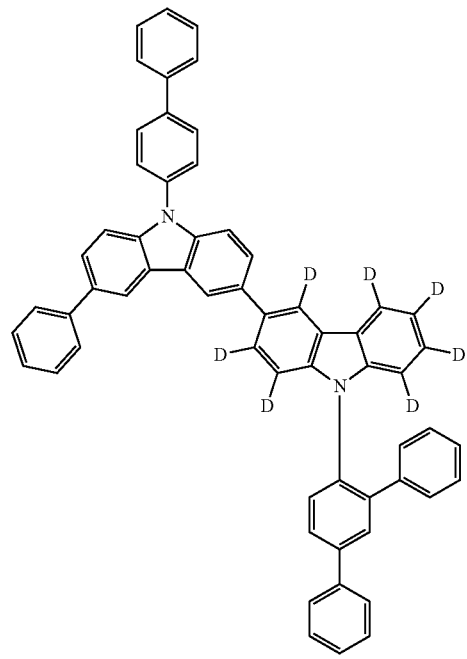
184
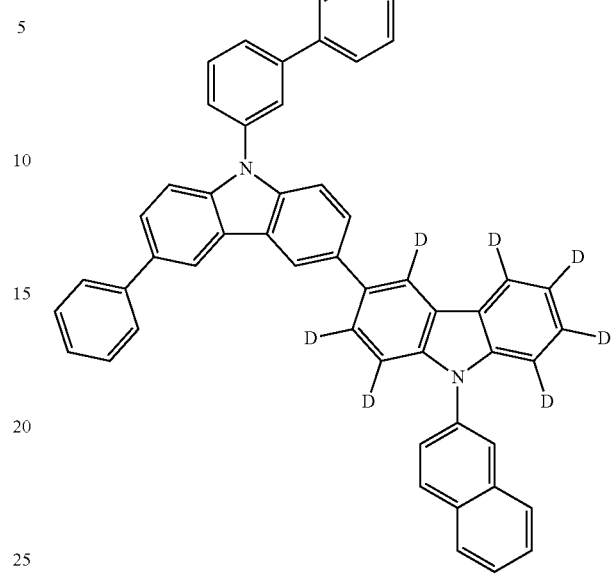
186
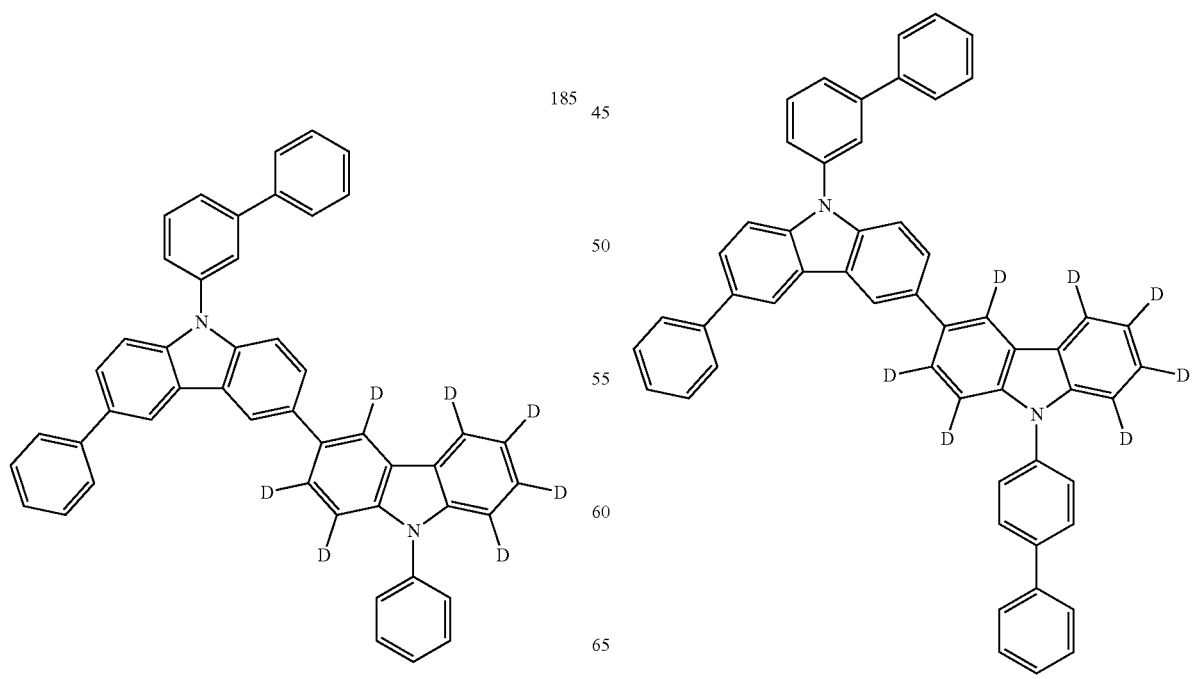
185
187

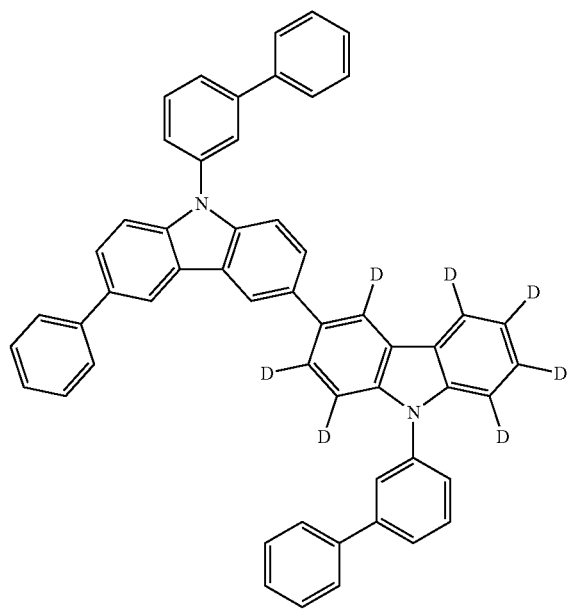

192
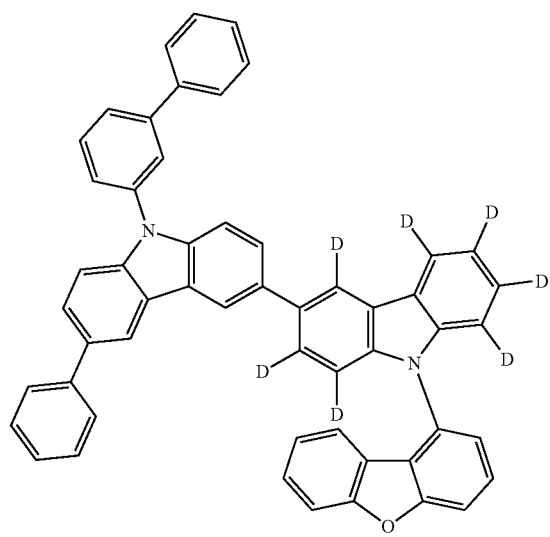
1943
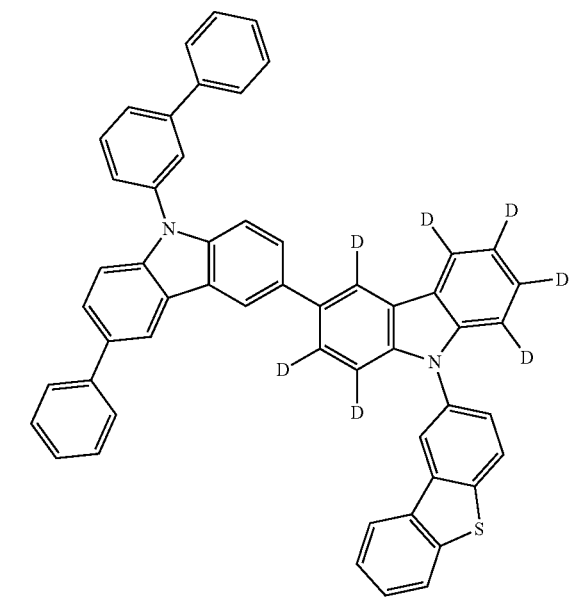
193
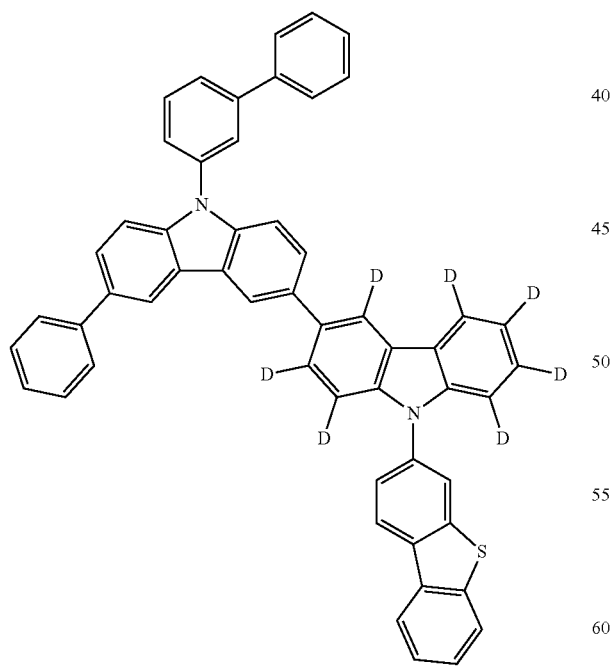
195
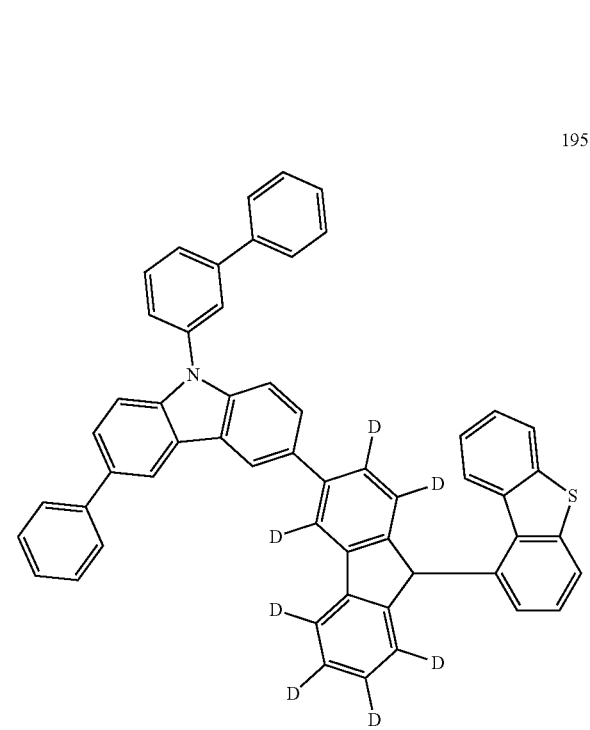

196

197

198

199

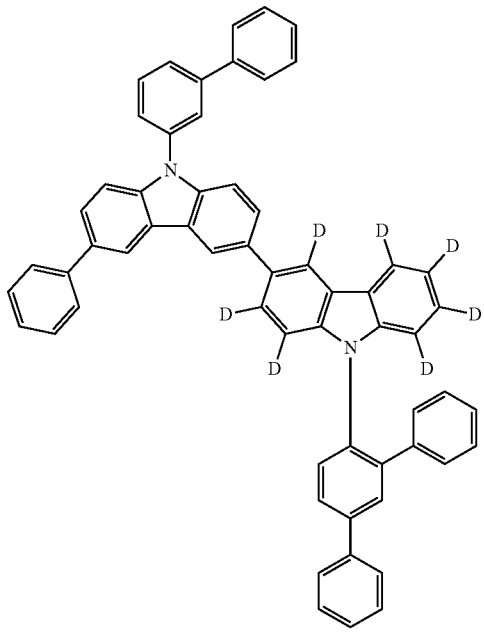
200
201
202
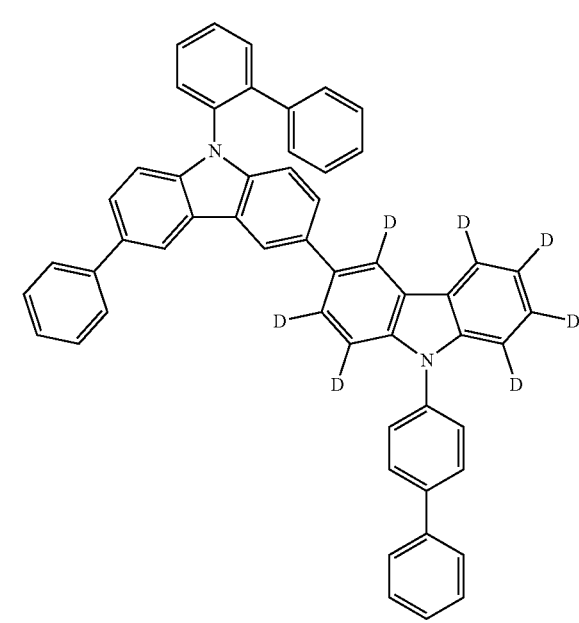
203
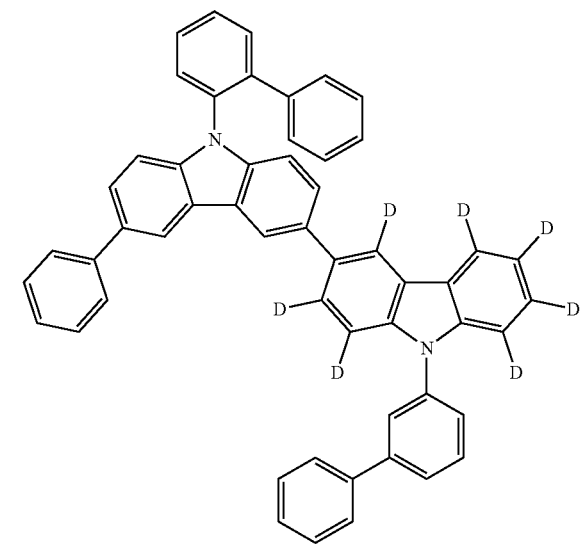
204

205
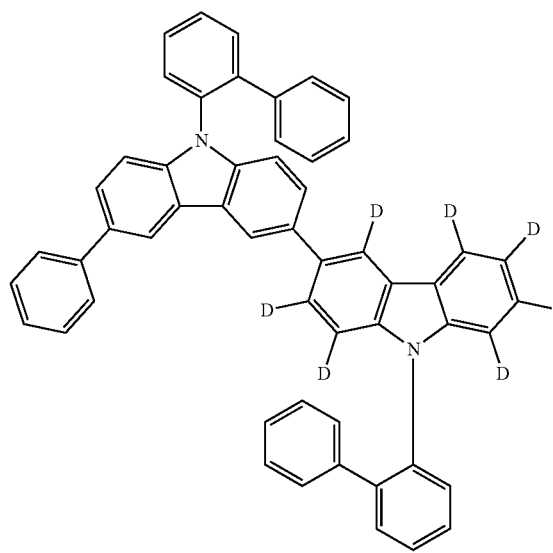
206
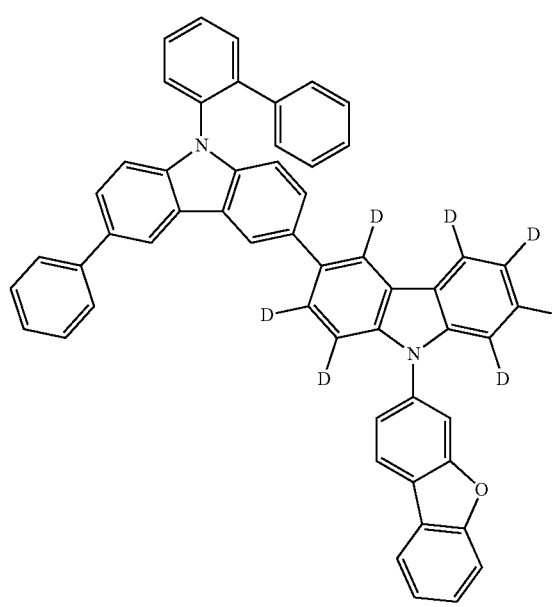
207
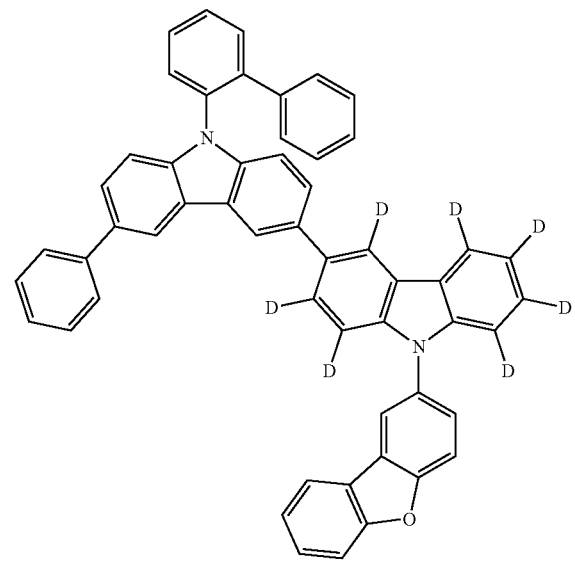
208
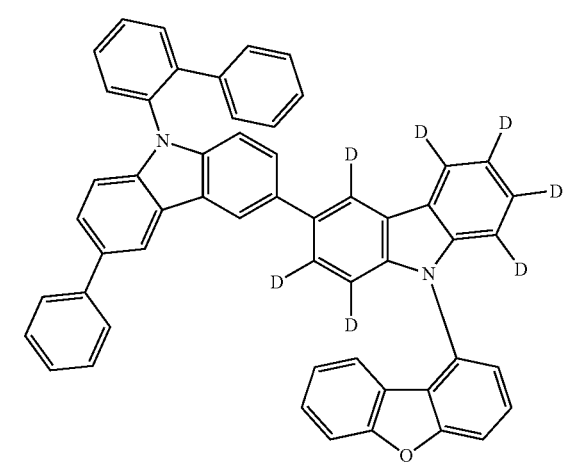
209
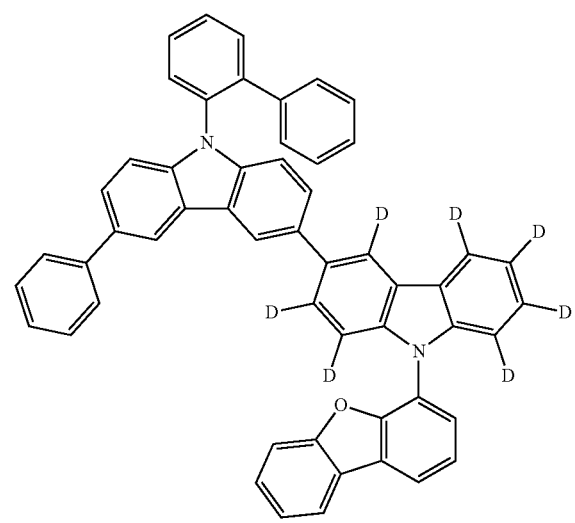

210
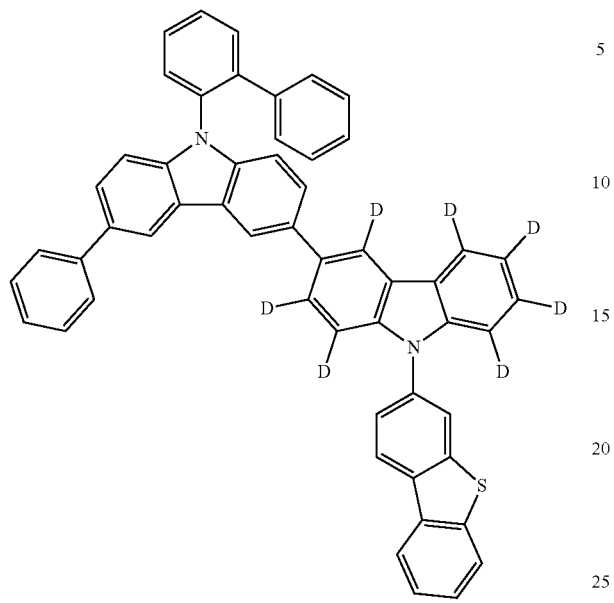
211
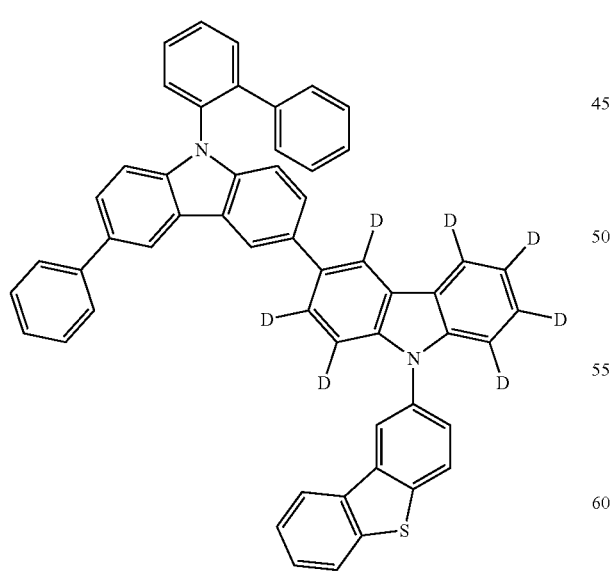
212
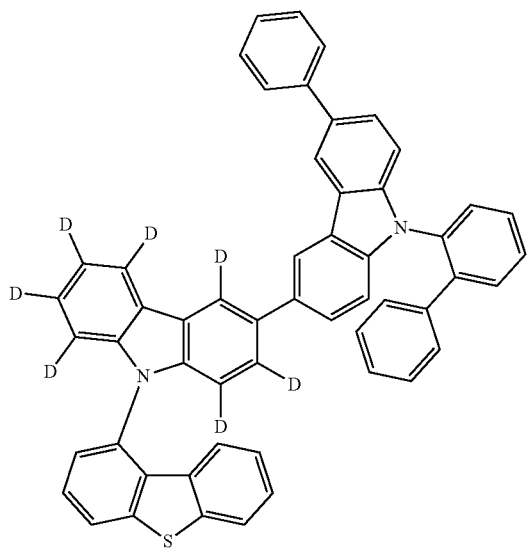
213
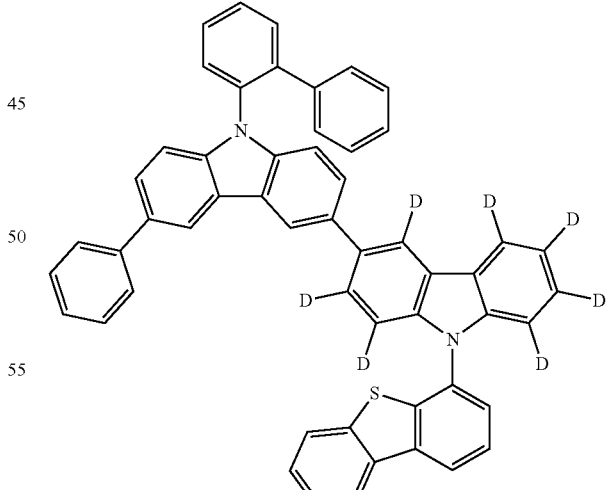

214
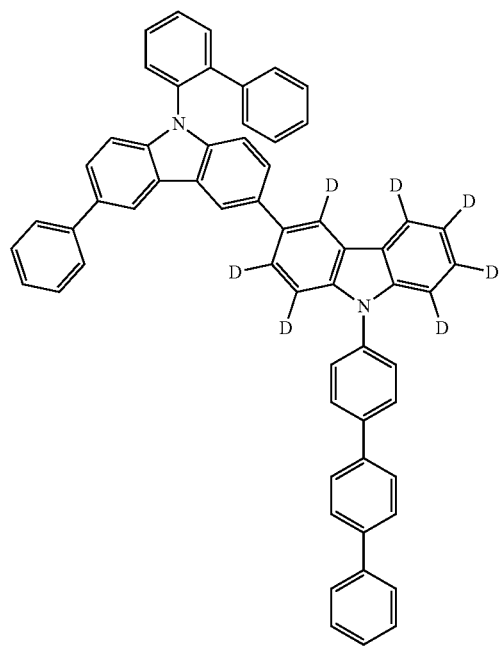
216
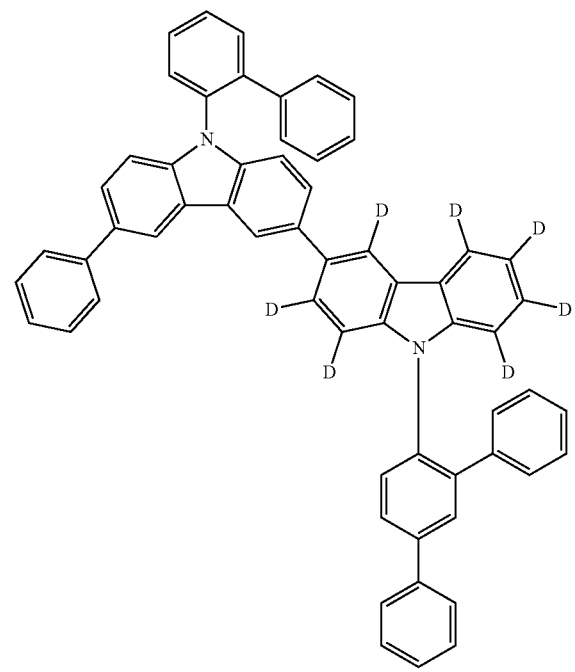
215
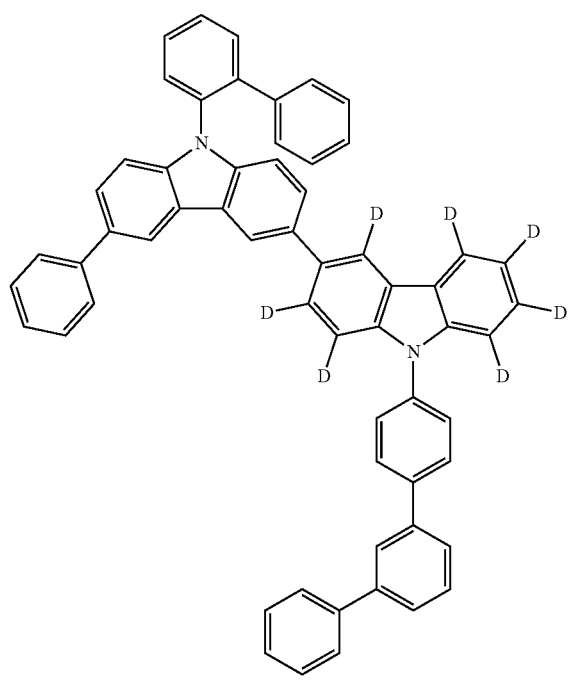
217
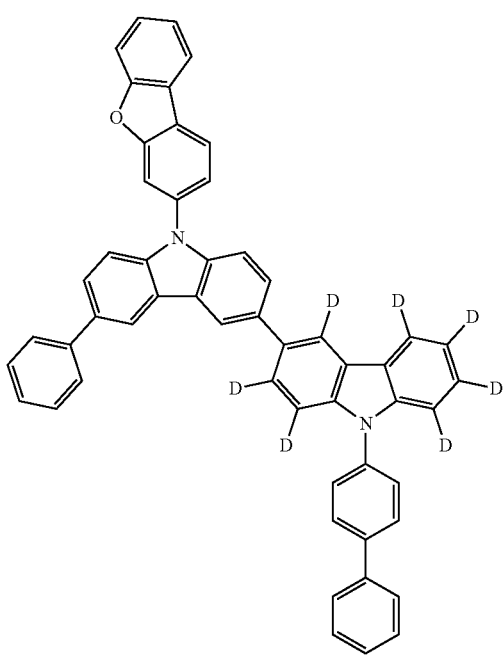

218
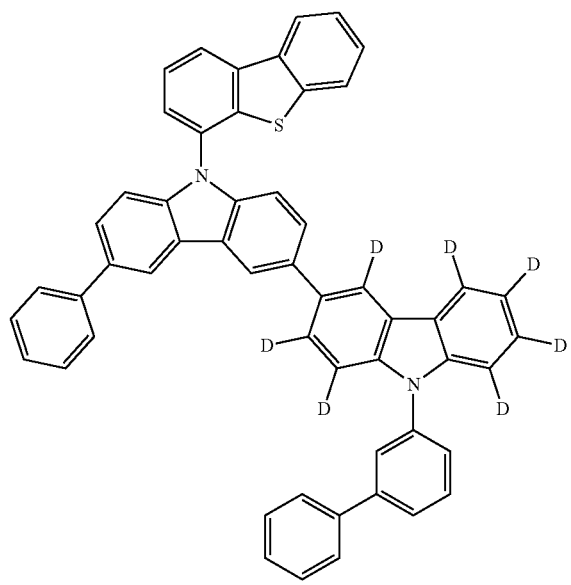
219
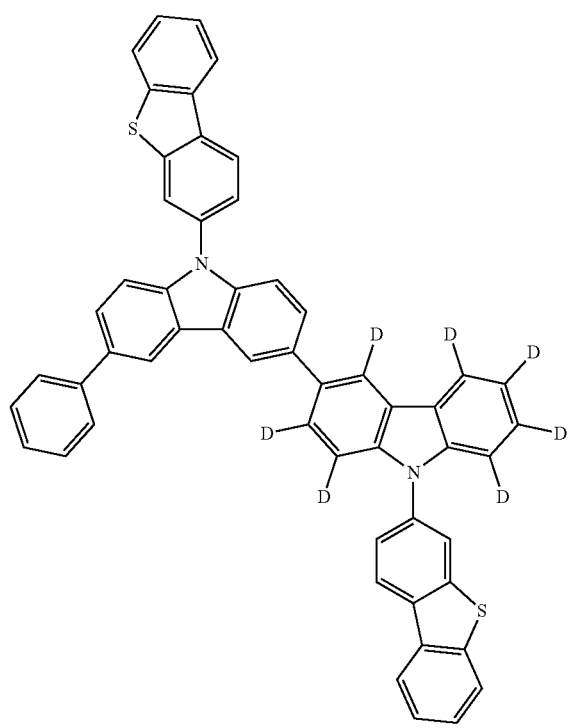
220
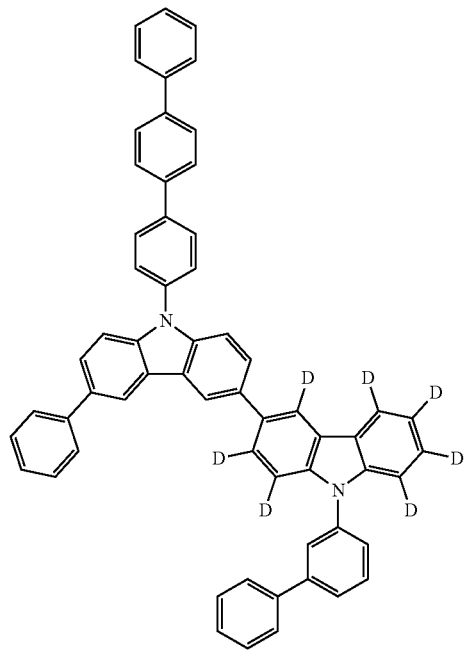
221
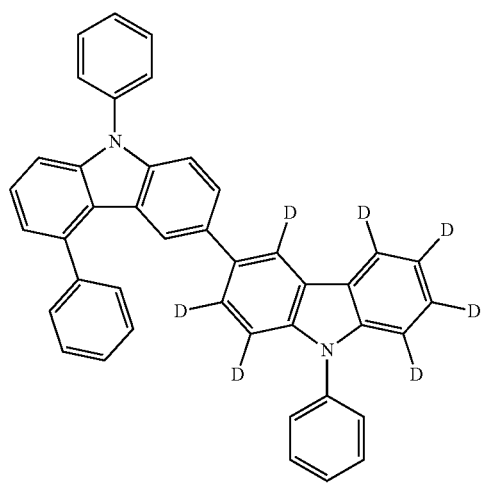
222
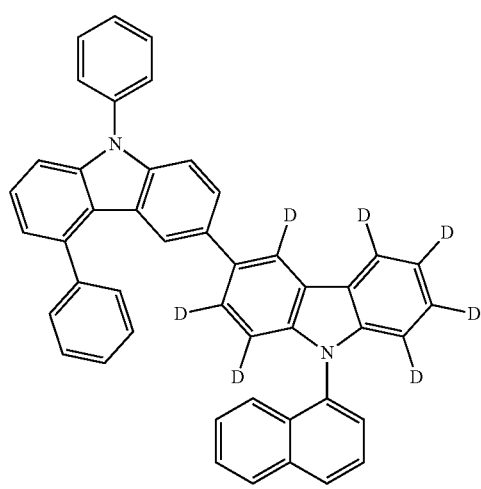

223
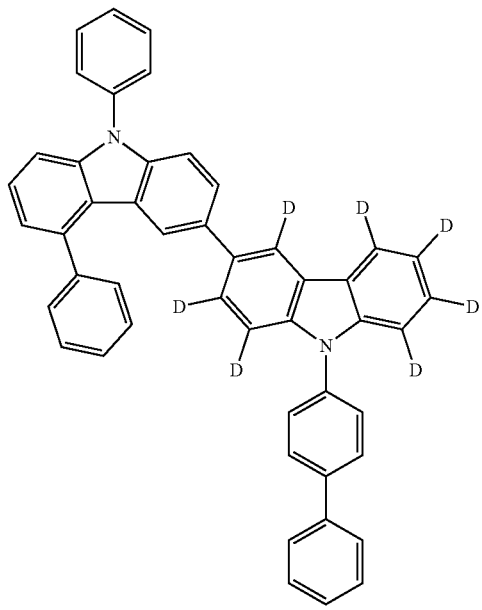
224
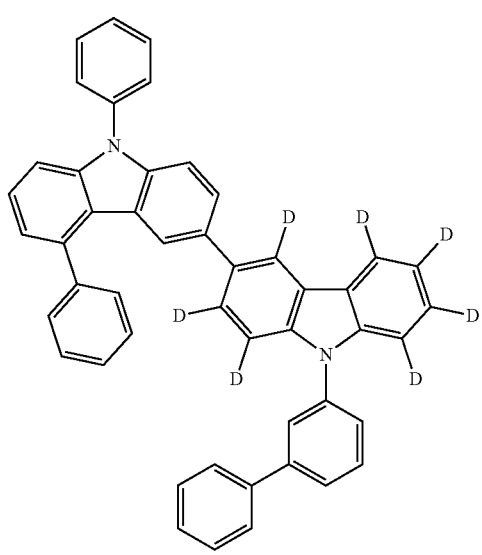
225
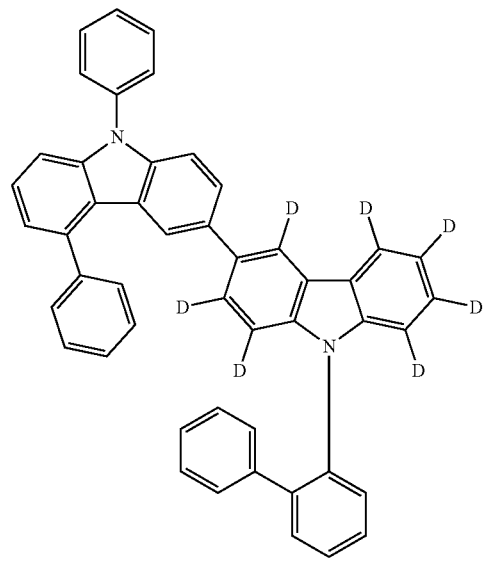
226
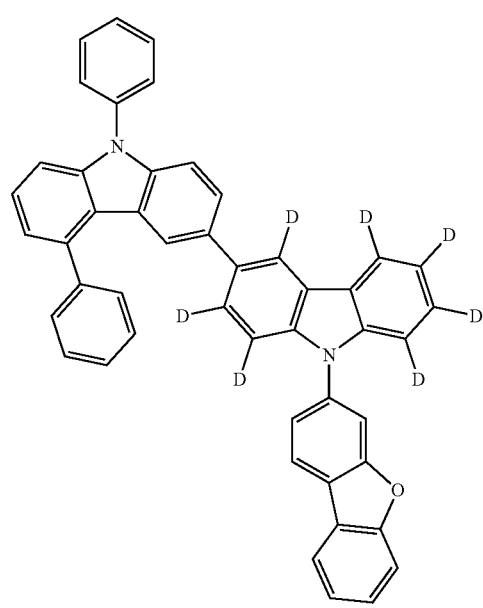

227
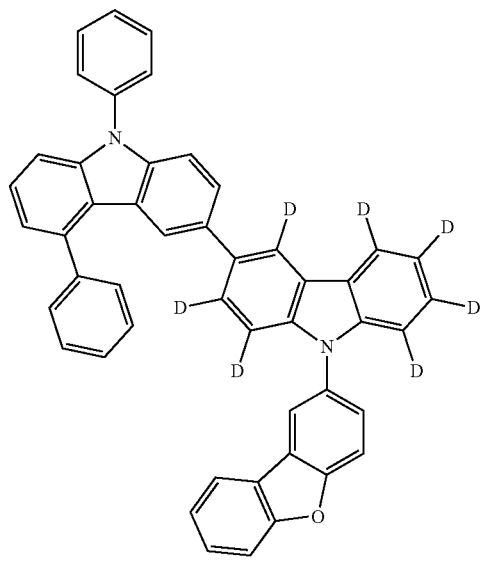
228
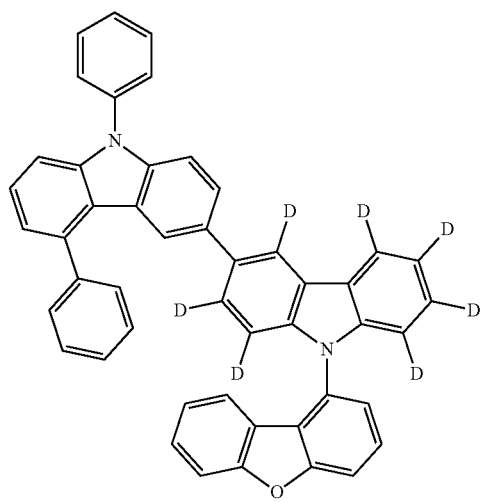
229
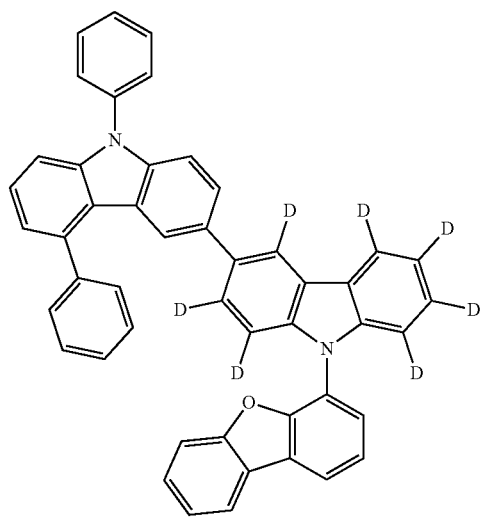
230
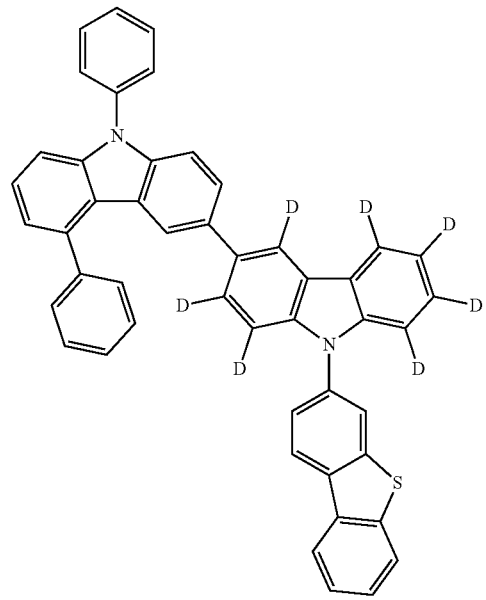
231
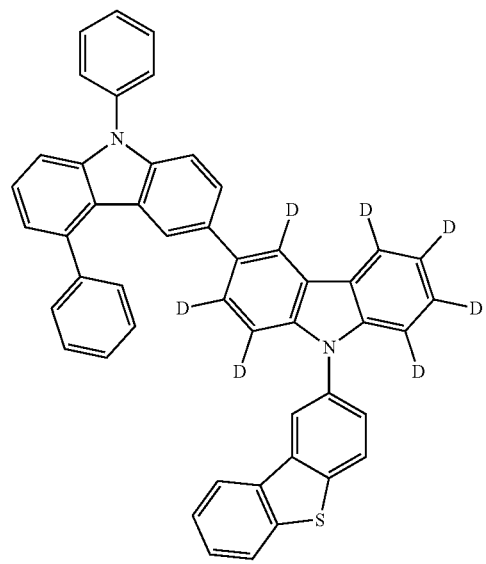
232
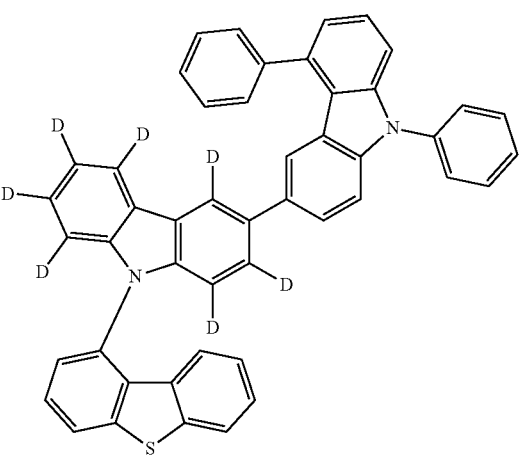

-continued
233
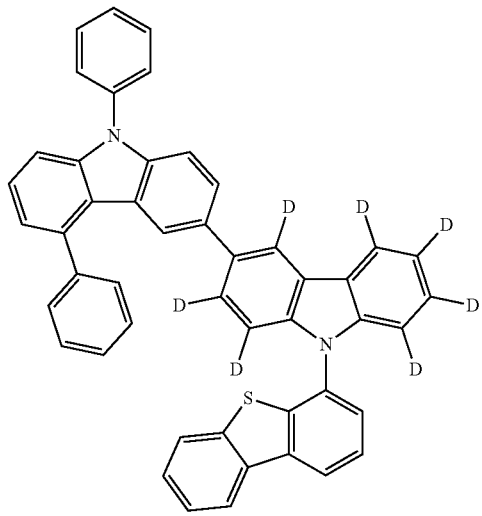
234
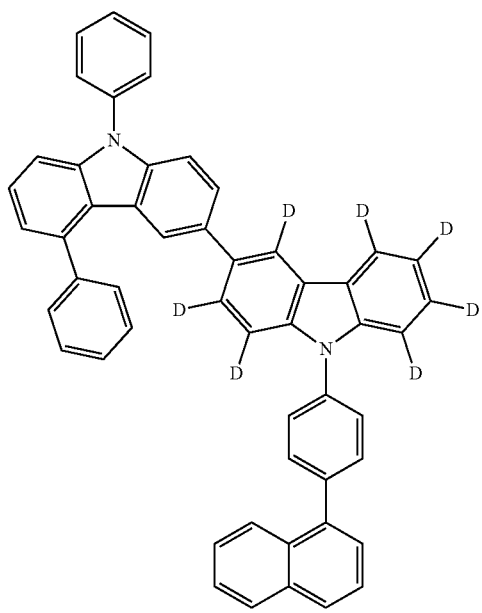
-continued
235
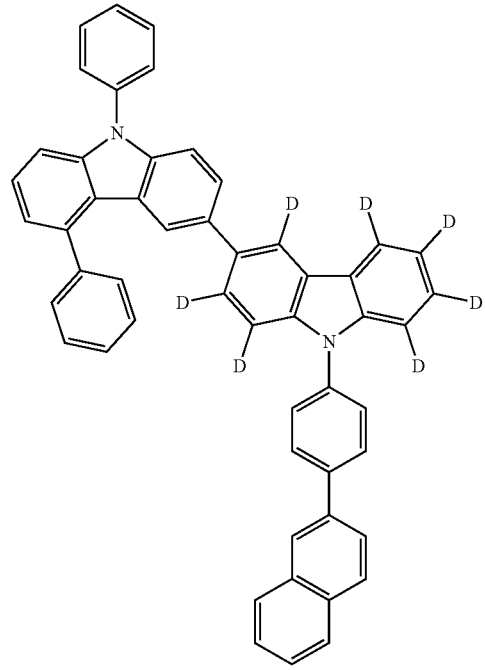
236
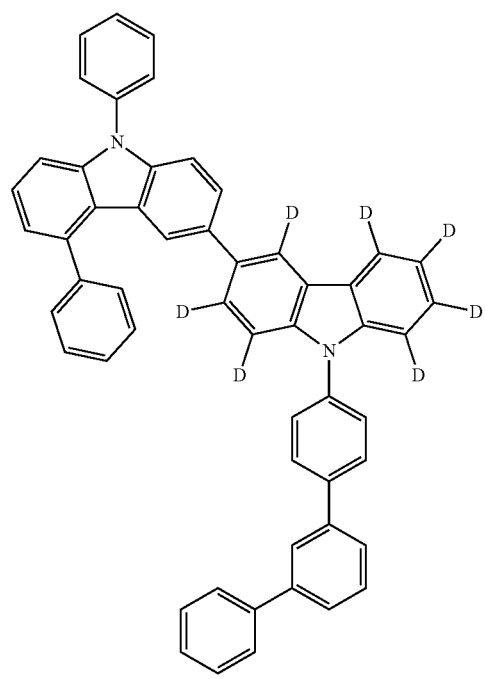

237
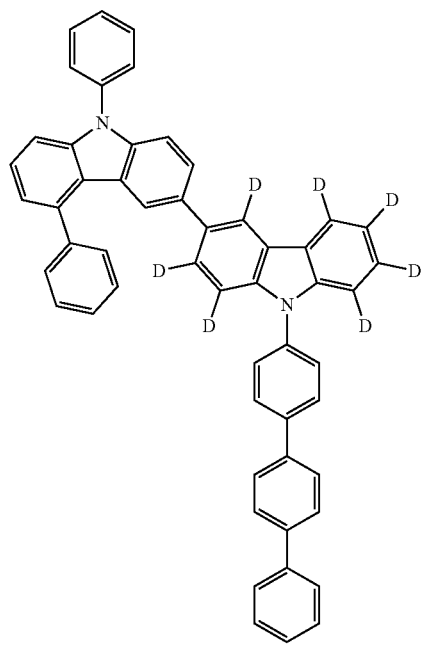
238
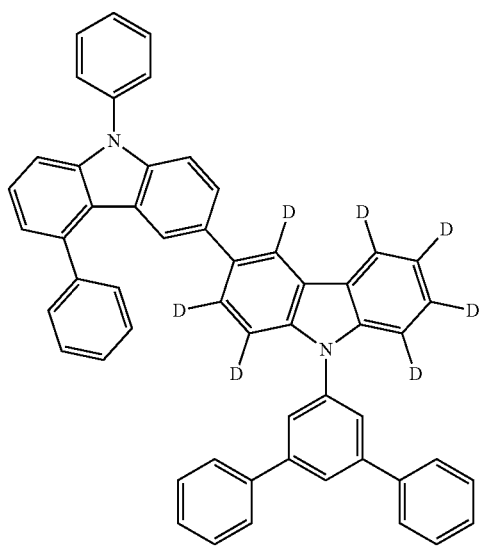
239
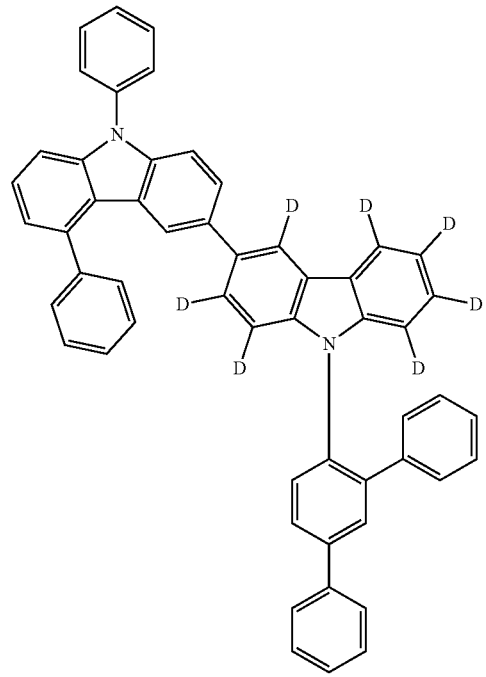
240
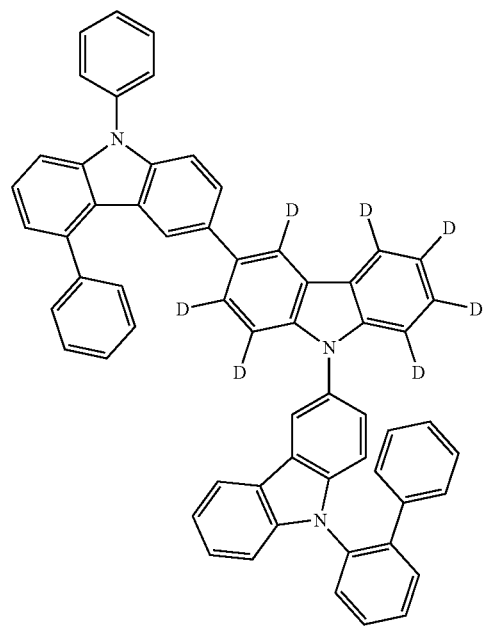

241
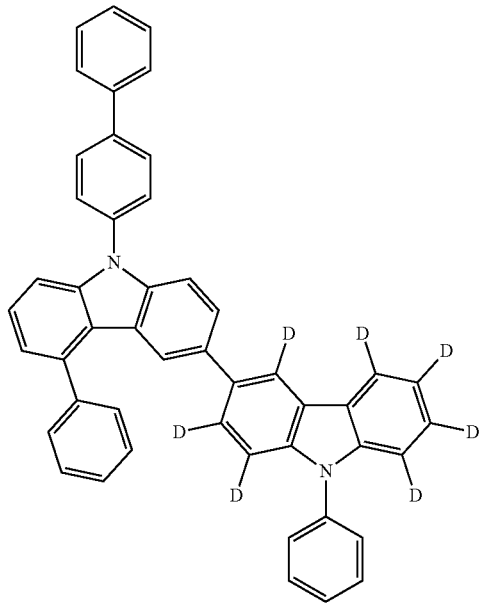
242
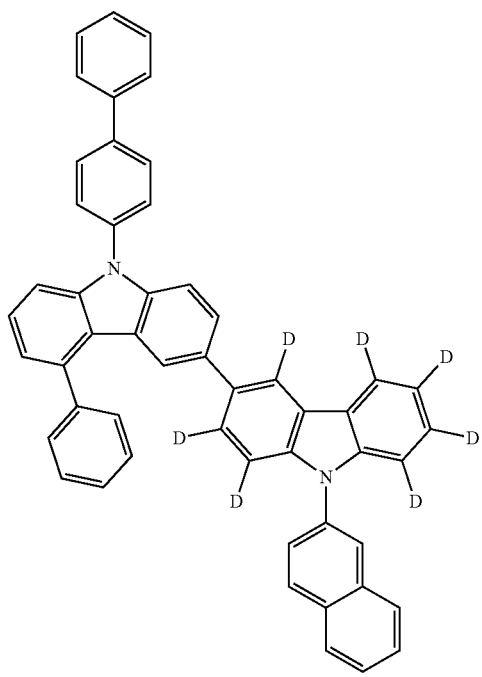
243
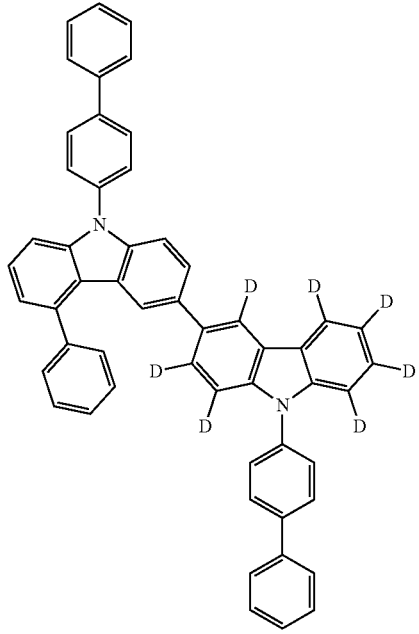
244
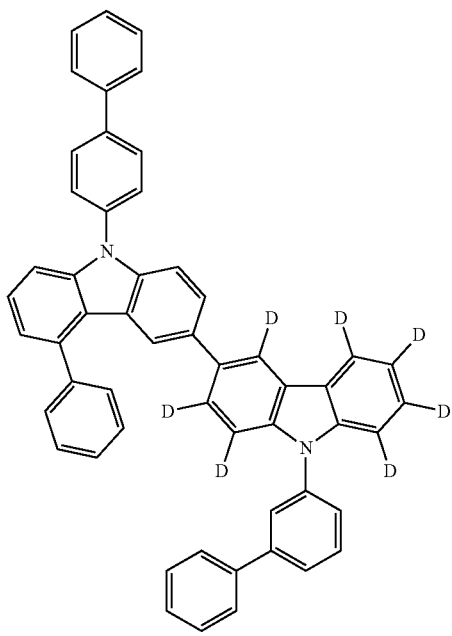

245
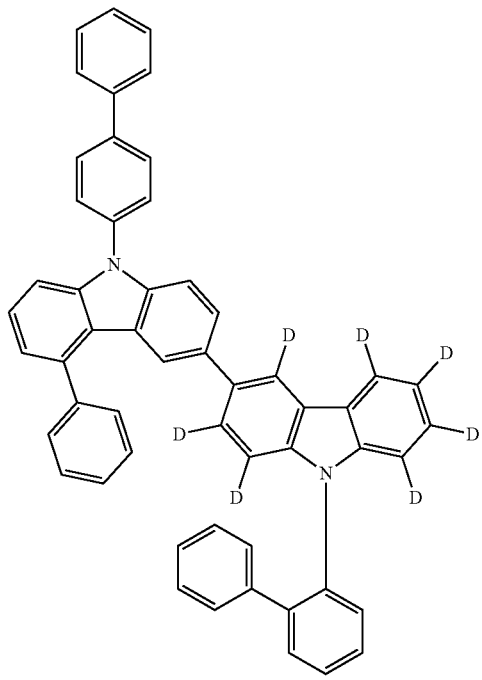
246
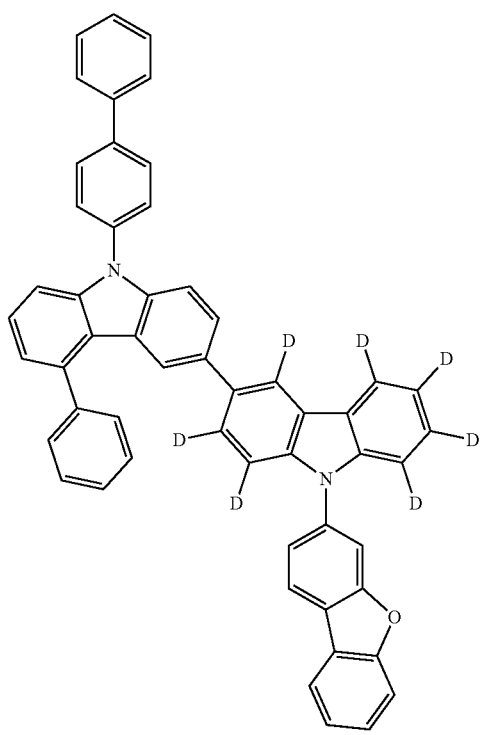
247
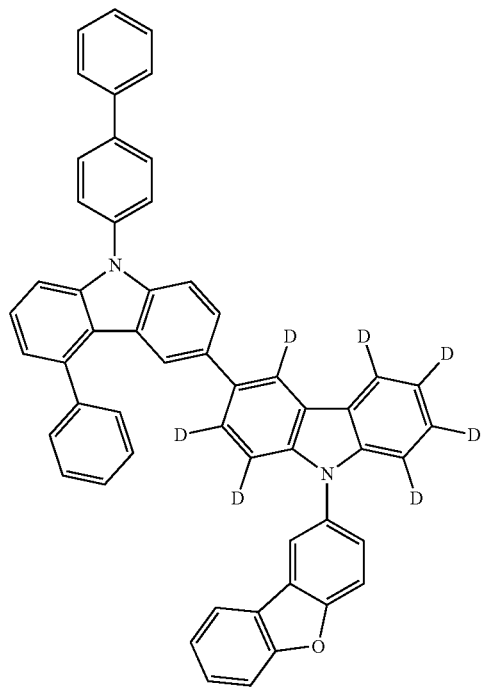
248
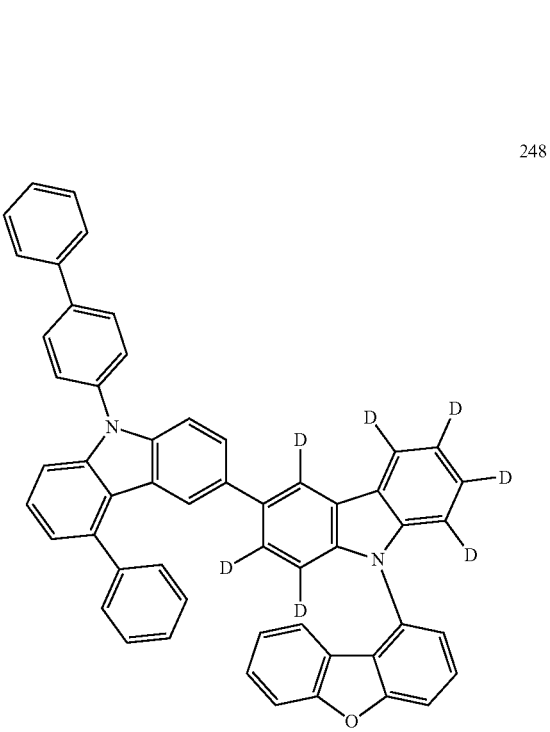

249
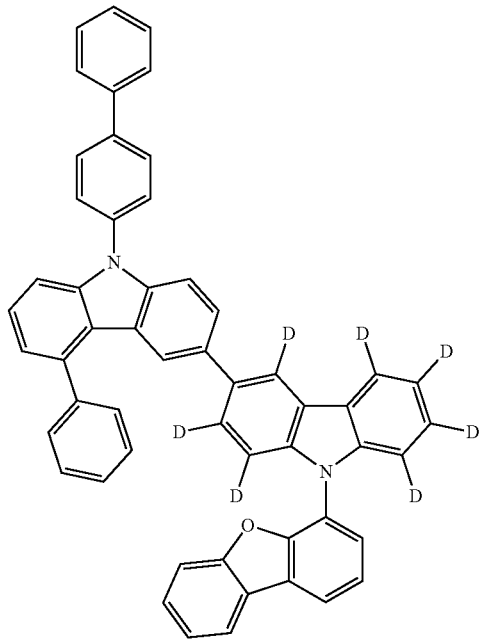
250
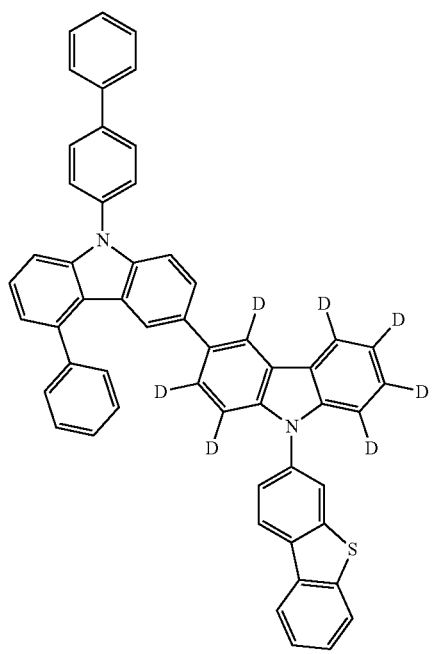
251
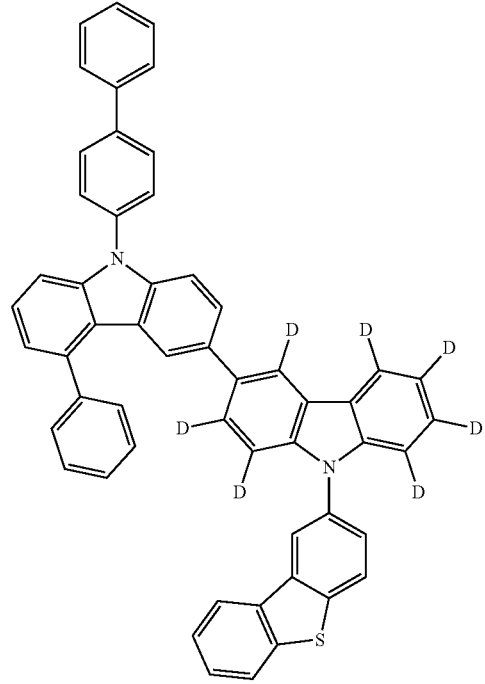
252
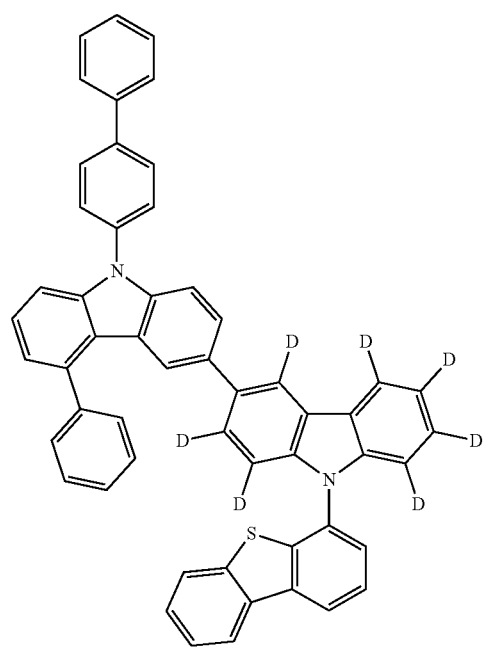

253
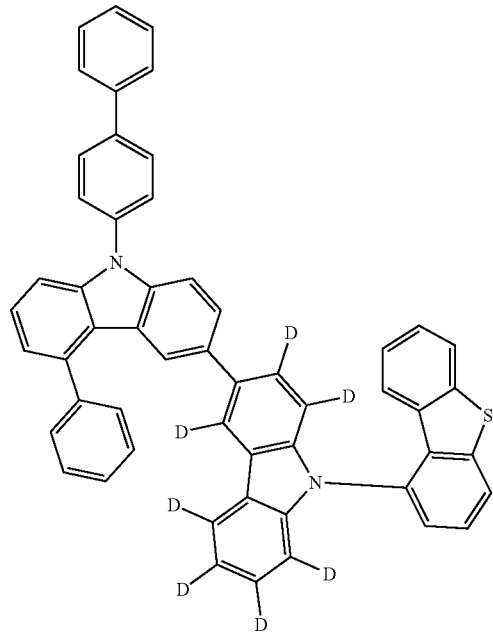
254
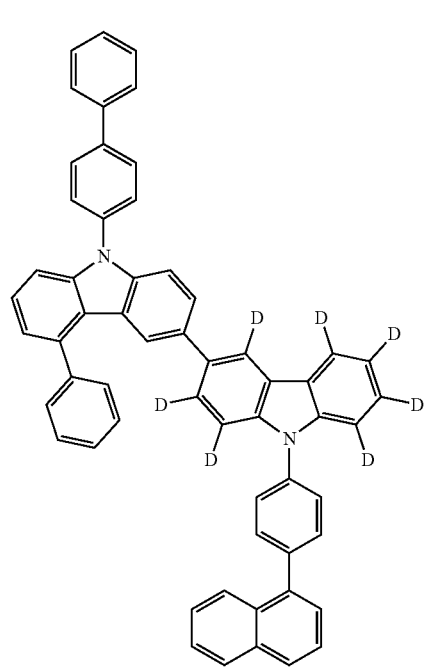
255
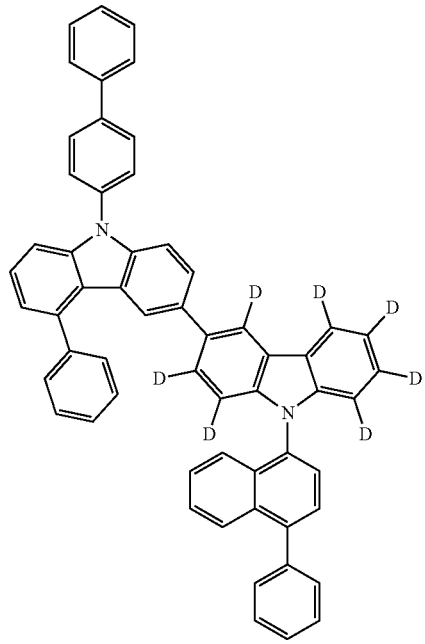
256
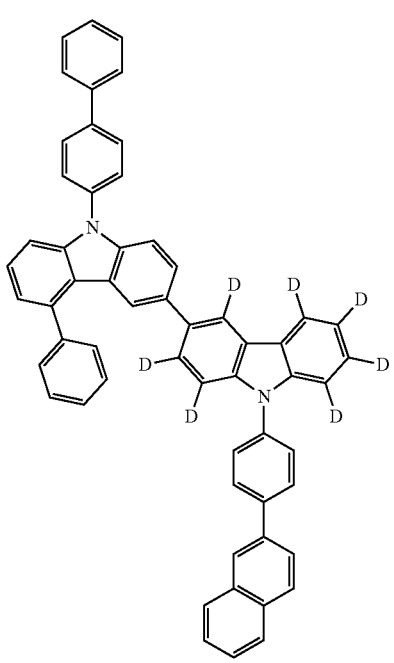

257
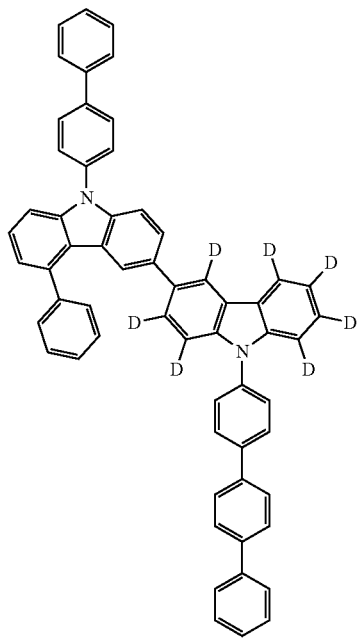
259
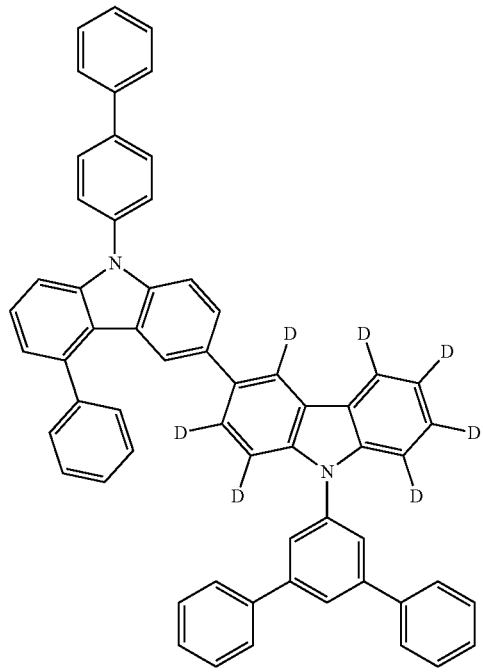
258
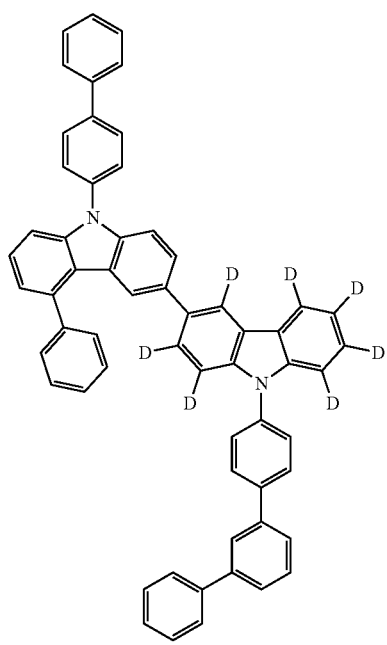
260
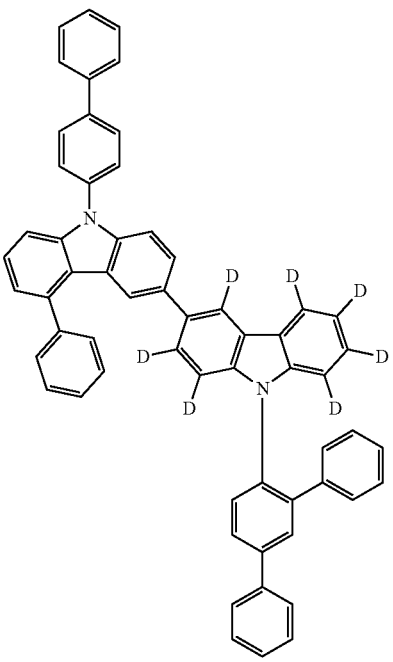

261
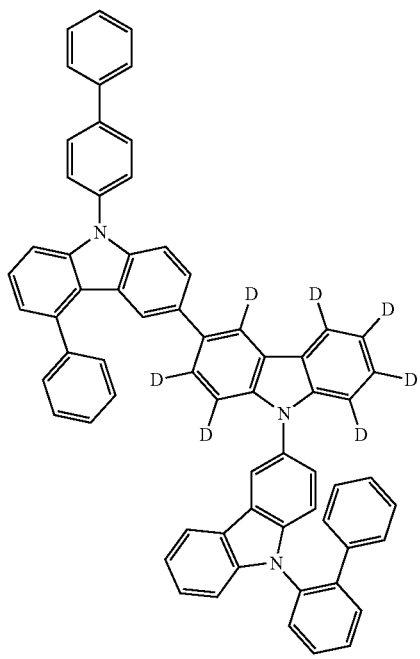
262
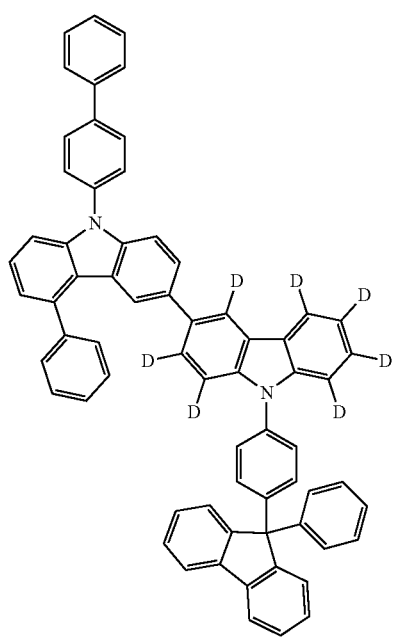
263
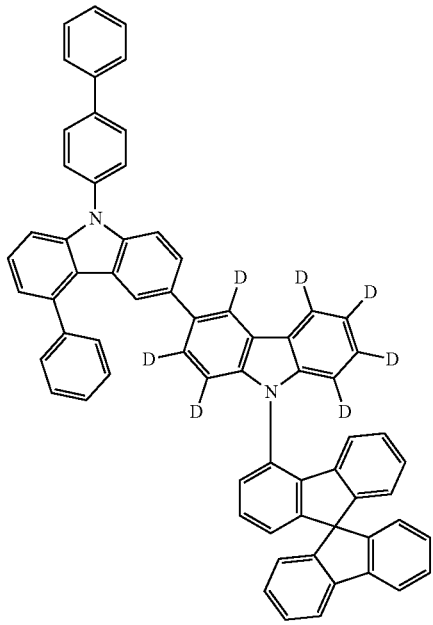
264
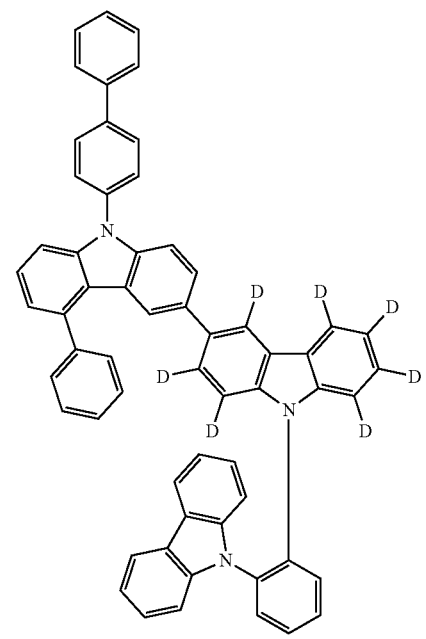

265
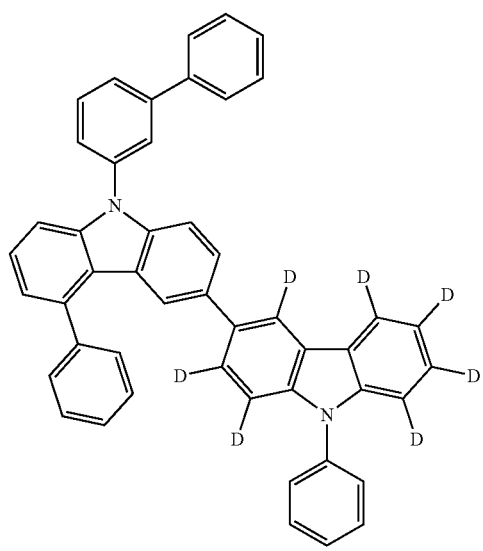
266
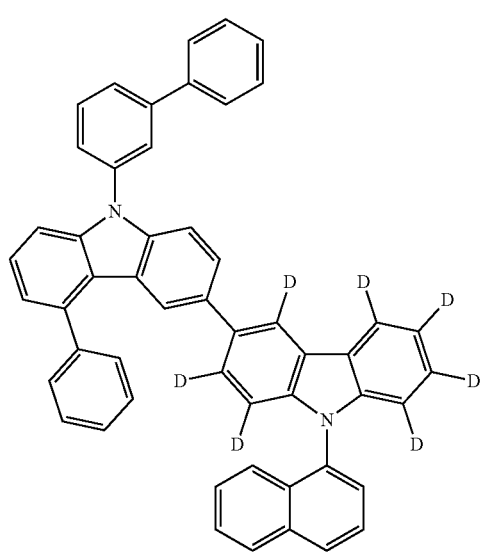
267
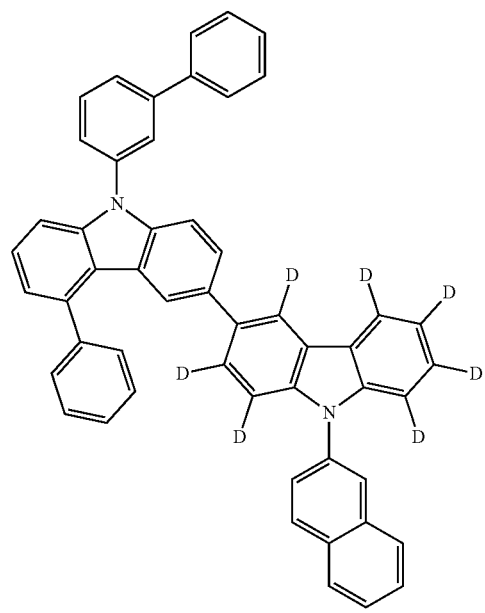
268
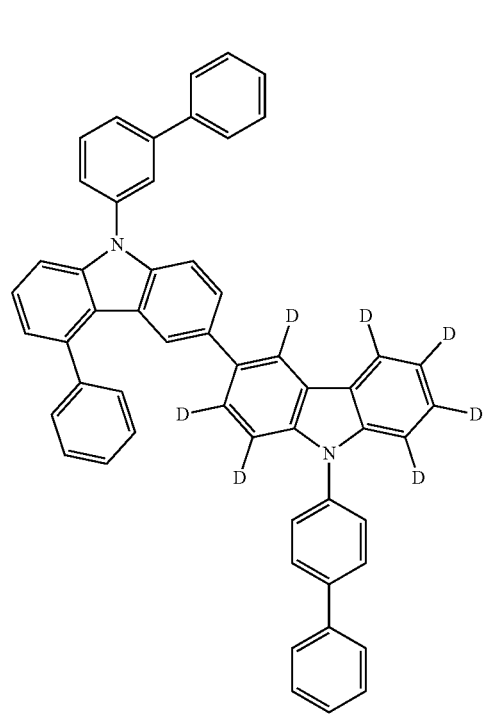

269
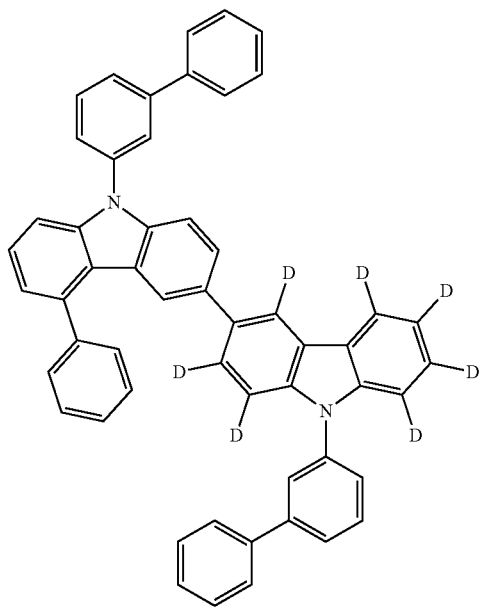
270
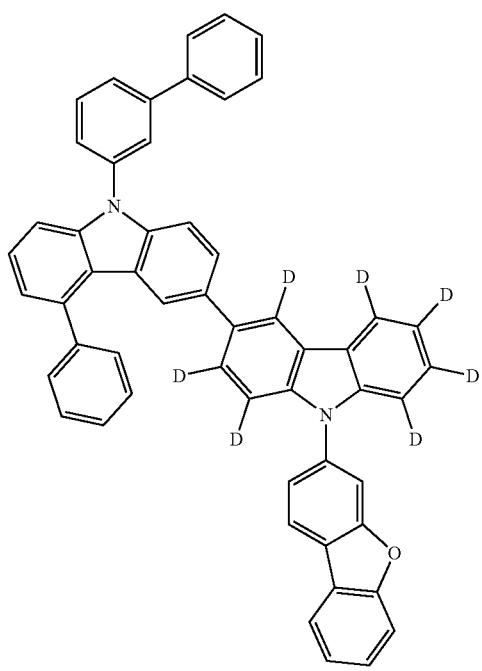
271
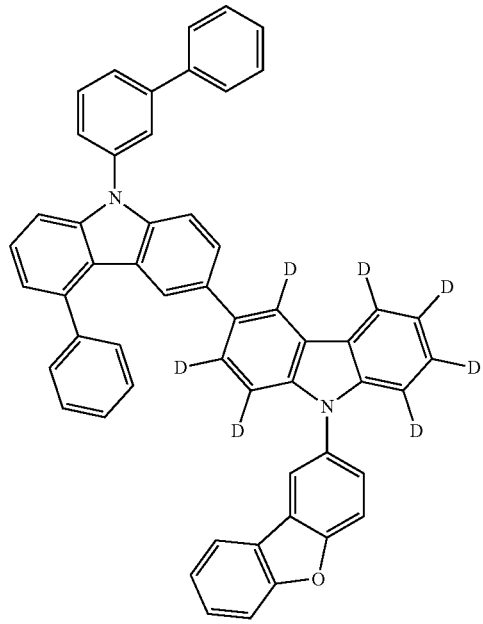
272
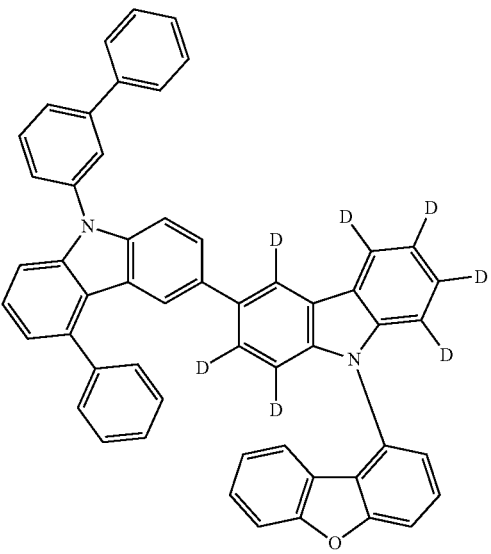

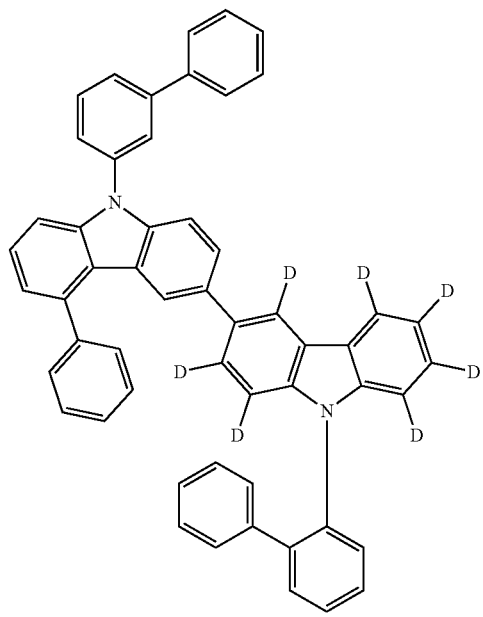
273
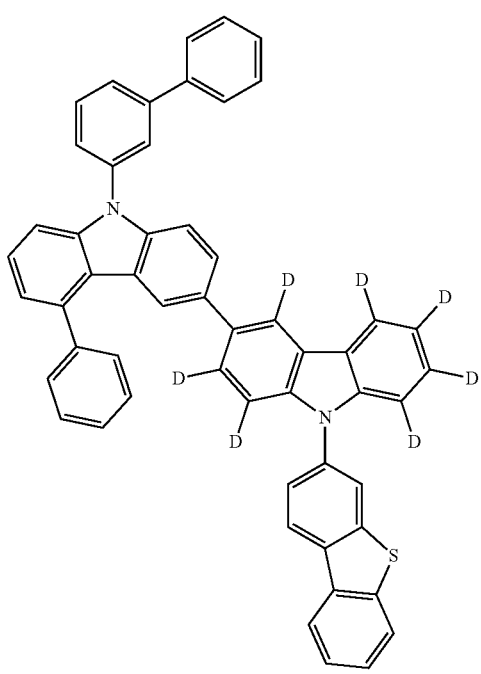
275
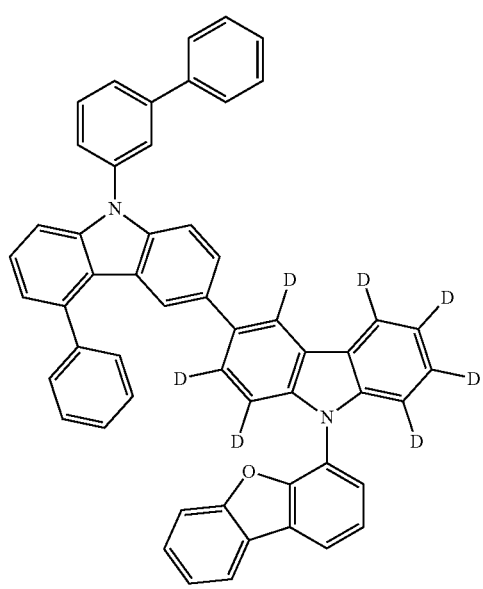
274
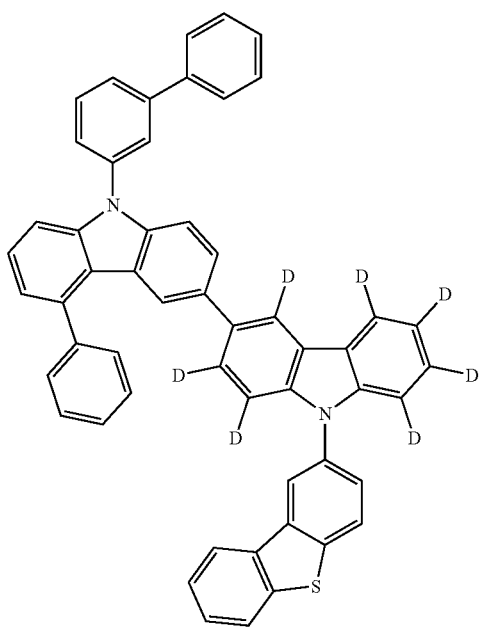
276

277
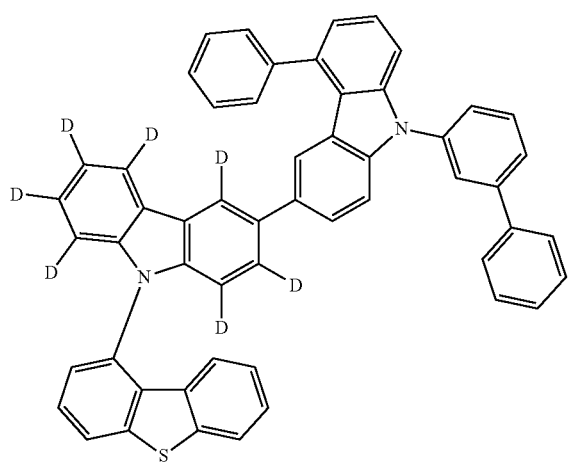
278
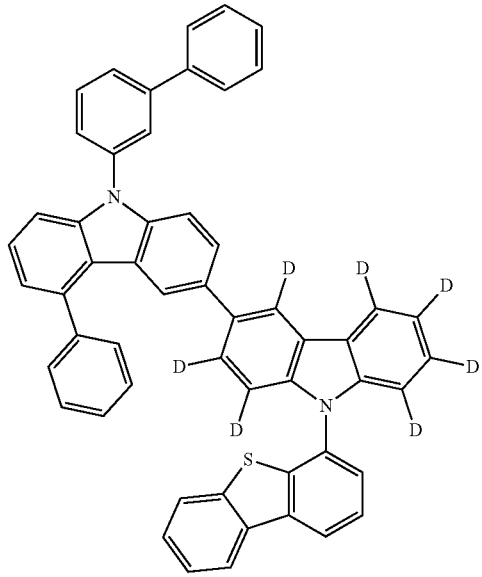
279
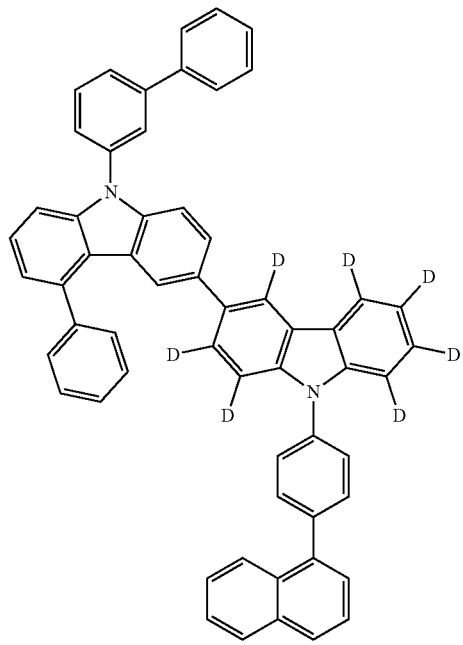
280
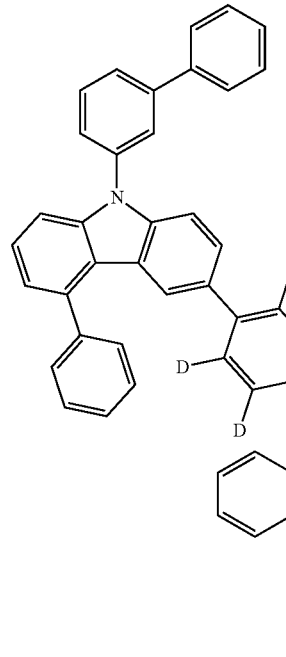

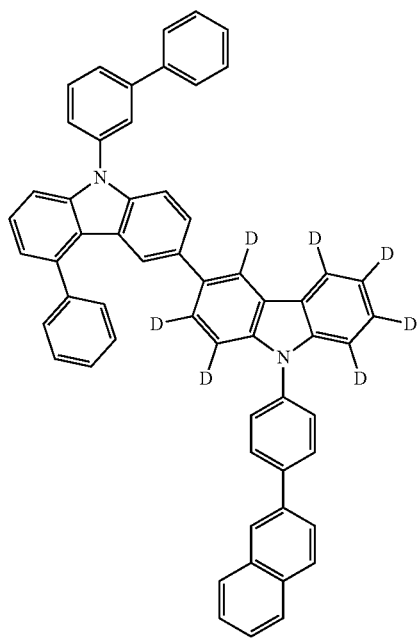
281
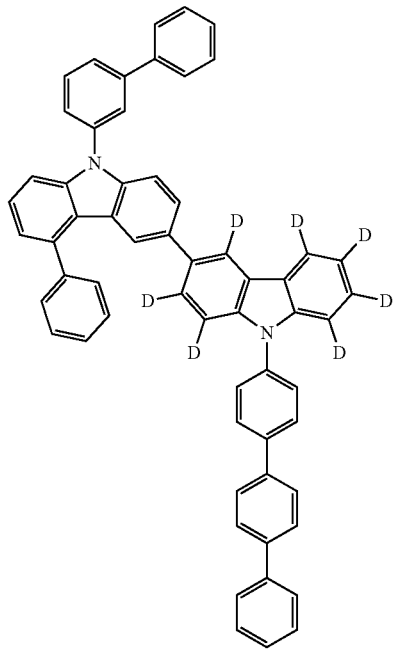
282
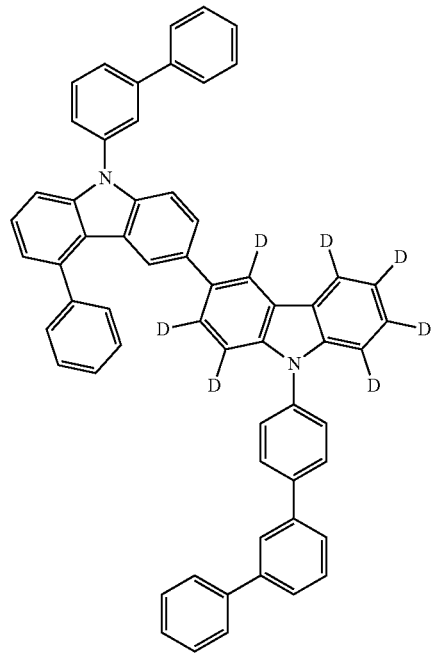
283
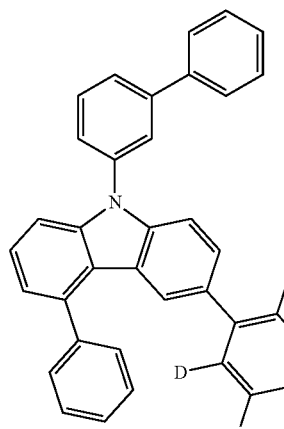
284

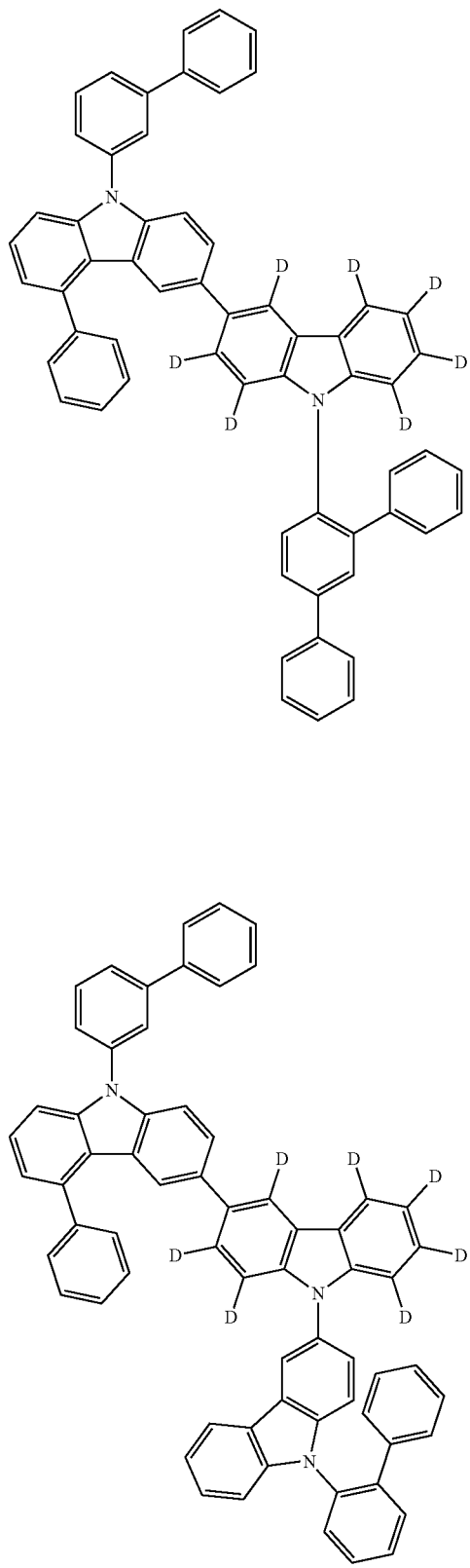
285
286
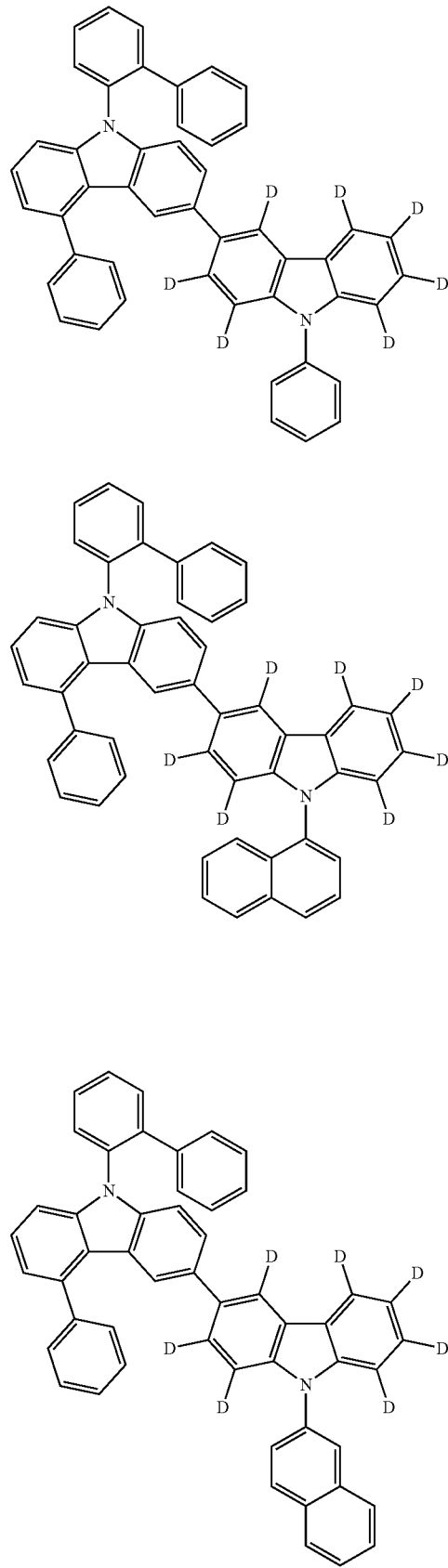
287
288
289

159
-continued
290
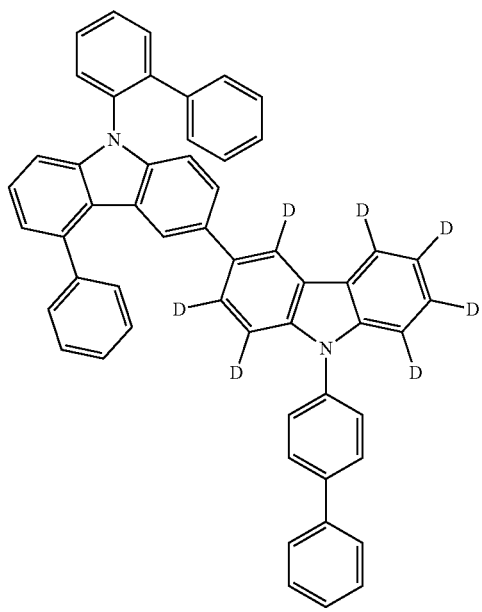
291
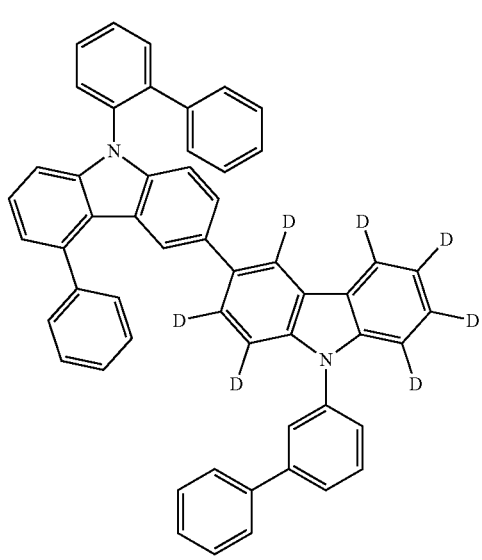
160
-continued
292
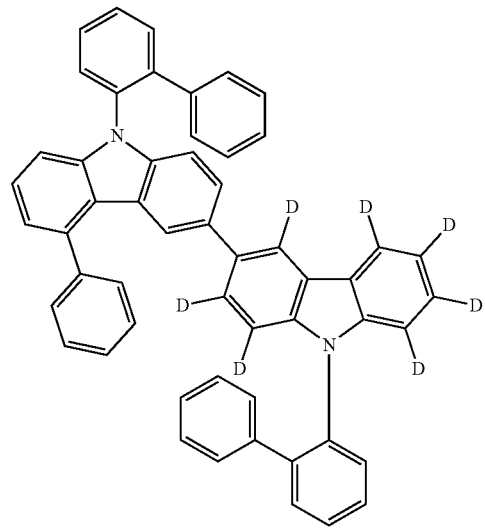
293
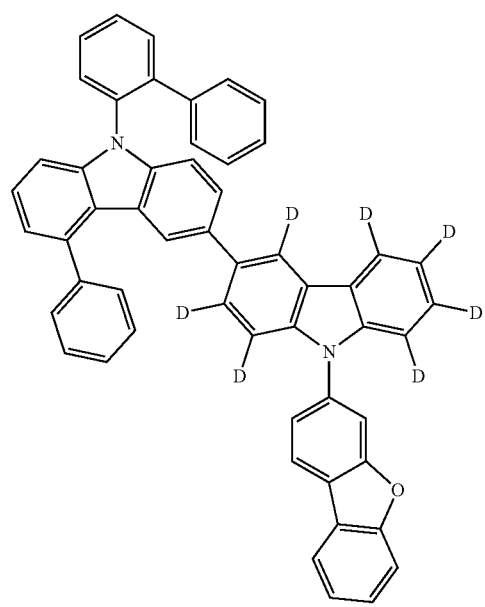

161
-continued
294
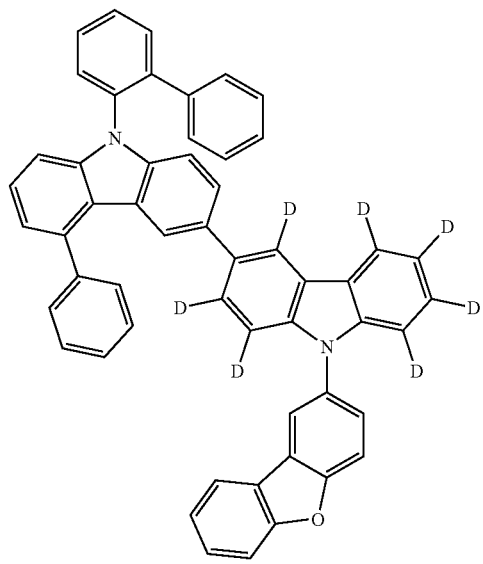
295
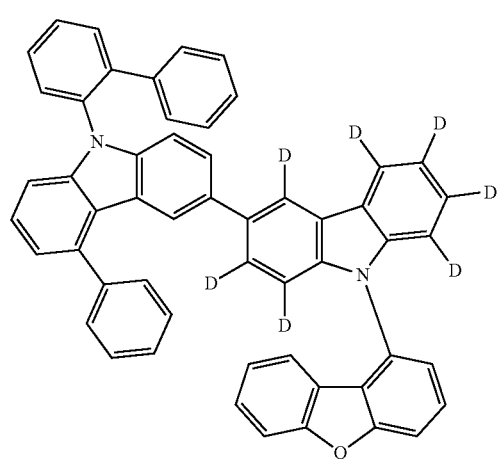
296
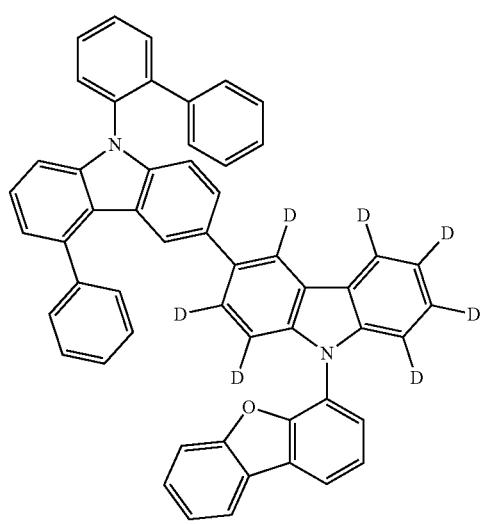
162
-continued
297
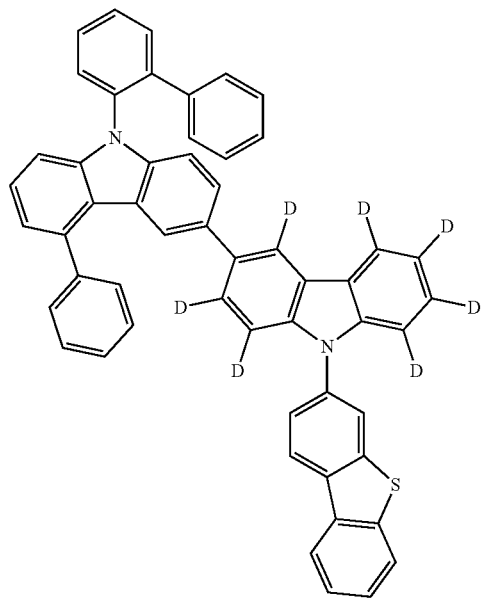
298
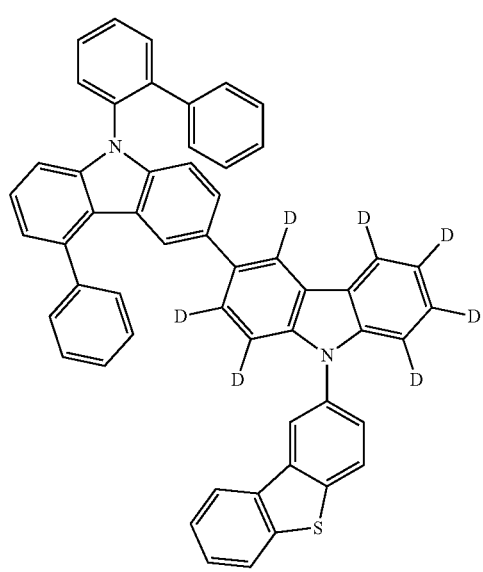

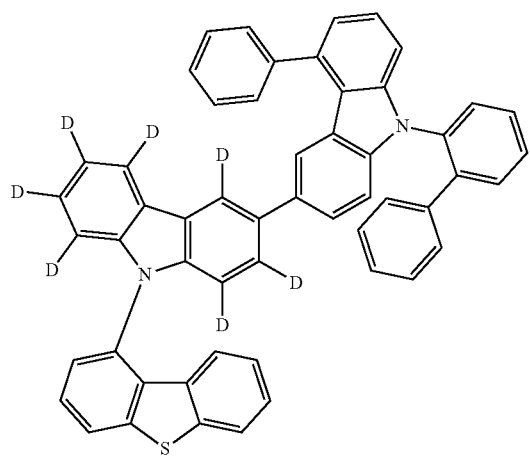
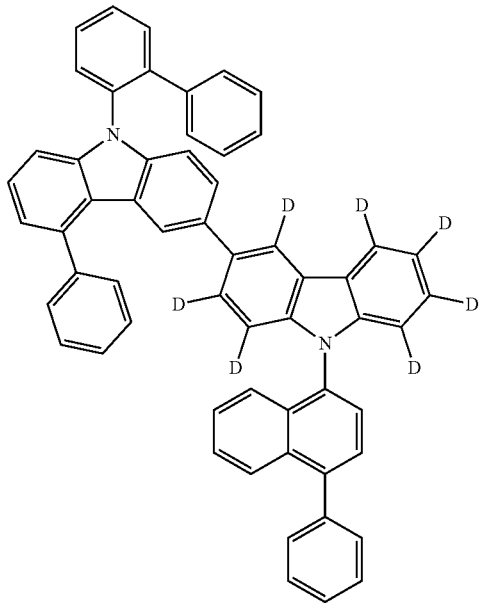
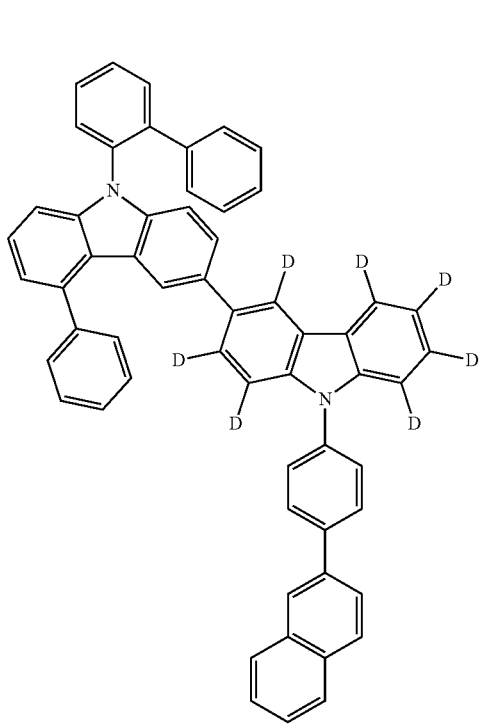

304
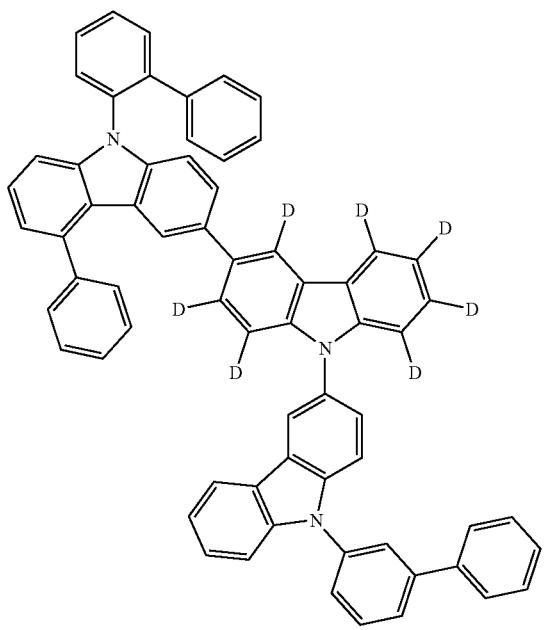
306
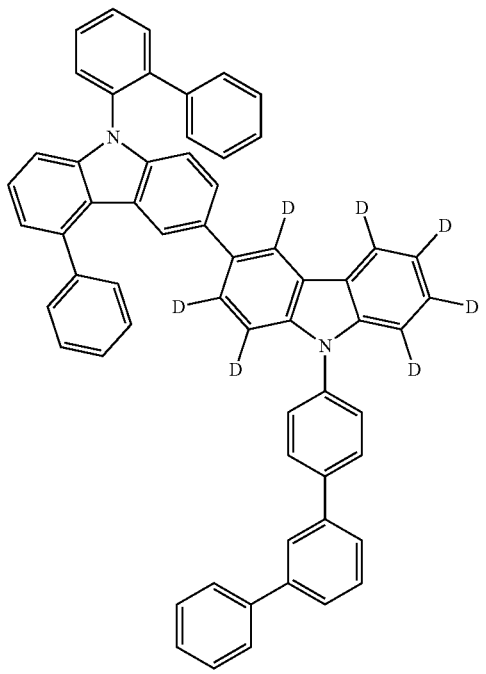
305
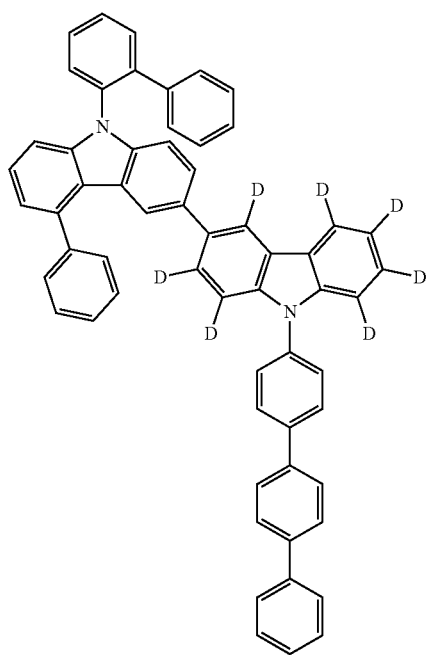
307
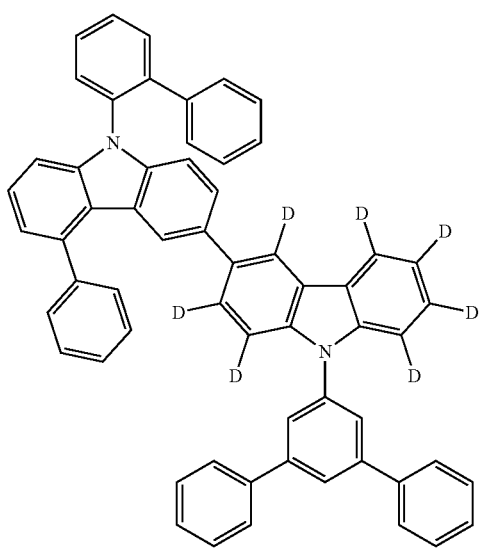

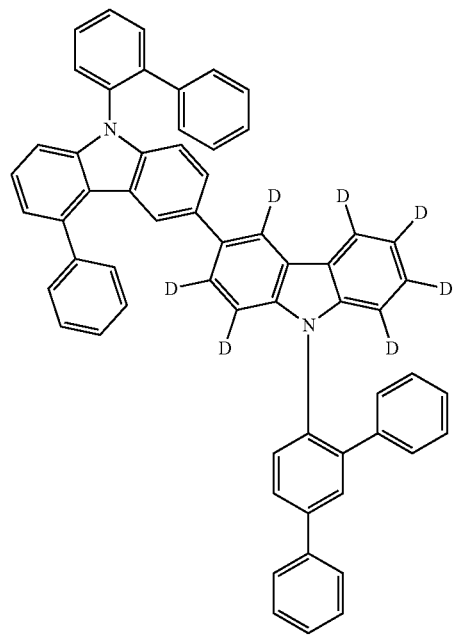
308
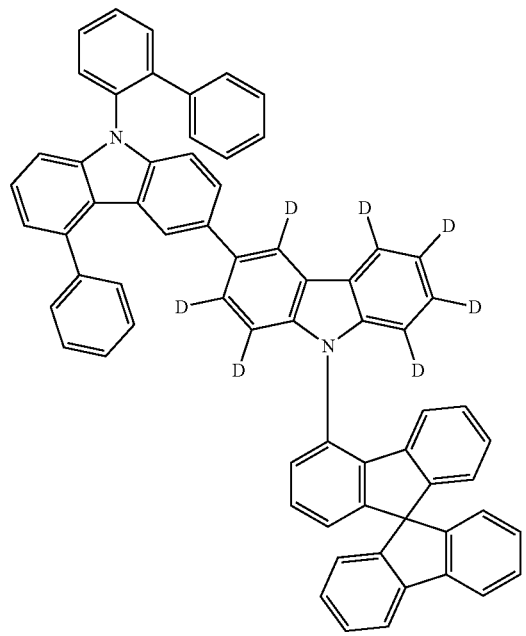
310
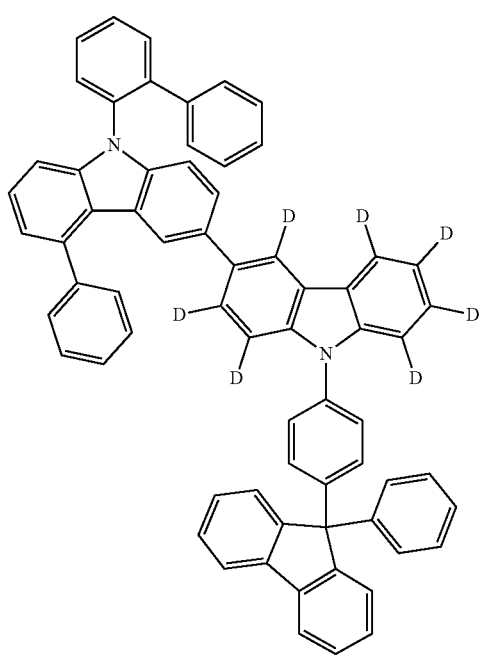
309
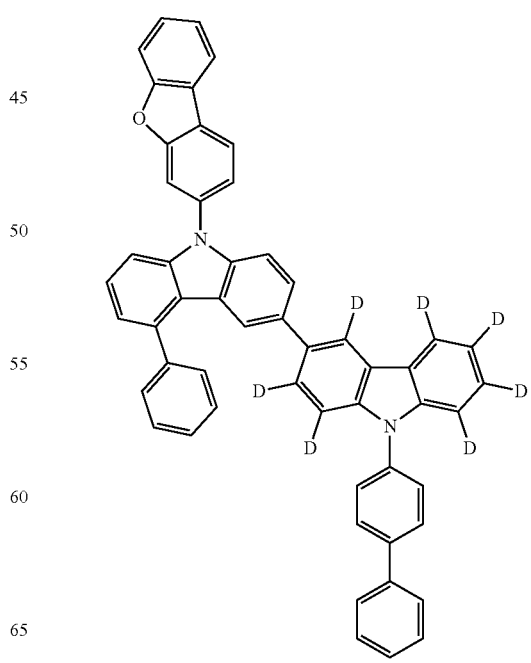
311

169
-continued
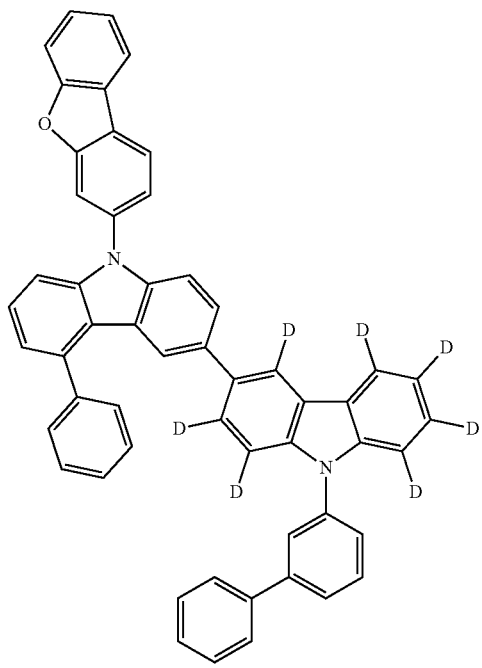
312
170
-continued
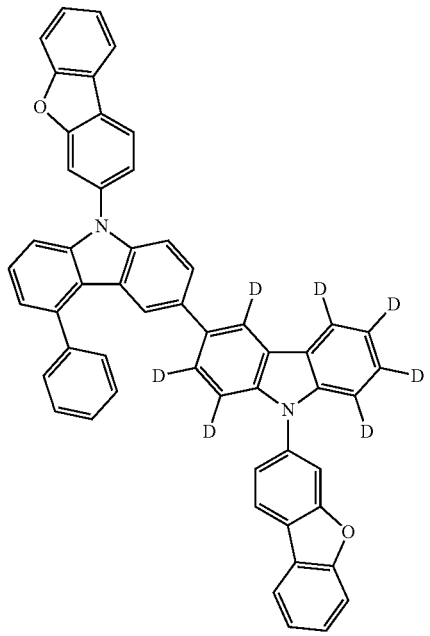
314
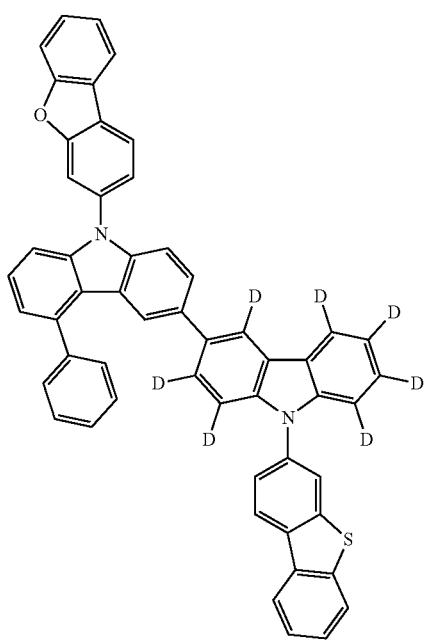
313
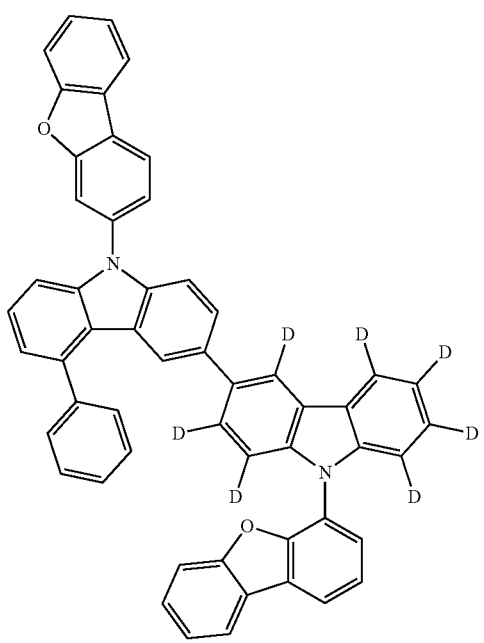
315

-continued
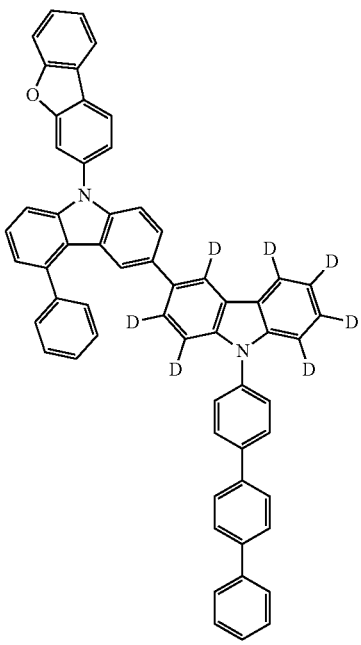
316
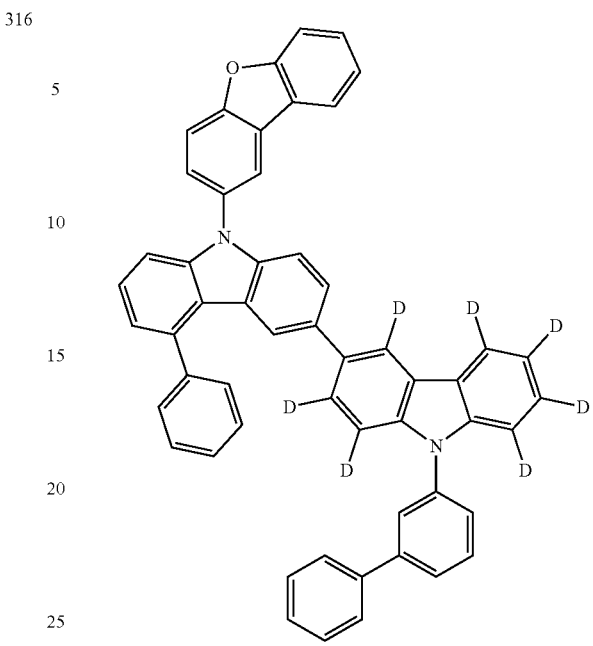
318
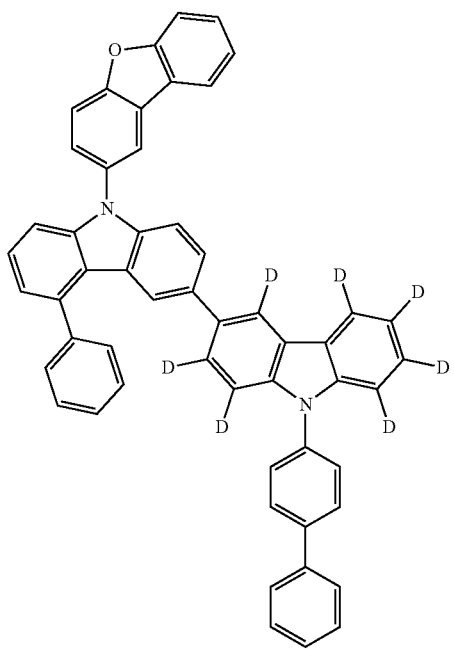
317
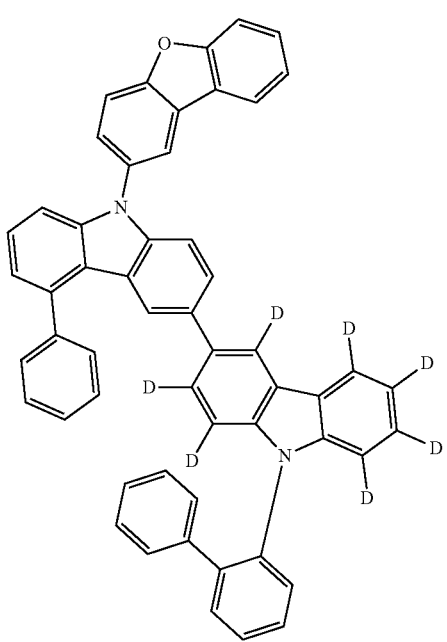
319

173
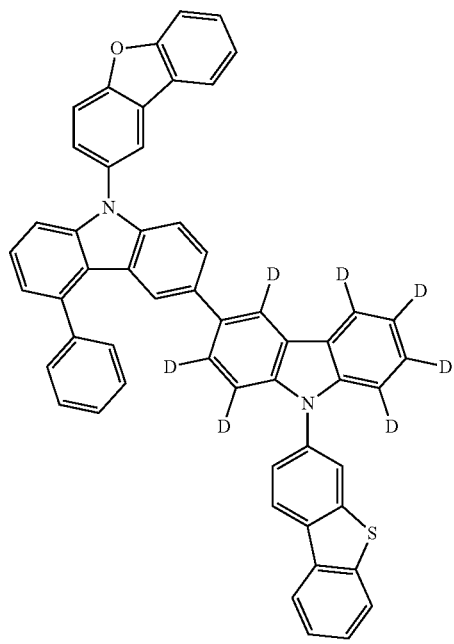
320
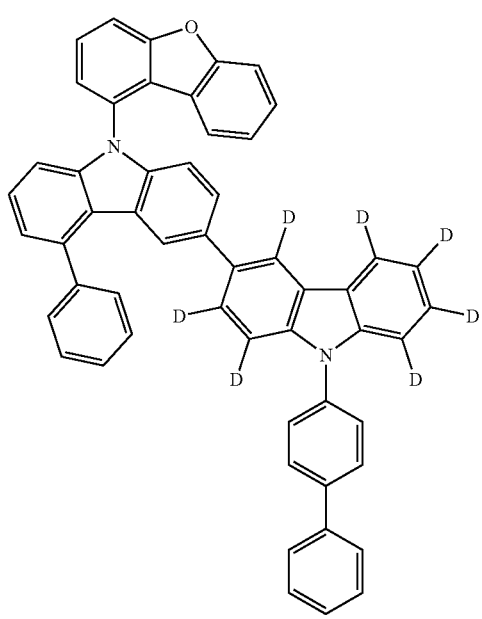
321
174
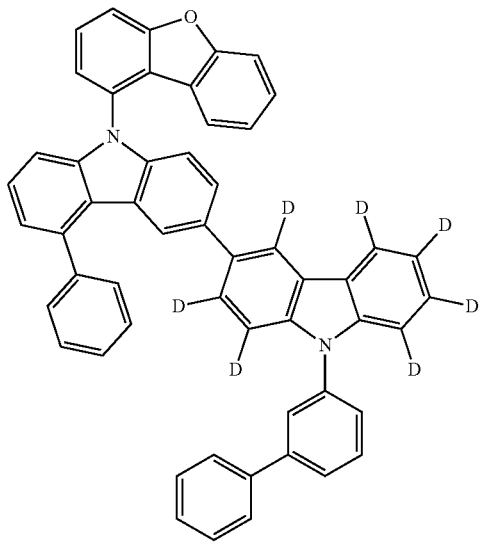
322
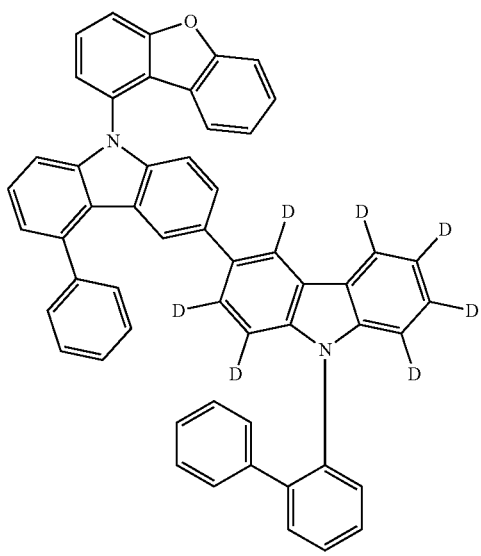
323

175
-continued
324
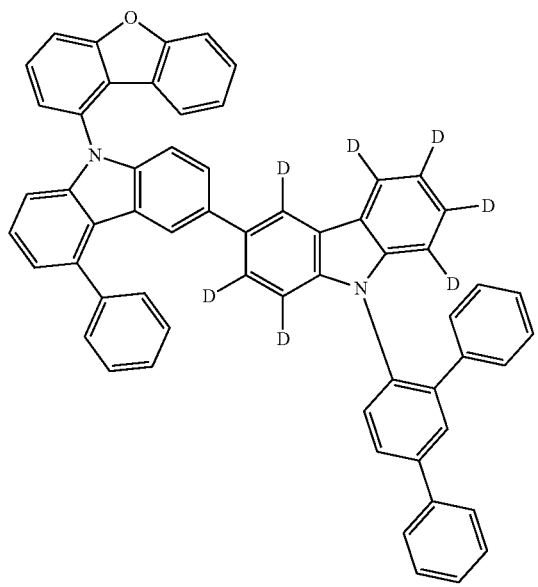
325
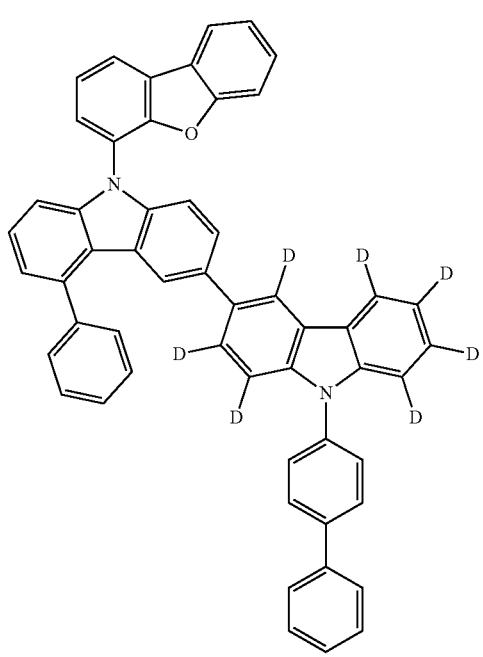
176
-continued
326
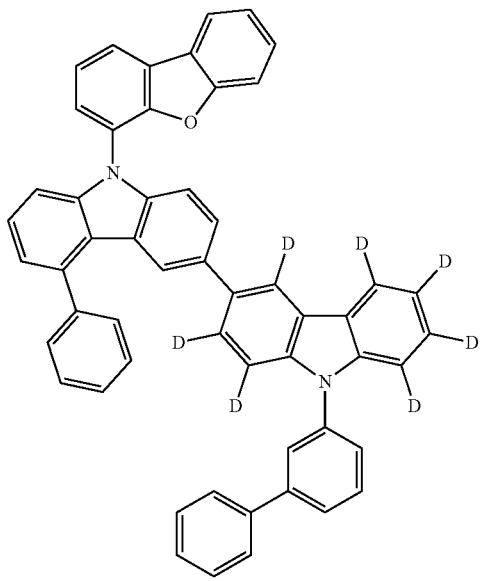
327
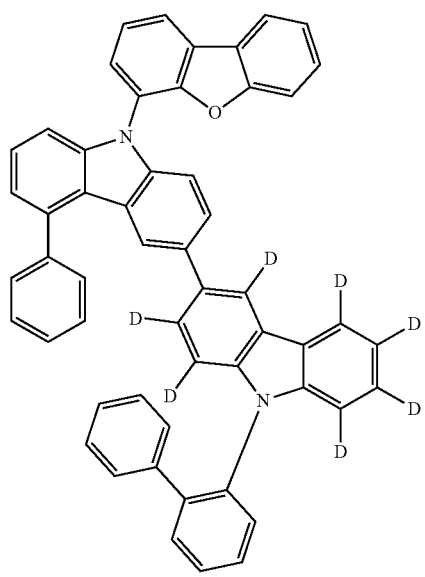

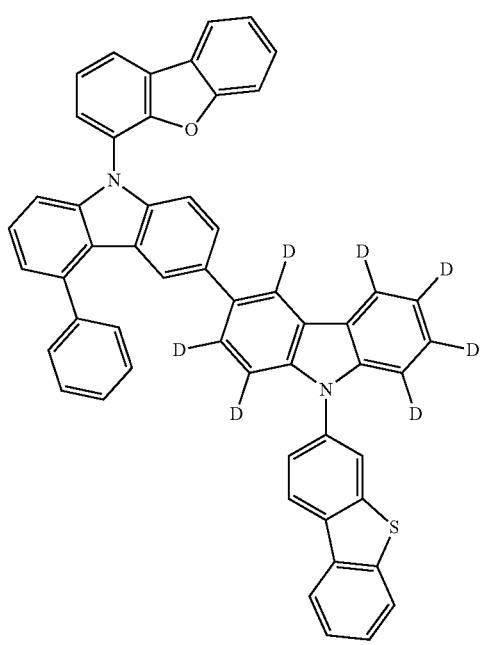
328
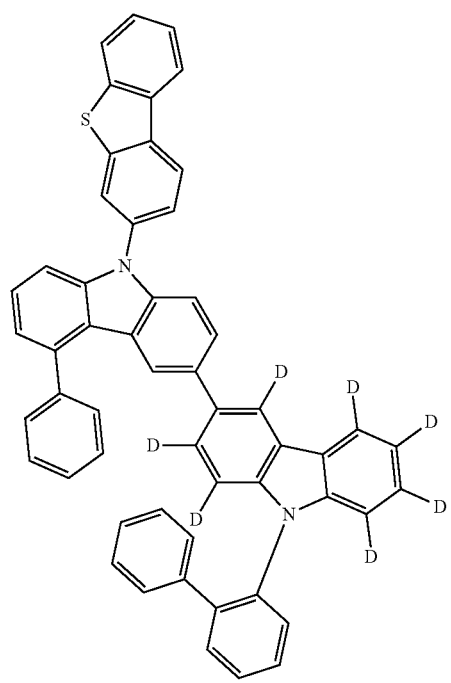
330
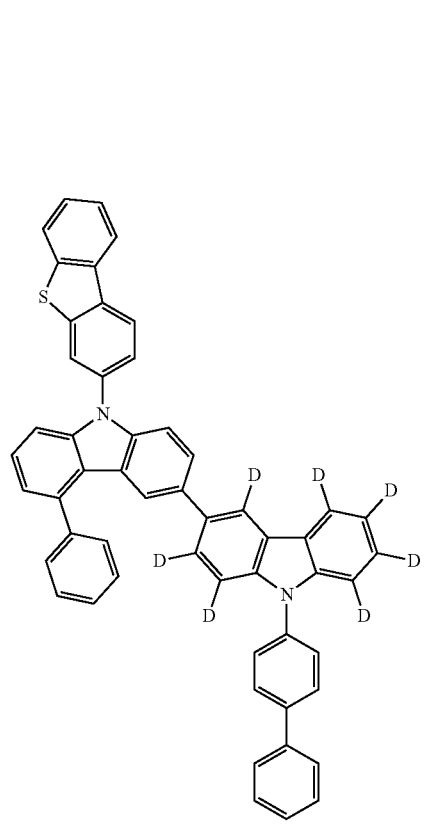
329
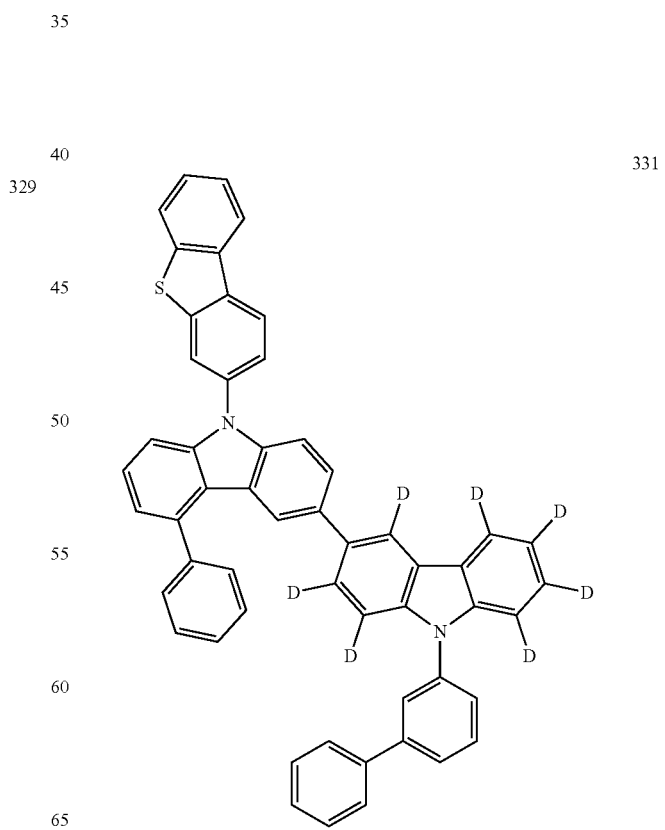
331

179
332
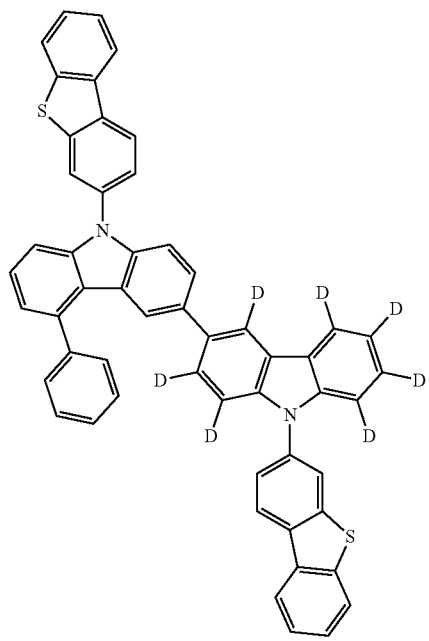
333
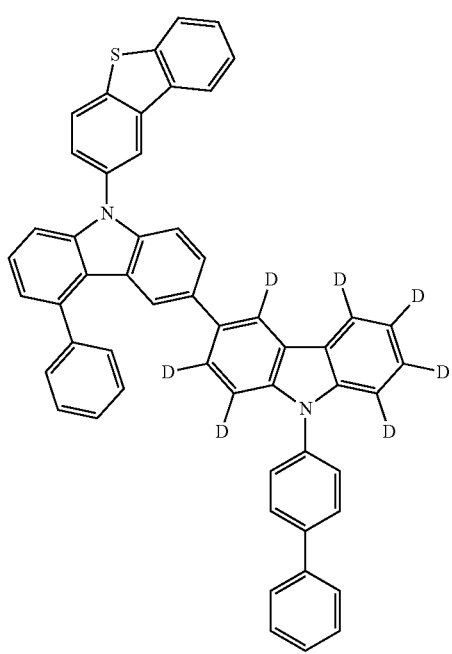
180
334
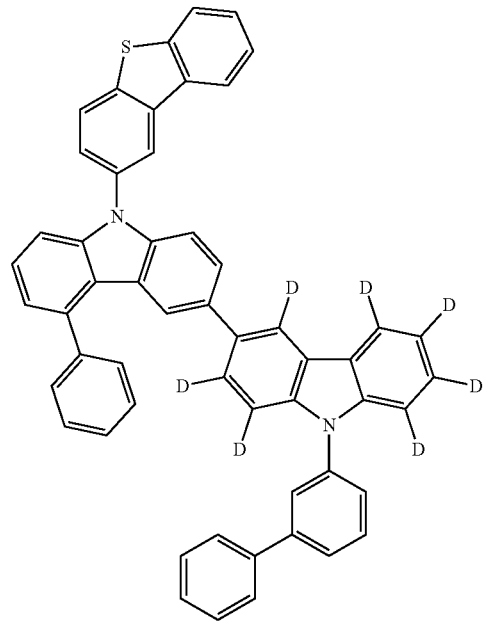
335
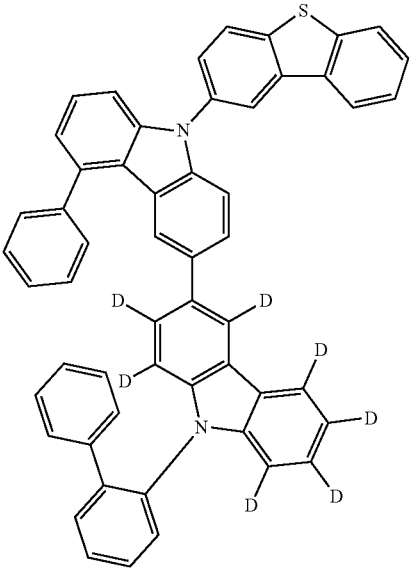

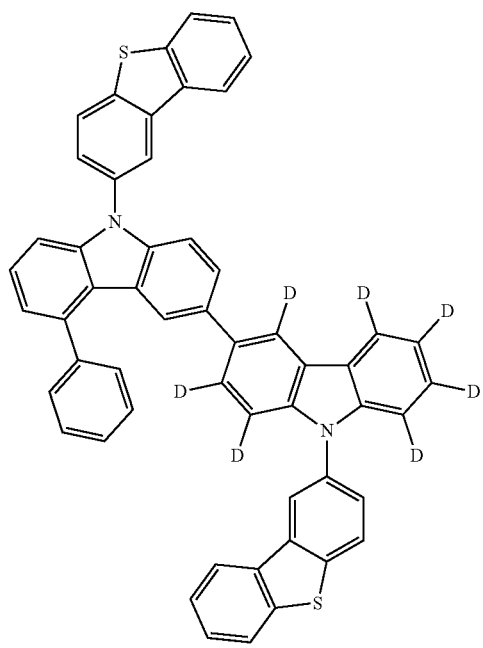
336
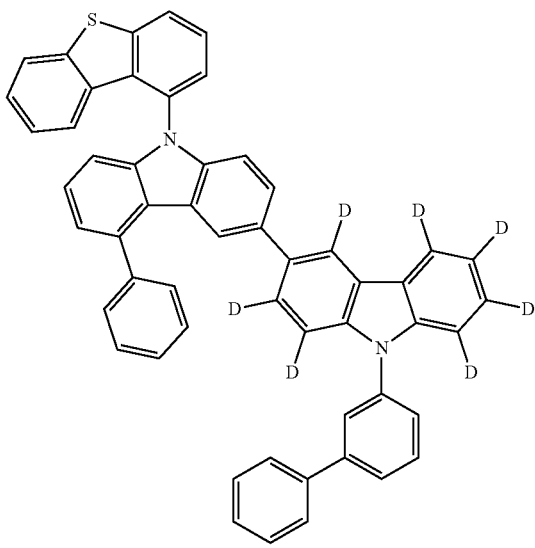
338
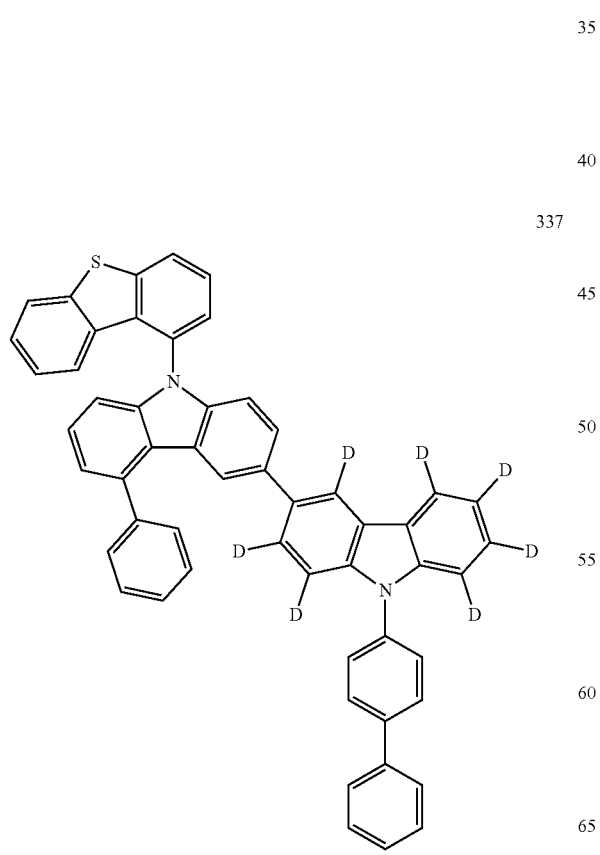
337
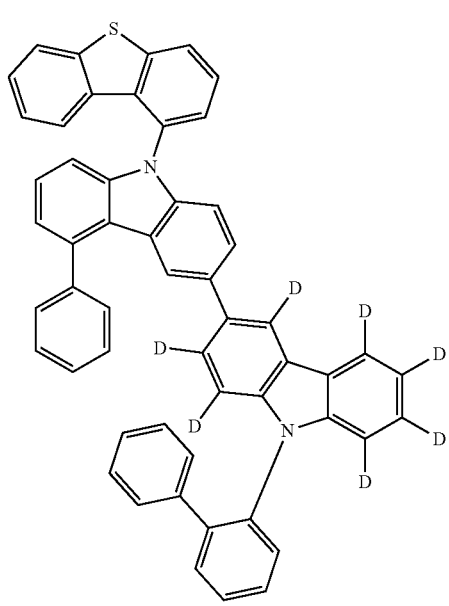
339

340
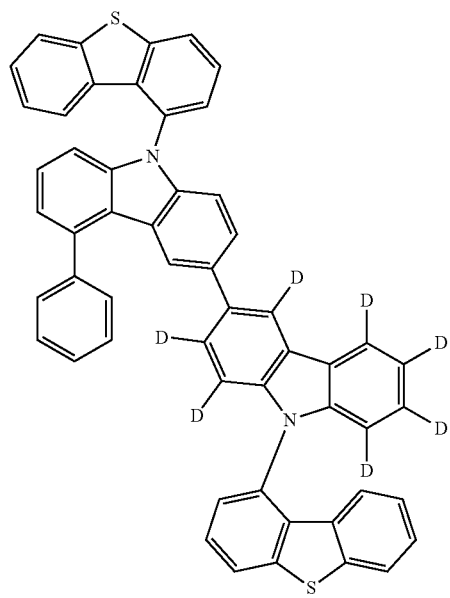
341
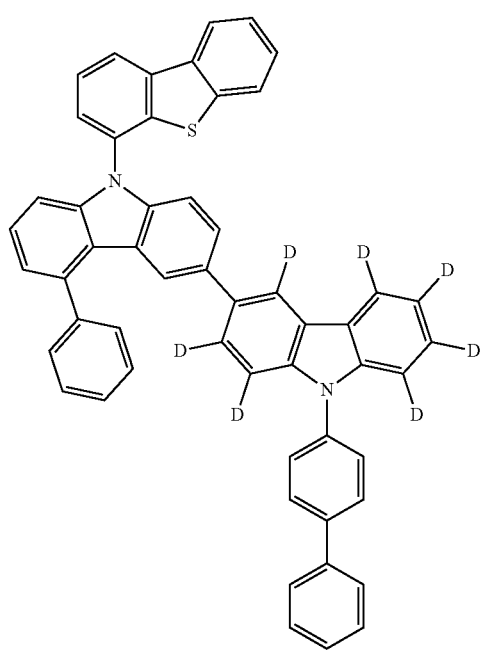
342
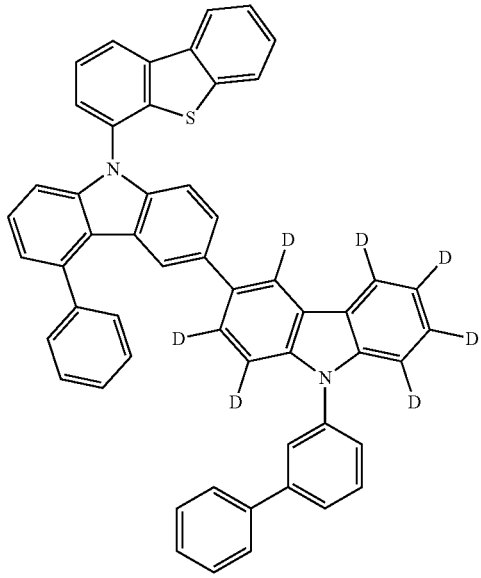
343
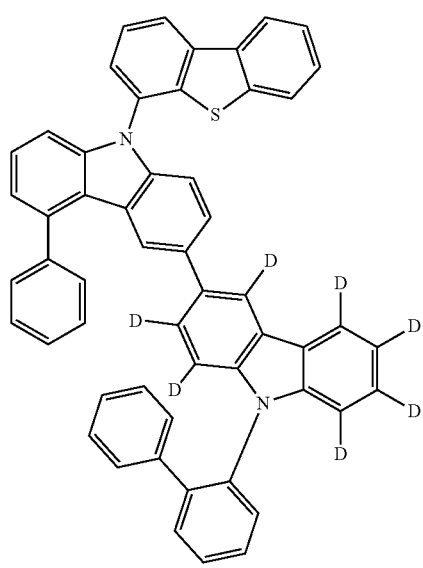
344
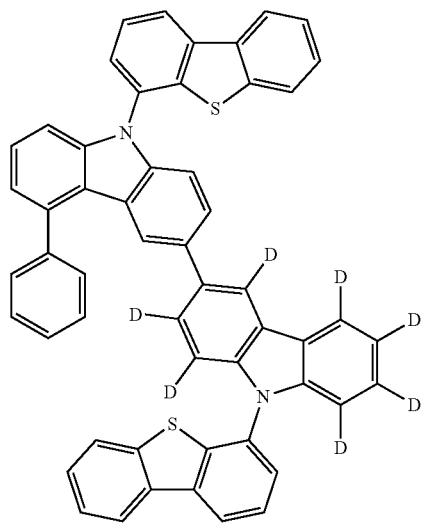

345
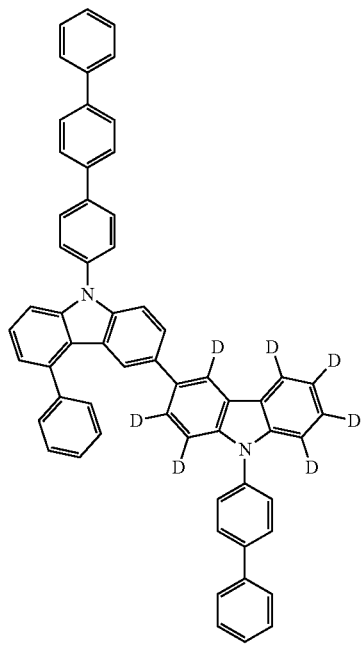
346
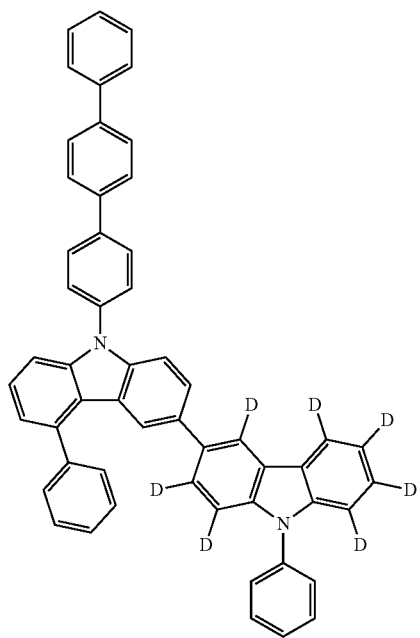
347
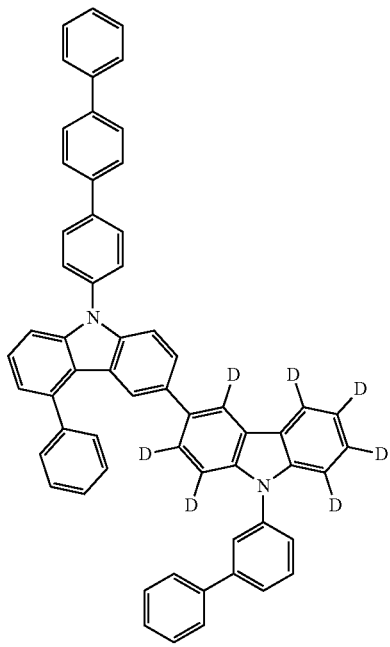
348
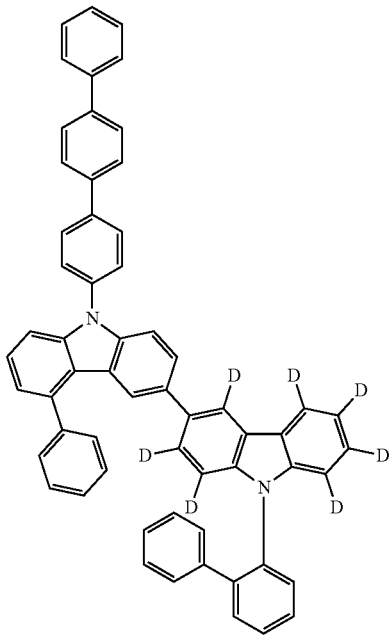

349
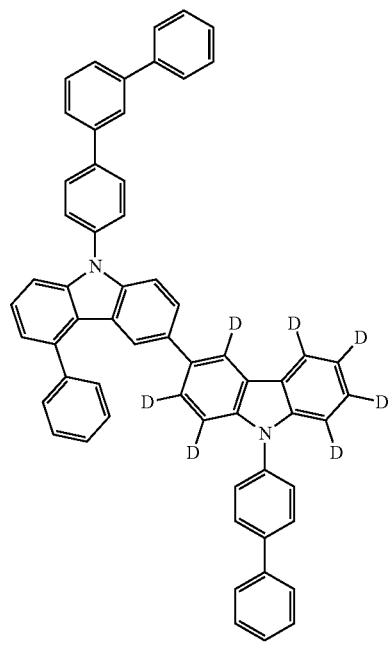
350
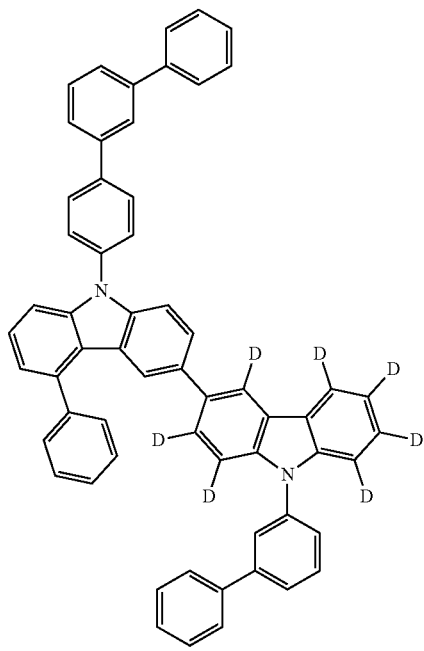
351
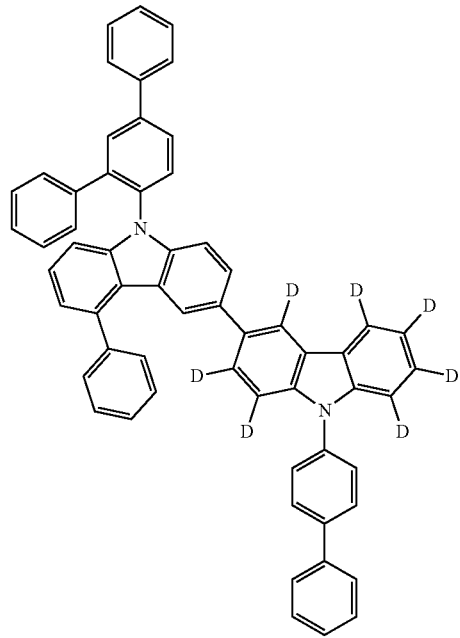
352
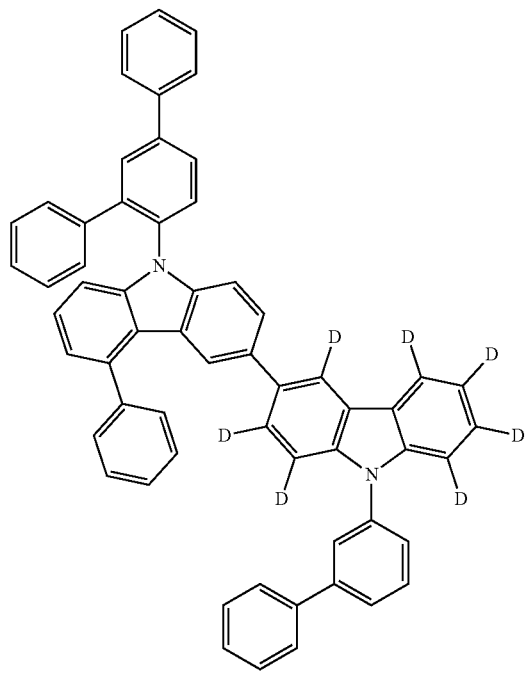

-continued
353
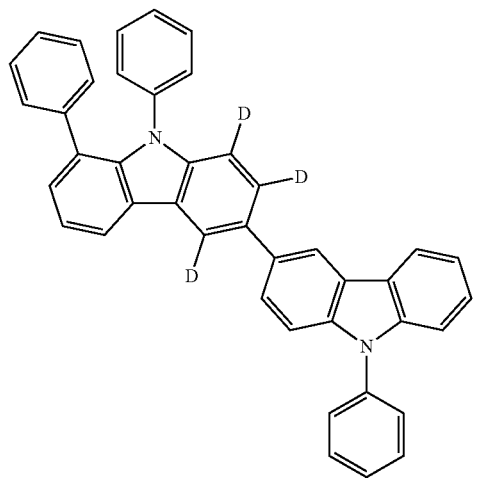
354
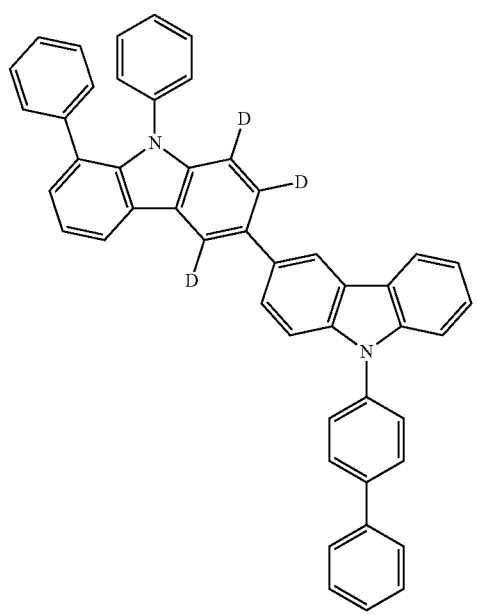
355
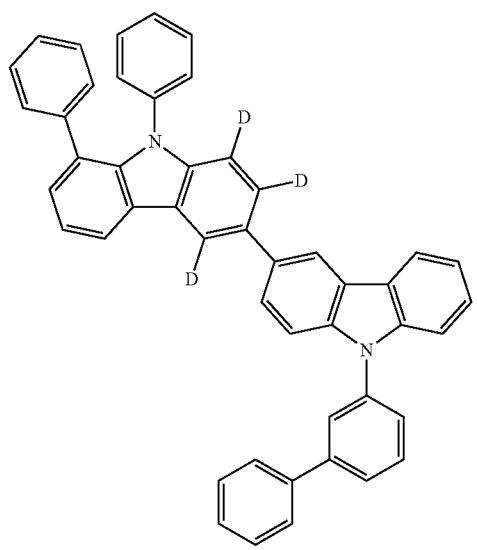
-continued
356
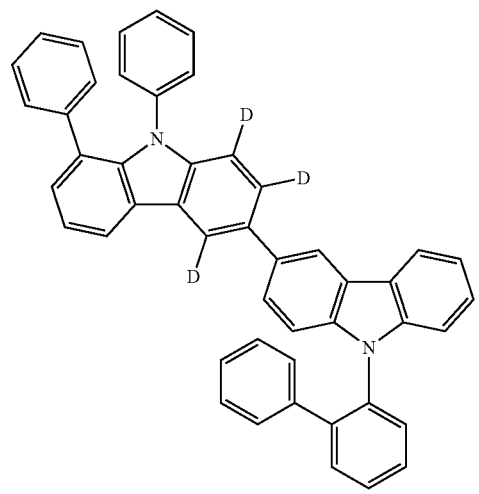
357
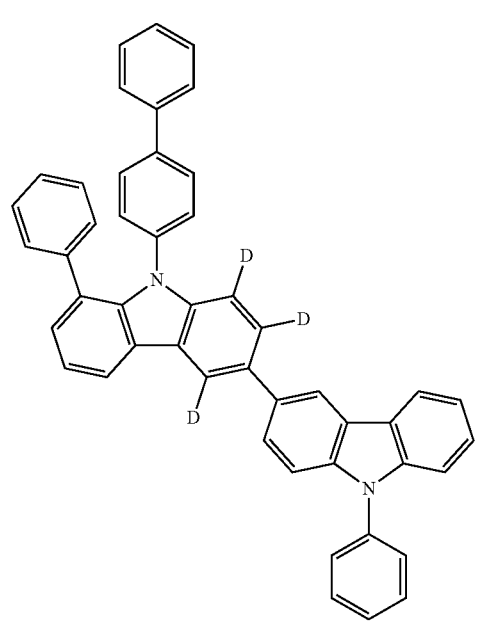
358
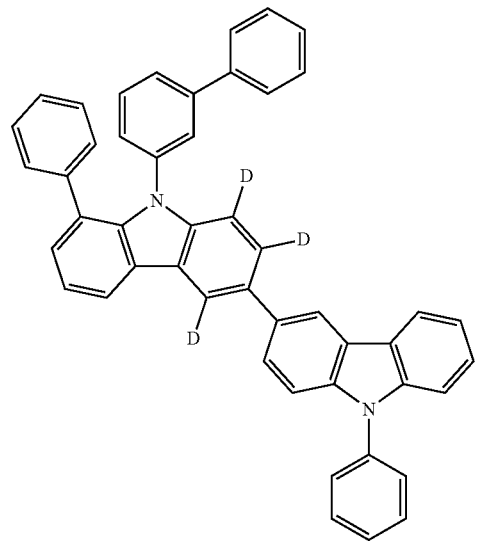

359
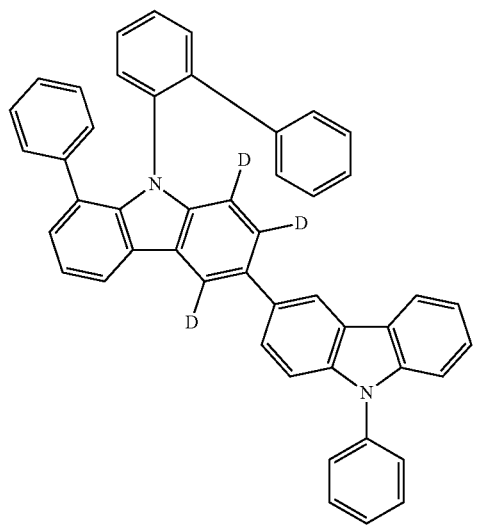
360
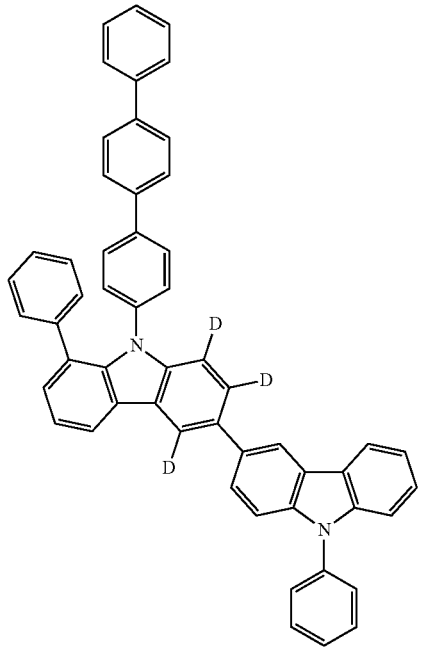
361
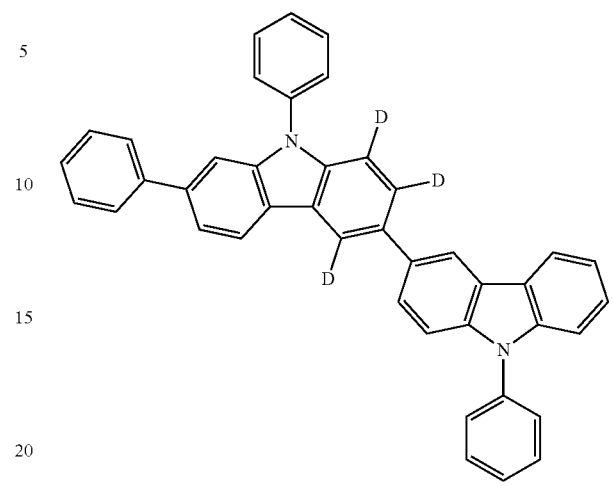
362
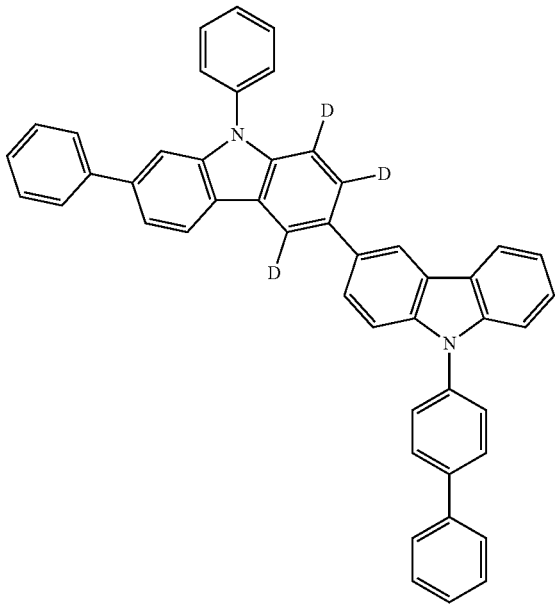

363
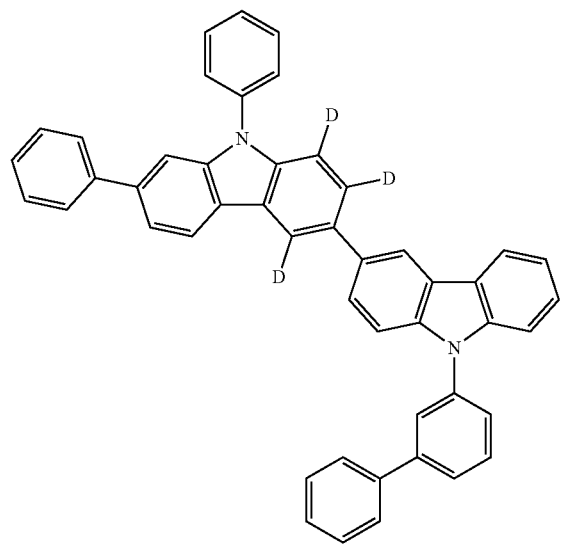
364
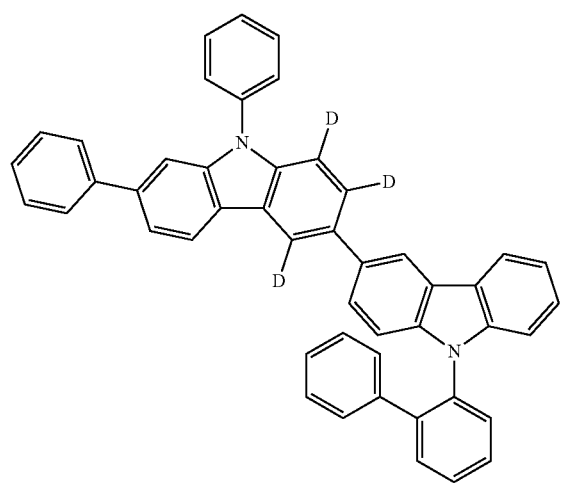
365
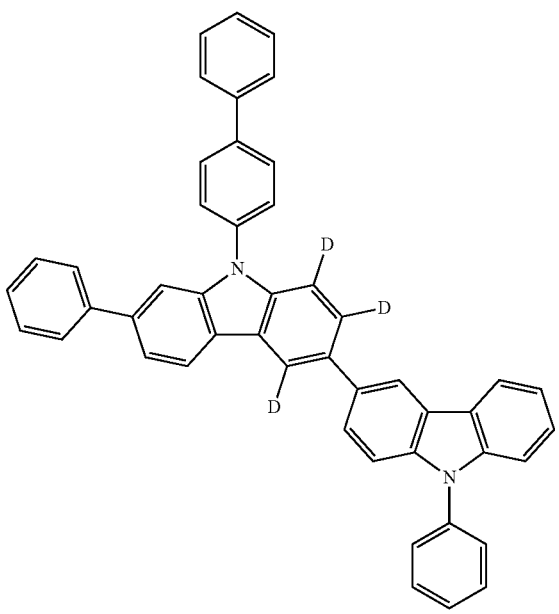
366
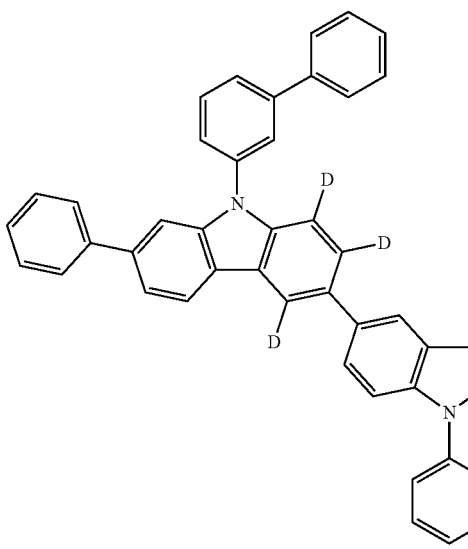

367
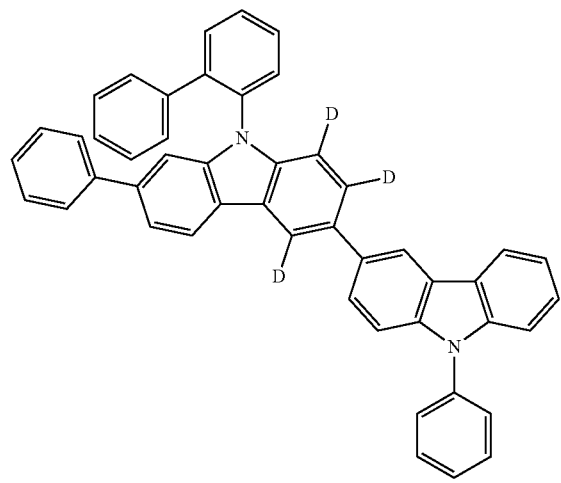
369
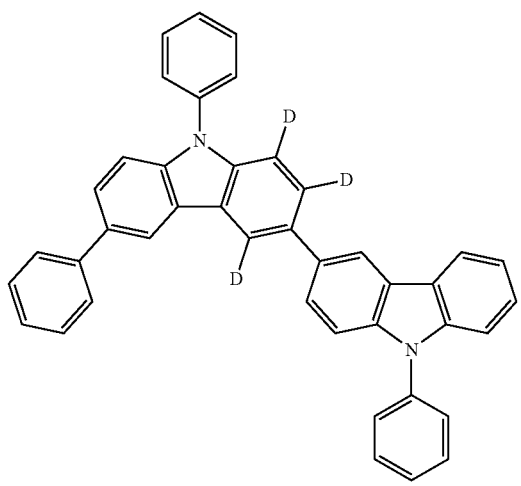
368
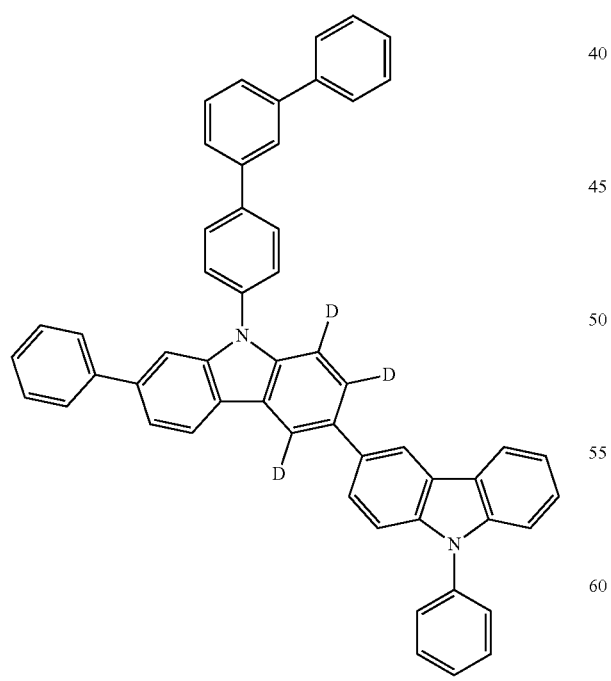
370
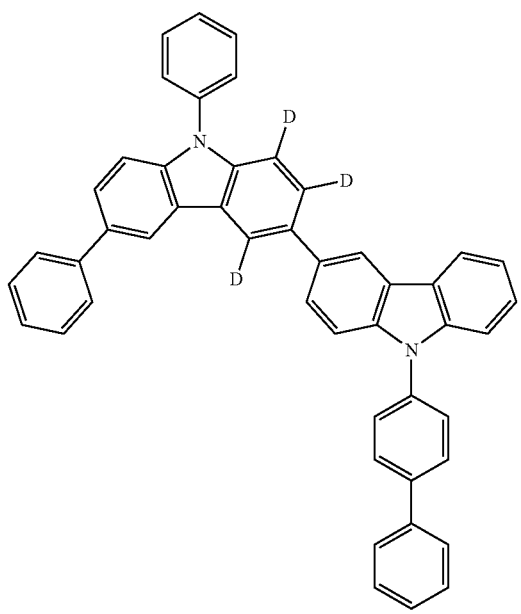

197
-continued
371
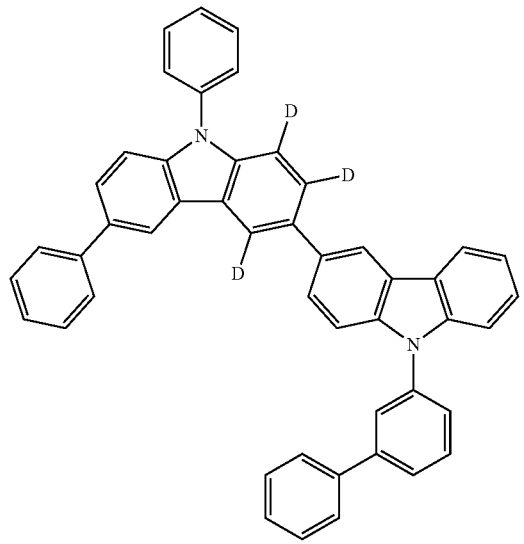
372
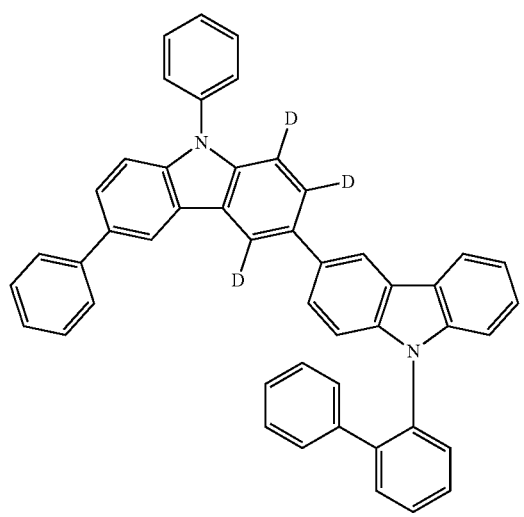
198
-continued
373
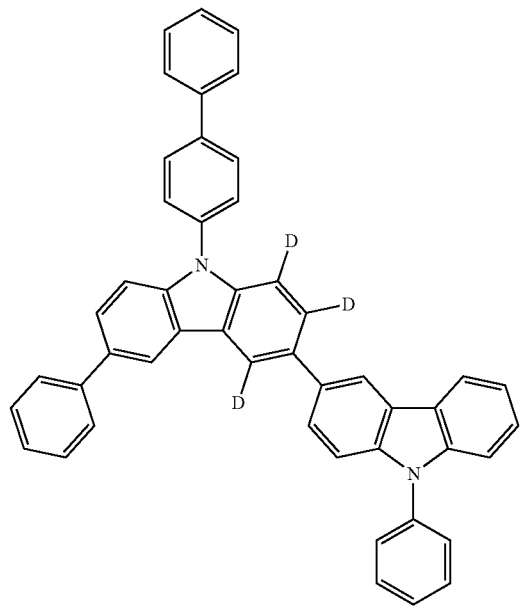
374
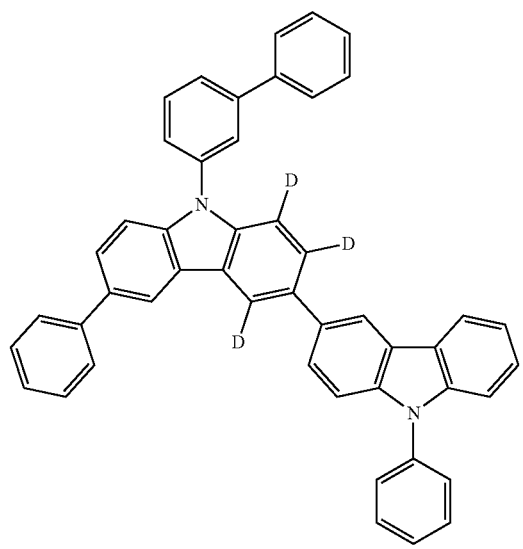

199
-continued
375
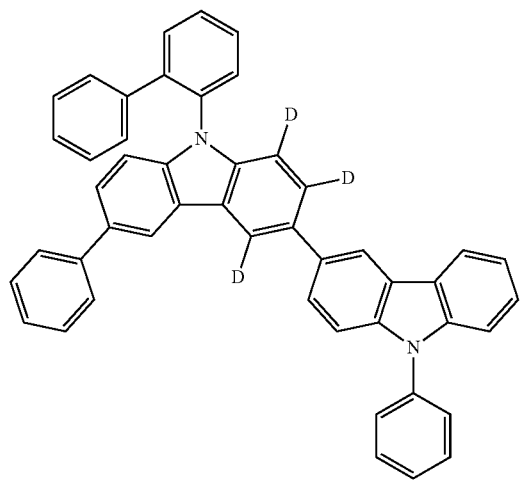
376
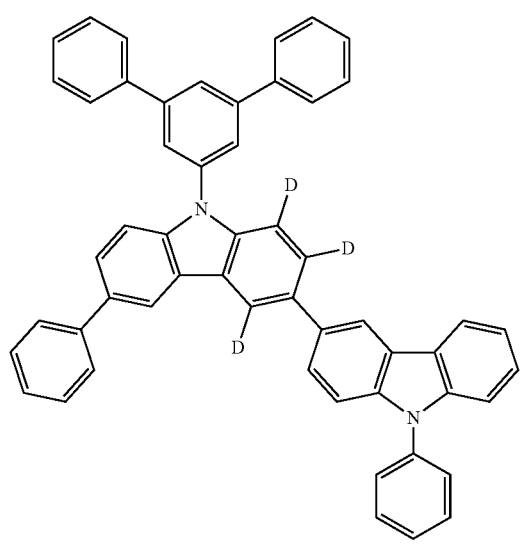
377
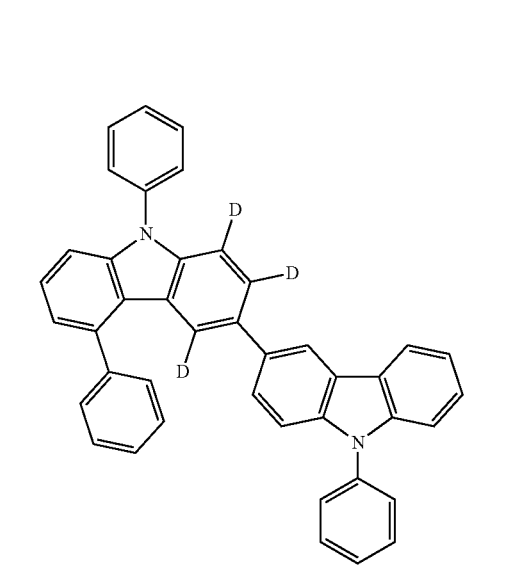
200
-continued
378
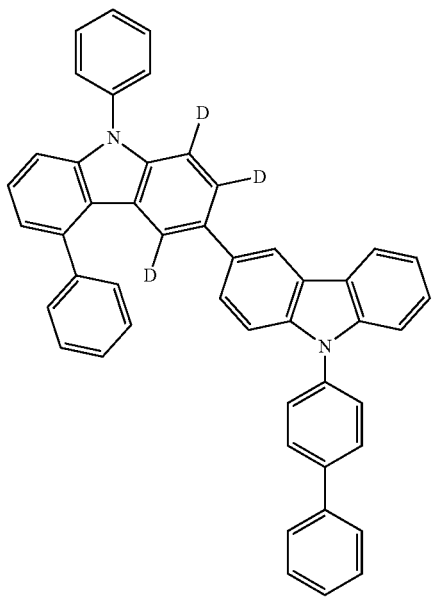
379
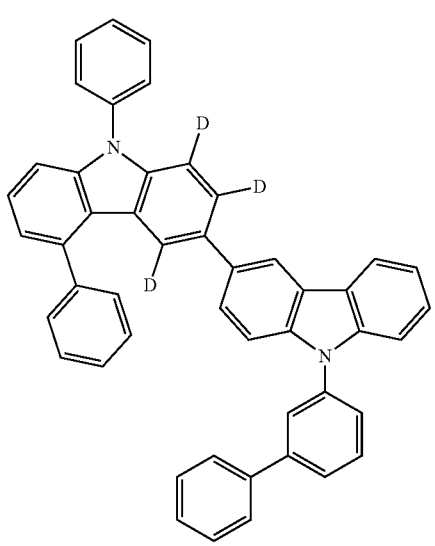
380
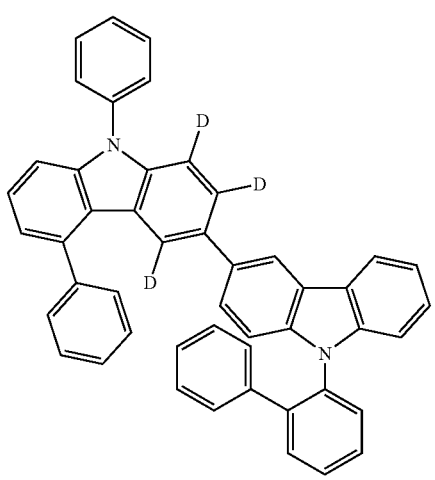

381
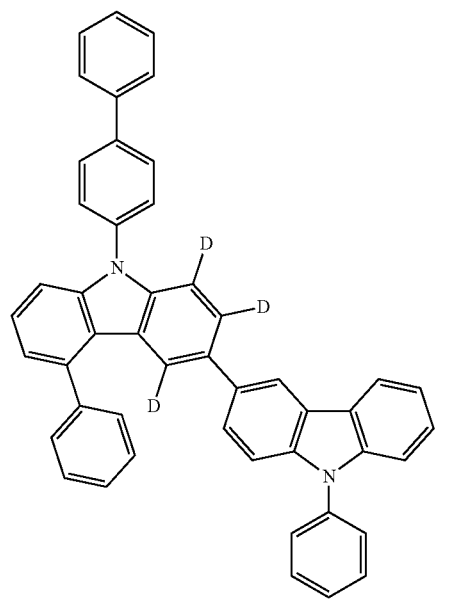
382
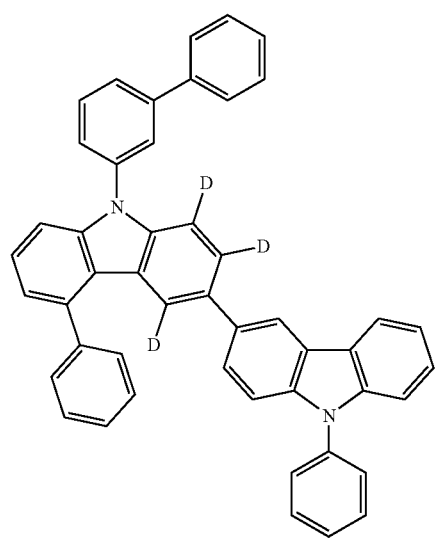
383
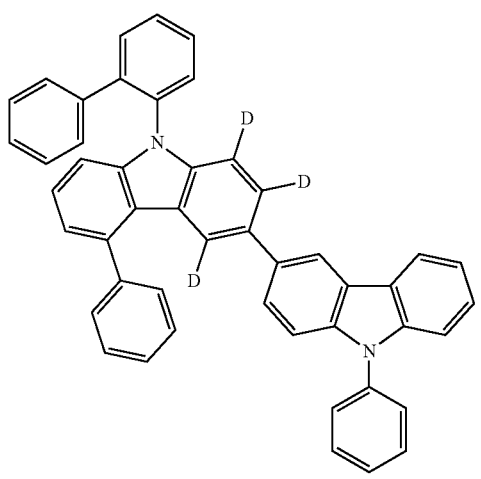
384
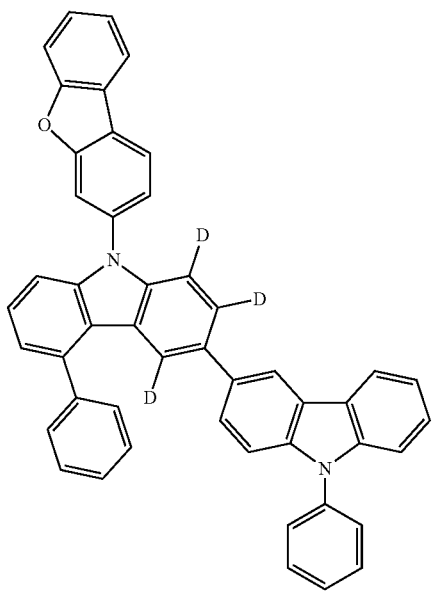
385
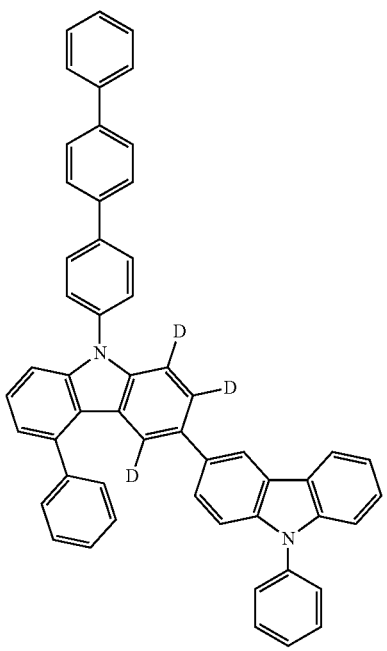

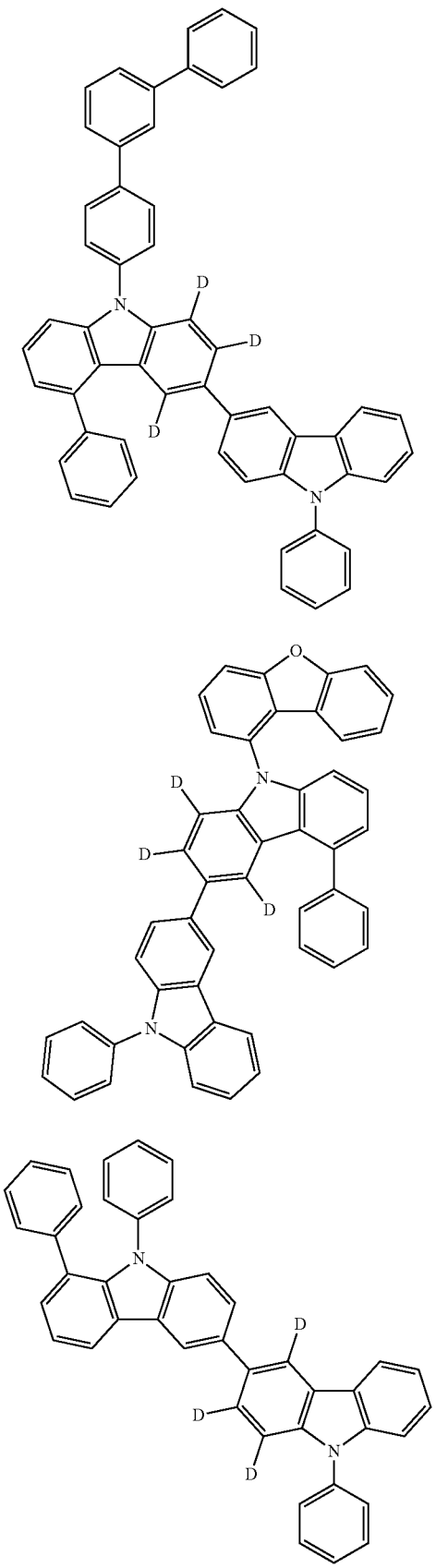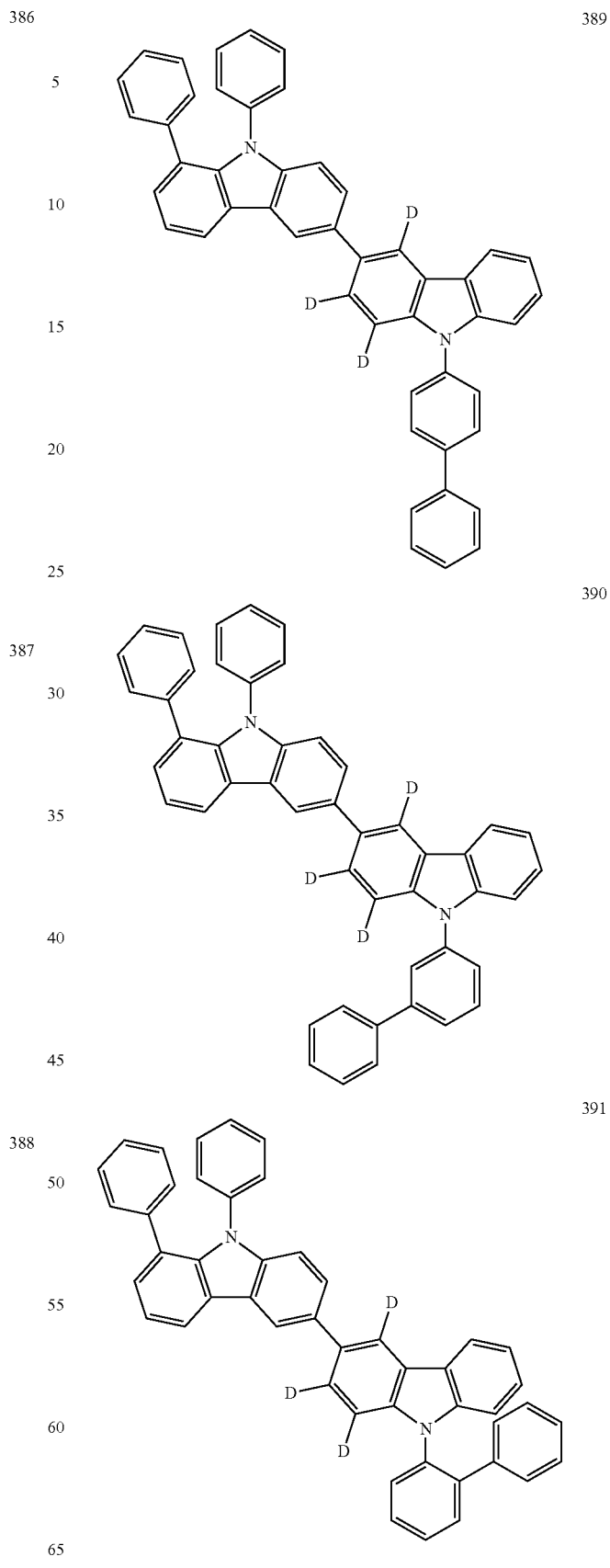

205
-continued
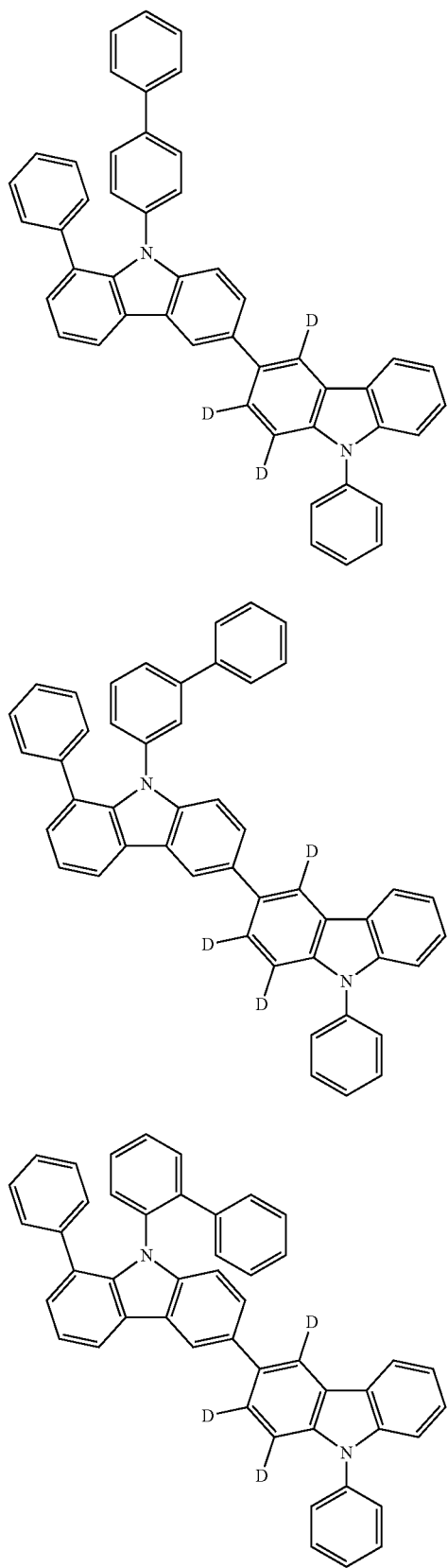
206
-continued
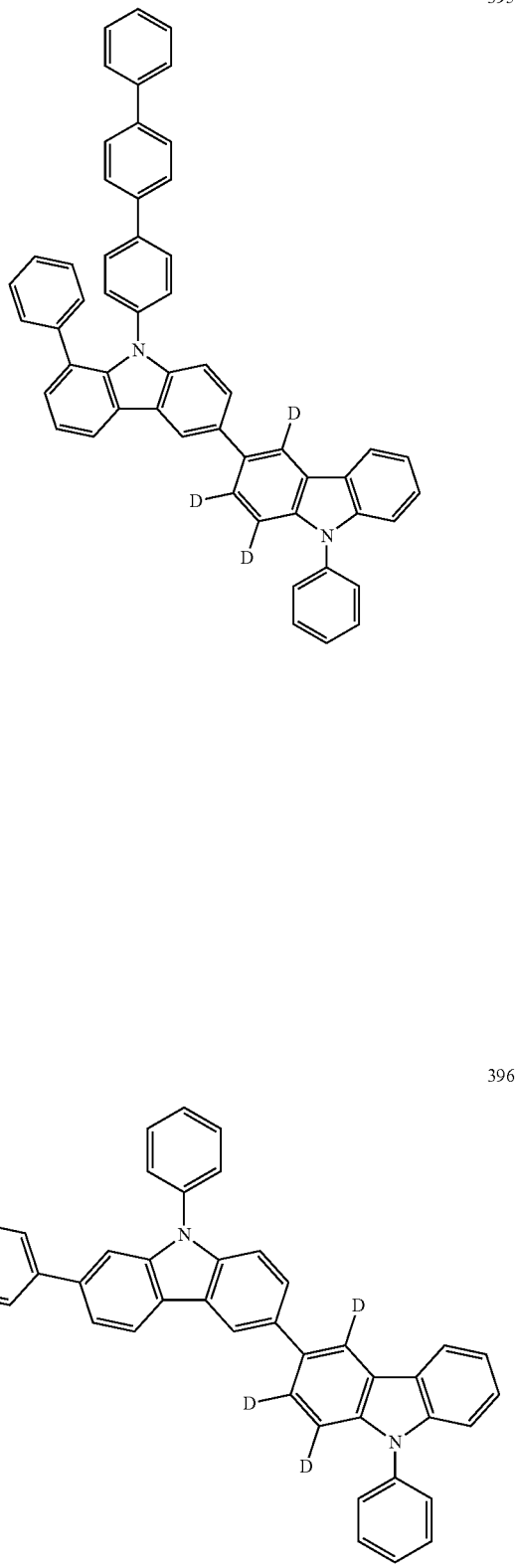

207
-continued
397
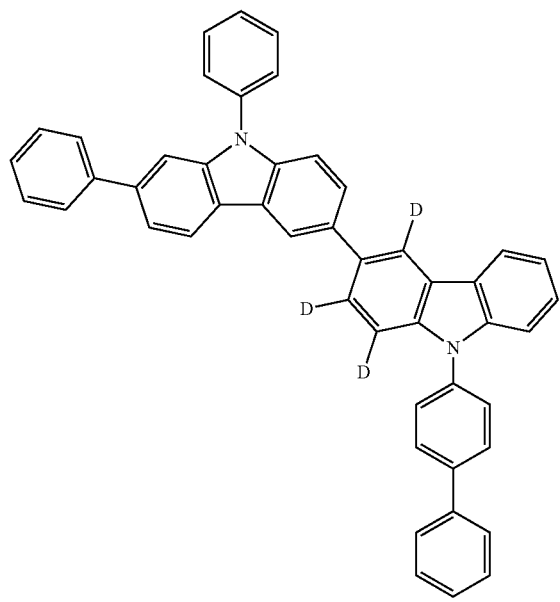
398
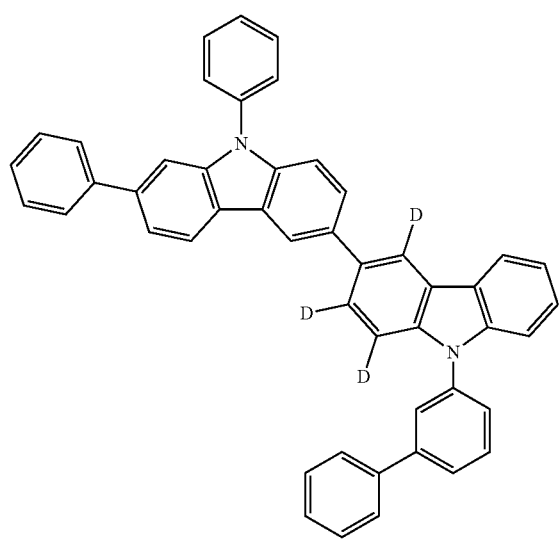
399
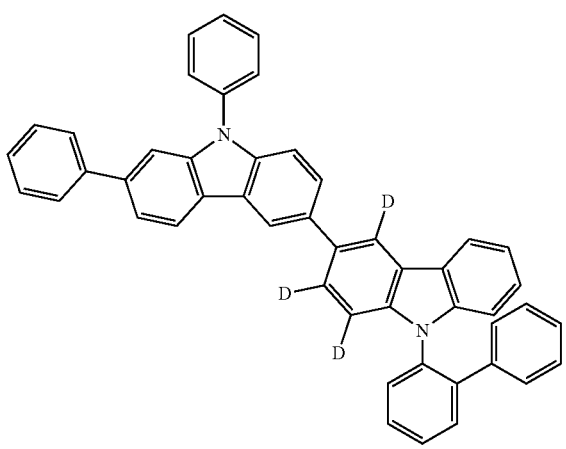
208
-continued
400
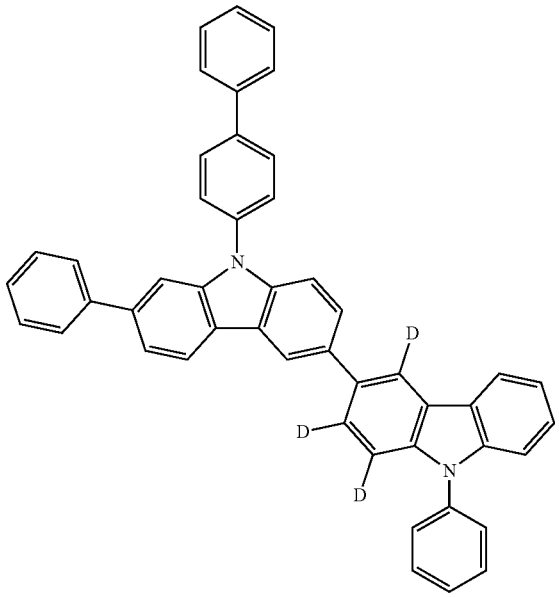
401
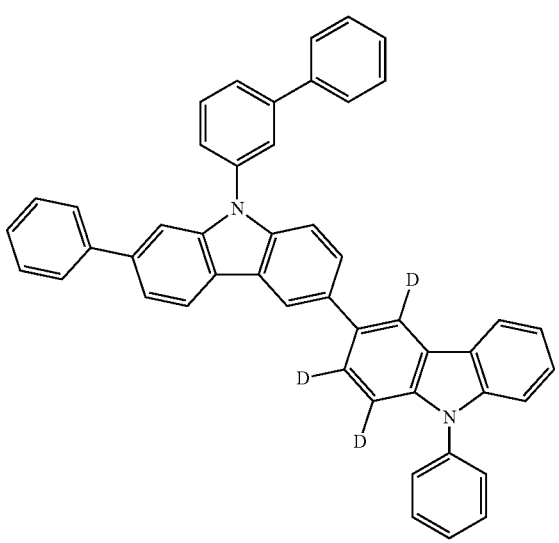
402
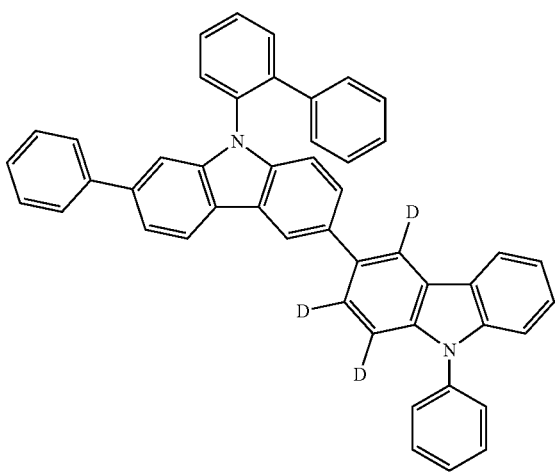

403
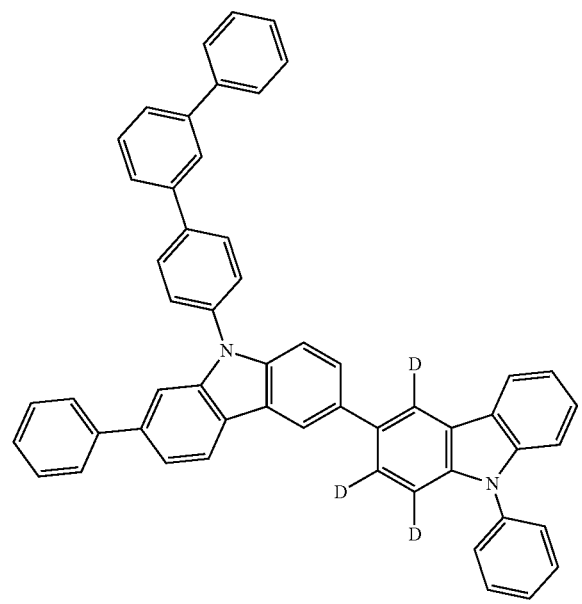
404
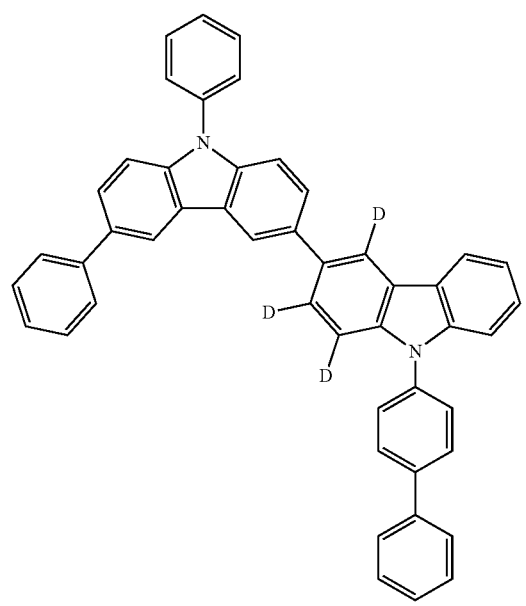
405
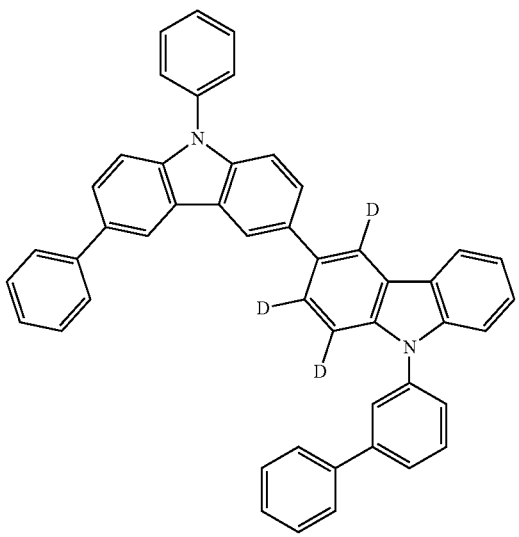
406
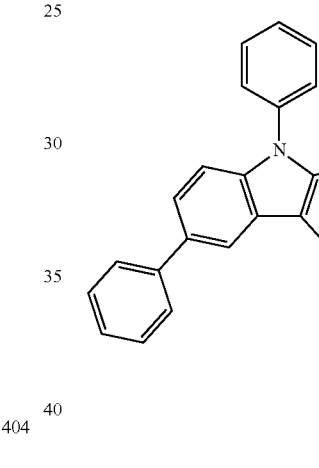
407
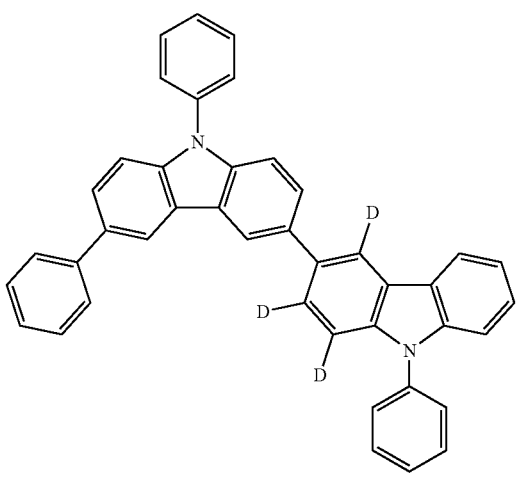

408
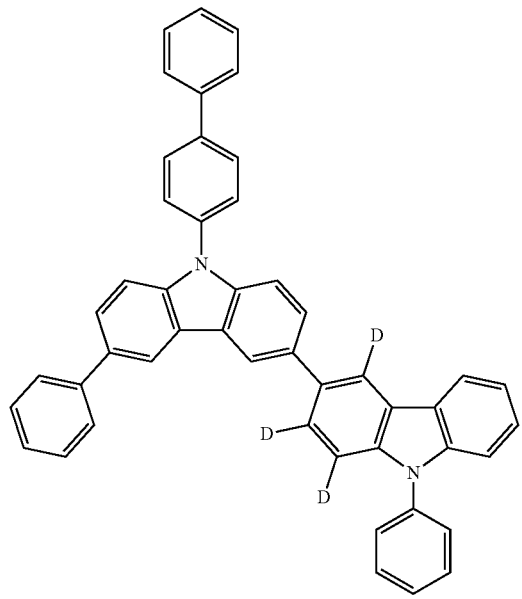
409
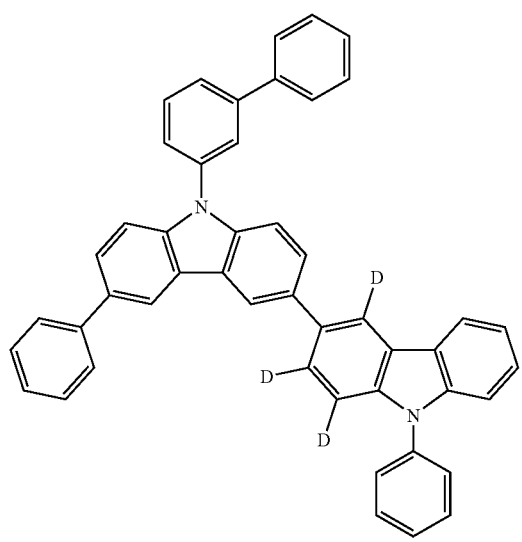
410
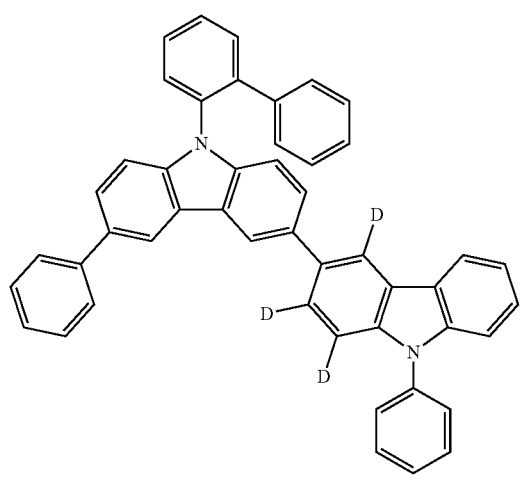
411
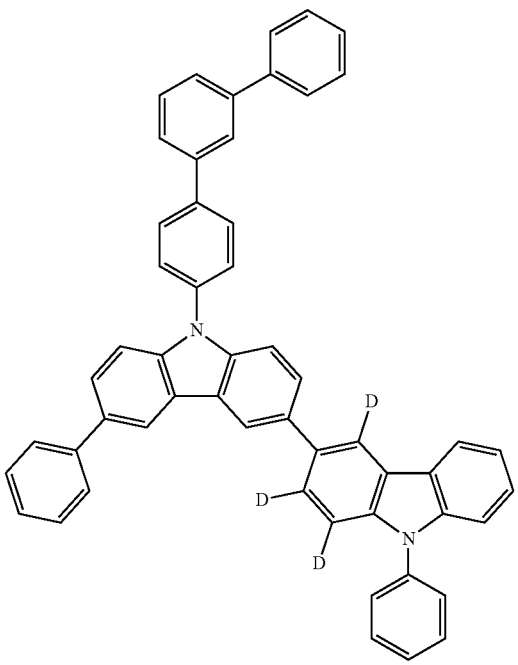
412
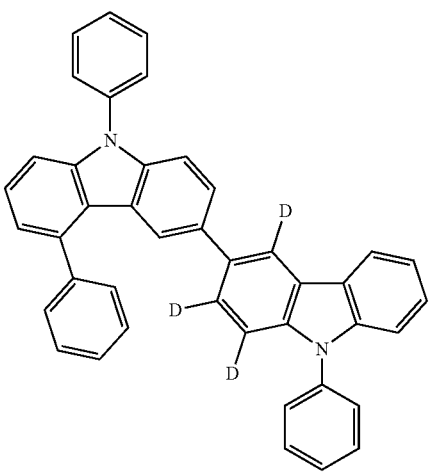

413
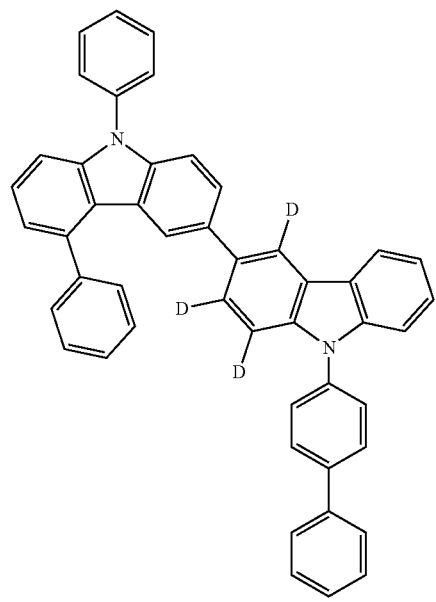
414
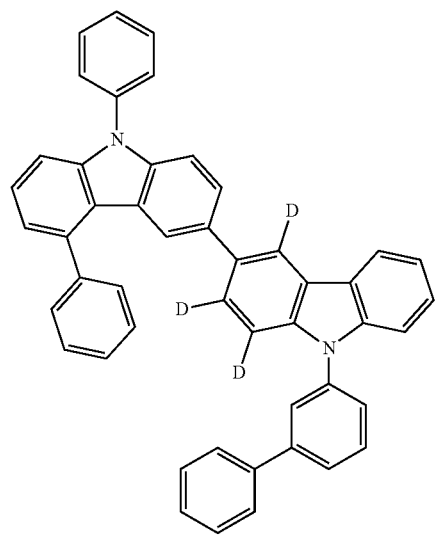
415
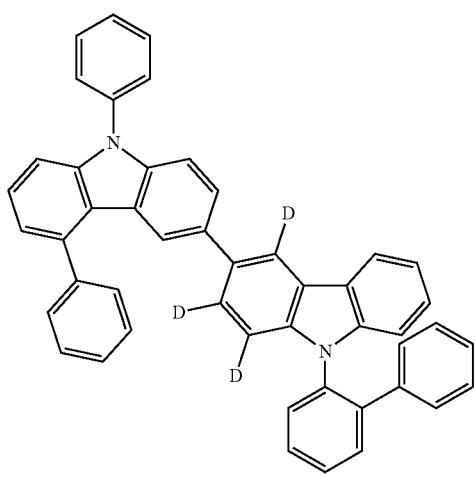
416
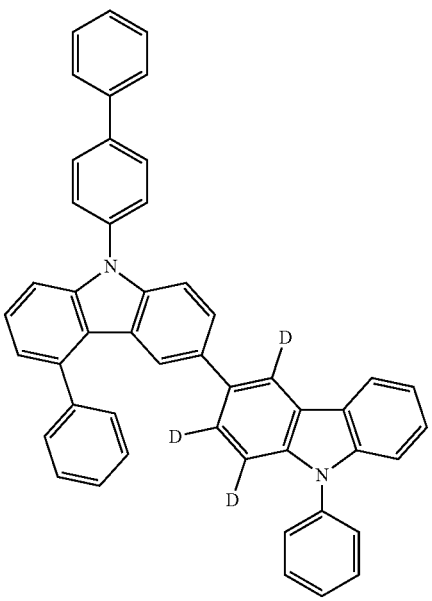
417
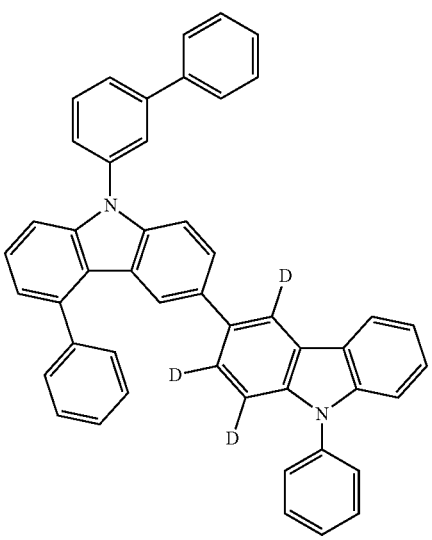
418
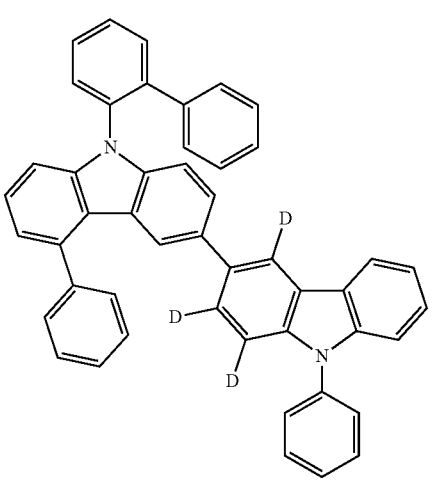

419
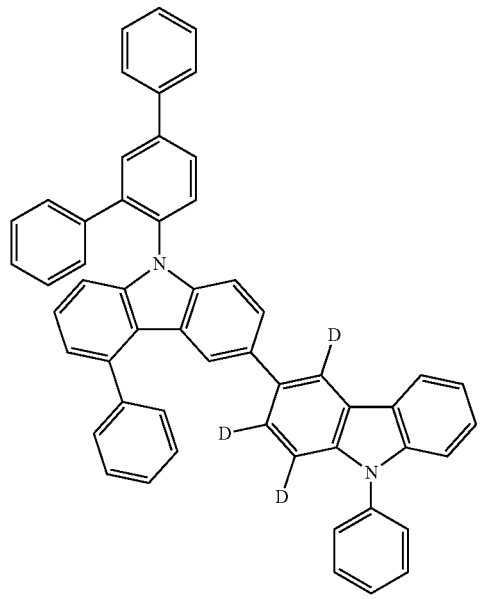
420
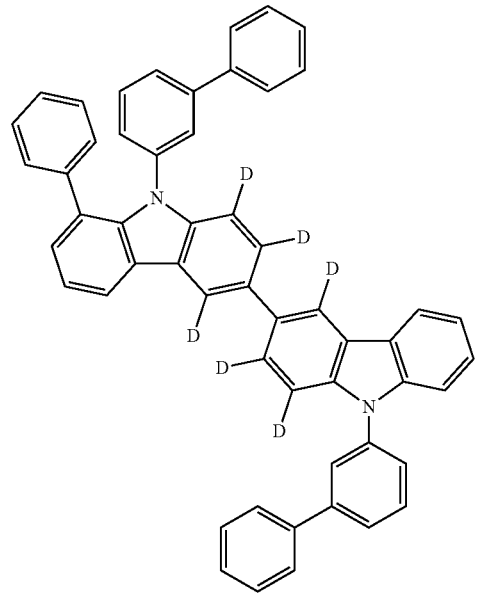
421
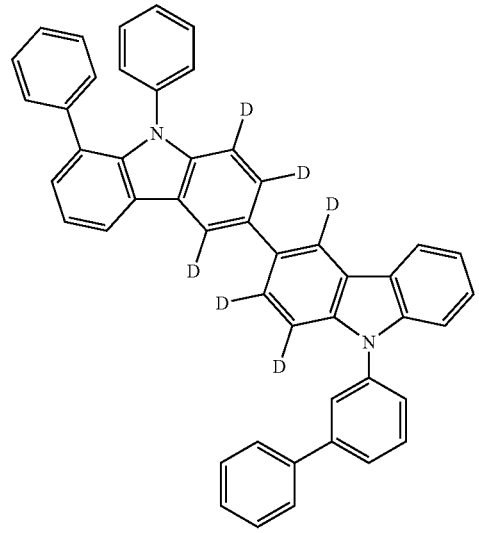
422
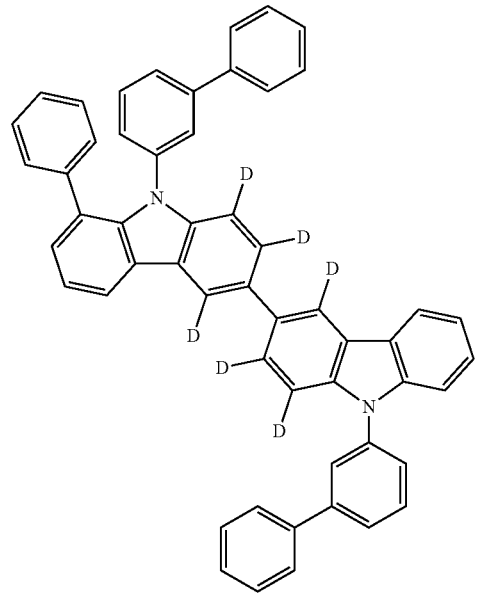

423
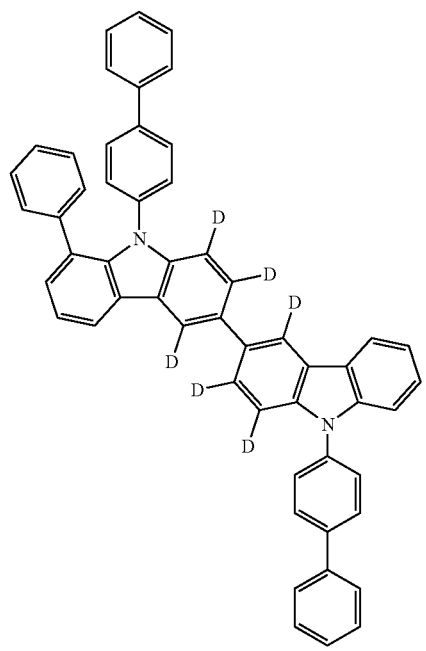
425
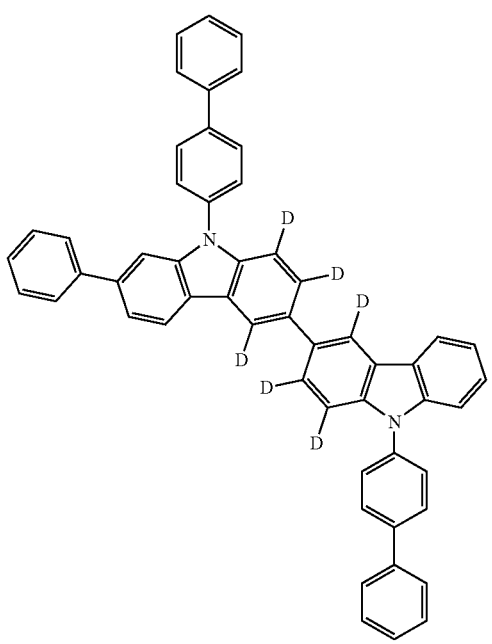
424
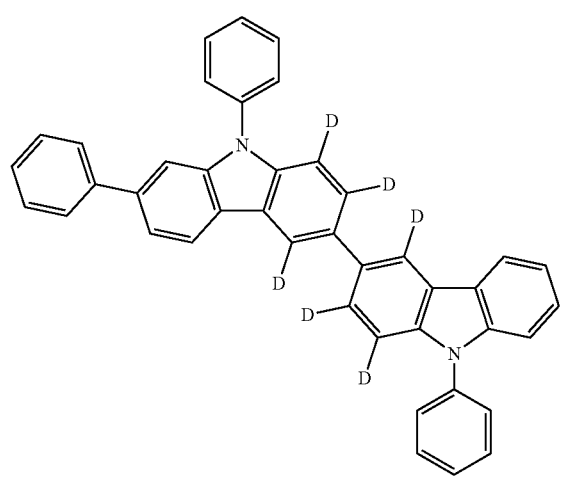
426
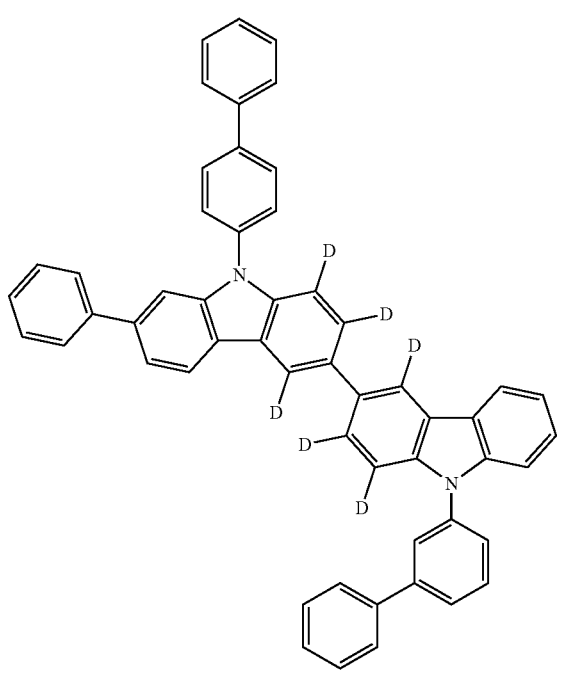

427
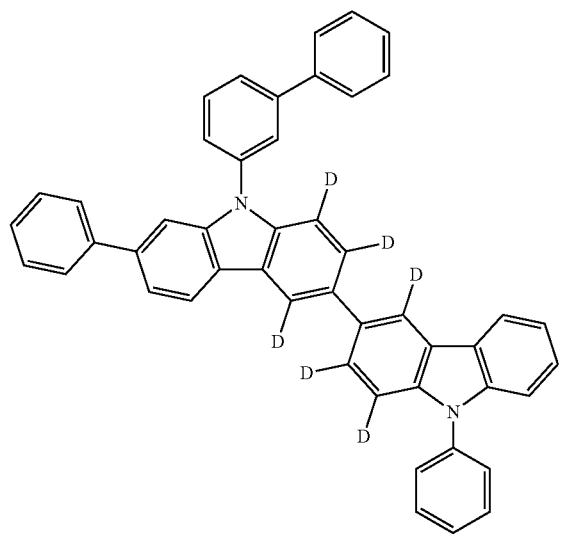
428
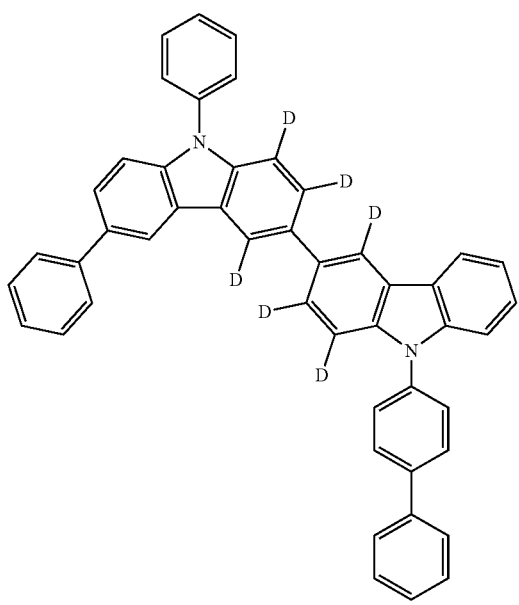
429
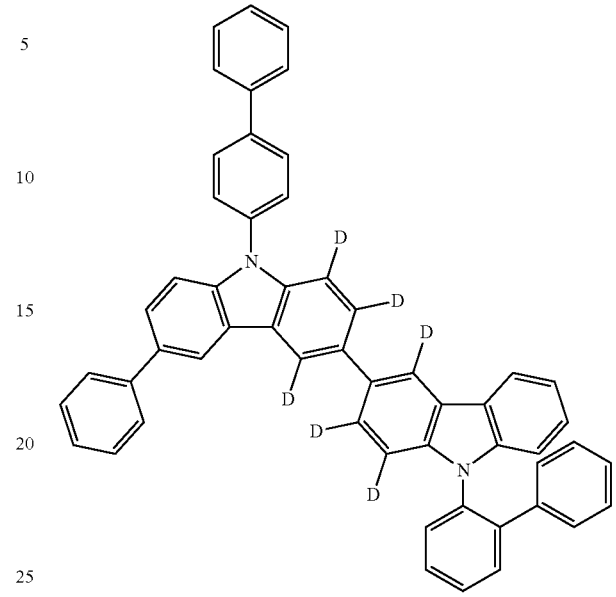
430
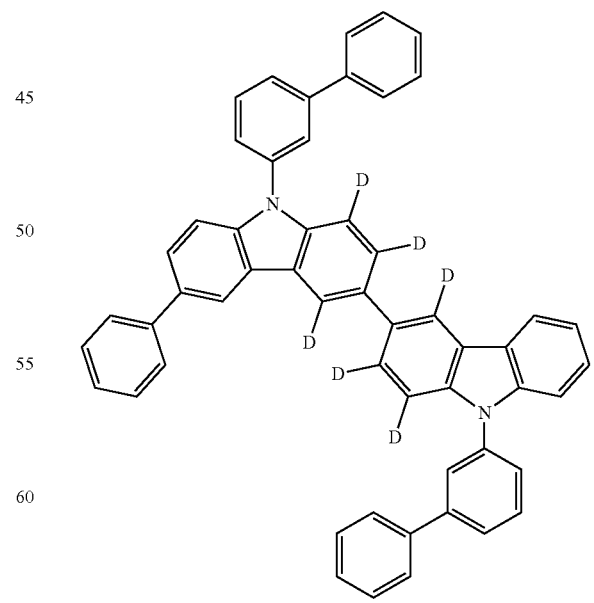

221
-continued
431
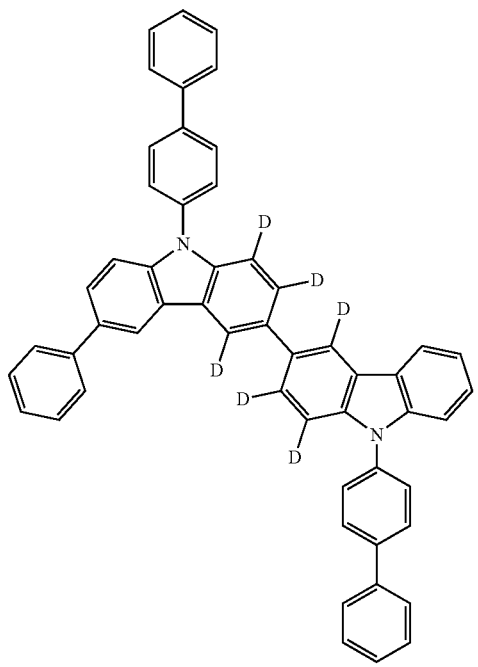
432
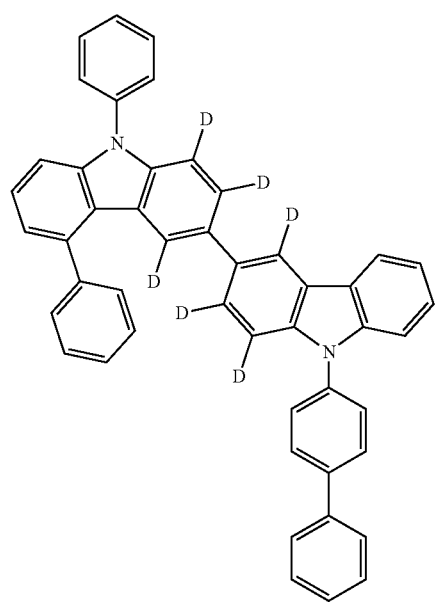
222
-continued
433
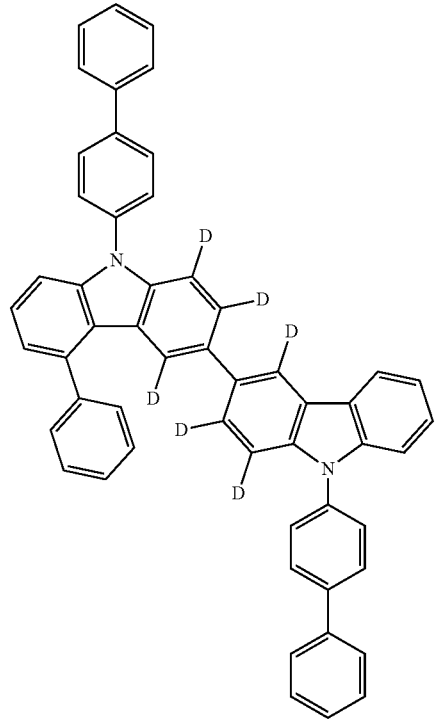
434
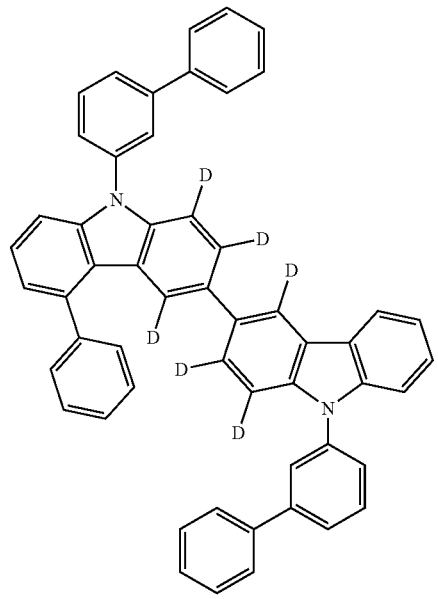

435
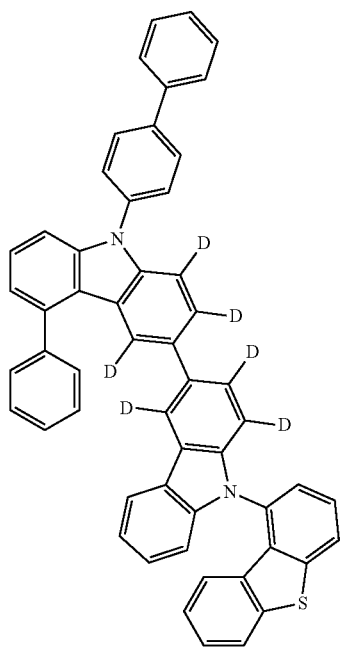
436
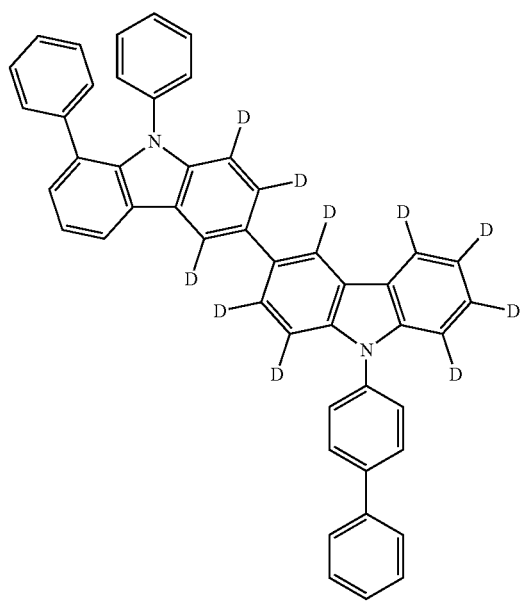
437
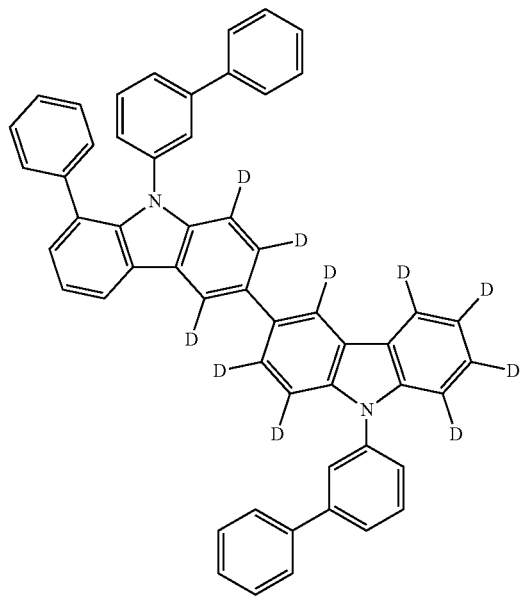
438
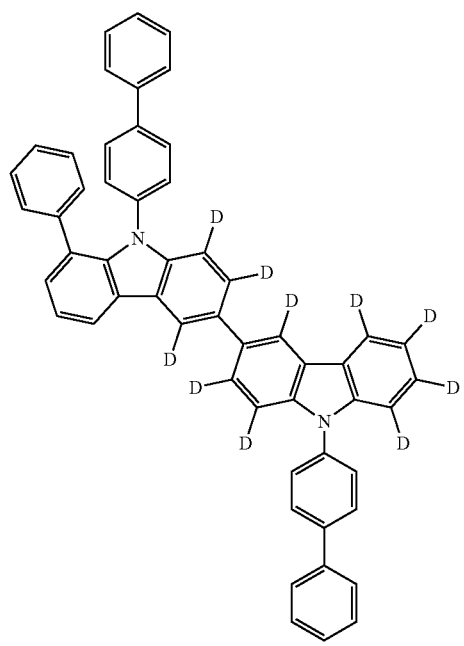

225
-continued
439
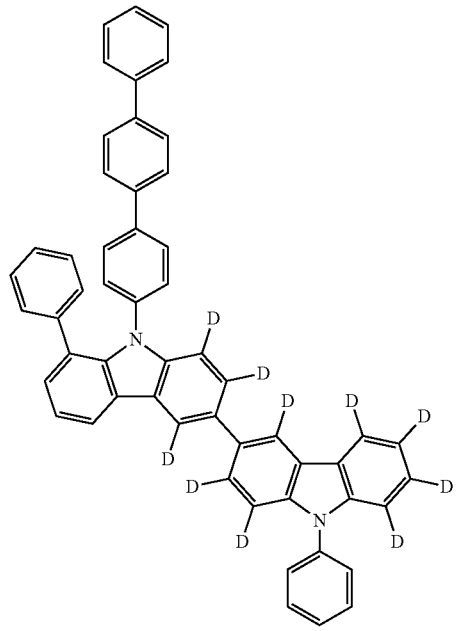
440
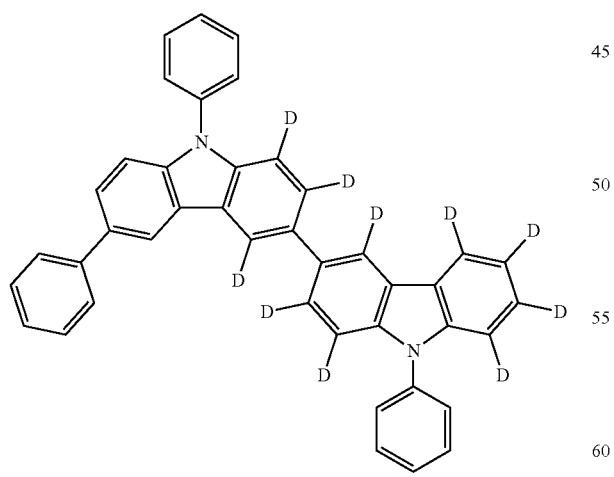
226
-continued
441
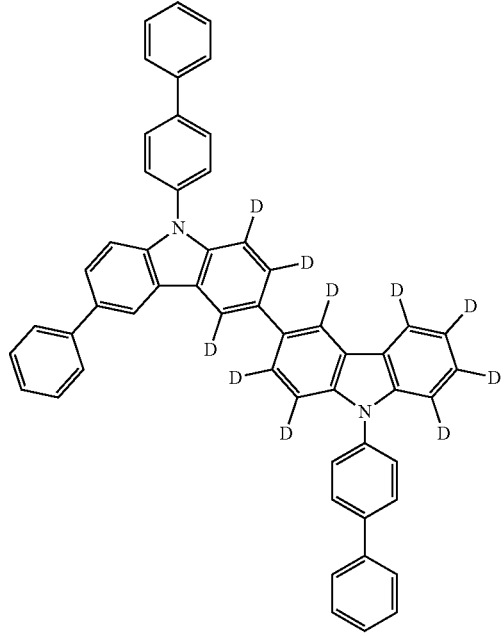
442
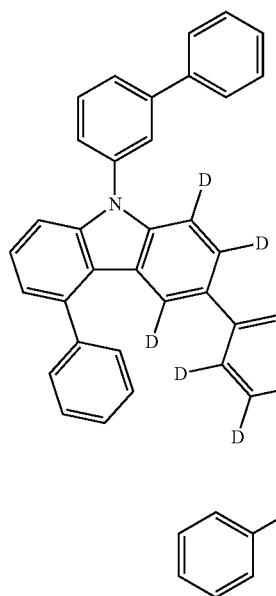

227
-continued
443
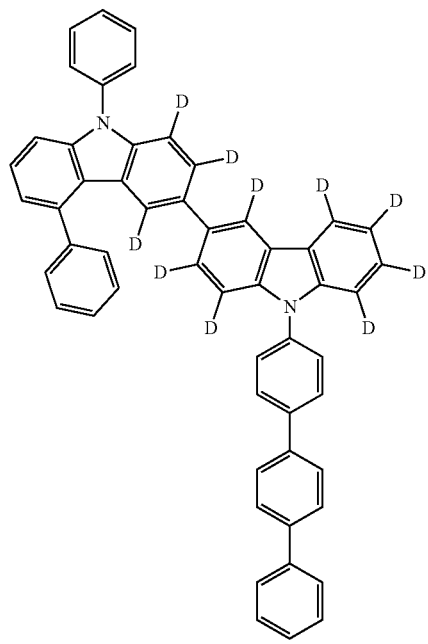
228
-continued
445
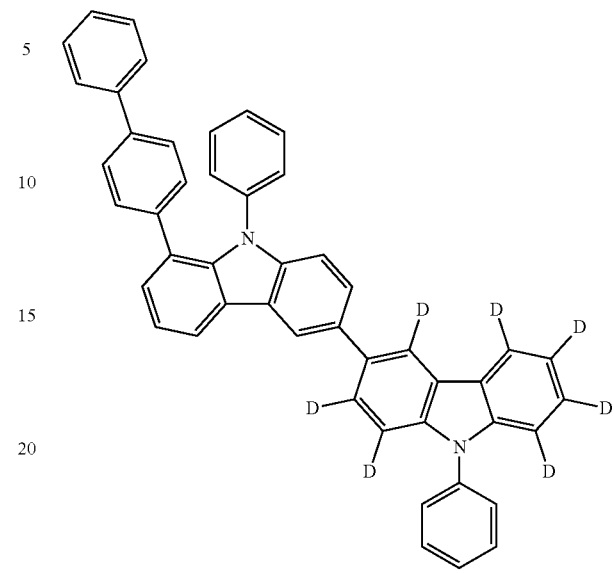
444
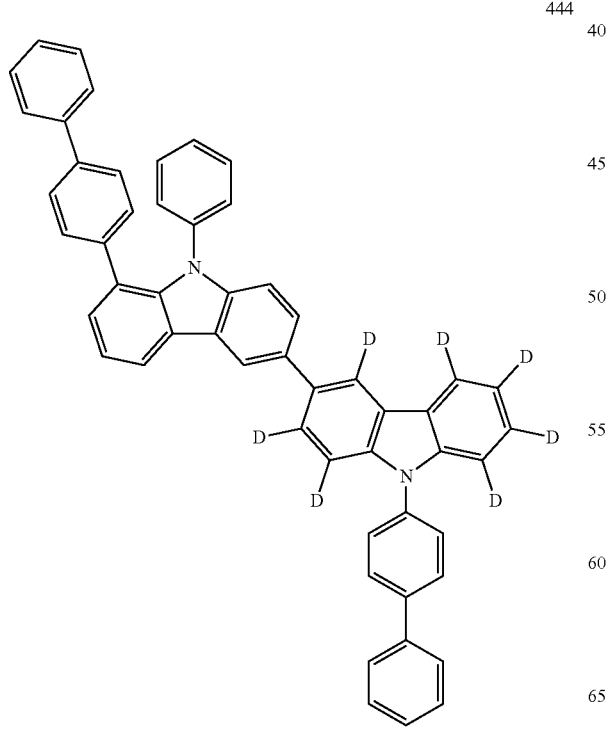
446
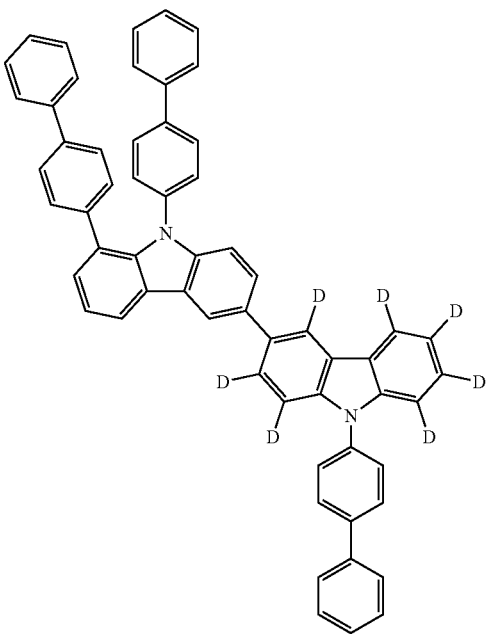

447
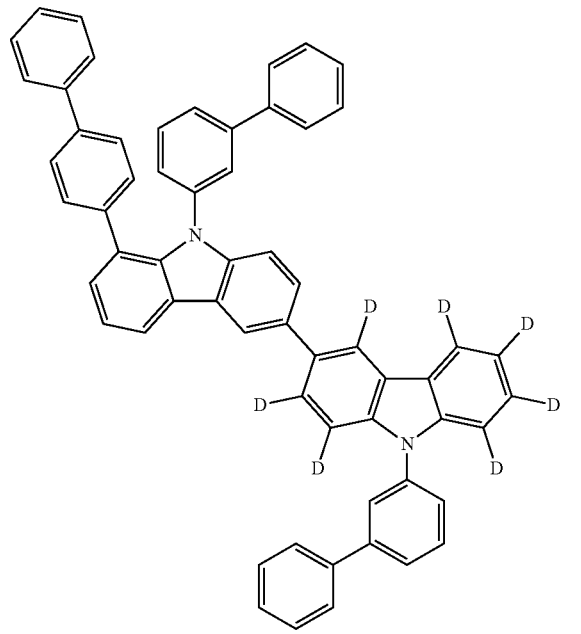
450
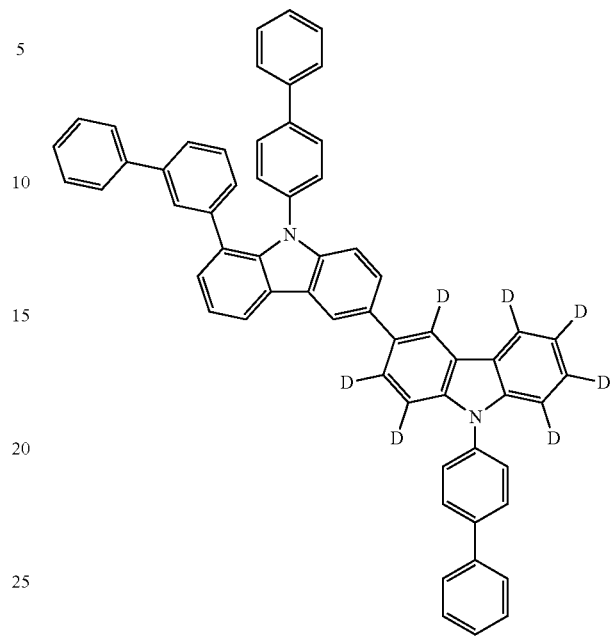
448
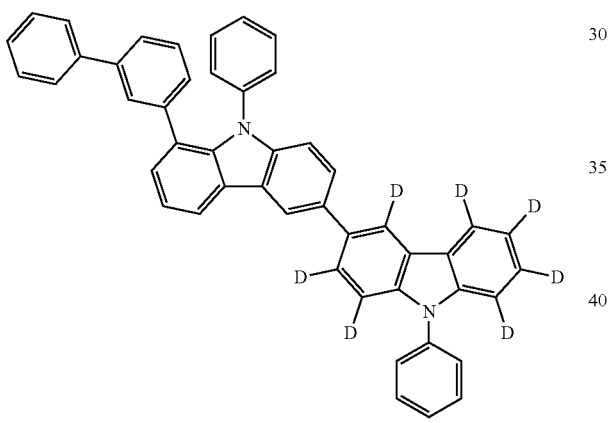
449
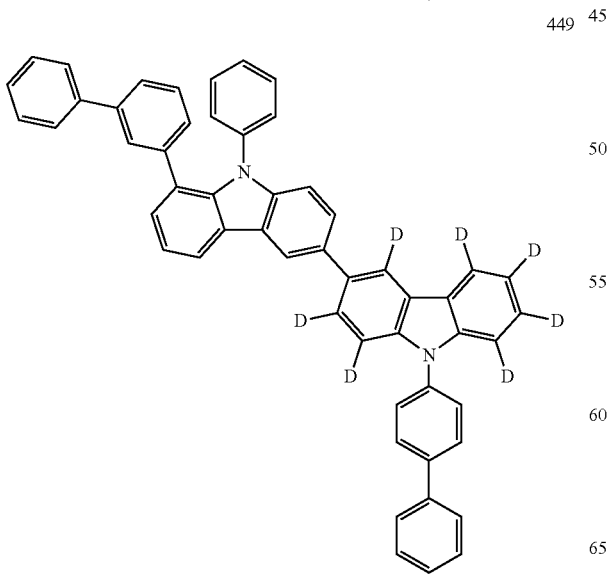
451
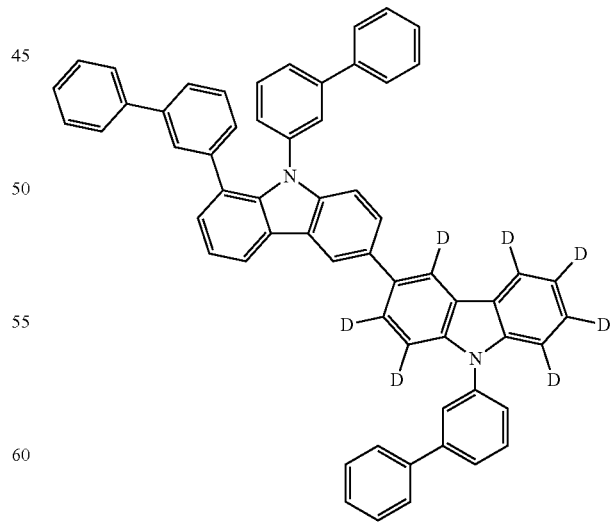

452
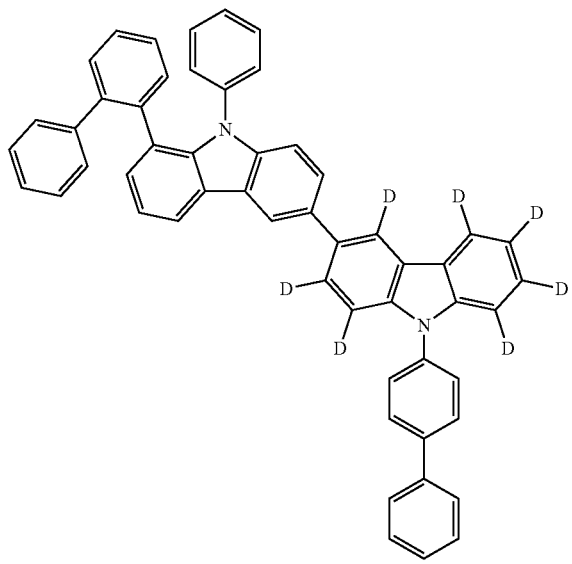
453
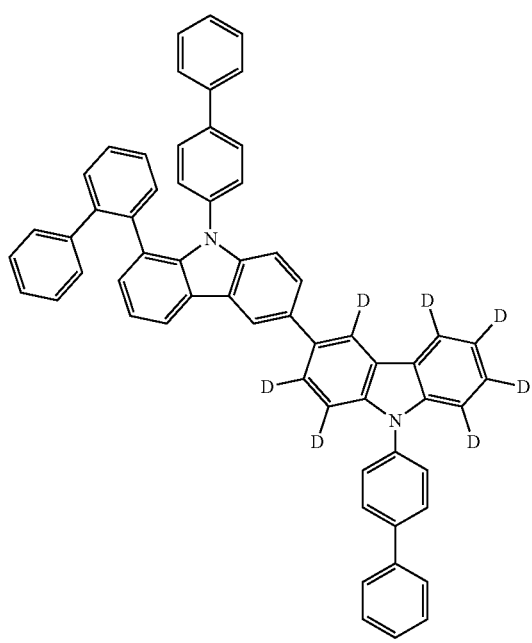
454
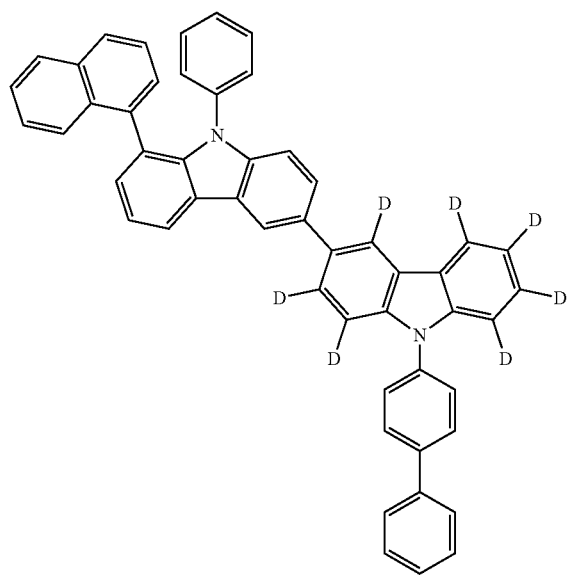
455
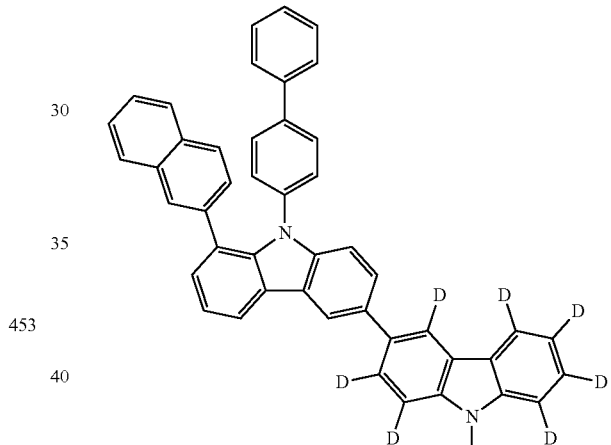
456
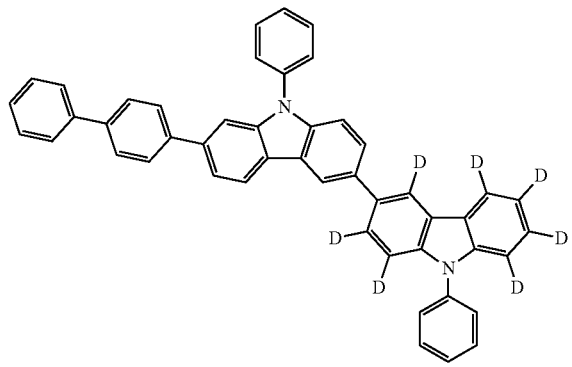

457
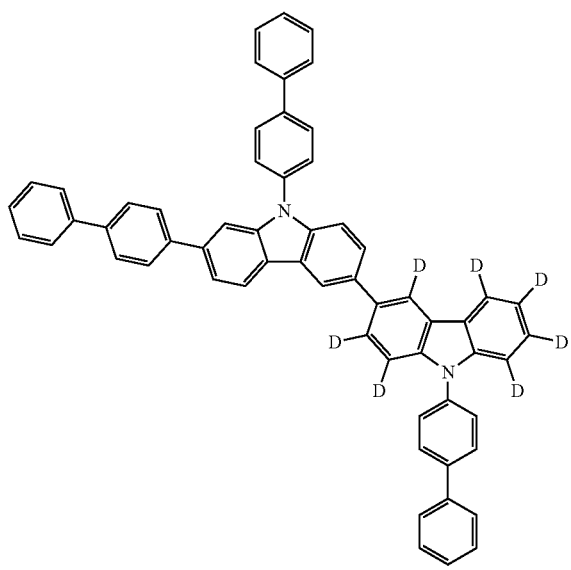
458
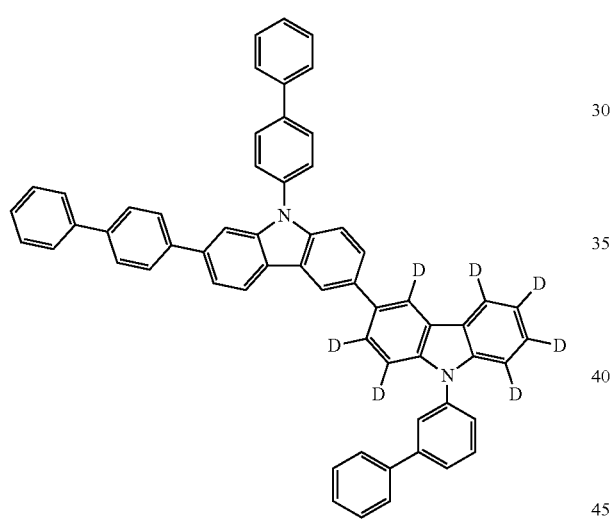
459
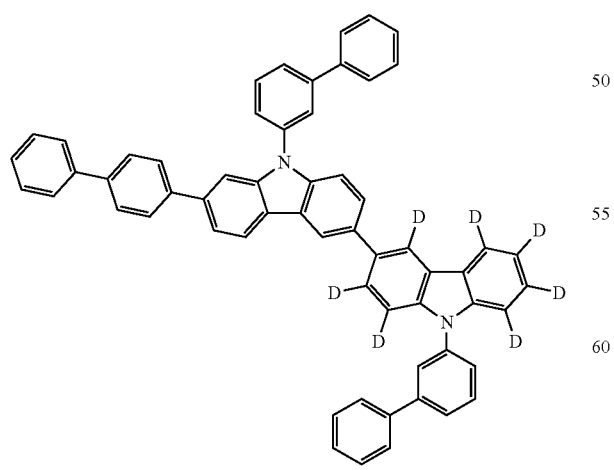
460
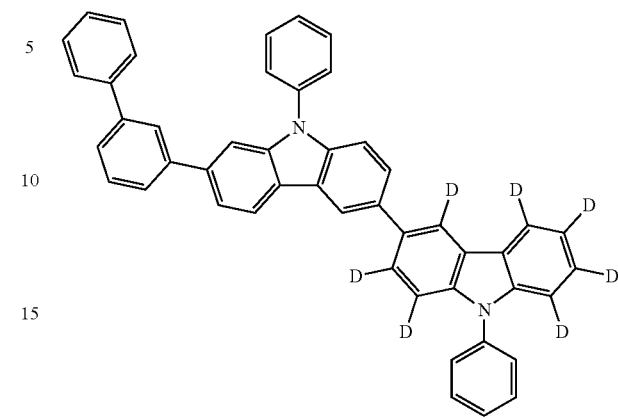
461
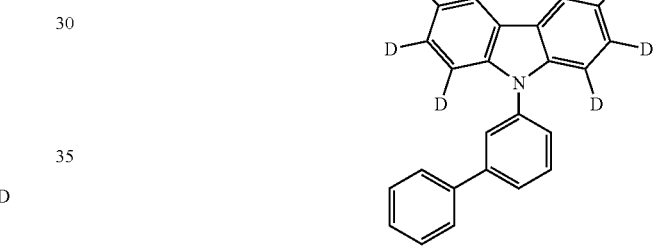
462
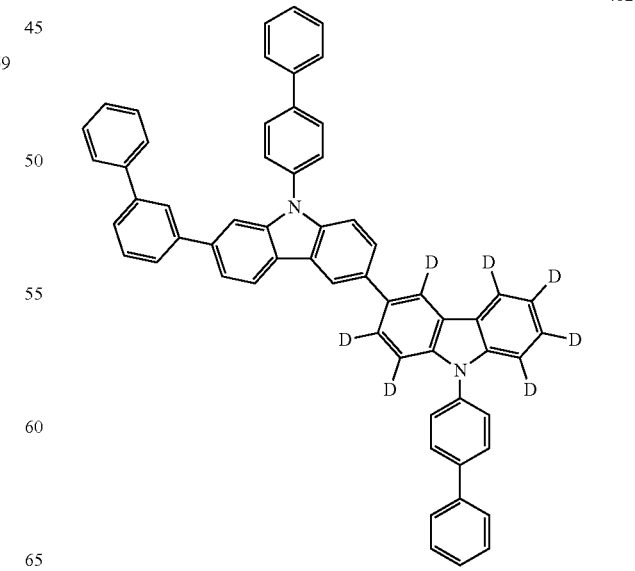

463
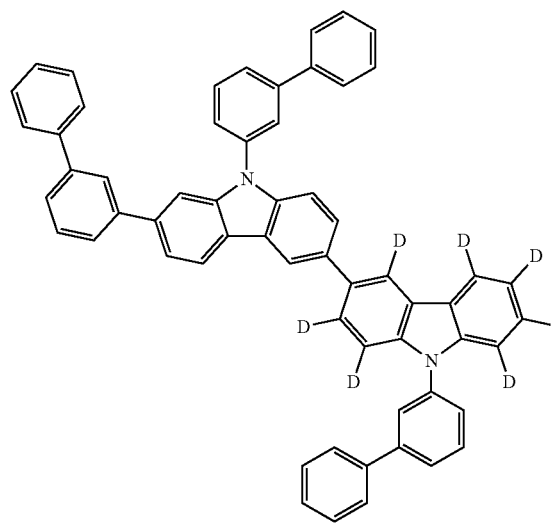
464
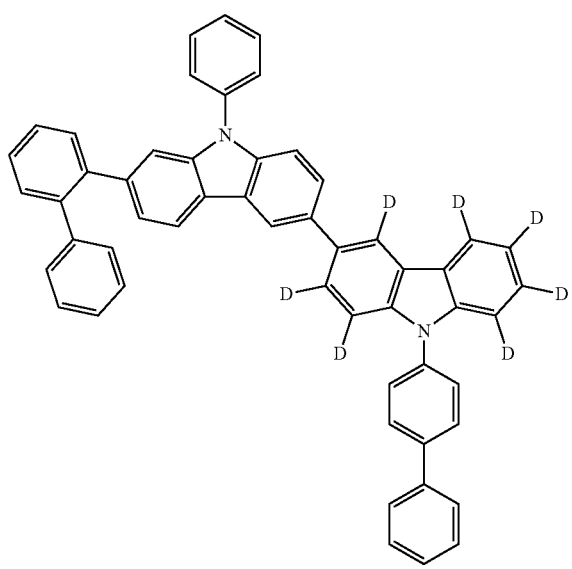
465
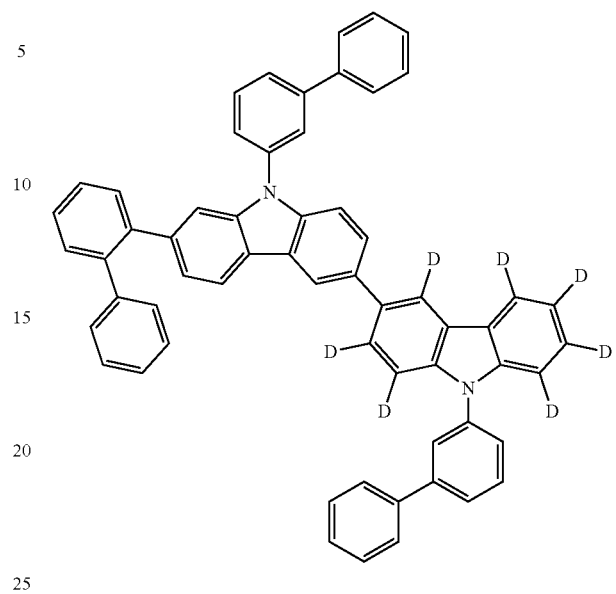
466
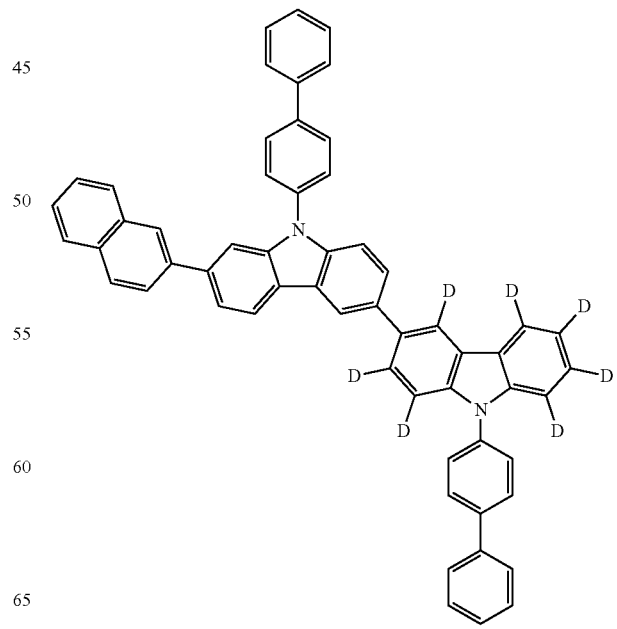

467
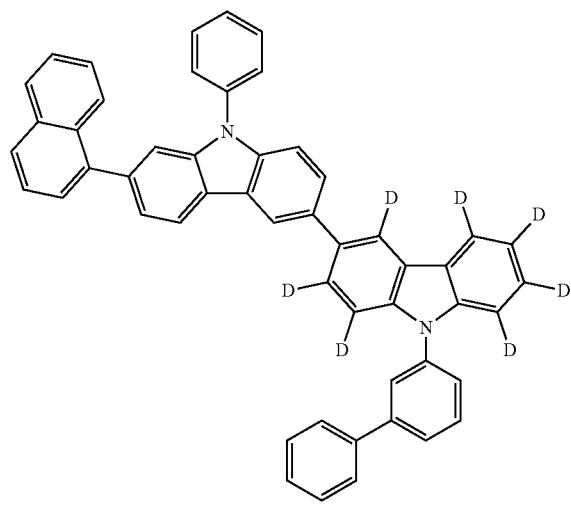
468
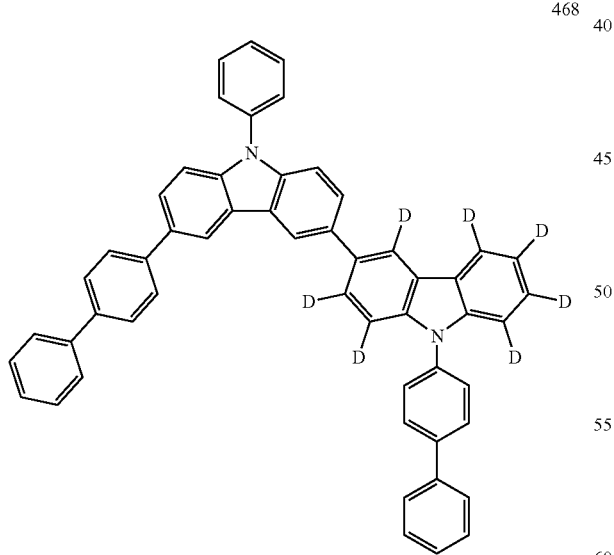
469
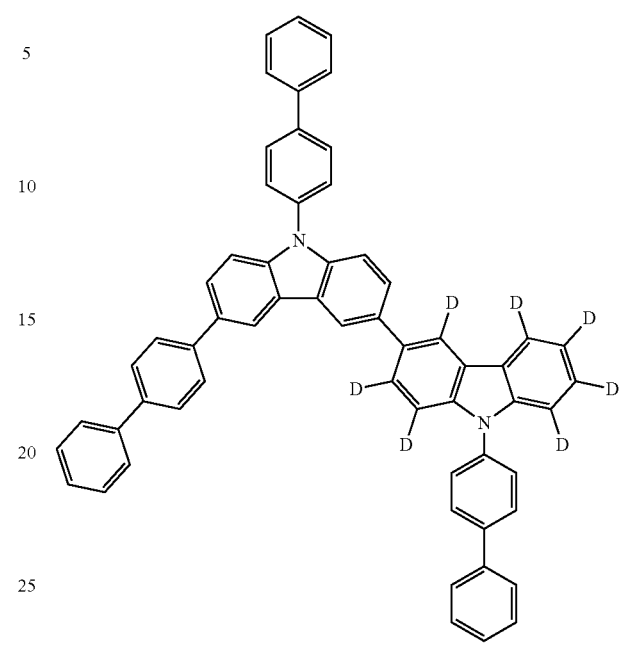
470
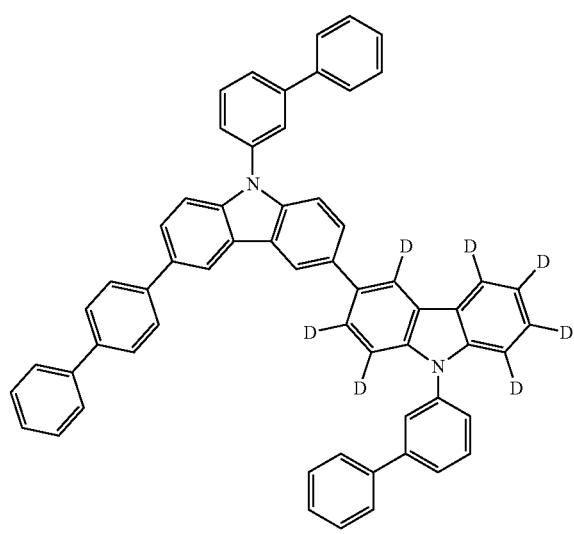

471
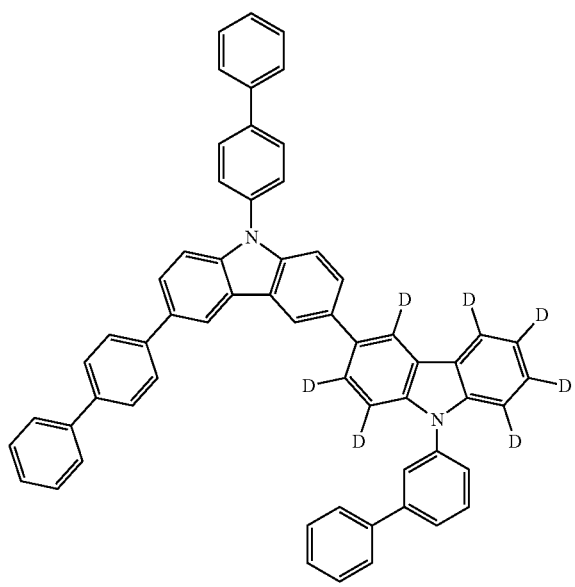
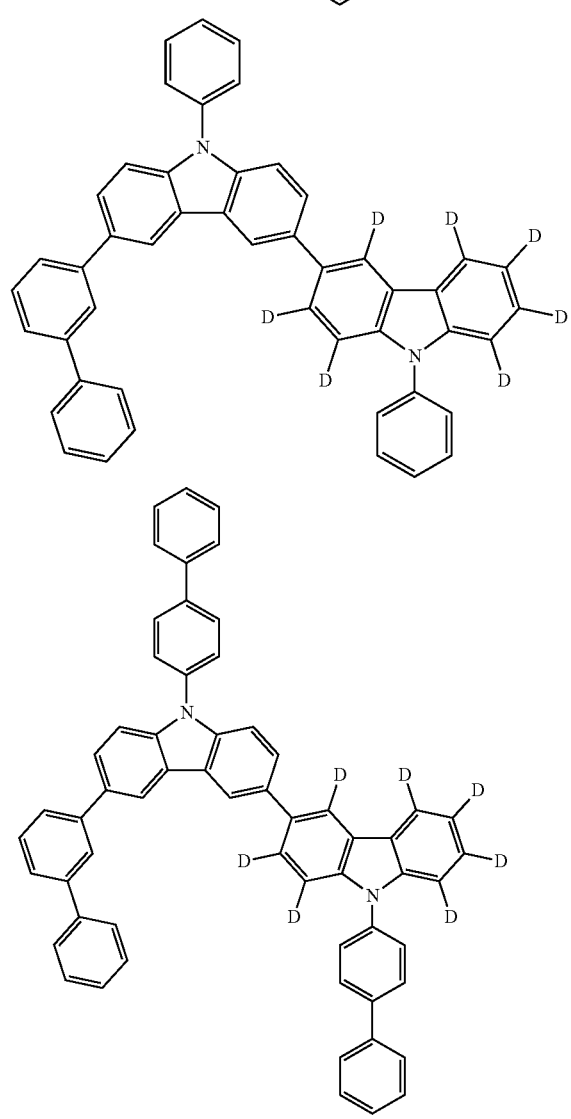
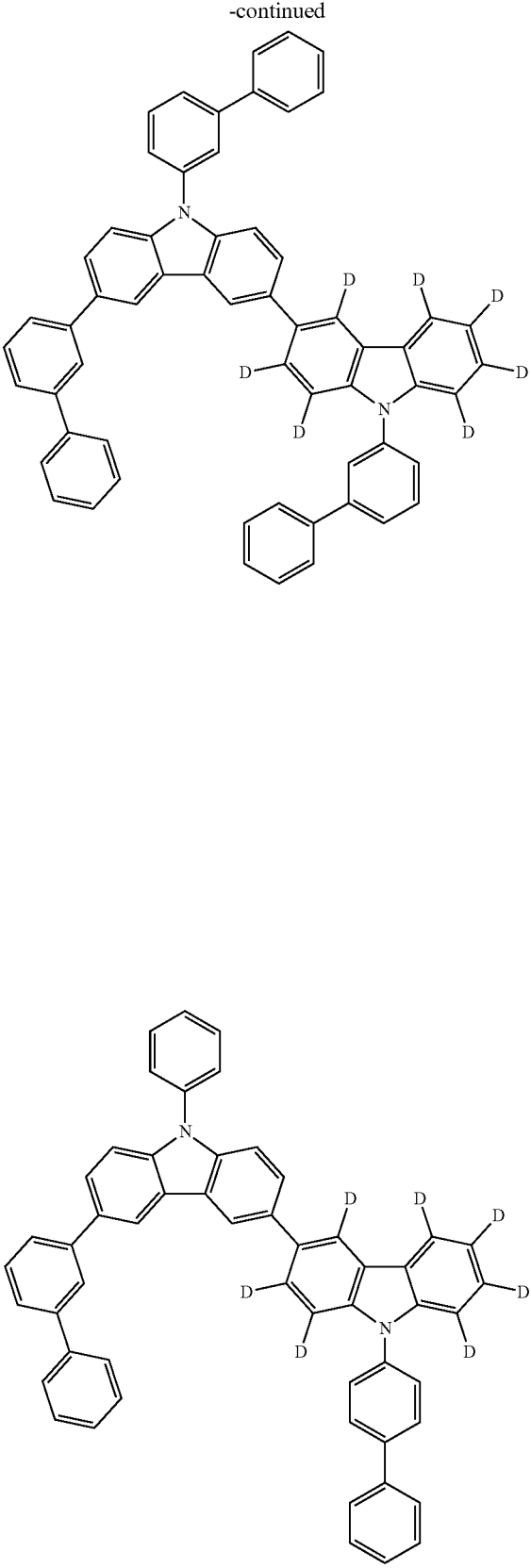

476
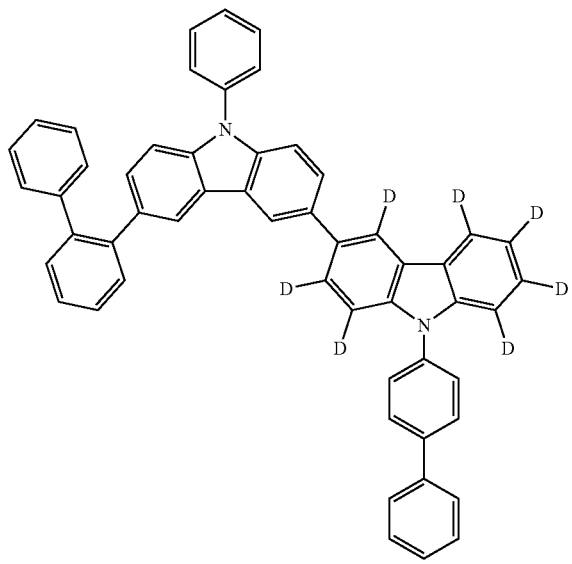
477
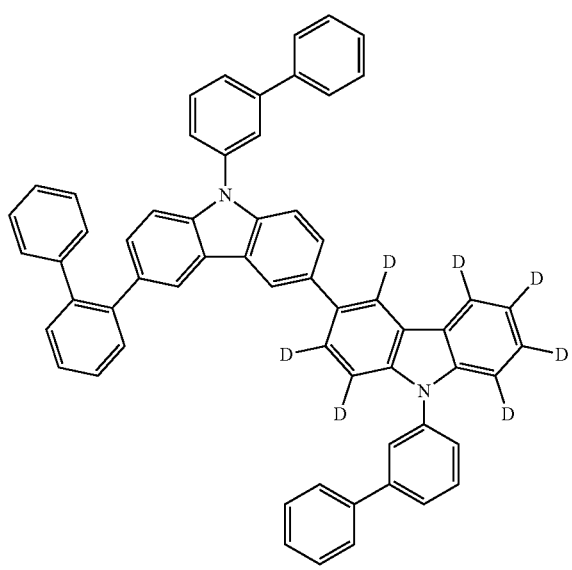
478
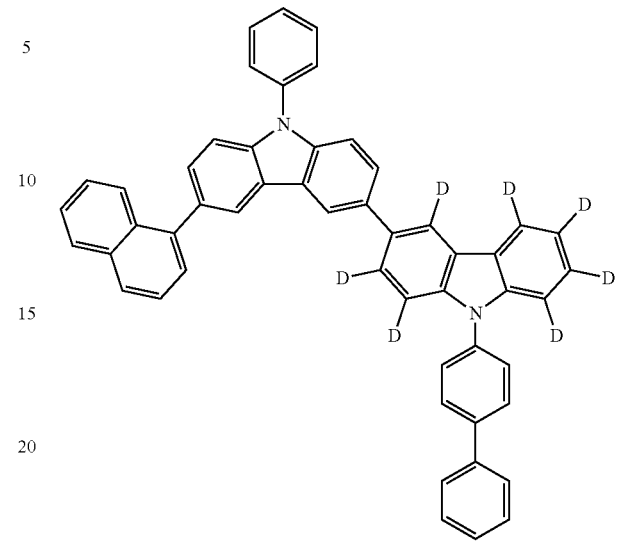
479
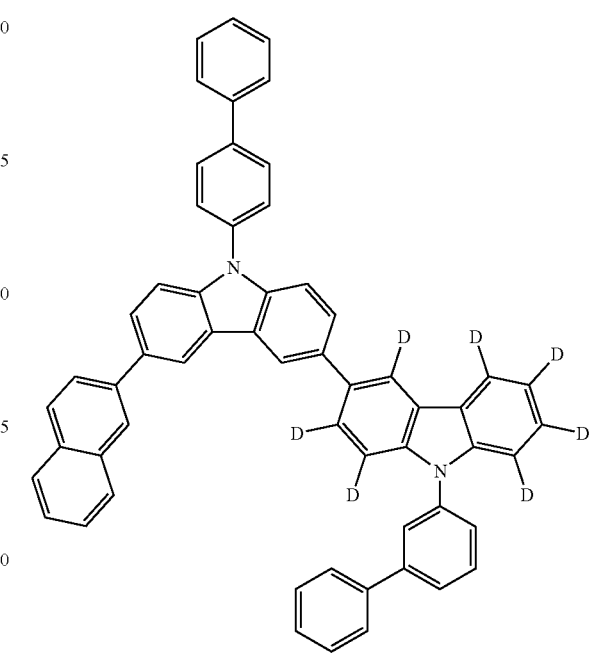

243
-continued
480
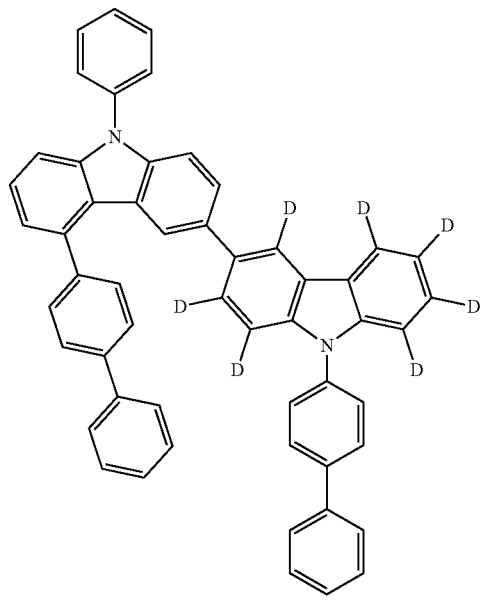
481
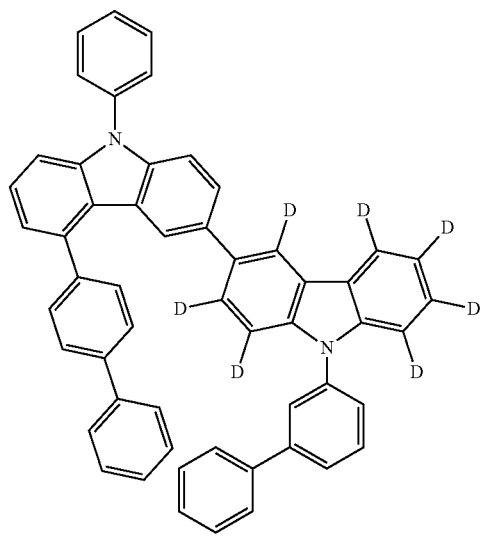
244
-continued
482
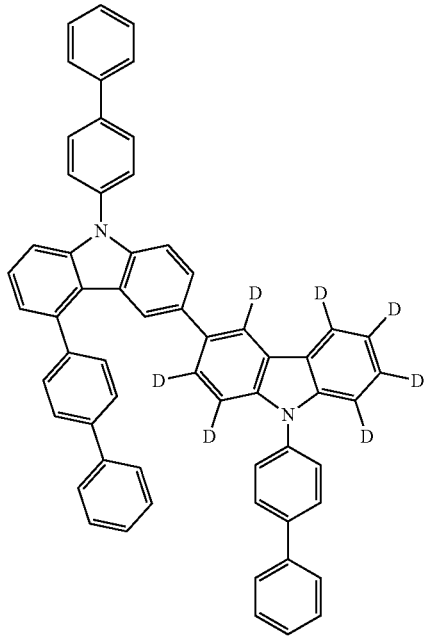
483
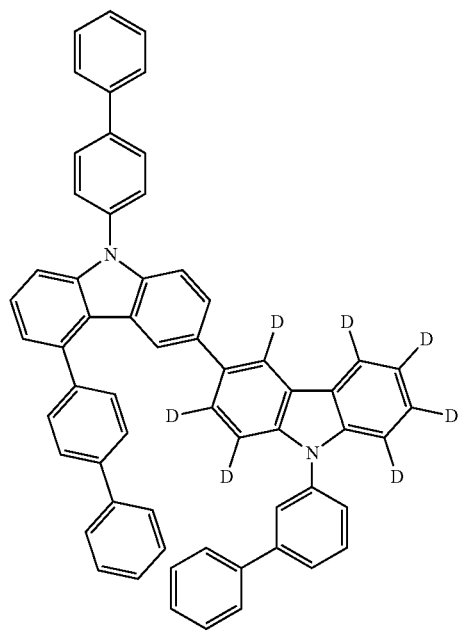

484
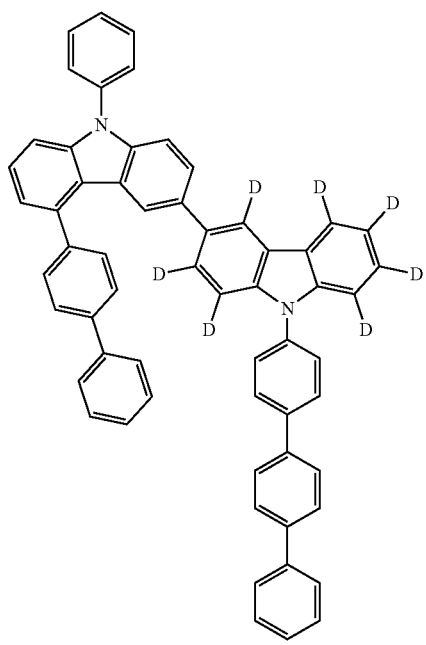
486
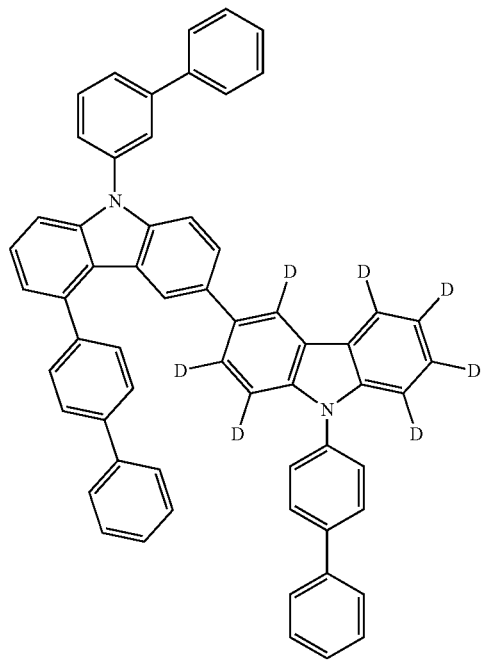
485
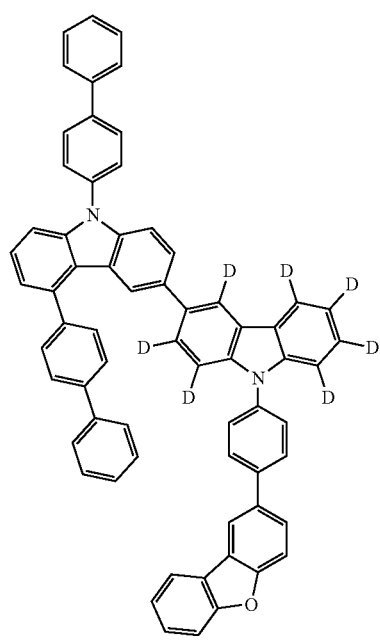
487
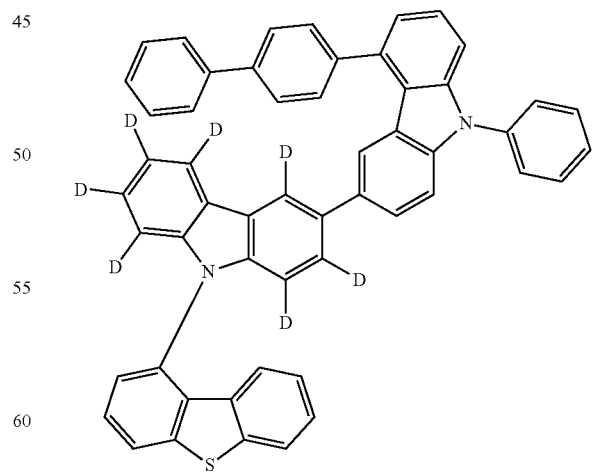

488
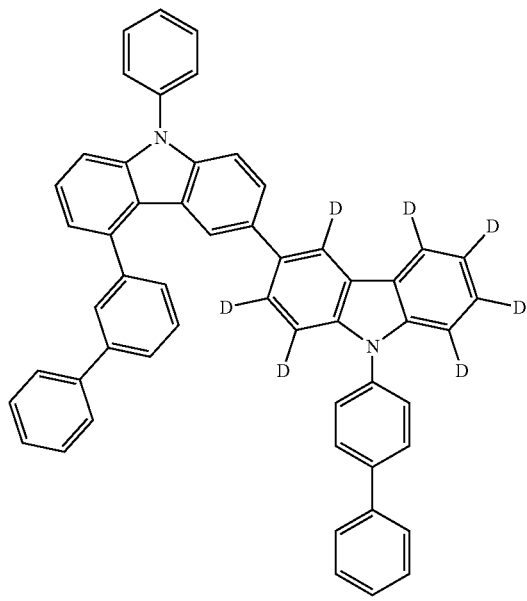
490
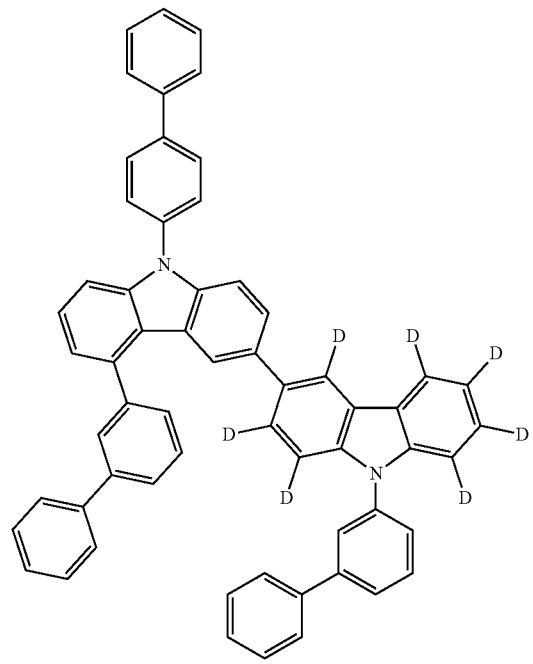
489
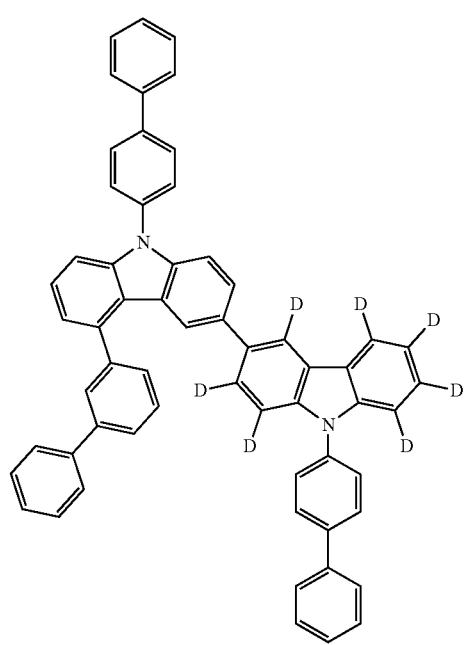
491
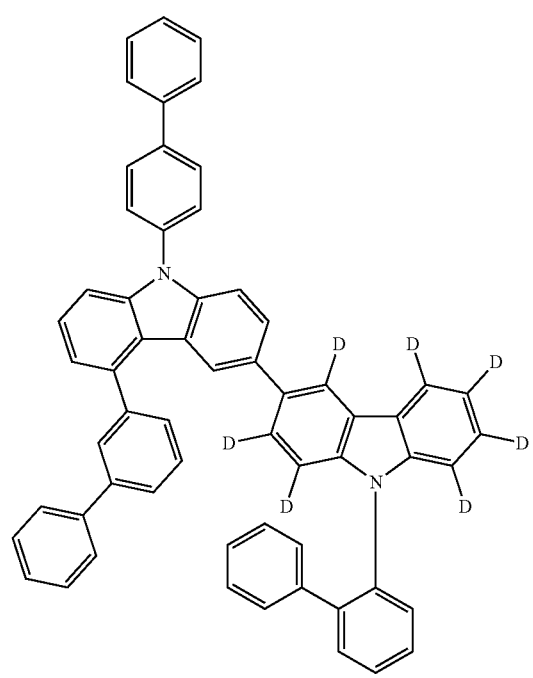

249
-continued
492
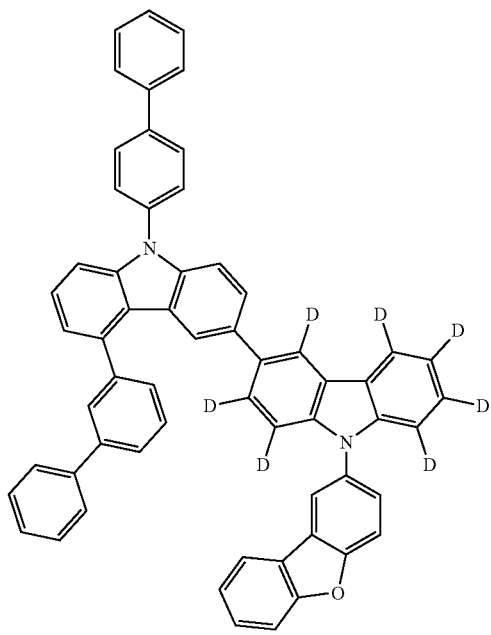
493
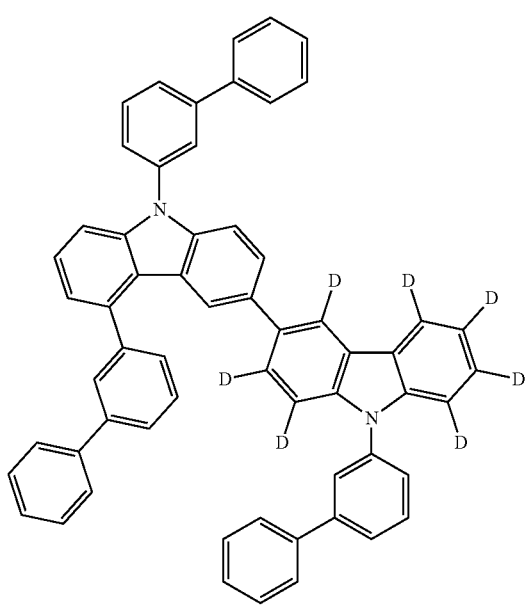
250
-continued
494
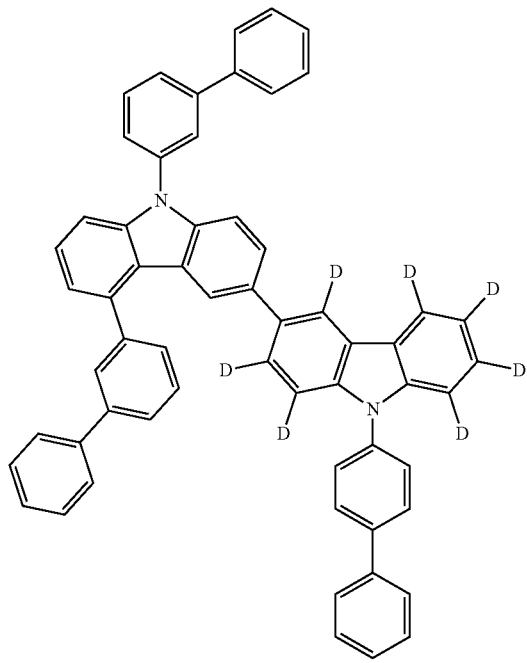
495
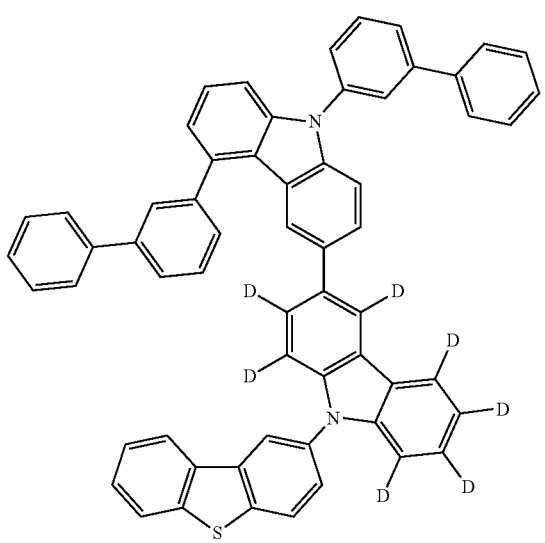

496
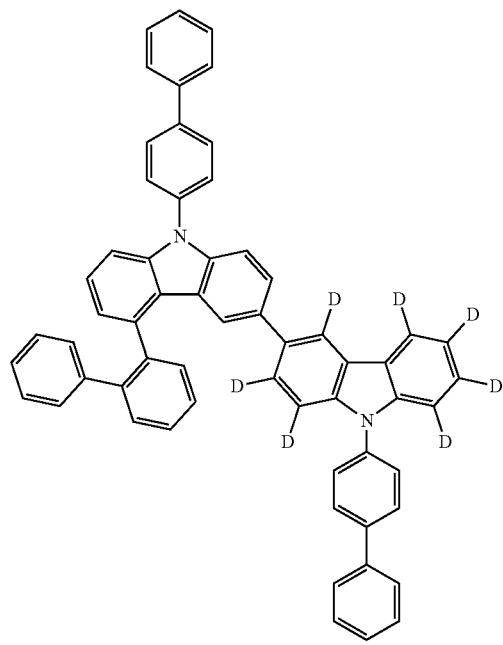
497
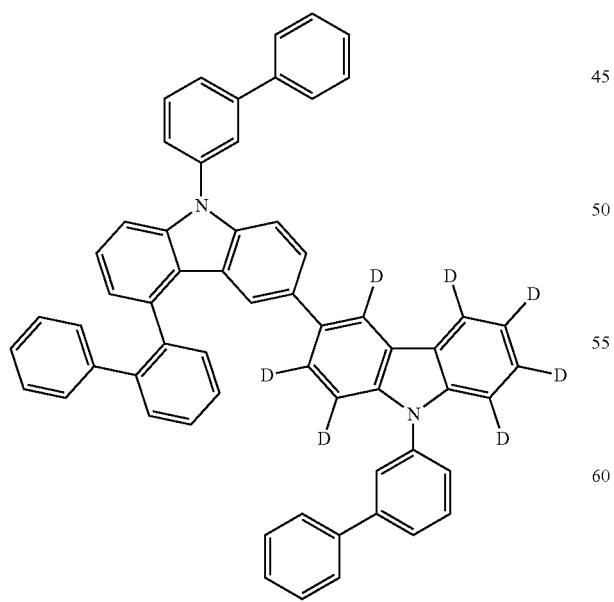
498
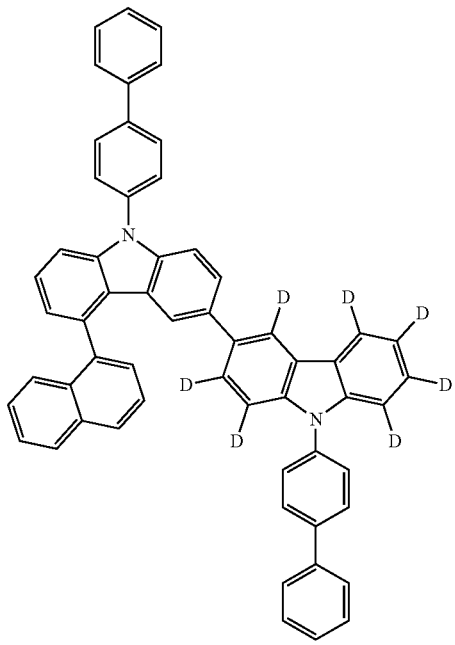
499
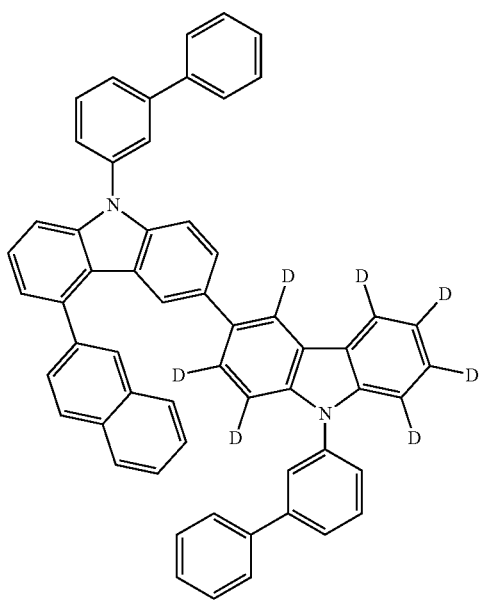

253
-continued
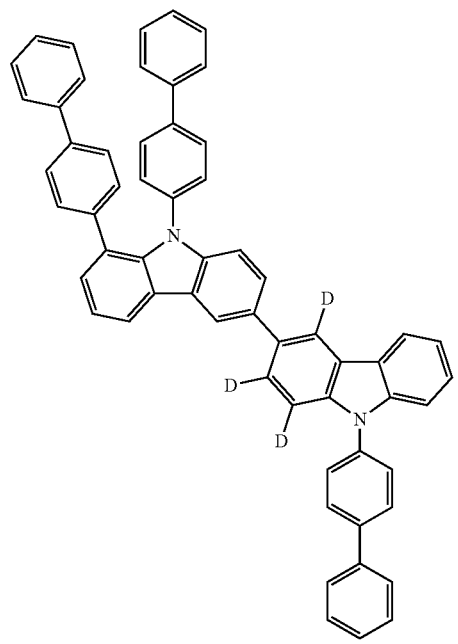
500
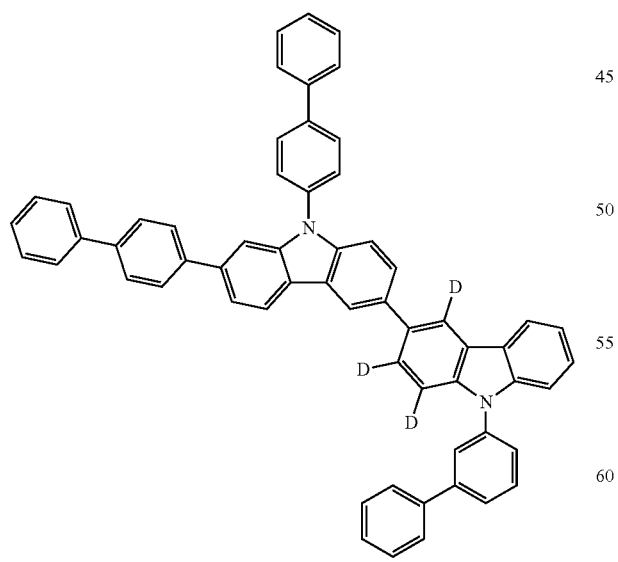
501
254
-continued
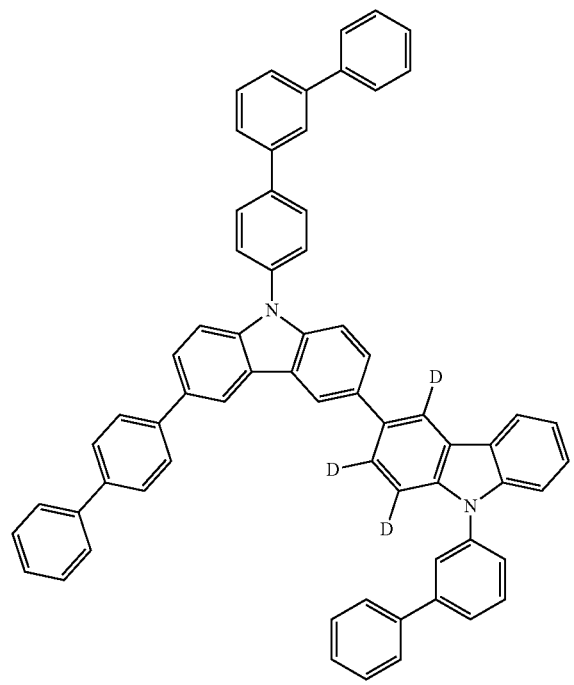
502
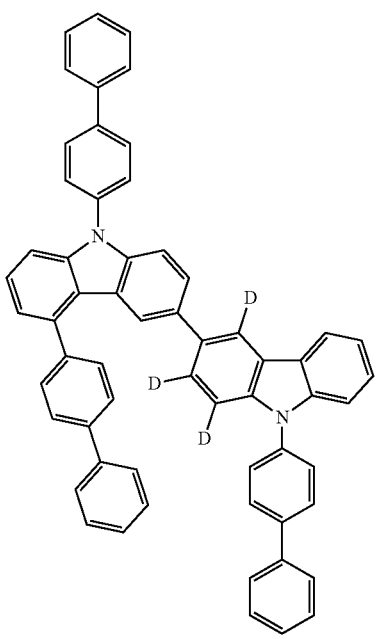
503

504
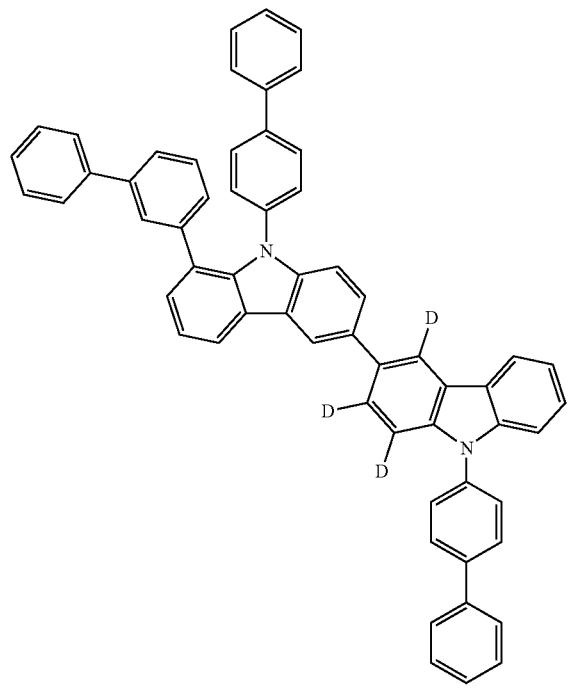
506
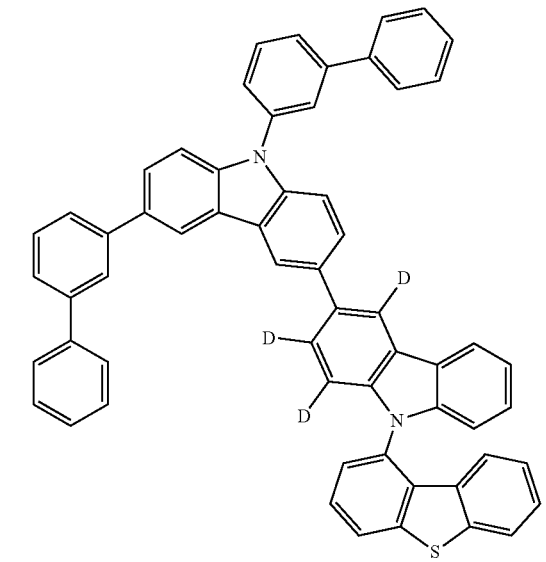
505
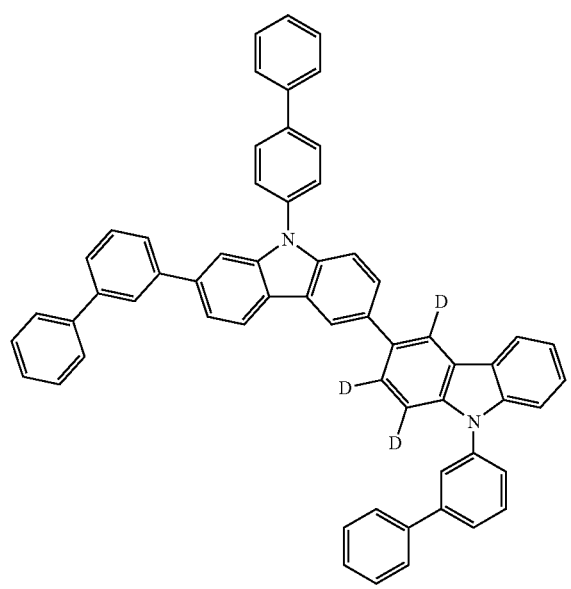
507
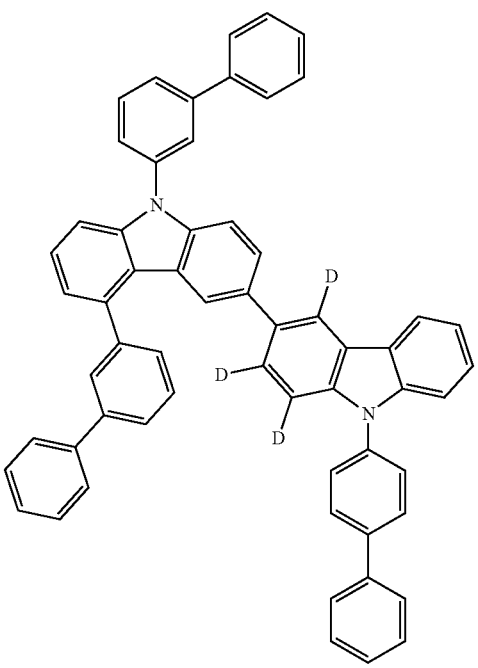

508
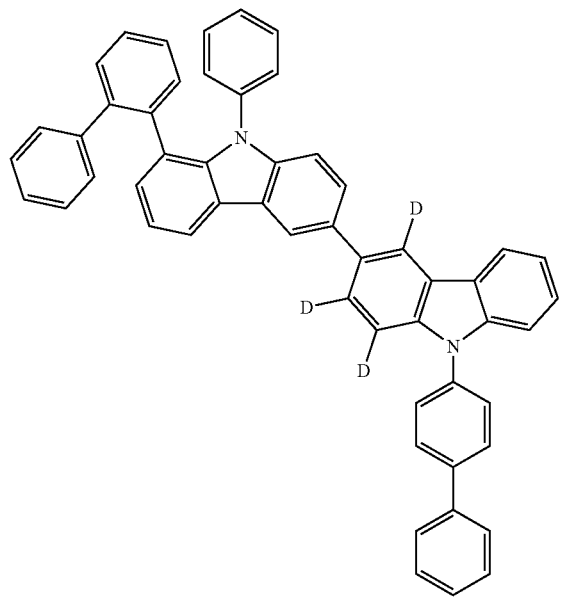
509
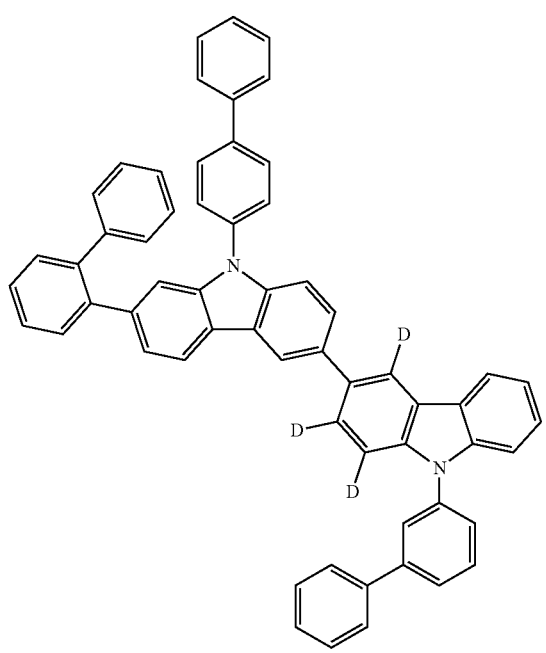
510
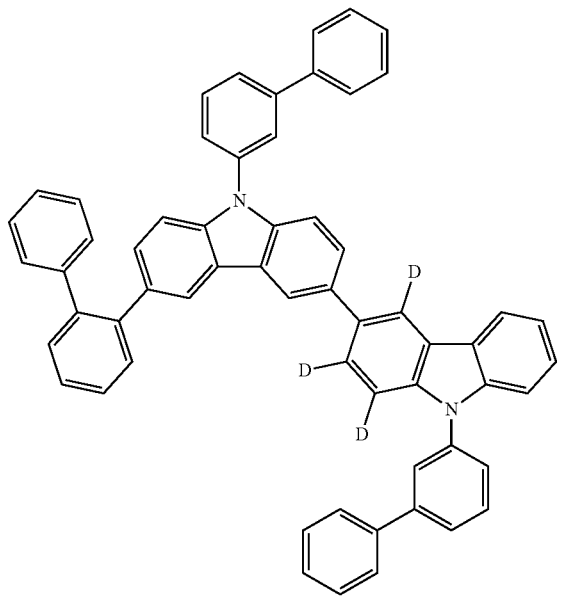
511
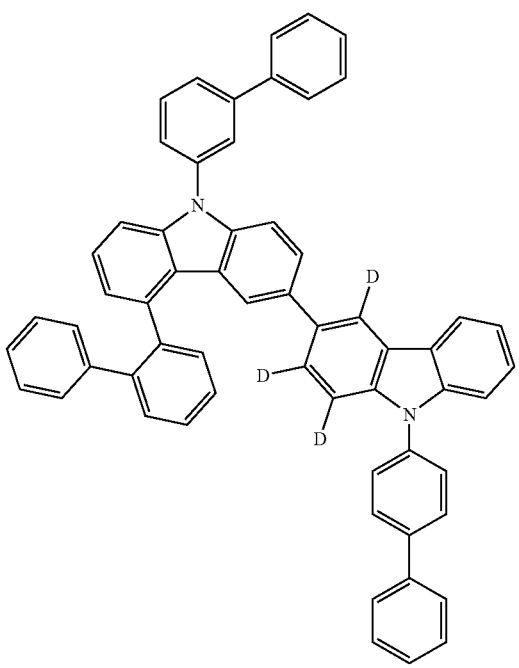

259
-continued
512
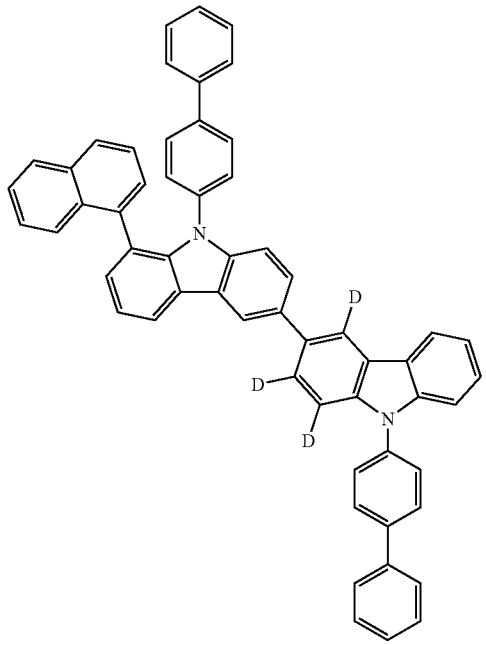
260
-continued
514
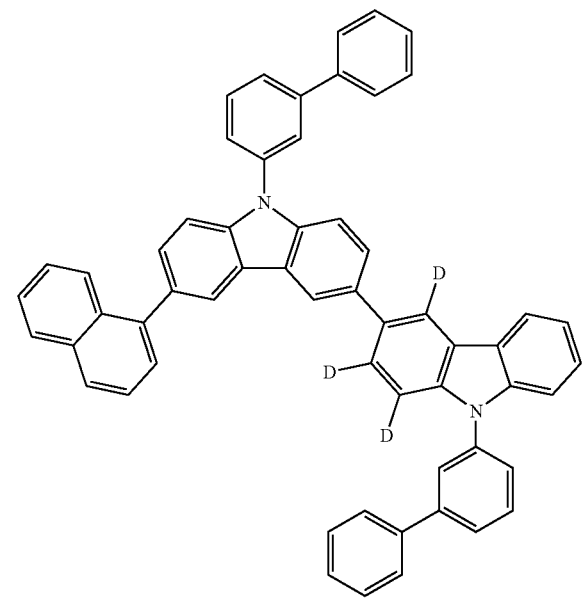
513
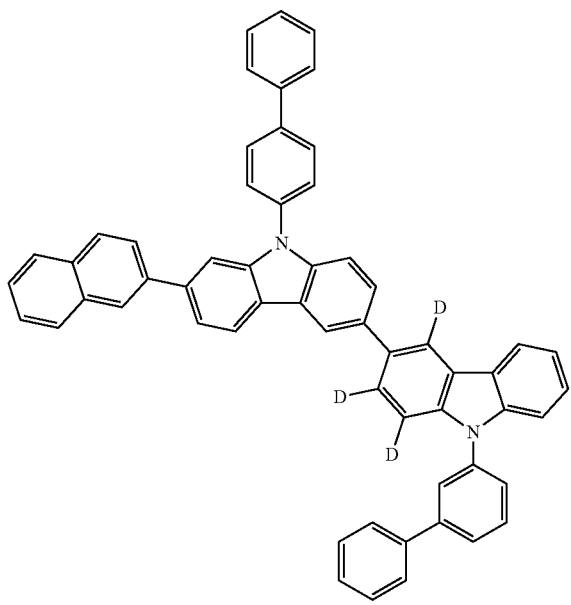
515
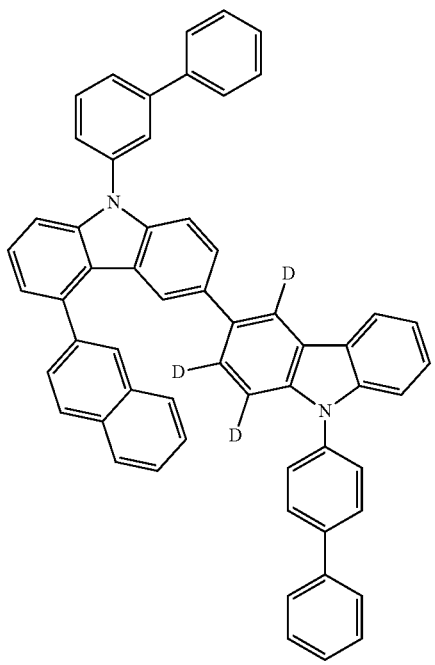

516
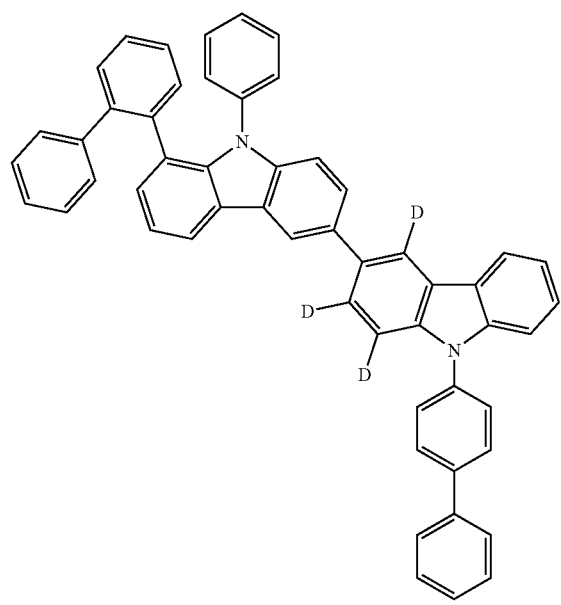
517
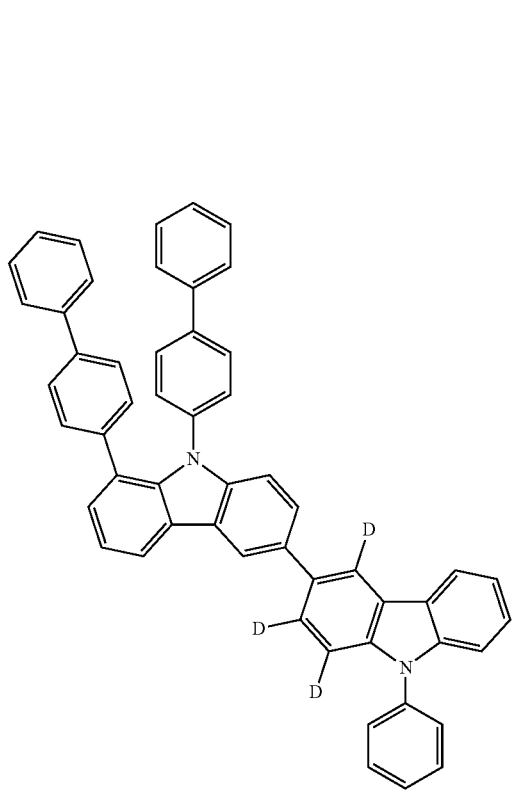
518
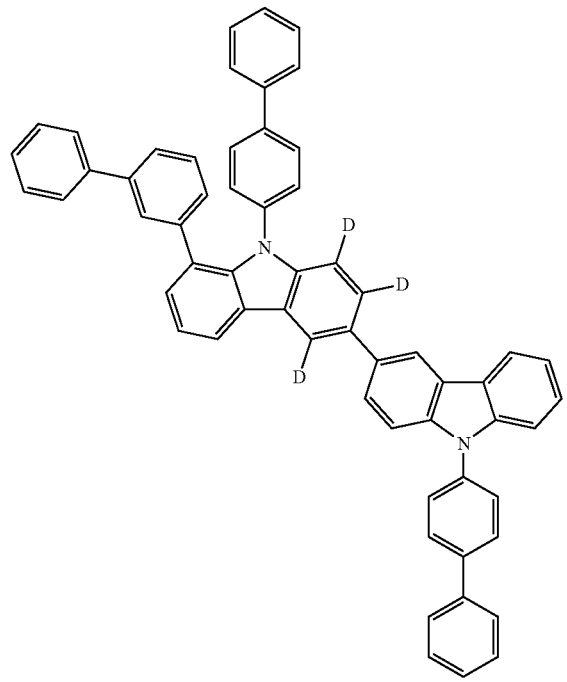
519
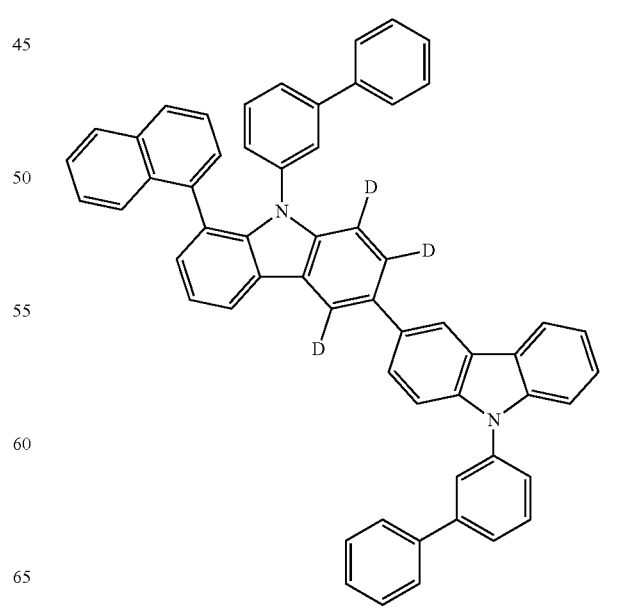

520
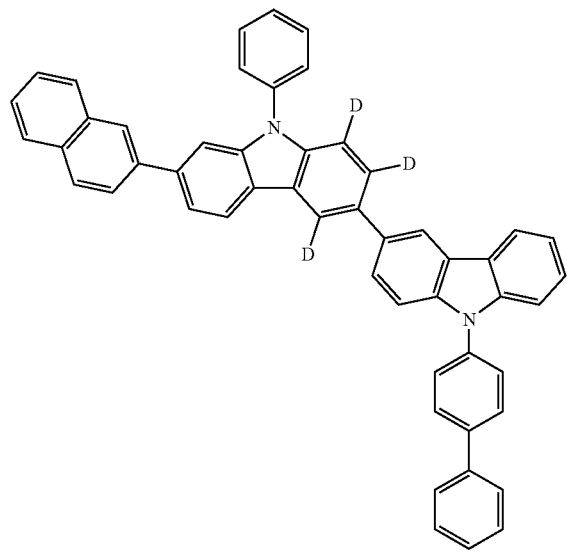
521
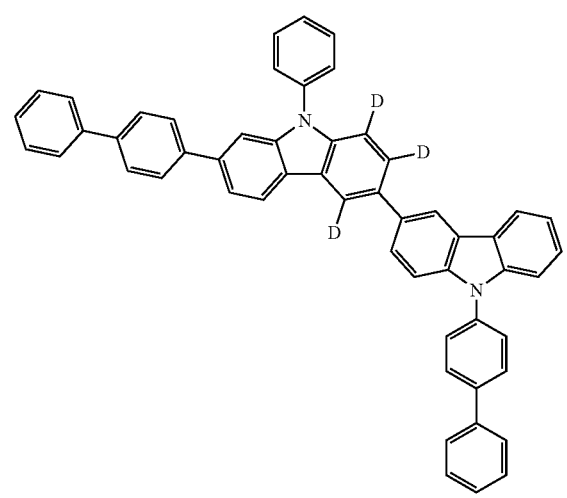
522
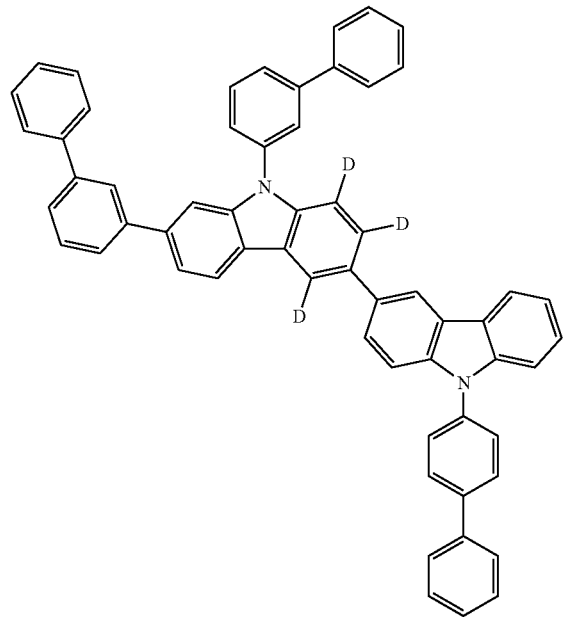
523
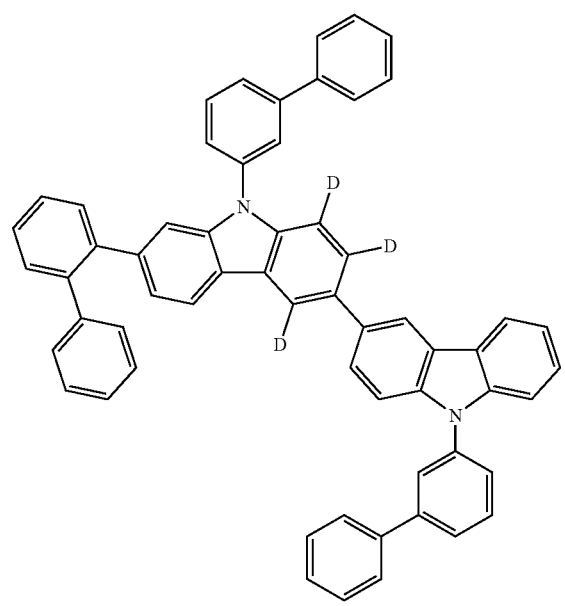

265
-continued
524
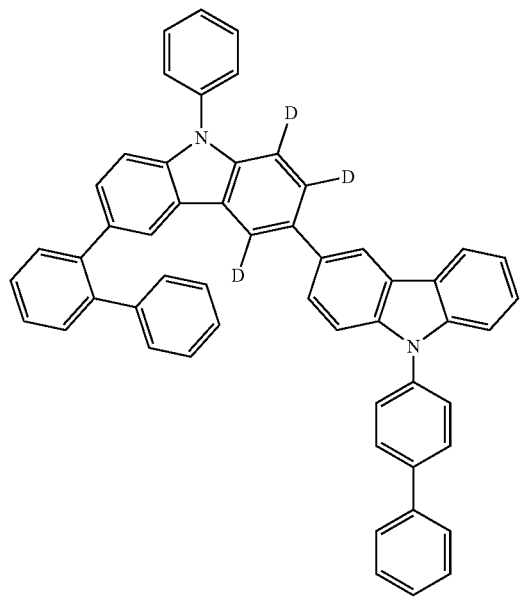
525
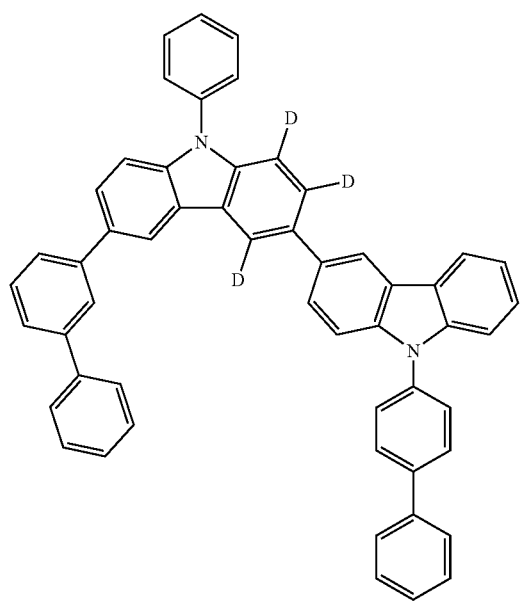
266
-continued
526
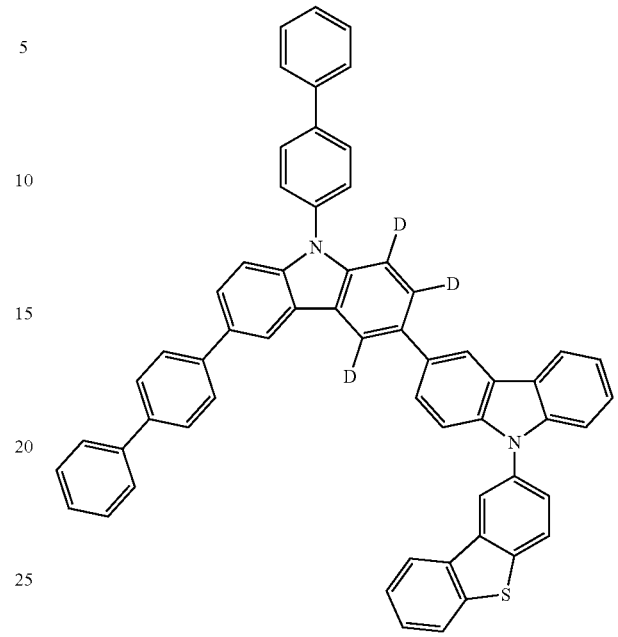
527
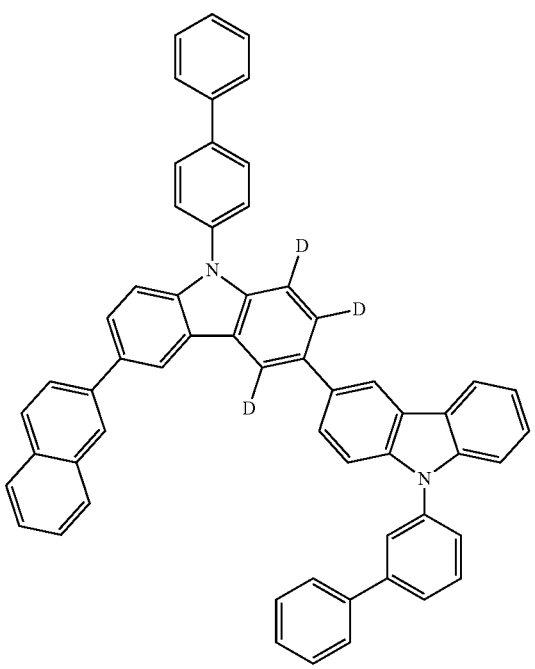

-continued
528
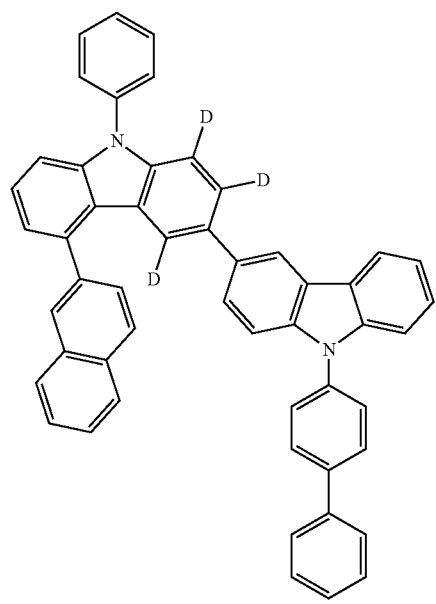
530
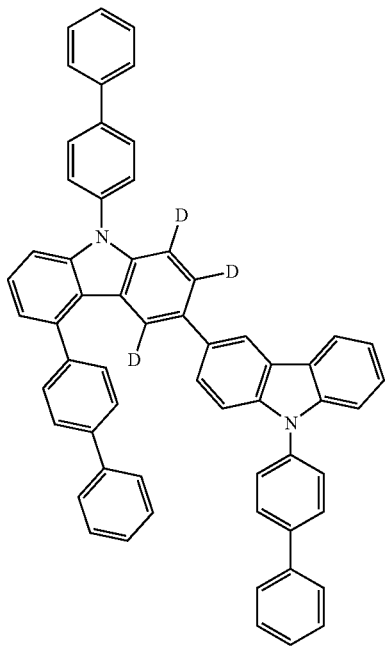
529
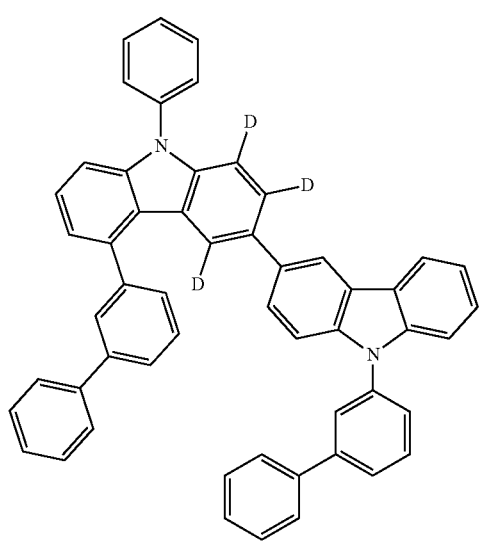
531
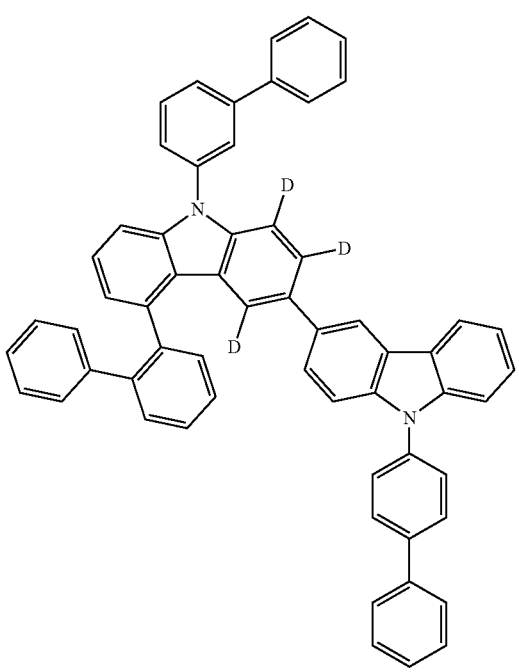

269
-continued
270
-continued
532
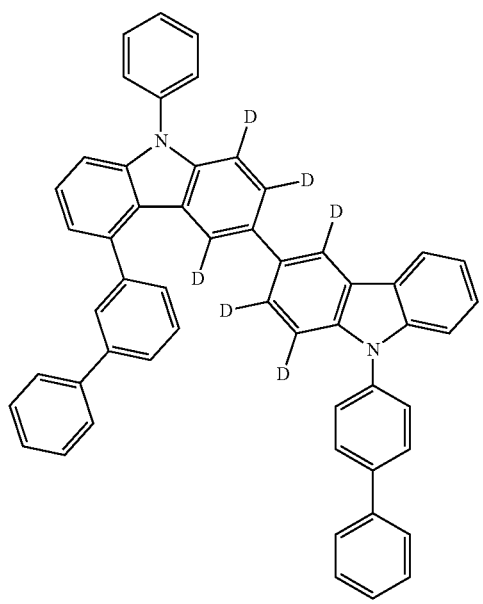
534
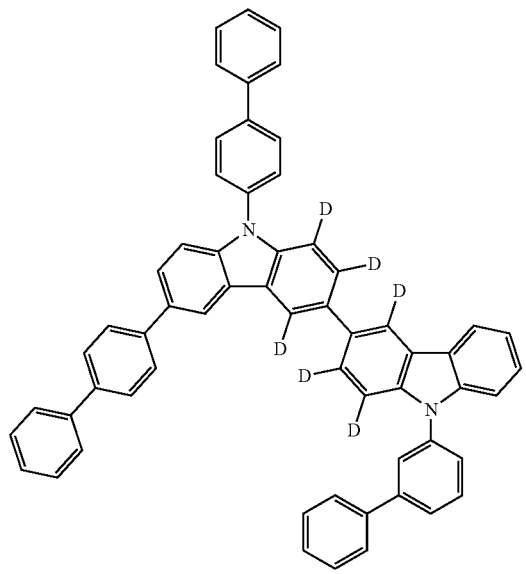
533
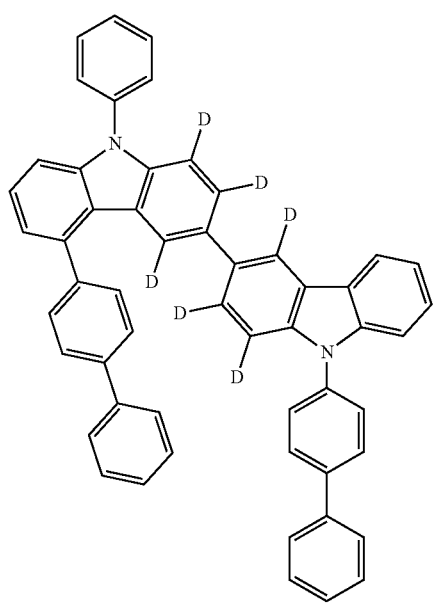
535
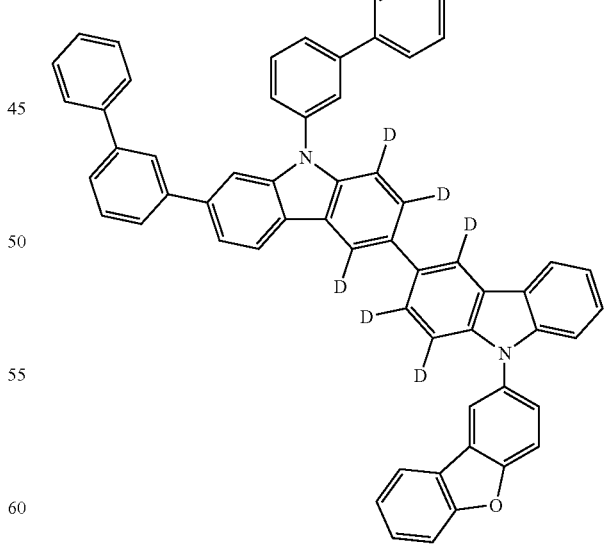

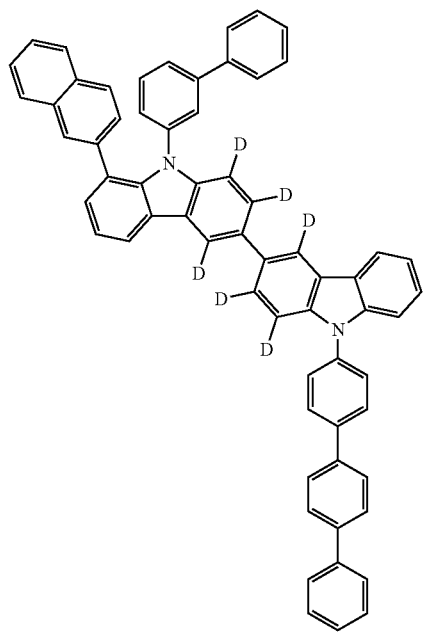
536
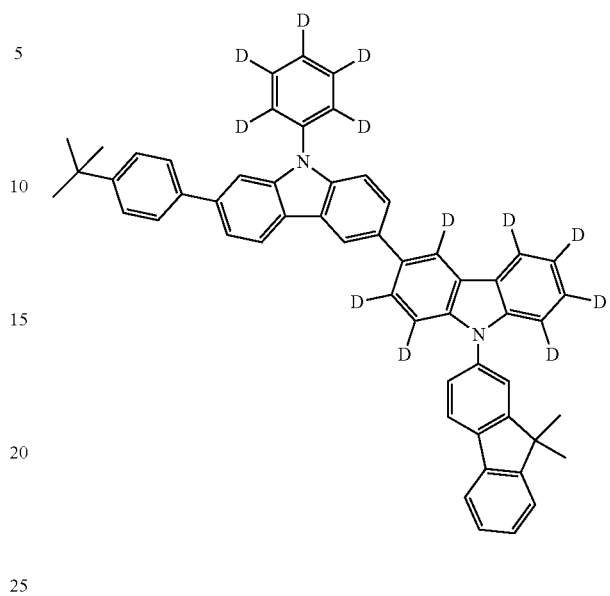
538
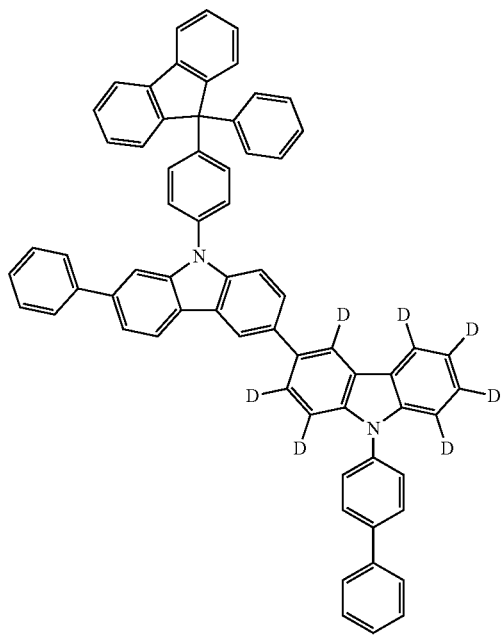
537
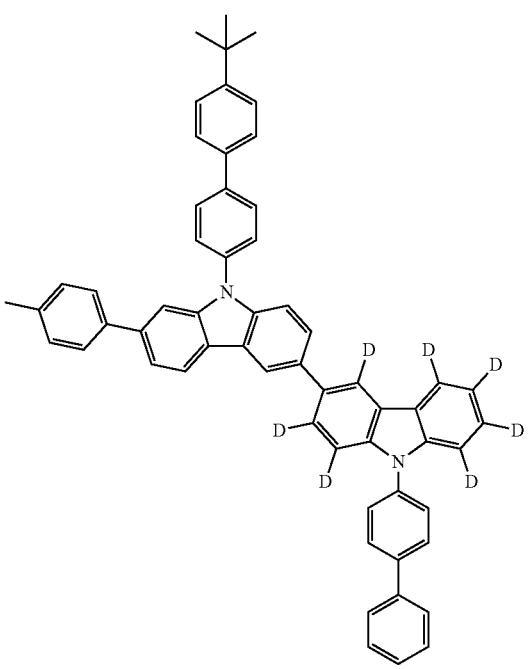
539

540
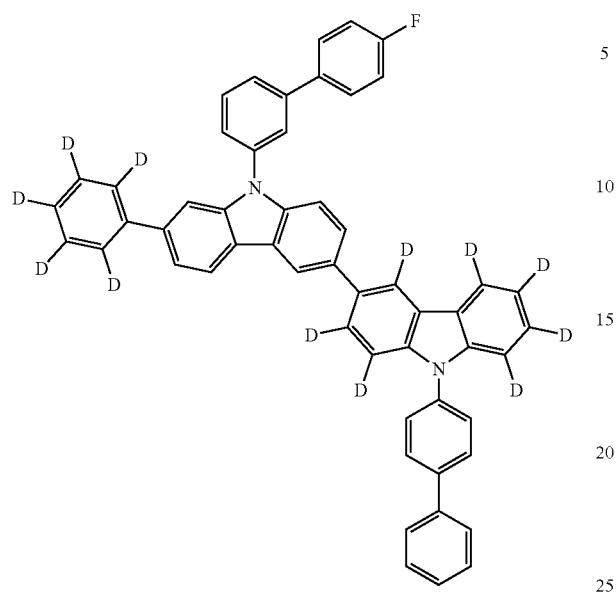
542
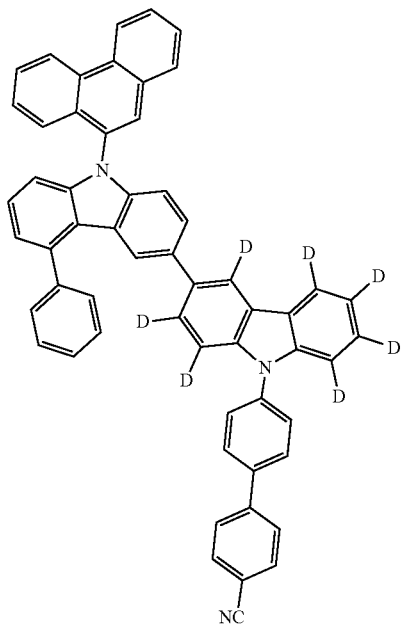
541
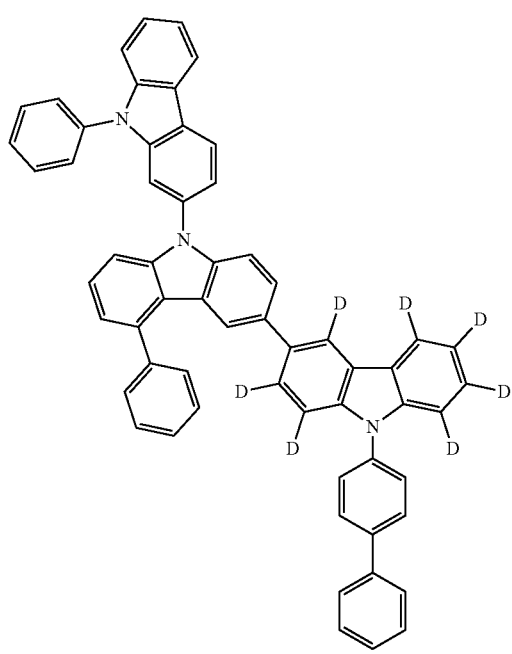
543
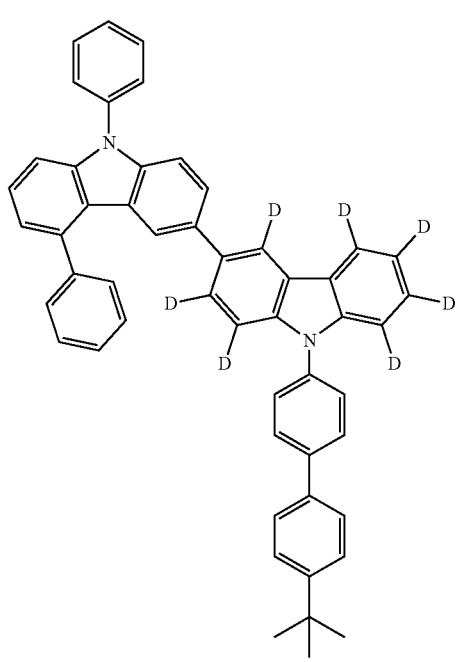

544
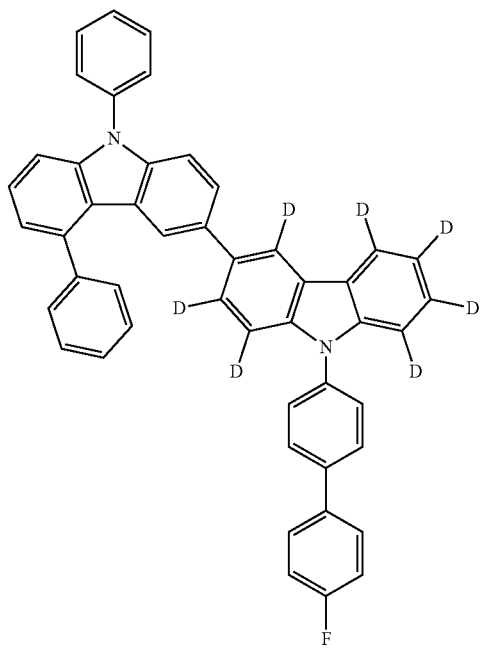
545
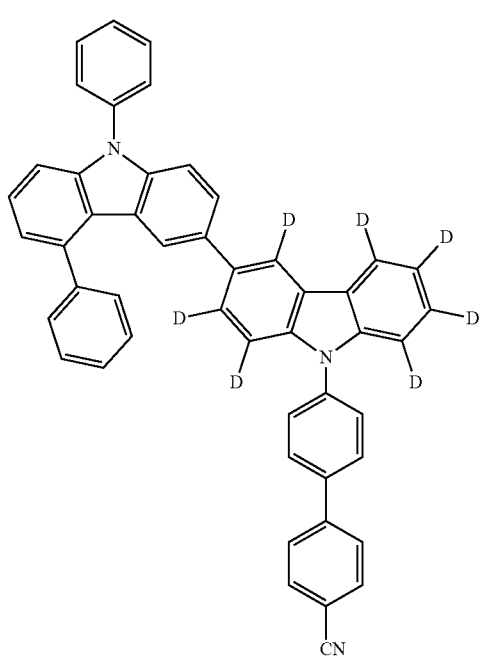
546
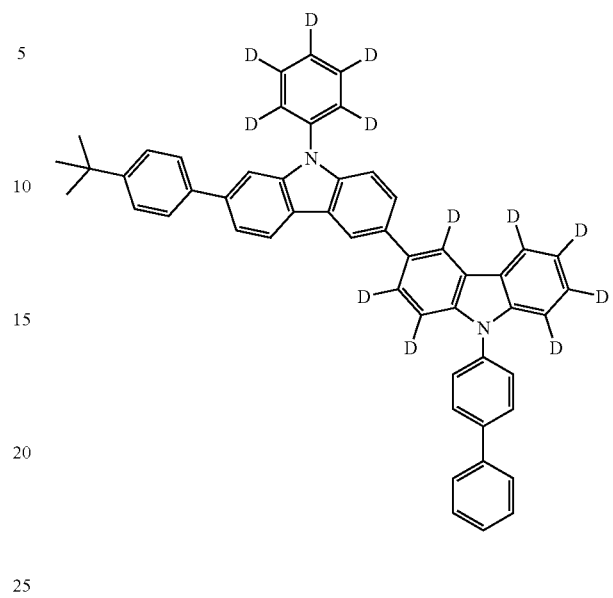
547
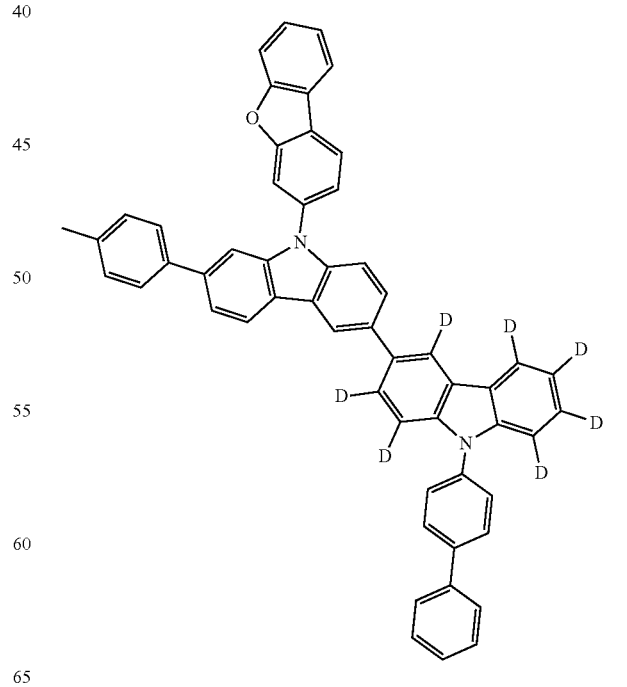

277
-continued
548
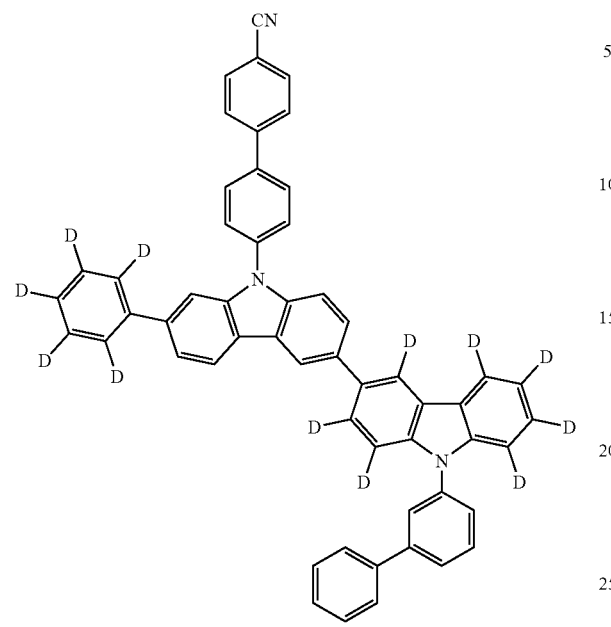
549
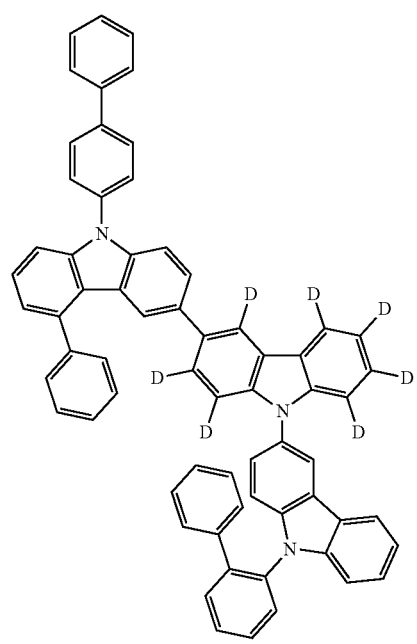
278
-continued
550
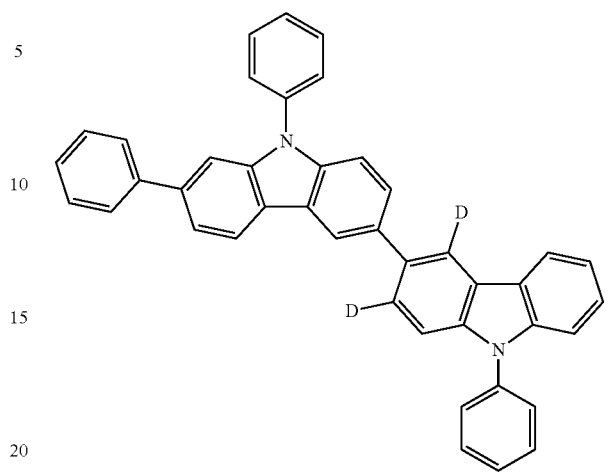
551
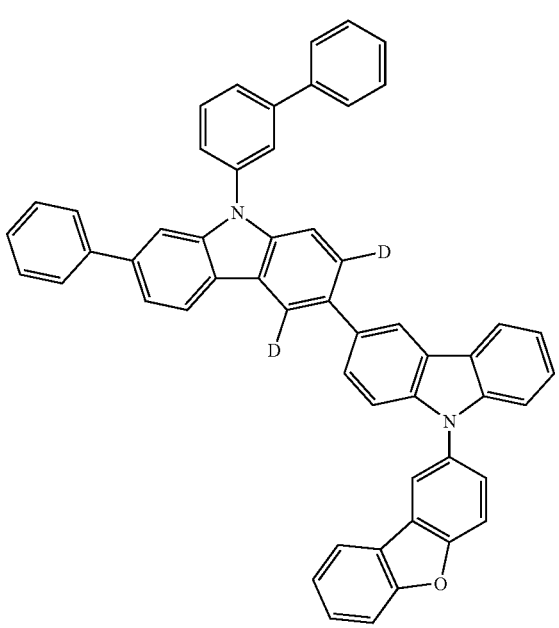

552
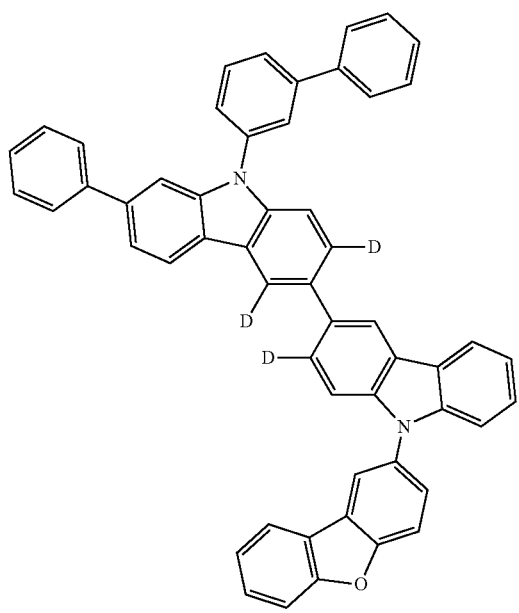
553
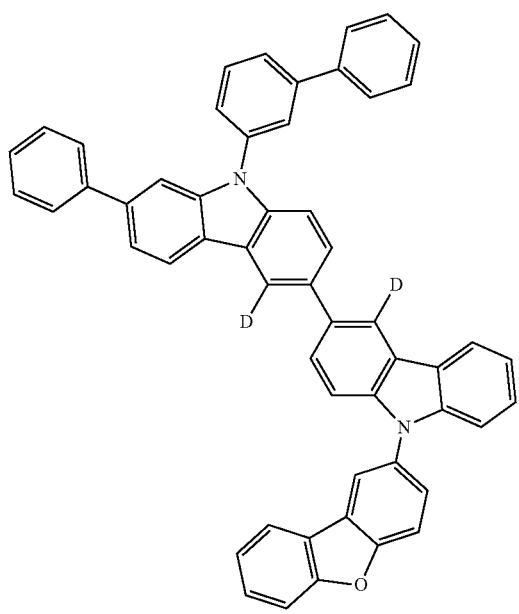
554
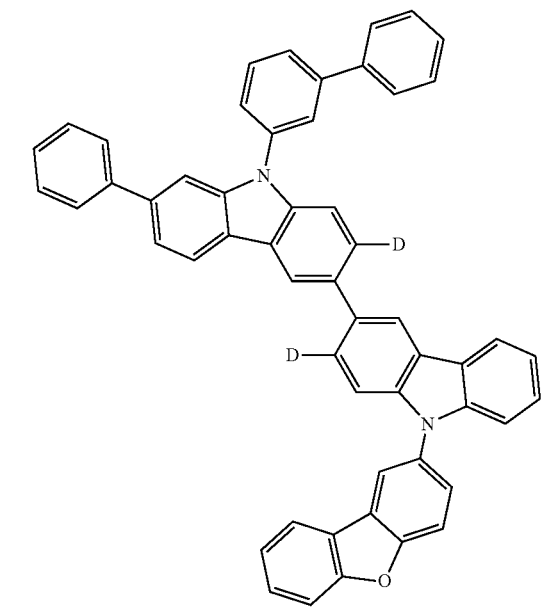
555
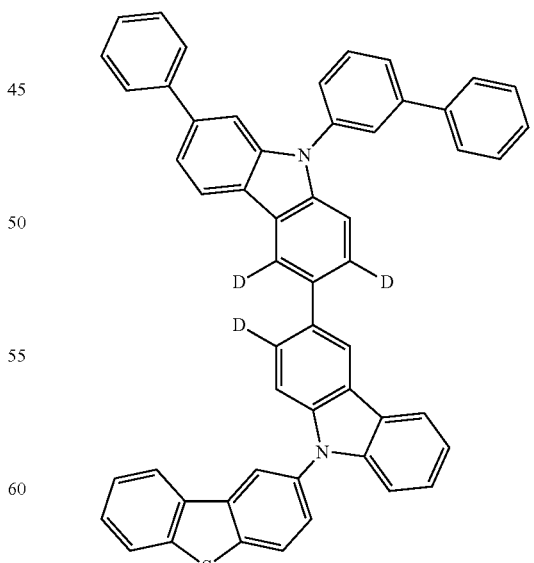

281
-continued
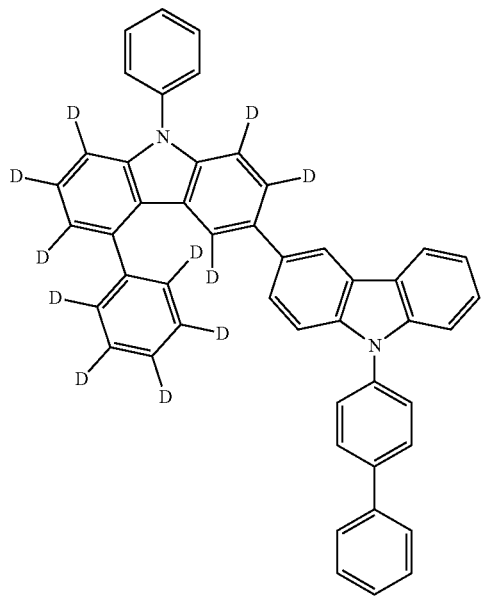
556
557
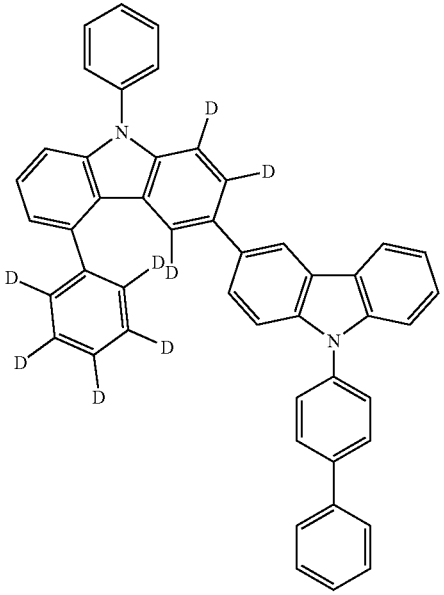
558
559
600
282
-continued
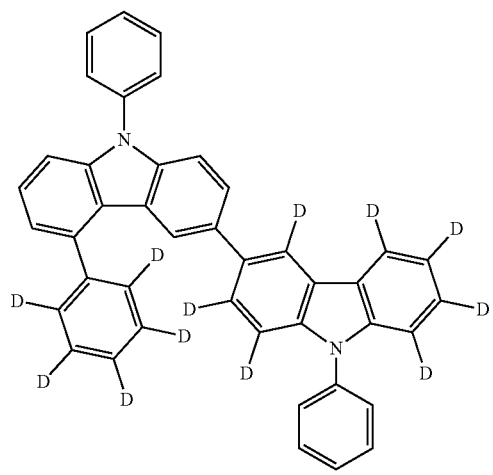
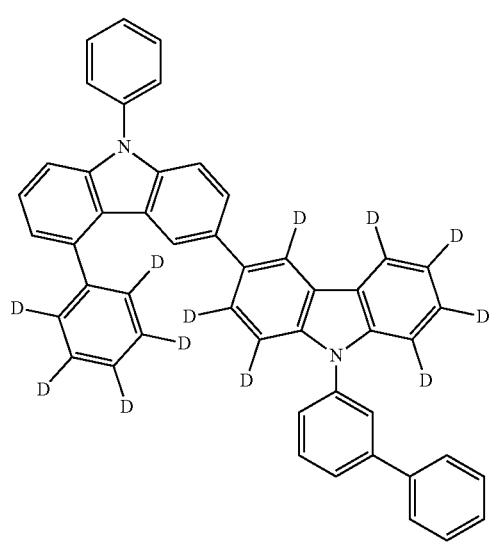

283
-continued
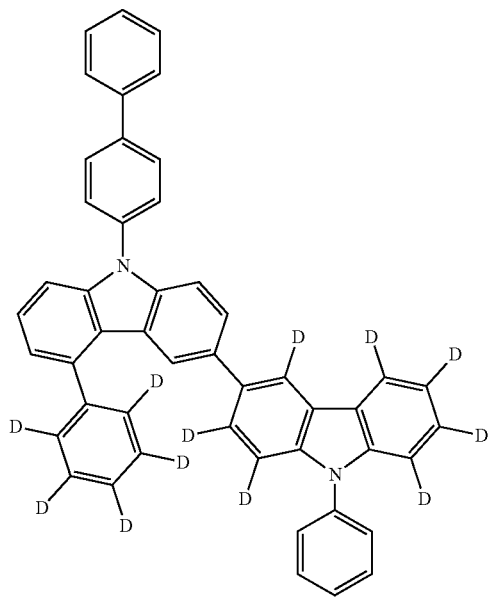
601
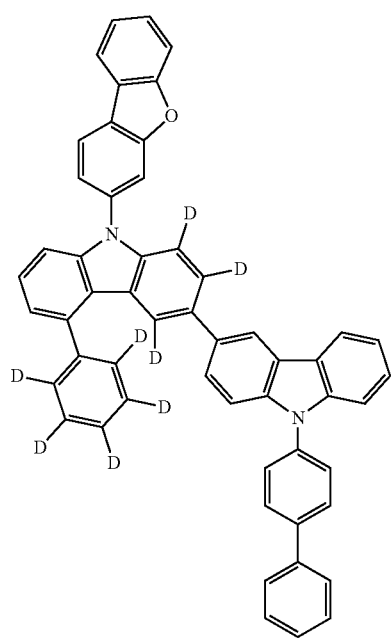
602
284
-continued
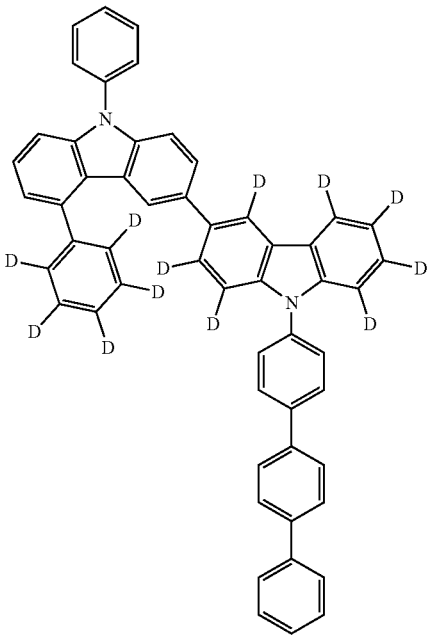
603
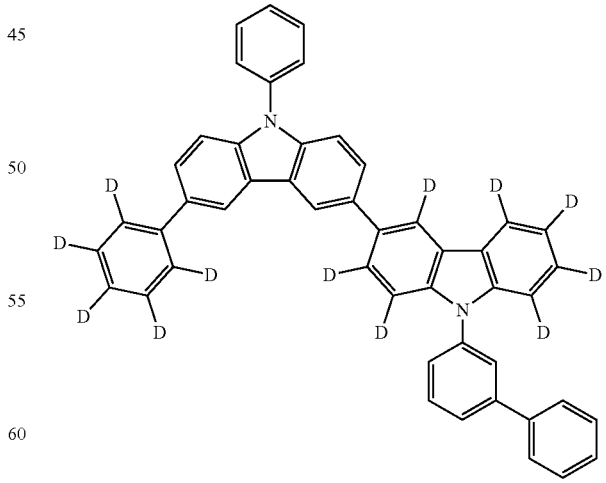
604

605
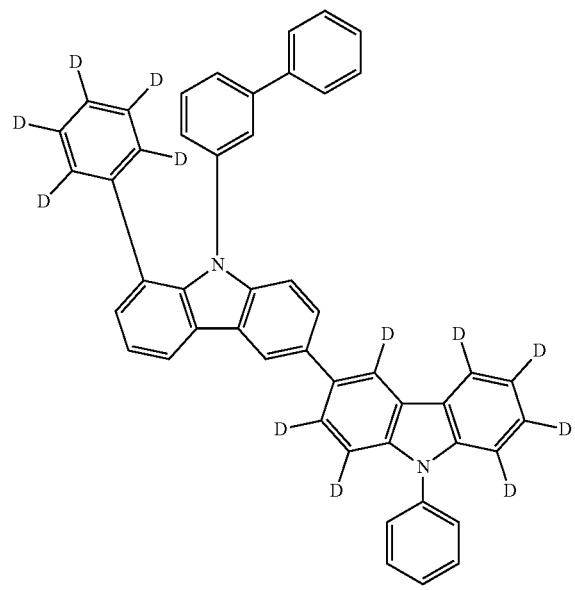
606
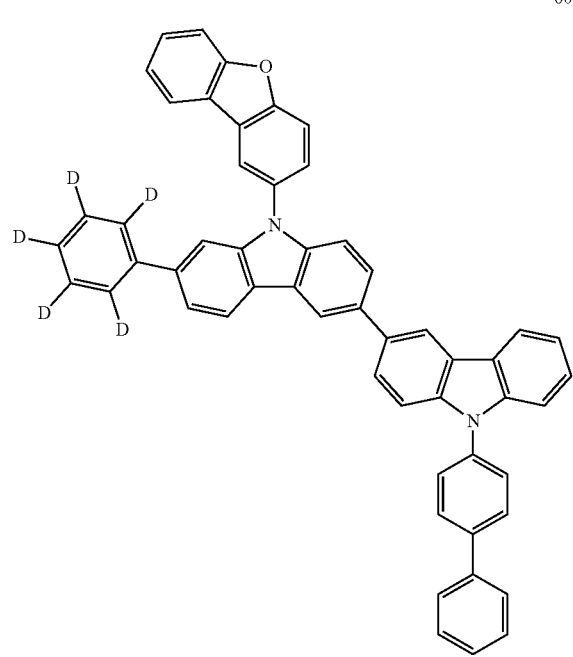
607
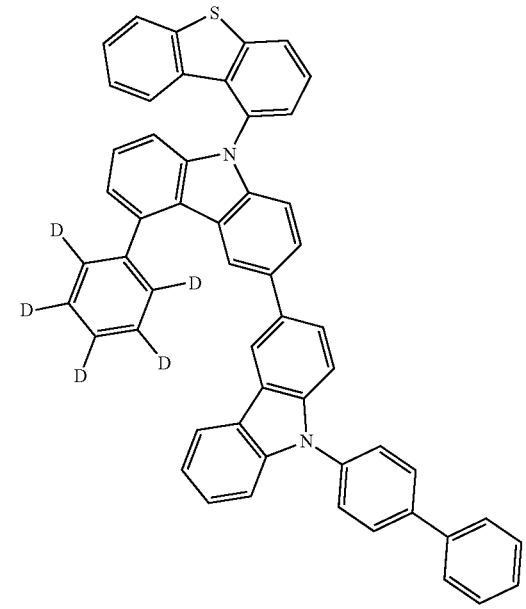
608
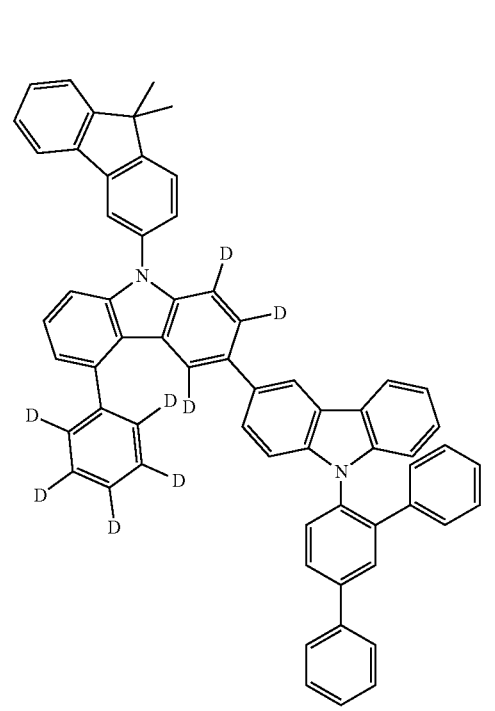

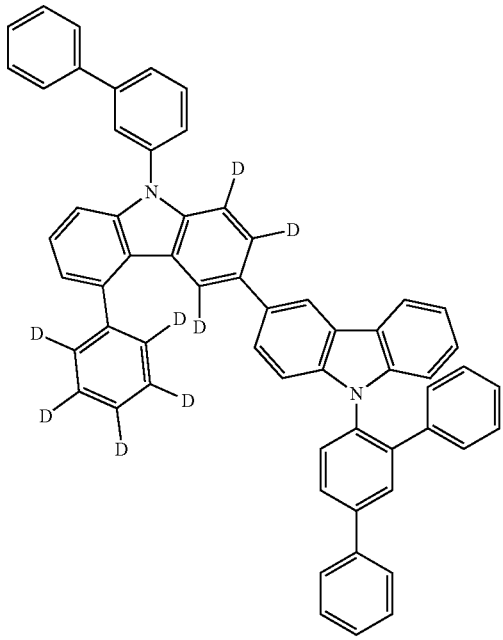

609

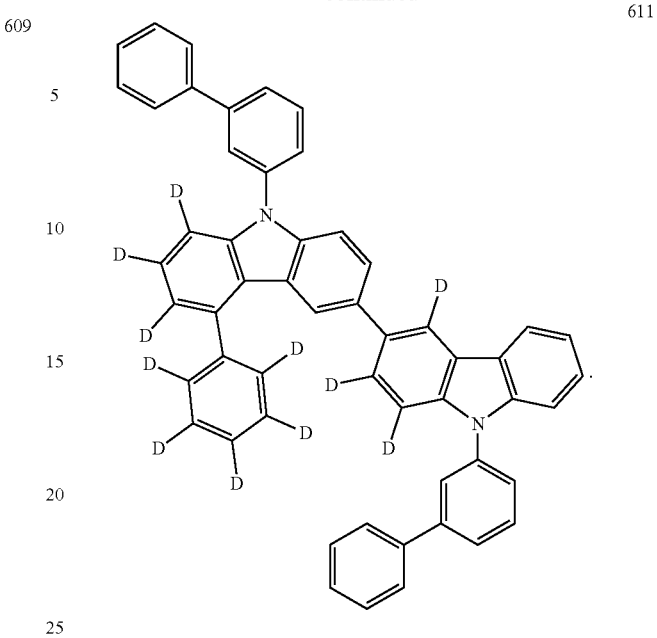

611

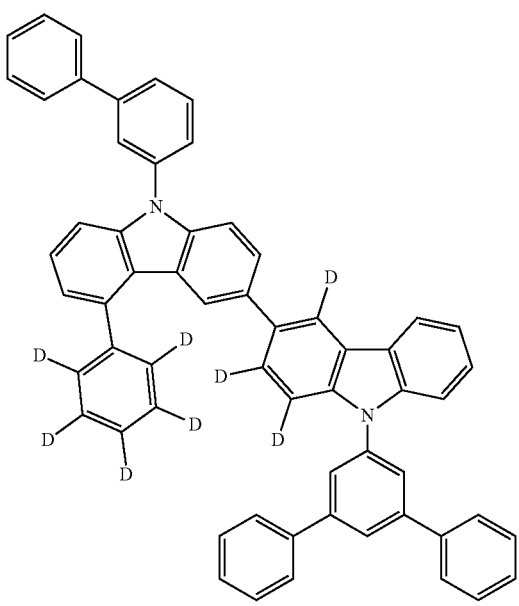

610

The present disclosure also provides an organic electroluminescent device, including an anode and a cathode which are oppositely disposed and at least one functional layer between the anode and the cathode, wherein the functional layer includes the organic compound of the present disclosure.

Further, the functional layer includes an organic light-emitting layer including the organic compound.

In one specific embodiment of the present disclosure, the organic electroluminescent device is a green phosphorescent organic electroluminescent device.

In one specific embodiment of the present disclosure, as shown in FIG. 1, the organic electroluminescent device of the present disclosure includes an anode 100, a cathode 200 and at least one functional layer 300 between the anode layer and the cathode layer. The functional layer 300 may include a hole injection layer 310, a hole transport layer 321, a hole auxiliary layer 322, an organic light-emitting layer 330, an electron transport layer 350, and an electron injection layer 360 which are stacked. The organic light-emitting layer 330 may contain the organic compound according to the first aspect of the present disclosure.

Optionally, the anode 100 includes the following anode materials, which are preferably materials with a large work function that facilitate hole injection into the functional layer. Specific examples of the anode materials include metals such as nickel, platinum, vanadium, chromium, copper, zinc, and gold, or their alloy; metal oxides such as zinc oxide, indium oxide, indium tin oxide (ITO) and indium zinc oxide (IZO); combined metals and oxides, such as ZnO:Al or $SnO_2$:Sb; or a conducting polymers such as poly(3-methylthiophene), poly [3,4-(ethylene-1,2-dioxy)thiophene] (PEDT), polypyrrole, and polyaniline, but are not limited to this. It preferably includes a transparent electrode containing indium tin oxide (ITO) as the anode.

Optionally, the hole transport layer 321 can include one or more hole transport materials, and the hole transport materials may be selected from a carbazole polymers, carbazole-linked triarylamine compounds or other types of compounds, which are not specially limited in the present disclosure. For example, in one embodiment of the present disclosure, the hole transport layer 321 is composed of HT-01.

Optionally, the hole auxiliary layer 322 may include one or more hole transport materials, and the hole transport materials may be selected from a carbazole polymers, carbazole-linked triarylamine compounds or other types of compounds, which are not specially limited in the present disclosure. For example, in one embodiment of the present disclosure, the hole auxiliary layer 322 is composed of HT-02.

Optionally, the organic light-emitting layer 330 may be composed of a single light-emitting material, or may also include a host material and a guest material. Optionally, the organic light-emitting layer 330 is composed of the host material and the guest material, holes injected into the organic light-emitting layer 330 and electrons injected into the organic light-emitting layer 330 can be recombined in the organic light-emitting layer 330 to form excitons, the excitons transfer energy to the host material, the host material transfers energy to the guest material, and then the guest material can emit light.

The guest material of the organic light-emitting layer 330 may be a compound having a condensed aryl ring or its derivative, a compound having a heteroaryl ring or its derivative, an aromatic amine derivative, or other materials, which is not specially limited in the present disclosure.

In one more specific embodiment of the present disclosure, the organic electroluminescent device is a green organic electroluminescent device, and the organic light-emitting layer 330 includes the organic compound described in the present disclosure, GH-N and a guest material Ir(m-ppy)$_3$.

The electron transport layer 350 can be of a single-layer structure or a multi-layer structure, which may include one or more electron transport materials, and the electron transport materials can be selected from a benzimidazole derivative, an oxadiazole derivative, a quinoxaline derivative or other electron transport materials, which are not specially limited in the present disclosure. For example, the electron transport layer 350 may be composed of ET-01 and LiQ.

Optionally, a hole blocking layer 340 may or may not be disposed between the organic light-emitting layer 330 and the electron transport layer 350. The hole blocking layer may include one or more hole blocking materials, which are not specially limited in the present disclosure.

Optionally, the cathode 200 includes the following cathode materials which are materials with a small work function that facilitate electron injection into the functional layer. Specific examples of the cathode materials include metals such as magnesium, calcium, sodium, potassium, titanium, indium, yttrium, lithium, gadolinium, aluminum, silver, tin, lead, or their alloys; or a plurality of layers of materials such as LiF/Al, Liq/Al, LiO$_2$/Al, LiF/Ca, LiF/Al, and BaF$_2$/Ca, but are not limited to this. A metal electrode including silver and magnesium as the cathode is preferably included.

Optionally, the hole injection layer 310 may also be arranged between the anode 100 and the hole transport layer 321 to enhance the ability to inject holes into the hole transport layer 321. The hole injection layer 310 can be made of a benzidine derivative, a starburst arylamine compound, a phthalocyanine derivative or other materials, which is not specially limited in the present disclosure. In one embodiment of the present disclosure, the hole injection layer 310 may be composed of F4-TCNQ.

Optionally, the electron injection layer 360 may also be arranged between the cathode 200 and the electron transport layer 350 to enhance the ability to inject electrons into the electron transport layer 350. The electron injection layer 360 may include an inorganic material such as an alkali metal sulfide and an alkali metal halide, or may include a complex of an alkali metal and an organic substance. In one embodiment of the present disclosure, the electron injection layer 360 may include ytterbium (Yb).

The present disclosure also provides an electronic apparatus, including the organic electroluminescent device described in the present disclosure.

Figure 2:
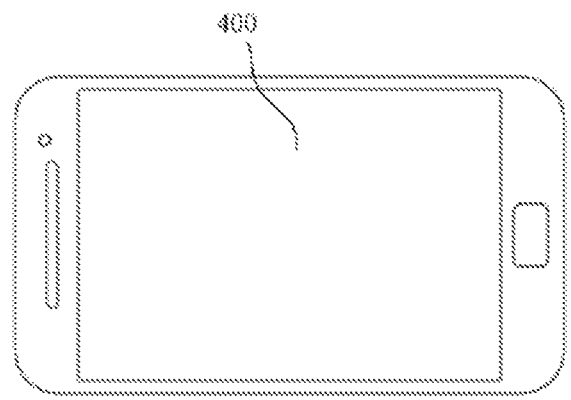
FIG. 2 is a structural schematic diagram of an electronic device according to an embodiment of the present disclosure.

For example, as shown in FIG. 2, the electronic apparatus provided by the present disclosure is an electronic apparatus 400, including the organic electroluminescent device described above. The electronic apparatus can be a display device, a lighting device, an optical communication device or other types of electronic devices, and may include, for example, but is not limited to, a computer screen, a mobile phone screen, a television, electronic paper, an emergency lighting lamp, an optical module and the like. Since the electronic apparatus 400 is provided with the above-described organic electroluminescent device, the electronic apparatus 400 has the same beneficial effects, which will not be repeated here.

The present disclosure will be described in detail with reference to examples, but the following description is intended to explain the present disclosure and is not intended to limit the scope of the present disclosure in any way. The examples only list the synthesis process of some compounds, and other compounds can also be obtained according to similar reaction steps.

Synthesis Examples

In the synthesis examples described below, unless otherwise stated, all temperatures are in degrees Celsius. Some reagents were purchased from commercial suppliers such as Aldrich Chemical Company, Arco Chemical Company and Alfa Chemical Company, and some intermediates that were not directly purchased were prepared from commercially available raw materials by a simple reaction and were used without further purification unless otherwise stated. The rest of the conventional reagents were purchased from Tianjin Haoyuyu chemical Co., Ltd., Tianjin Fuchen chemical reagent factory, Wuhan Xinhuayuan technology development Co., Ltd., Qingdao Tenglong chemical reagent Co., Ltd., Qingdao ocean chemical plant and the like. Reactions in the synthesis examples were generally carried out under a positive pressure of nitrogen or argon or an anhydrous solvent was sleeved with a drying tube (unless otherwise stated); in the reactions, reaction flasks were stoppered with suitable rubber stoppers and substrates were injected into the reaction flasks by a syringe. Each glassware used was dried.

During purification, a chromatographic column was a silica gel column and silica gel (100-200 mesh) was purchased from the Qingdao ocean chemical plant.

In the synthesis examples, low resolution mass spectrometry (MS) data were determined by using Agilent 6120 Quadrupole HPLC-M (column model: Zorbax SB-C18, 2.1× 30 mm, 3.5 μm, 6 min, and a flow rate of 0.6 mL/min). Mobile phase: 5-95% (a ratio of acetonitrile containing 0.1% formic acid in water containing 0.1% formic acid), using electrospray ionization (ESI) at 210 nm/254 nm with UV detection.

Nuclear magnetic resonance hydrogen spectrum: Bruker 400 MHz nuclear magnetic resonance spectrometer with CD$_2$Cl$_2$ as a solvent (in ppm) and TMS (0 ppm) as a reference standard at room temperature.

Synthesis of Intermediate K-1

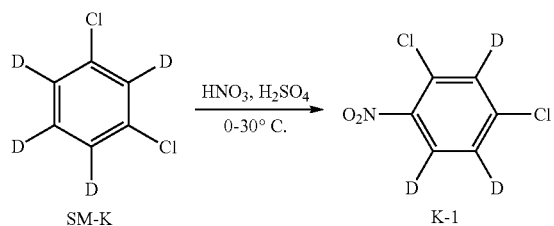

1,3-Dichlorobenzene-D4 (30.0 g, 198.65 mmol) was placed in a four-necked flask, the temperature was controlled at 25° C., fuming nitric acid (13.77 g, 218.51 mmol) and concentrated sulfuric acid (19.48 g, 198.65 mmol) were sequentially added dropwise, after adding dropwise was completed, the mixture was allowed to stand for layering, an organic phase was separated, and dried over anhydrous magnesium sulfate, and a solvent was removed under reduced pressure to obtain an intermediate K-1 (30.99 g; 80%).

Synthesis of Intermediate S-1

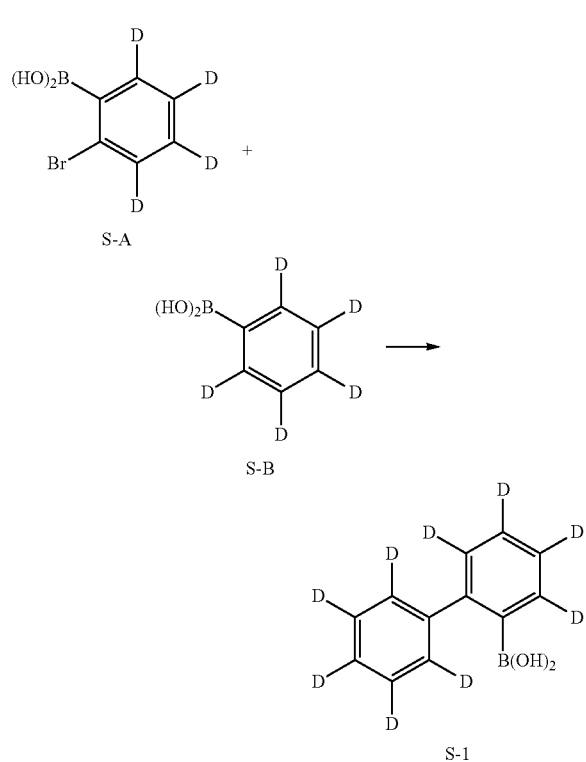

S-A (30 g, 146.41 mmol), S-B (18.59 g, 146.41 mmol), tetrakis(triphenylphosphine)palladium (8.45 g, 7.32 mmol), tetrabutylammonium bromide (2.36 g, 7.32 mmol), potassium carbonate (30.35 g, 219.62 mmol), toluene (240 mL), ethanol (120 mL), and deionized water (60 mL) were added into a dry 500 mL round bottom flask replace with nitrogen, and the mixture was heated to 75 to 80° C. under stirring for 8 h; the reaction mixture was then cooled to room temperature, deionized water (200 mL) was added, stirring was performed for 15 min, an organic phase was separated, and dried over anhydrous magnesium sulfate, and a solvent was removed under reduced pressure; and the obtained crude product was purified by silica gel column chromatography using dichloromethane/n-heptane as a mobile phase to obtain an intermediate S-1 (9.1 g; 30%).

Synthesis of Intermediate A-1

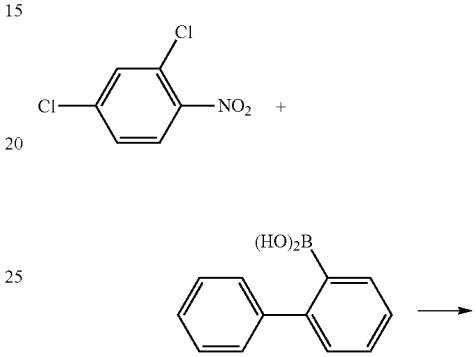

2,4-dichloronitrobenzene (30 g, 156.26 mmol), 2-biphenylboronic acid (34.04 g, 171.88 mmol), tetrakis(triphenylphosphine)palladium (3.6 g, 3.12 mmol), tetrabutylammonium bromide (1.00 g, 3.13 mmol), potassium carbonate (64.79 g, 468.77 mmol), toluene (240 mL), ethanol (120 mL), and deionized water (60 mL) were added into a dry 500 mL round bottom flask replaced with nitrogen, and the mixture was heated to 75 to 80° C. under stirring for 8 h; the reaction mixture was then cooled to room temperature, deionized water (200 mL) was added, stirring was performed for 15 min, an organic phase was separated, and dried over anhydrous magnesium sulfate, and a solvent was removed under reduced pressure; and the obtained crude product was purified by silica gel column chromatography using dichloromethane/n-heptane in a ratio of 1:6 as a mobile phase to obtain an intermediate A-1 (33.87 g; 70%).

Referring to the synthesis method of intermediate A-1, raw material 1 in Table 1 replaces 2,4-dichloronitrobenzene, and SM-X replaced 2-biphenylboronic acid, and intermediate A-X in Table 1 was synthesized:

TABLE 1
| Raw material 1 | SM-X | Intermediate A-X | Yield (%) |
|---|---|---|---|
| 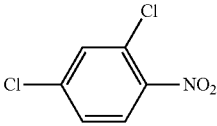 | 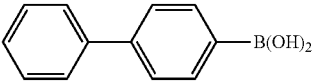 | 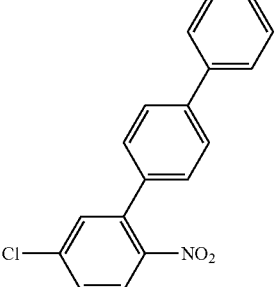<br>A-2 | 73 |
| | 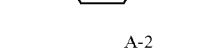 | <br>A-3 | 68 |
| 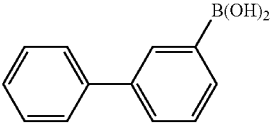 [SMILES: OB(O)c1cccc(-c2ccccc2)c1]<br>K-1 | 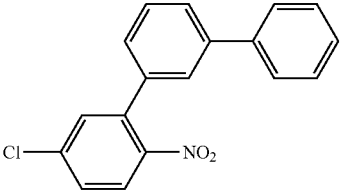 | <br>A-4 | 72 |
|  | 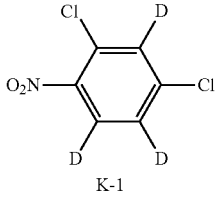 | 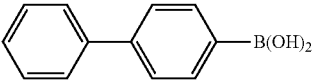 [SMILES: OB(O)c1ccc(-c2ccccc2)cc1]<br>A-5 | 70 |
| 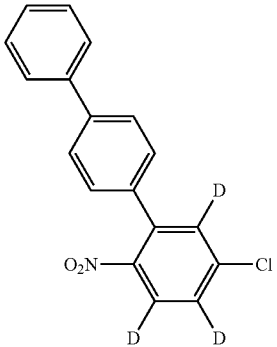 [SMILES: [2H]c1c([2H])c([N+](=O)[O-])c(-c2ccc(-c3ccccc3)cc2)c([2H])c1Cl] |  | <br>A-6 | 65 |

TABLE 1-continued
| Raw material 1 | SM-X | Intermediate A-X | Yield (%) |
|---|---|---|---|
| 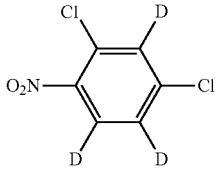 [SMILES: [2H]c1c([2H])c([N+](=O)[O-])c(Cl)c([2H])c1Cl] | 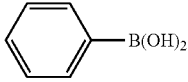 | 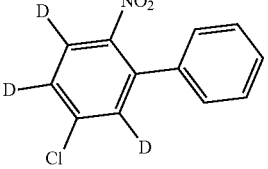<br>A-7 | 74 |
| 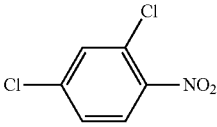 [SMILES: O=[N+]([O-])c1ccc(Cl)cc1Cl] | 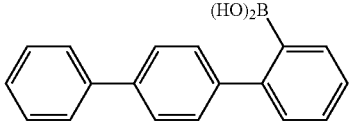 | 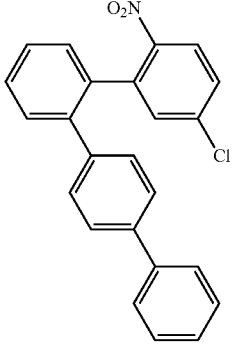 [SMILES: O=[N+]([O-])c1ccc(Cl)cc1-c1ccccc1-c1ccc(-c2ccccc2)cc1]<br>A-8 | 66 |
| 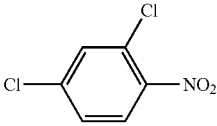 [SMILES: O=[N+]([O-])c1ccc(Cl)cc1Cl] | 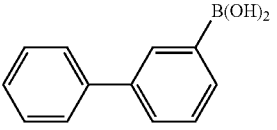 | 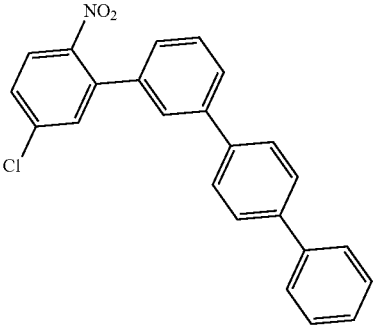 [SMILES: O=[N+]([O-])c1ccc(Cl)cc1-c1cccc(-c2ccc(-c3ccccc3)cc2)c1]<br>A-9 | 62 |
| 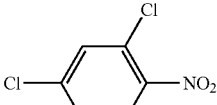 | 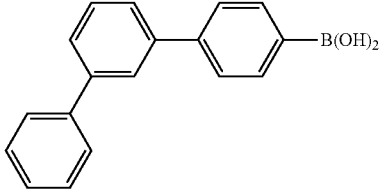 | 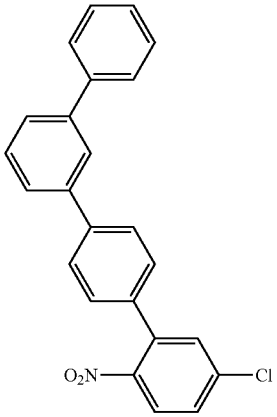 [SMILES: O=[N+]([O-])c1ccc(Cl)cc1-c1ccc(-c2cccc(-c3ccccc3)c2)cc1]<br>A-10 | 60 |

TABLE 1-continued
| Raw material 1 | SM-X | Intermediate A-X | Yield (%) |
|---|---|---|---|
| 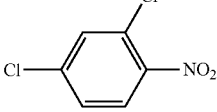 | 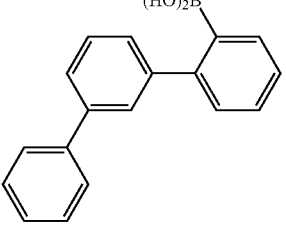 | 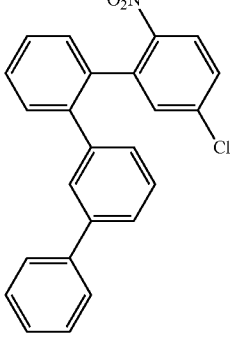<br>A-11 | 59 |
| 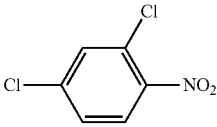 | 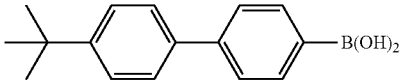 | 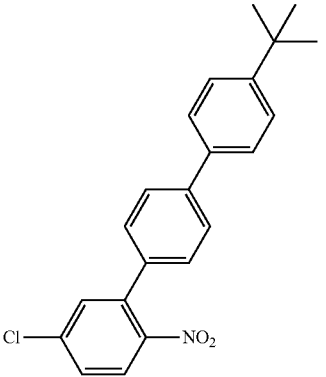 [SMILES: CC(C)(C)c1ccc(-c2ccc(-c3cc(Cl)ccc3[N+](=O)[O-])cc2)cc1]<br>A-12 | 63 |
| 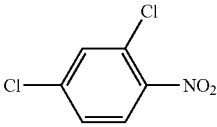 [SMILES: O=[N+]([O-])c1ccc(Cl)cc1Cl] | 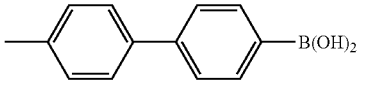 | 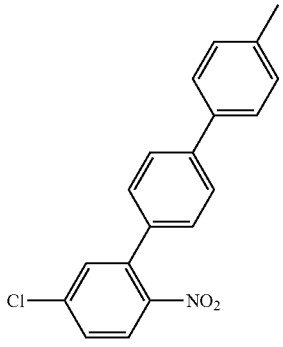 [SMILES: Cc1ccc(-c2ccc(-c3cc(Cl)ccc3[N+](=O)[O-])cc2)cc1]<br>A-13 | 55 |
| 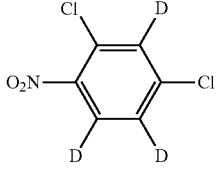 [SMILES: [2H]c1c([2H])c([N+](=O)[O-])c(Cl)c([2H])c1Cl] | 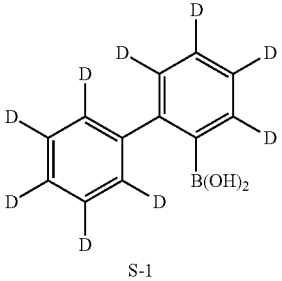<br>S-1 | 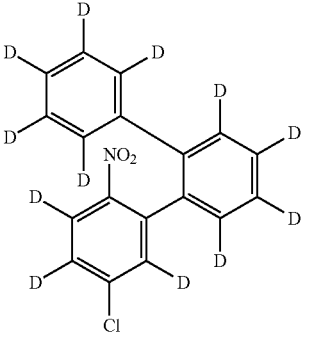 [SMILES: [2H]c1c([2H])c([2H])c(-c2c([2H])c([2H])c([2H])c([2H])c2-c2c([2H])c(Cl)c([2H])c([2H])c2[N+](=O)[O-])c([2H])c1[2H]]<br>A-15 | 60 |

TABLE 1-continued

| Raw material 1 | SM-X | Intermediate A-X | Yield (%) |
|---|---|---|---|
| (structure) | S-2 | A-16 | 58 |
| (structure) | S-2 | A-17 | 62 |

Synthesis of Intermediate B-1

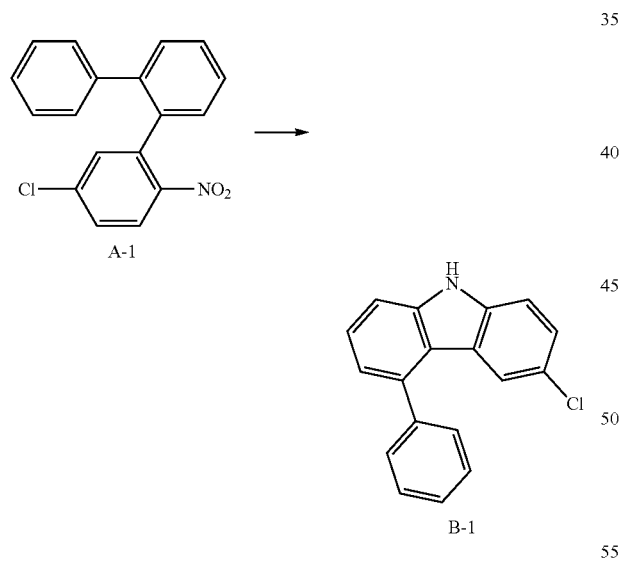

The intermediate A-1 (30 g, 96.85 mmol), triphenylphosphine (63.51 g, 242.14 mmol), and ortho-dichlorobenzene (300 mL) were added into a dry round bottom flask replaced with nitrogen, and the mixture was heated to 170° C. under stirring for 18 h; the reaction mixture was then cooled to room temperature, ortho-dichlorobenzene was removed by atmospheric distillation, toluene (200 mL) was added, stirring was performed for 15 min, and a solvent was removed under reduced pressure; and the obtained crude product was purified by silica gel column chromatography using dichloromethane/n-heptane as a mobile phase to obtain an intermediate B-1 (13.45 g; 50%).

Referring to the synthesis method of intermediate B-1, replaced intermediate A-1 with intermediate A-1 to synthesize intermediate B-X in the table 2:
TABLE 2
| Intermediate A-X | Intermediate B-X | Yield (%) |
|---|---|---|
| 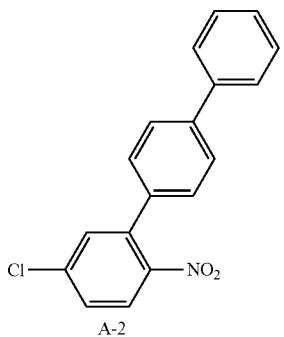<br>A-2 | 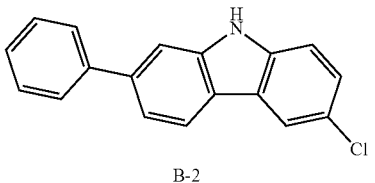<br>B-2 | 49 |
| 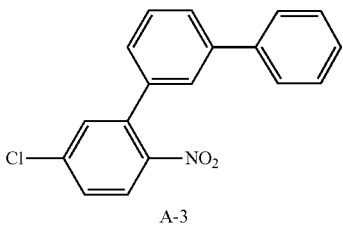<br>A-3 | 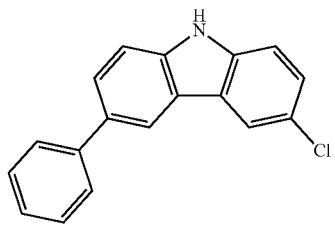<br>B-3 | 21 |
|  | 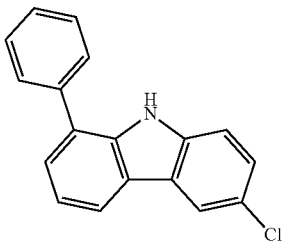<br>B-4 | 23 |
| 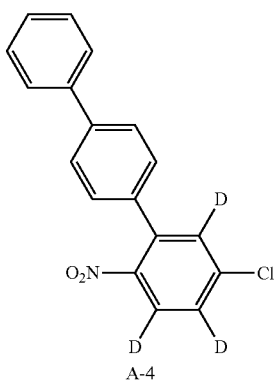<br>A-4 | 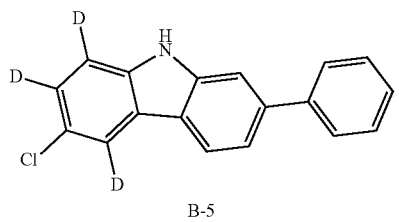<br>B-5 | 48 |
| 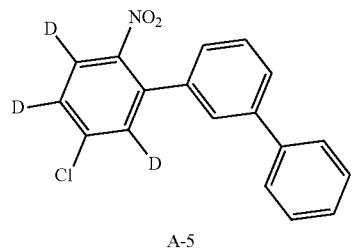 [SMILES: [2H]c1c([2H])c([N+](=O)[O-])c(-c2cccc(-c3ccccc3)c2)c([2H])c1Cl ; "A-5"]<br>A-5 | 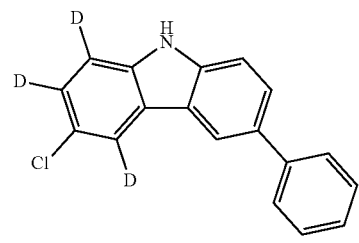<br>B-6 | 24 |

TABLE 2-continued

| Intermediate A-X | Intermediate B-X | Yield (%) |
|---|---|---|
| A-5 | B-7 | 20 |
| A-6 | B-8 | 50 |
| A-7 | B-9 | 46 |
| A-8 | B-10 | 40 |
| A-9 | B-11 | 25 |

TABLE 2-continued
| Intermediate A-X | Intermediate B-X | Yield (%) |
|---|---|---|
| 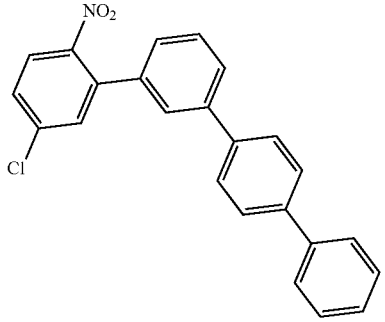<br>A-9 | 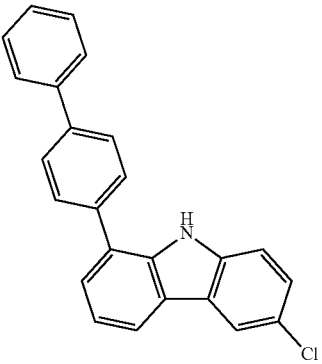<br>B-12 | 20 |
| 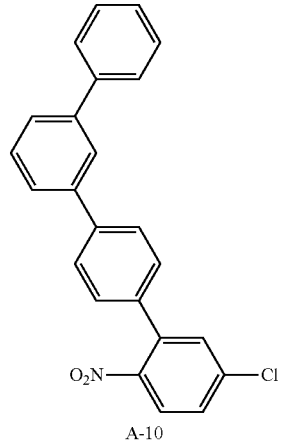<br>A-10 | 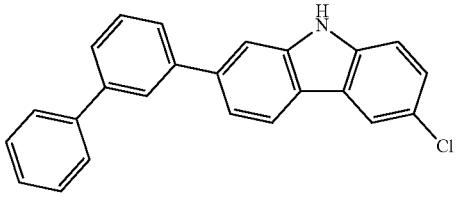<br>B-13 | 43 |
| 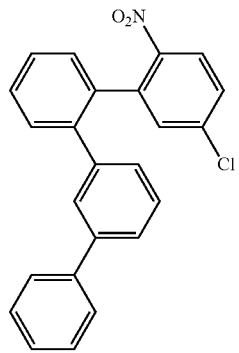<br>A-11 | 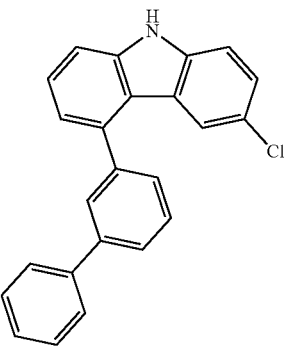<br>B-14 | 45 |

TABLE 2-continued

| Intermediate A-X | Intermediate B-X | Yield (%) |
|---|---|---|
| A-12 | B-15 | 50 |
| A-13 | B-16 | 47 |
| A-14 | B-17 | 45 |
| A-15 | B-18 | 38 |

TABLE 2-continued

| Intermediate A-X | Intermediate B-X | Yield (%) |
|---|---|---|
| A-16 | B-19 | 35 |
| A-17 | B-20 | 39 |

Synthesis of intermediate C-1

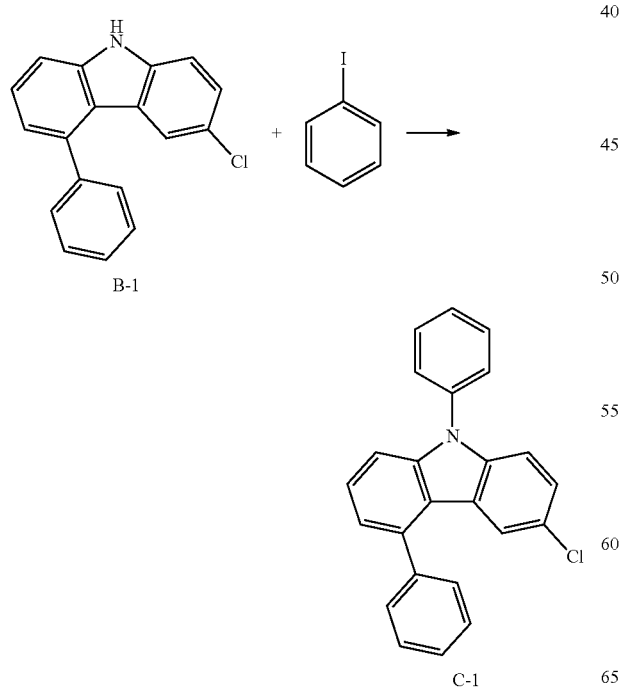

The intermediate B-1 (15 g, 54.0 mmol), iodobenzene (16.53 g, 81.0 mmol), cuprous iodide (1.03 g, 5.4 mmol), potassium carbonate (18.63 g, 135.01 mmol), o-phenanthroline (0.54 g, 2.7 mmol), 18-crown-6 (1.43 g, 5.4 mmol), and DMF (150 mL) were added into a dry round bottom flask replaced with nitrogen, and the mixture was heated to 150° C. under stirring for 16 h; the reaction mixture was then cooled to room temperature, ethyl acetate (200 mL) and deionized water (200 mL) were added, stirring was performed for 15 min, an organic phase was separated, and dried over anhydrous magnesium sulfate, and a solvent was removed under reduced pressure; and the obtained crude product was purified by silica gel column chromatography using dichloromethane/n-heptane as a mobile phase to obtain an intermediate C-1 (12.4 g; 65%).

Referring to the synthesis method of intermediate C-1, intermediate B-X in Table 3 below replaced intermediate B-1, raw material 2 replaced iodobenzene, and intermediate C-X in Table 3 below was synthesized:

TABLE 3

| Intermediate B-X | Raw material 2 | Intermediate C-X | Yield % |
|---|---|---|---|
| B-1 | 4-iodobiphenyl | C-2 | 58 |
| B-1 | 3-iodobiphenyl | C-3 | 62 |
| B-1 | 2-iodobiphenyl | C-4 | 65 |

TABLE 3-continued
| Intermediate B-X | Raw material 2 | Intermediate C-X | Yield % |
|---|---|---|---|
| 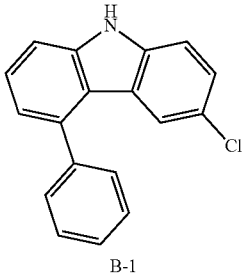<br>B-1 | 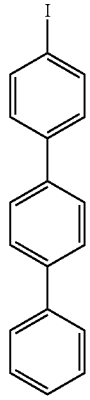 [SMILES: Ic1ccc(-c2ccc(-c3ccccc3)cc2)cc1] | 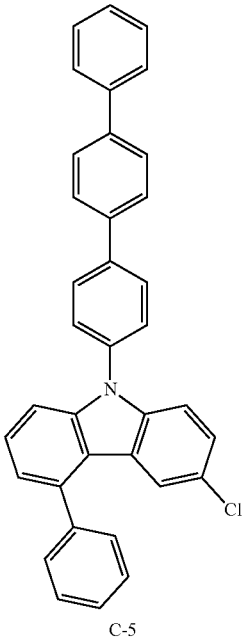<br>C-5 | 55 |
| 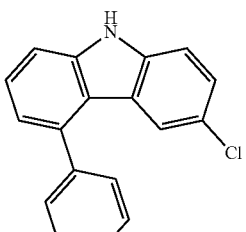<br>B-1 | 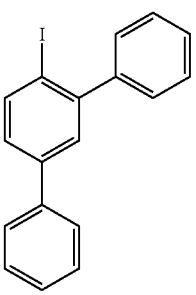 [SMILES: Ic1ccc(-c2ccccc2)cc1-c1ccccc1] | 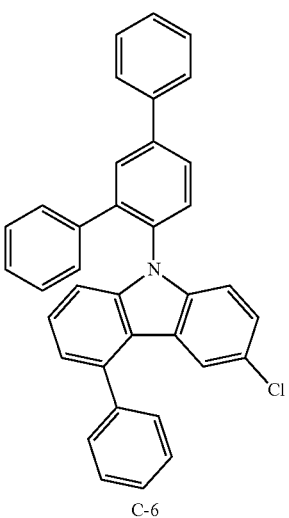<br>C-6 | 53 |

TABLE 3-continued
| Intermediate B-X | Raw material 2 | Intermediate C-X | Yield % |
|---|---|---|---|
| 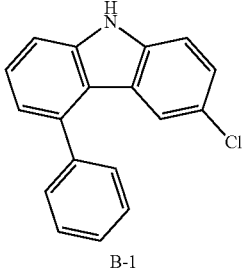 B-1 | 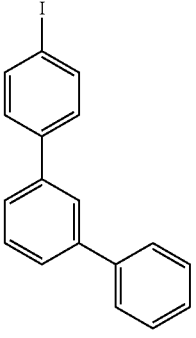 [SMILES: Ic1ccc(-c2cccc(-c3ccccc3)c2)cc1] | 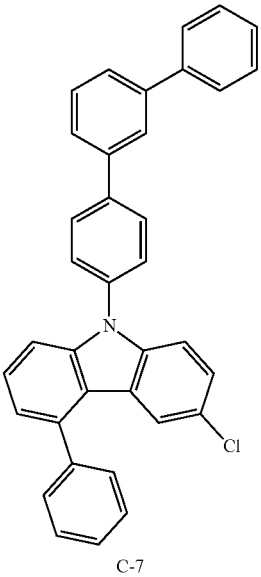 C-7 | 50 |
| 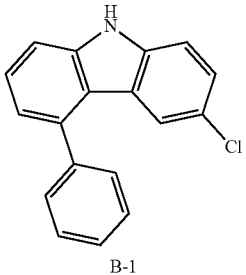 B-1 | 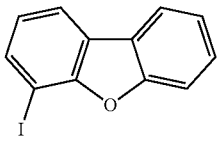 [SMILES: Ic1cccc2c1oc1ccccc12] | 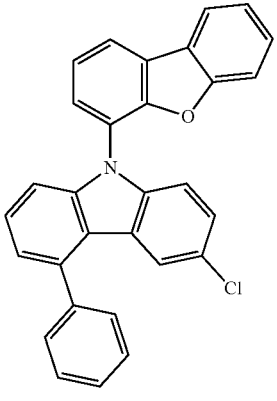 C-8 | 61 |
| 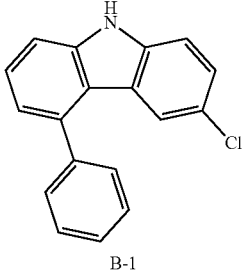 B-1 | 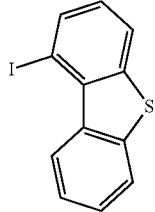 [SMILES: Ic1cccc2sc3ccccc3c12] | 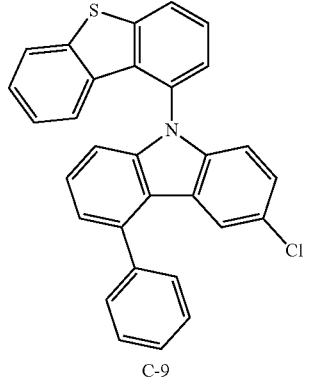 C-9 | 58 |

TABLE 3-continued
| Intermediate B-X | Raw material 2 | Intermediate C-X | Yield % |
|---|---|---|---|
| 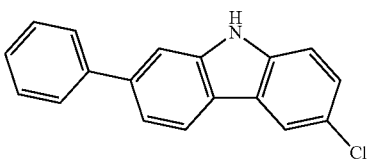 B-2 | 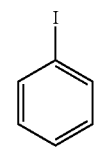 | 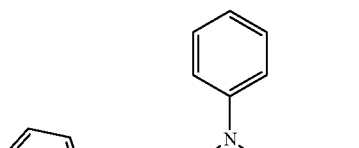 C-10 | 68 |
| 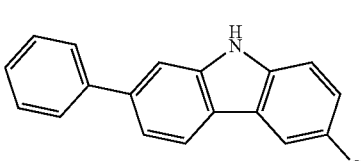 B-2 | 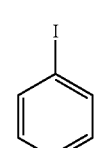 | 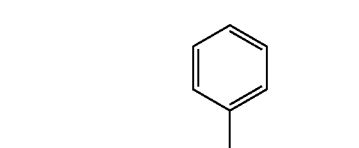 C-11 | 63 |
| 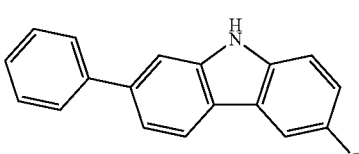 B-2 | 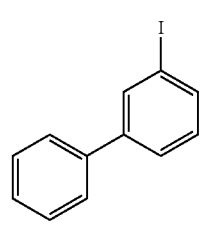 [SMILES: Ic1cccc(-c2ccccc2)c1] | 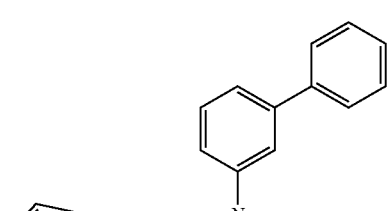 C-12 | 64 |
| 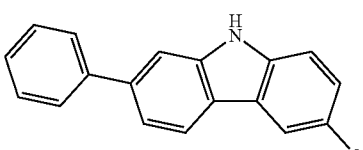 B-2 | 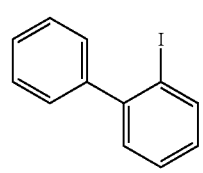 [SMILES: Ic1ccccc1-c1ccccc1] | 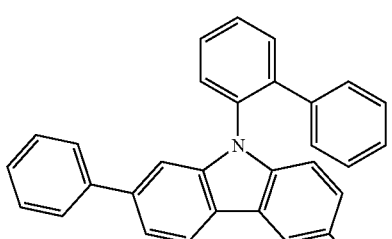 C-13 | 58 |

TABLE 3-continued
| Intermediate B-X | Raw material 2 | Intermediate C-X | Yield % |
|---|---|---|---|
| 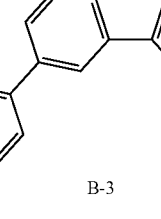 B-3 | 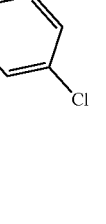 | 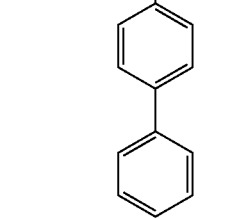 C-14 | 61 |
|  B-3 |  |  C-15 | 62 |
| 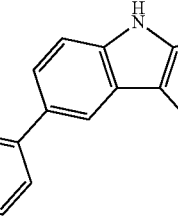 B-3 | 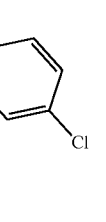 | 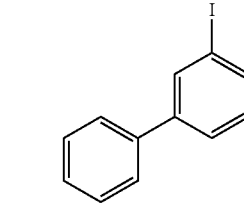 C-16 | 61 |

TABLE 3-continued

| Intermediate B-X | Raw material 2 | Intermediate C-X | Yield % |
|---|---|---|---|
| B-4 | 4-iodobiphenyl | C-17 | 60 |
| B-4 | 3-iodobiphenyl | C-18 | 65 |
| B-4 | 2-iodobiphenyl | C-19 | 61 |
| B-5 | 4-iodobiphenyl | C-20 | 63 |

TABLE 3-continued

| Intermediate B-X | Raw material 2 | Intermediate C-X | Yield % |
|---|---|---|---|
| B-6 | (3-iodobiphenyl) | C-21 | 65 |
| B-7 | (iodobenzene) | C-22 | 60 |
| B-8 | (iodobenzene) | C-23 | 61 |
| B-9 | (4-iodobiphenyl) | C-24 | 62 |

TABLE 3-continued

| Intermediate B-X | Raw material 2 | Intermediate C-X | Yield % |
|---|---|---|---|
| B-9 | iodobenzene | C-25 | 59 |
| B-10 | iodobenzene | C-26 | 57 |
| B-10 | 4-iodobiphenyl | C-27 | 60 |

TABLE 3-continued
| Intermediate B-X | Raw material 2 | Intermediate C-X | Yield % |
|---|---|---|---|
| 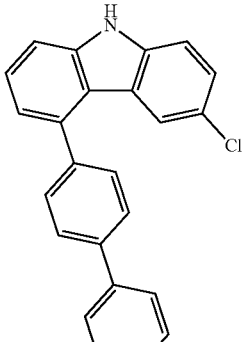 B-10 | 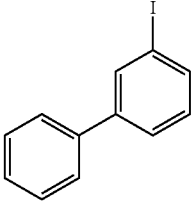 [SMILES: Ic1cccc(-c2ccccc2)c1] | 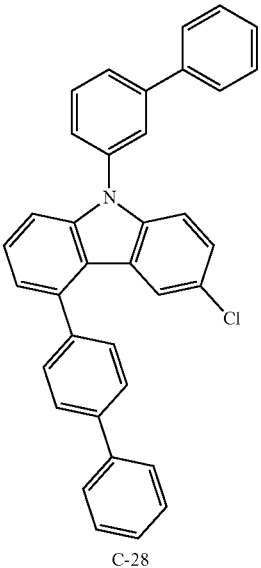 C-28 | 63 |
| 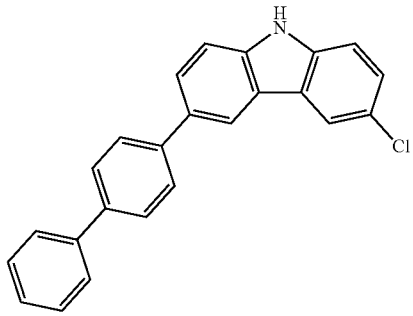 B-11 | 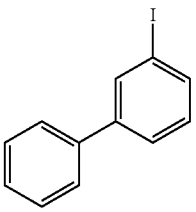 [SMILES: Ic1cccc(-c2ccccc2)c1] | 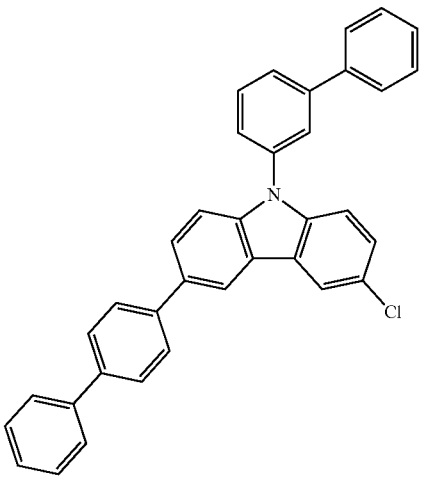 C-29 | 61 |
| 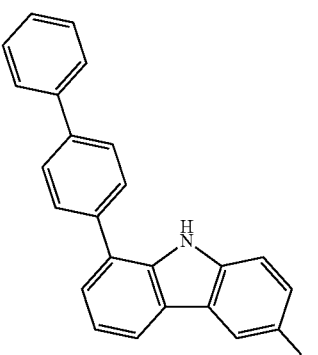 B-12 | 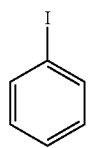 | 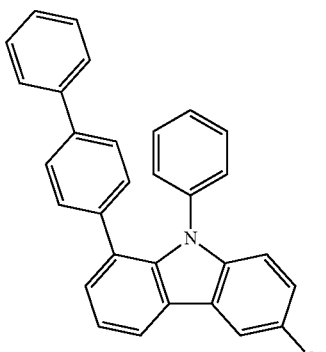 C-30 | 60 |

TABLE 3-continued
| Intermediate B-X | Raw material 2 | Intermediate C-X | Yield % |
|---|---|---|---|
| 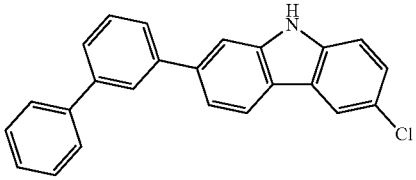 B-13 | 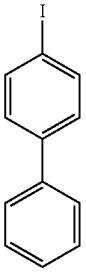 [SMILES: Ic1ccc(-c2ccccc2)cc1] | 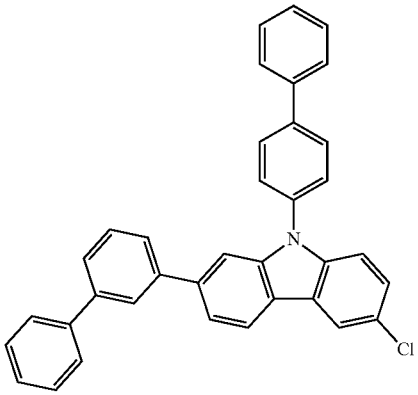 C-31 | 56 |
| 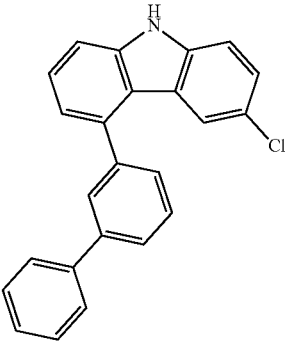 B-14 | 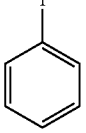 | 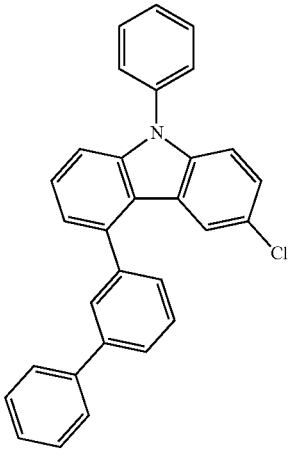 C-32 | 57 |
| 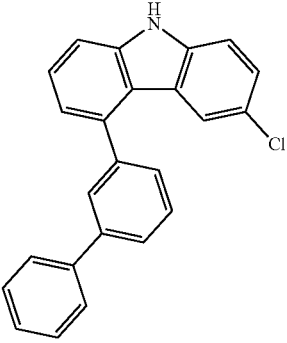 B-14 | 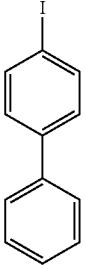 [SMILES: Ic1ccc(-c2ccccc2)cc1] | 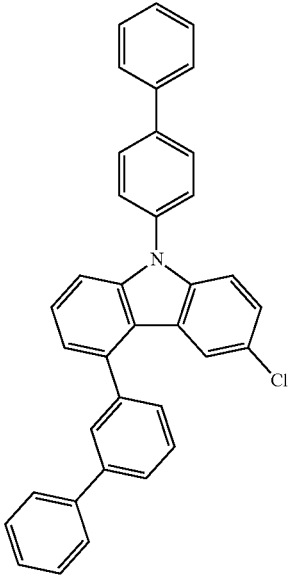 C-33 | 59 |

TABLE 3-continued
| Intermediate B-X | Raw material 2 | Intermediate C-X | Yield % |
|---|---|---|---|
| 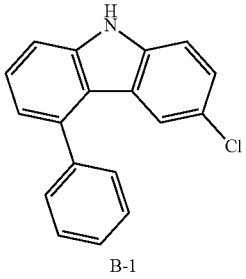 B-1 | 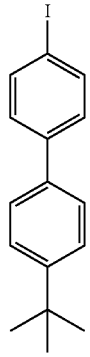 [SMILES: CC(C)(C)c1ccc(-c2ccc(I)cc2)cc1] | 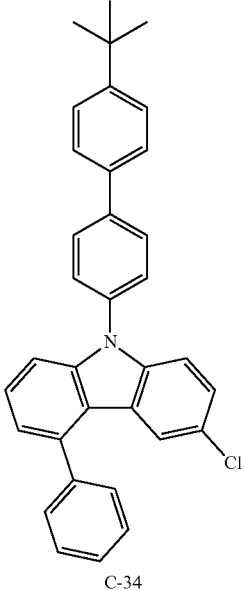 C-34 | 50 |
| 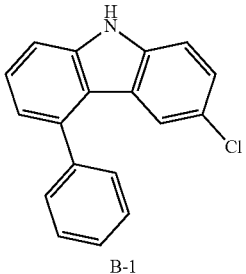 B-1 | 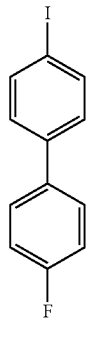 [SMILES: Fc1ccc(-c2ccc(I)cc2)cc1] | 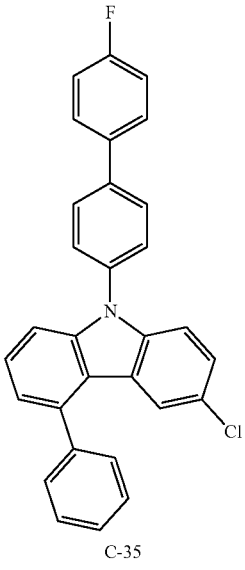 C-35 | 47 |
| 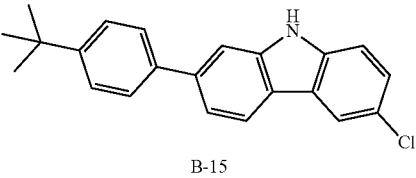 B-15 | 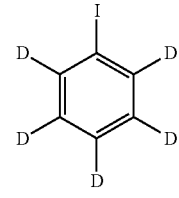 [SMILES: [2H]c1c([2H])c([2H])c(I)c([2H])c1[2H]] | 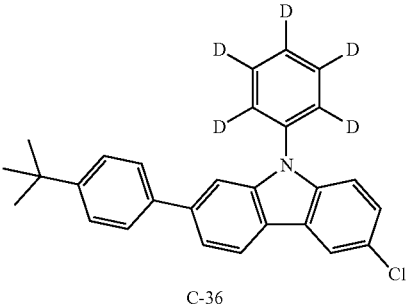 C-36 | 55 |

TABLE 3-continued
| Intermediate B-X | Raw material 2 | Intermediate C-X | Yield % |
|---|---|---|---|
| 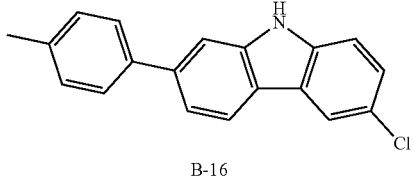 B-16 | 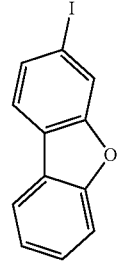 [SMILES: Ic1ccc2c(c1)oc1ccccc12] | 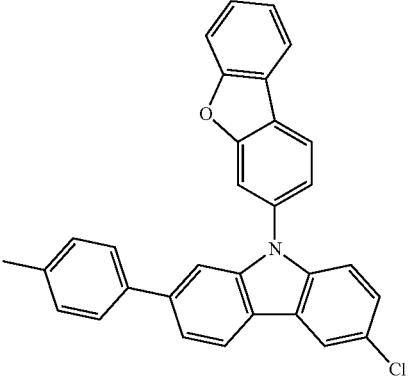 C-37 | 51 |
| 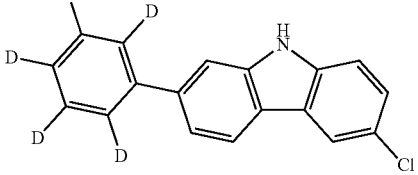 B-17 | 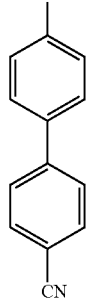 | 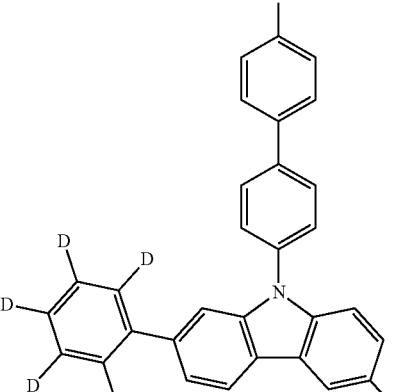 C-38 | 48 |
| 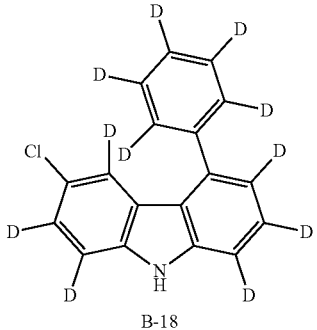 B-18 | 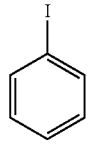 | 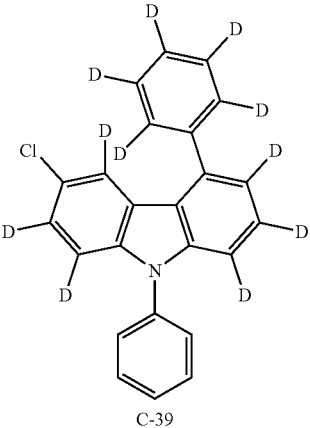 C-39 | 55 |

TABLE 3-continued
| Intermediate B-X | Raw material 2 | Intermediate C-X | Yield % |
|---|---|---|---|
| B-19 | phenyl iodide | C-40 | 52 |
| B-20 | phenyl iodide | C-41 | 49 |
Synthesis of Intermediate CM-1
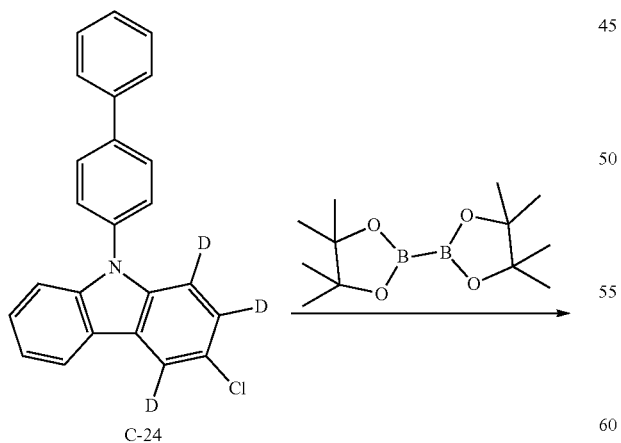
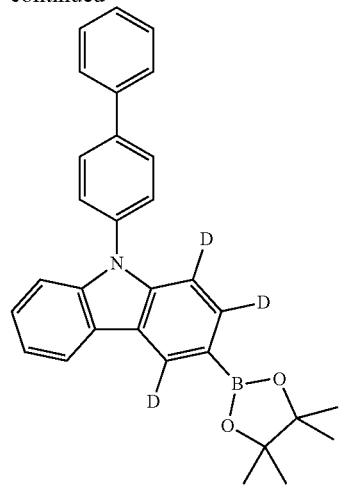
The intermediate C-24 (20 g, 56.04 mmol), bis(pinacolato)diboron (21.35 g, 84.06 mmol), tris(dibenzylideneacetone)dipalladium (1.54 g, 1.68 mmol), potassium acetate (11.00 g, 112.09 mmol), 2-dicyclohexylphosphino-2',4',6'-triisopropylbiphenyl (1.60 g, 3.36 mmol), and 1,4-dioxane (200 mL) were added into a dry round bottom flask replaced with nitrogen, and the mixture was heated to 100° C. under stirring for 16 h; the reaction mixture was then cooled to room temperature, ethyl acetate (200 mL) and deionized water (200 mL) were added, stirring was performed for 15 min, an organic phase was separated, and dried over anhydrous magnesium sulfate, and a solvent was removed under reduced pressure; and the obtained crude product was purified by silica gel column chromatography using dichloromethane/n-heptane as a mobile phase to obtain CM-1 (17.6 g; 70%).

Referring to the synthesis method of CM-1, the intermediate C-25 in Table 4 replaced the intermediate C-24, and the intermediate CM-2 in Table 4 below was synthesized:

TABLE 4

| Intermediate C-25 | CM-X | Yield (%) |
|---|---|---|
| 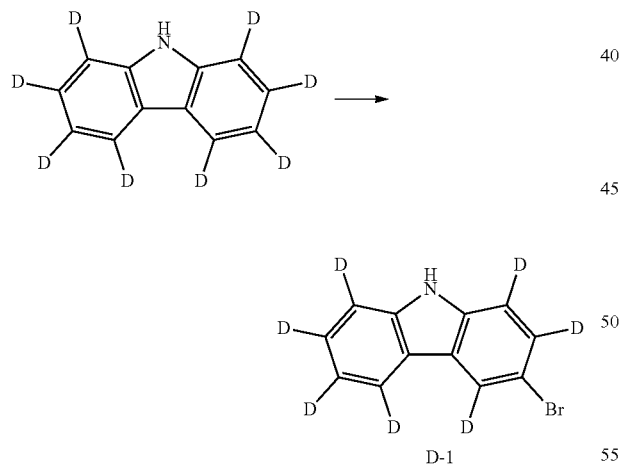 | | 75 |

Synthesis of Intermediate D-1

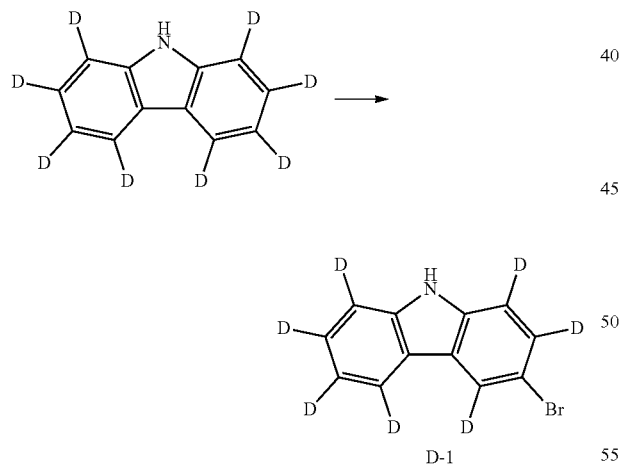

Deuterated carbazole (20 g, 114.12 mmol), N-bromosuccinimide (NBS) (50.78 g, 285.29 mmol), and DMF (200 mL) were added into a dry round bottom flask replaced with nitrogen, and the mixture was stirred at room temperature for 16 h; and then ethyl acetate (200 mL) and deionized water (200 mL) were added to the reaction mixture, an organic phase was separated, and dried over anhydrous magnesium sulfate, and a solvent was removed under reduced pressure to obtain an intermediate D-1 (12.42 g; 43%).

Synthesis of Intermediate E-1

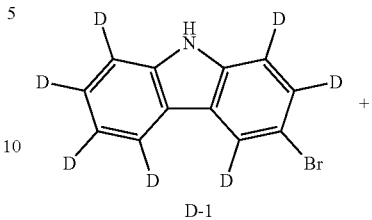

D-1

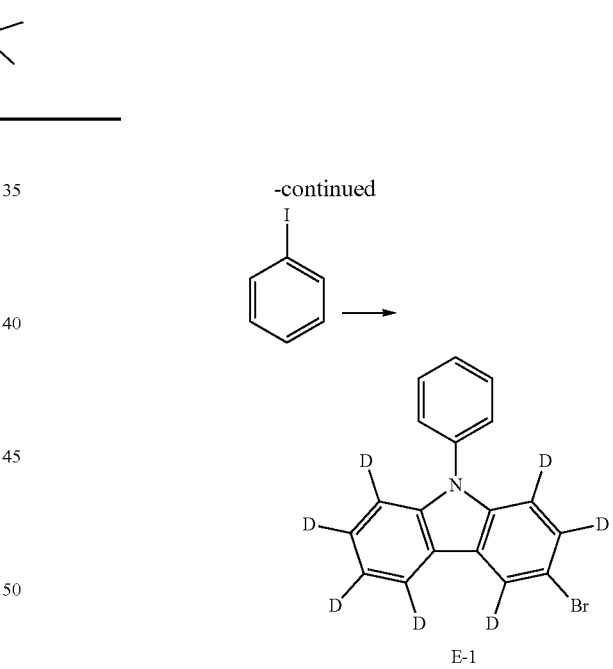

E-1

The intermediate D-1 (10 g, 39.50 mmol), iodobenzene (12.08 g, 59.25 mmol), cuprous iodide (0.75 g, 3.95 mmol), potassium carbonate (13.65 g, 98.76 mmol), o-phenanthroline (0.39 g, 1.98 mmol), 18-crown-6 (1.04 g, 3.95 mmol), and DMF (100 mL) were added into a dry round bottom flask replaced with nitrogen, and the mixture was heated to 150° C. under stirring for 16 h; the reaction mixture was then cooled to room temperature, ethyl acetate (200 mL) and deionized water (200 mL) were added, stirring was performed for 15 min, an organic phase was separated, and dried over anhydrous magnesium sulfate, and a solvent was removed under reduced pressure; and the obtained crude product was purified by silica gel column chromatography using dichloromethane/n-heptane as a mobile phase to obtain an intermediate E-1 (6.89 g; 53%).

Referring to the synthesis method of intermediate E-1, raw material 3 in Table 5 replaced iodobenzene, and the intermediate E-X in the following Table 5 was synthesized:

TABLE 5

| Intermediate D-1 | Raw material 3 | Intermediate E-X | Yield % |
|---|---|---|---|
| (D-substituted carbazole with Br) | 4-iodobiphenyl | E-2 | 54 |
| (D-substituted carbazole with Br) | 3-iodobiphenyl | E-3 | 56 |
| (D-substituted carbazole with Br) | 2-iodobiphenyl | E-4 | 51 |

TABLE 5-continued

| Intermediate D-1 | Raw material 3 | Intermediate E-X | Yield % |
|---|---|---|---|
| (carbazole-d6, Br) | 4-iodo-p-terphenyl | E-5 | 53 |
| (carbazole-d6, Br) | iodo-m-terphenyl | E-6 | 49 |
| (carbazole-d6, Br) | 4-iodo-3'-phenylbiphenyl | E-7 | 51 |

TABLE 5-continued

| Intermediate D-1 | Raw material 3 | Intermediate E-X | Yield % |
|---|---|---|---|
| | | E-8 | 50 |
| | | E-9 | 62 |
| | | E-10 | 56 |
| | | E-11 | 61 |

TABLE 5-continued

| Intermediate D-1 | Raw material 3 | Intermediate E-X | Yield % |
|---|---|---|---|
| (structure) | (structure) | E-12 | 63 |
| (structure) | (structure) | E-13 | 58 |
| (structure) | (structure) | E-14 | 61 |

TABLE 5-continued

| Intermediate D-1 | Raw material 3 | Intermediate E-X | Yield % |
|---|---|---|---|
| 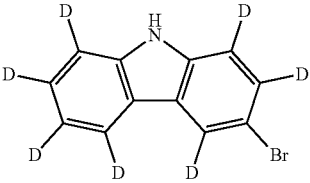 [SMILES: [2H]c1c([2H])c([2H])c2c([nH]c3c([2H])c([2H])c(Br)c([2H])c32)c1[2H]] | 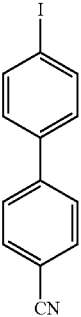 | 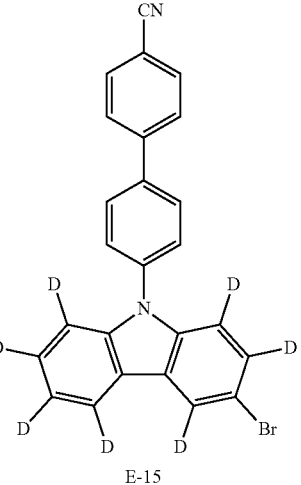\
E-15 | 64 |
| 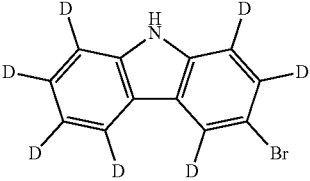 [SMILES: [2H]c1c([2H])c([2H])c2c([nH]c3c([2H])c([2H])c(Br)c([2H])c32)c1[2H]] | 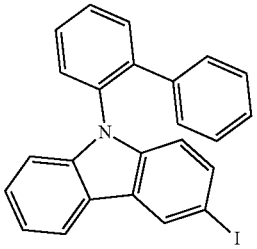 [SMILES: Ic1ccc2c(c1)c1ccccc1n2-c1ccccc1-c1ccccc1] | 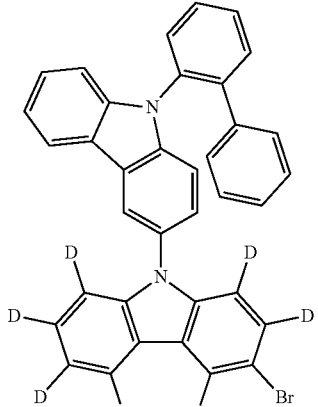\
E-16 | 66 |

Synthesis of Intermediate F-1

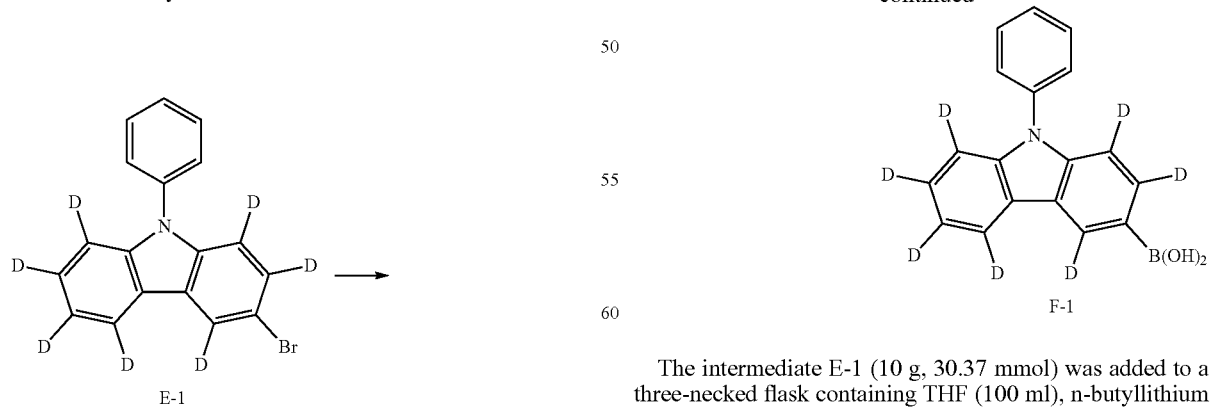

The intermediate E-1 (10 g, 30.37 mmol) was added to a three-necked flask containing THF (100 ml), n-butyllithium (2.07 g, 31.89 mmol) was added dropwise at −80° C., heat preservation was performed for 1 h after adding dropwise was completed, trimethyl borate (4.73 g, 45.56 mmol) was added dropwise, heat preservation was continued to be performed for 1 h, the reaction solution was raised to room temperature, and stirred overnight. Hydrochloric acid (2 mol/L) was added into the reaction solution to adjust a pH to be neutral, filtration was performed to obtain a white crude product, and the obtained crude product was pulped with n-heptane to obtain an intermediate F-1 (5.36 g, yield: 60%).

Referring to the synthesis method of intermediate F-1, raw material 4 in Table 6 replaced E-1 and intermediate F-X in Table 6 below was synthesized:

TABLE 6

| Raw material 4 | Intermediate F-X | Yield % |
|---|---|---|
| E-2 | F-2 | 55 |
| E-3 | F-3 | 62 |
| E-4 | F-4 | 59 |

TABLE 6-continued

| Raw material 4 | Intermediate F-X | Yield % |
|---|---|---|
| E-5 | F-5 | 58 |
| E-6 | F-6 | 56 |
| E-7 | F-7 | 53 |

TABLE 6-continued

| Raw material 4 | Intermediate F-X | Yield % |
| --- | --- | --- |
| E-8 | F-8 | 50 |
| E-9 | F-9 | 55 |
| E-10 | F-10 | 51 |
| E-11 | F-11 | 60 |

TABLE 6-continued

| Raw material 4 | Intermediate F-X | Yield % |
|---|---|---|
| E-12 | F-12 | 52 |
| E-13 | F-13 | 50 |
| E-14 | F-14 | 63 |

TABLE 6-continued
| Raw material 4 | Intermediate F-X | Yield % |
|---|---|---|
| E-15 | F-15 | 59 |
| E-16 | F-16 | 55 |
Synthesis of Compound 221
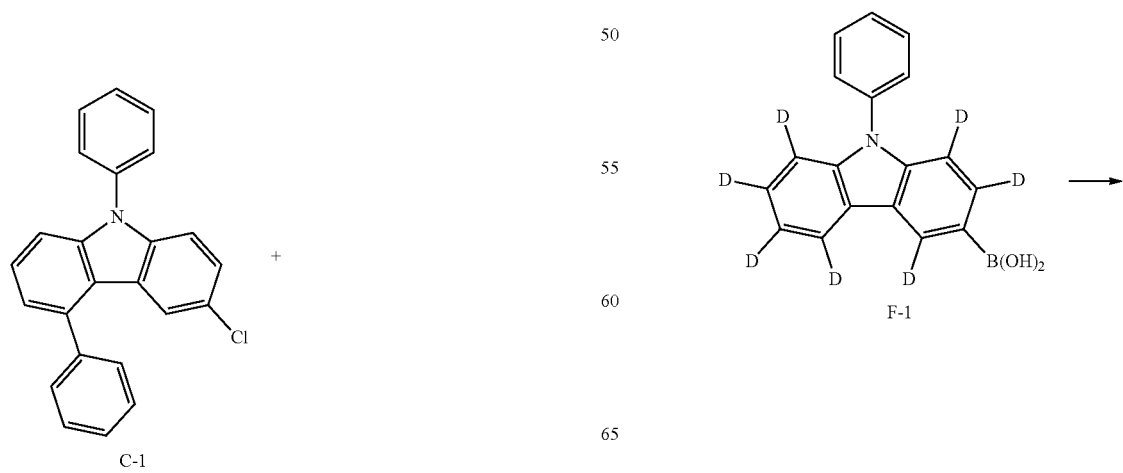

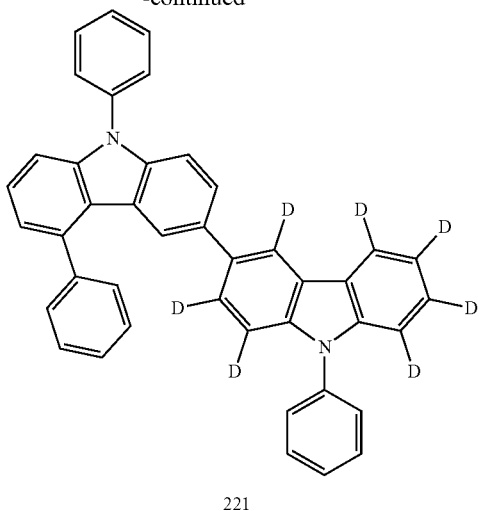

221

The intermediate C-1 (10 g, 28.26 mmol), the intermediate F-1 (8.72 g, 29.67 mmol), palladium acetate (0.06 g, 0.28 mmol), X-Phos (0.27 g, 0.56 mmol), potassium carbonate (7.81 g, 56.52 mmol), toluene (80 mL), ethanol (40 mL), and deionized water (20 mL) were added into a dry round bottom flask replaced with nitrogen, and the mixture was heated to 75 to 80° C. under stirring for 8 h; the reaction mixture was then cooled to room temperature, deionized water (200 mL) was added, stirring was performed for 15 min, an organic phase was separated, and dried over anhydrous magnesium sulfate, and a solvent was removed under reduced pressure; and the obtained crude product was purified by silica gel column chromatography using dichloromethane/n-heptane as a mobile phase to obtain a compound 221 (12.03 g; 75%).

Referring to the method of synthesis of compound 221, raw material C replaced intermediate C-1 in Table 7, and raw material F replaced intermediate F-1 to synthesize the compounds in Table 7:

TABLE 7
| Raw material C | Raw material F | Compound | Yield % |
|---|---|---|---|
| 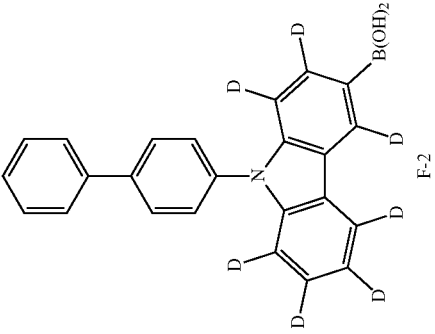 C-1 | 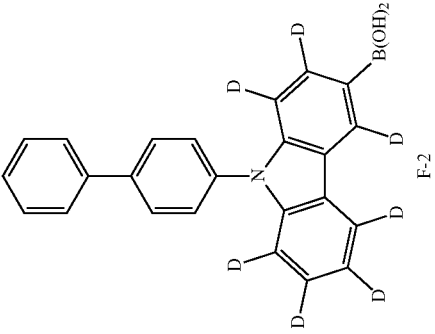 F-2 | 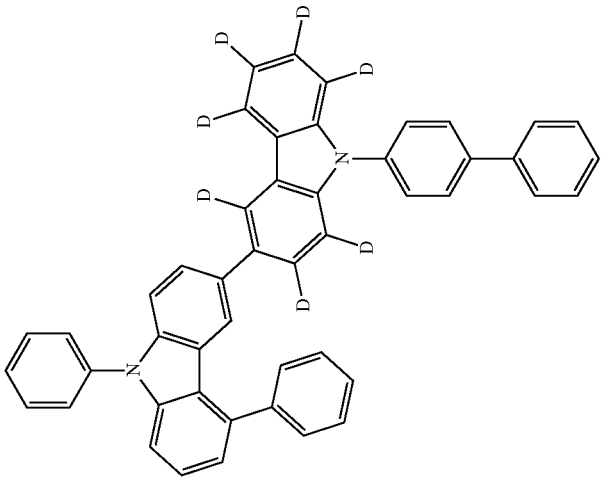 223 | 70 |

TABLE 7-continued
| Raw material C | Raw material F | Compound | Yield % |
|---|---|---|---|
| 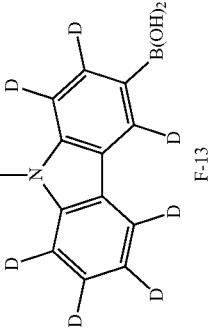 | 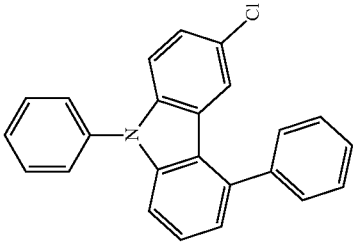 | 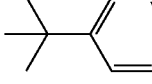 543 | 68 |

TABLE 7-continued

| Raw material C | Raw material F | Compound | Yield % |
|---|---|---|---|
| (structure) | F-14 | 544 | 65 |

TABLE 7-continued

| Raw material C | Raw material F | Compound | Yield % |
|---|---|---|---|
| (structure with Cl) | F-15 | 545 | 60 |

TABLE 7-continued

| Raw material C | Raw material F | Compound | Yield % |
|---|---|---|---|
| C-1 | F-5 | 237 | 71 |

TABLE 7-continued
| Raw material C | Raw material F | Compound | Yield % |
|---|---|---|---|
| 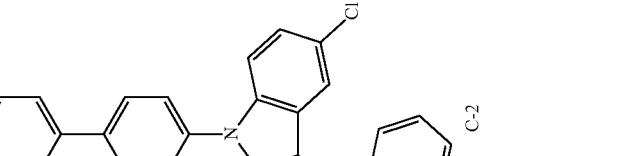 C-2 | 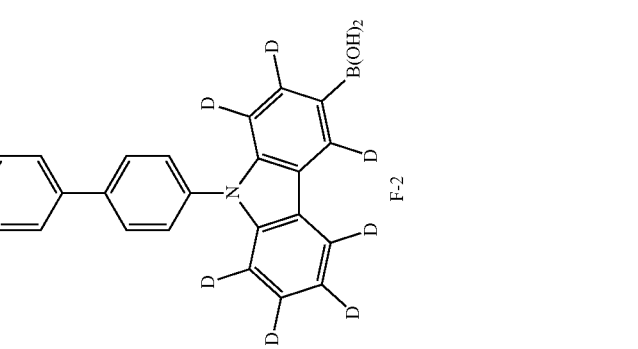 F-2 | 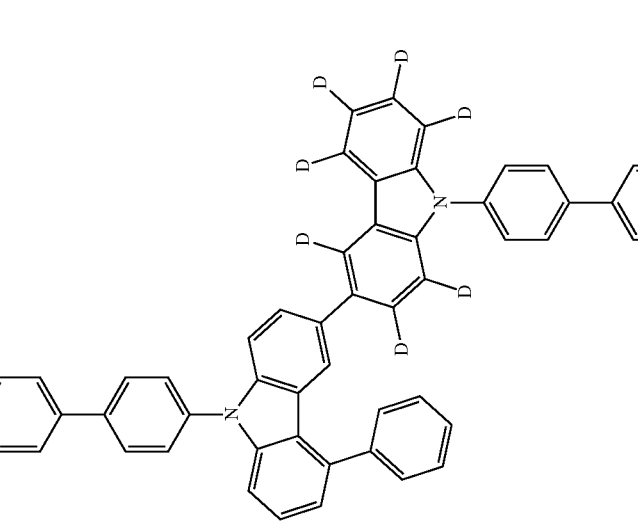 243 | 73 |

TABLE 7-continued

| Raw material C | Raw material F | Compound | Yield % |
|---|---|---|---|
| C-2 | F-16 | 549 | 69 |

TABLE 7-continued

| Raw material C | Raw material F | Compound | Yield % |
|---|---|---|---|
| C-2 | F-3 | 244 | 71 |

TABLE 7-continued

| Raw material C | Raw material F | Compound | Yield % |
|---|---|---|---|
| C-2 | F-8 | 249 | 75 |

TABLE 7-continued

| Raw material C | Raw material F | Compound | Yield % |
|---|---|---|---|
| C-2 | F-9 | 253 | 71 |

TABLE 7-continued
| Raw material C | Raw material F | Compound | Yield % |
|---|---|---|---|
| 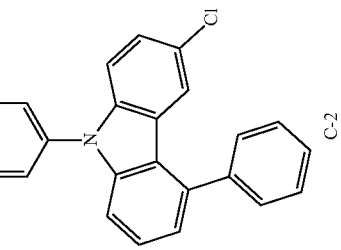 C-2 | 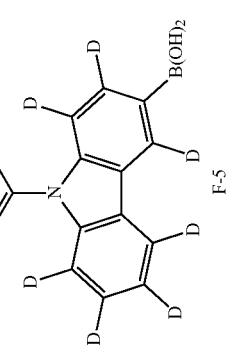 F-5 | 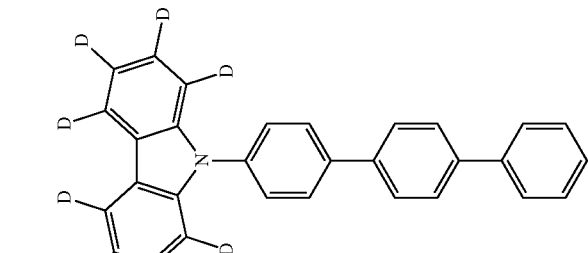 257 | 72 |

TABLE 7-continued

| Raw material C | Raw material F | Compound | Yield % |
|---|---|---|---|
| C-3 | F-2 | 268 | 72 |

TABLE 7-continued

| Raw material C | Raw material F | Compound | Yield % |
|---|---|---|---|
| C-3 | F-3 | 269 | 70 |

TABLE 7-continued
| Raw material C | Raw material F | Compound | Yield % |
|---|---|---|---|
| 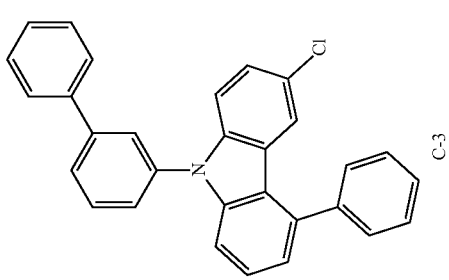 C-3 | 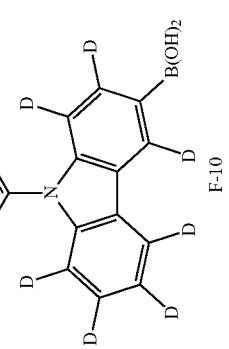 F-10 | 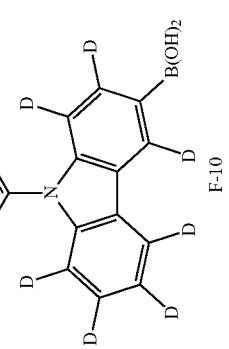 270 | 74 |

TABLE 7-continued

| Raw material C | Raw material F | Compound | Yield % |
|---|---|---|---|
| C-3 | F-11 | 276 | 70 |

TABLE 7-continued

| Raw material C | Raw material F | Compound | Yield % |
|---|---|---|---|
| C-3 | F-6 | 285 | 69 |

TABLE 7-continued

| Raw material C | Raw material F | Compound | Yield % |
|---|---|---|---|
| C-4 | F-2 | 290 | 70 |

TABLE 7-continued

| Raw material C | Raw material F | Compound | Yield % |
|---|---|---|---|
| C-4 | F-3 | 291 | 74 |

TABLE 7-continued

| Raw material C | Raw material F | Compound | Yield % |
|---|---|---|---|
| C-5 | F-2 | 345 | 78 |

TABLE 7-continued
| Raw material C | Raw material F | Compound | Yield % |
|---|---|---|---|
| 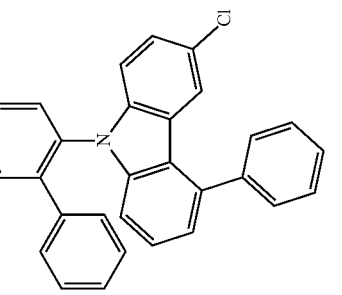<br>C-6 | 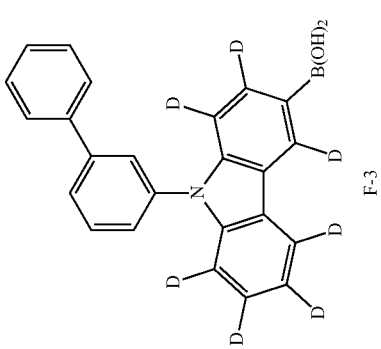<br>F-3 | 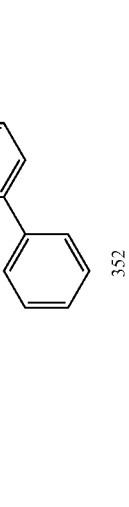<br>352 | 73 |

TABLE 7-continued

| Raw material C | Raw material F | Compound | Yield % |
|---|---|---|---|
| C-7 | F-2 | 349 | 75 |

TABLE 7-continued

| Raw material C | Raw material F | Compound | Yield % |
|---|---|---|---|
| C-8 | F-2 | 325 | 73 |

TABLE 7-continued

| Raw material C | Raw material F | Compound | Yield % |
|---|---|---|---|
| C-9 | F-2 | 337 | 78 |

TABLE 7-continued

| Raw material C | Raw material F | Compound | Yield % |
|---|---|---|---|
| C-10 | F-2 | 74 | 77 |

TABLE 7-continued

| Raw material C | Raw material F | Compound | Yield % |
|---|---|---|---|
| C-11 | F-2 | 99 | 74 |

TABLE 7-continued

| Raw material C | Raw material F | Compound | Yield % |
|---|---|---|---|
| C-12 | F-3 | 120 | 70 |

TABLE 7-continued

| Raw material C | Raw material F | Compound | Yield % |
|---|---|---|---|
| C-13 | F-1 | 133 | 71 |

TABLE 7-continued

| Raw material C | Raw material F | Compound | Yield % |
|---|---|---|---|
| C-14 | F-1 | 169 | 78 |

TABLE 7-continued

| Raw material C | Raw material F | Compound | Yield % |
|---|---|---|---|
| C-15 | F-5 | 197 | 76 |

TABLE 7-continued

| Raw material C | Raw material F | Compound | Yield % |
|---|---|---|---|
| C-16 | F-12 | 213 | 72 |

TABLE 7-continued

| Raw material C | Raw material F | Compound | Yield % |
|---|---|---|---|
| C-17 | F-2 | 22 | 76 |

TABLE 7-continued

| Raw material C | Raw material F | Compound | Yield % |
|---|---|---|---|
| C-18 | F-3 | 40 | 73 |

TABLE 7-continued

| Raw material C | Raw material F | Compound | Yield % |
|---|---|---|---|
| C-19 | F-10 | 54 | 71 |

TABLE 7-continued

| Raw material C | Raw material F | Compound | Yield % |
|---|---|---|---|
| C-22 | | 354 | 70 |

TABLE 7-continued

| Raw material C | Raw material F | Compound | Yield % |
|---|---|---|---|
| C-20 | | 365 | 73 |

TABLE 7-continued

| Raw material C | Raw material F | Compound | Yield % |
|---|---|---|---|
| C-21 | | 374 | 72 |

TABLE 7-continued

| Raw material C | Raw material F | Compound | Yield % |
|---|---|---|---|
| C-23 | | 378 | 71 |

TABLE 7-continued

| Raw material C | Raw material F | Compound | Yield % |
|---|---|---|---|
| C-10 | CM-1 | 397 | 73 |

TABLE 7-continued

| Raw material C | Raw material F | Compound | Yield % |
|---|---|---|---|
| C-2 | CM-2 | 408 | 71 |

TABLE 7-continued

| Raw material C | Raw material F | Compound | Yield % |
|---|---|---|---|
| C-1 | CM-1 | 413 | 75 |

TABLE 7-continued

| Raw material C | Raw material F | Compound | Yield % |
|---|---|---|---|
| C-30 | F-2 | 444 | 70 |

TABLE 7-continued

| Raw material C | Raw material F | Compound | Yield % |
|---|---|---|---|
| C-31 | F-2 | 462 | 73 |

TABLE 7-continued

| Raw material C | Raw material F | Compound | Yield % |
|---|---|---|---|
| C-29 | F-3 | 470 | 71 |

TABLE 7-continued

| Raw material C | Raw material F | Compound | Yield % |
|---|---|---|---|
| C-26 | F-2 | 480 | 74 |

TABLE 7-continued

| Raw material C | Raw material F | Compound | Yield % |
|---|---|---|---|
| C-27 | F-2 | 482 | 70 |

TABLE 7-continued

| Raw material C | Raw material F | Compound | Yield % |
|---|---|---|---|
| C-27 | F-3 | 483 | 73 |

TABLE 7-continued

| Raw material C | Raw material F | Compound | Yield % |
|---|---|---|---|
| C-28 | F-2 | 486 | 71 |

TABLE 7-continued
| Raw material C | Raw material F | Compound | Yield % |
|---|---|---|---|
| 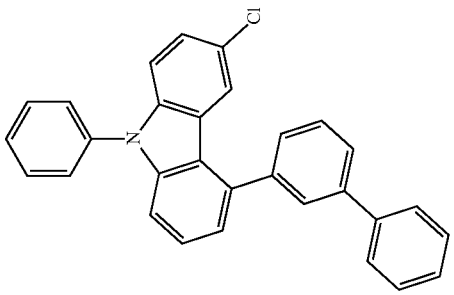 C-32 | 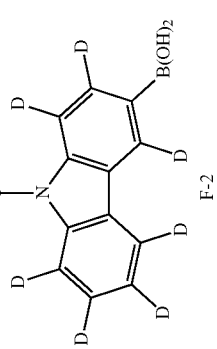 F-2 | 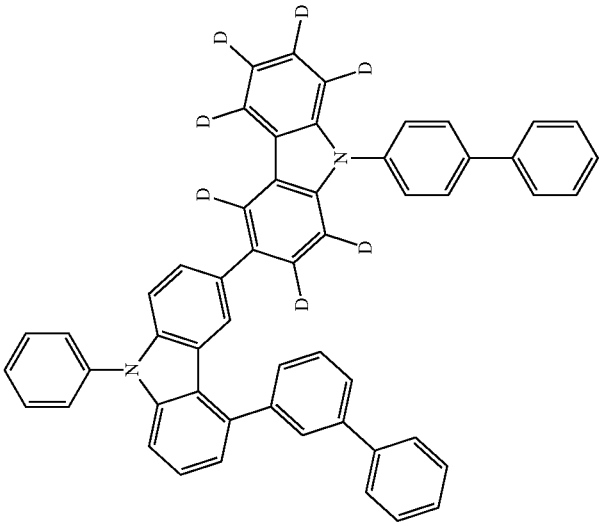 488 | 70 |

TABLE 7-continued
| Raw material C | Raw material F | Compound | Yield % |
|---|---|---|---|
| 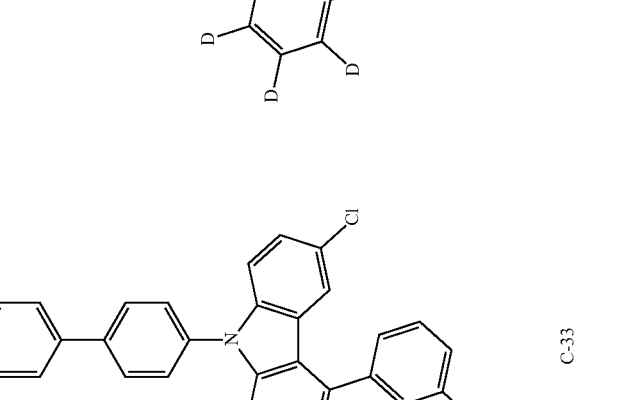 C-33 | 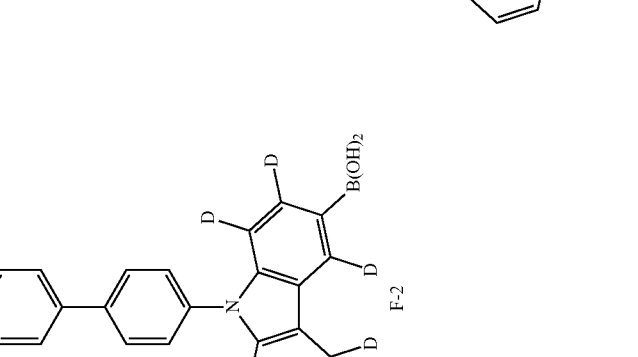 F-2 | 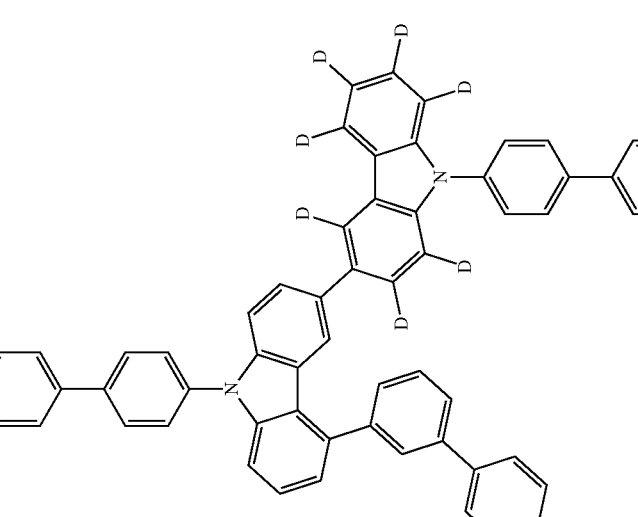 489 | 74 |

TABLE 7-continued

| Raw material C | Raw material F | Compound | Yield % |
|---|---|---|---|
| C-33 | F-3 | 490 | 71 |

TABLE 7-continued

| Raw material C | Raw material F | Compound | Yield % |
|---|---|---|---|
| C-36 | F-13 | 546 | 65 |

TABLE 7-continued

| Raw material C | Raw material F | Compound | Yield % |
|---|---|---|---|
| C-37 | F-2 | 547 | 55 |

TABLE 7-continued

| Raw material C | Raw material F | Compound | Yield % |
|---|---|---|---|
| C-38 | F-3 | 548 | 57 |

TABLE 7-continued
| Raw material C | Raw material F | Compound | Yield % |
|---|---|---|---|
| 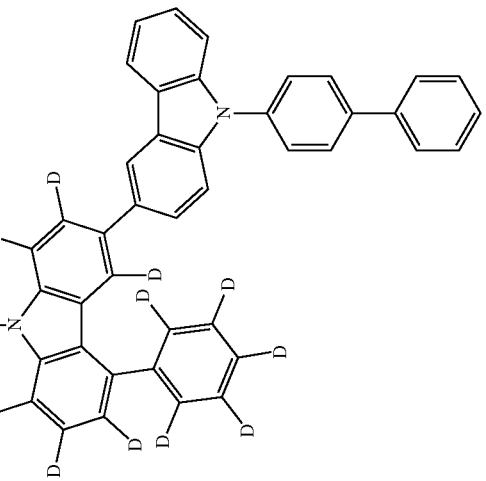 C-39 | 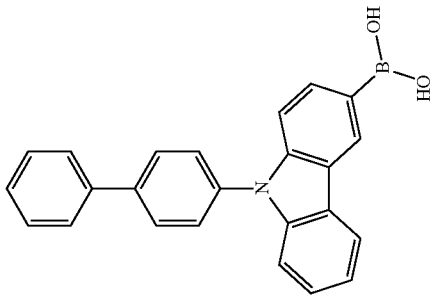 | 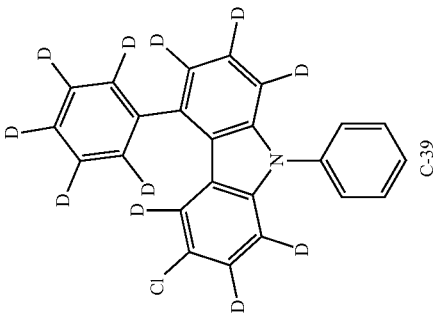 556 | 51 |

TABLE 7-continued

| Raw material C | Raw material F | Compound | Yield % |
|---|---|---|---|
| C-40 | | 558 | 48 |

TABLE 7-continued

| Raw material C | Raw material F | Compound | Yield % |
|---|---|---|---|
| C-41 | F-2 | 559 | 53 |

The compounds synthesized above were subjected to mass spectrometry and the data obtained are shown in Table 8 below:

TABLE 8

| Compound No. | Mass spectrum ([M + H]$^+$) | Compound No. | Mass spectrum ([M + H]$^+$) |
|---|---|---|---|
| 221 | 568.3 | 223 | 644.3 |
| 237 | 720.3 | 243 | 720.3 |
| 244 | 720.2 | 249 | 734.3 |
| 253 | 750.3 | 257 | 796.3 |
| 268 | 720.4 | 269 | 720.3 |
| 270 | 734.3 | 276 | 750.3 |
| 285 | 796.4 | 290 | 720.3 |
| 291 | 720.3 | 345 | 796.4 |
| 352 | 796.4 | 349 | 796.4 |
| 325 | 734.3 | 337 | 750.3 |
| 74 | 644.3 | 99 | 720.3 |
| 120 | 720.3 | 133 | 644.3 |
| 169 | 644.3 | 197 | 796.4 |
| 213 | 750.3 | 22 | 720.3 |
| 40 | 720.3 | 54 | 734.3 |
| 354 | 640.3 | 365 | 640.3 |
| 374 | 640.4 | 378 | 640.2 |
| 397 | 640.2 | 408 | 640.3 |
| 413 | 640.3 | 444 | 720.3 |
| 462 | 796.4 | 470 | 796.4 |
| 480 | 720.3 | 482 | 796.3 |
| 483 | 796.3 | 486 | 796.5 |
| 488 | 720.2 | 489 | 796.2 |
| 490 | 796.4 | 543 | 700.3 |
| 544 | 662.3 | 545 | 669.3 |
| 546 | 723.3 | 547 | 748.3 |
| 548 | 750.3 | 549 | 885.3 |
| 556 | 648.3 | 558 | 645.3 |
| 559 | 649.3 | | |

NMR data of some compounds are shown in Table 9 below:

TABLE 9

| Compound | NMR data |
|---|---|
| Compound 223 | $^1$HNMR (400 MHZ, CD$_2$Cl$_2$): δ7.82-7.88 (d, 2H), δ7.78-7.82 (s, 1H), δ7.58-7.78 (m, 13H), δ7.35-7.58 (m, 7H), δ7.07-7.25 (d, 2H). |
| Compound 268 | $^1$HNMR (400 MHZ, CD$_2$Cl$_2$): δ7.83-7.91 (m, 3H), δ7.79-7.83 (s, 1H), δ7.57-7.79 (m,14H), δ7.43-7.57 (m, 8H), δ7.35-7.42 (t, 2H), δ7.15-7.24 (m, 1H). |

Manufacture and Evaluation of Organic Electroluminescent Device

Example 1 Green Organic Electroluminescent Device

Anode preparation: an ITO substrate having a thickness of 1460 Å was cut into a size of 40 mm×40 mm×0.5 mm, an experimental substrate with cathode, anode and insulating layer patterns was obtained by using a photoetching process, and surface treatment was performed by utilizing UV ozone and O$_2$:N$_2$ plasma to increase the work function of the anode and remove scum.

F4-TCNQ was vacuum evaporated on the experimental substrate (the anode) with a thickness of 110 Å as a hole injection layer (HIL), and HT-01 was evaporated on the hole injection layer to form a hole transport layer of 1120 Å.

HT-02 was vacuum evaporated on the hole transport layer to form a hole adjusting layer of 320 Å.

GH-N, the compound 221 and Ir(mppy)$_3$ were co-evaporated on the hole adjusting layer at a film thickness ratio of 45%:45%:10% to form an organic light-emitting layer (G-EML) with a thickness of 300 Å.

ET-01 and LiQ were evaporated at a film thickness ratio of 1:1 to form an electron transport layer (ETL) with a thickness of 350 Å, Yb was evaporated on the electron transport layer to form an electron injection layer (EIL) with a thickness of 15 Å, and then magnesium (Mg) and silver (Ag) were vacuum evaporated on the electron injection layer at a film thickness ratio of 1:9 to form a cathode having a thickness of 125 Å.

In addition, an organic capping layer (CPL) of 600 Å was evaporated on the above cathode, thus completing the manufacture of the green organic electroluminescent device.

Examples 2 to 57

An organic electroluminescent device was manufactured by the same method as that in Example 1 except that compounds shown in Table 10 below were used instead of the compound 221 when forming the organic light-emitting layer.

Comparative Example 1

An organic electroluminescent device was manufactured by the same method as that in Example 1 except that the compound 221 was replaced by a compound I when forming the organic light-emitting layer.

Comparative Example 2

An organic electroluminescent device was manufactured by the same method as that in Example 1 except that compound 221 was replaced by a compound II when forming the organic light-emitting layer.

Comparative Example 3

An organic electroluminescent device was manufactured by the same method as that in Example 1 except that the compound 221 was replaced by a compound III when forming the organic light-emitting layer.

The structures of materials used in Examples 1 to 57 and Comparative examples 1 to 3 above are shown below:

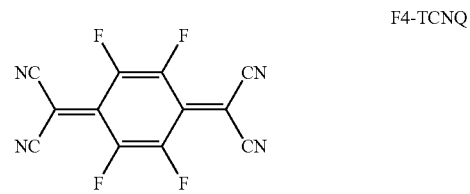

F4-TCNQ

-continued
HT-01
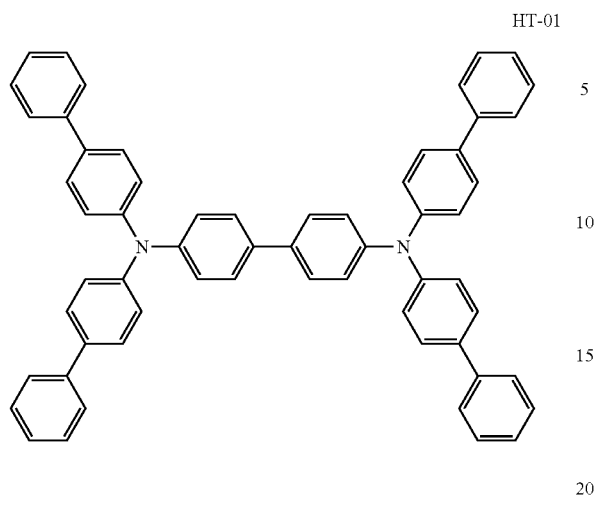
ET-01
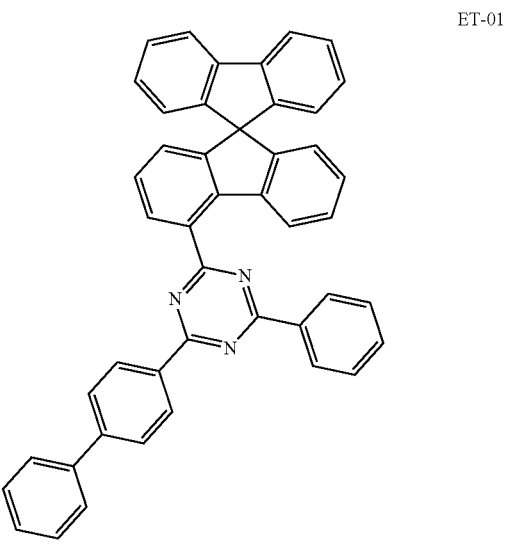
LiQ
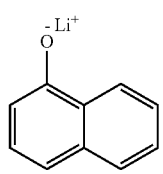
HT-02
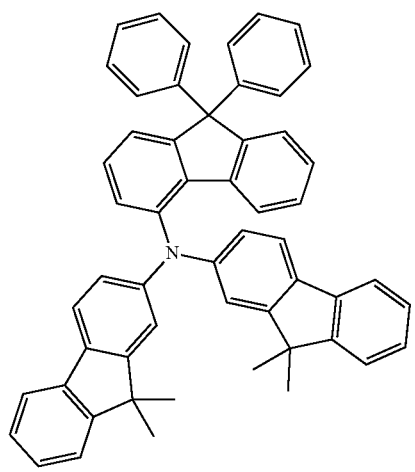
CPL
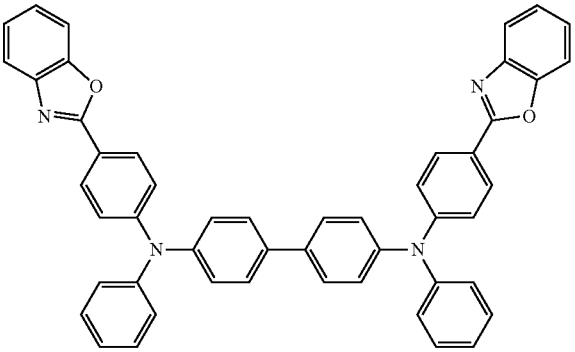
Ir(mppy)₃
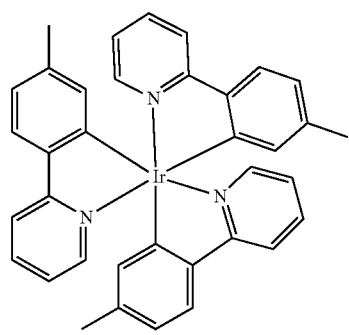
GH-N
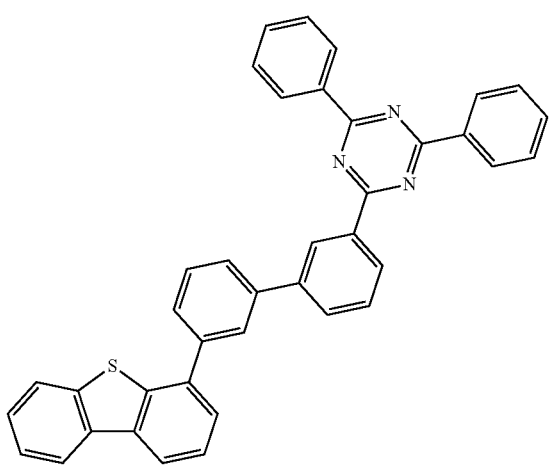

-continued

Compound I

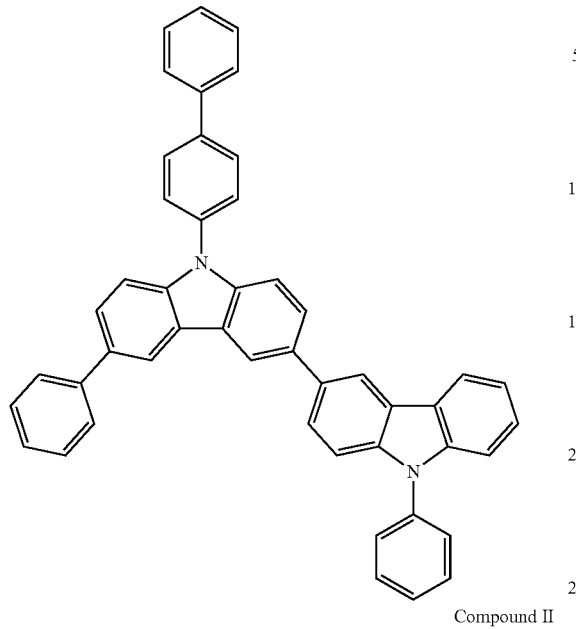

Compound II

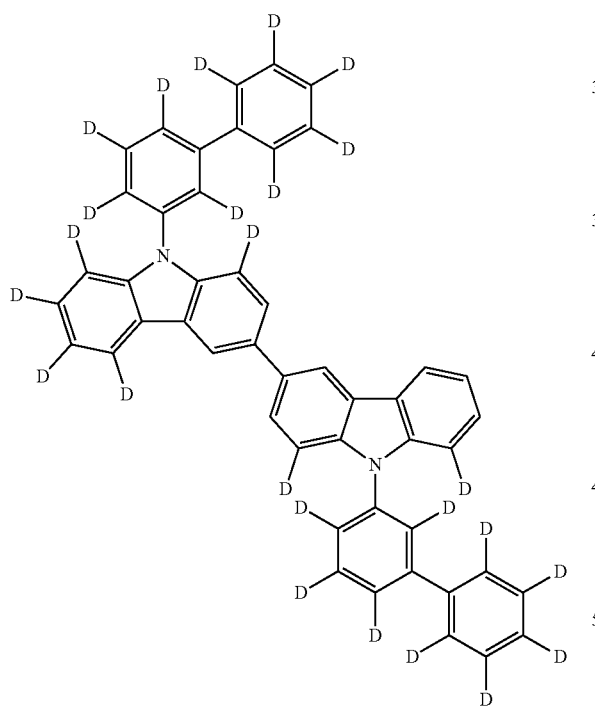

-continued

Compound III

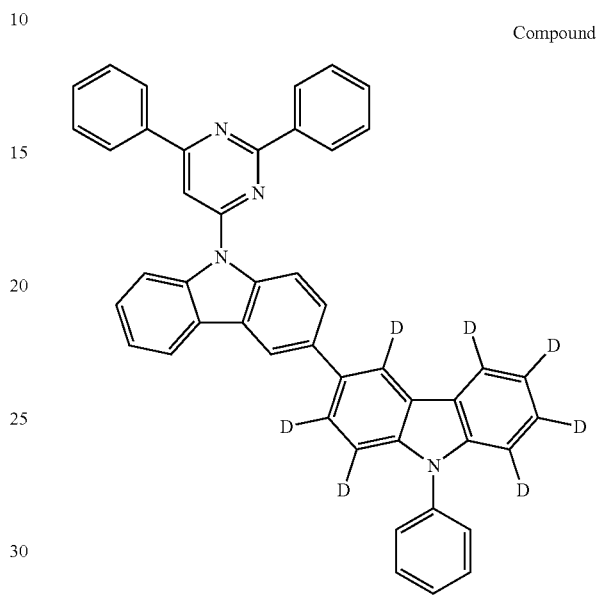

For the organic electroluminescent devices manufactured above, the performance of the device was analyzed under the condition of 15 mA/cm², and the results are shown in Table 10 below:

TABLE 10

| No. | Compound | Operating voltage (V) | Current efficiency Cd/A | Power efficiency lm/W | CIE-X | CIE-Y | EQE % | Service life (T95, hrs) @ 20 mA/cm² |
|---|---|---|---|---|---|---|---|---|
| Example 1 | 221 | 4.15 | 105.81 | 80.11 | 0.22 | 0.73 | 25.41 | 366 |
| Example 2 | 223 | 4.16 | 104.72 | 79.10 | 0.22 | 0.73 | 25.10 | 366 |
| Example 3 | 237 | 4.17 | 106.33 | 80.30 | 0.22 | 0.73 | 25.52 | 372 |
| Example 4 | 243 | 4.19 | 105.62 | 79.22 | 0.22 | 0.73 | 25.32 | 373 |
| Example 5 | 244 | 4.13 | 105.40 | 80.12 | 0.22 | 0.73 | 25.31 | 370 |
| Example 6 | 249 | 4.18 | 105.21 | 79.00 | 0.22 | 0.73 | 25.22 | 364 |

TABLE 10-continued

| No. | Compound | Operating voltage (V) | Current efficiency Cd/A | Power efficiency lm/W | CIE-X | CIE-Y | EQE % | Service life (T95, hrs) @ 20 mA/cm² |
|---|---|---|---|---|---|---|---|---|
| Example 7 | 253 | 4.16 | 105.82 | 79.90 | 0.22 | 0.73 | 25.40 | 371 |
| Example 8 | 257 | 4.20 | 104.92 | 78.52 | 0.22 | 0.73 | 25.20 | 375 |
| Example 9 | 268 | 4.19 | 105.43 | 79.02 | 0.22 | 0.73 | 25.33 | 368 |
| Example 10 | 269 | 4.14 | 104.73 | 79.51 | 0.22 | 0.73 | 25.14 | 365 |
| Example 11 | 270 | 4.19 | 105.10 | 78.81 | 0.22 | 0.73 | 25.26 | 375 |
| Example 12 | 276 | 4.13 | 105.84 | 80.52 | 0.22 | 0.73 | 25.44 | 376 |
| Example 13 | 285 | 4.16 | 105.83 | 79.93 | 0.22 | 0.73 | 25.41 | 379 |
| Example 14 | 290 | 4.19 | 106.00 | 79.50 | 0.22 | 0.73 | 24.99 | 374 |
| Example 15 | 291 | 4.18 | 106.51 | 80.00 | 0.22 | 0.73 | 25.61 | 380 |
| Example 16 | 345 | 4.18 | 105.12 | 79.04 | 0.22 | 0.73 | 25.27 | 368 |
| Example 17 | 352 | 4.21 | 105.90 | 79.21 | 0.22 | 0.73 | 25.45 | 370 |
| Example 18 | 349 | 4.17 | 106.01 | 79.83 | 0.22 | 0.73 | 25.42 | 364 |
| Example 19 | 354 | 4.14 | 98.10 | 74.33 | 0.22 | 0.73 | 23.63 | 338 |
| Example 20 | 325 | 4.21 | 106.03 | 79.15 | 0.22 | 0.73 | 25.44 | 371 |
| Example 21 | 337 | 4.20 | 105.86 | 79.24 | 0.22 | 0.73 | 25.47 | 373 |
| Example 22 | 74 | 4.18 | 105.85 | 79.55 | 0.22 | 0.73 | 25.46 | 369 |
| Example 23 | 99 | 4.13 | 106.50 | 81.00 | 0.22 | 0.73 | 25.62 | 375 |
| Example 24 | 120 | 4.14 | 104.91 | 79.60 | 0.22 | 0.73 | 25.28 | 378 |
| Example 25 | 365 | 4.20 | 101.10 | 75.64 | 0.22 | 0.73 | 24.30 | 341 |
| Example 26 | 133 | 4.18 | 105.12 | 79.08 | 0.22 | 0.73 | 25.29 | 374 |
| Example 27 | 169 | 4.17 | 104.83 | 78.92 | 0.22 | 0.73 | 25.18 | 370 |
| Example 28 | 197 | 4.19 | 106.54 | 79.84 | 0.22 | 0.73 | 25.63 | 381 |
| Example 29 | 213 | 4.17 | 105.33 | 79.41 | 0.22 | 0.73 | 25.32 | 379 |
| Example 30 | 374 | 4.19 | 100.31 | 75.23 | 0.22 | 0.73 | 24.10 | 342 |
| Example 31 | 22 | 4.18 | 105.24 | 79.03 | 0.22 | 0.73 | 25.25 | 375 |
| Example 32 | 40 | 4.13 | 104.74 | 79.70 | 0.22 | 0.73 | 25.17 | 368 |
| Example 33 | 54 | 4.15 | 104.60 | 79.18 | 0.22 | 0.73 | 25.19 | 365 |
| Example 34 | 378 | 4.13 | 100.42 | 76.42 | 0.22 | 0.73 | 24.10 | 339 |
| Example 35 | 397 | 4.14 | 100.83 | 76.55 | 0.22 | 0.73 | 24.21 | 340 |
| Example 36 | 444 | 4.20 | 101.03 | 75.50 | 0.22 | 0.73 | 24.25 | 377 |
| Example 37 | 462 | 4.18 | 99.21 | 74.60 | 0.22 | 0.73 | 23.86 | 367 |
| Example 38 | 470 | 4.21 | 98.72 | 73.71 | 0.22 | 0.73 | 23.75 | 374 |
| Example 39 | 408 | 4.16 | 98.61 | 74.41 | 0.22 | 0.73 | 23.70 | 337 |
| Example 40 | 480 | 4.14 | 99.74 | 75.70 | 0.22 | 0.73 | 23.92 | 369 |
| Example 41 | 482 | 4.14 | 99.70 | 75.65 | 0.22 | 0.73 | 23.94 | 377 |
| Example 42 | 483 | 4.13 | 99.05 | 75.35 | 0.22 | 0.73 | 23.84 | 374 |
| Example 43 | 486 | 4.21 | 100.61 | 75.12 | 0.22 | 0.73 | 24.11 | 368 |
| Example 44 | 413 | 4.17 | 99.62 | 75.00 | 0.22 | 0.73 | 23.90 | 340 |
| Example 45 | 488 | 4.21 | 98.92 | 73.84 | 0.22 | 0.73 | 23.77 | 365 |
| Example 46 | 489 | 4.15 | 100.70 | 75.74 | 0.22 | 0.73 | 24.20 | 372 |
| Example 47 | 490 | 4.18 | 100.93 | 75.86 | 0.22 | 0.73 | 24.24 | 370 |
| Example 48 | 543 | 4.16 | 99.34 | 75.05 | 0.22 | 0.73 | 23.78 | 365 |
| Example 49 | 544 | 4.18 | 99.31 | 74.62 | 0.22 | 0.73 | 23.83 | 369 |
| Example 50 | 545 | 4.13 | 100.26 | 76.55 | 0.22 | 0.73 | 24.12 | 371 |
| Example 51 | 546 | 4.18 | 100.02 | 75.11 | 0.22 | 0.73 | 24.00 | 377 |
| Example 52 | 547 | 4.19 | 99.03 | 74.23 | 0.22 | 0.73 | 23.82 | 372 |
| Example 53 | 548 | 4.18 | 99.81 | 75.07 | 0.22 | 0.73 | 23.89 | 373 |
| Example 54 | 549 | 4.12 | 99.72 | 74.44 | 0.22 | 0.73 | 23.91 | 372 |
| Example 55 | 556 | 4.18 | 99.3 | 74.61 | 0.22 | 0.73 | 23.87 | 339 |
| Example 56 | 558 | 4.15 | 98.54 | 74.56 | 0.22 | 0.73 | 23.64 | 337 |
| Example 57 | 559 | 4.14 | 106.27 | 80.60 | 0.22 | 0.73 | 25.51 | 380 |
| Comparative example 1 | Compound I | 4.24 | 87.50 | 64.79 | 0.22 | 0.73 | 21.00 | 300 |
| Comparative example 2 | Compound II | 4.31 | 86.00 | 62.65 | 0.22 | 0.73 | 20.60 | 278 |
| Comparative example 3 | Compound III | 4.70 | 41.58 | 27.78 | 0.22 | 0.73 | 9.97 | 128 |

From the data shown in Table 10 above, it can be seen that the compounds of the present disclosure, when used as a host of the organic light-emitting layer of the green organic electroluminescent device, significantly improved the device performance compared with Comparative examples 1 to 3. For the organic compound of the present disclosure, the service life was improved by at least 12.3% and the current efficiency was improved by at least 12.1% compared with Comparative examples 1 to 3.

According to the organic compound provided by the present disclosure, specific 3,3-bicarbazole is used as a parent core, deuteration is performed in at least two ortho positions of a connecting bond of bicarbazole, and aryl is connected to one carbazole ring, and an electron donating group is connected to biscarbazole, and such a specific combination reduces the twist angle between two carbazole rings, and improves the conjugation, thus improving the hole mobility and charge transport balance of a host material. The organic compound is applied to a hole-type host material in a host material for a light-emitting layer of a phosphorescent organic electroluminescent device, in particular a green organic electroluminescent device, so that the light-emitting layer has good hole transport properties, and the efficiency of recombination of electrons and holes to form excitons is increased, thus making the device have a reduced voltage, and improving the luminous efficiency and service life characteristics of the device.

Other embodiments of the present disclosure will be readily conceived by those skilled in the art after taking into account the description and practicing the present disclosure disclosed here. The present disclosure is intended to cover any variations, uses or adaptive variations of the present disclosure, and the variations, uses or adaptive variations follow the general principles of the present disclosure and include the common general knowledge or conventional technical means in the art, which is not disclosed in the present disclosure. The description and examples are considered only exemplary, and the true scope and spirit of the present disclosure are indicated by the following claims.

It should be understood that the present disclosure is not limited to the precise structures that have been described above and shown in the drawings, and that various modifications and changes can be made without departing from its scope. The scope of the present disclosure is limited only by the following claims.

What is claimed is:

1. An organic compound, having a structure represented by a formula 1:

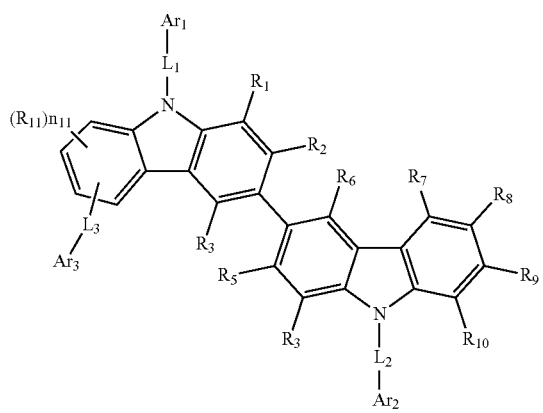

Formula 1 wherein $L_1$ and $L_2$ are respectively and independently selected from a single bond, substituted or unsubstituted phenylene, substituted or unsubstituted naphthylene, substituted or unsubstituted biphenylene, substituted or unsubstituted carbazolylene, substituted or unsubstituted dibenzofurylene, and substituted or unsubstituted dibenzothienylene;

$L_3$ is selected from a single bond or phenylene;

$Ar_1$ and $Ar_2$ are respectively and independently selected from substituted or unsubstituted phenyl, substituted or unsubstituted naphthyl, substituted or unsubstituted biphenyl, substituted or unsubstituted terphenyl, substituted or unsubstituted phenanthryl, substituted or unsubstituted fluorenyl, substituted or unsubstituted dibenzofuranyl, substituted or unsubstituted carbazolyl, and substituted or unsubstituted dibenzothienyl;

$Ar_3$ is selected from substituted or unsubstituted phenyl, substituted or unsubstituted naphthyl, and substituted or unsubstituted biphenyl;

$R_1$, $R_2$, $R_3$, $R_4$, $R_5$, $R_6$, $R_7$, $R_8$, $R_9$ and $R_{10}$ are respectively and independently selected from hydrogen or deuterium, and at least two of $R_2$, $R_3$, $R_5$ and $R_6$ are deuterium;

$R_{11}$ is selected from hydrogen or deuterium;

$n_{11}$ is the number of $R_{11}$, and is selected from 1, 2 or 3, and when $n_{11}$ is greater than 1, any two $R_{11}$ are the same or different;

substituents in $L_1$ and $L_2$ are the same or different, and are respectively and independently selected from deuterium, fluorine, cyano, methyl, ethyl, n-propyl, isopropyl, tert-butyl, and phenyl;

substituents in $Ar_1$ and $Ar_2$ are the same or different, and are respectively and independently selected from deuterium, fluorine, cyano, methyl, ethyl, n-propyl, isopropyl, tert-butyl, phenyl, and naphthyl;

optionally, any two adjacent substituents in $Ar_1$ and $Ar_2$ form a fluorene ring; and substituents in $Ar_3$ are the same or different, and are respectively and independently selected from deuterium, fluorine, cyano, methyl, ethyl, n-propyl, isopropyl, tert-butyl, and phenyl.

2. The organic compound according to claim 1, having a structure represented by a formula 2:

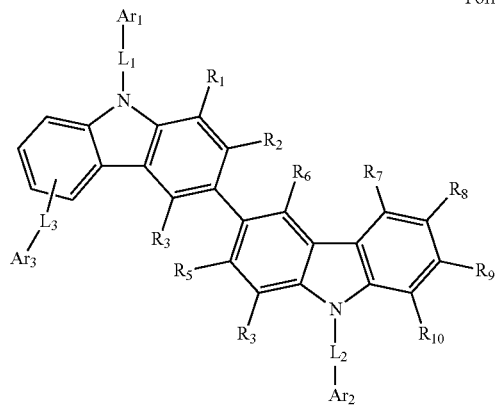

Formula 2 wherein $L_1$ and $L_2$ are respectively and independently selected from a single bond, substituted or unsubstituted phenylene, substituted or unsubstituted naphthylene, substituted or unsubstituted biphenylene, substituted or unsubstituted carbazolylene, substituted or unsubstituted dibenzofurylene, and substituted or unsubstituted dibenzothienylene;

$L_3$ is selected from a single bond or phenylene;

$Ar_1$ and $Ar_2$ are respectively and independently selected from substituted or unsubstituted phenyl, substituted or unsubstituted naphthyl, substituted or unsubstituted biphenyl, substituted or unsubstituted terphenyl, substituted or unsubstituted phenanthryl, substituted or unsubstituted fluorenyl, substituted or unsubstituted dibenzofuranyl, substituted or unsubstituted carbazolyl, and substituted or unsubstituted dibenzothienyl;

$Ar_3$ is selected from substituted or unsubstituted phenyl, substituted or unsubstituted naphthyl, and substituted or unsubstituted biphenyl;

$R_1$, $R_2$, $R_3$, $R_4$, $R_5$, $R_6$, $R_7$, $R_8$, $R_9$ and $R_{10}$ are respectively and independently selected from hydrogen or deuterium, and at least two of $R_2$, $R_3$, $R_5$ and $R_6$ are deuterium;

substituents in $L_1$ and $L_2$ are the same or different, and are respectively and independently selected from deuterium, fluorine, cyano, methyl, ethyl, n-propyl, isopropyl, tert-butyl, and phenyl;

substituents in Ar$_1$ and Ar$_2$ are the same or different, and are respectively and independently selected from deuterium, fluorine, cyano, methyl, ethyl, n-propyl, isopropyl, tert-butyl, phenyl, and naphthyl;

optionally, any two adjacent substituents in Ar$_1$ and Ar$_2$ form a fluorene ring; and substituents in Ara are the same or different, and are respectively and independently selected from deuterium, fluorine, cyano, methyl, ethyl, n-propyl, isopropyl, tert-butyl, and phenyl.

3. The organic compound according to claim 1, wherein Ar$_1$ and Ar$_2$ are respectively and independently selected from a substituted or unsubstituted group W, wherein the unsubstituted group W is selected from the group consisting of:

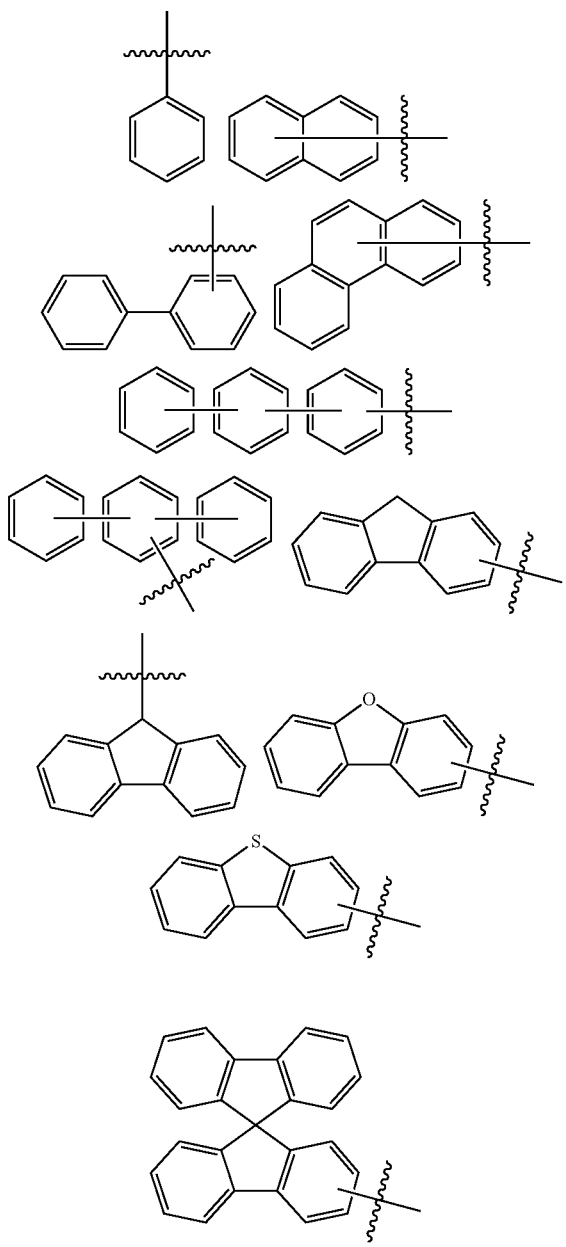

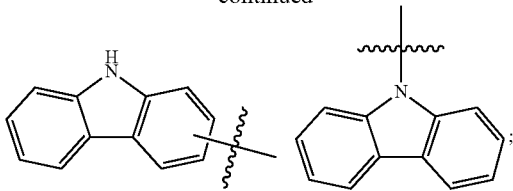

wherein ⫲ represents a chemical bond; the substituted group W contains one or more substituents selected from deuterium, fluorine, cyano, methyl, ethyl, n-propyl, isopropyl, tert-butyl, phenyl, and naphthyl; and when the substituted group W contains a plurality of substituents, the substituents are the same or different.

4. The organic compound according to claim 1, wherein R$_1$, R$_2$ and R$_3$ are all deuterium, or R$_4$, R$_5$ and R$_6$ are all deuterium.

5. The organic compound according to claim 1, wherein R$_4$, R$_5$, R$_6$, R$_7$, R$_8$, R$_9$ and R$_{10}$ are all deuterium.

6. The organic compound according to claim 1, wherein the organic compound is selected from the group consisting of:

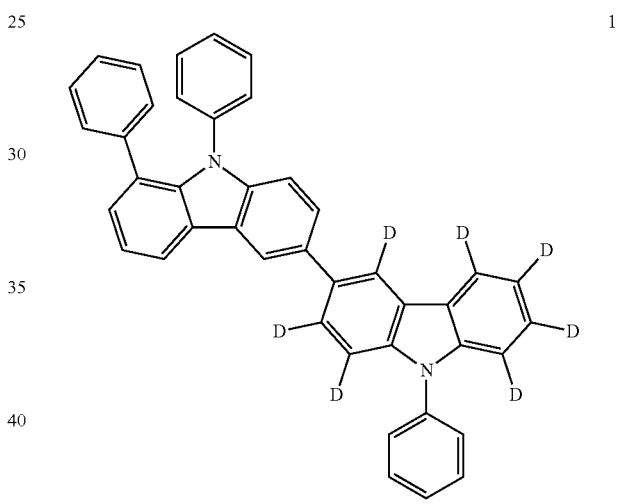

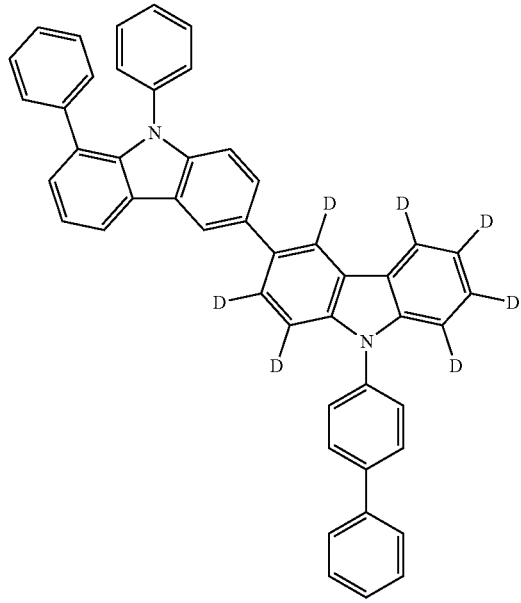

485
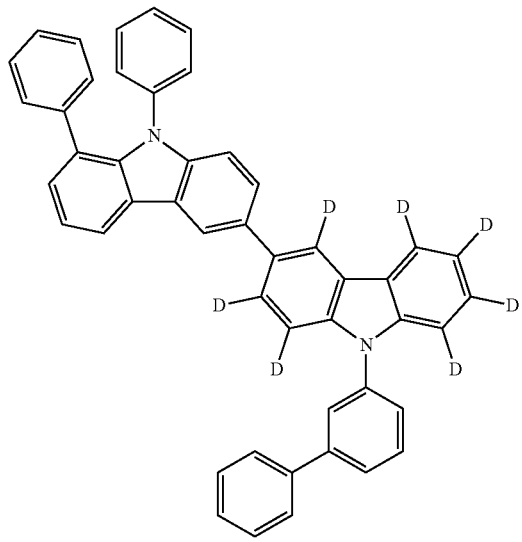
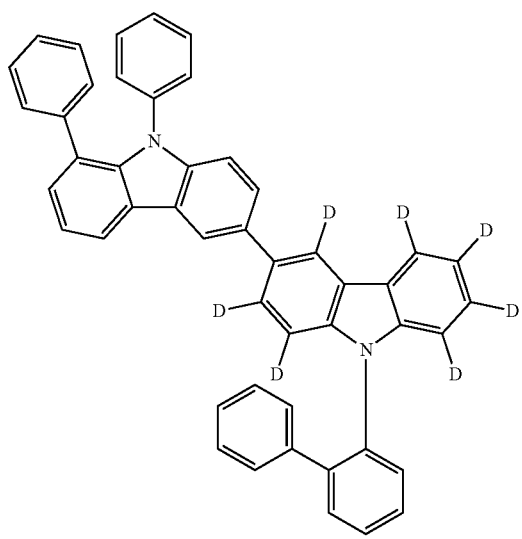
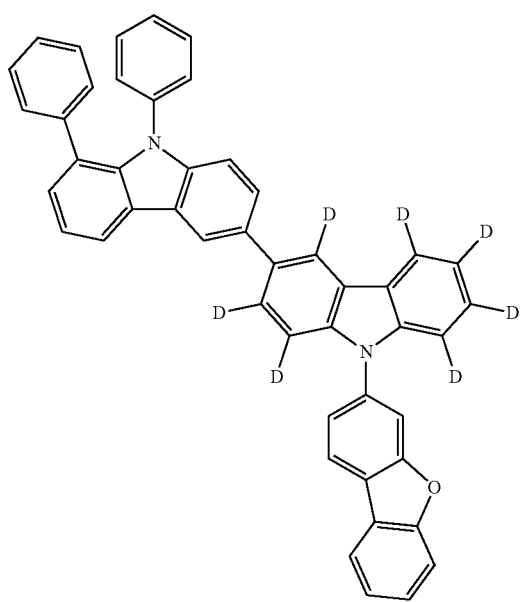
486
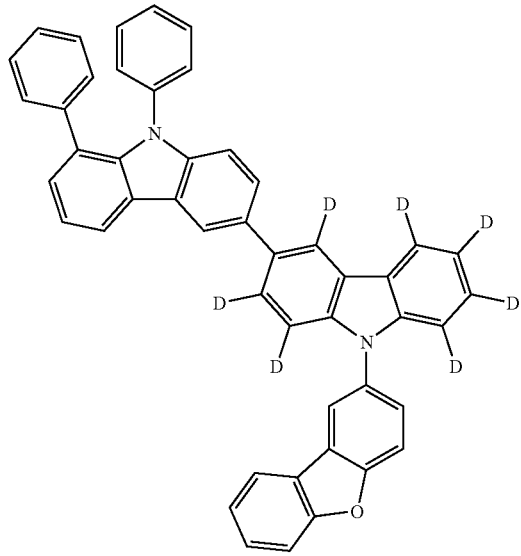
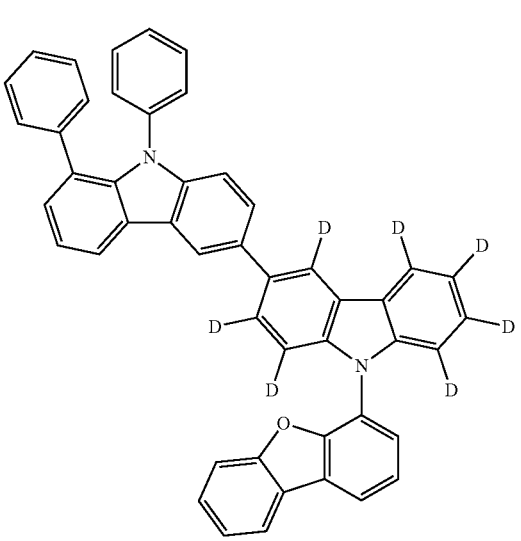

487
-continued
488
-continued
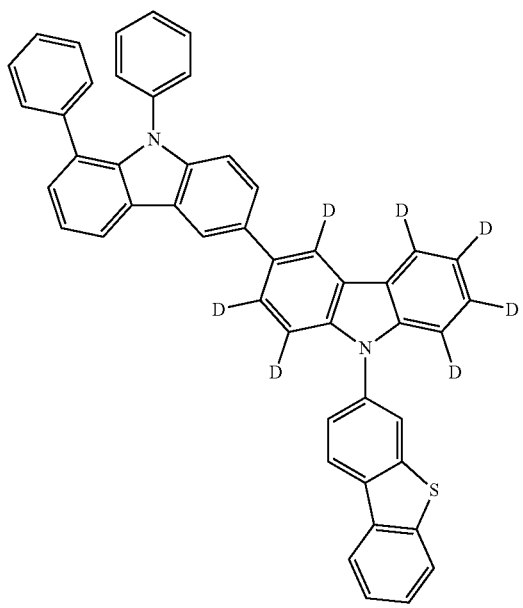
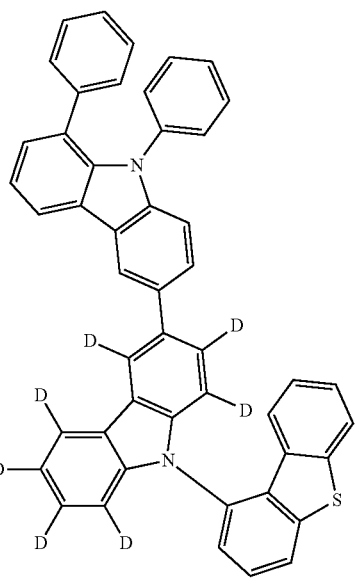

15
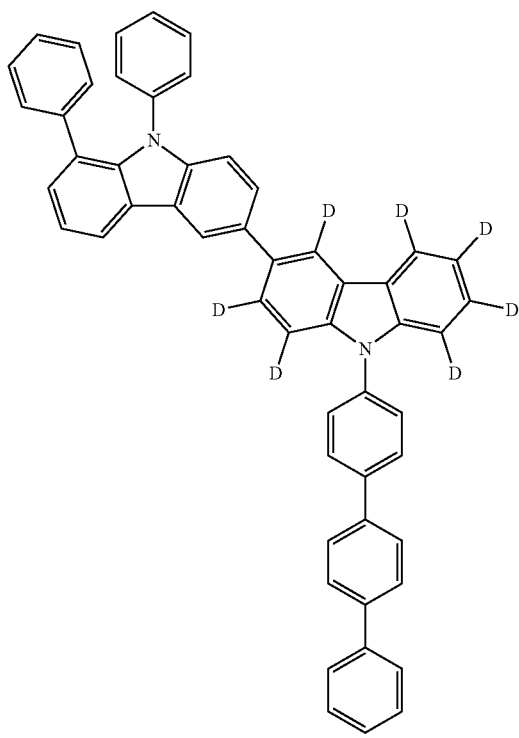
16
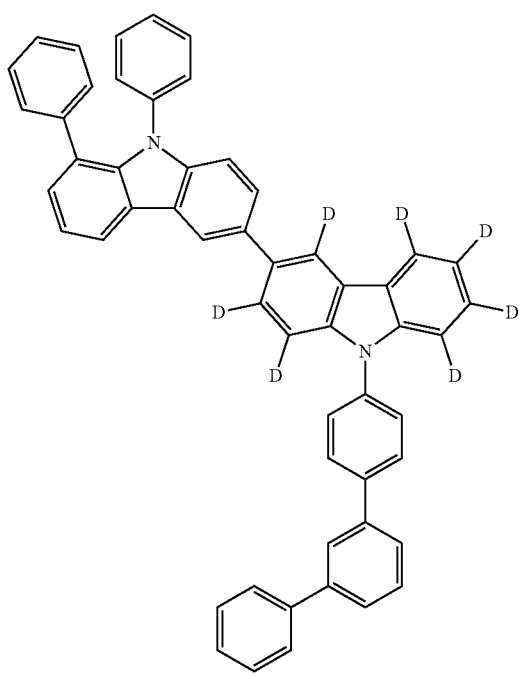
17
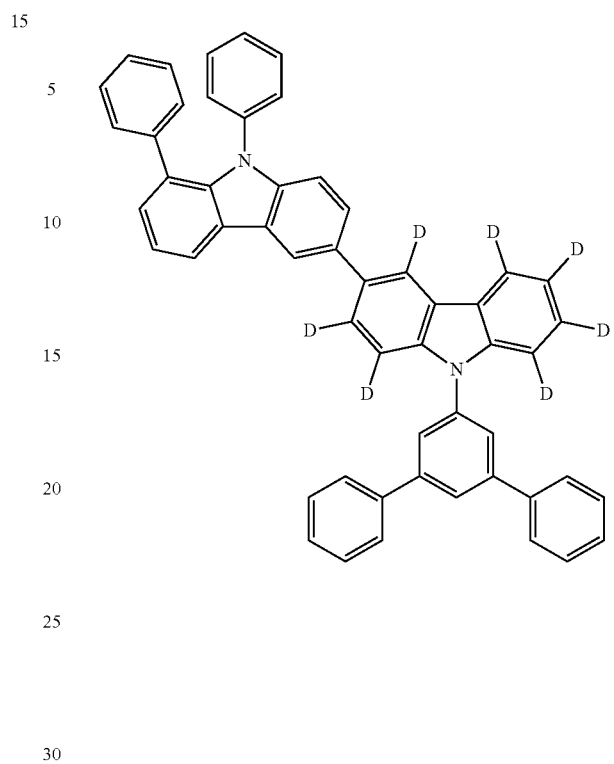
18

491
-continued
19
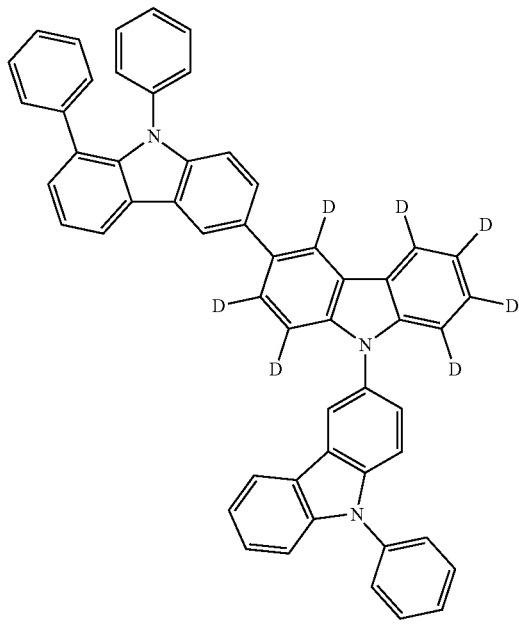
492
-continued
22
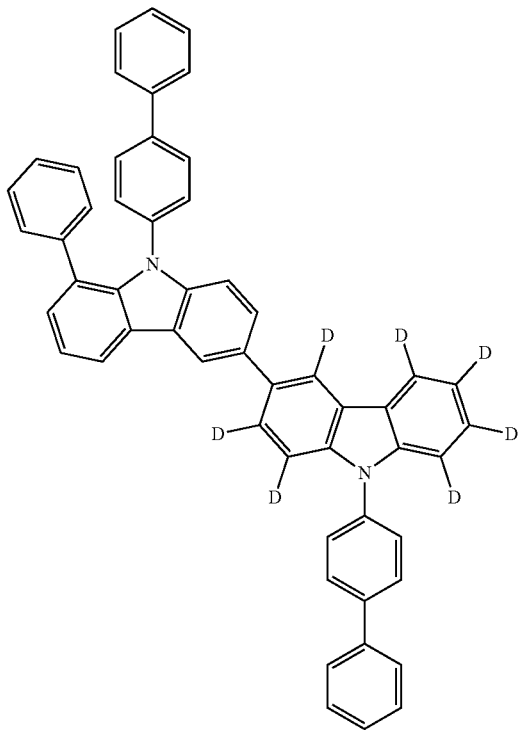
21
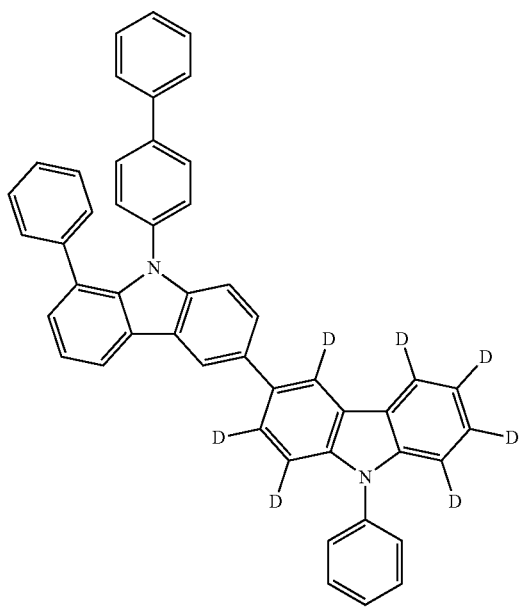
23
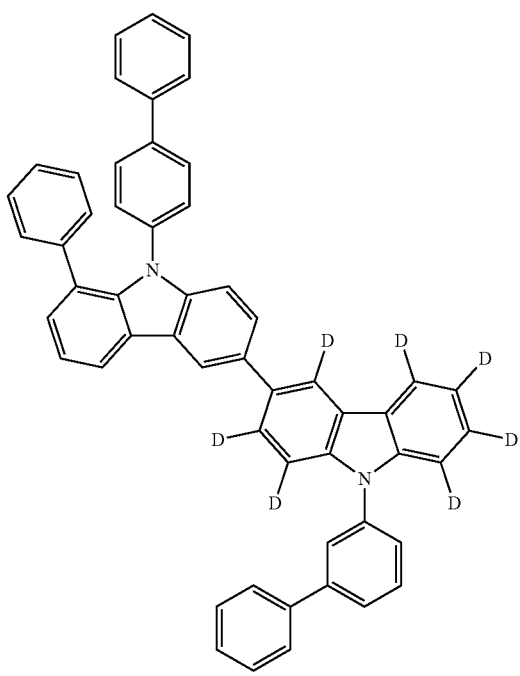

-continued
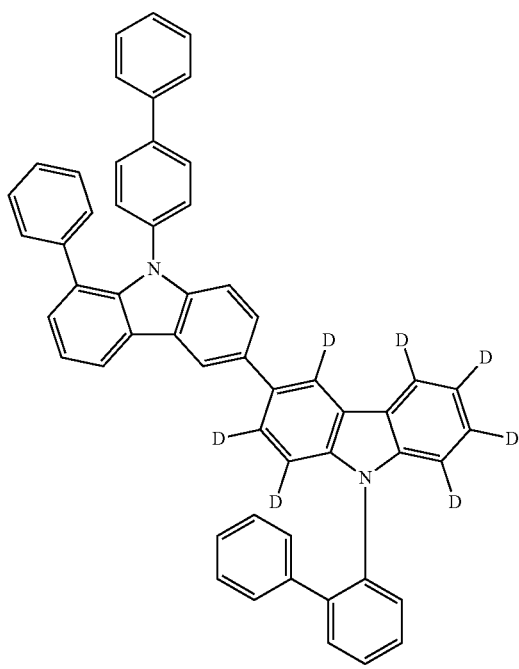
24
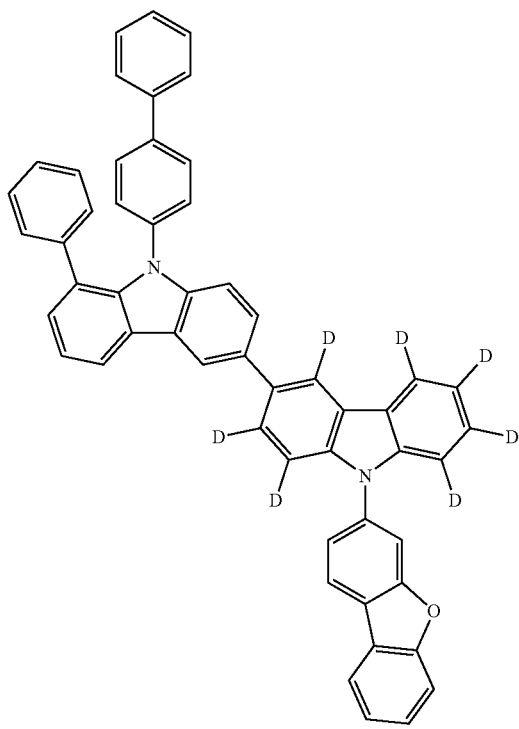
25
-continued
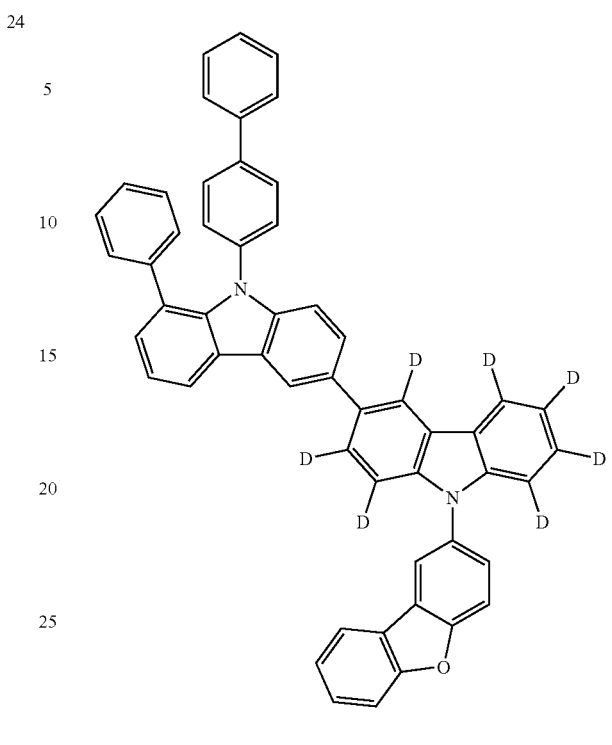
26
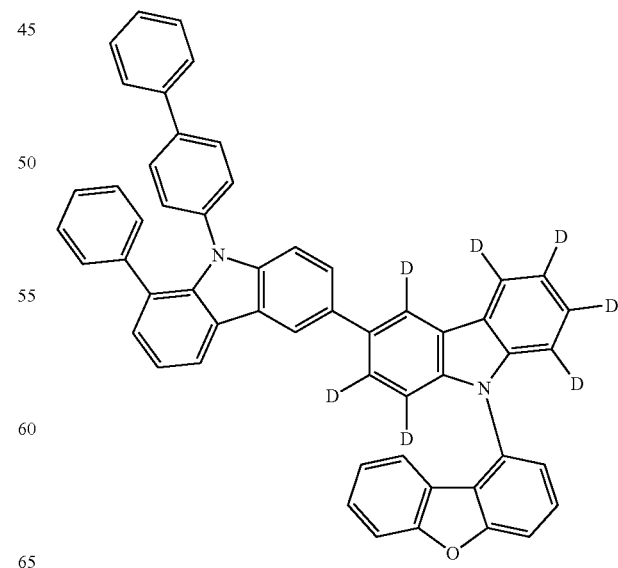
27

-continued
28
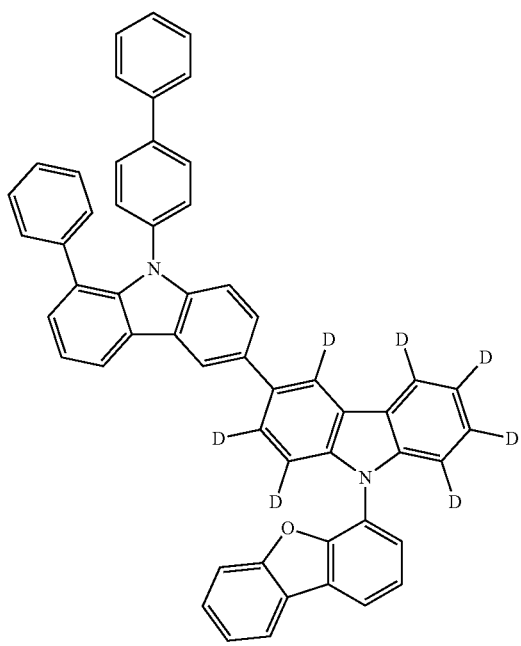
29
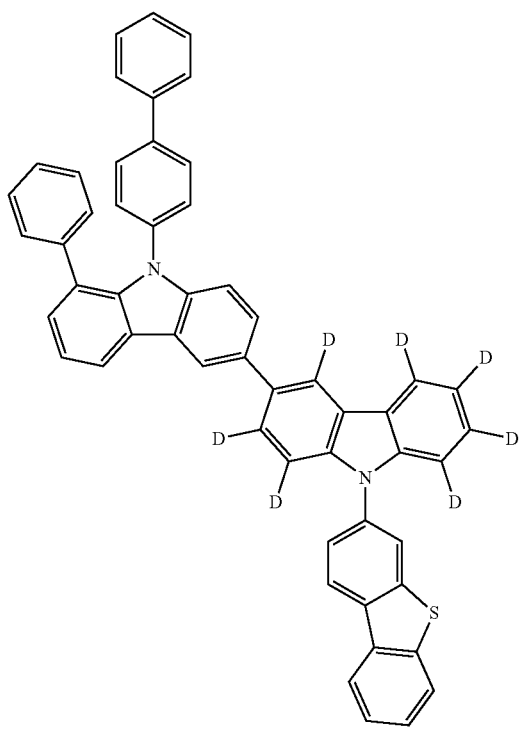
-continued
30
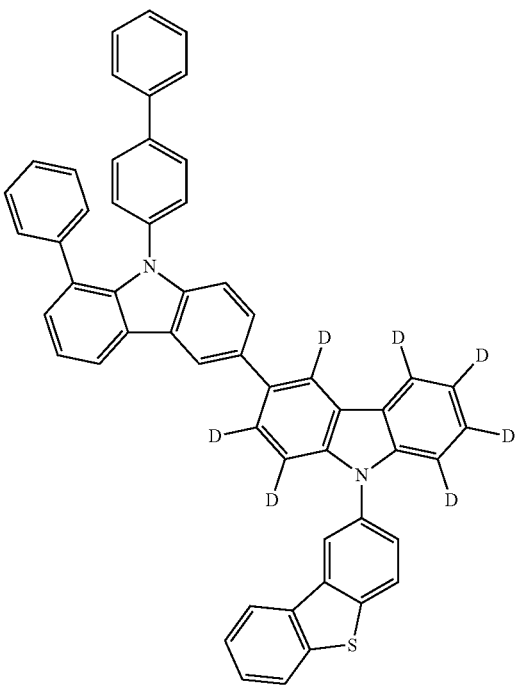
31
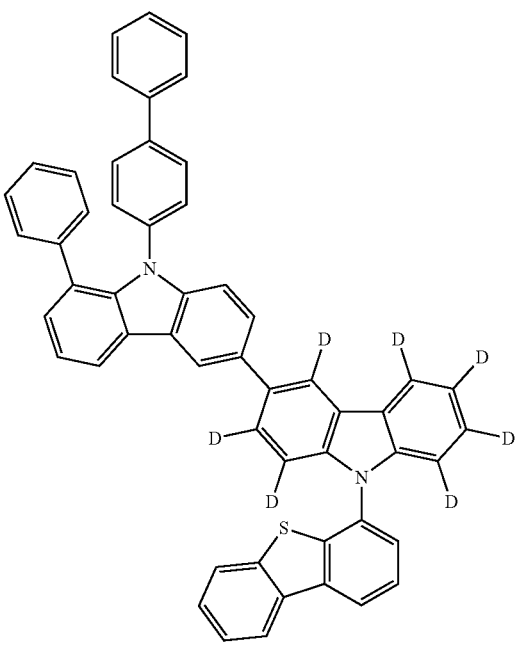

497
-continued
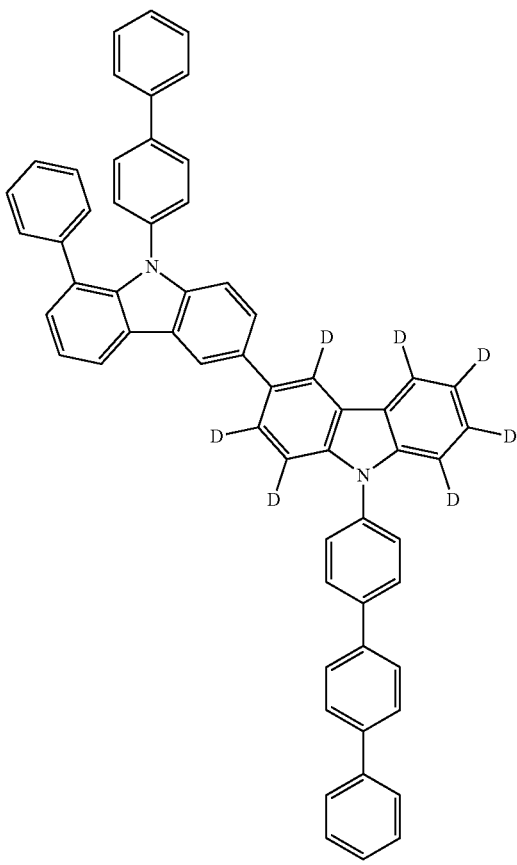
34
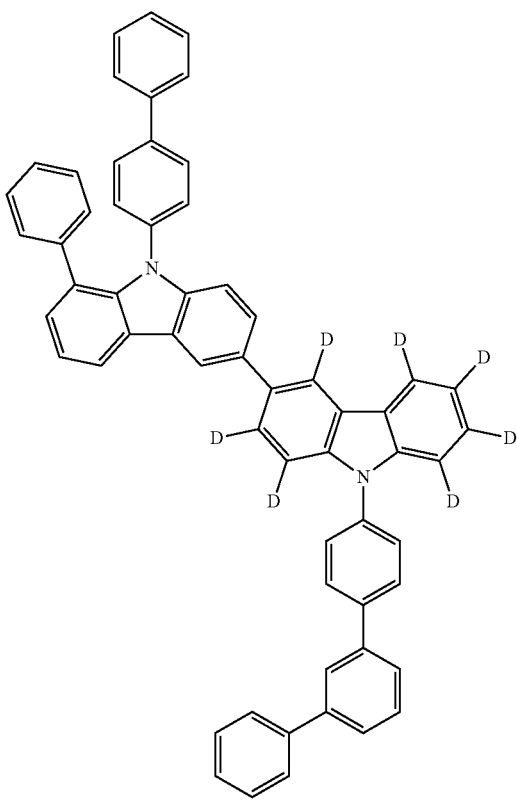
498
-continued
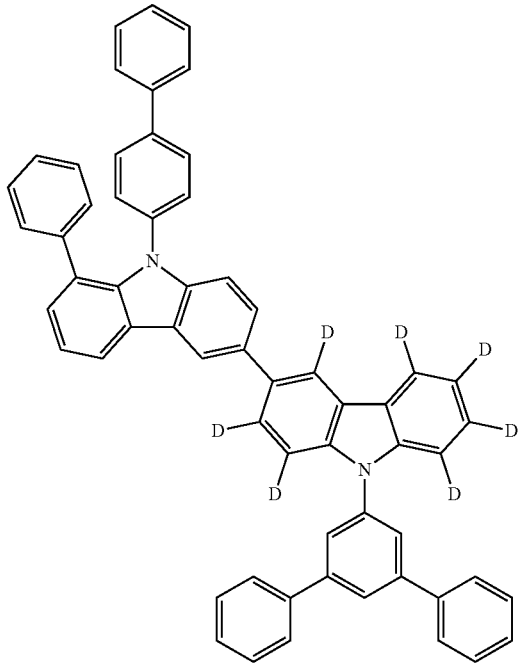
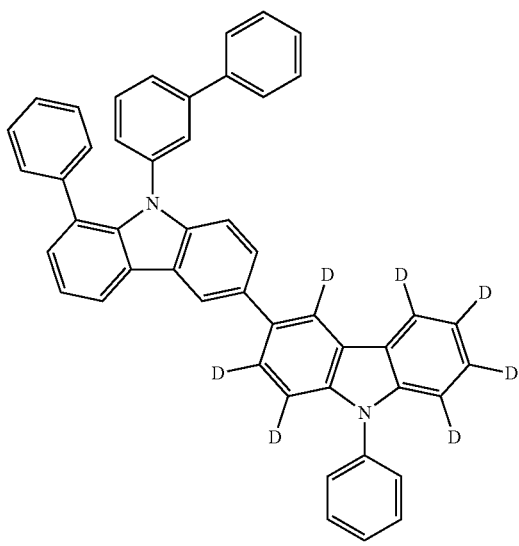

499
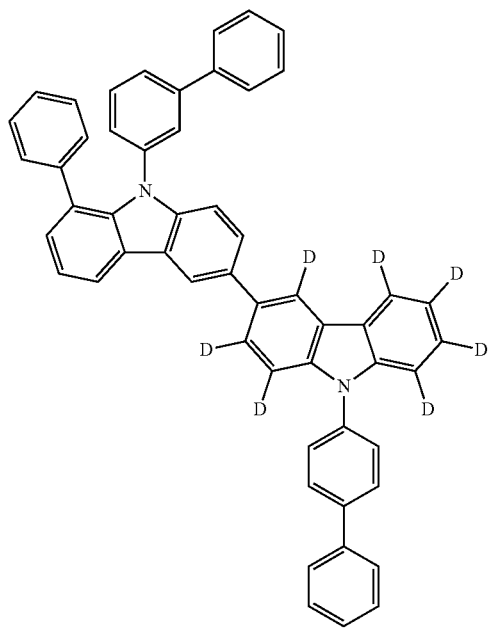
500
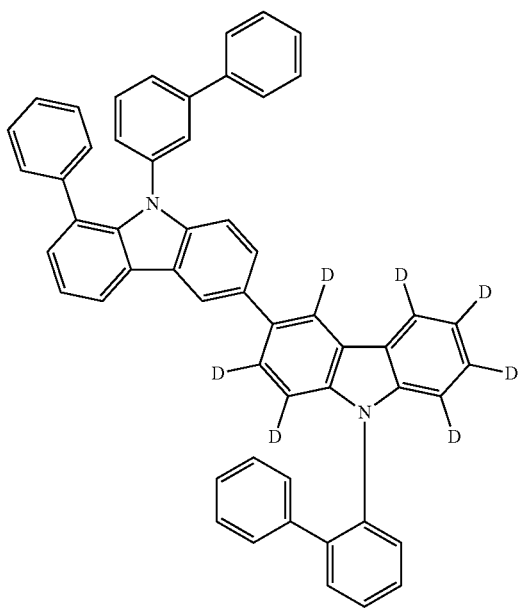
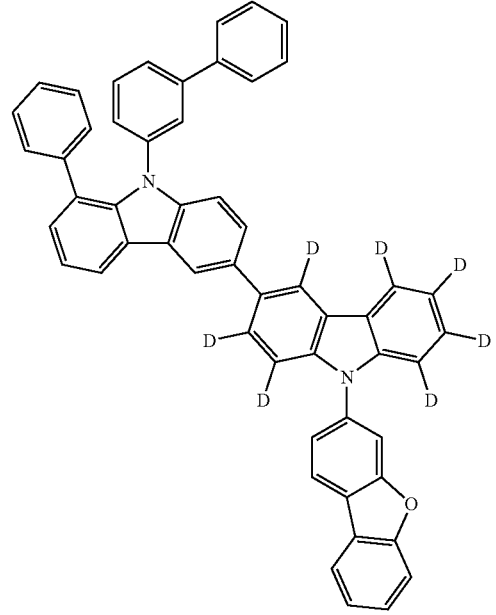

501
-continued
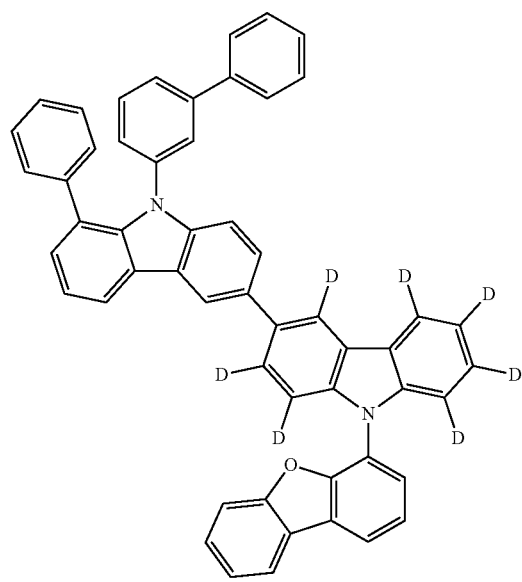
43
502
-continued
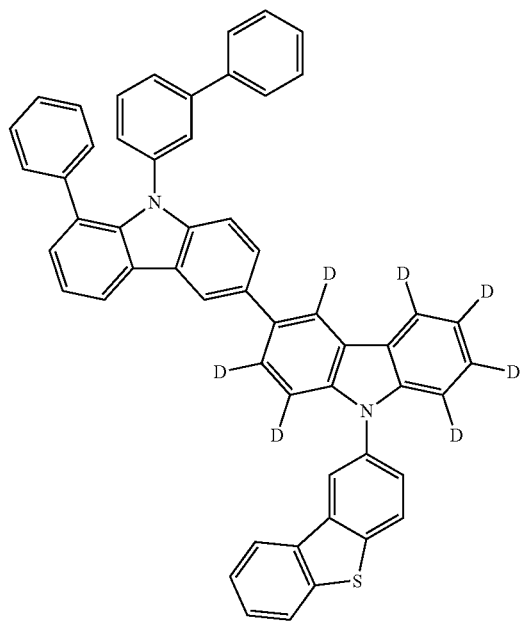
45
44
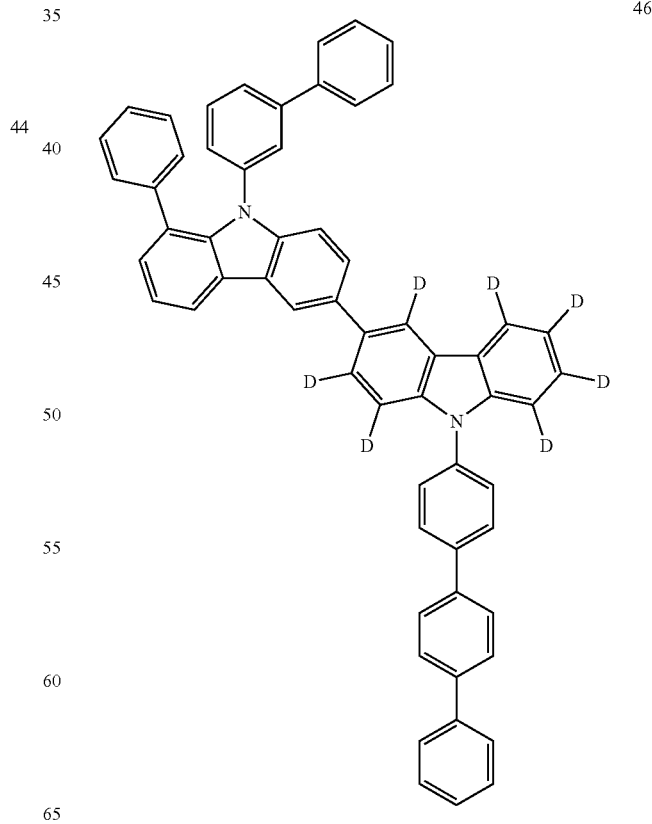
46

503
47
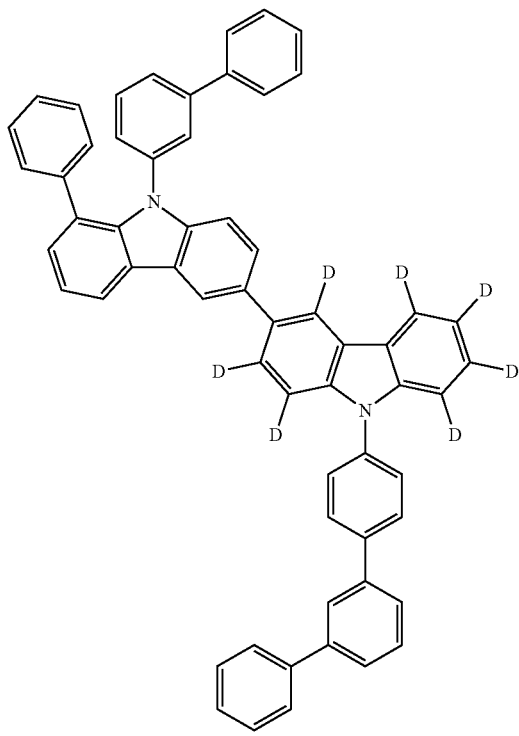
48
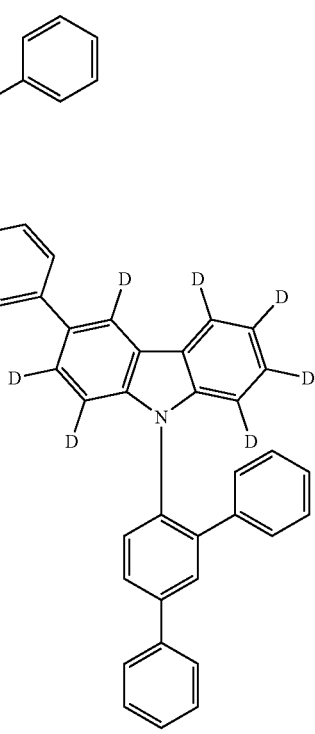
504
49
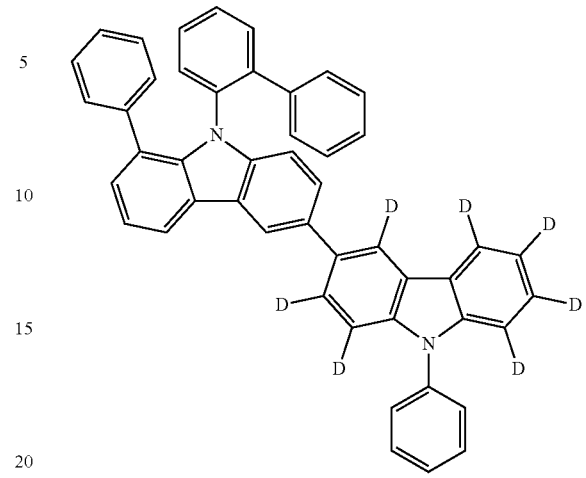
51
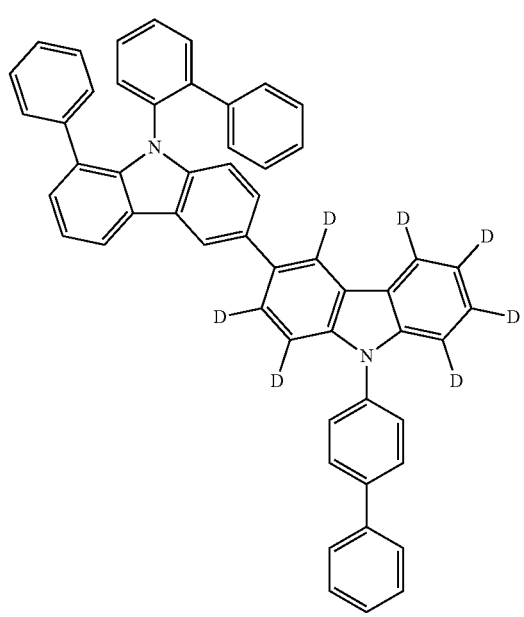
52
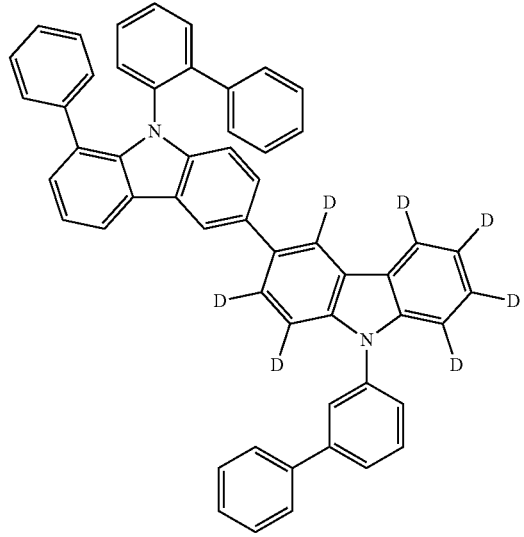

505
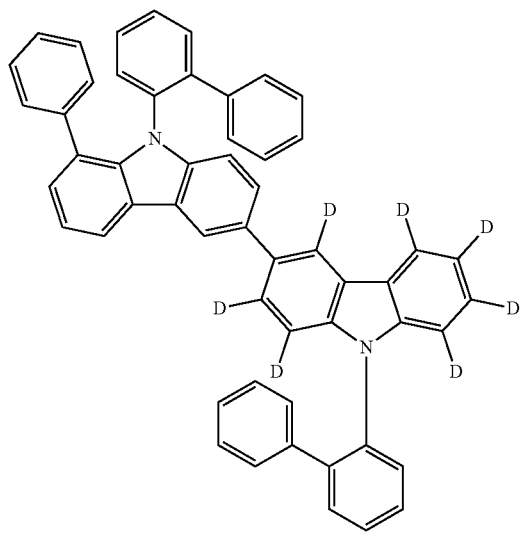
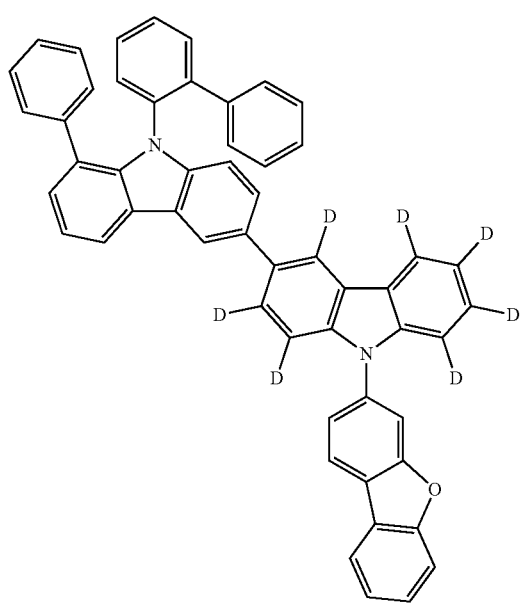
506
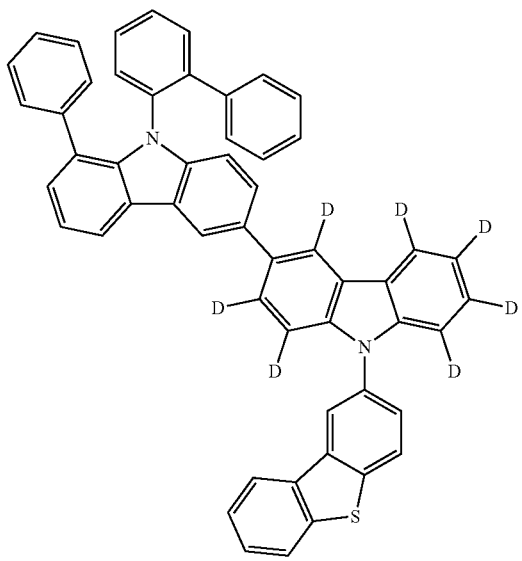
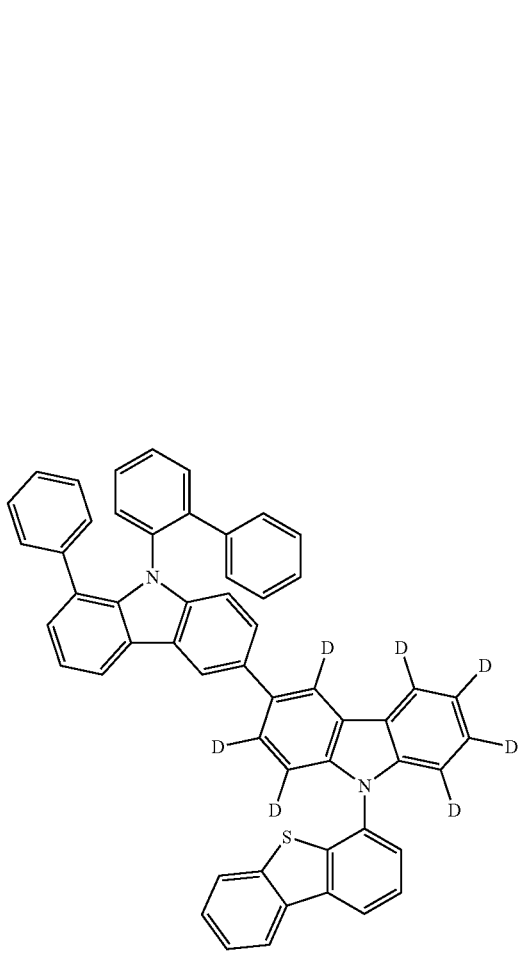

507
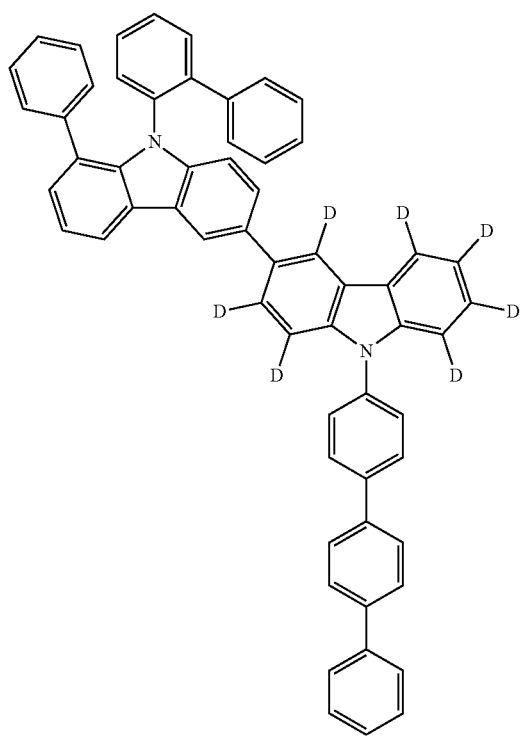
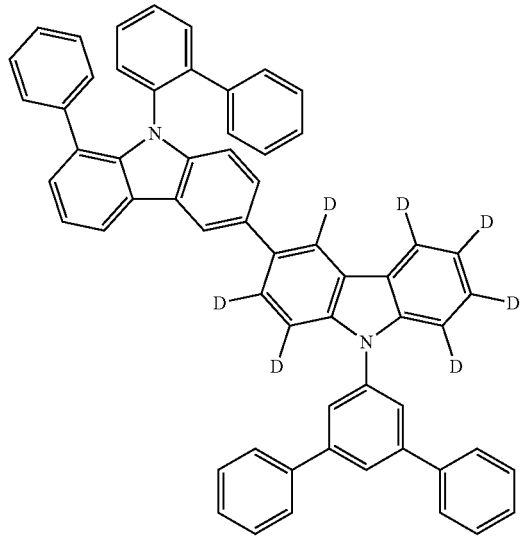
508
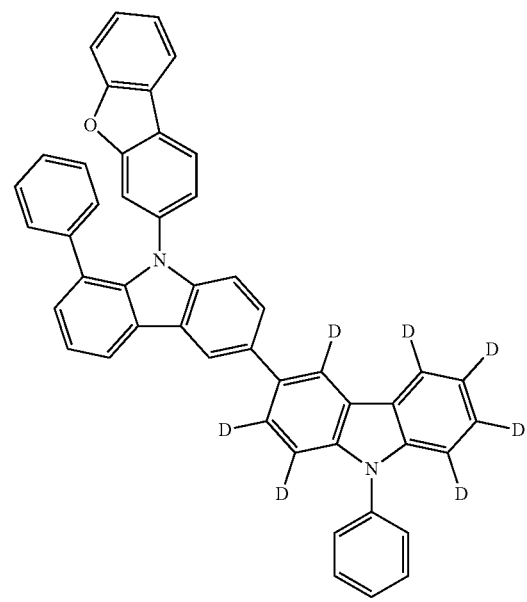
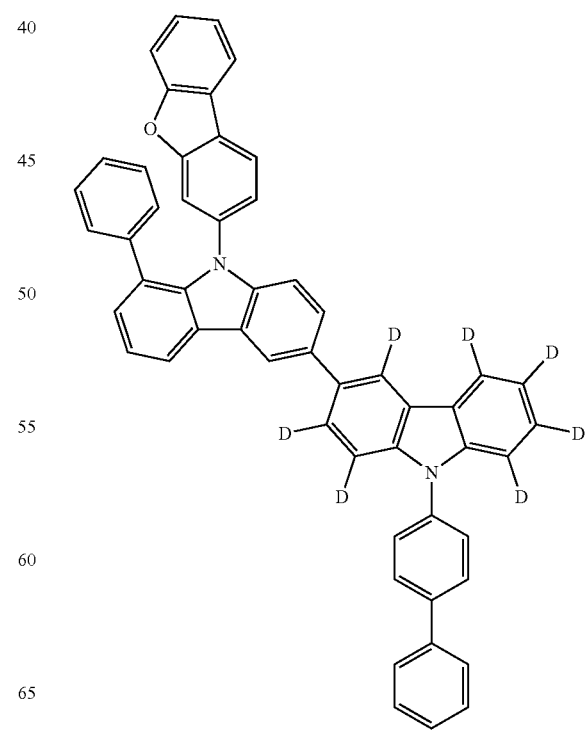

509
-continued
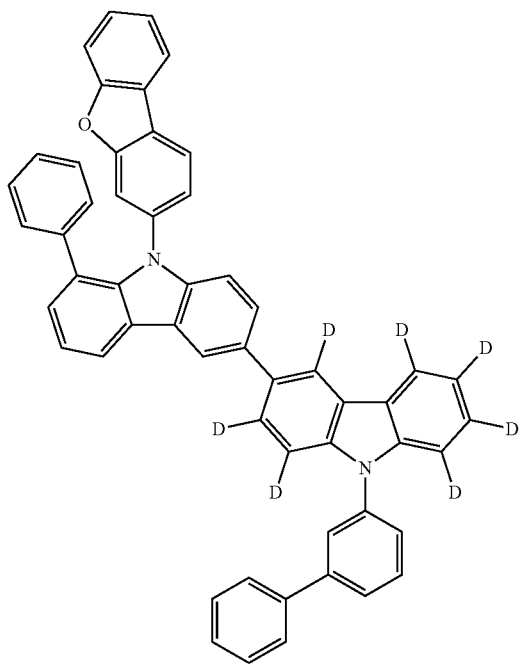
510
-continued
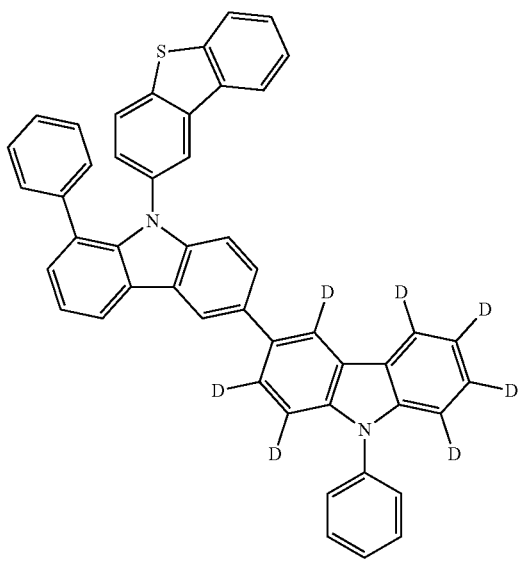
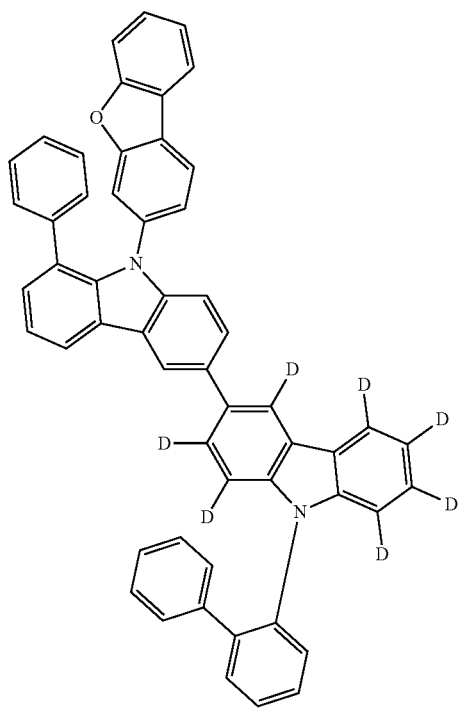
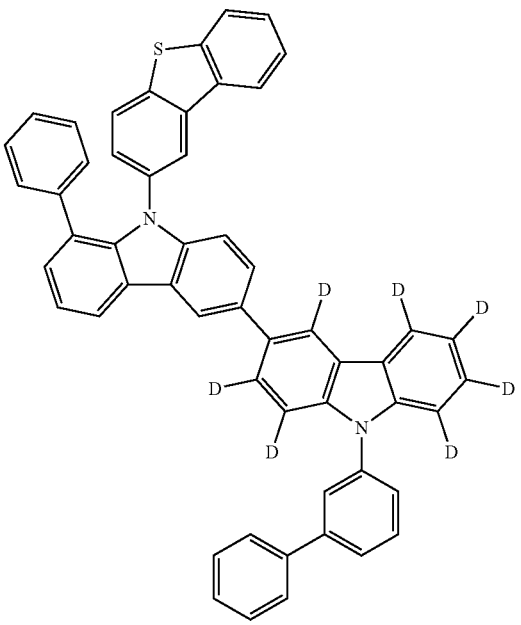

511
-continued
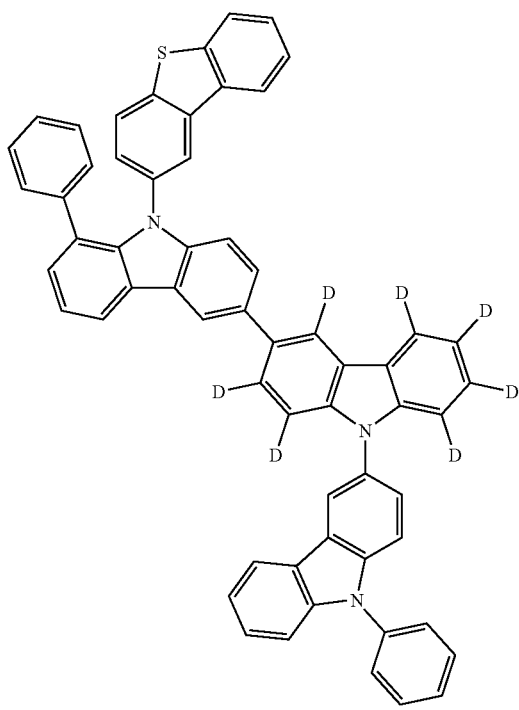
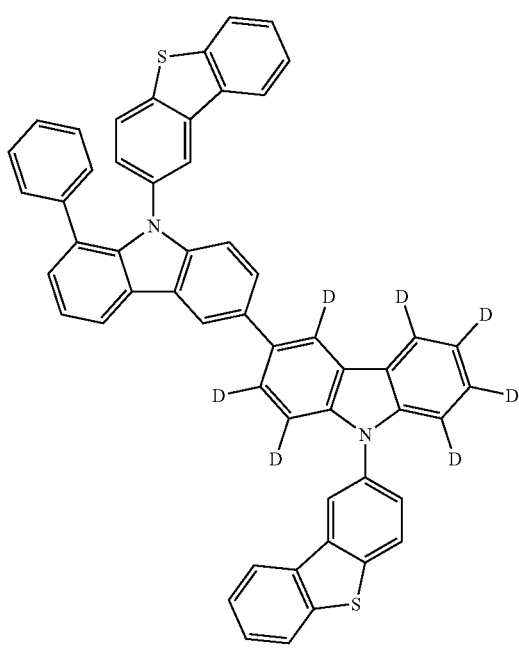
512
-continued
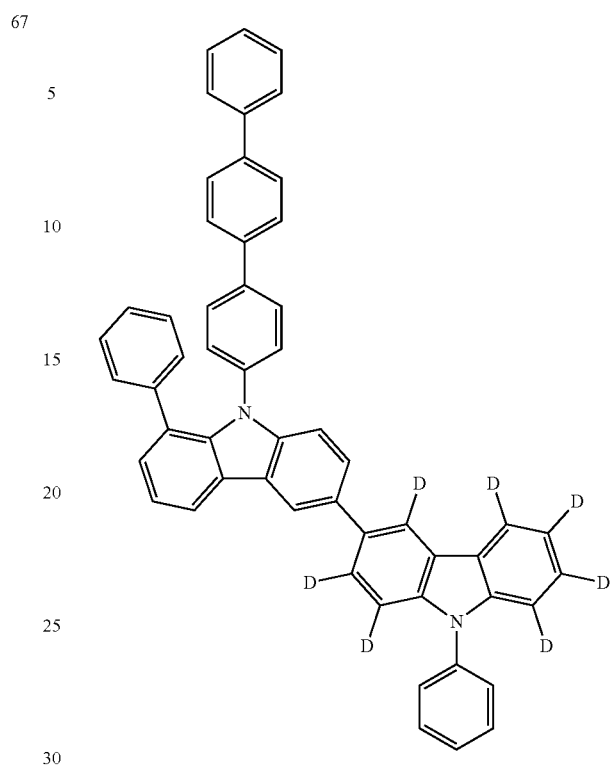
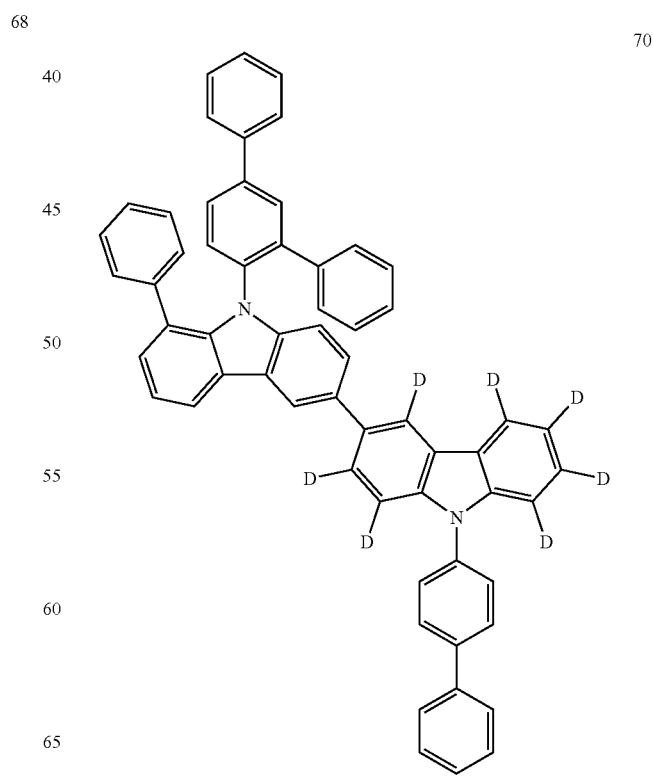

73
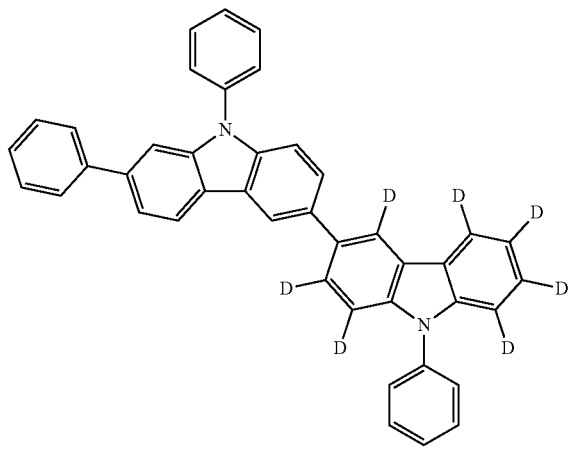
74
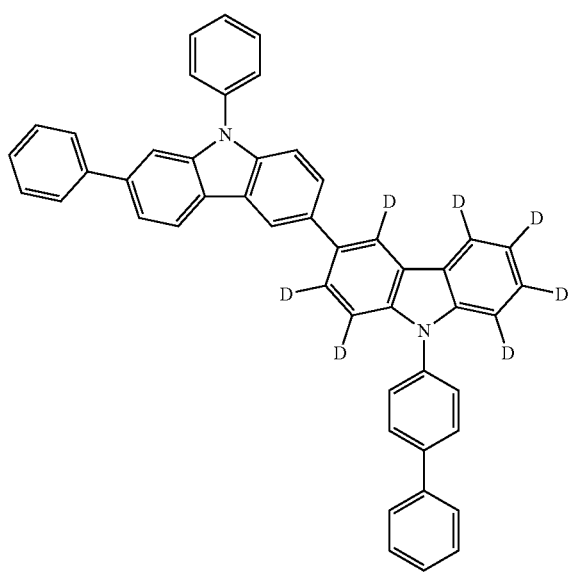
75
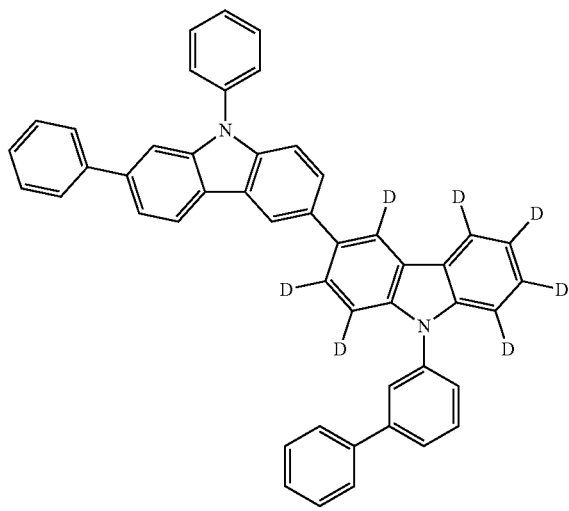
76
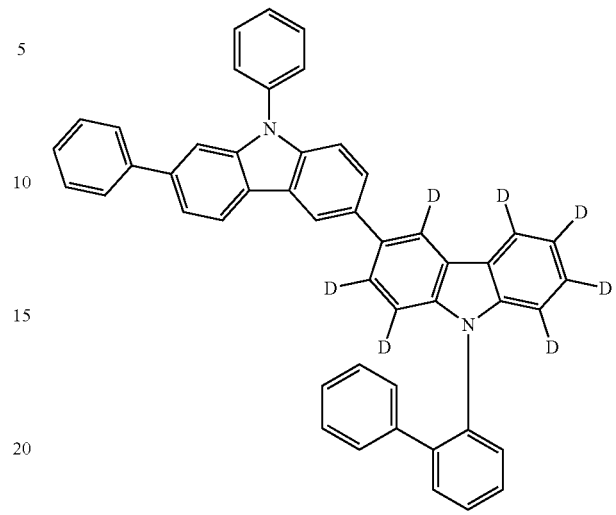
77
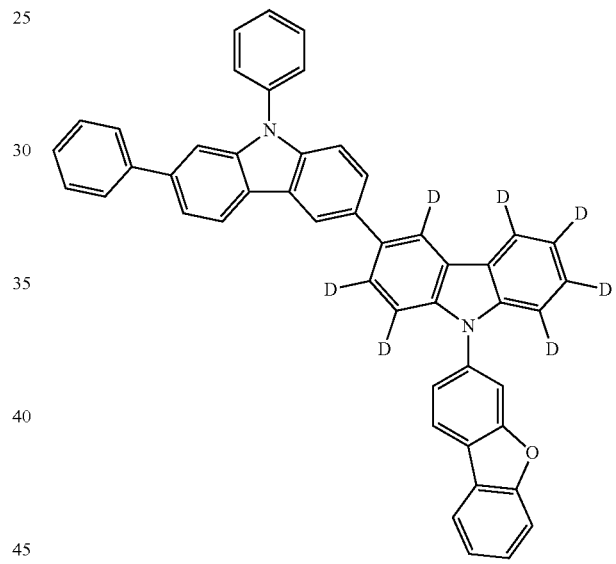
78
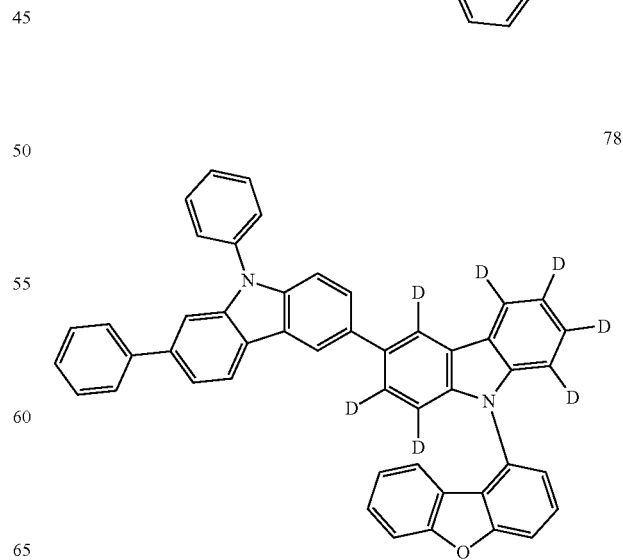

515
-continued
79
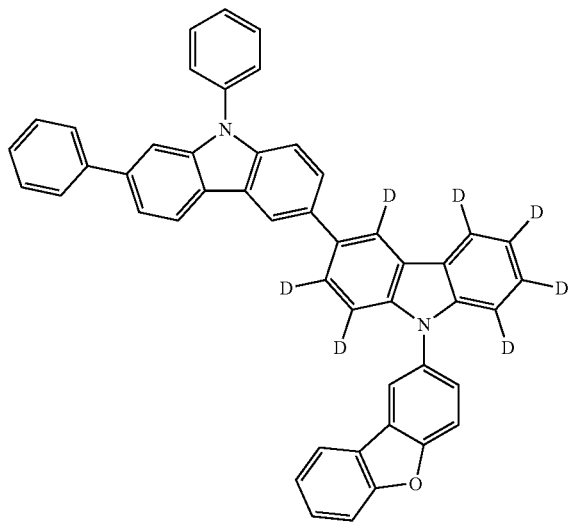
80
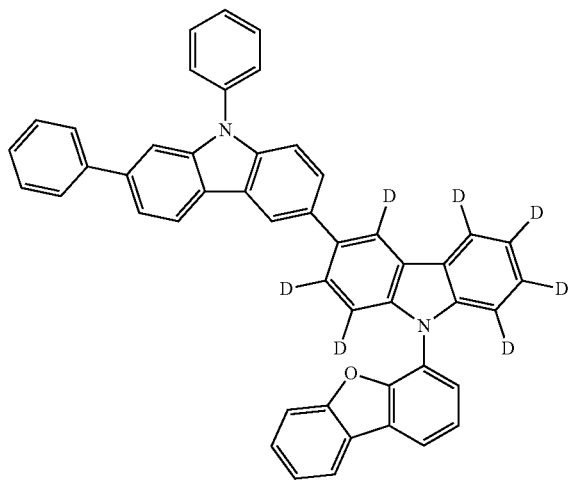
81
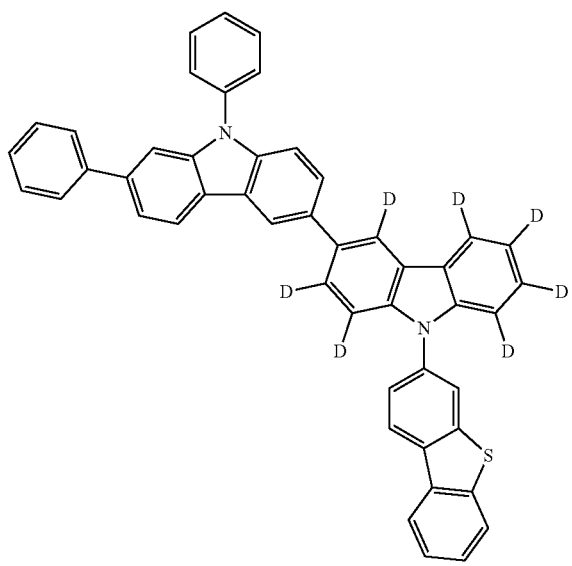
516
-continued
82
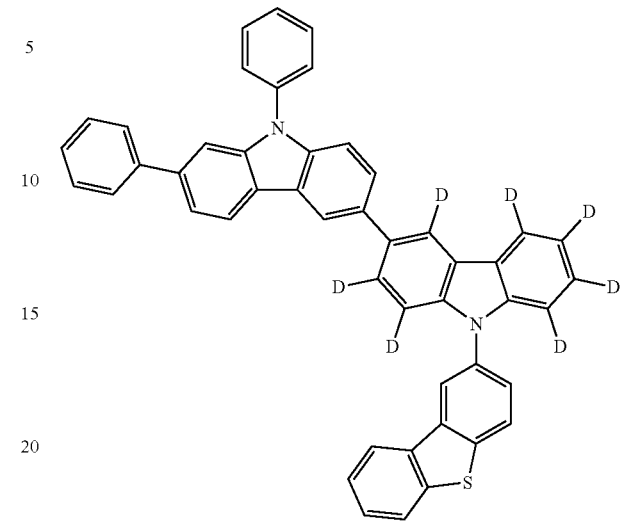
83
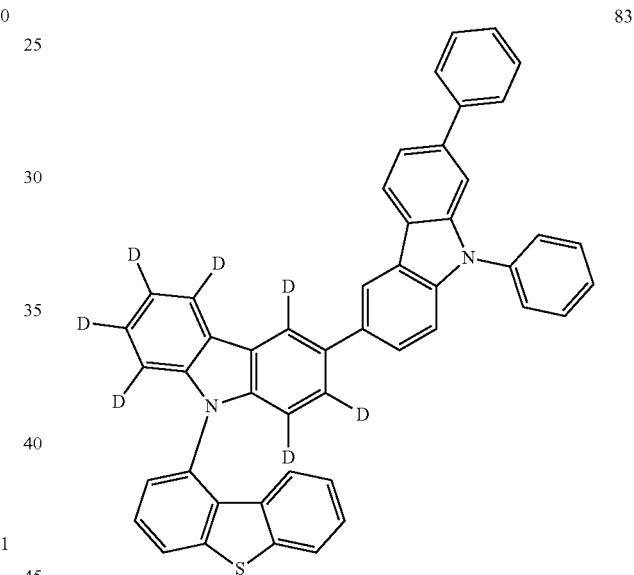
84

517
-continued
88
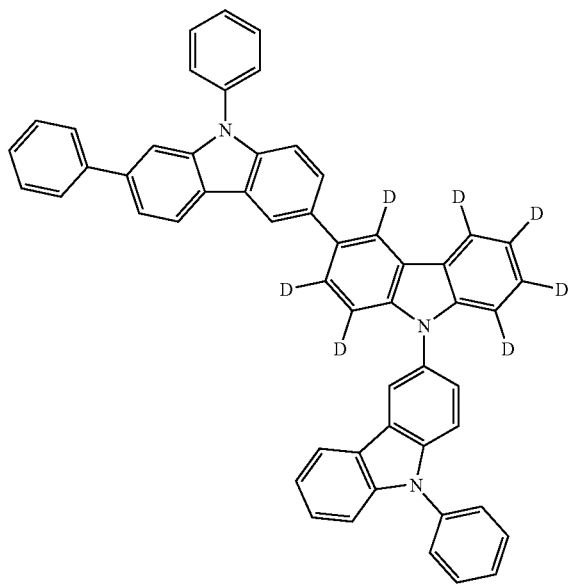
89
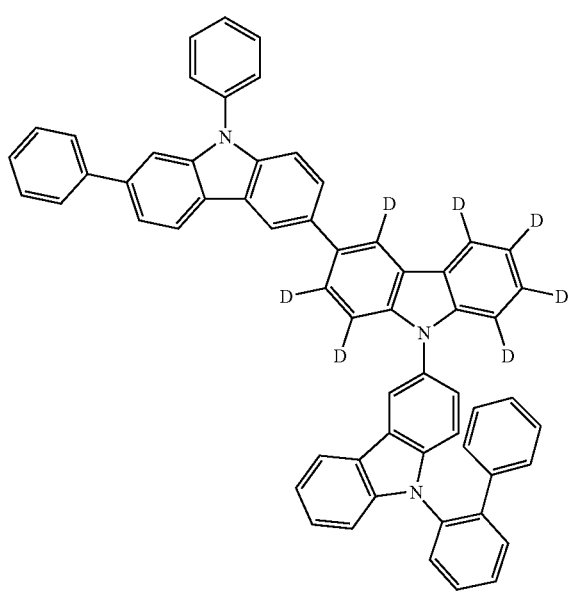
518
-continued
90
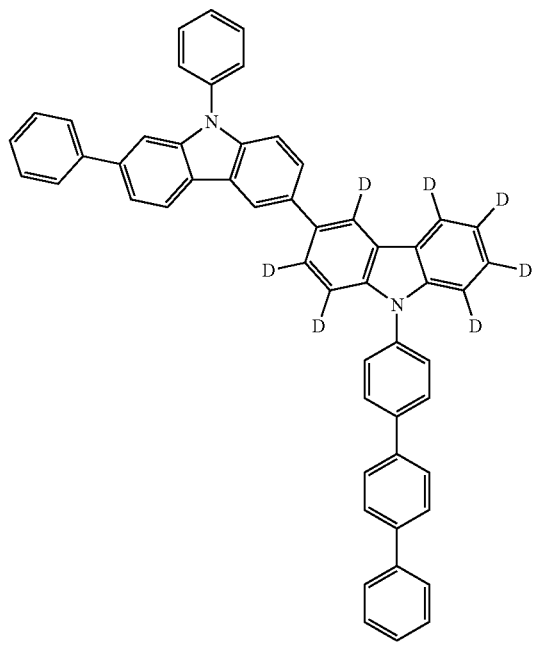
91
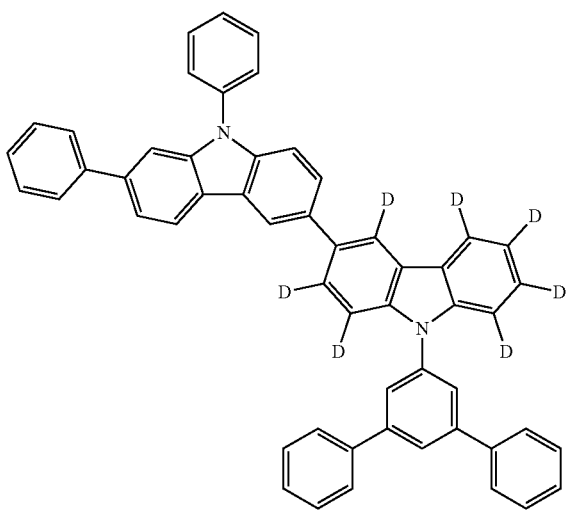

92
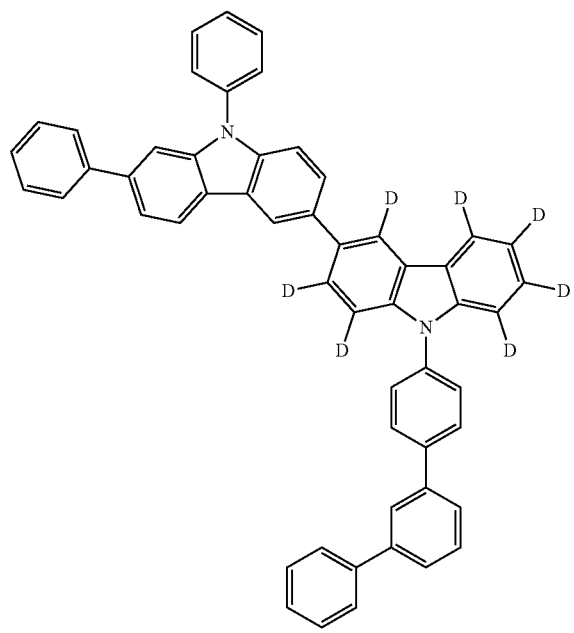
93
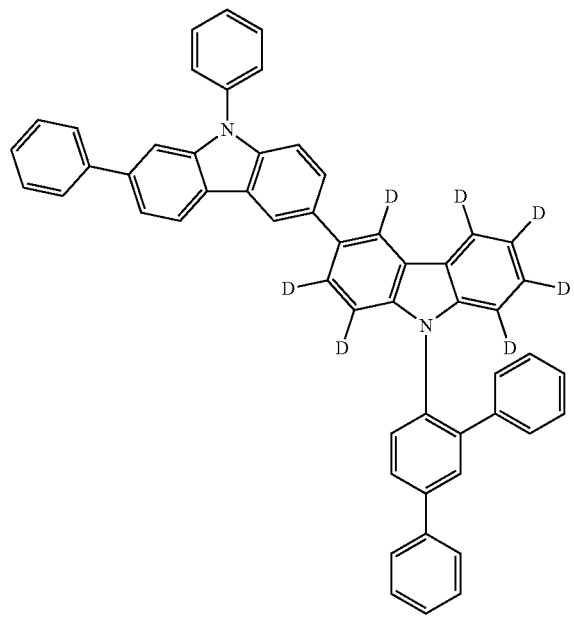
97
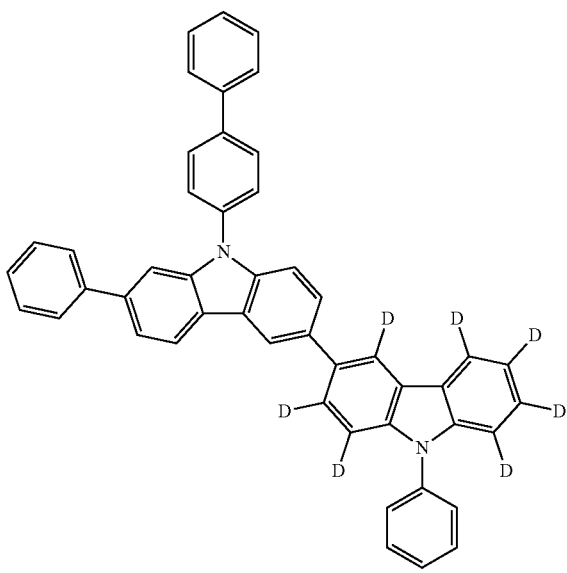
99
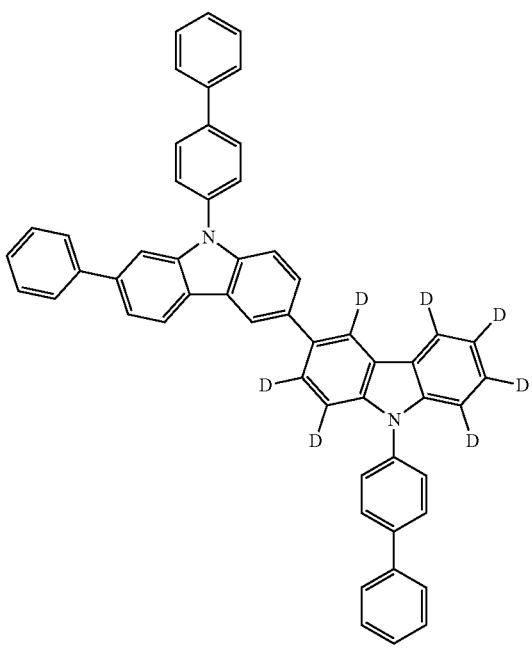

521
-continued
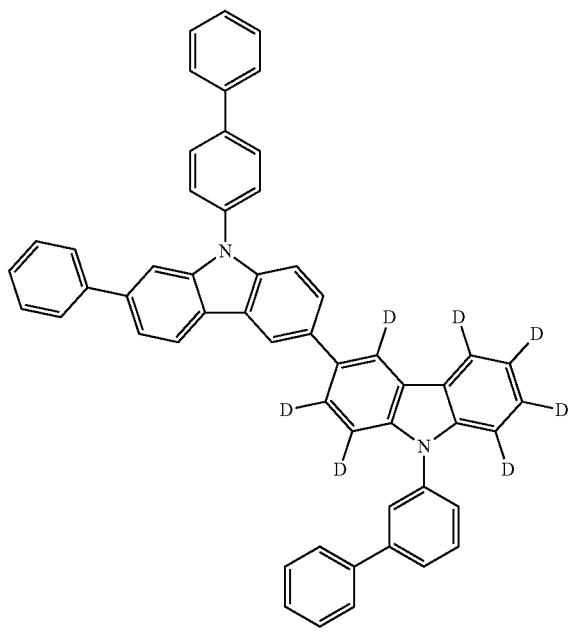
100
522
-continued
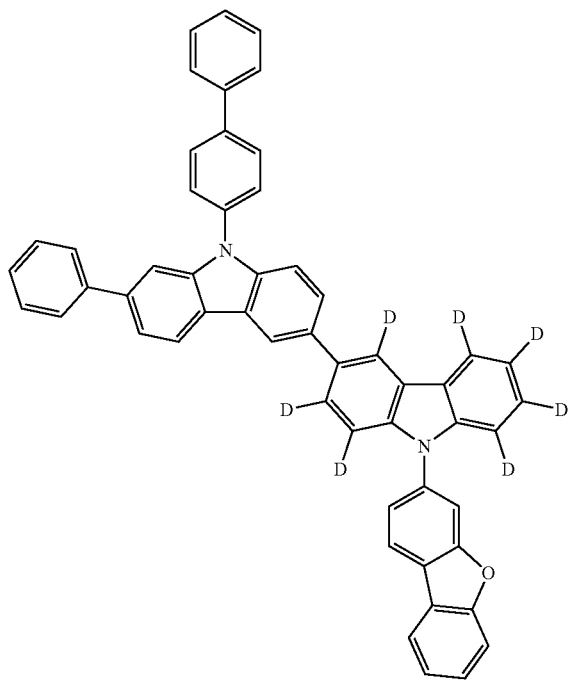
102
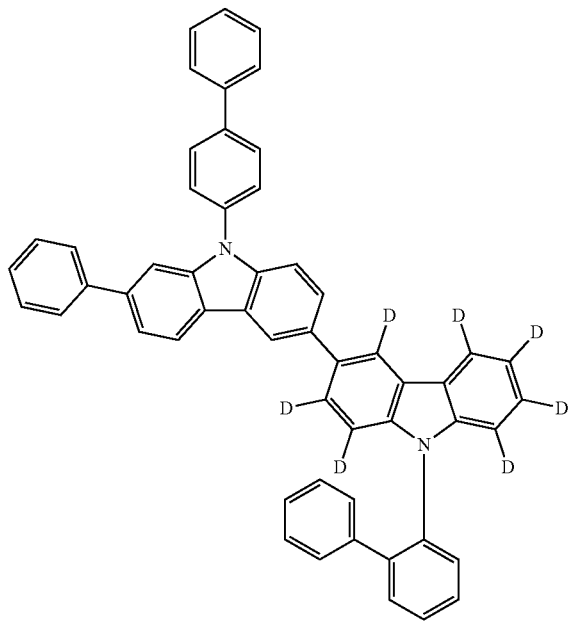
101
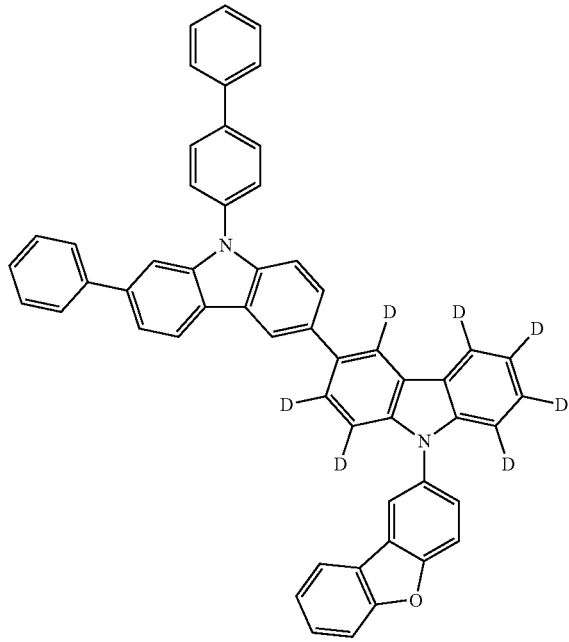
103

523
-continued
104
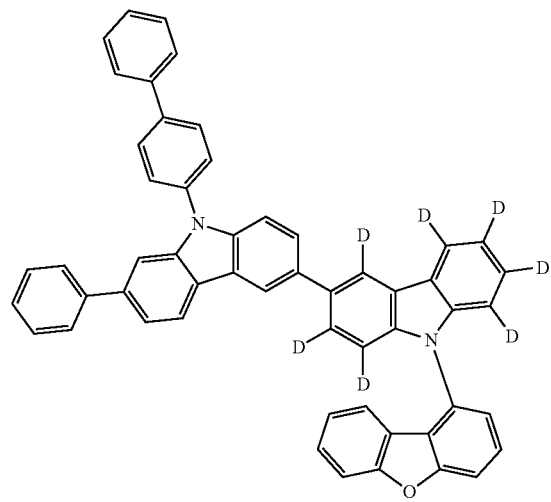
105
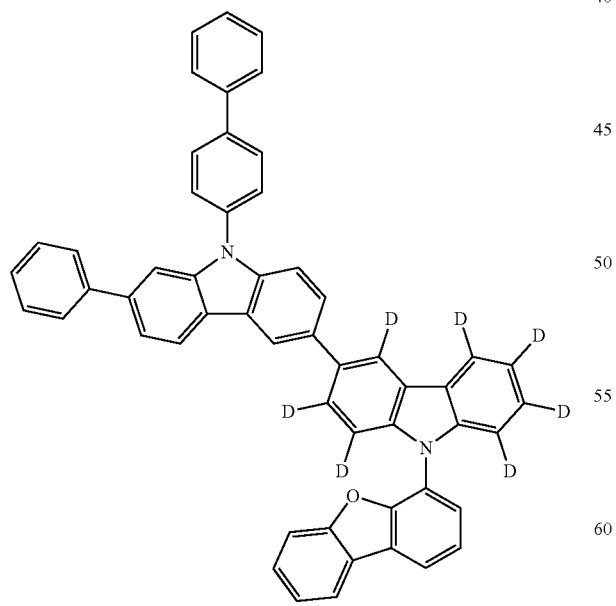
524
-continued
106
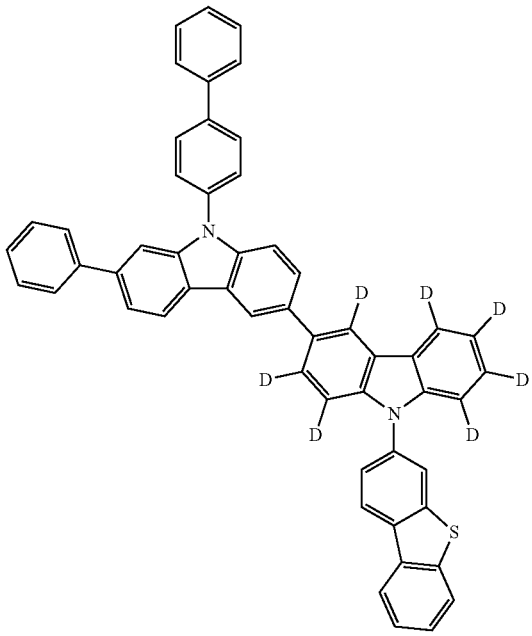
107

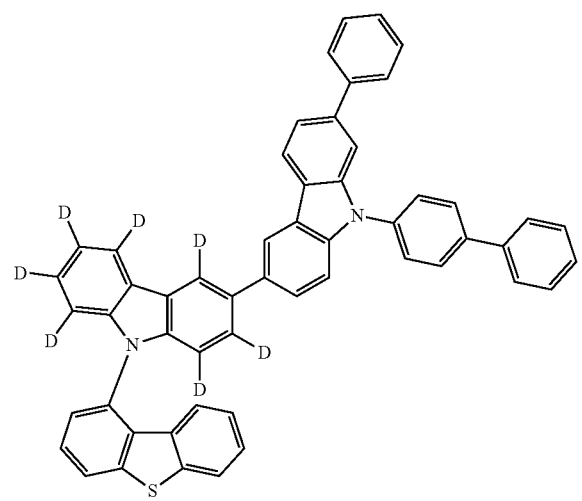
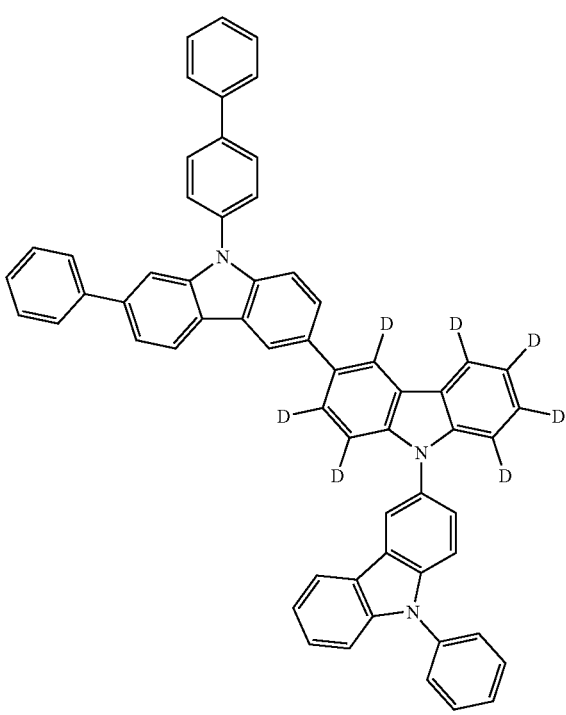
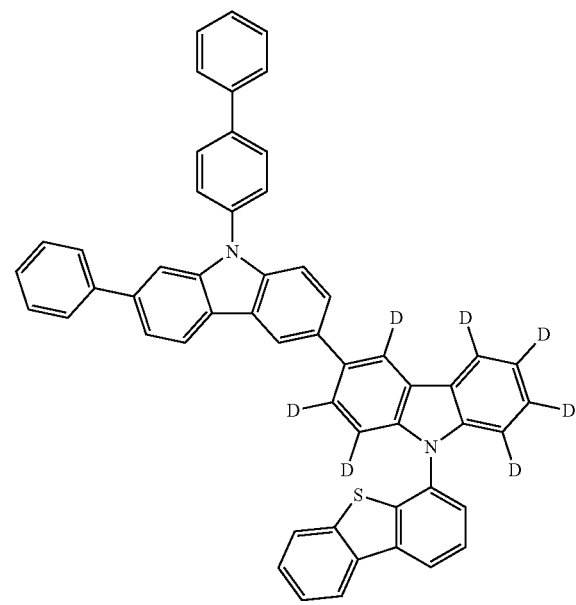

527
-continued
113
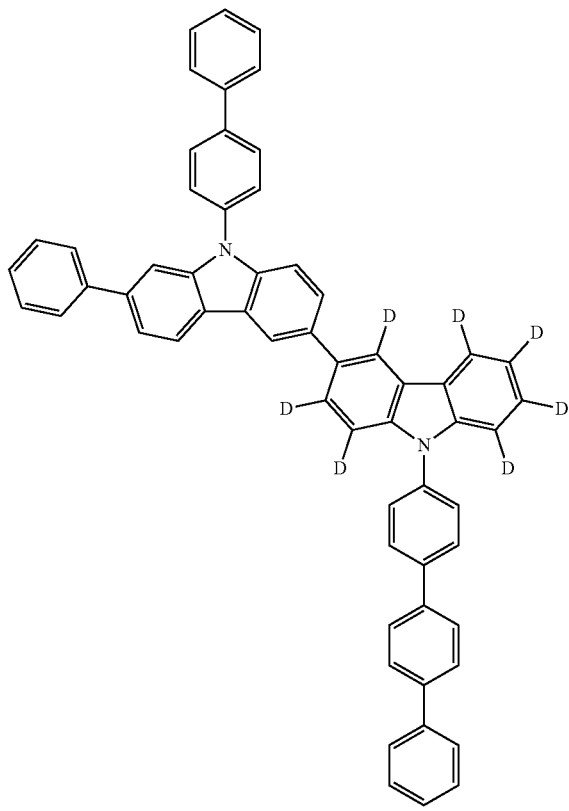
114
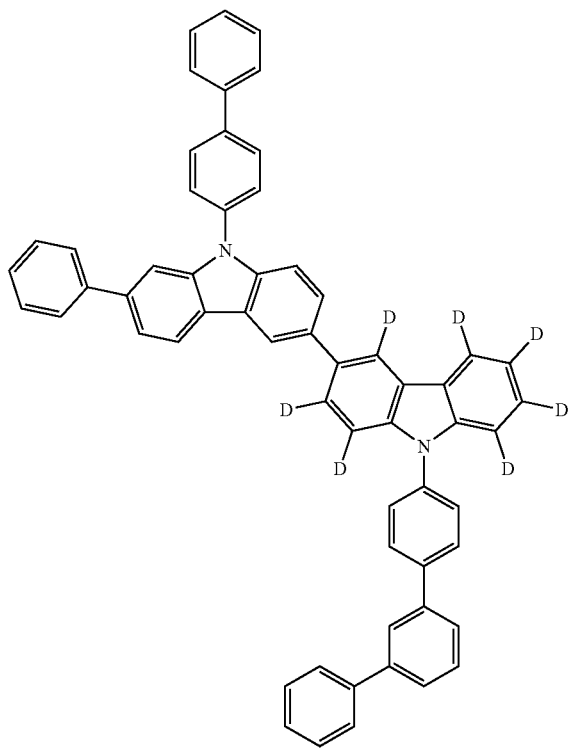
528
-continued
115
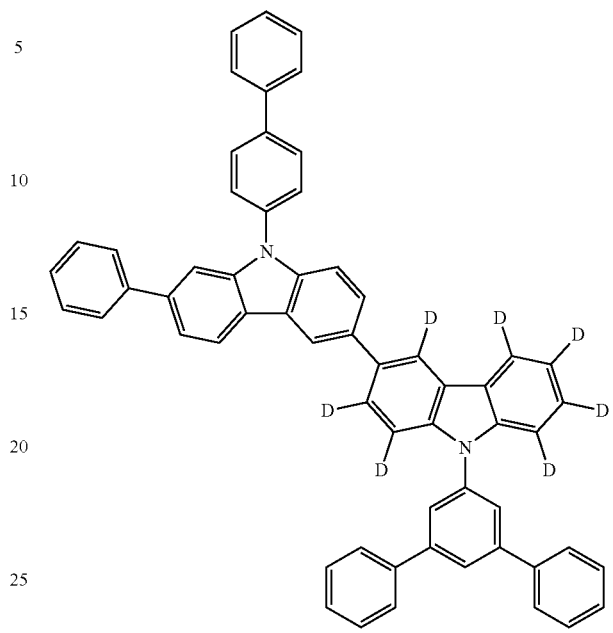
116
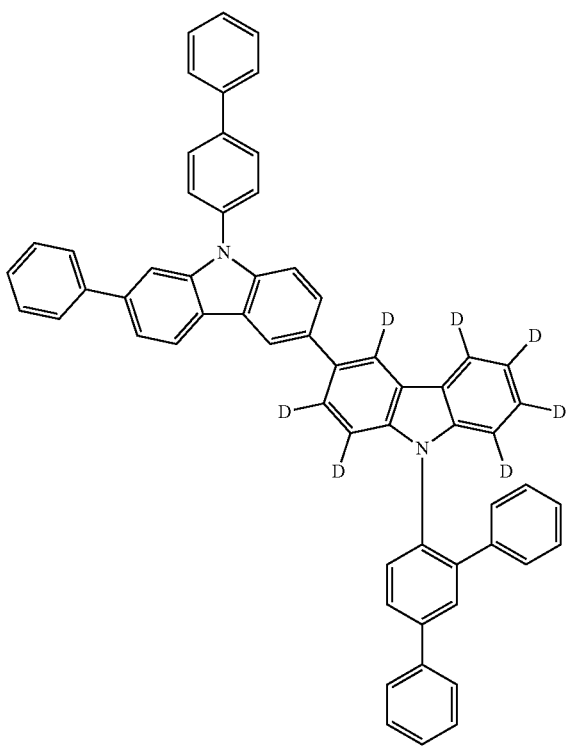

117
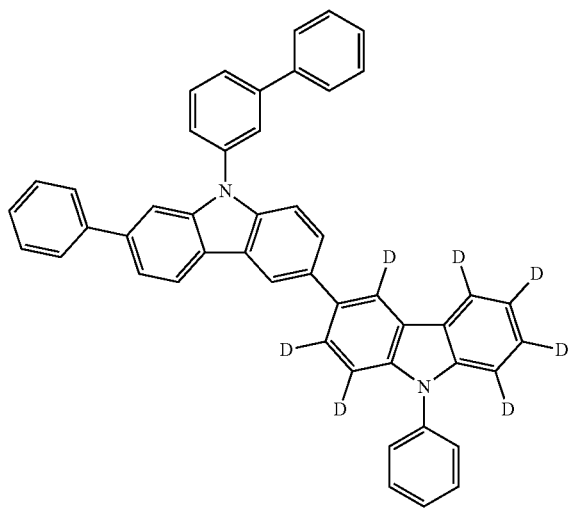
119
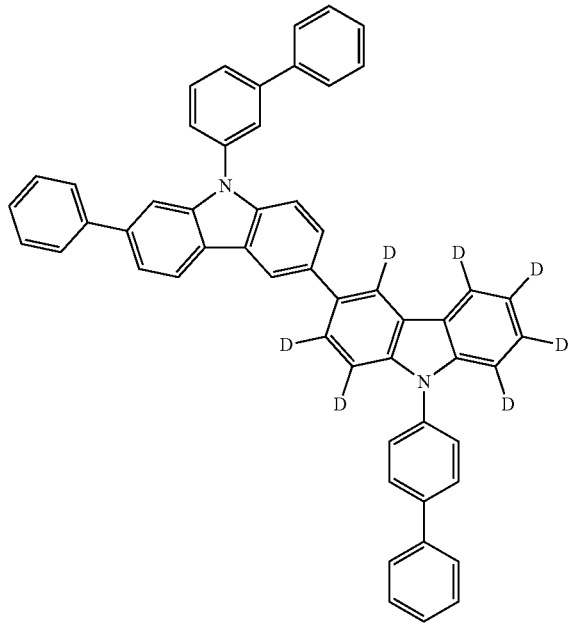
120
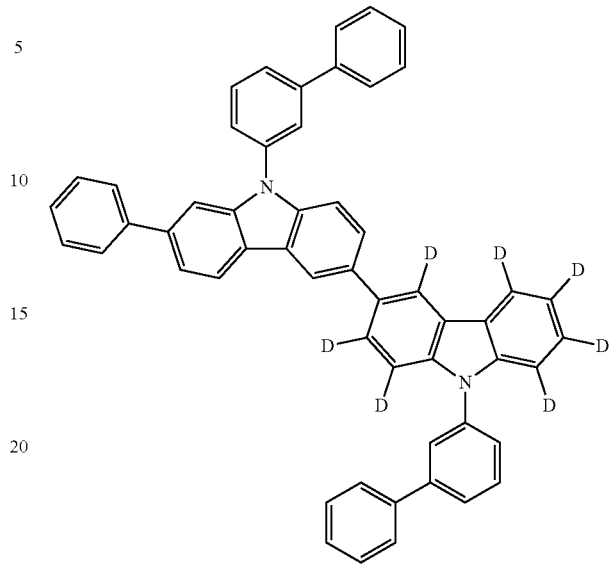
121
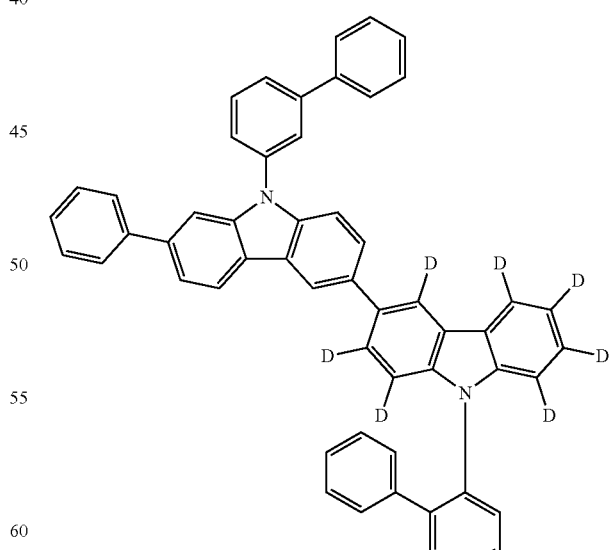

531
122
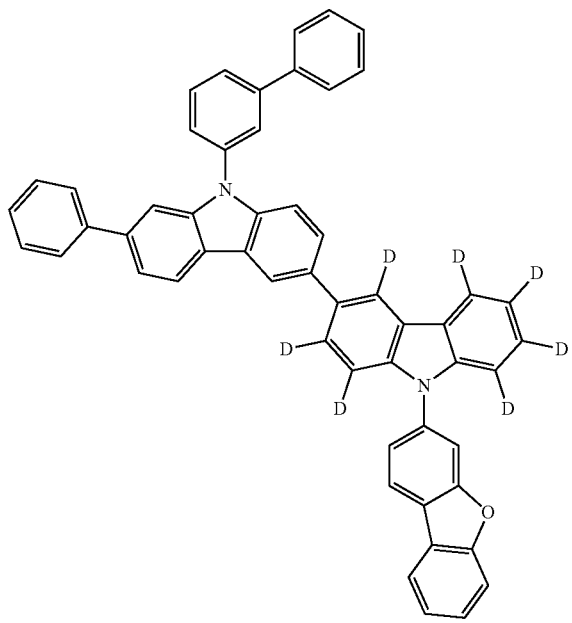
123
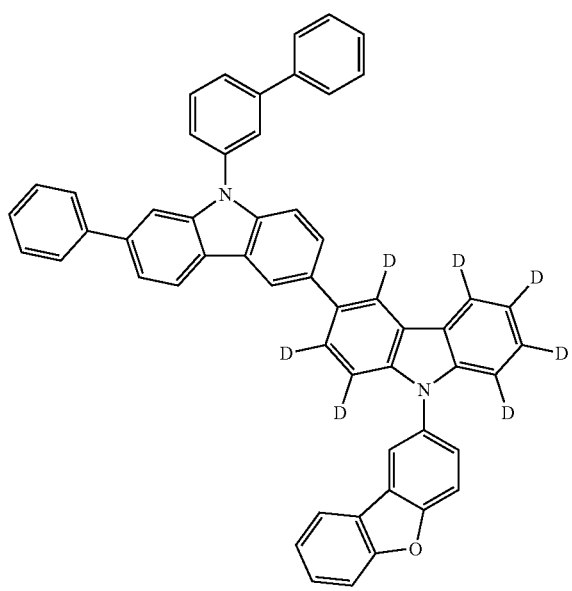
532
124
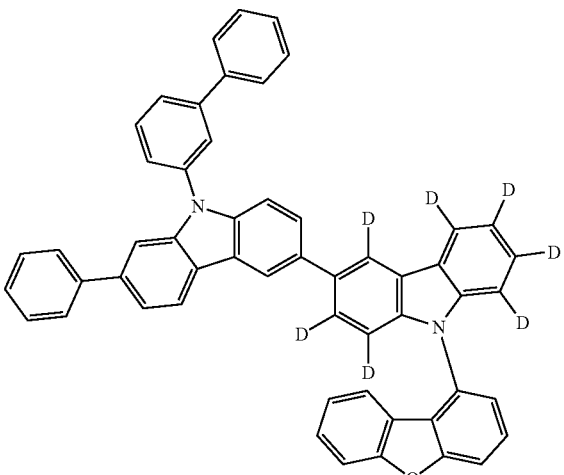
125
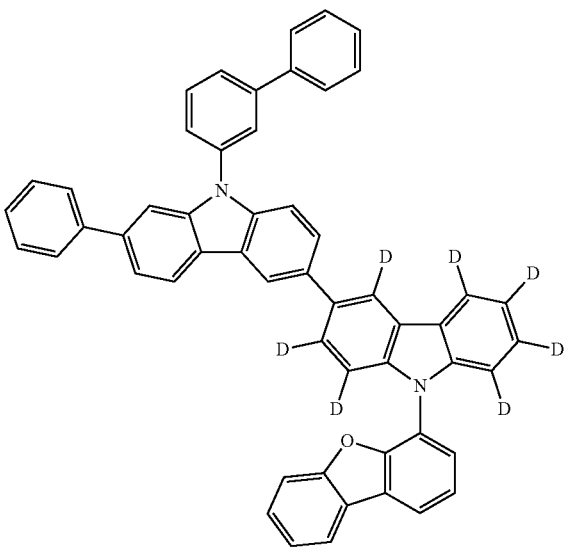

126
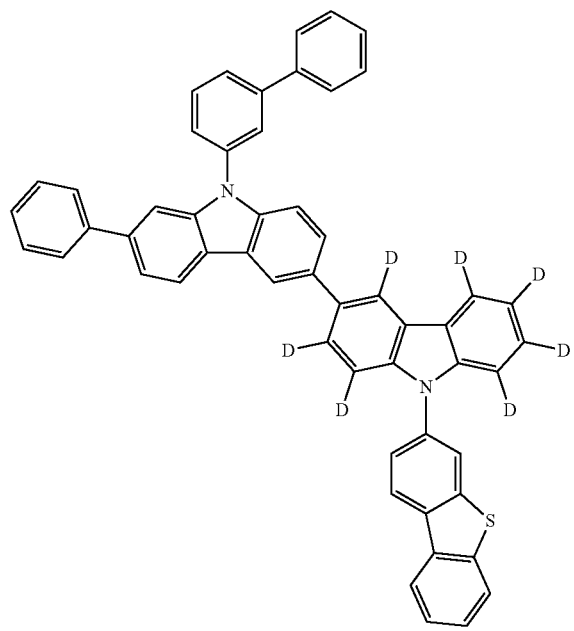
127
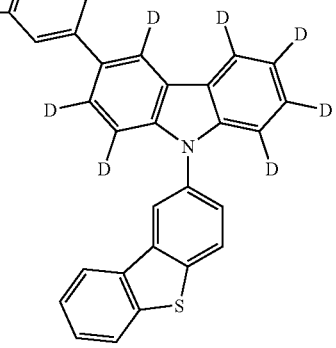
129
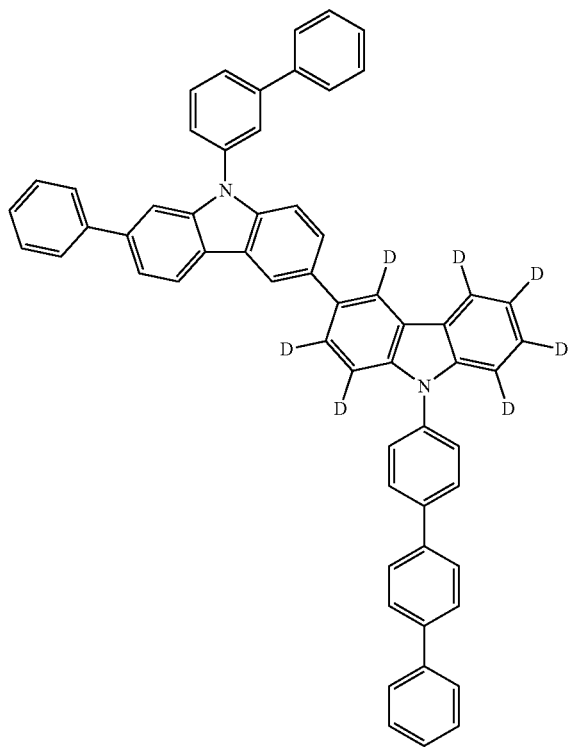
130
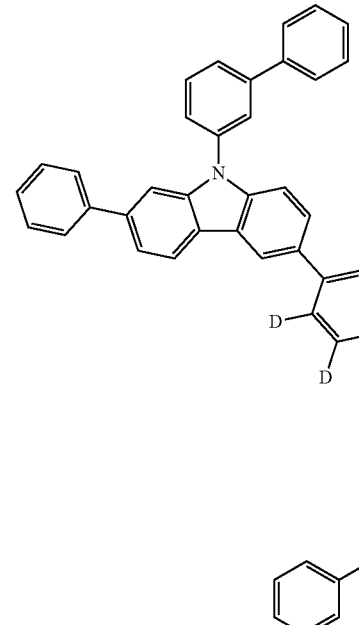

131
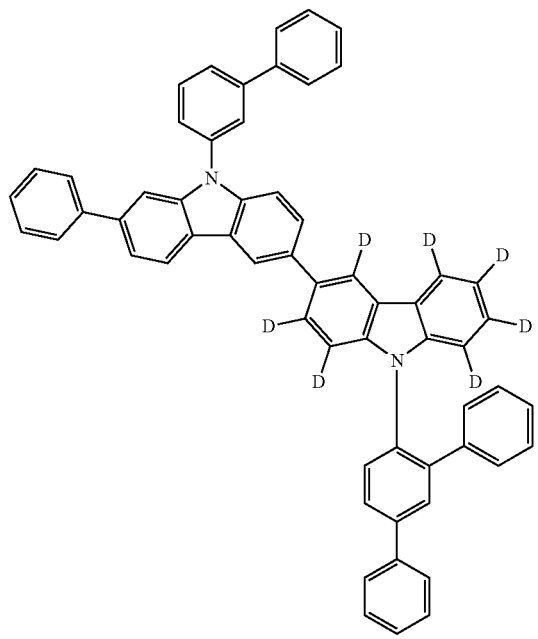
132
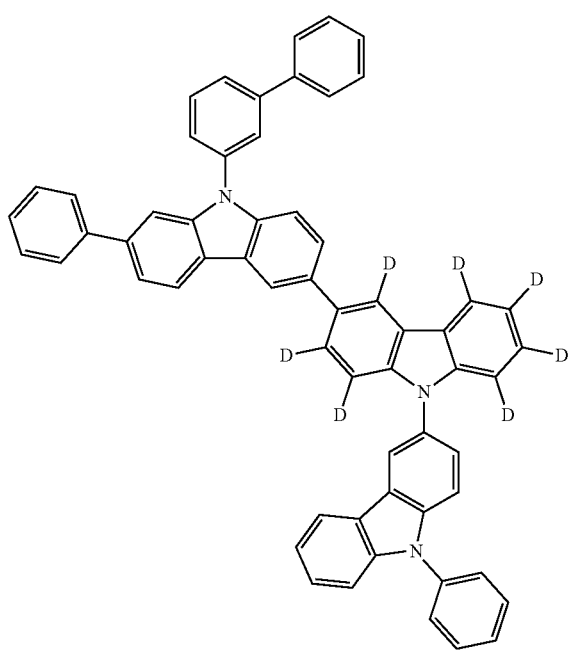
133
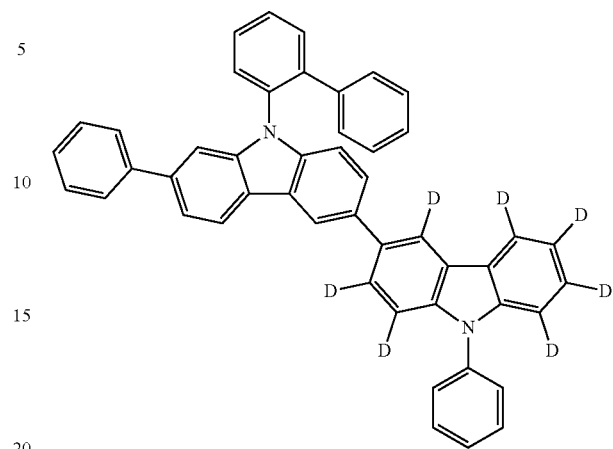
134
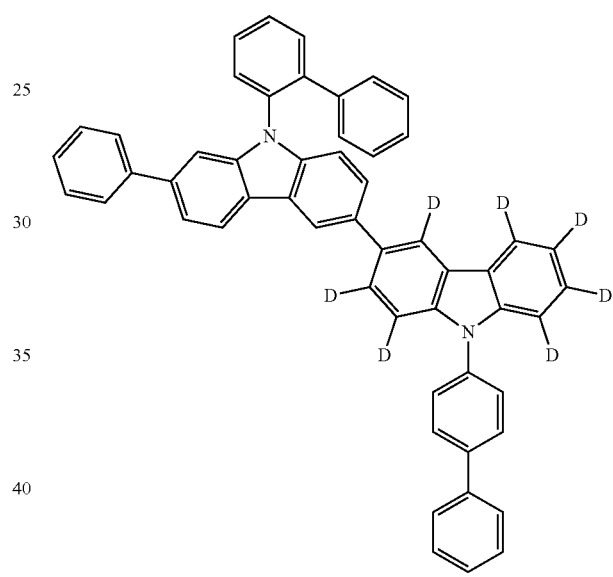
135
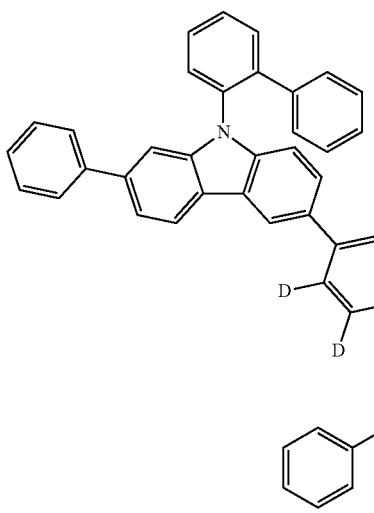

537
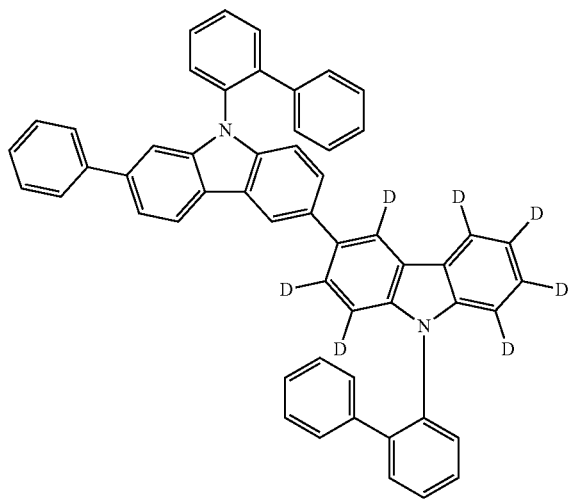
136
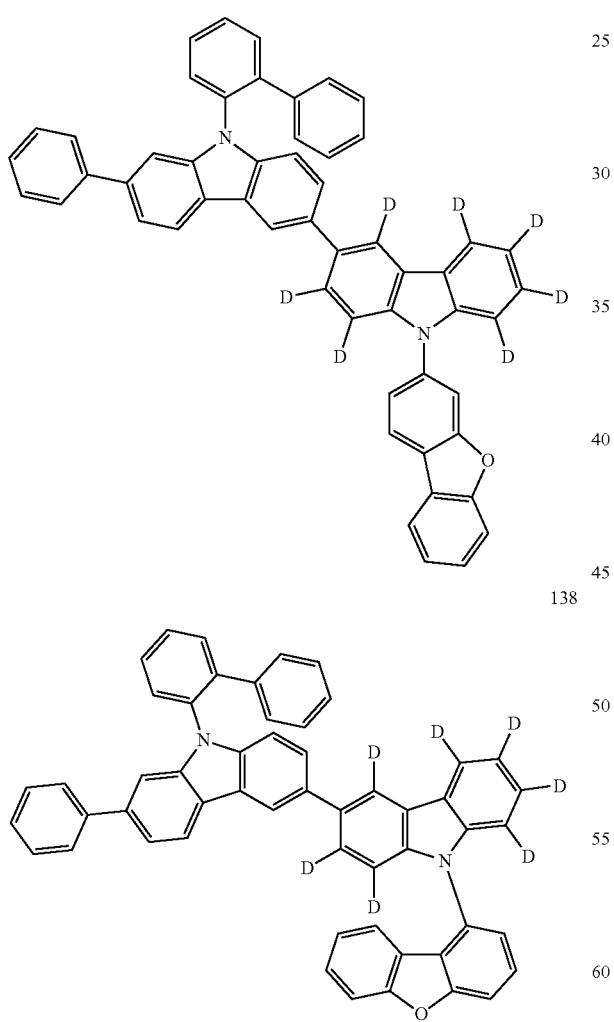
137
138
538
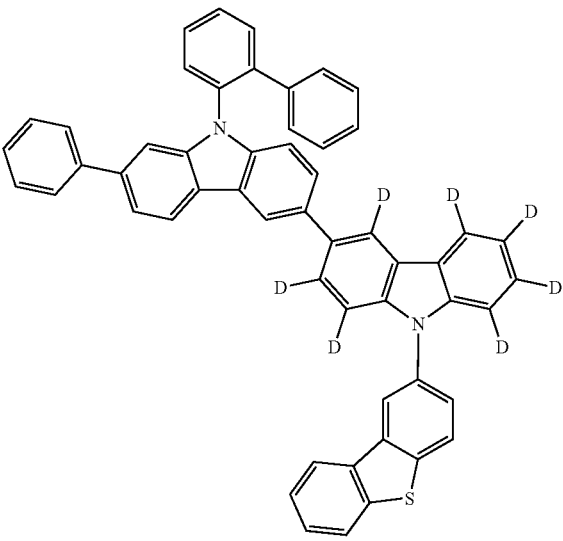
139
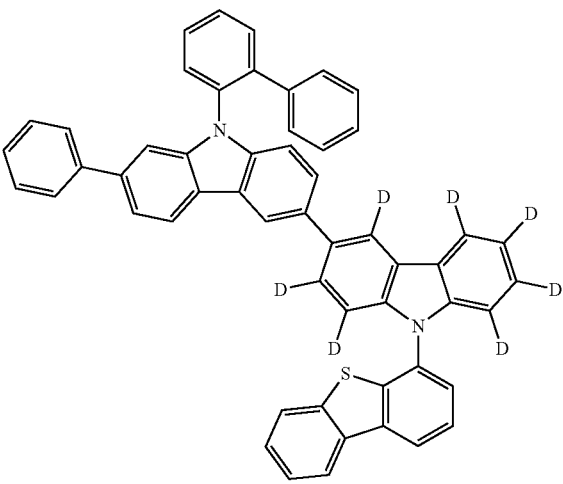
140

539
-continued
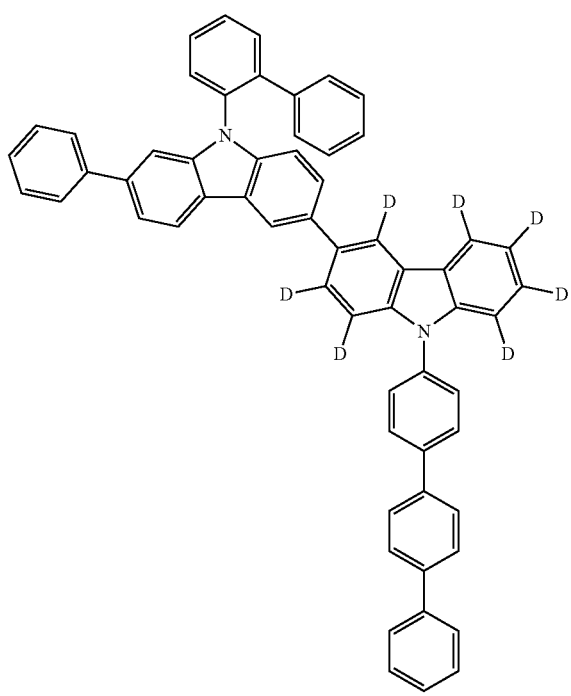
141
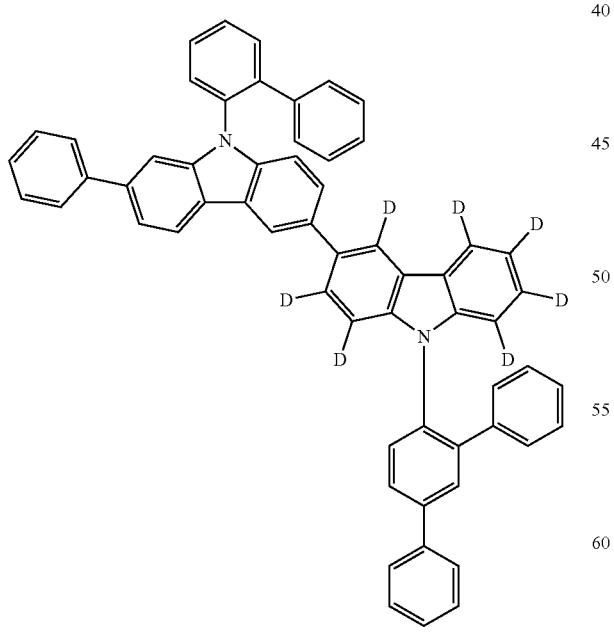
142
540
-continued
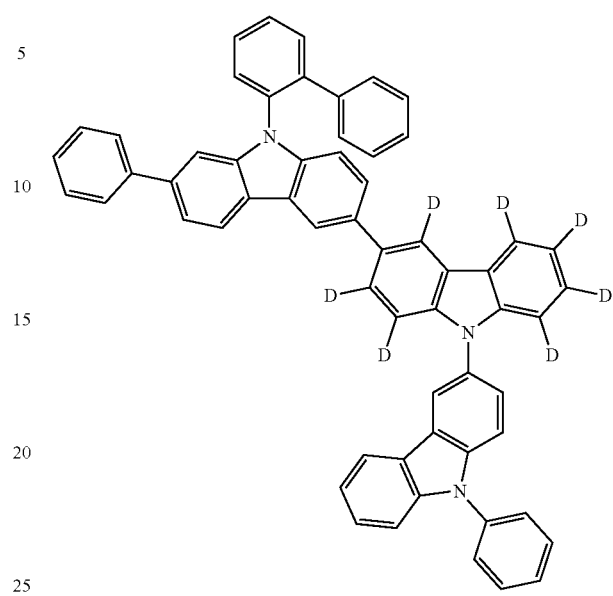
143
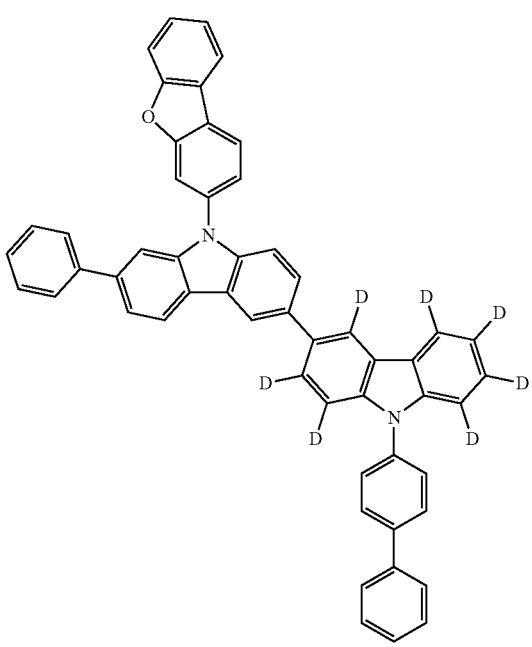
145

541
-continued
146
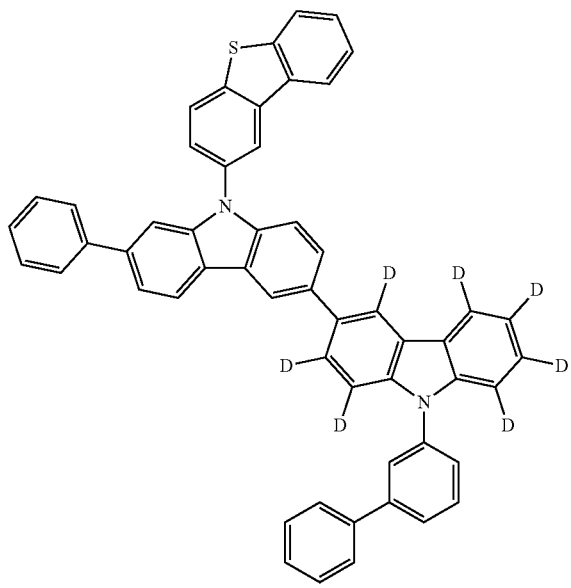
147
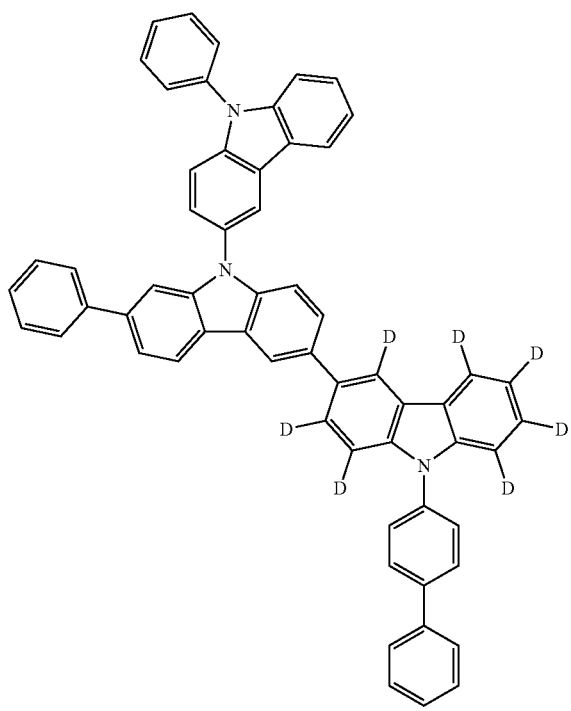
542
-continued
148
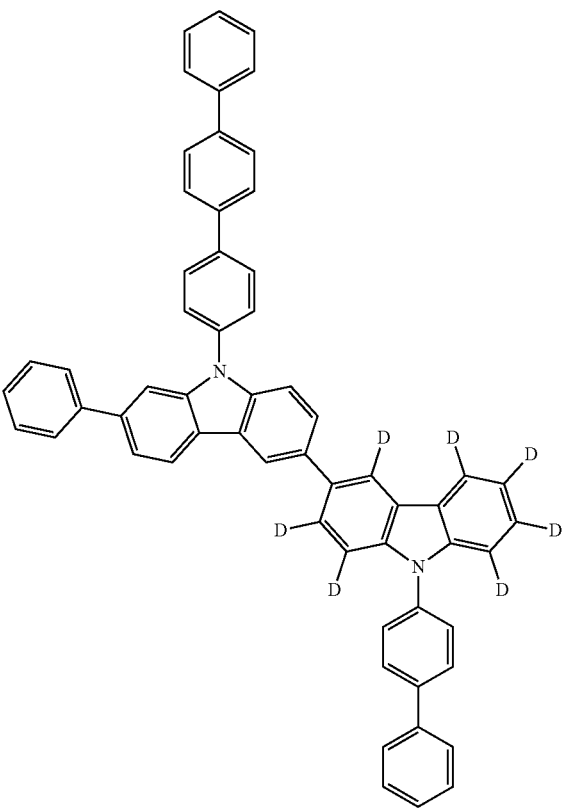
149
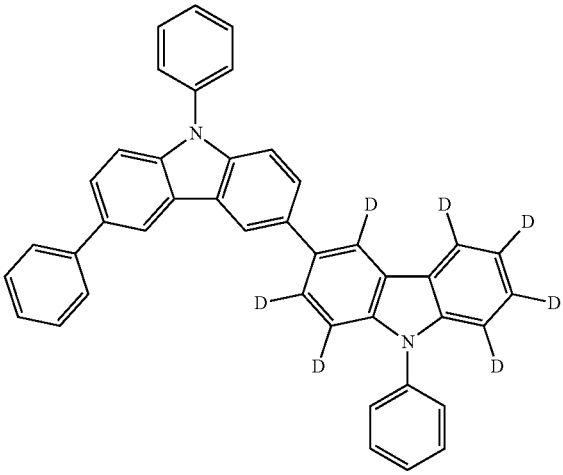

151
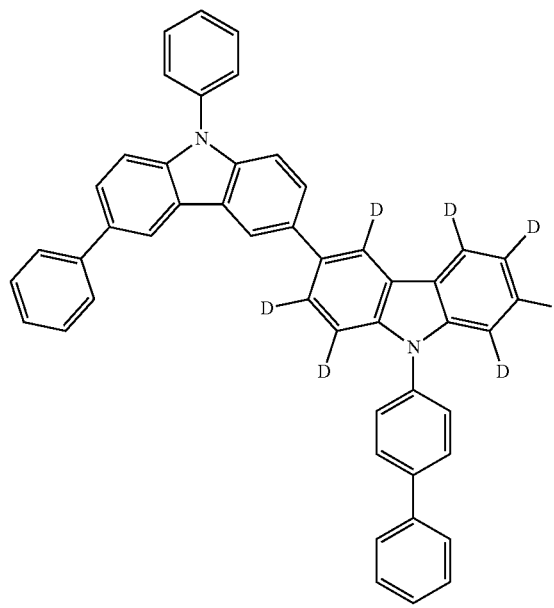
152
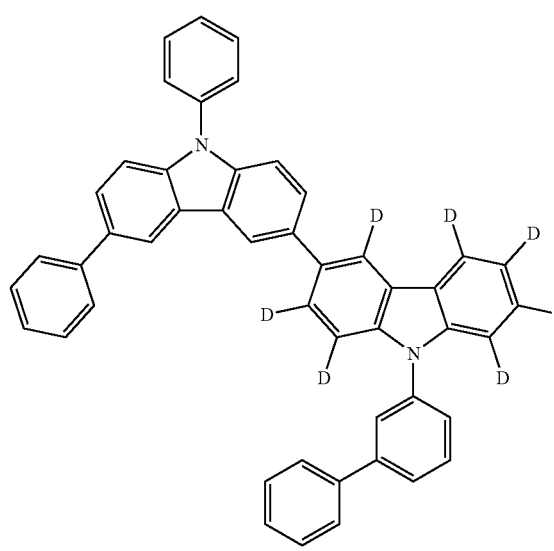
153
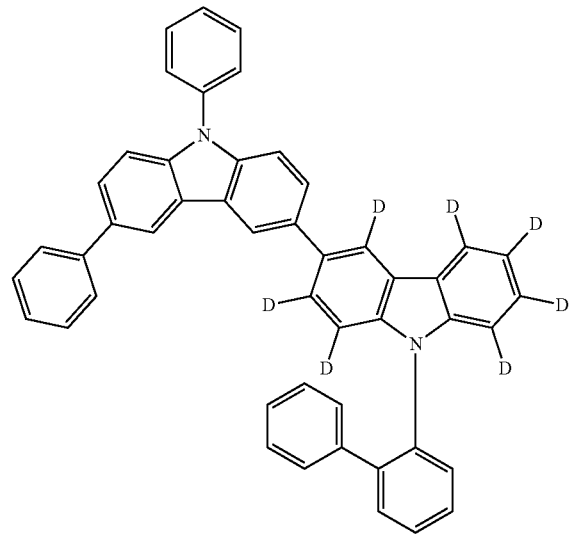
154
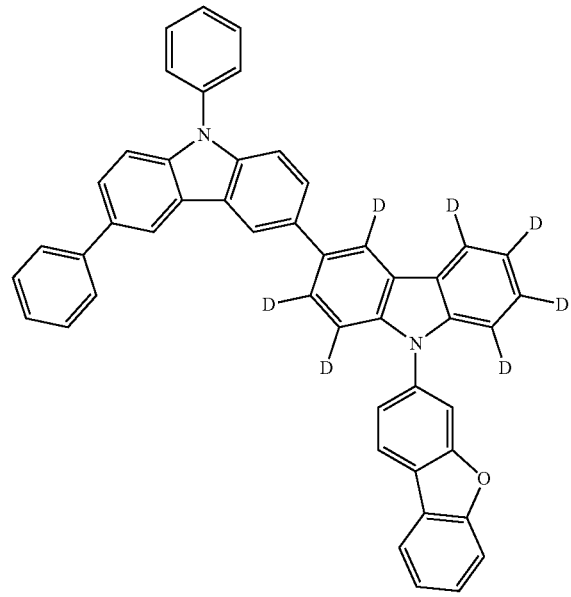

155
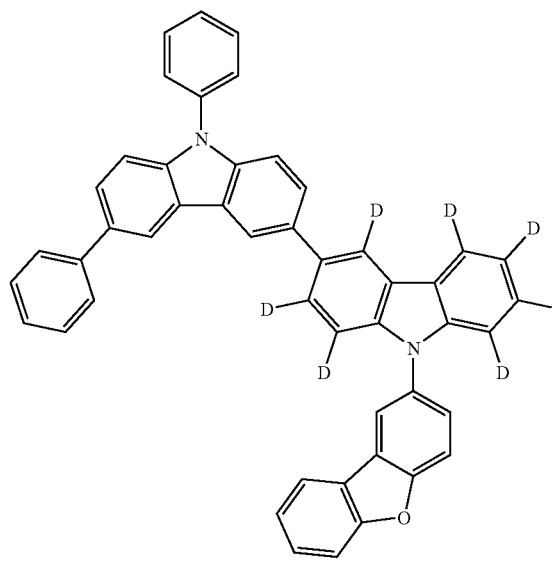
156
158
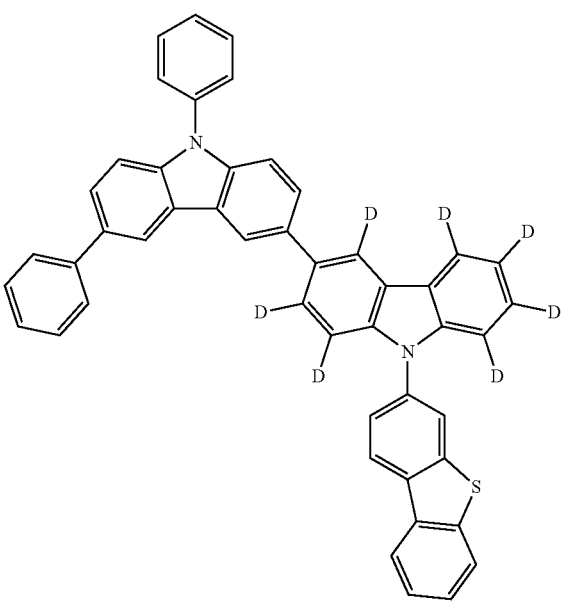
157
159
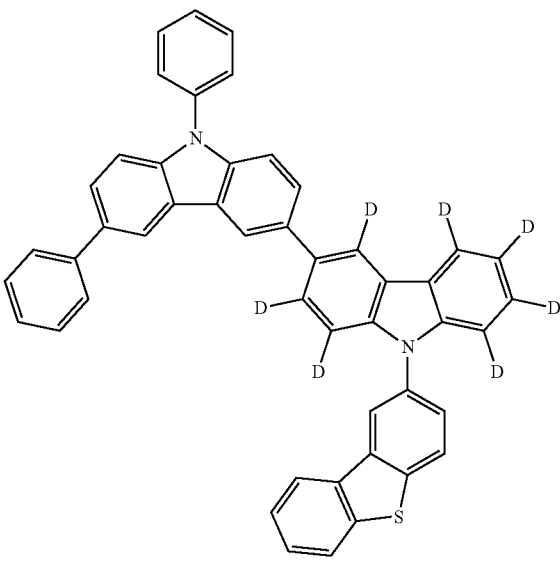

160
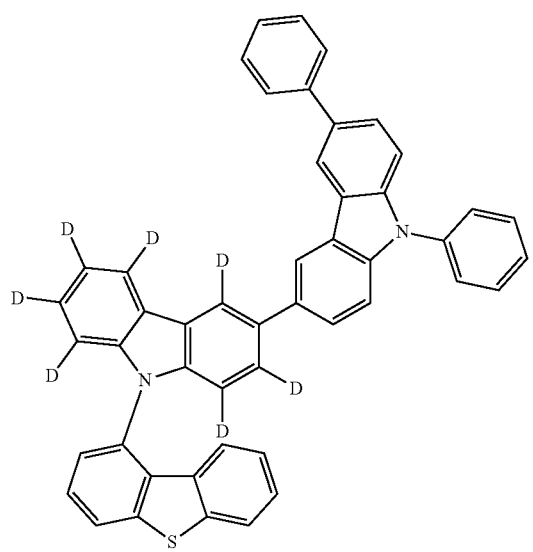
161
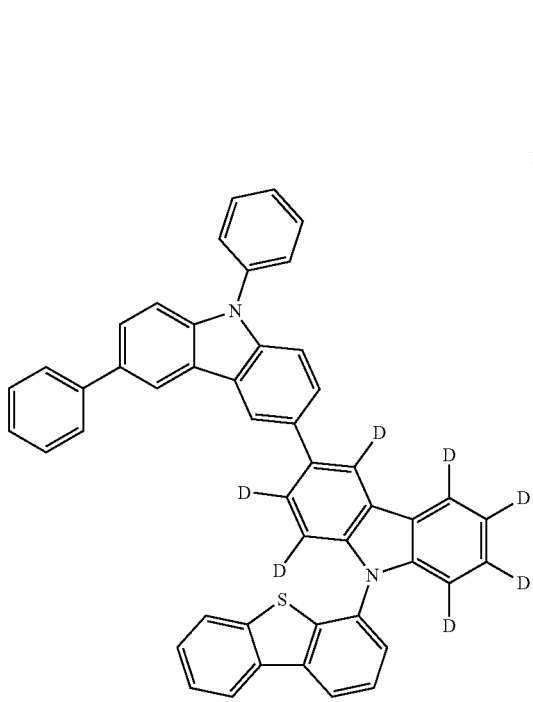
163
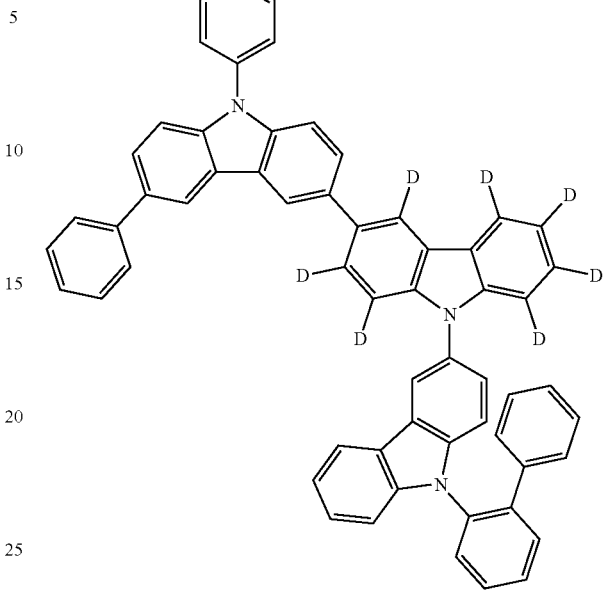
164
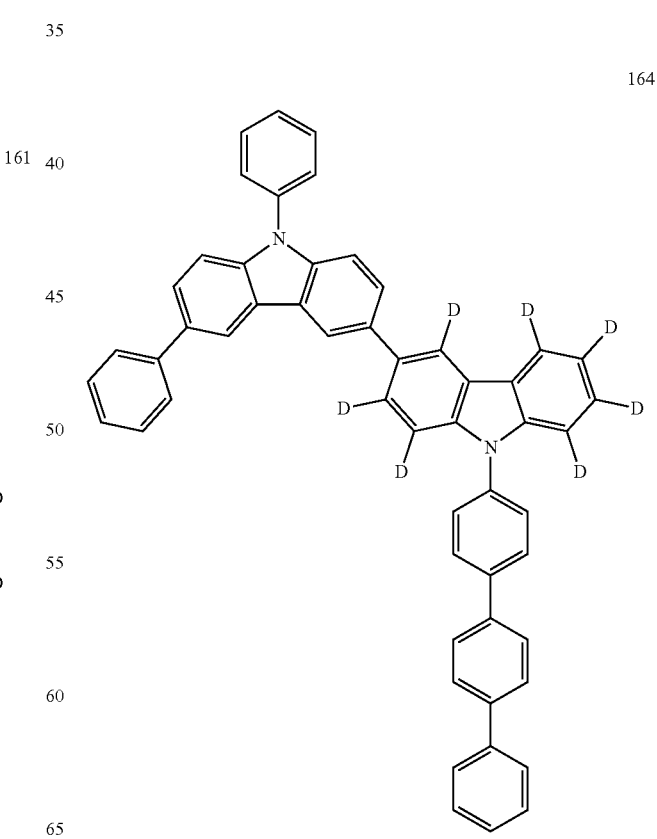

549
-continued
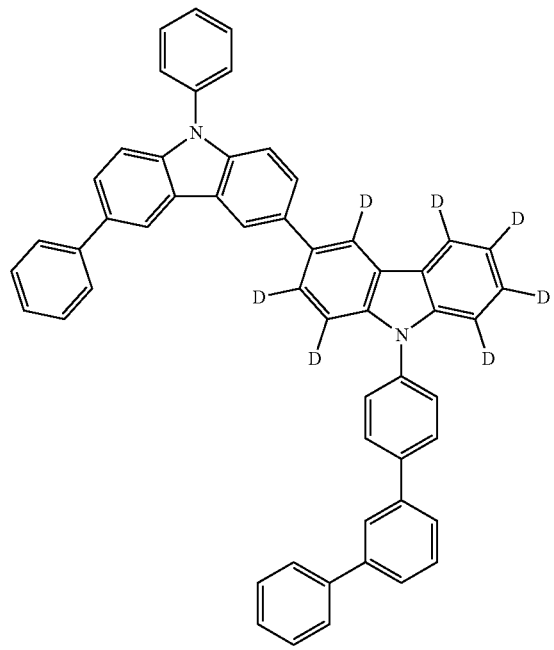
165
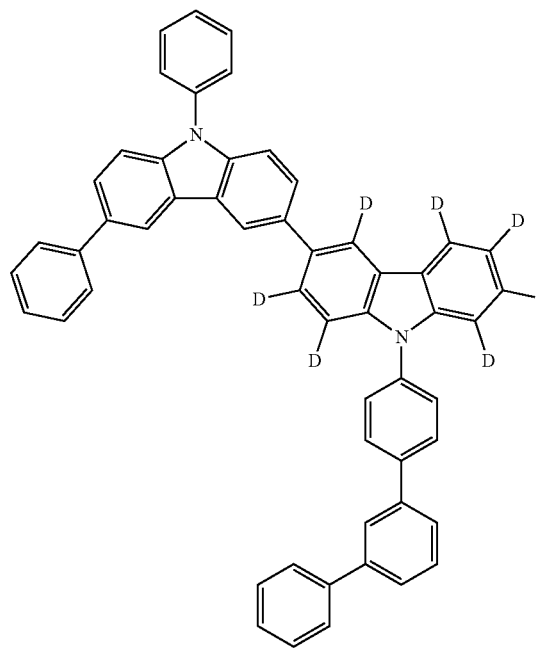
166
550
-continued
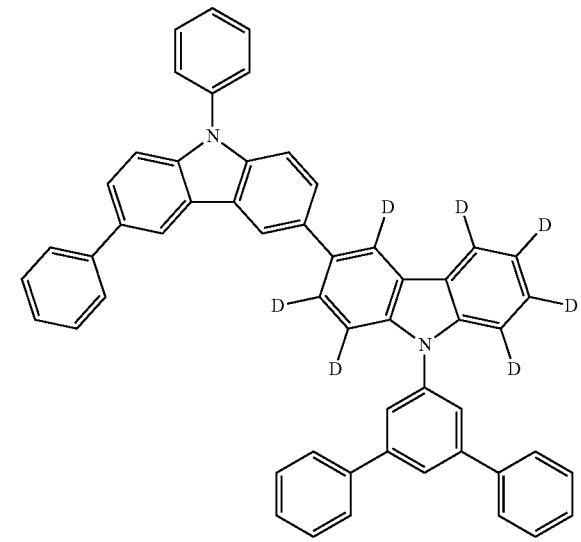
167
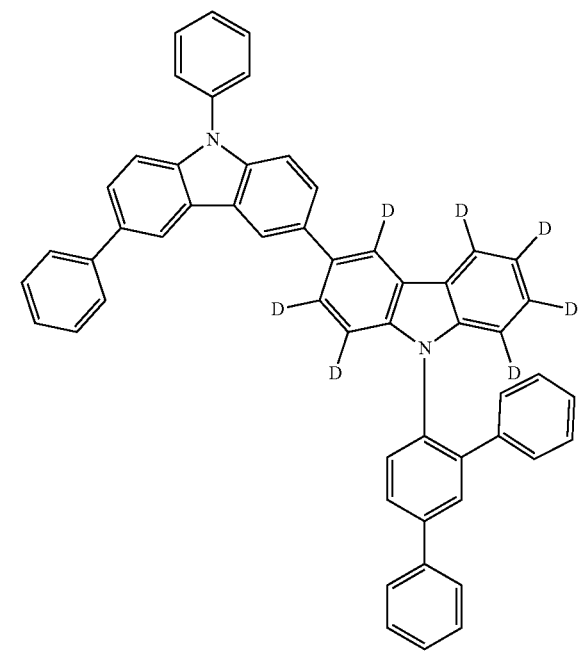
167'

551
-continued
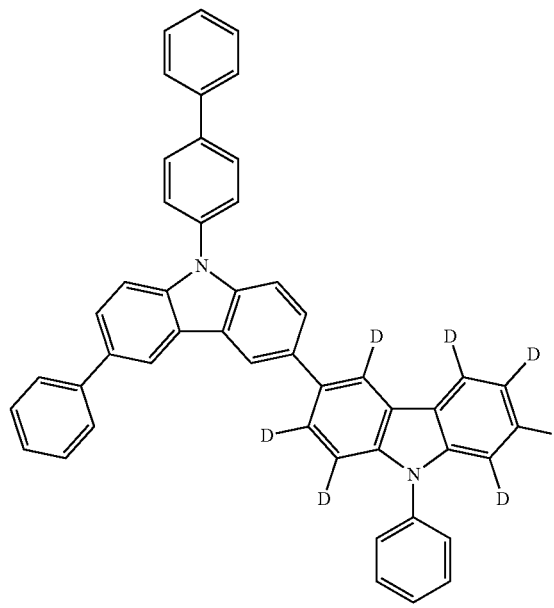
169
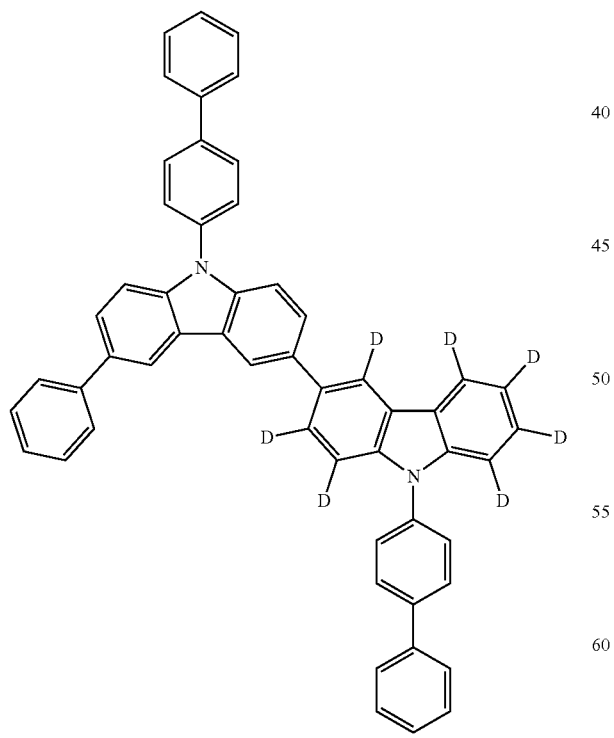
170
552
-continued
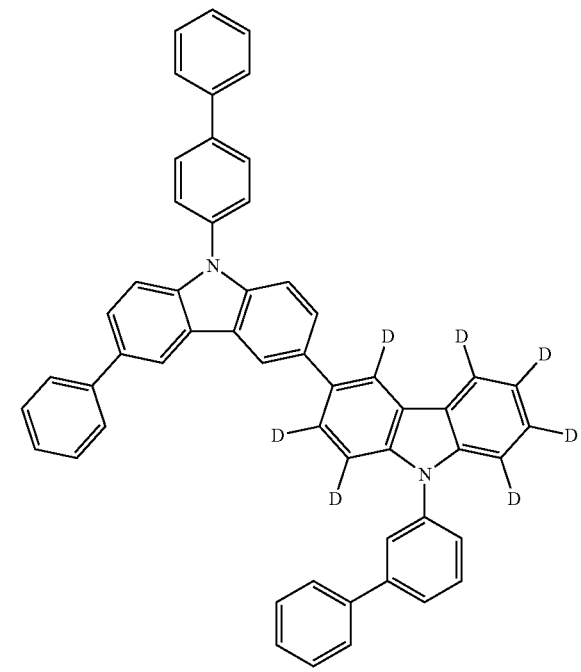
171
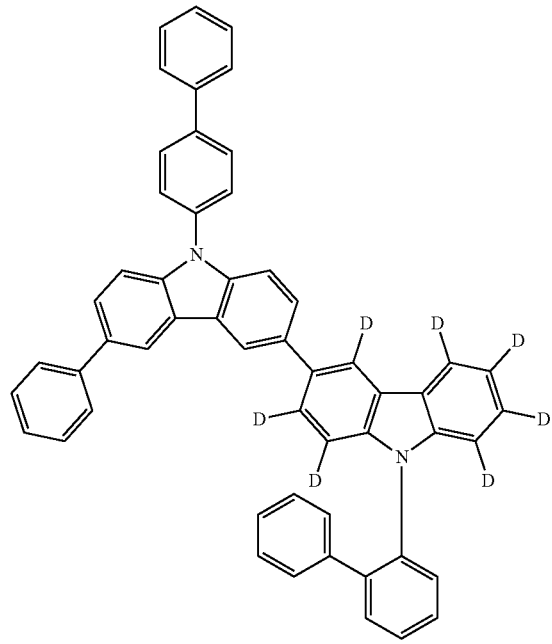
172

173
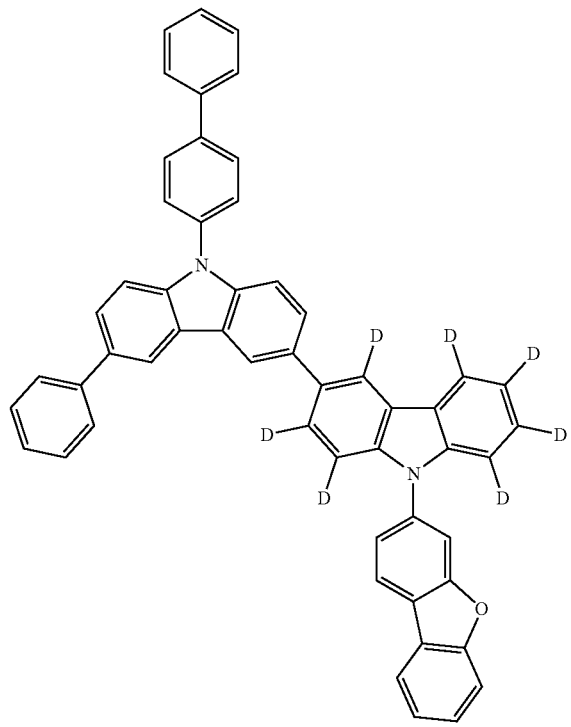
174
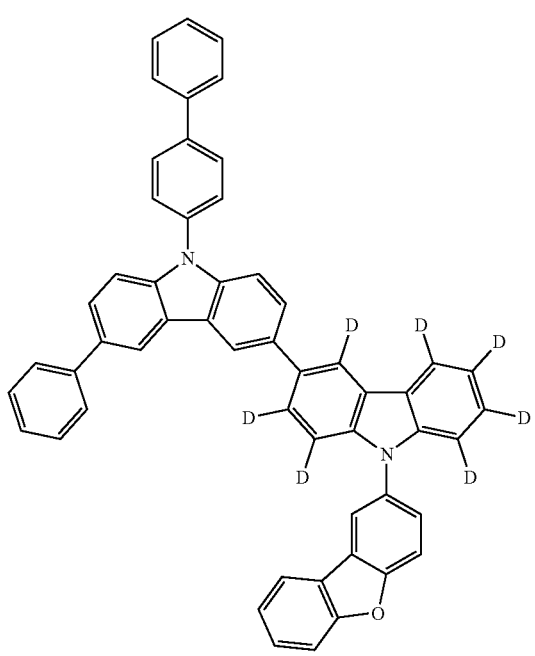
175
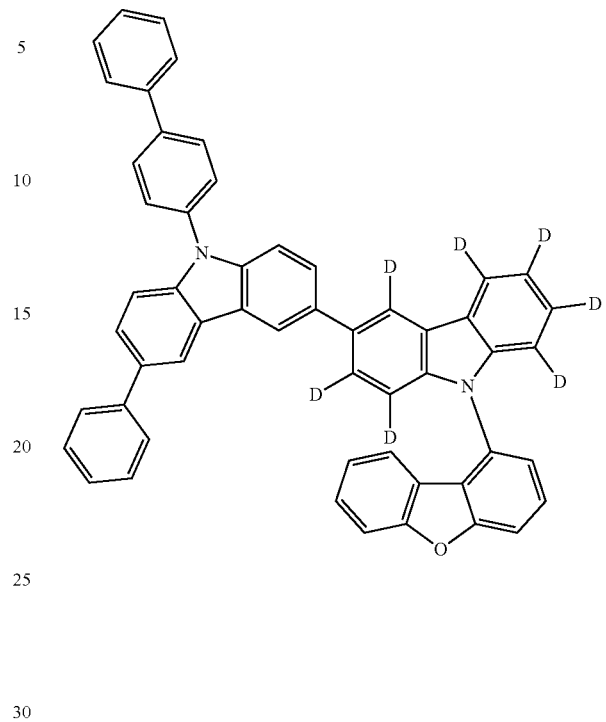
176
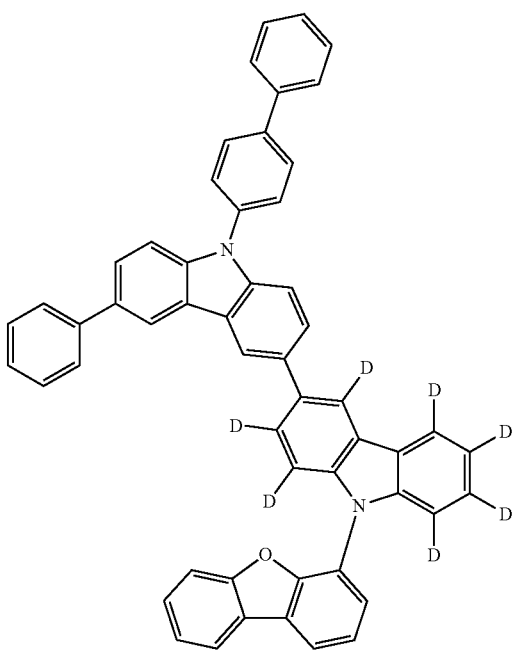

555
-continued
177
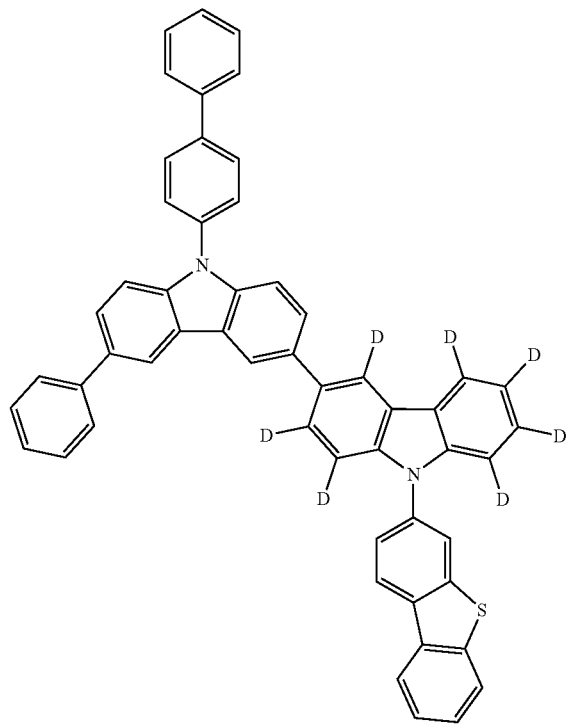
178
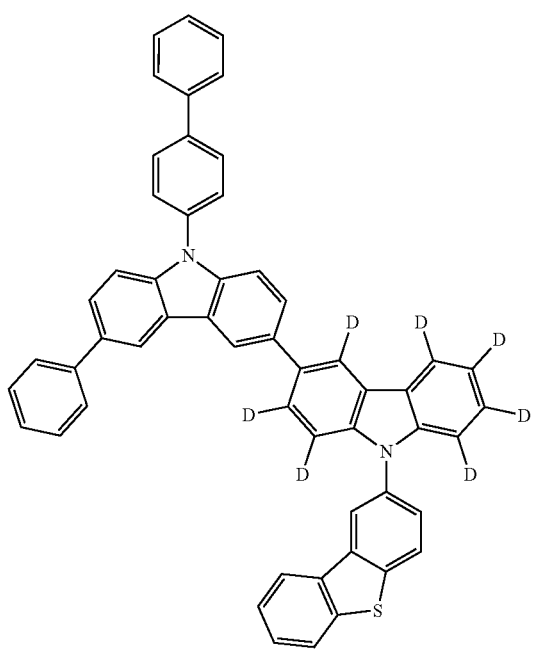
556
-continued
179
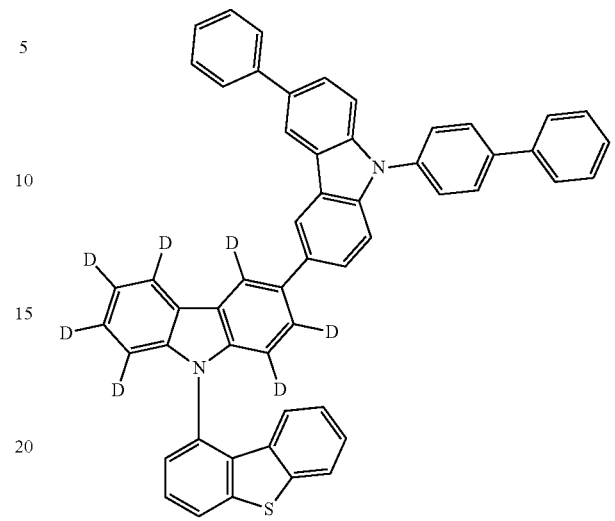
181
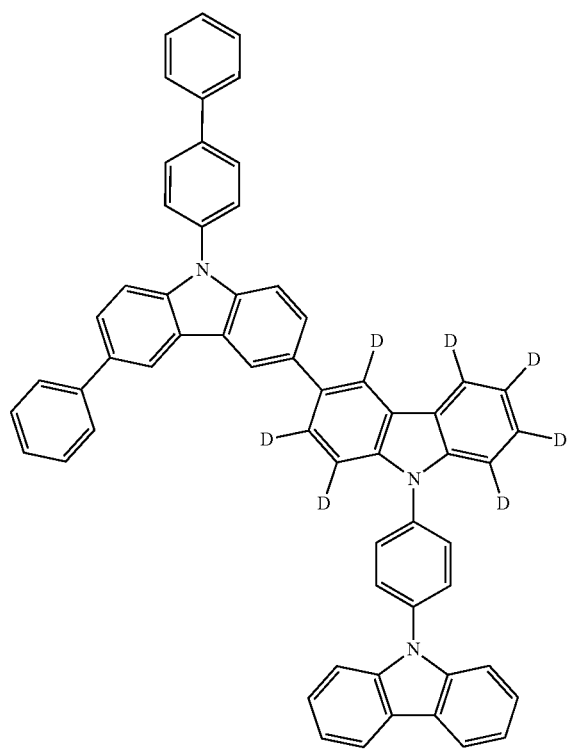

182
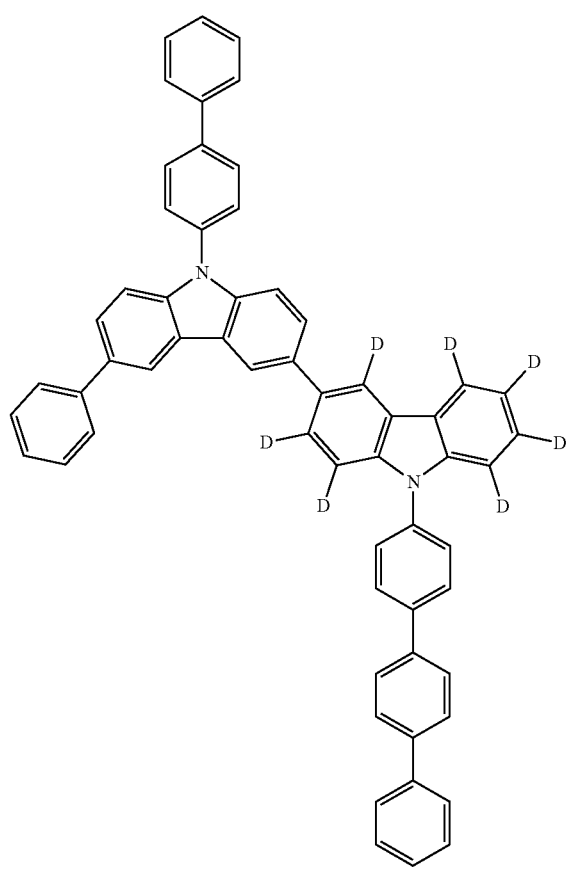
183
184
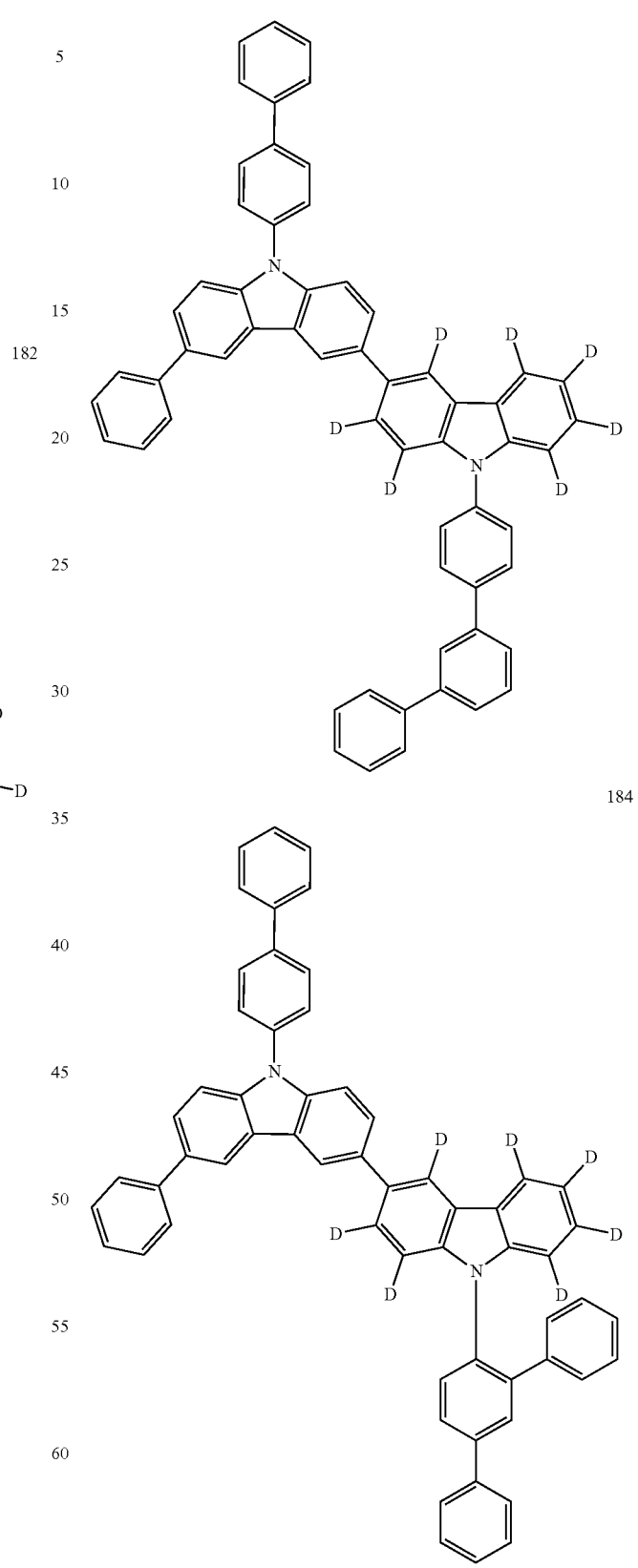

185
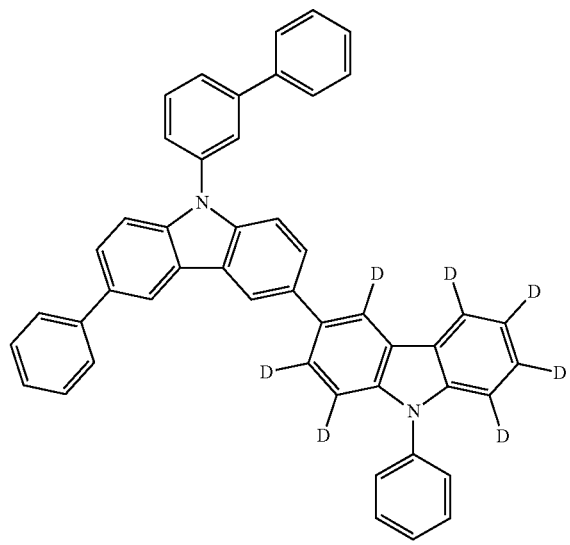
187
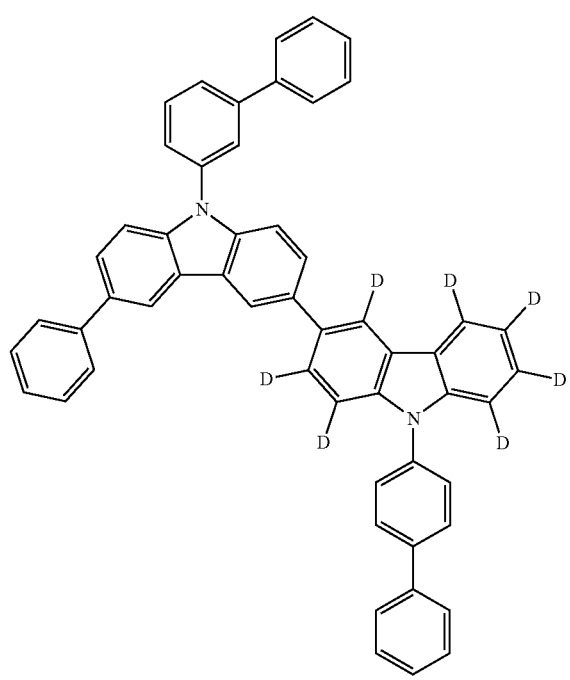
188
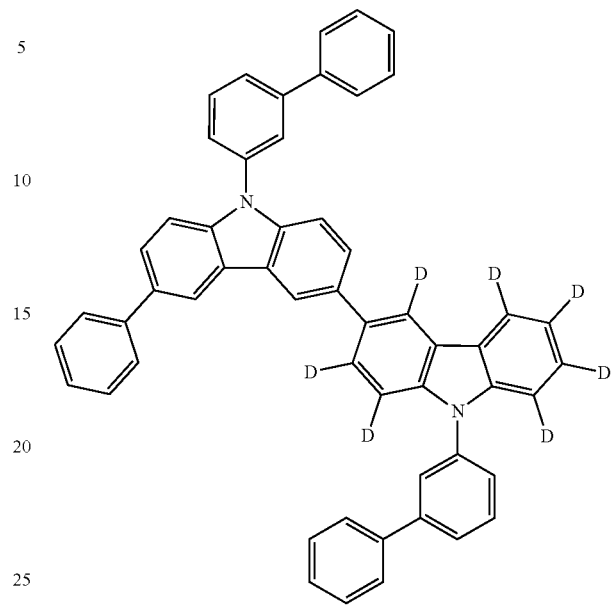
189
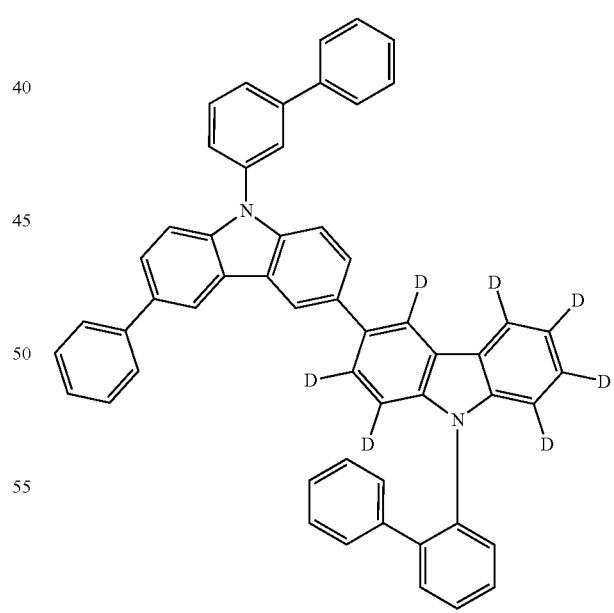

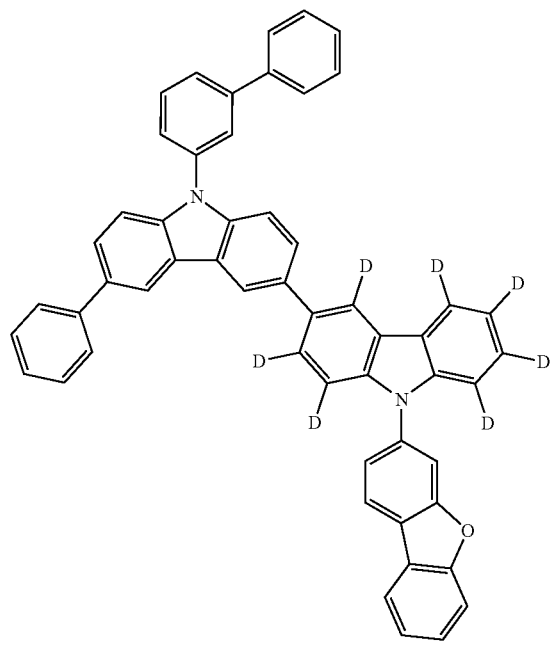
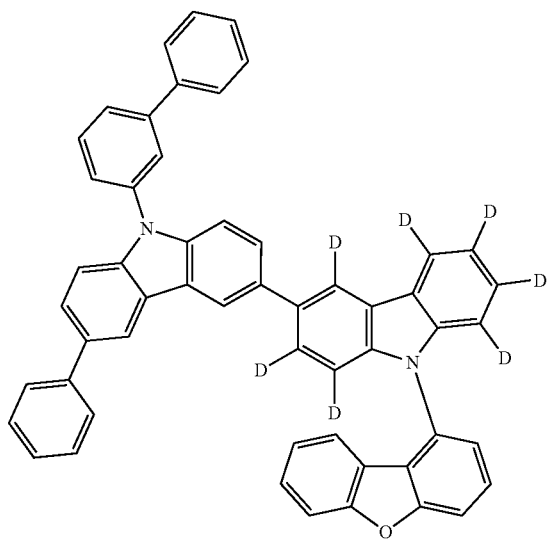
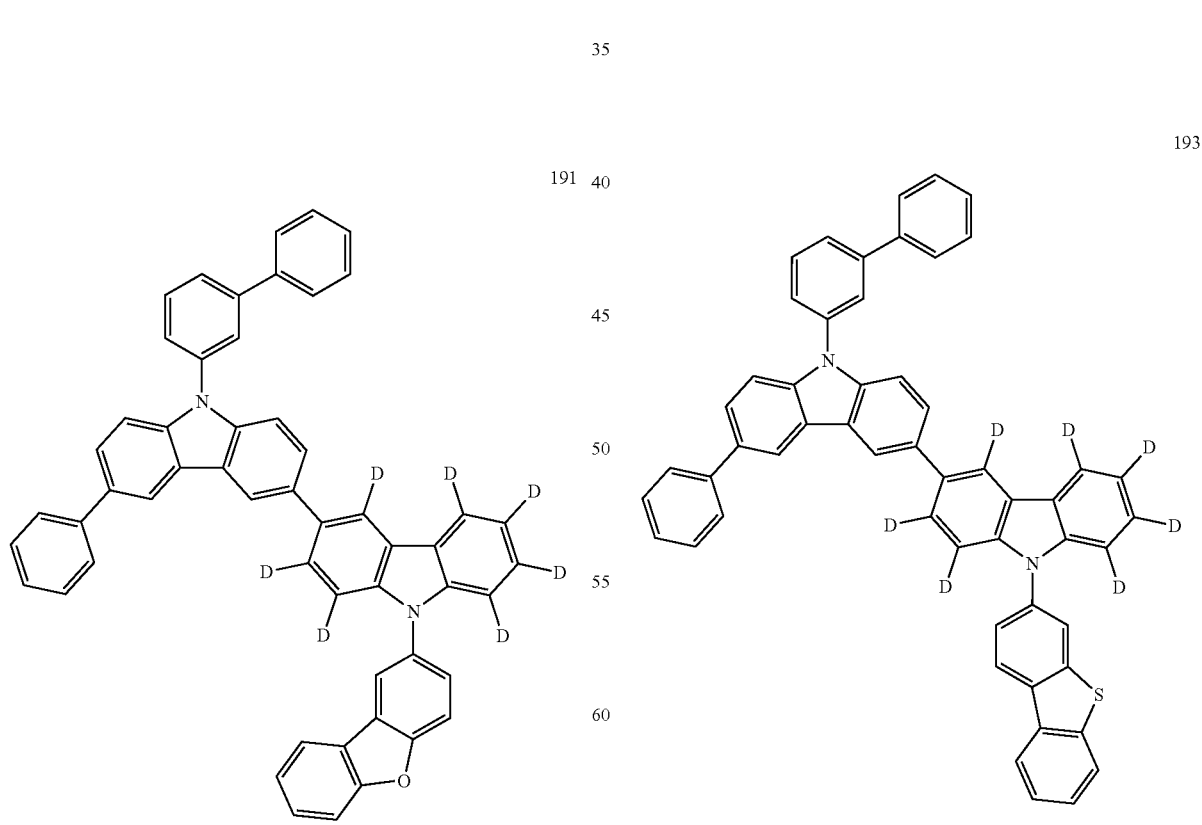

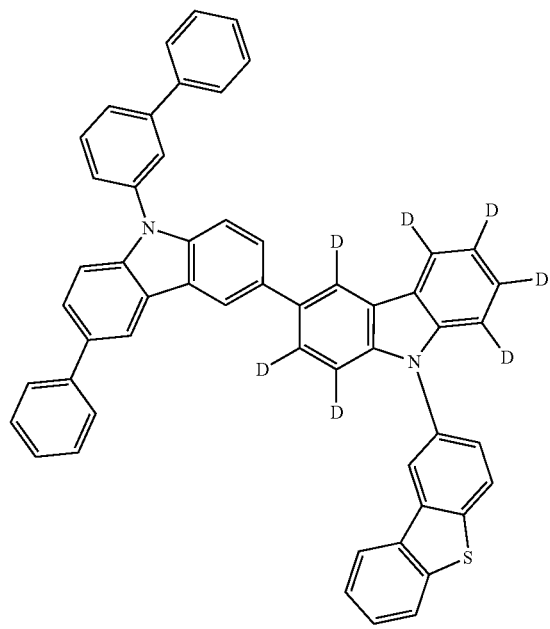
194
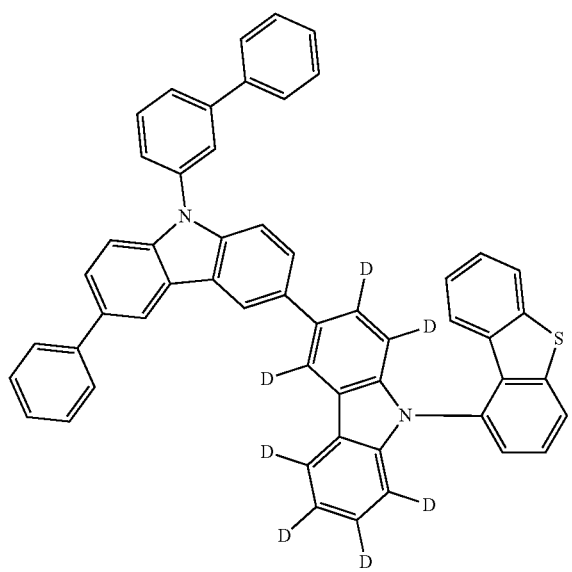
195
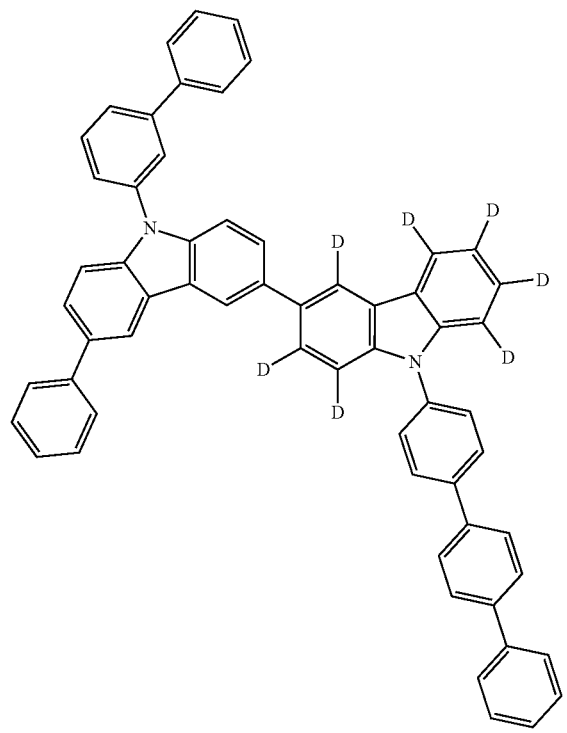
197
198

199
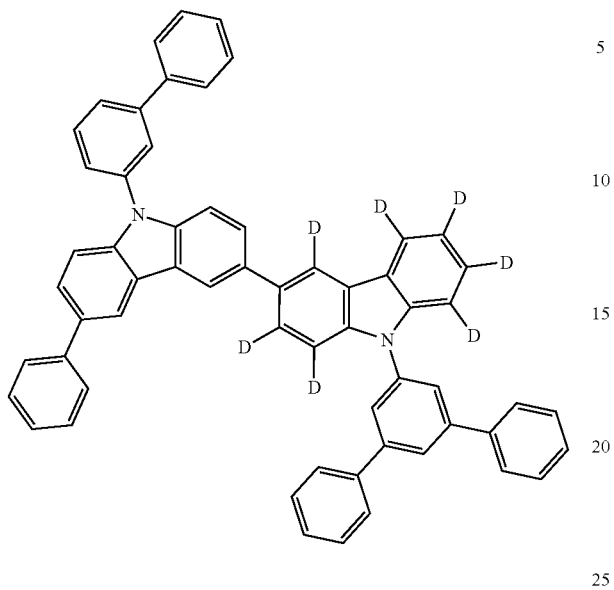
200
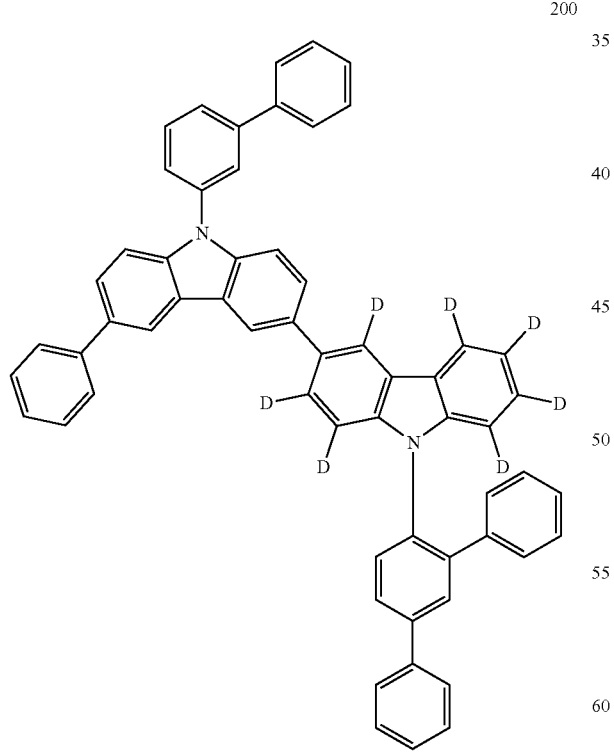
201
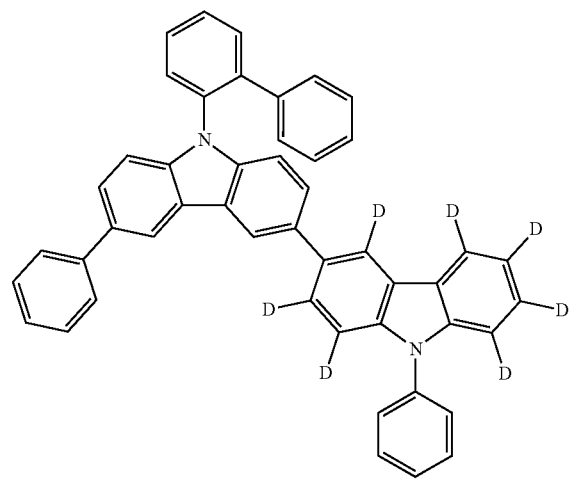
203

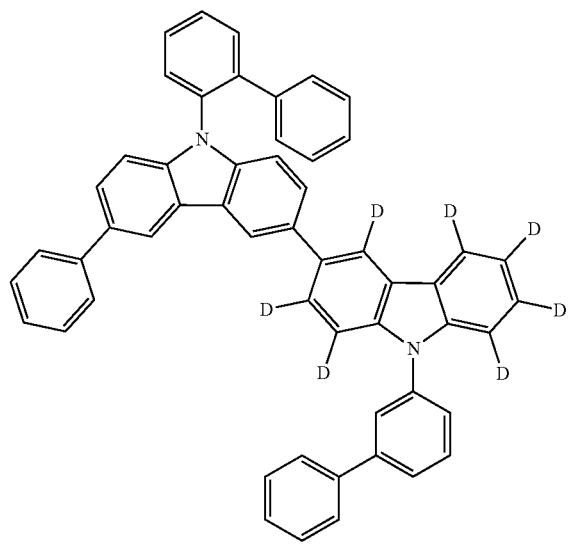
204
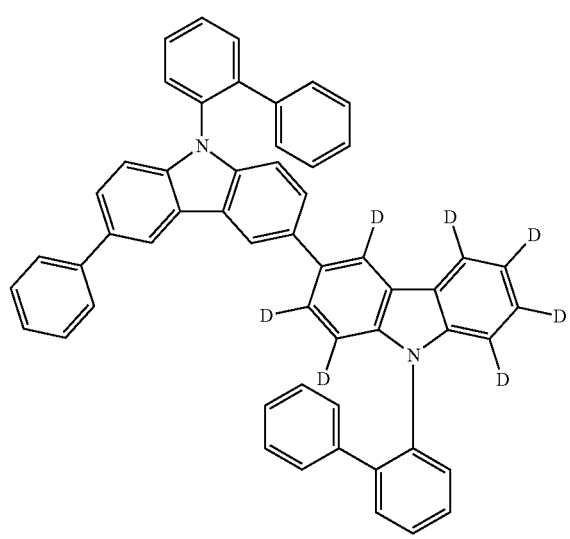
205
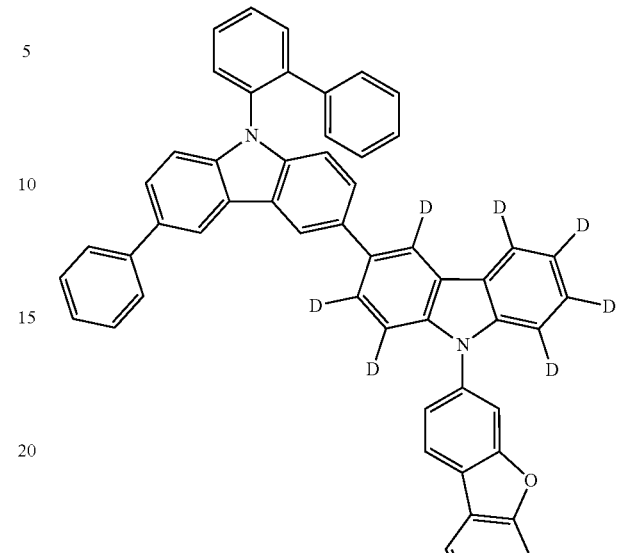
206
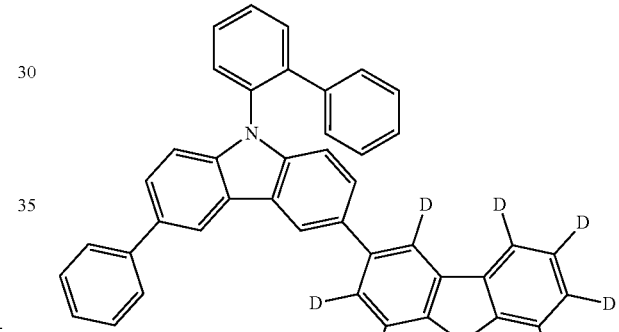
207
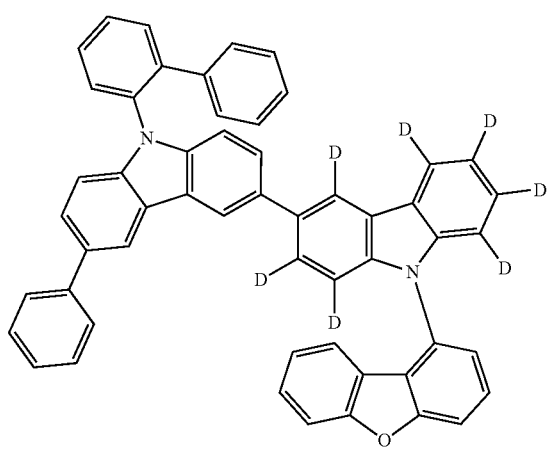
208

209
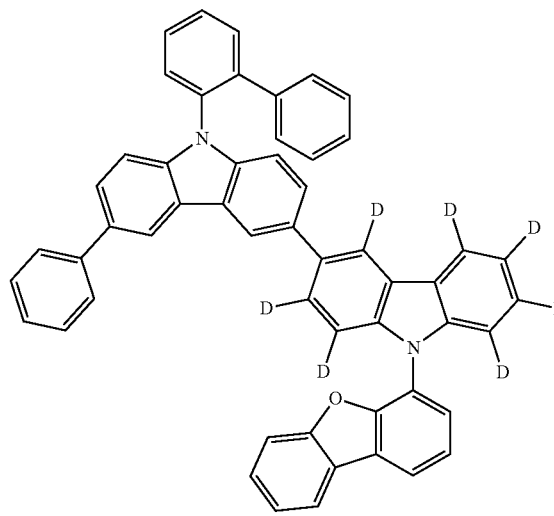
210
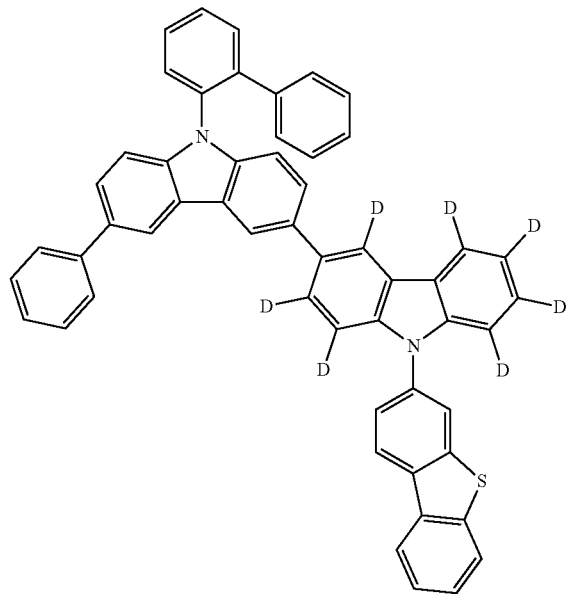
211
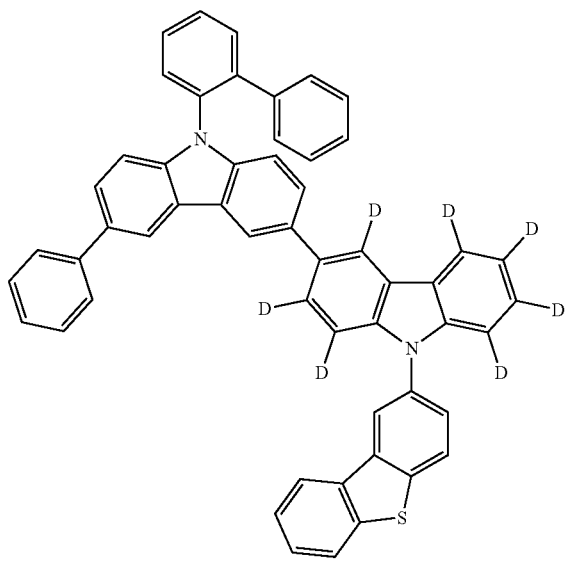
212
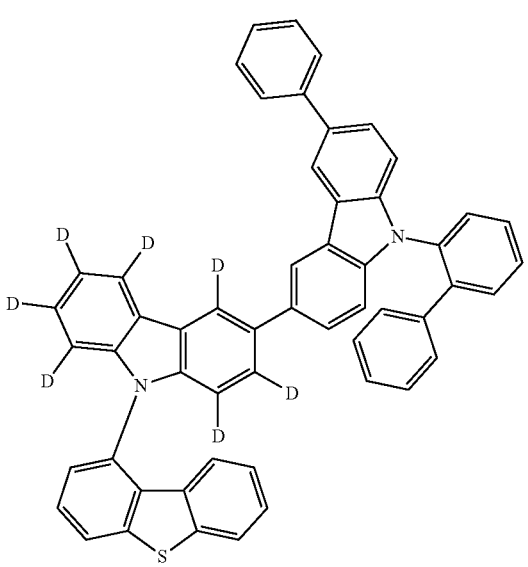

571
-continued
213
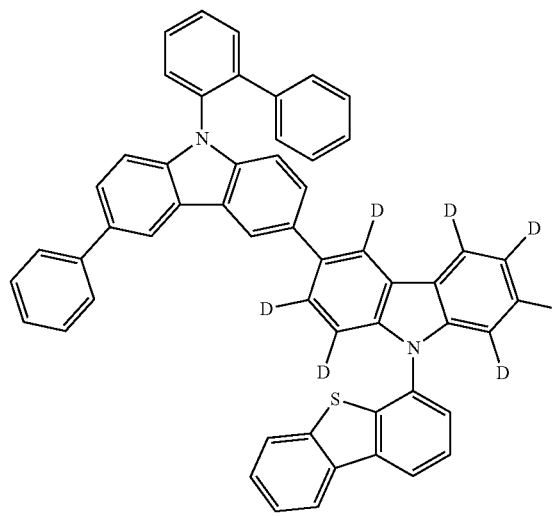
214
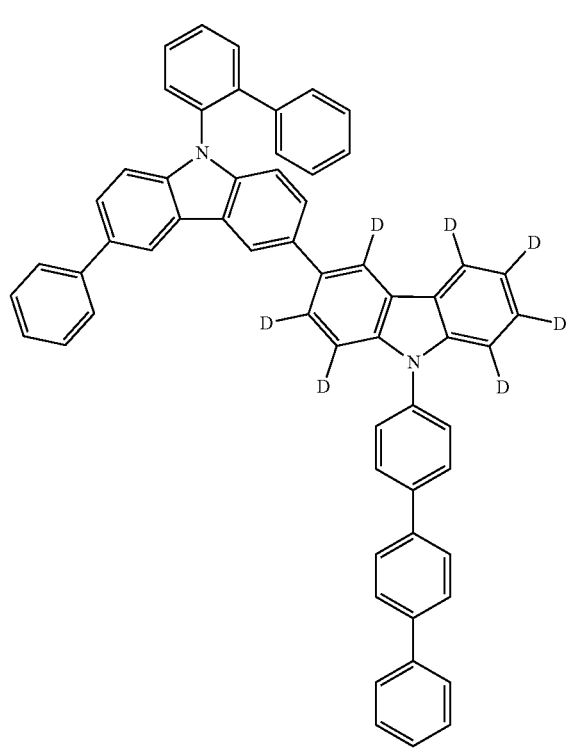
572
-continued
215
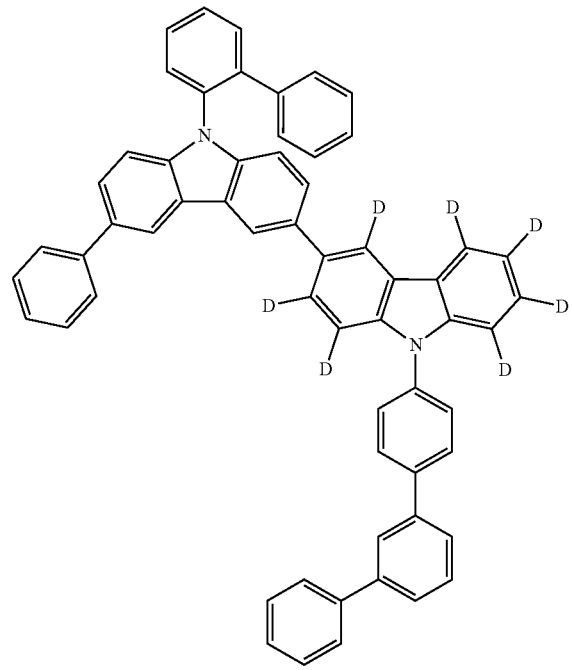
216
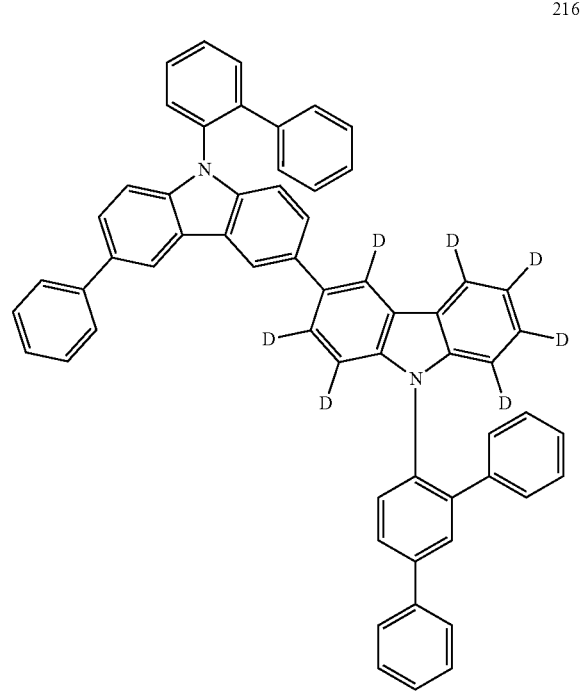

217
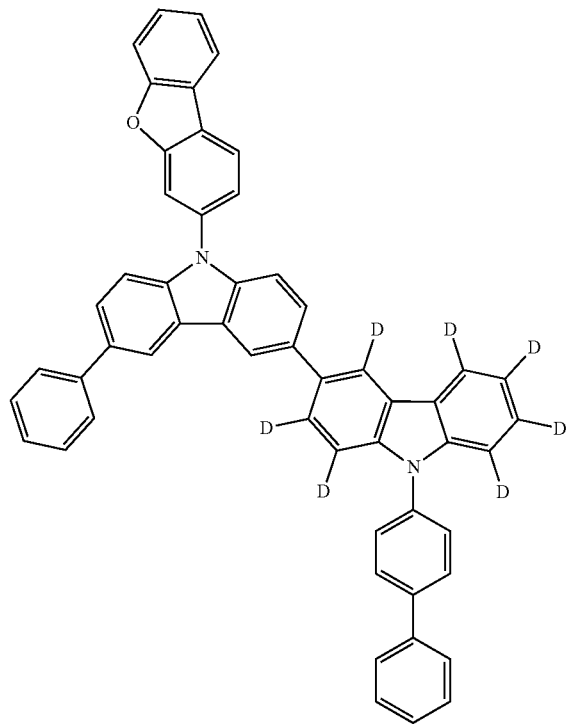
219
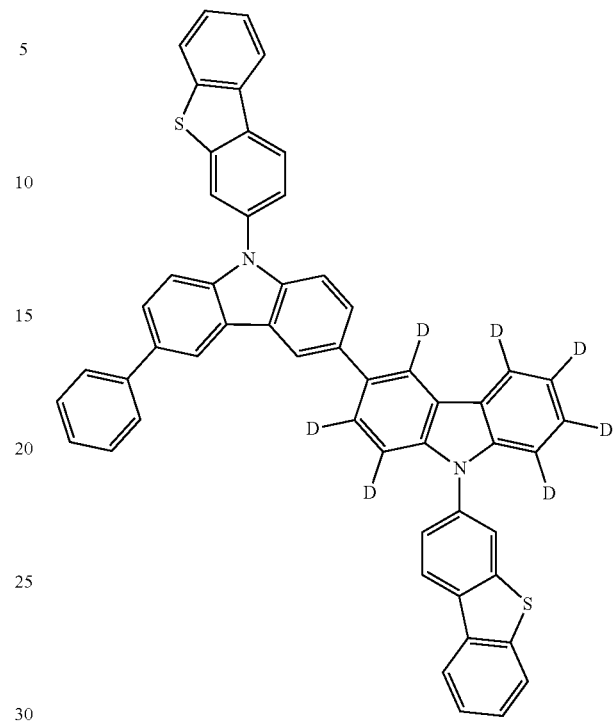
218
220
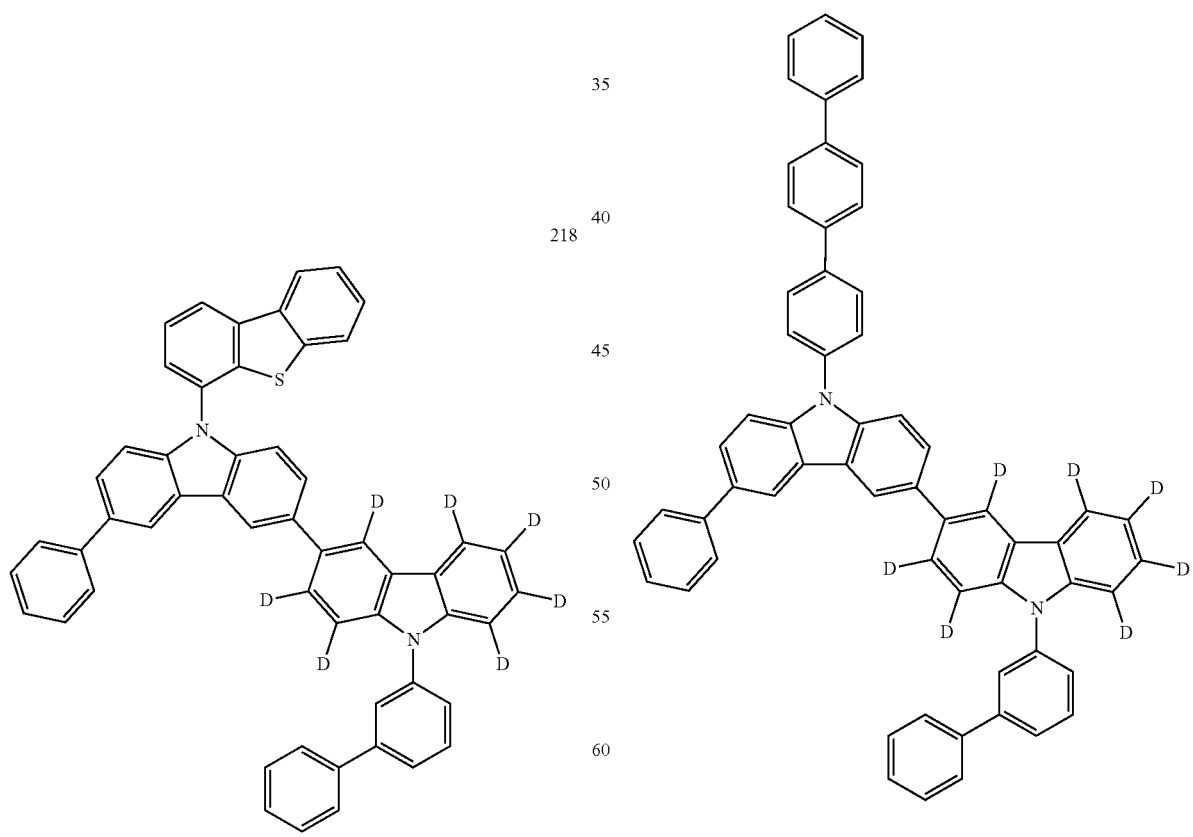

575
-continued
221
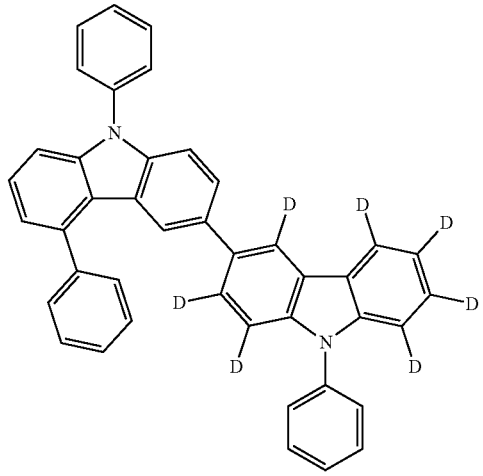
223
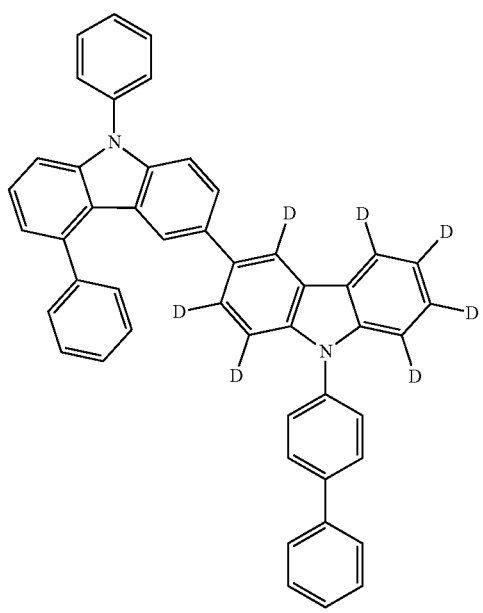
224
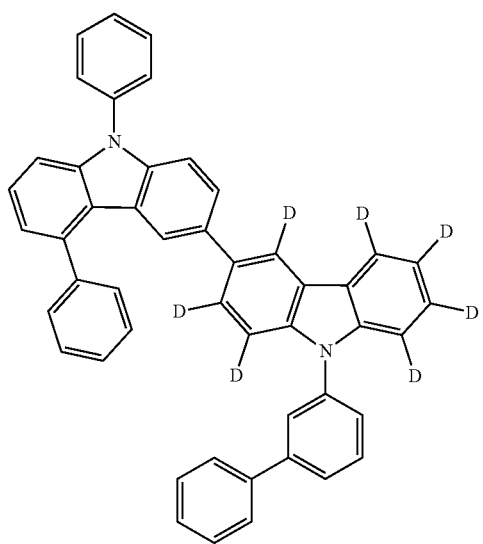
576
-continued
225
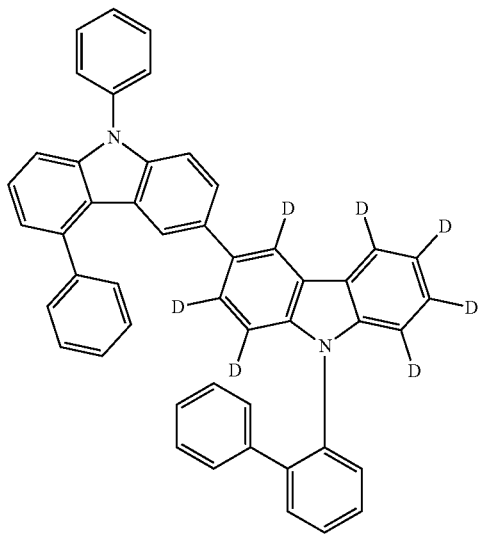
226
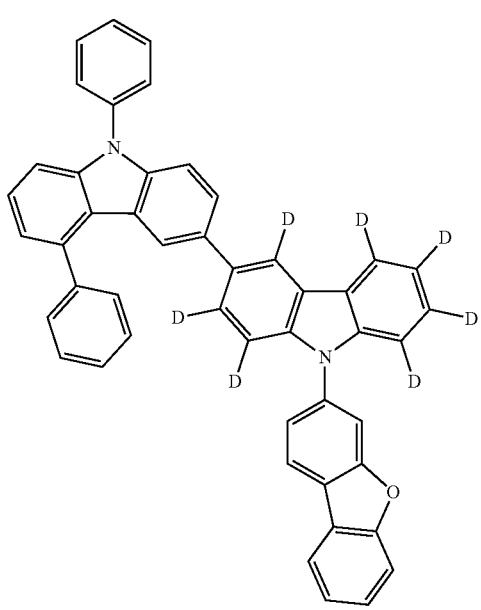

577
-continued
227
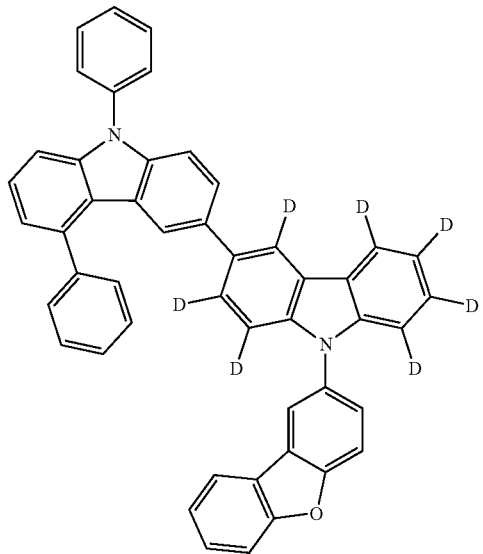
228
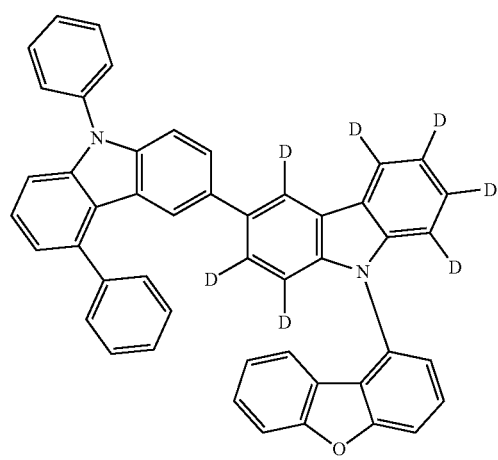
229
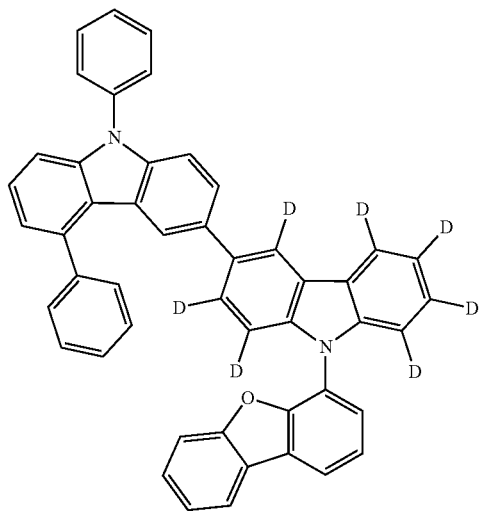
578
-continued
230
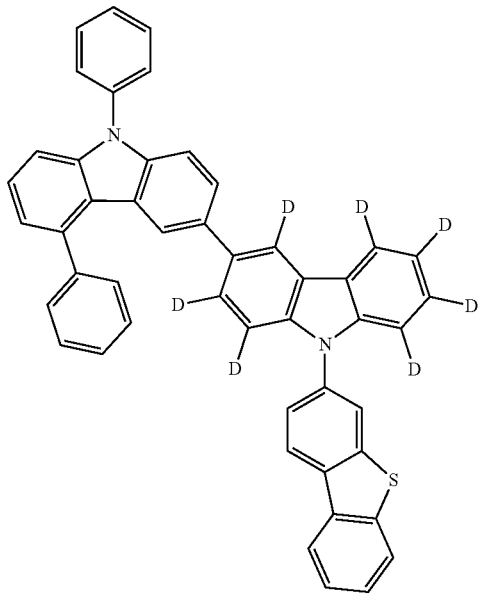
231
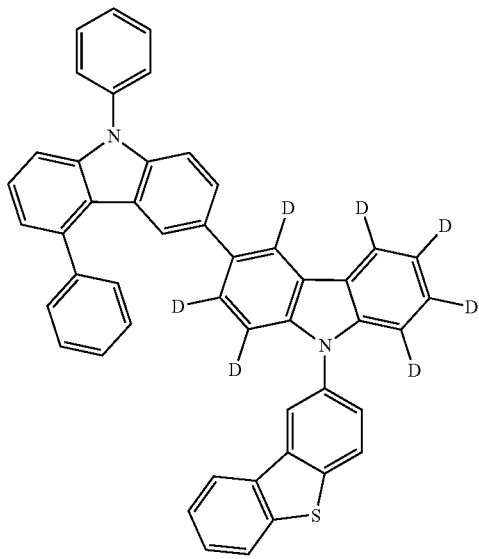
232
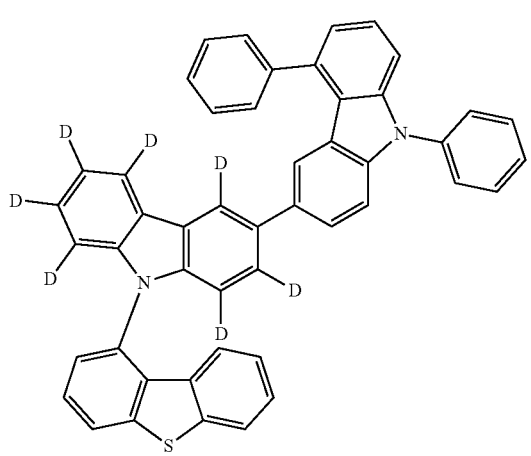

233
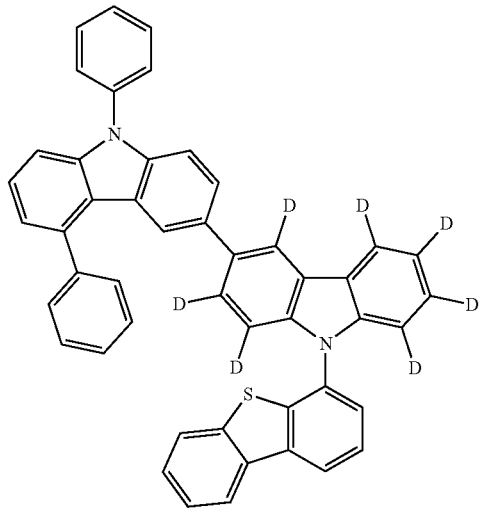
236
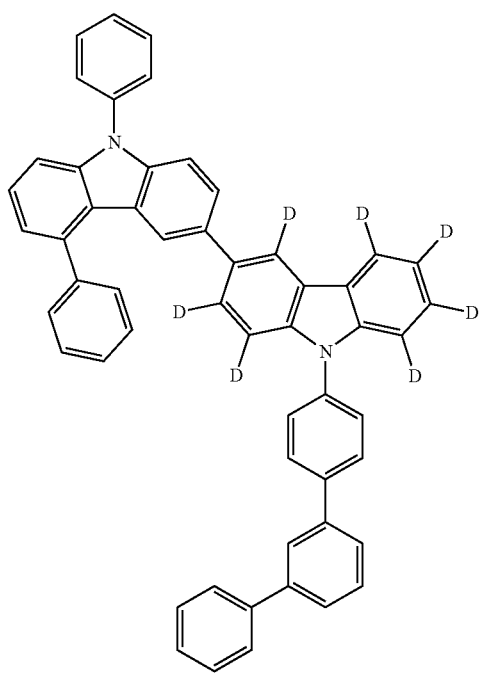
237
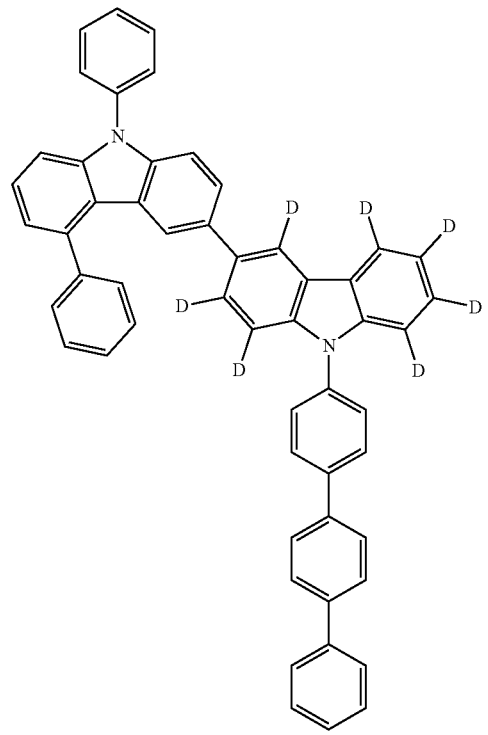
238
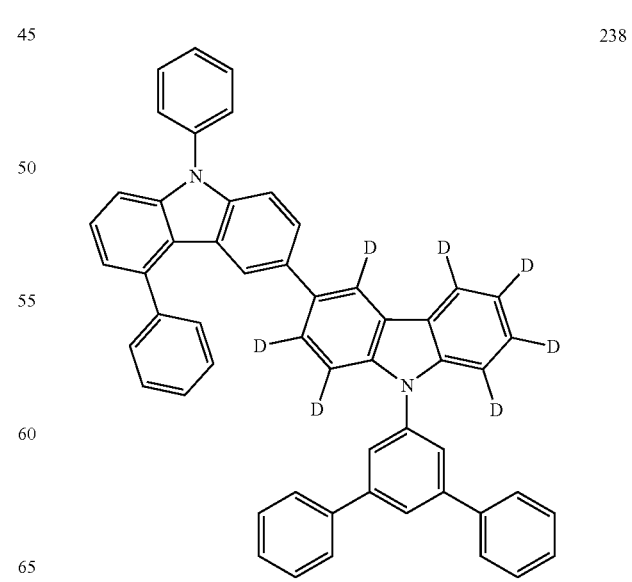

581
-continued
238
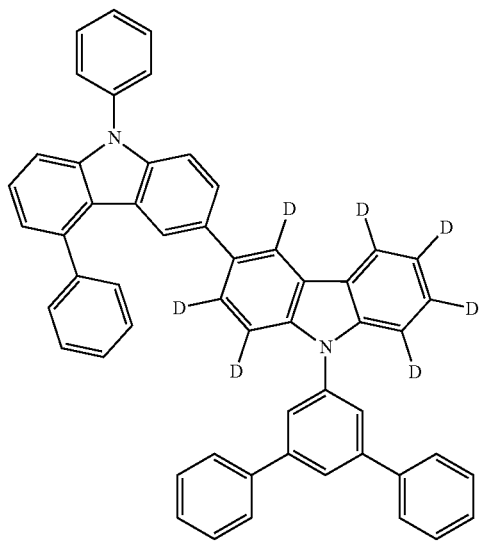
239
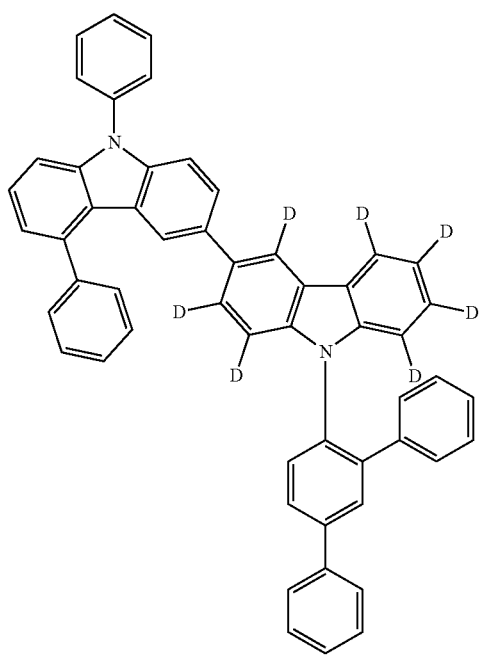
582
-continued
240
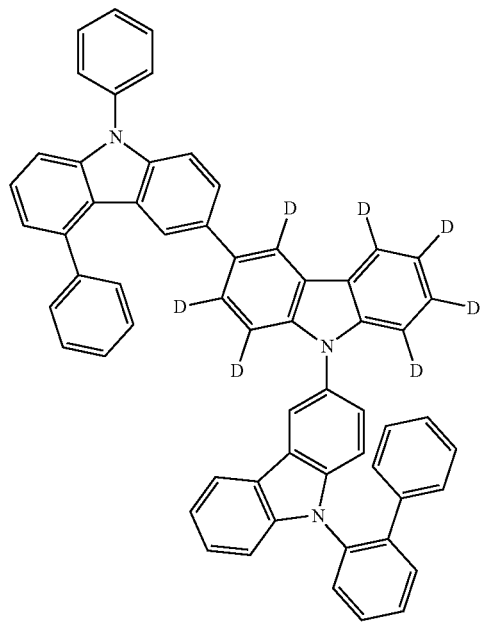
241
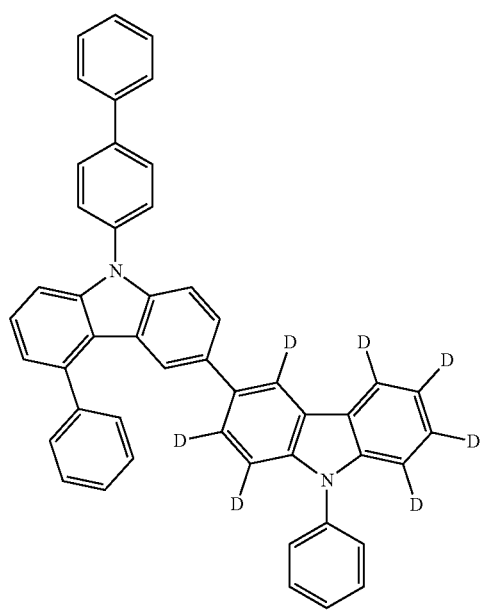

243
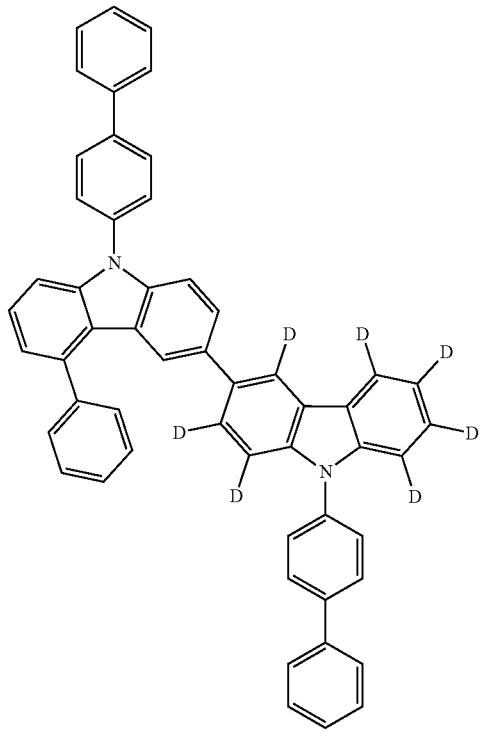
244
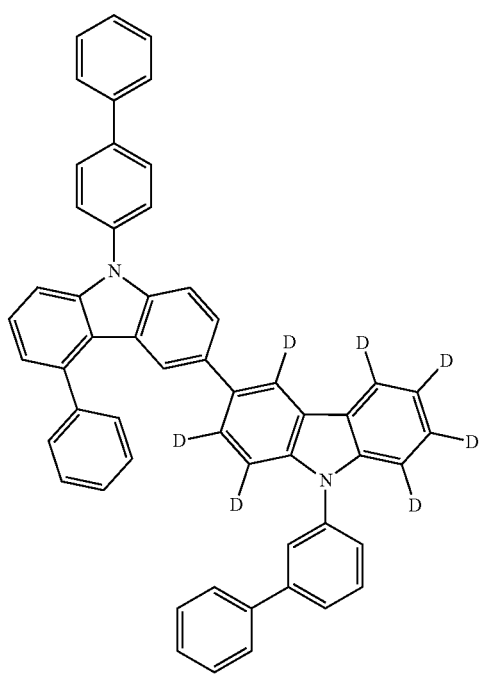
245
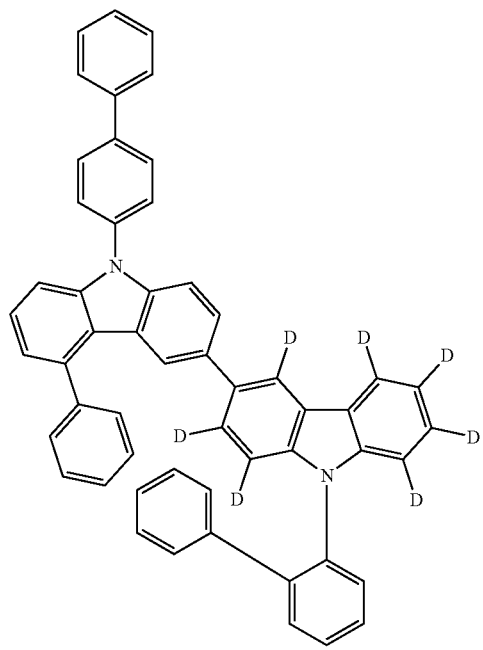
246
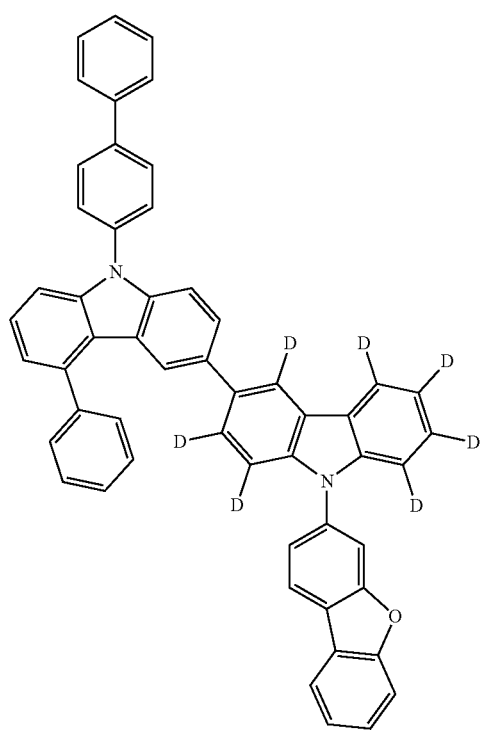

247
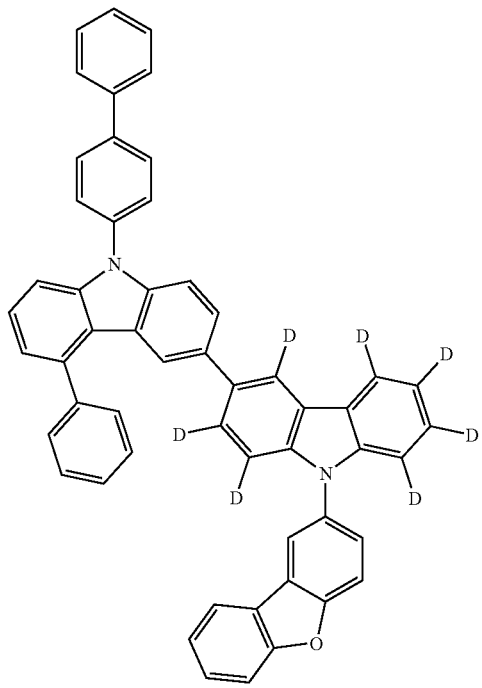
249
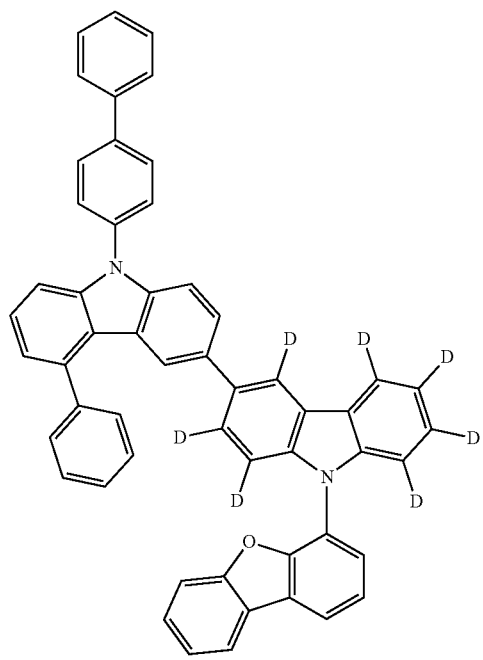
248
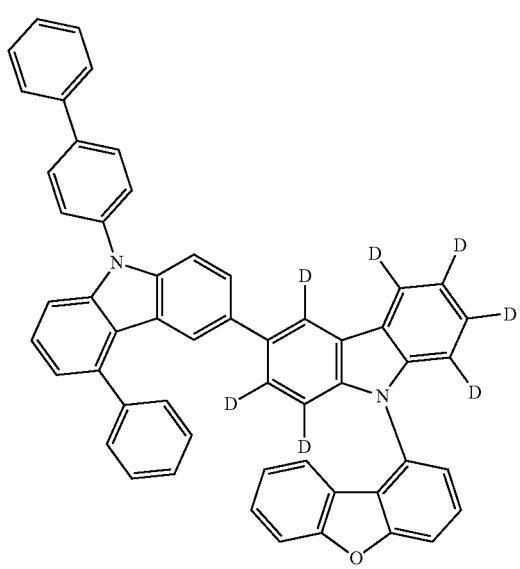
250
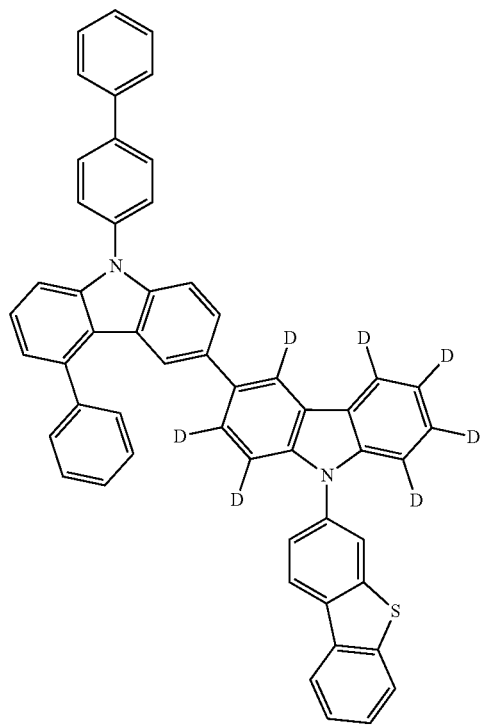

251
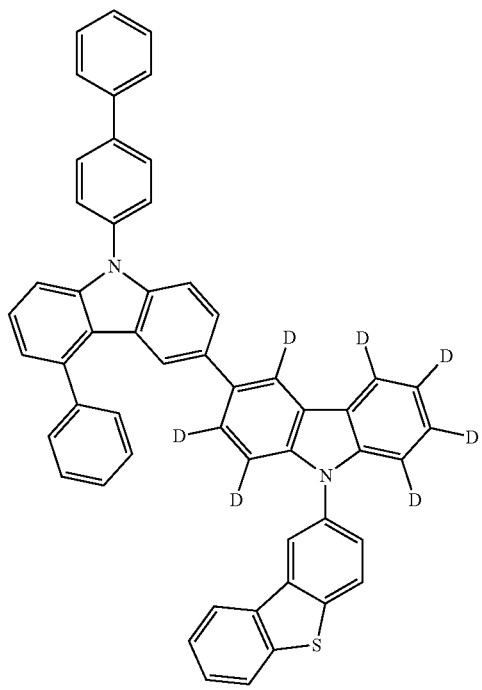
252
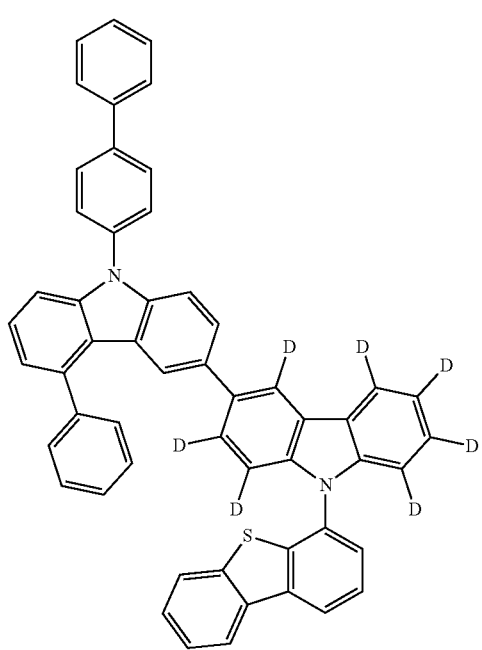
253
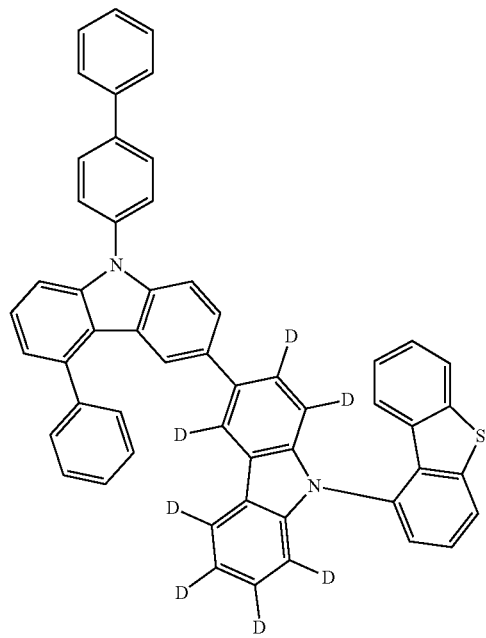
257
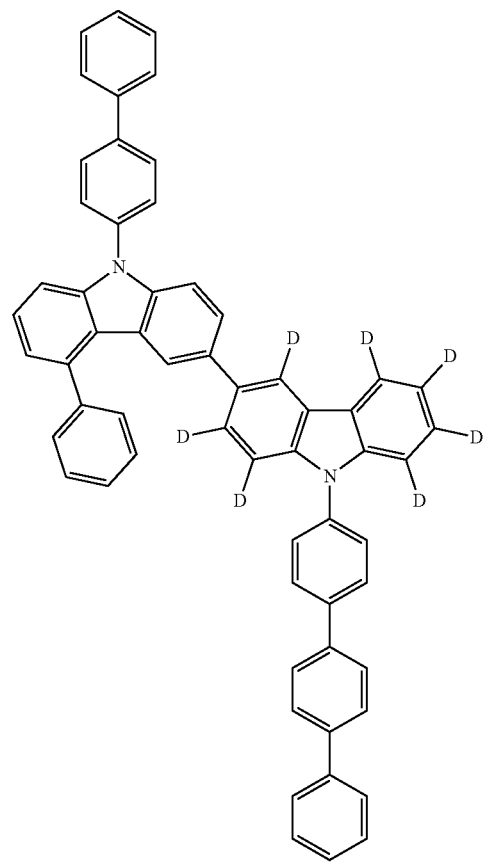

258
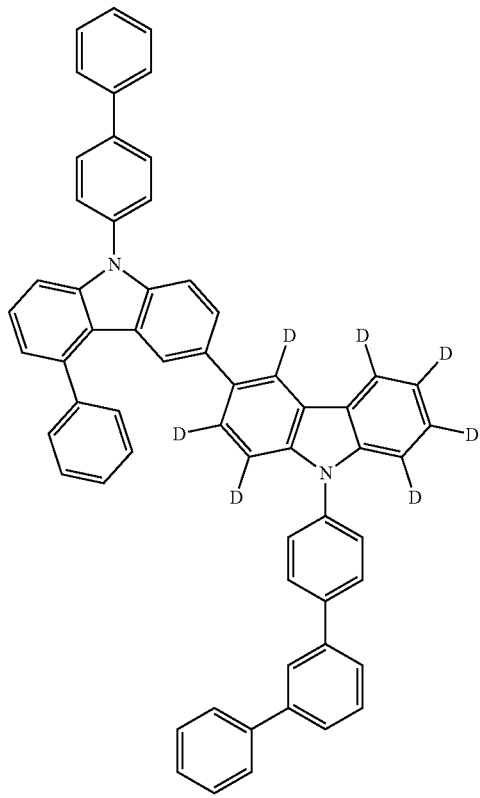
259
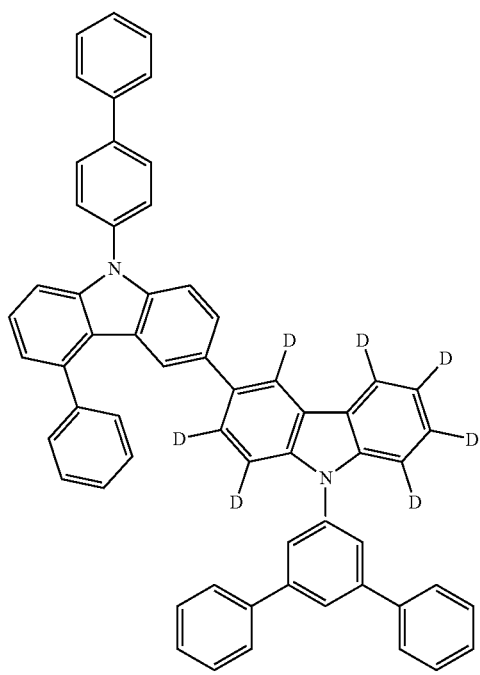
260
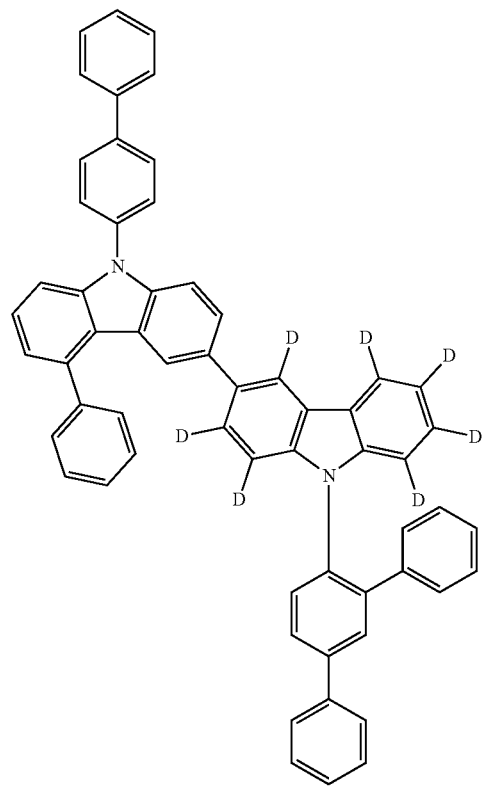
261
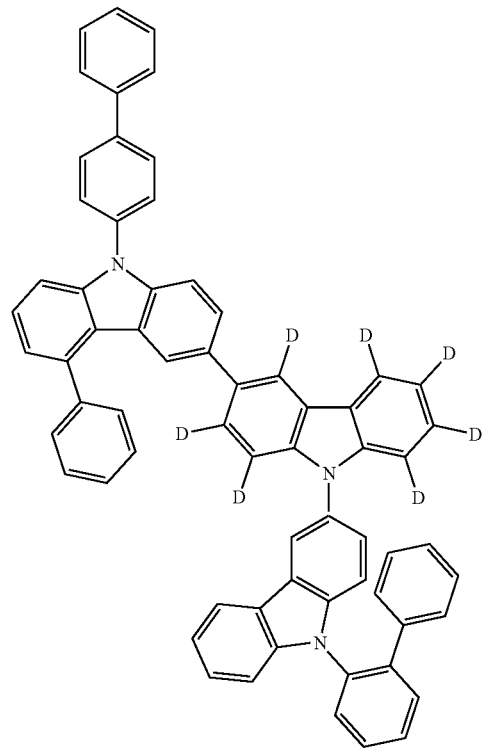

591
-continued
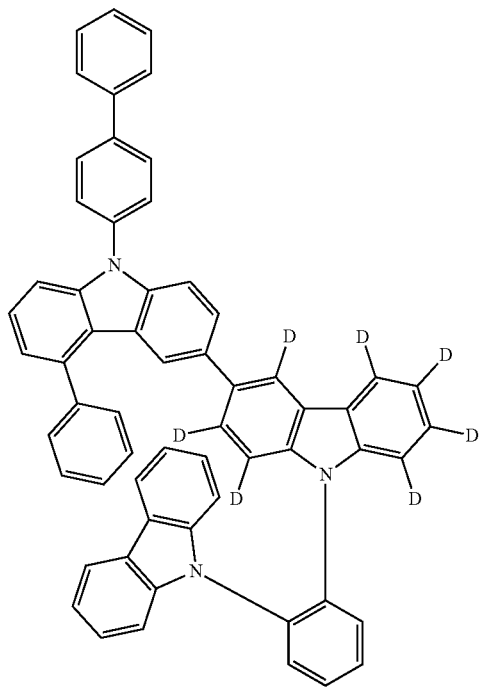
264
592
-continued
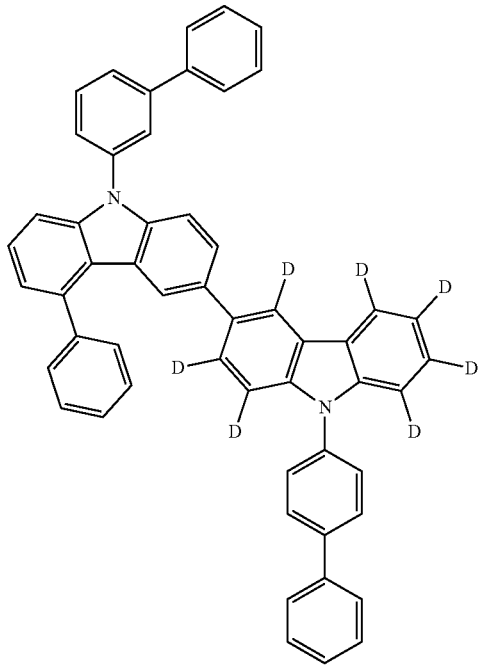
268
265
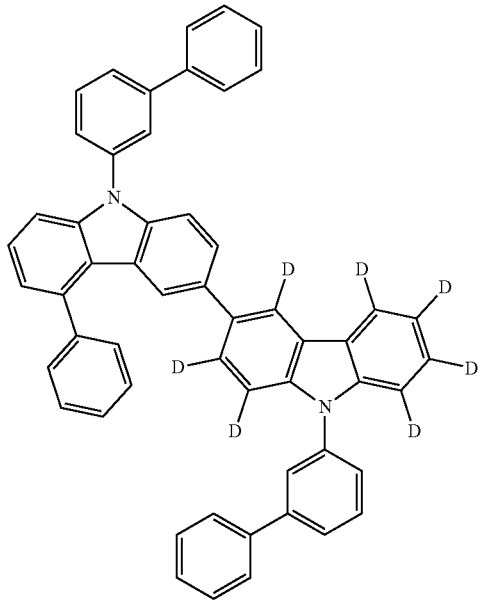
269

593
270
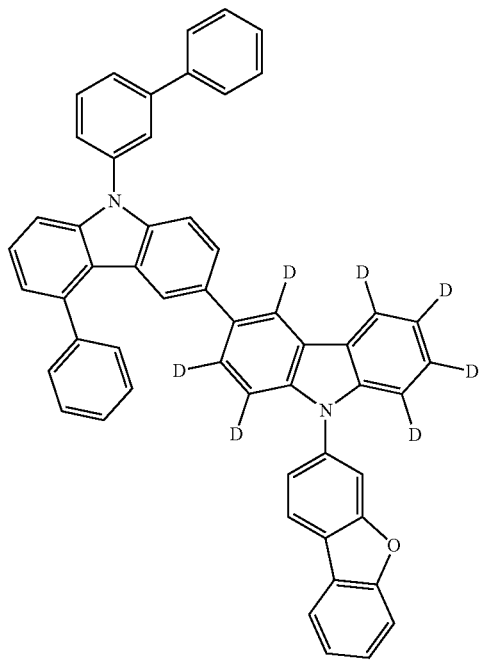
271
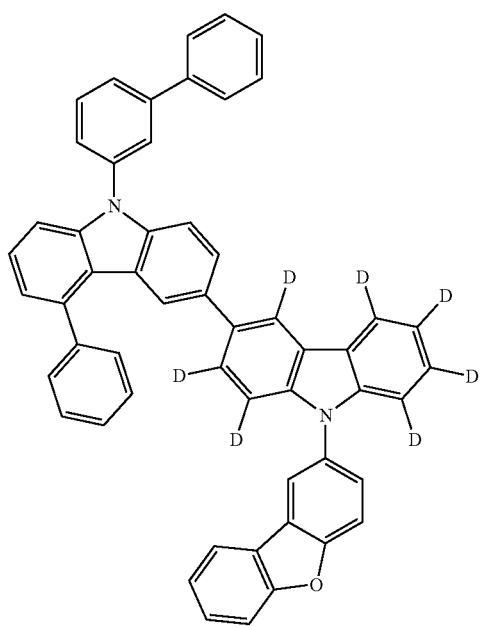
594
272
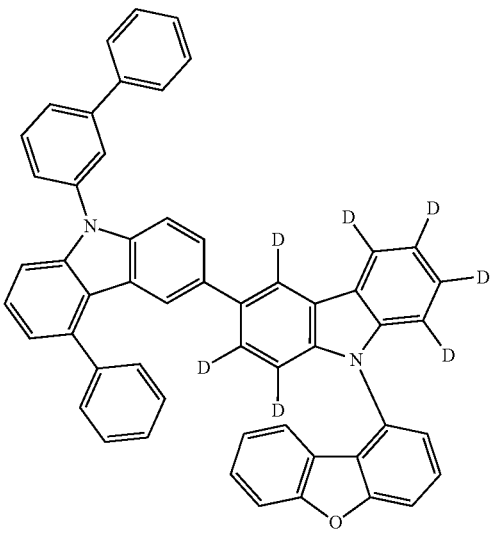
273
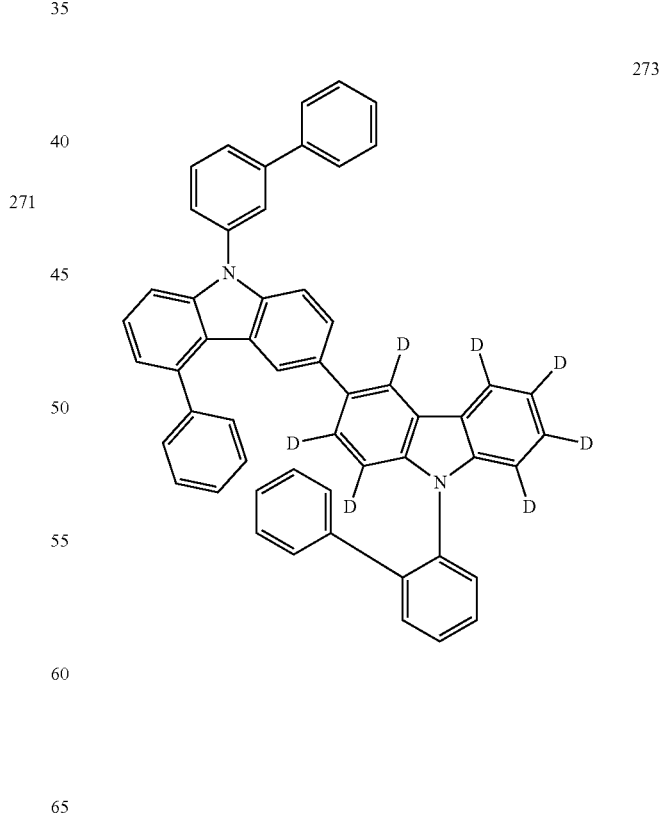

274
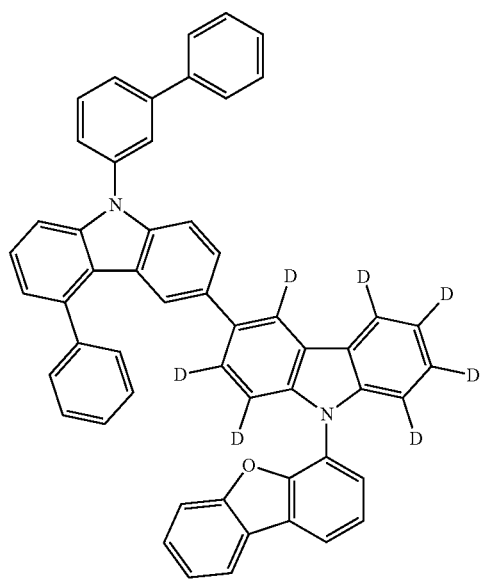
276
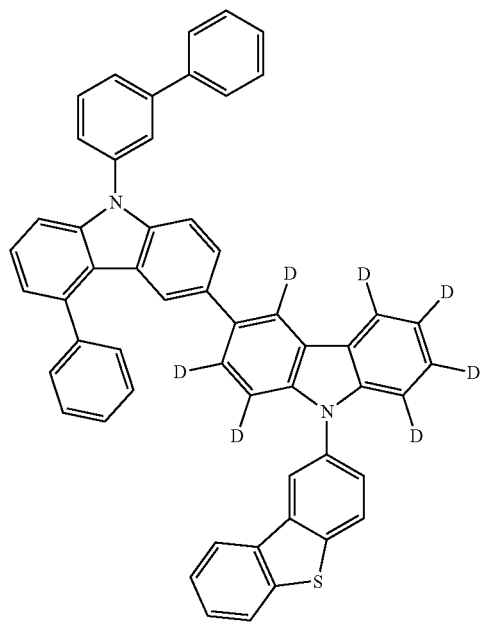
275
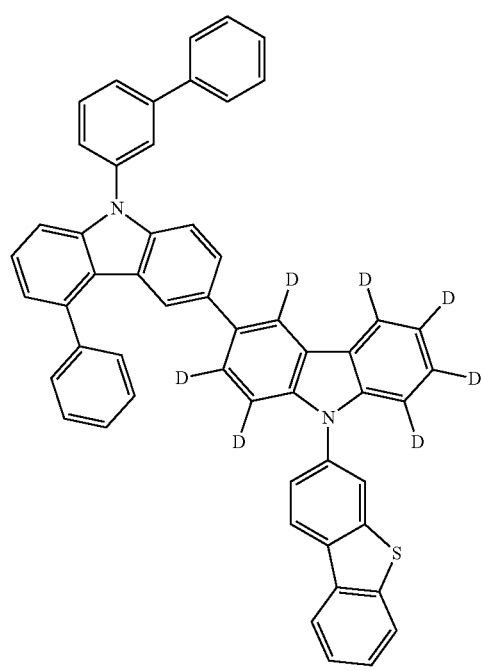
277
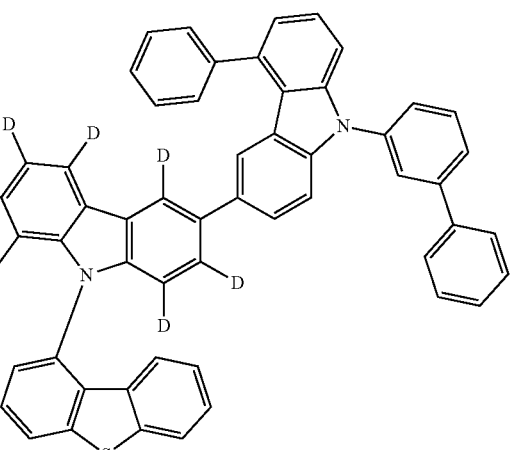

597
-continued
278
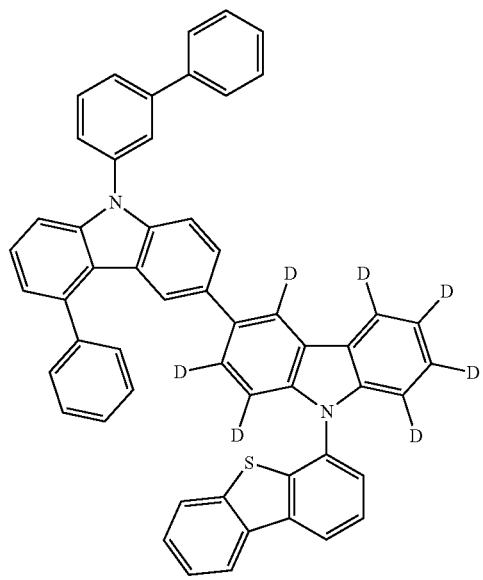
282
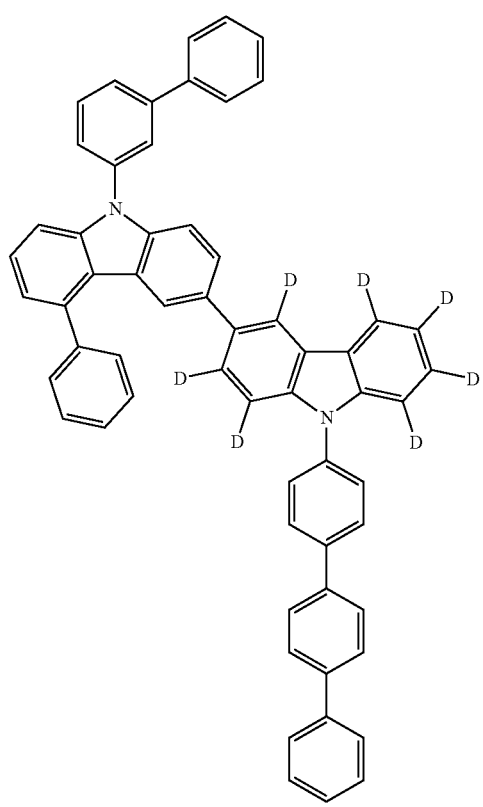
598
-continued
283
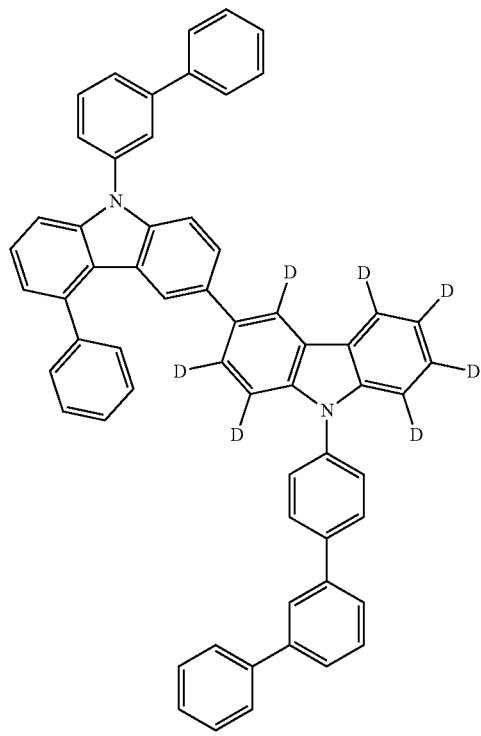
284
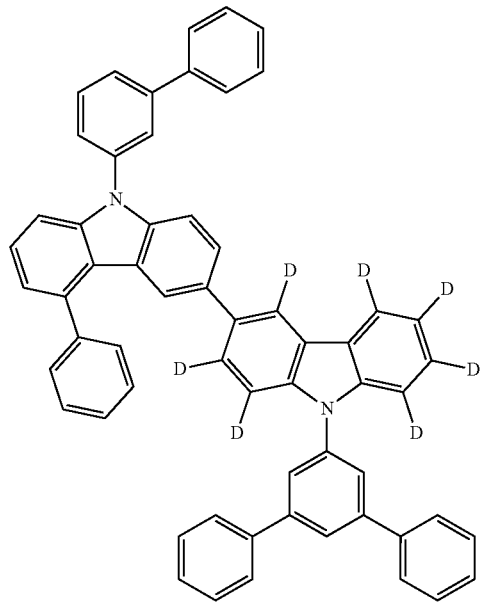

599
-continued
285
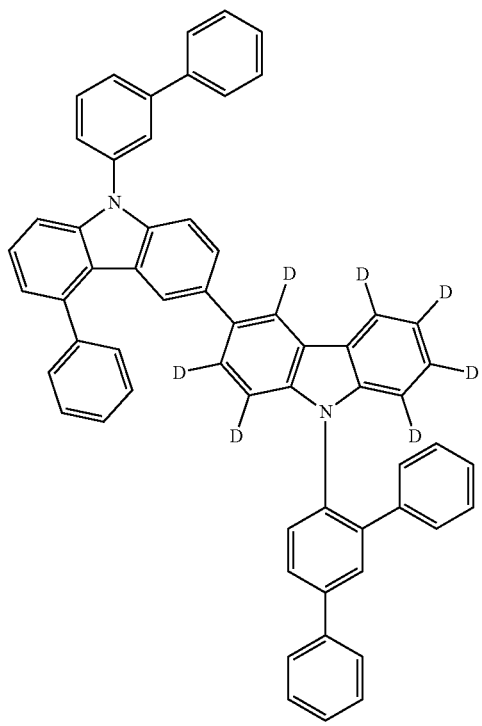
286
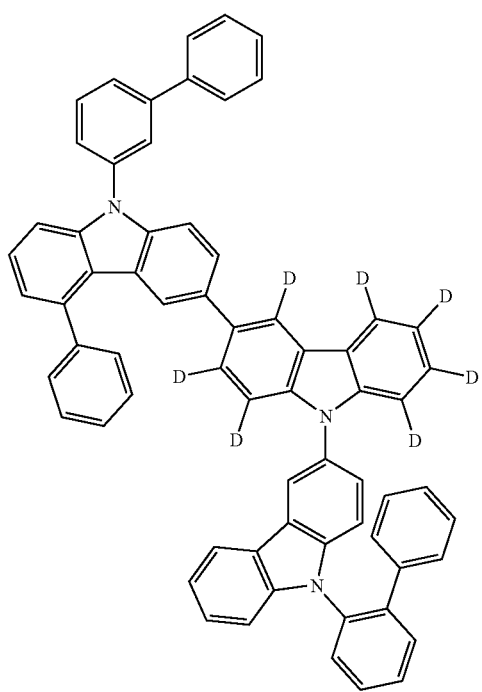
600
-continued
287
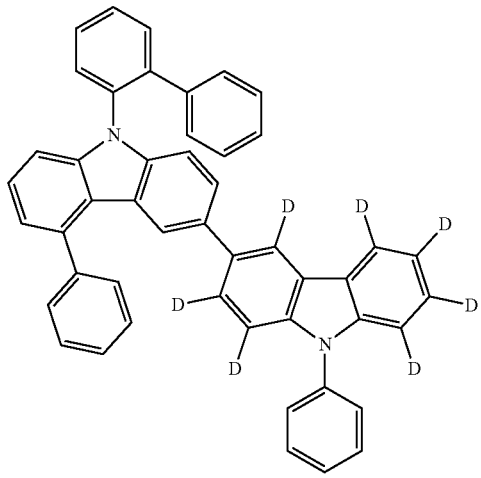
290
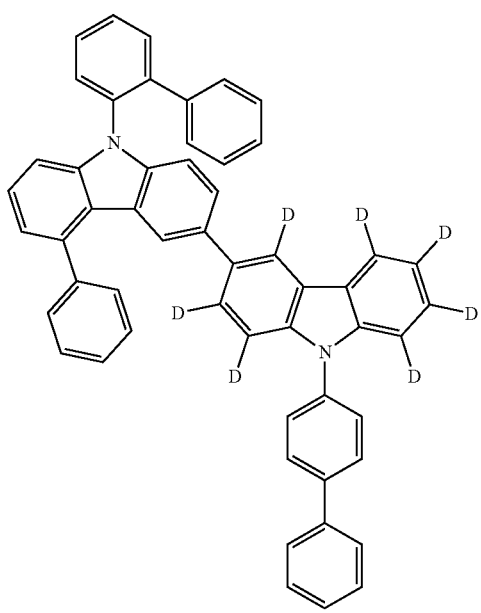
291
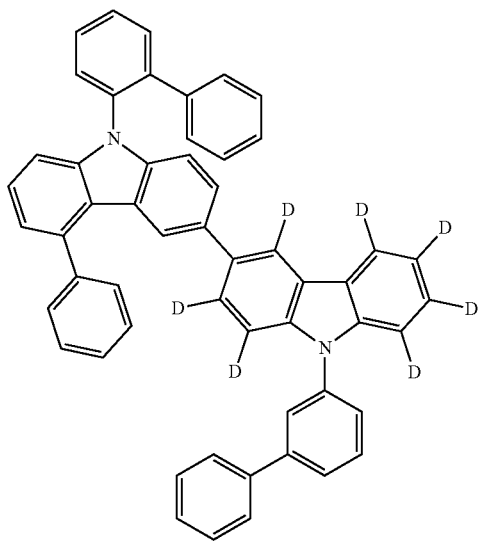

601
-continued
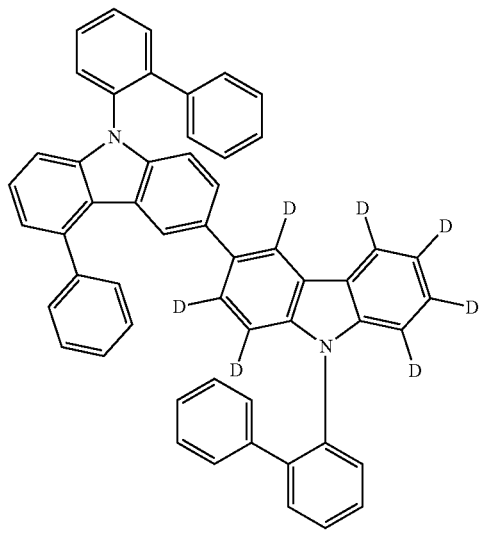
292
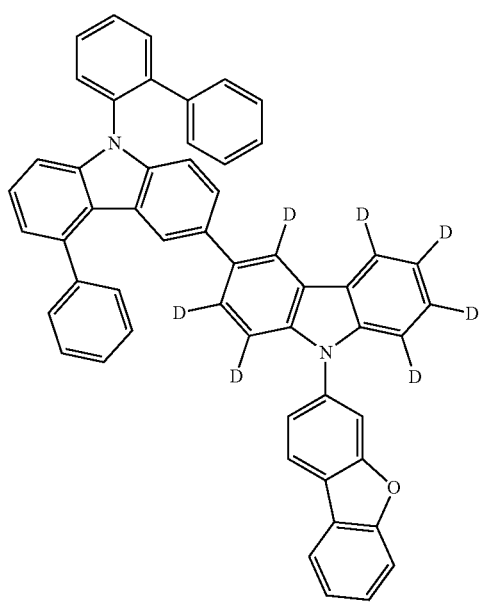
293
602
-continued
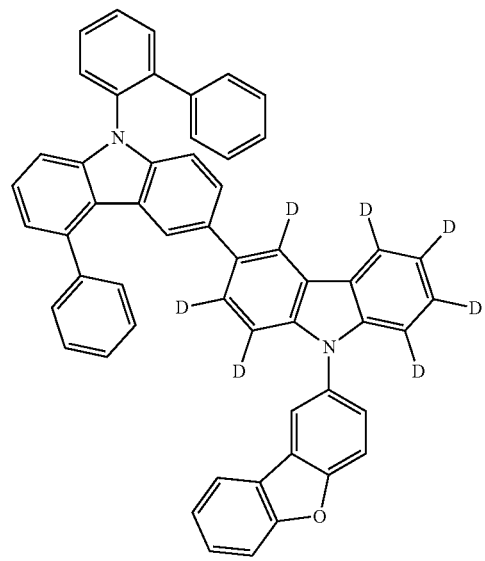
294
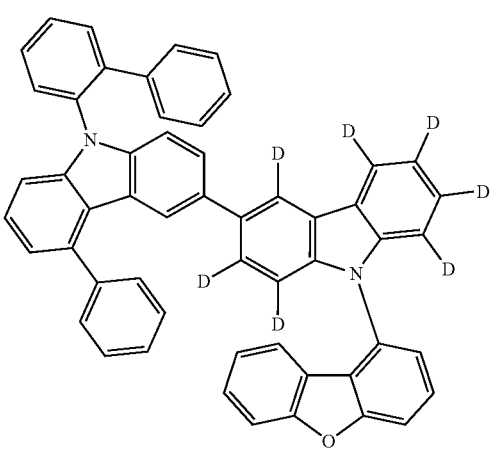
295
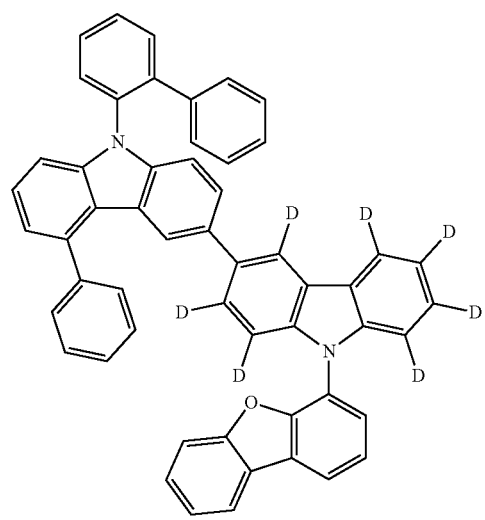
296

297
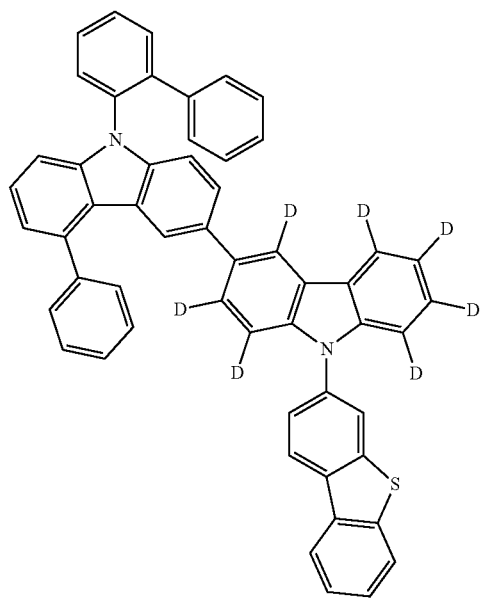
298
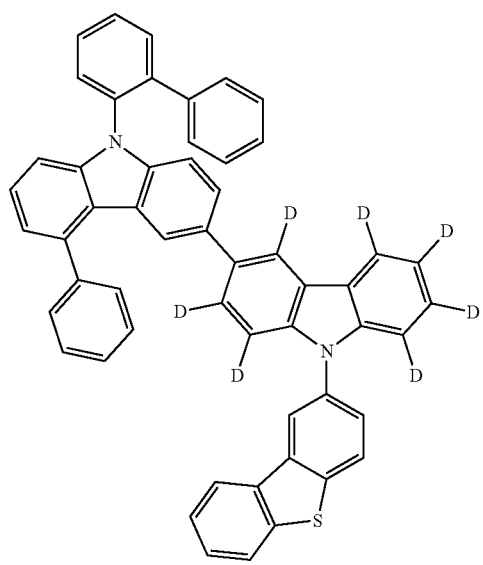
299
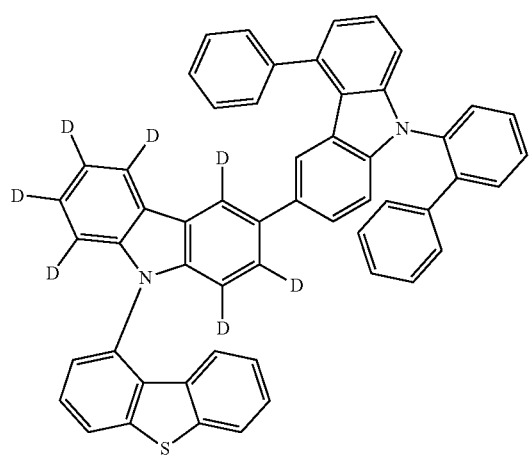
300
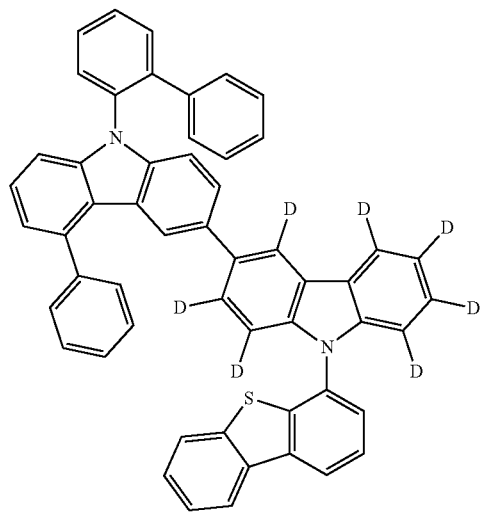
304
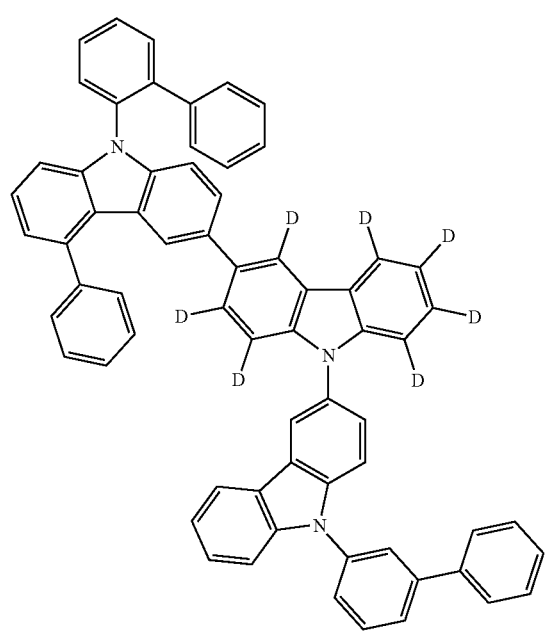

605
-continued
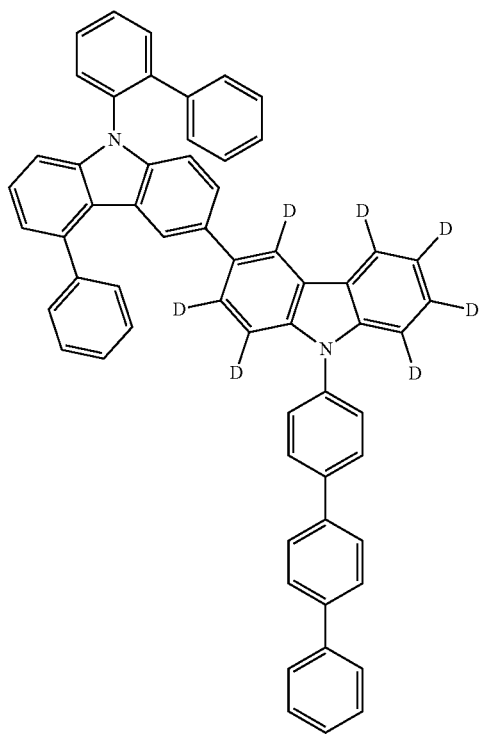
305
606
-continued
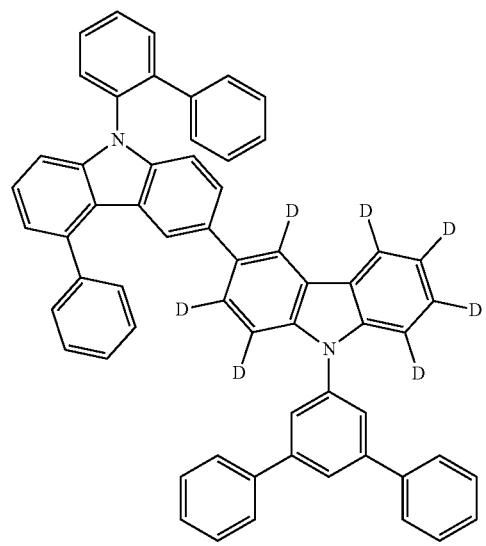
307
306
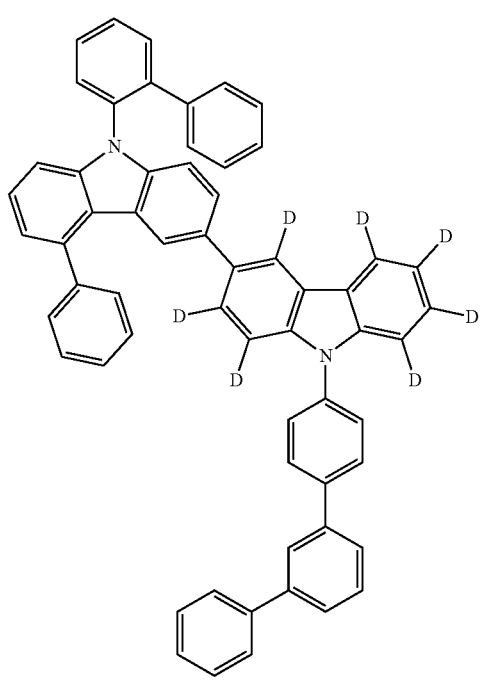
308
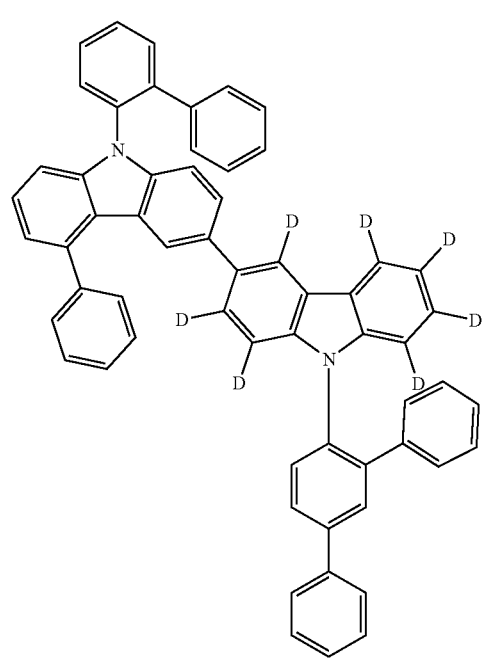

607
-continued
311
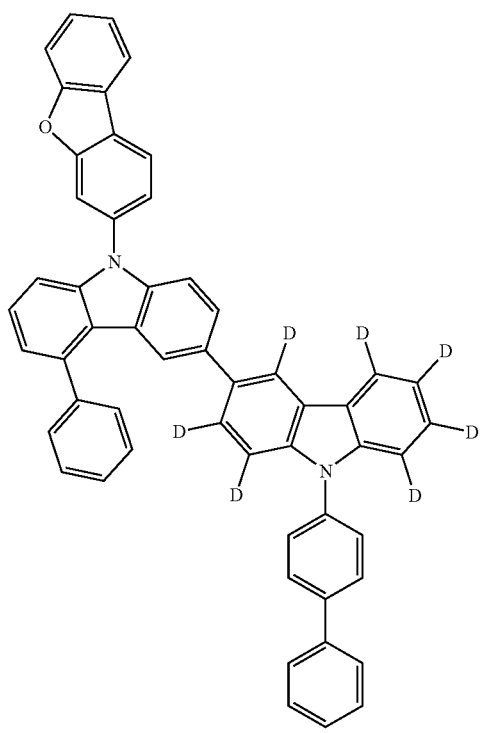
312
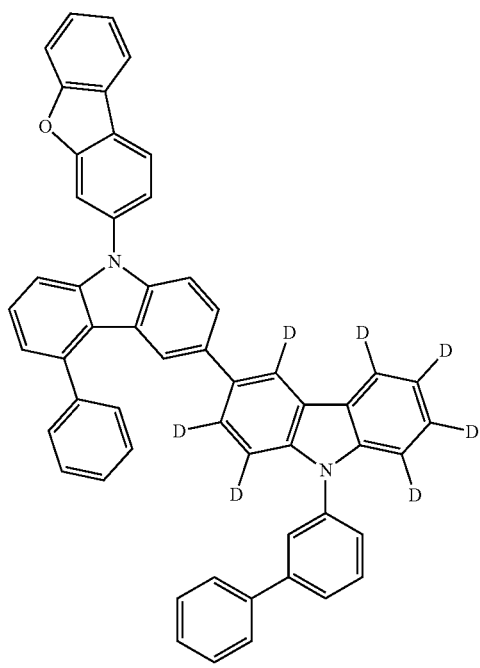
608
-continued
313
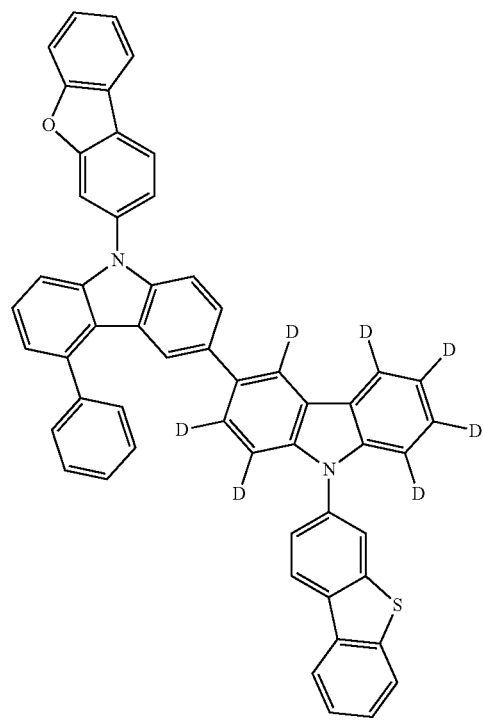
314
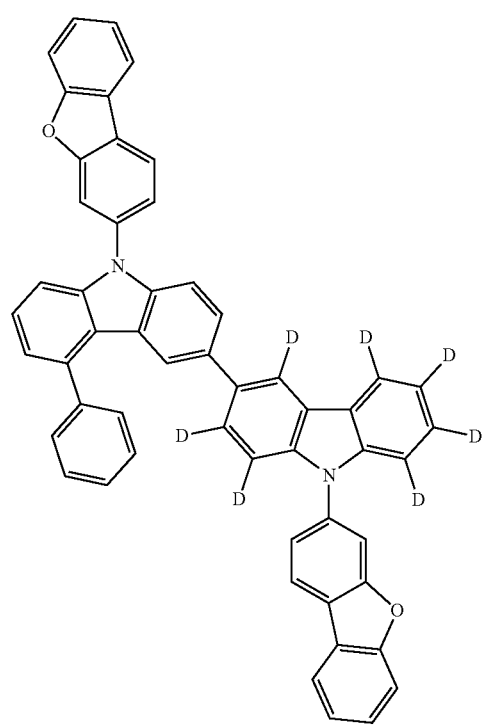

609
-continued
315
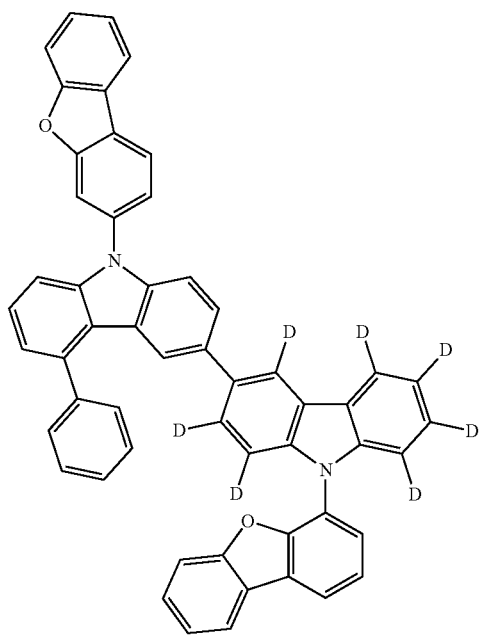
316
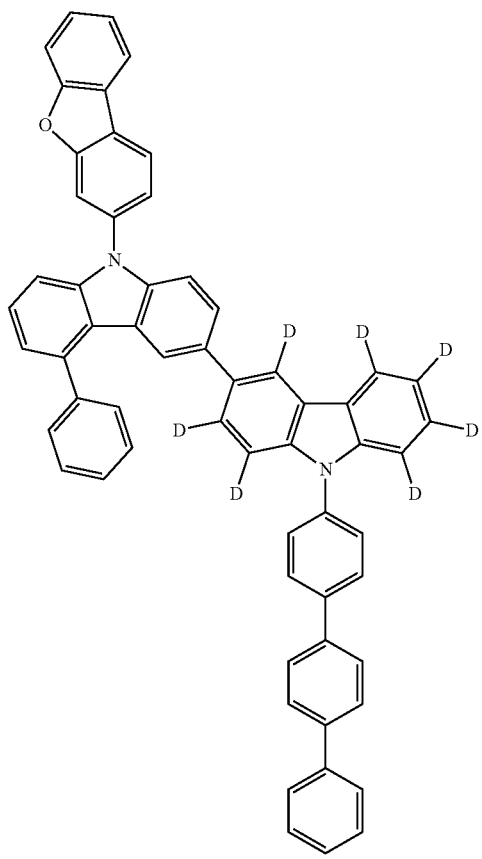
610
-continued
317
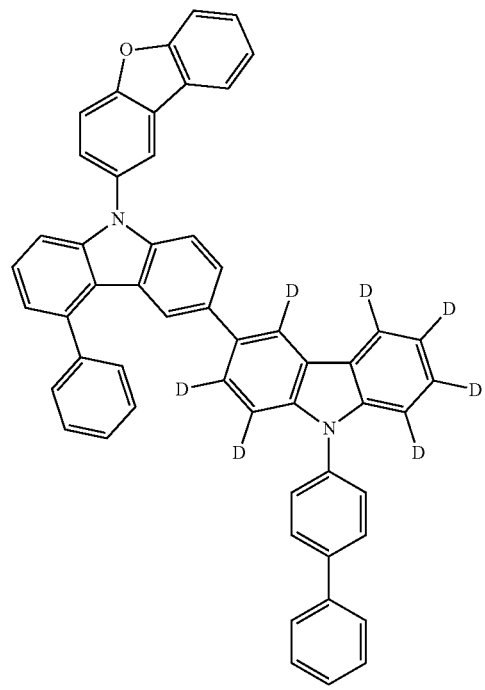
318
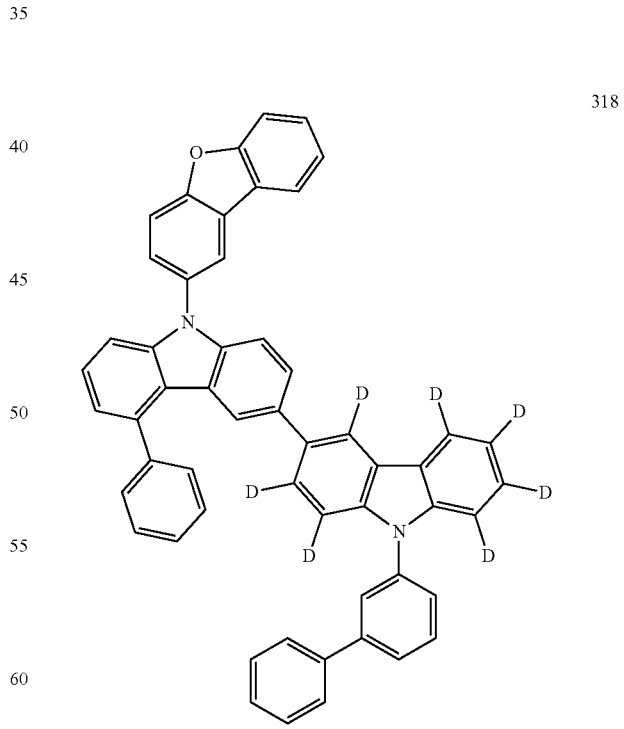

611
-continued
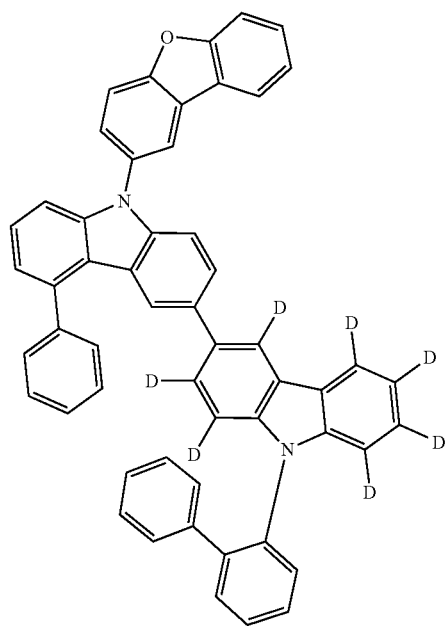
319
612
-continued
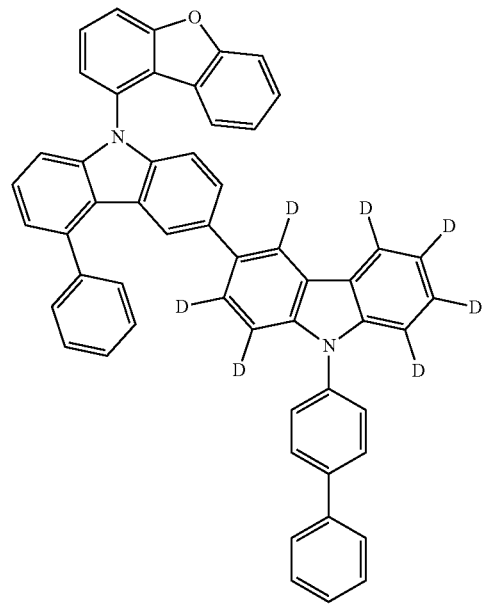
321
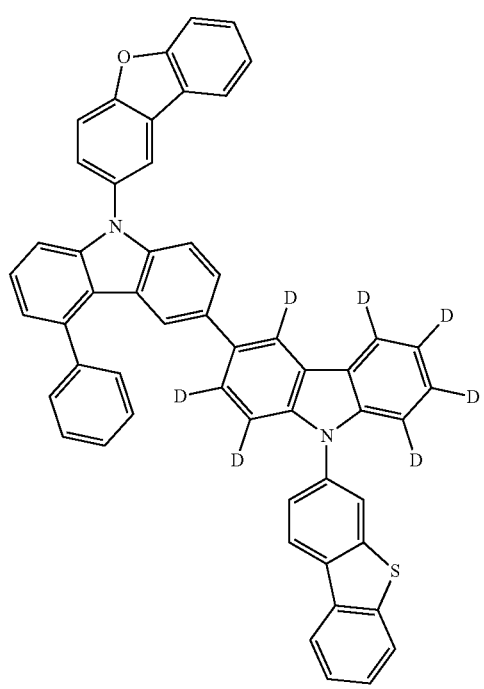
320
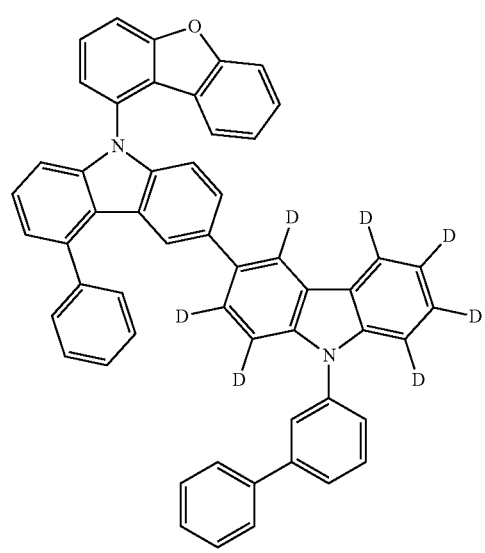
322

-continued
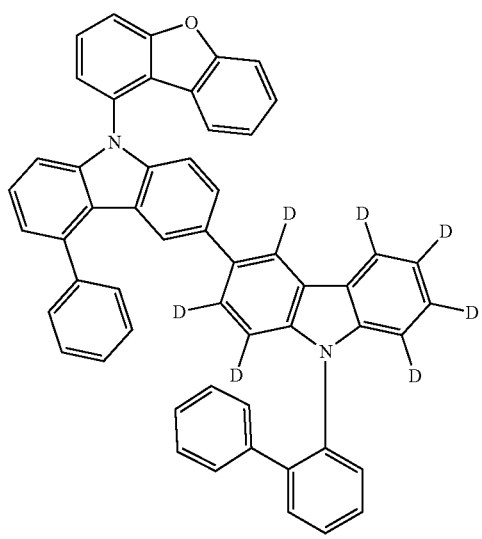
323
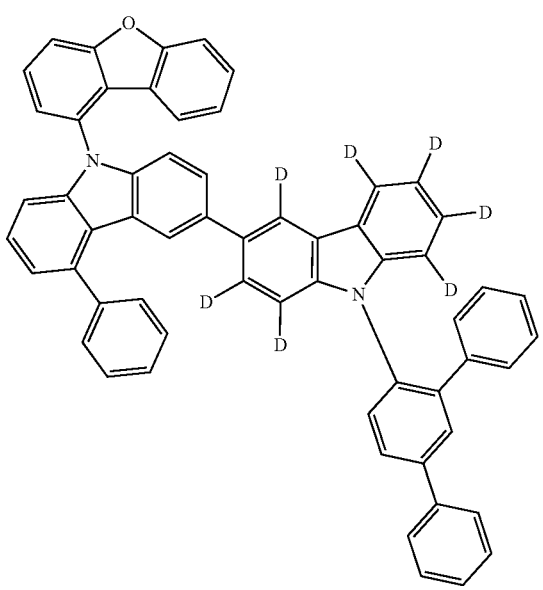
324
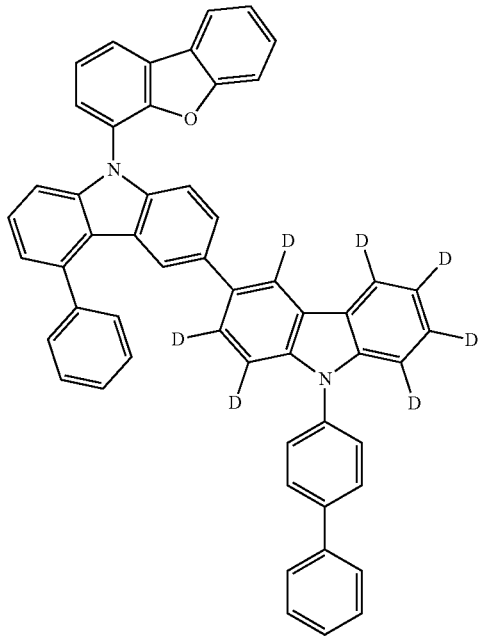
325
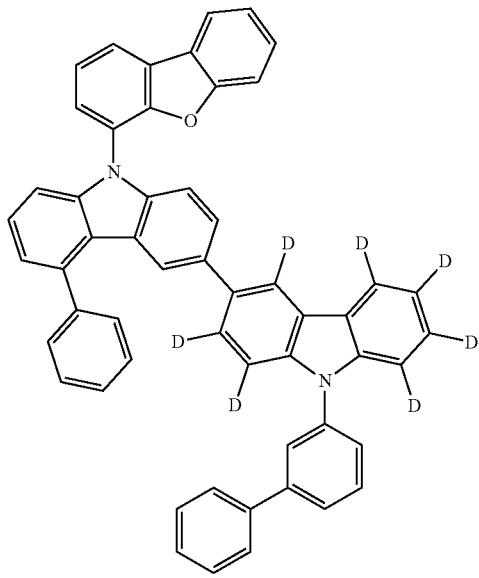
326

327
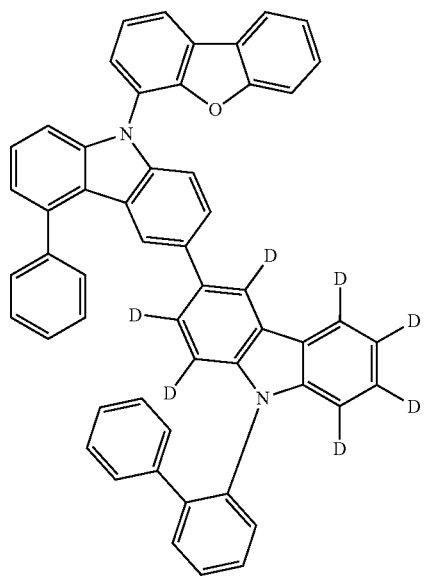
328
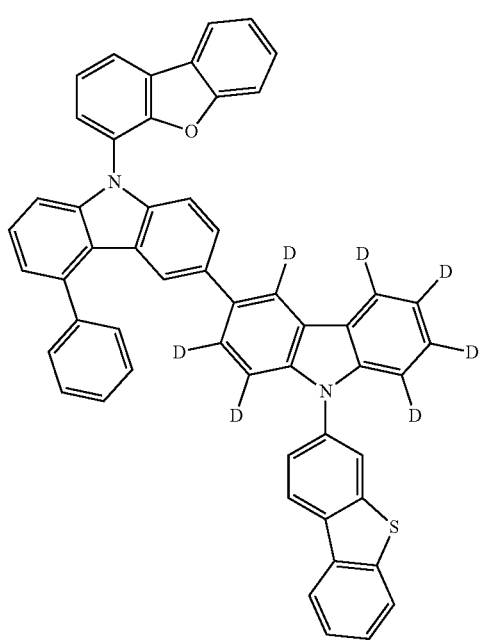
329
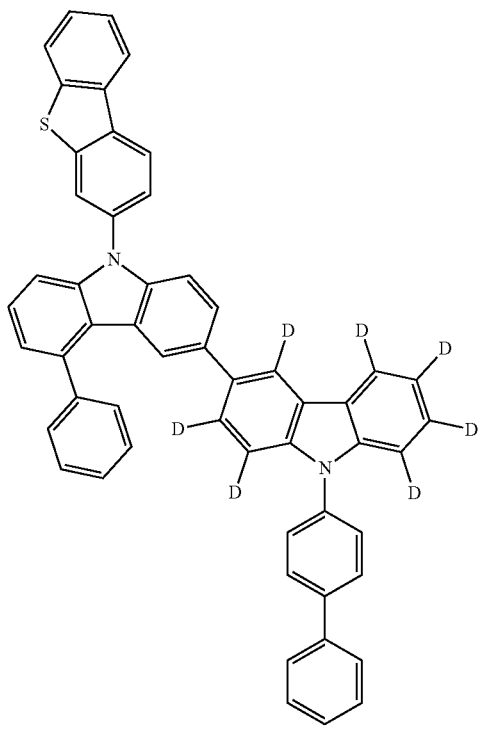
330
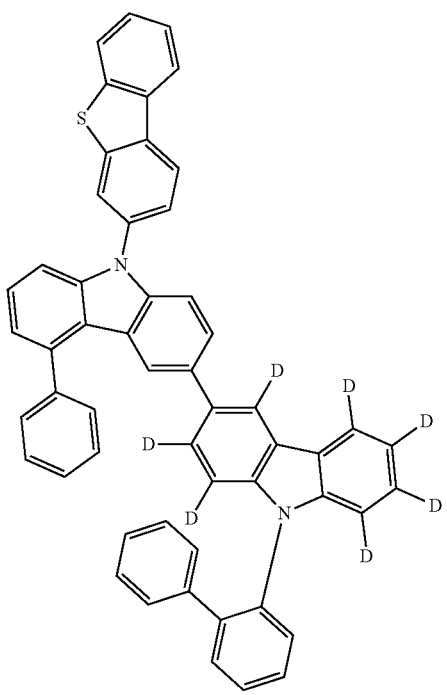

617
-continued
331
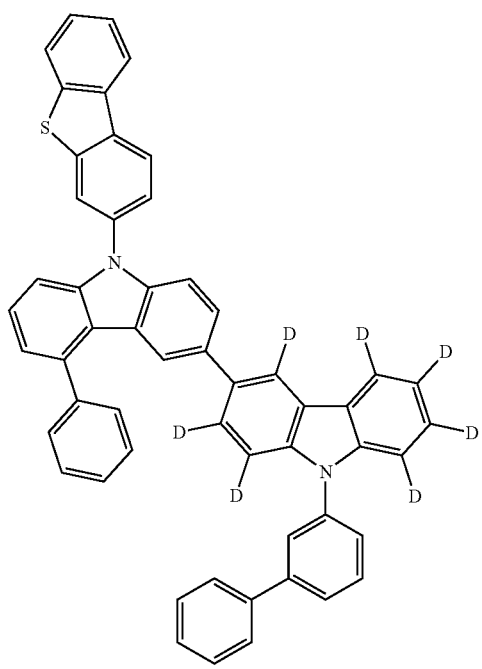
332
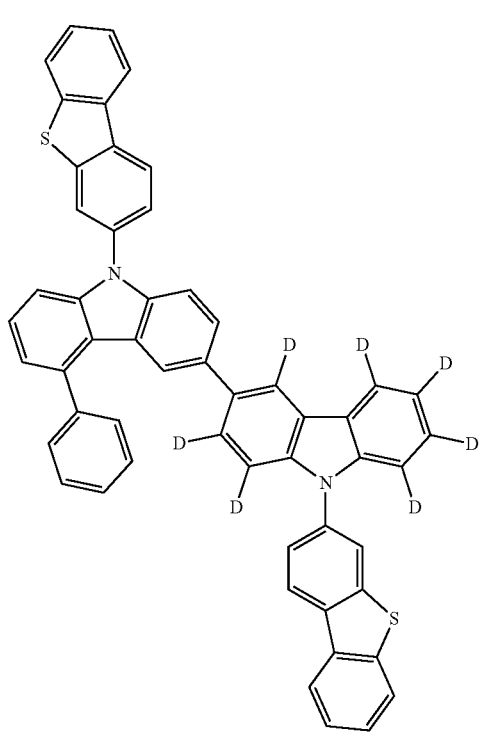
618
-continued
333
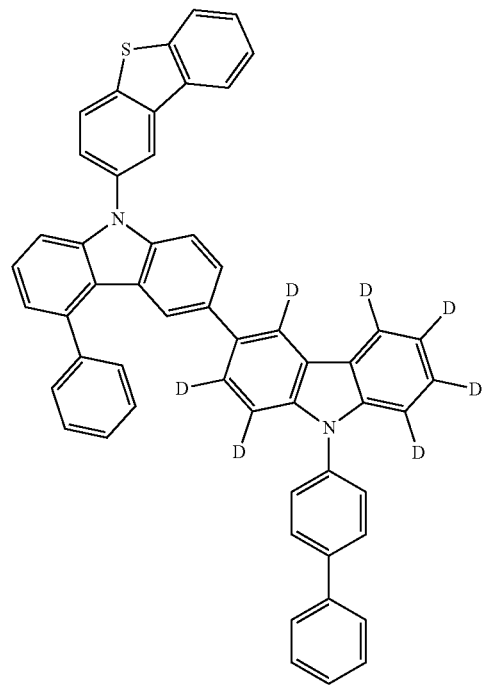
334
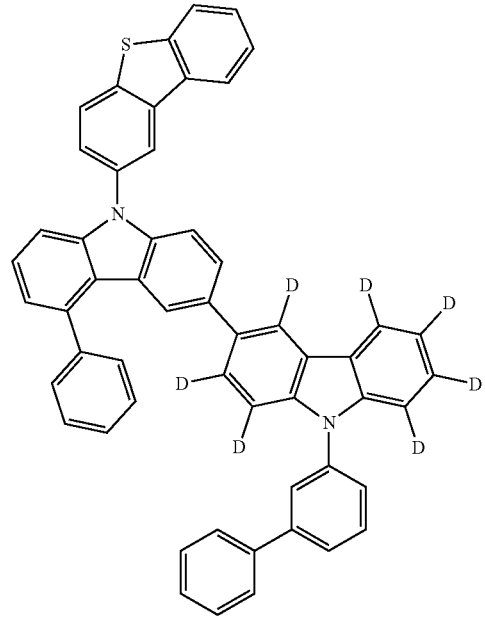

619
-continued
335
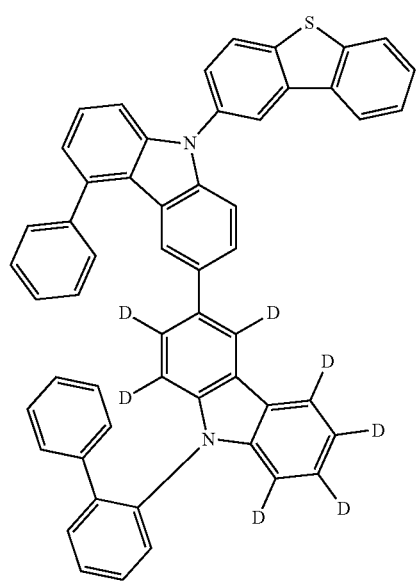
336
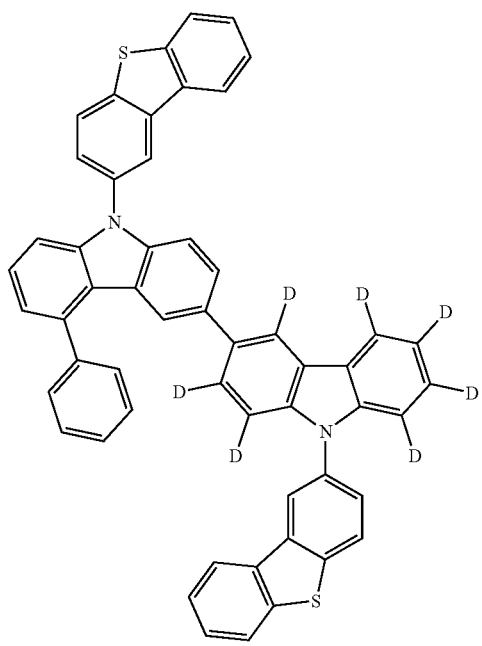
620
-continued
337
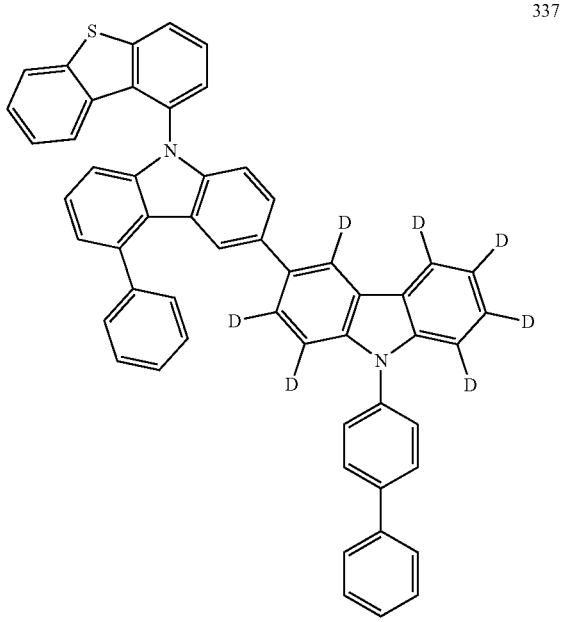
338

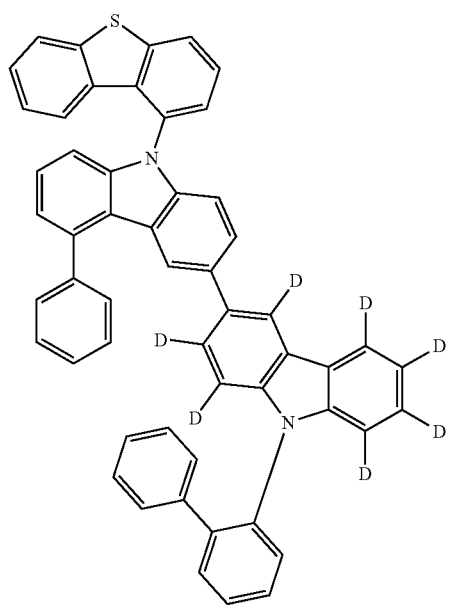
339
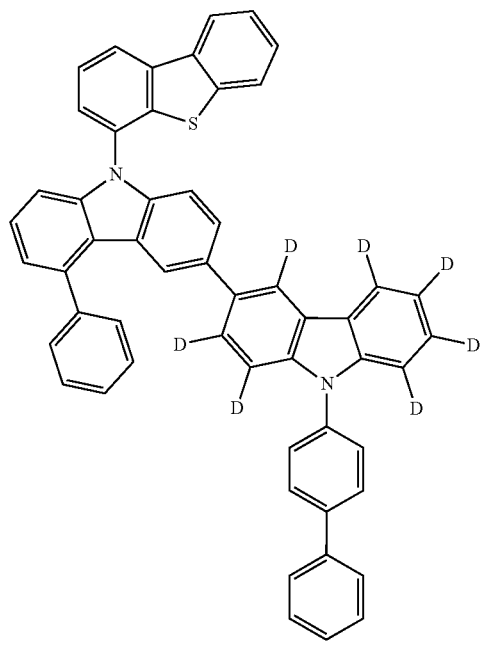
341
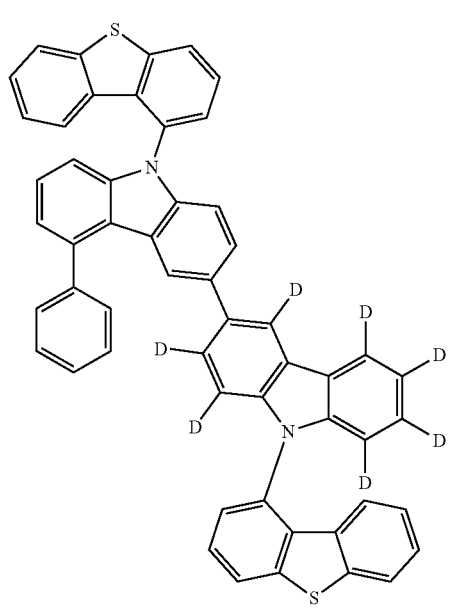
340
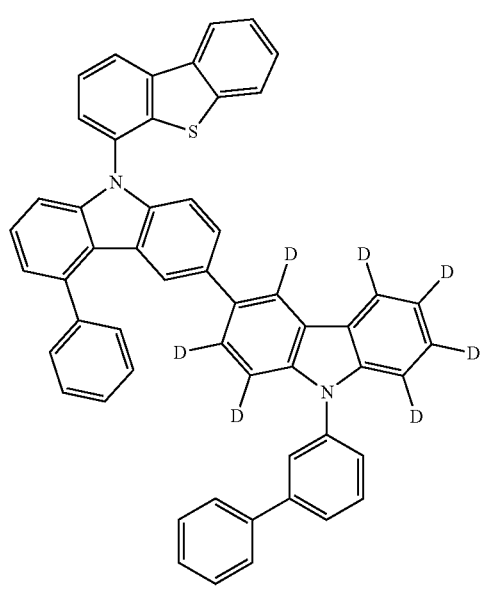
342

623
-continued
343
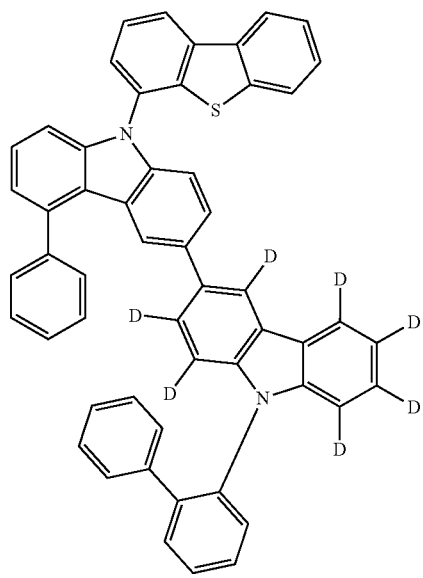
344
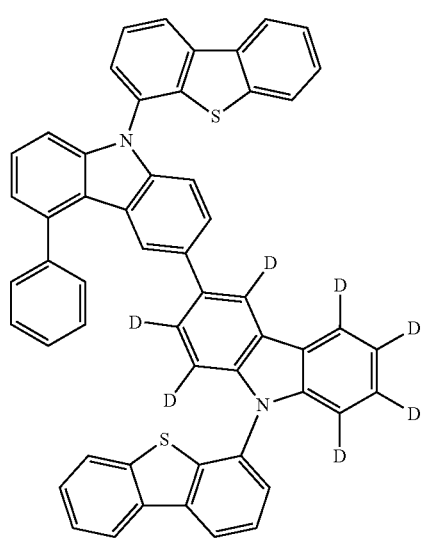
624
-continued
345
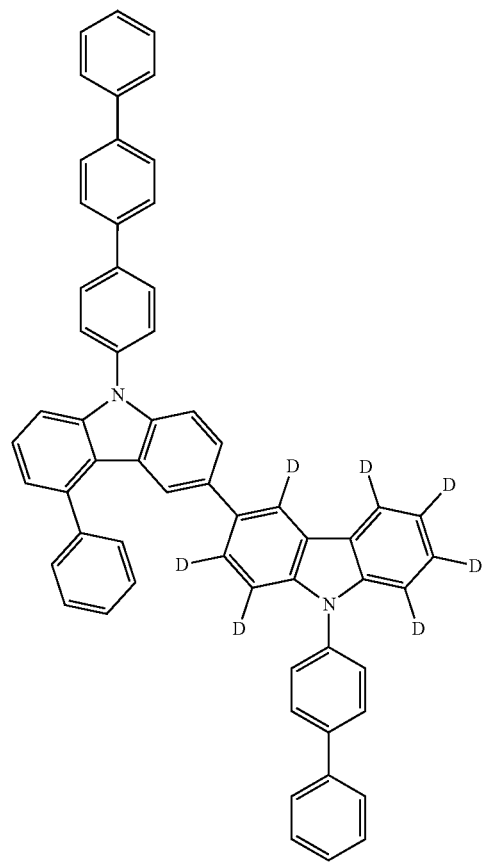
346
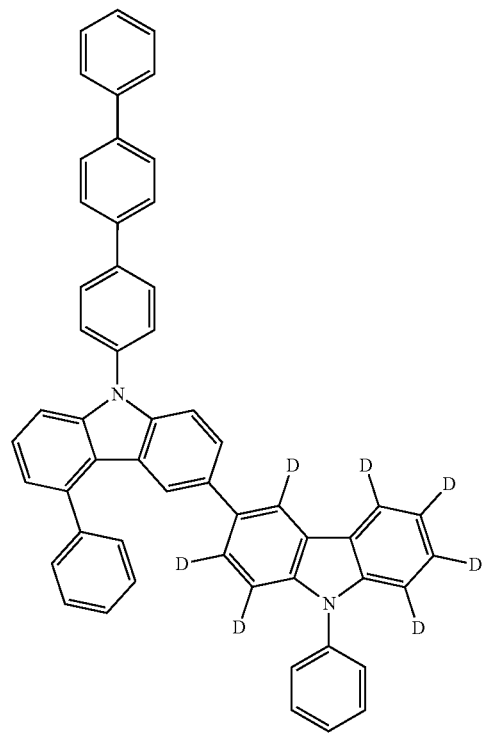

625
-continued
347
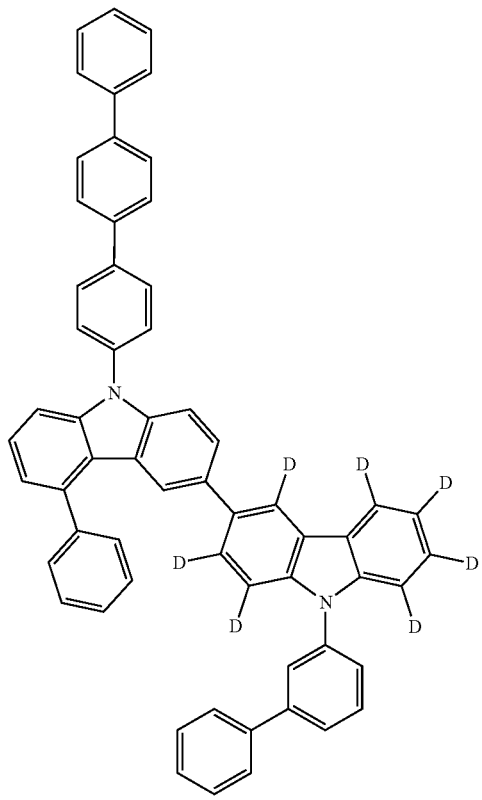
348
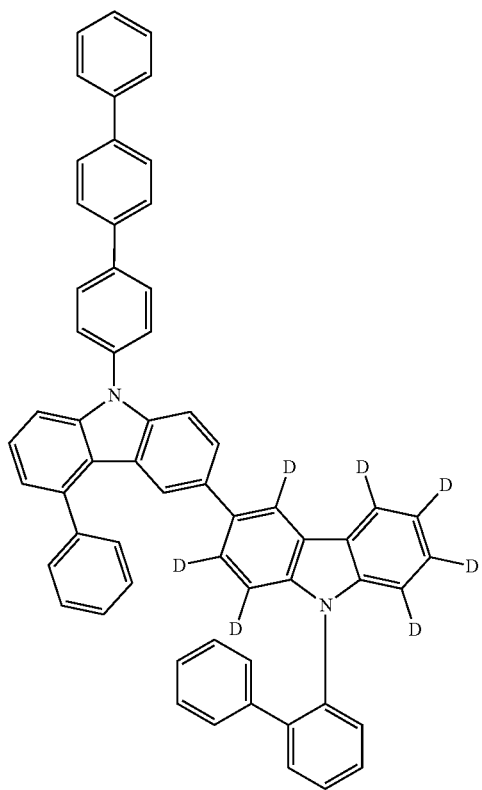
626
-continued
349
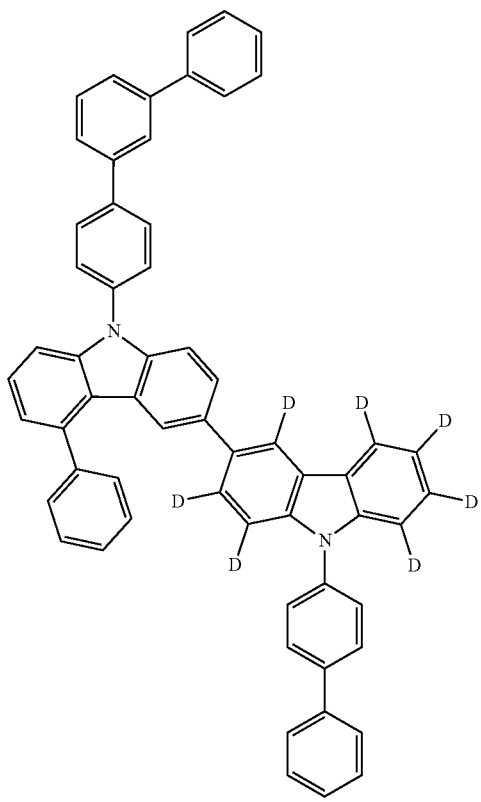
350
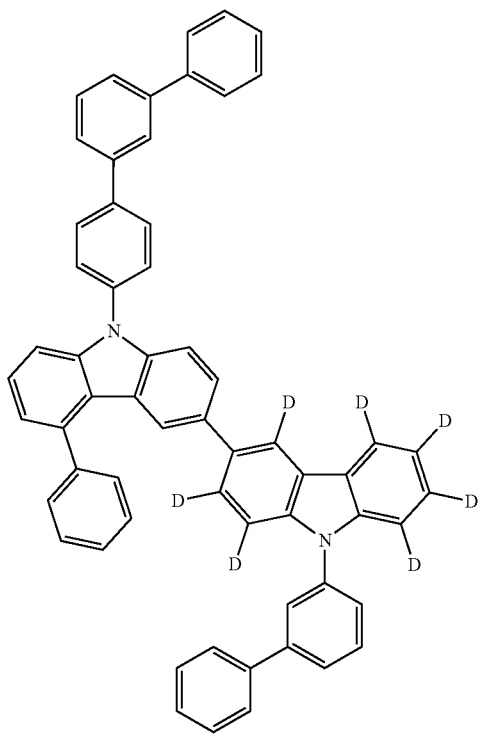

627
-continued
628
-continued
351
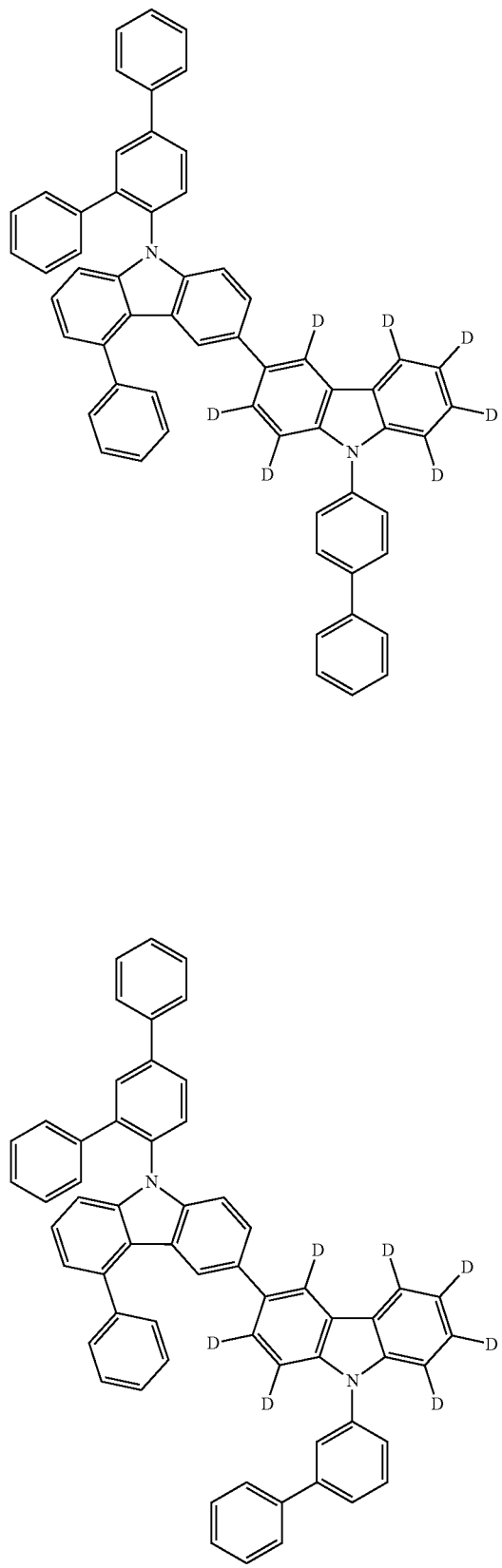
353
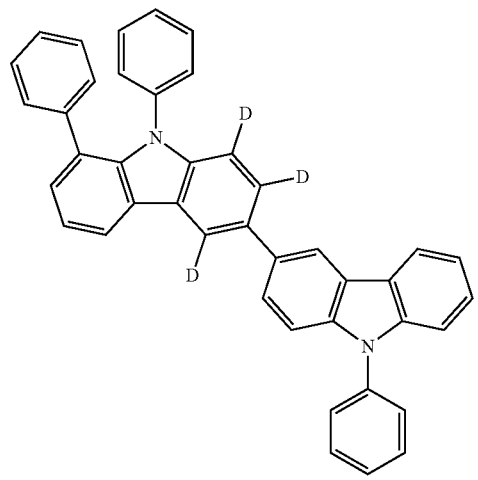
354
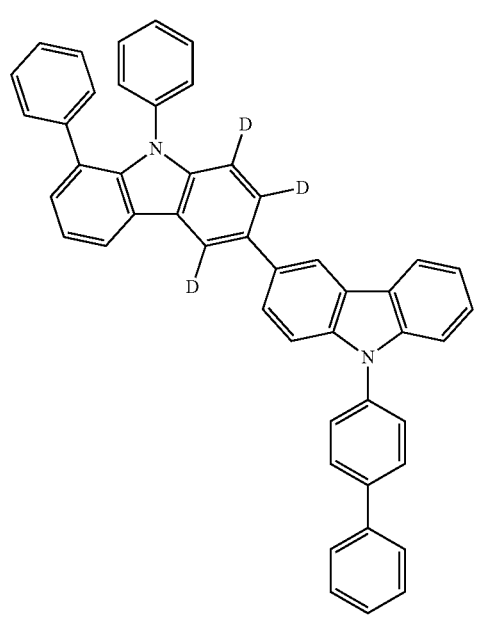
352
355
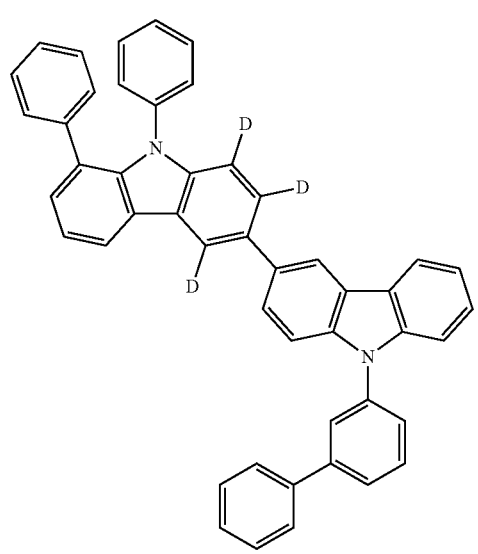

356
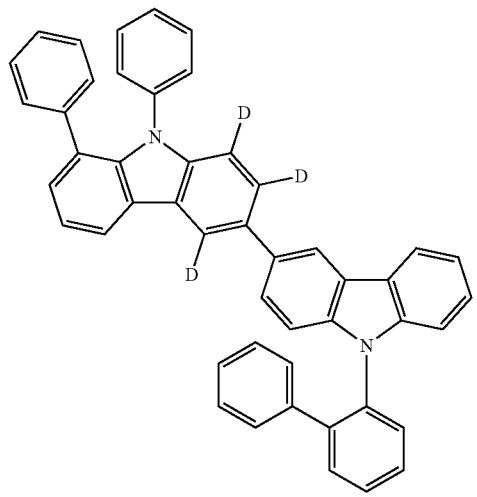
357
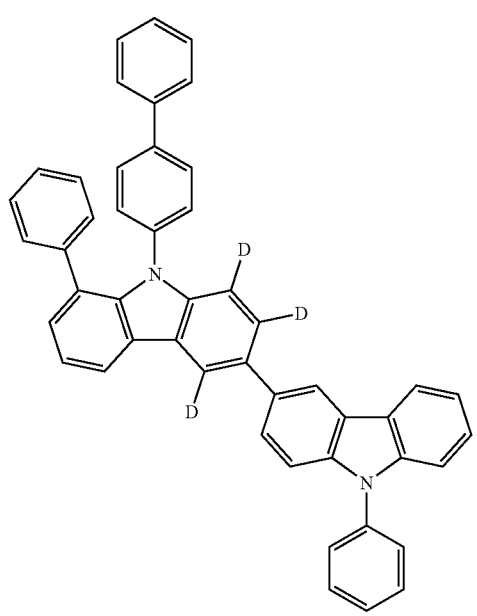
358
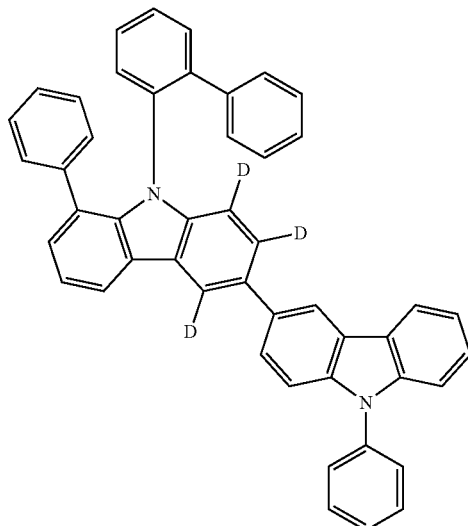
359
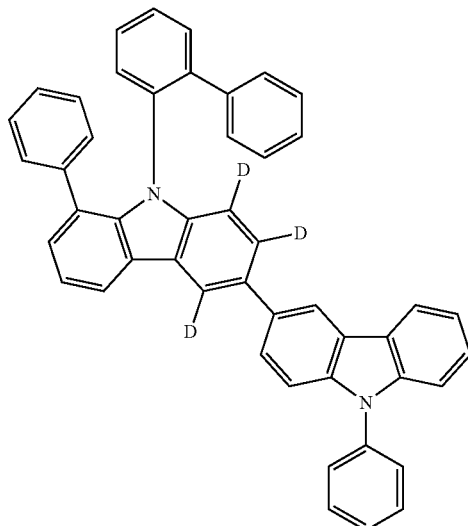
360
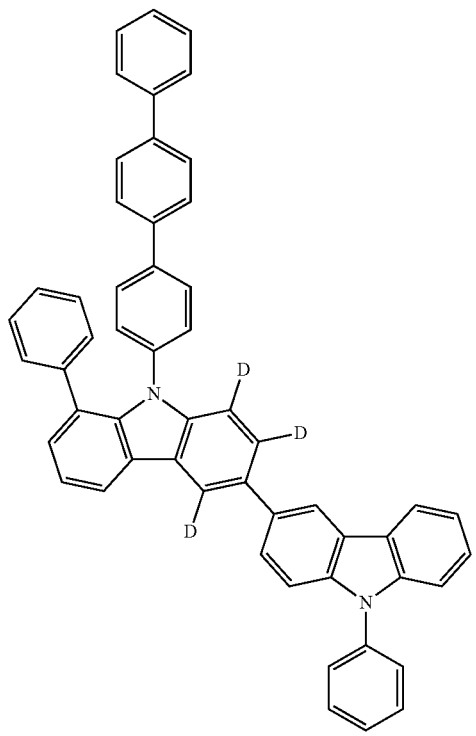

361
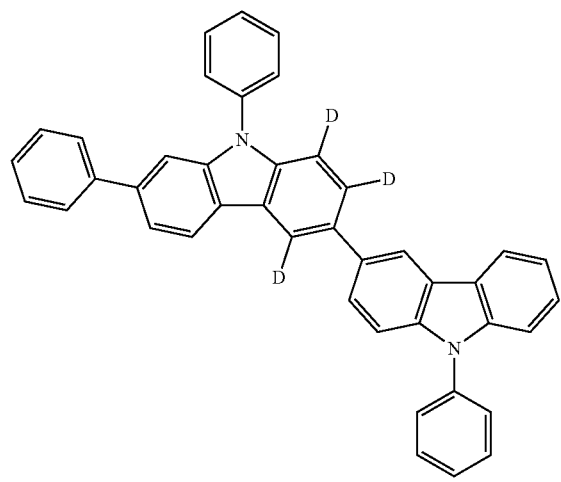
362
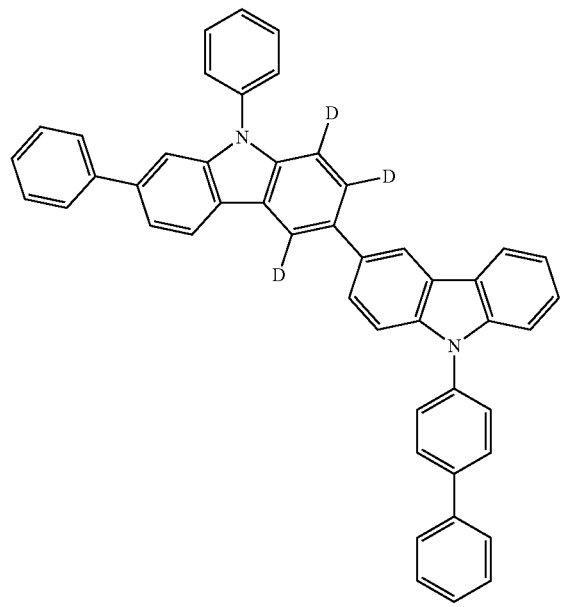
363
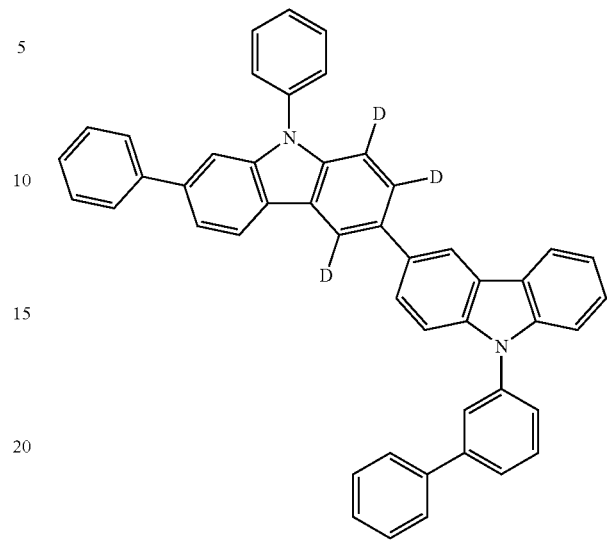
364

365
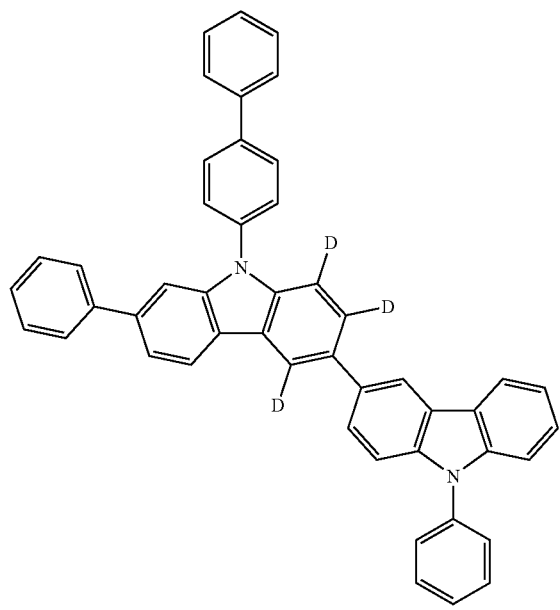
366
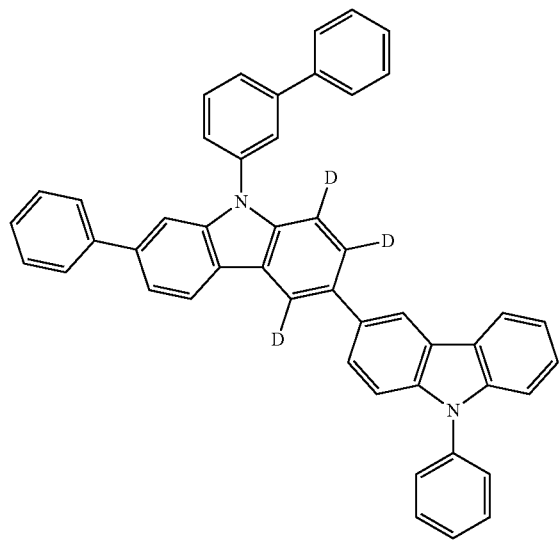
367
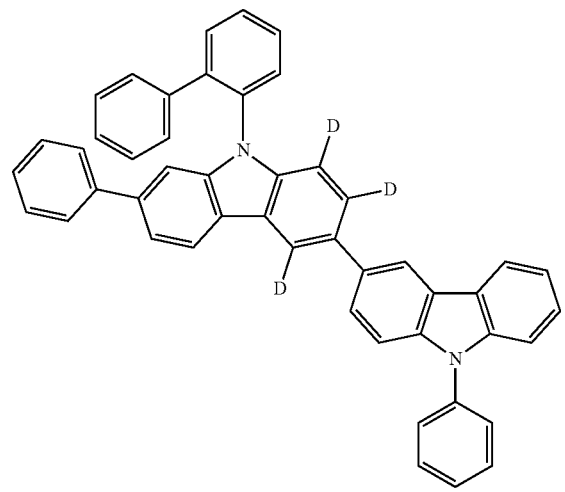
368
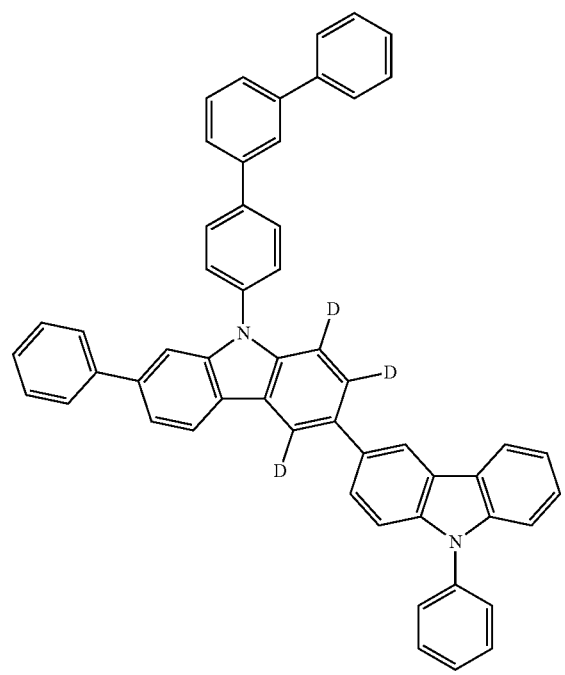

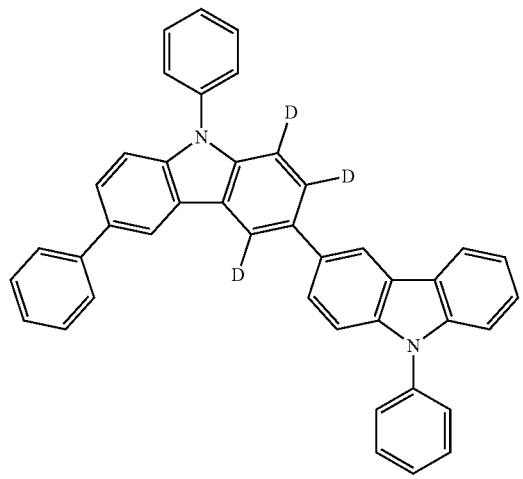
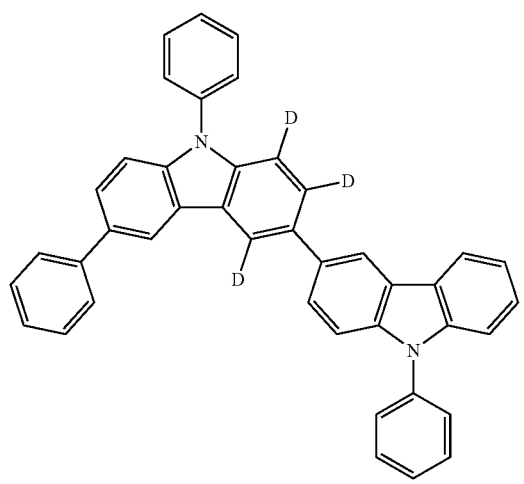
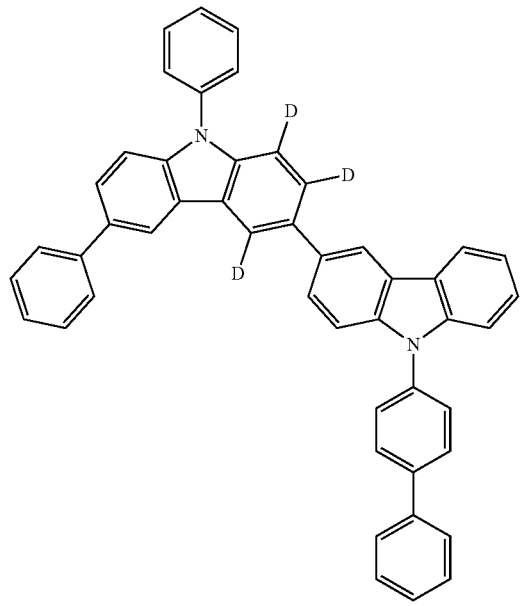
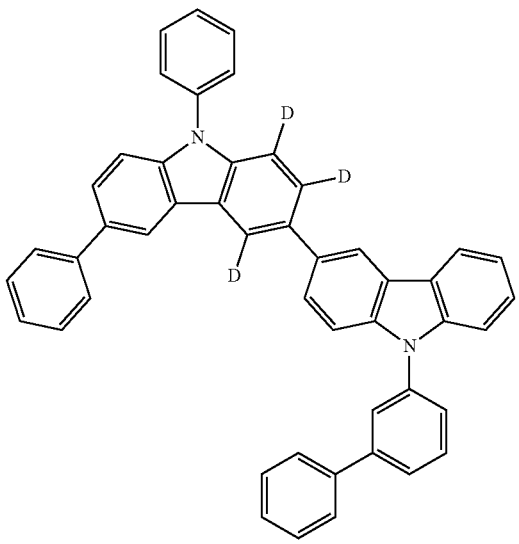
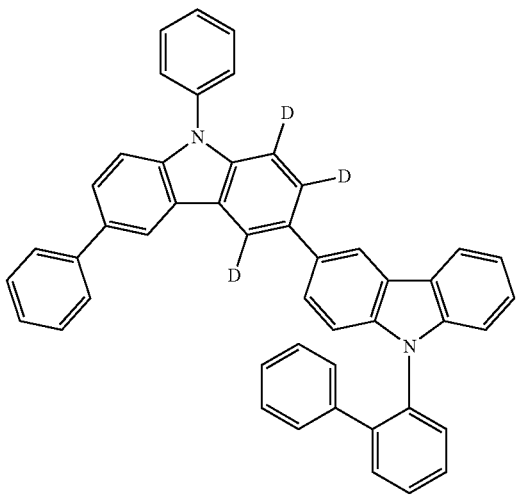

373
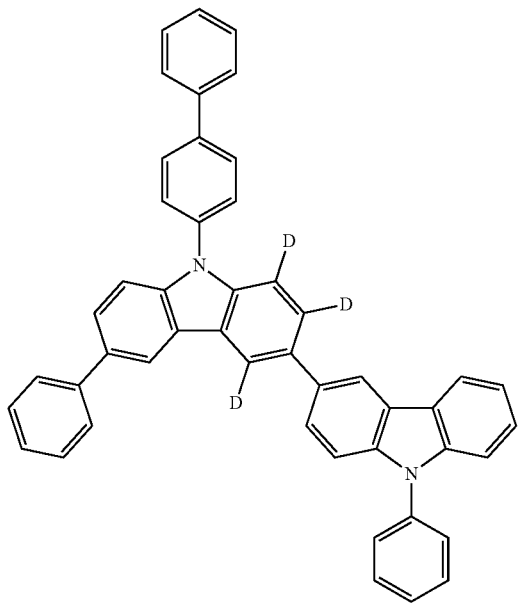
374
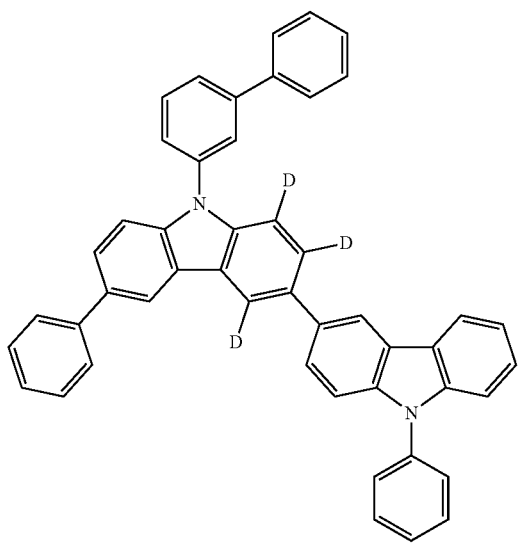
375
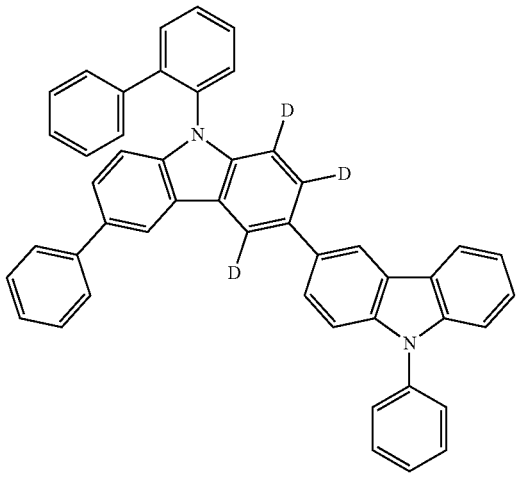
376
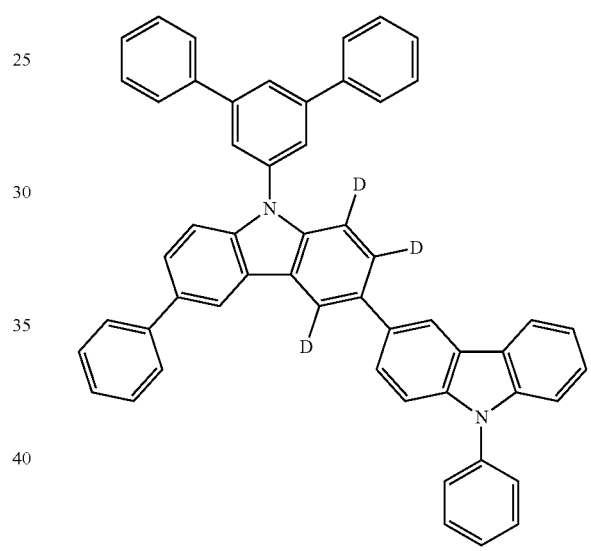
377
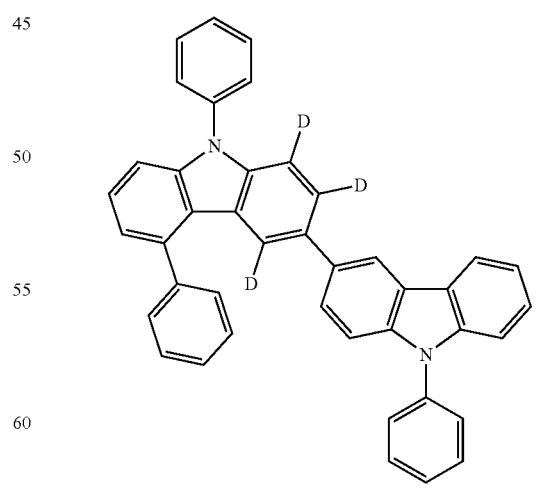

378
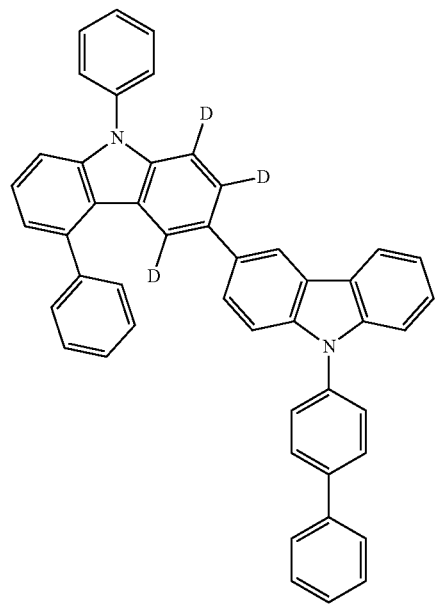
379
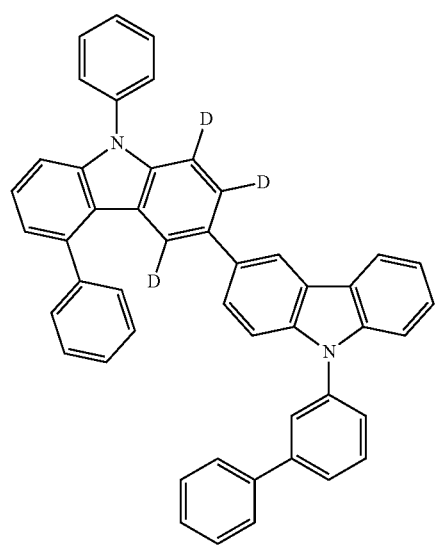
380
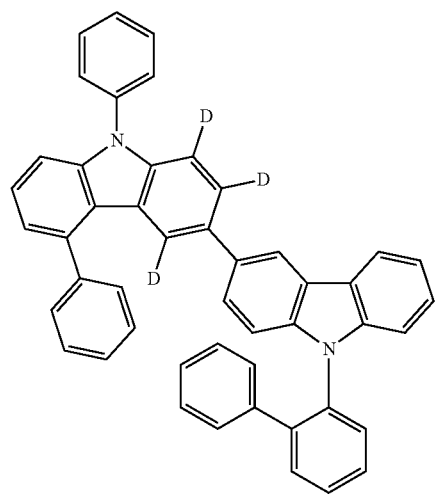
381
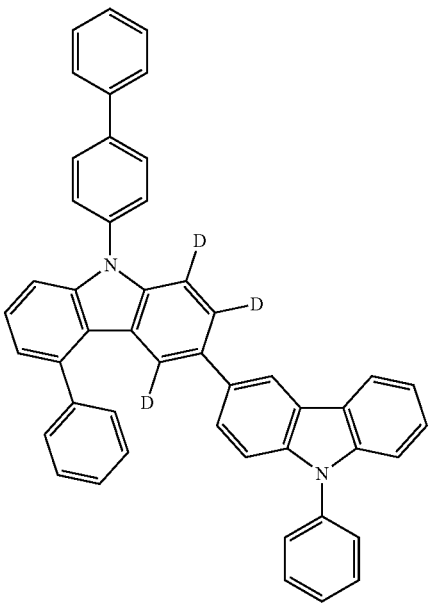
382
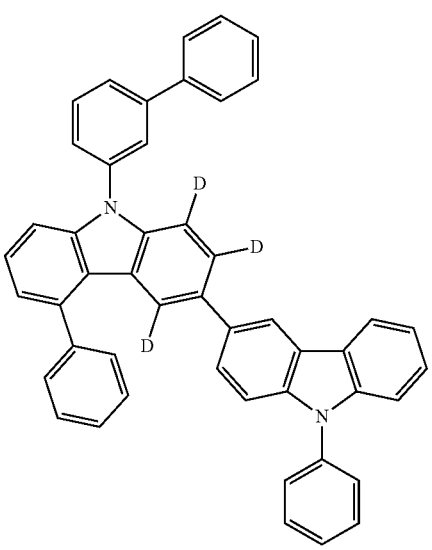
383
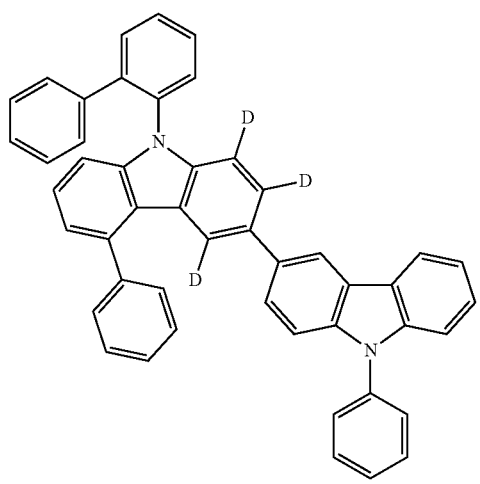

641
-continued
384
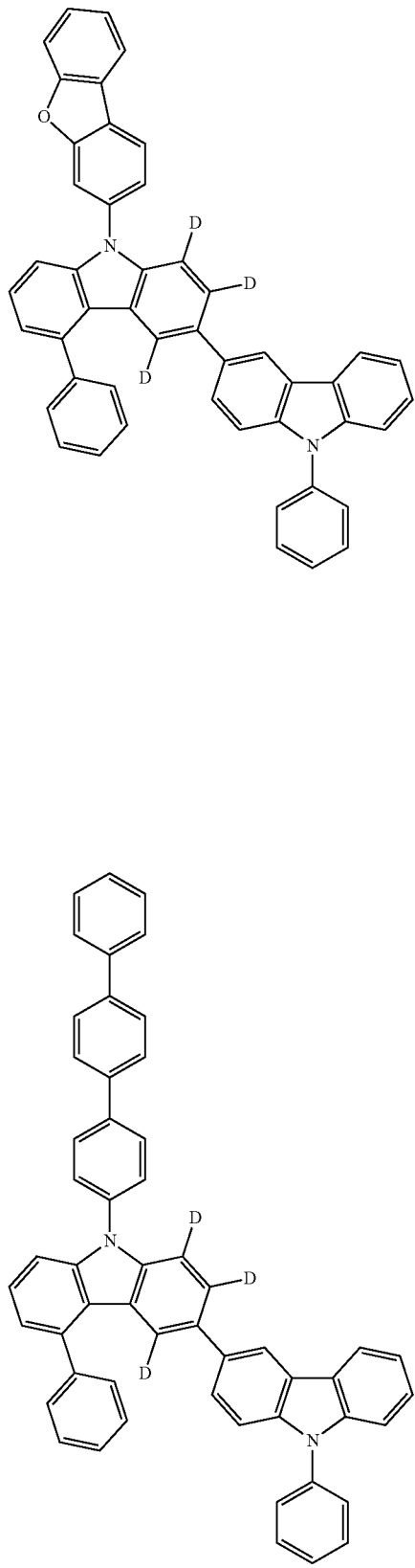
385
642
-continued
386
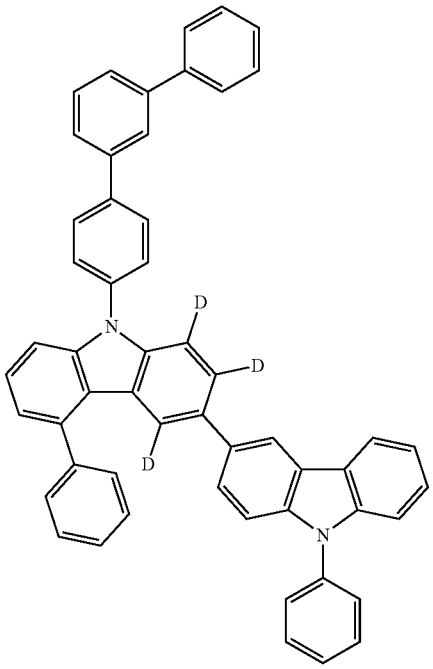
387
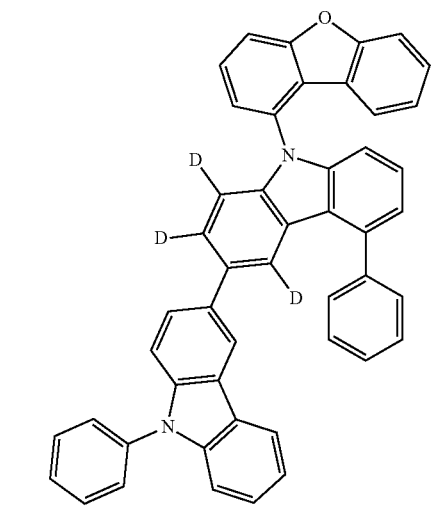
388
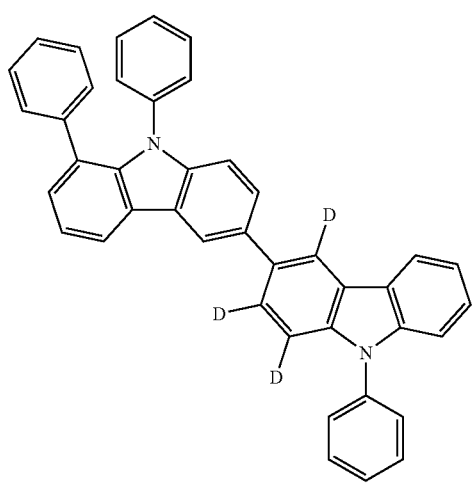

389
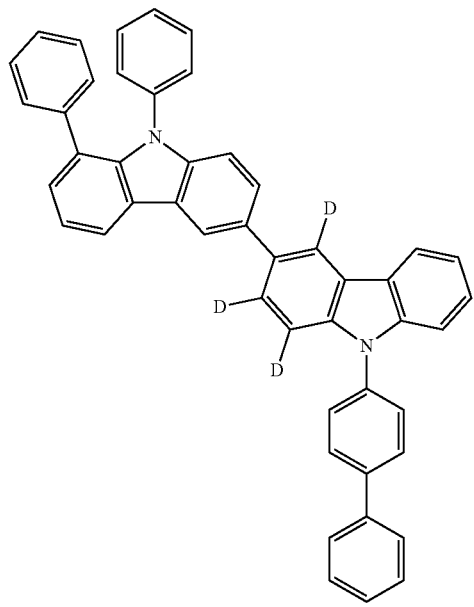
390
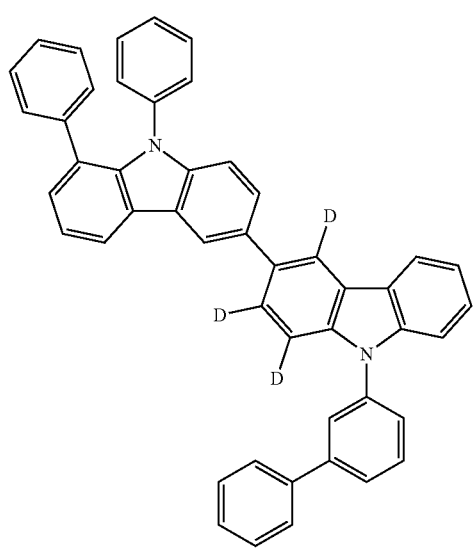
391
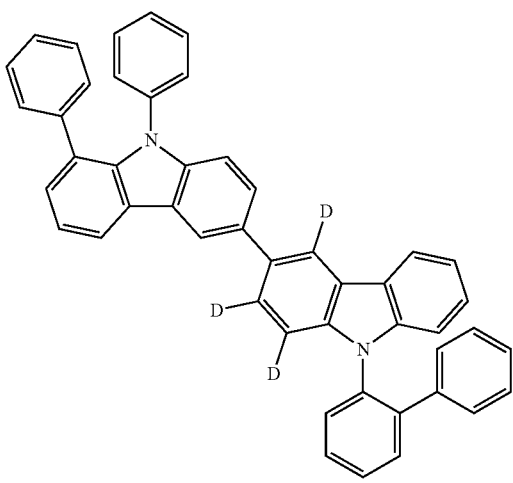
392
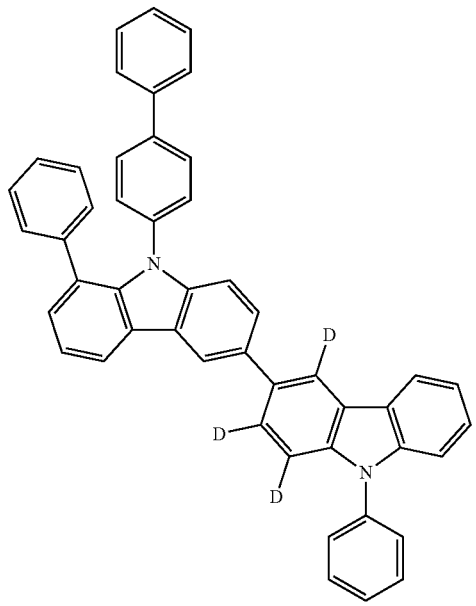
393
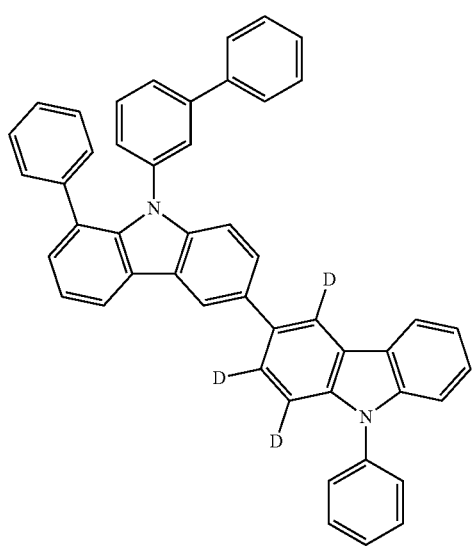
394
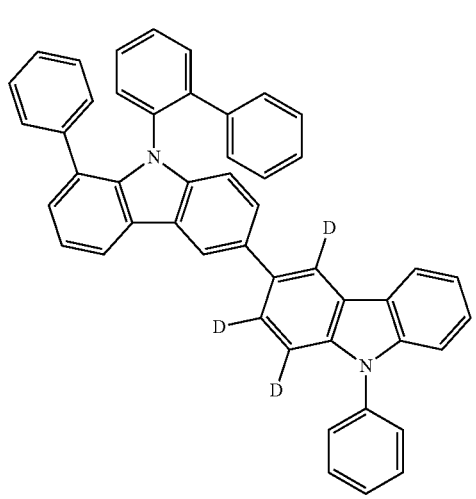

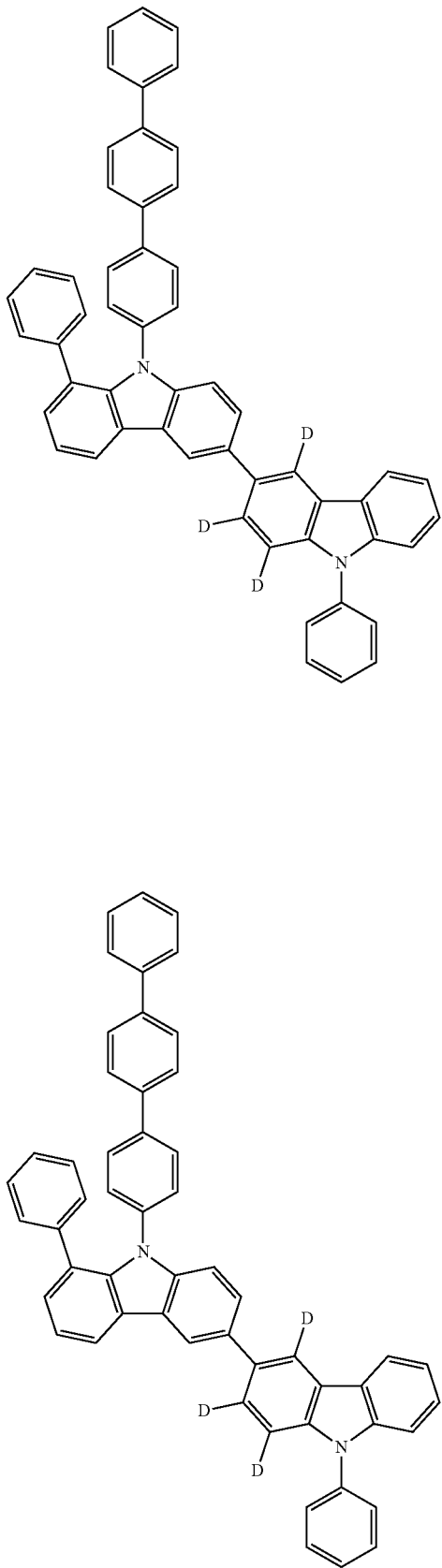
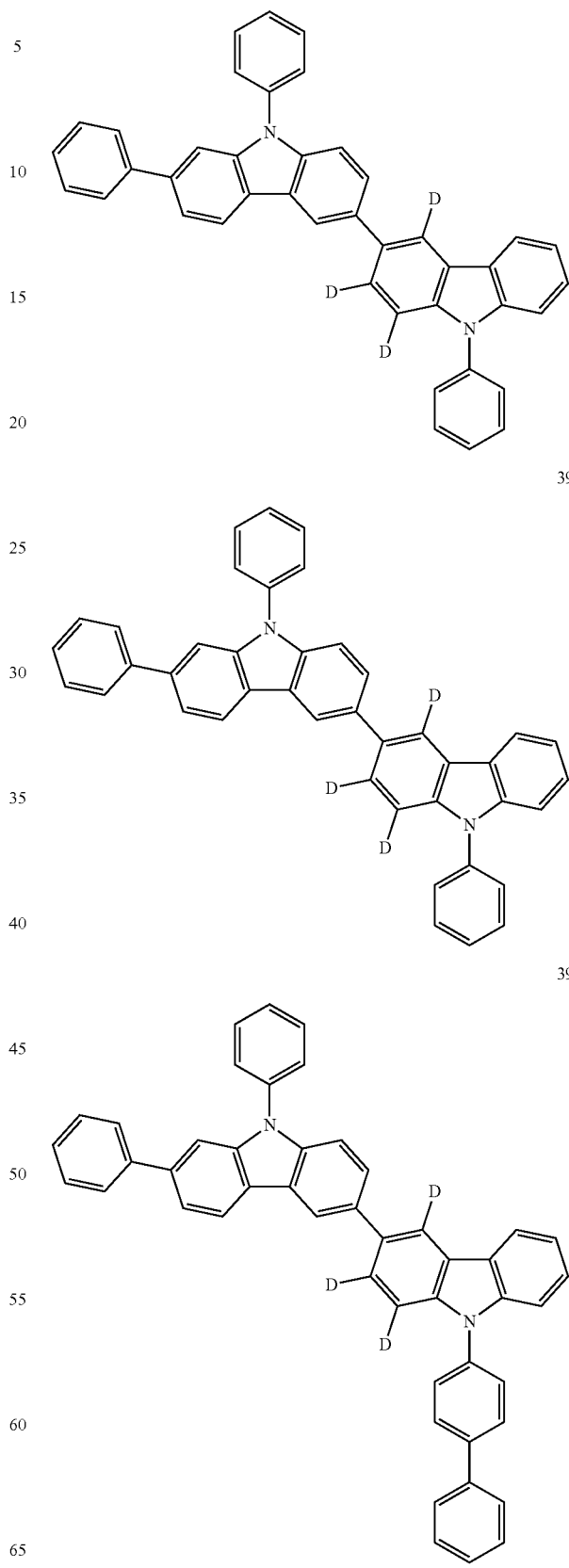

398
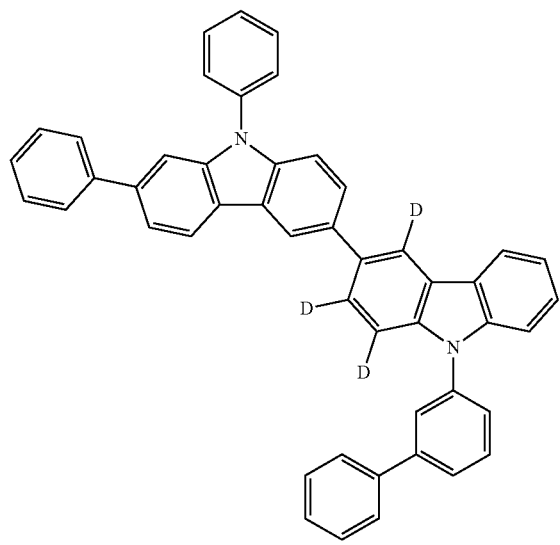
399
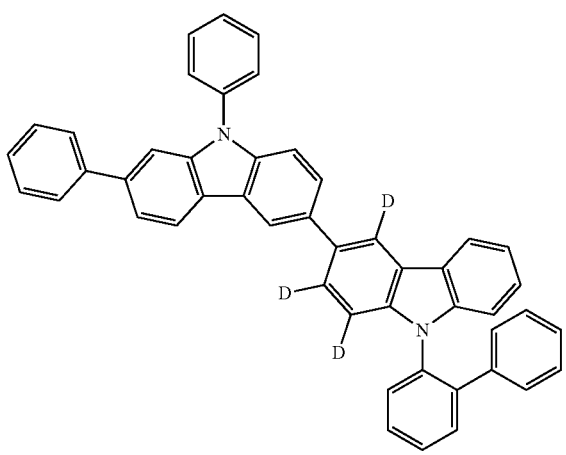
400
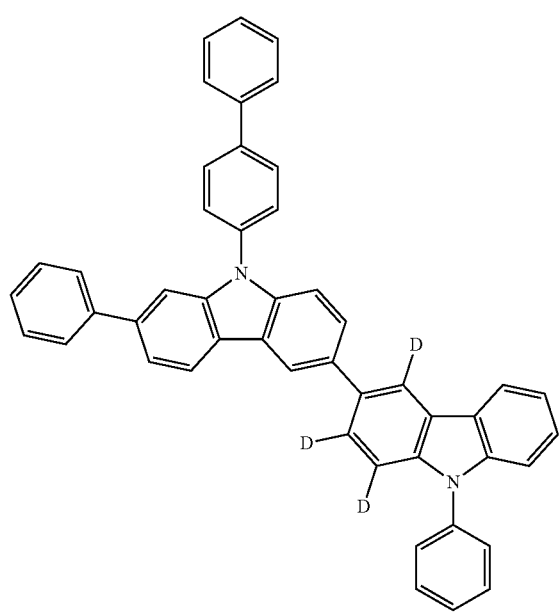
401
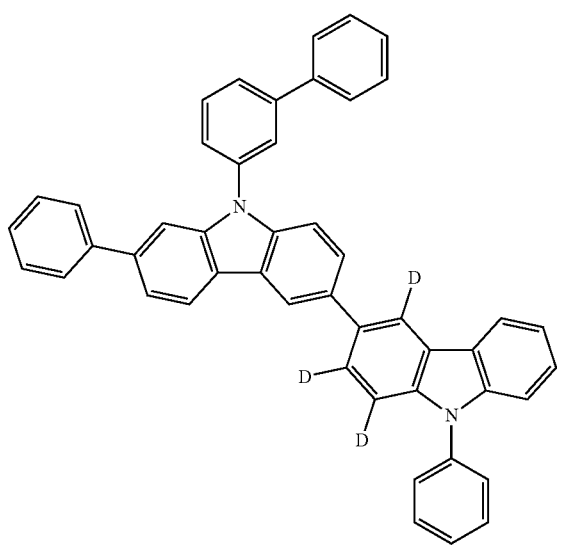
402
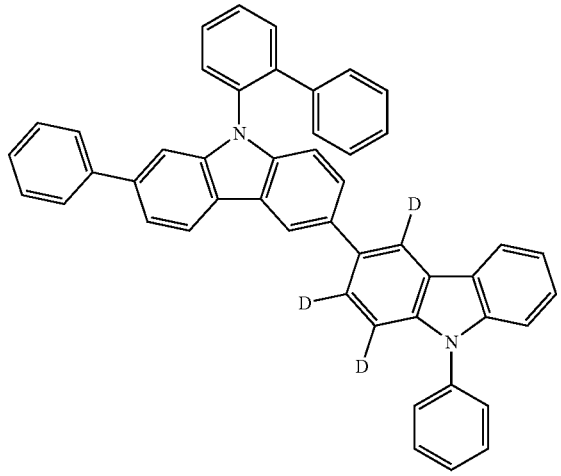

403
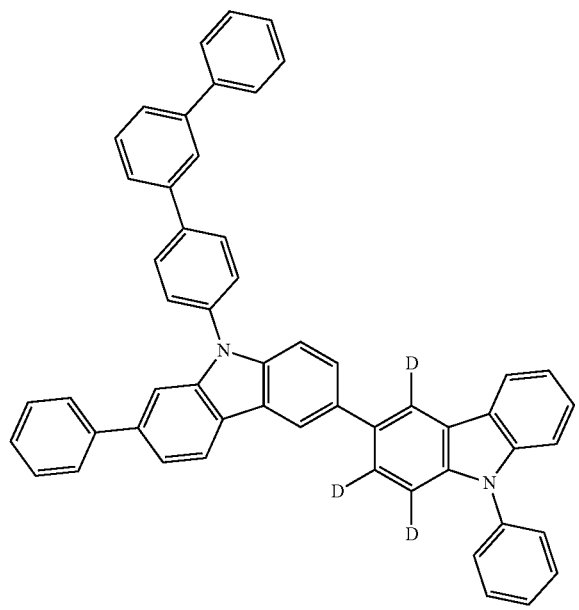
404
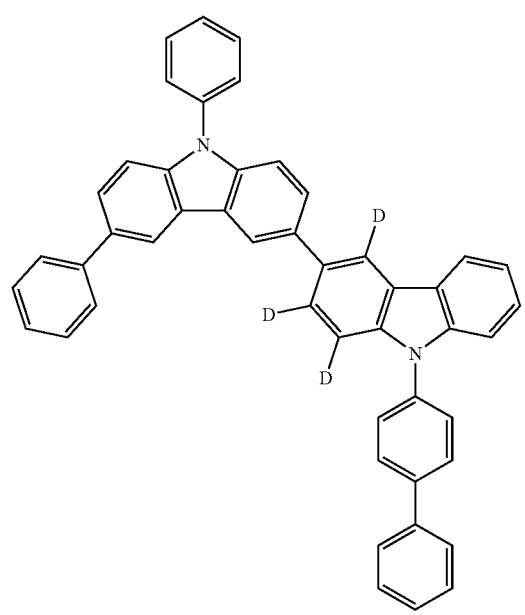
405
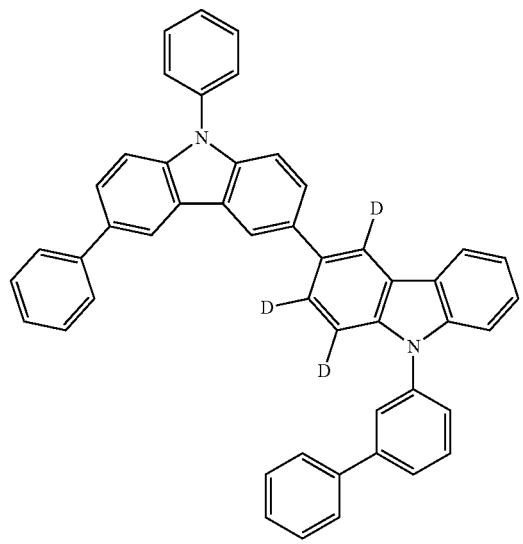
406
407
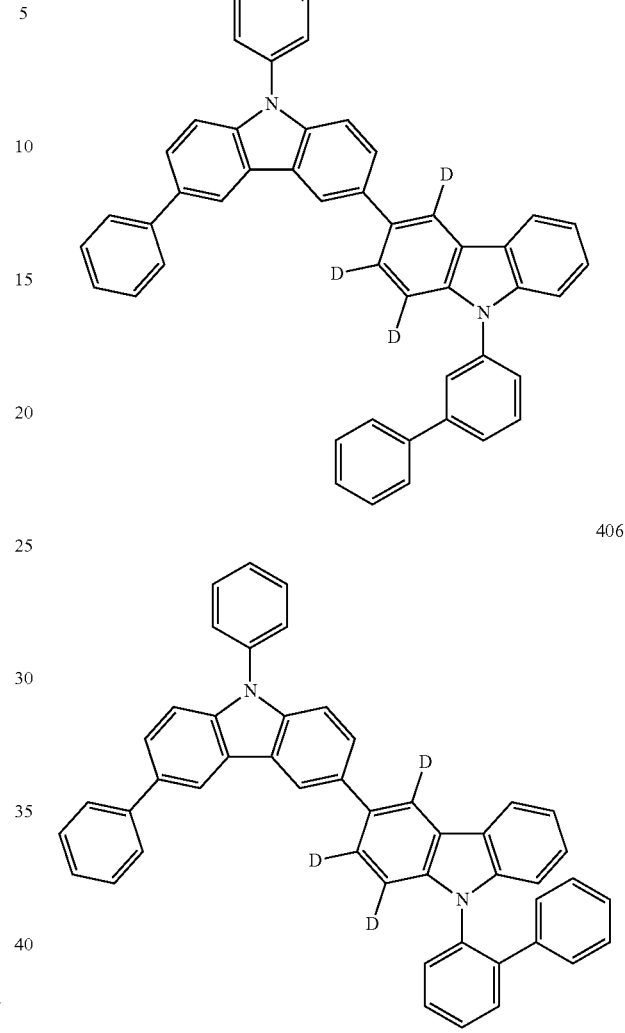

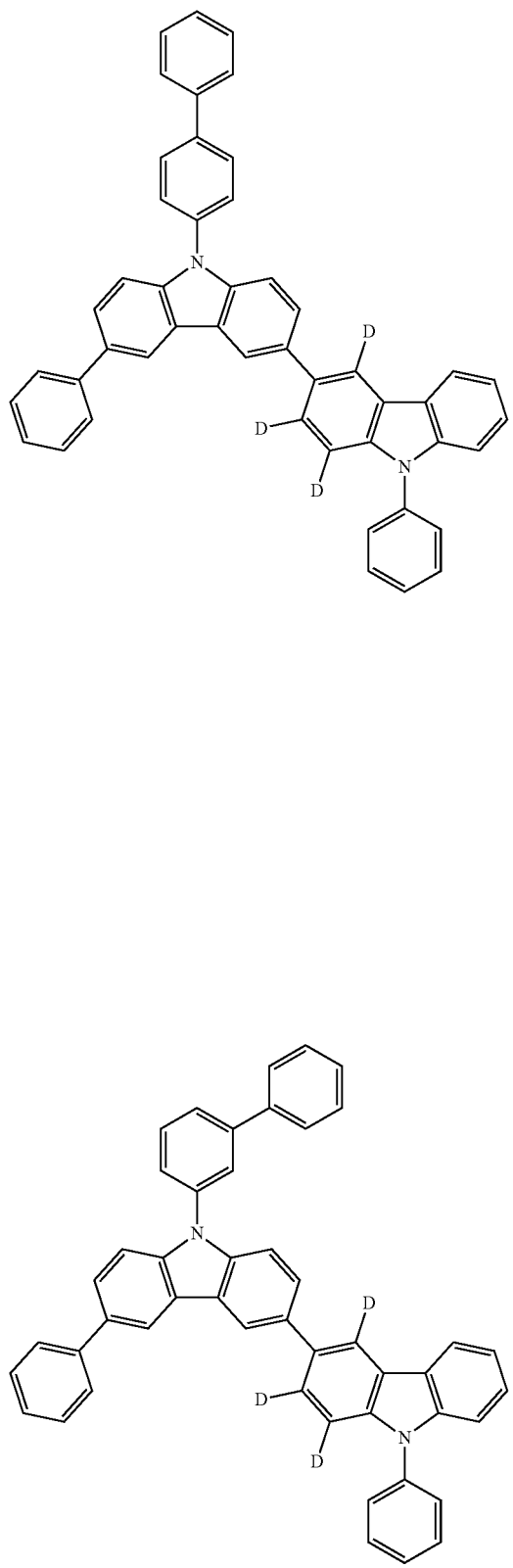
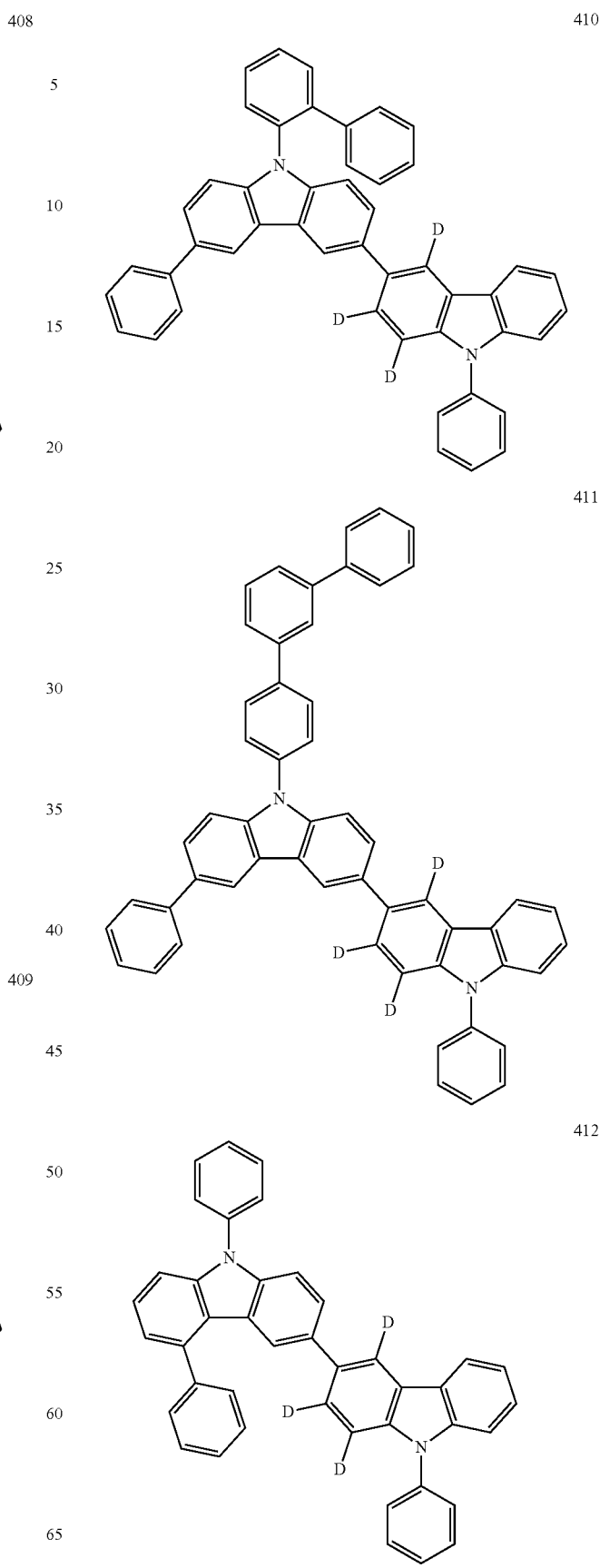

412
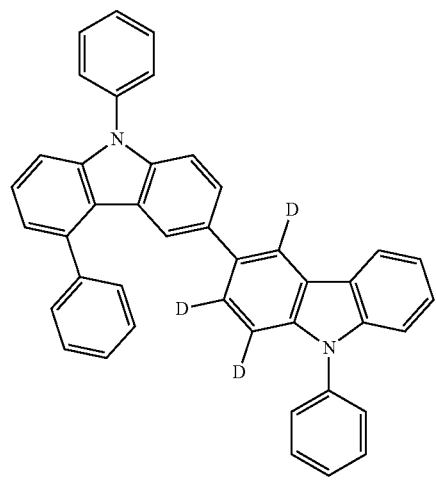
413
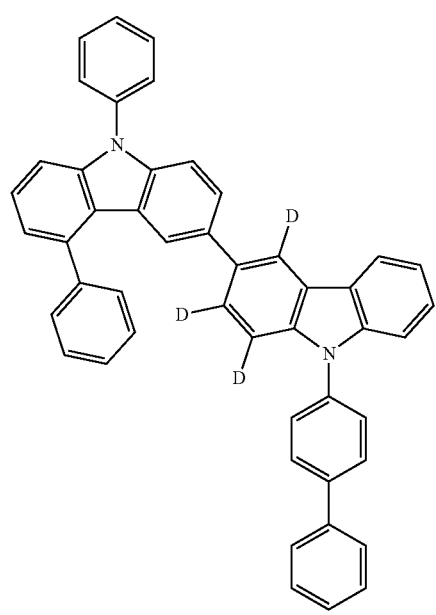
414
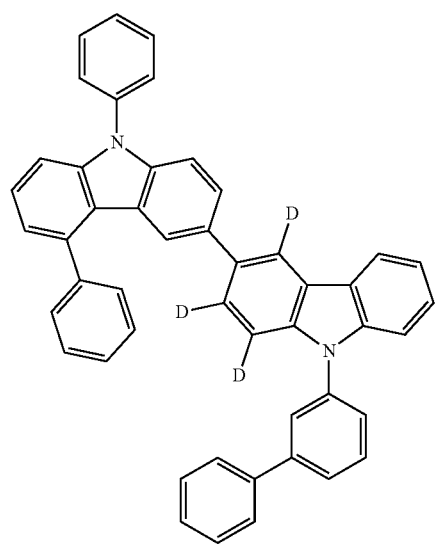
415
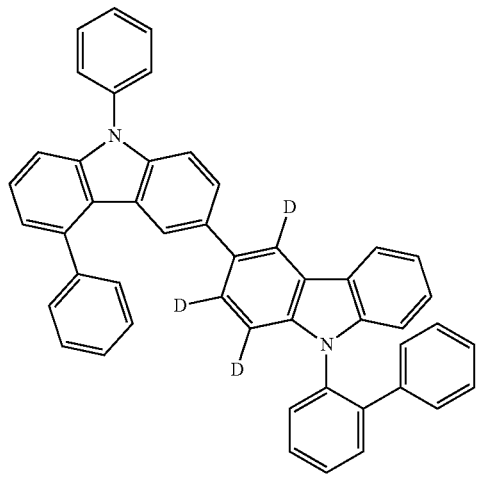
416
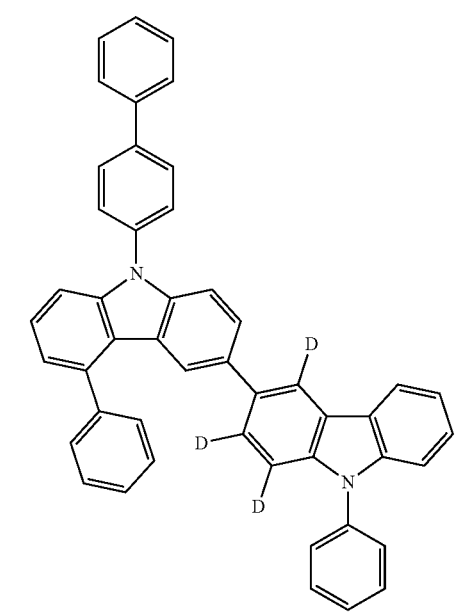
417
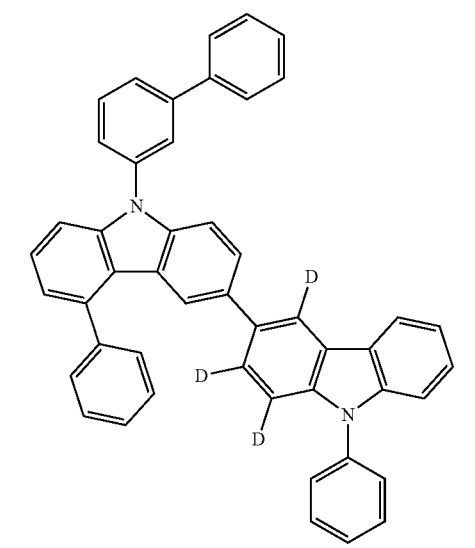

655
-continued
418
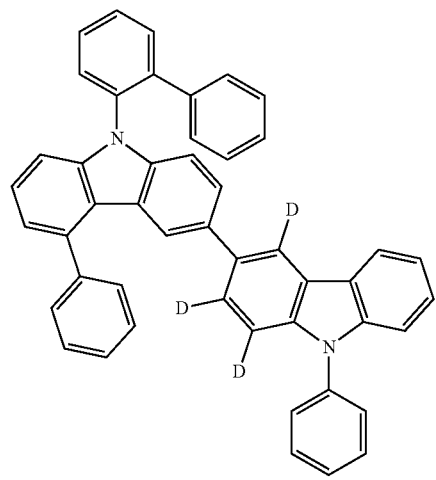
419
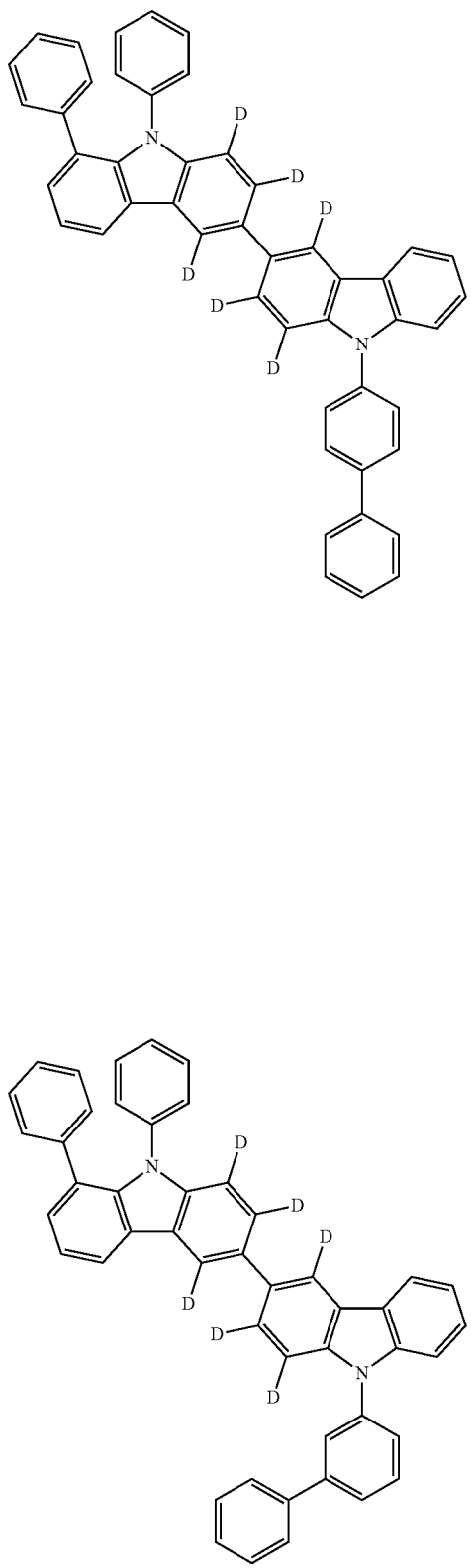
656
-continued
420
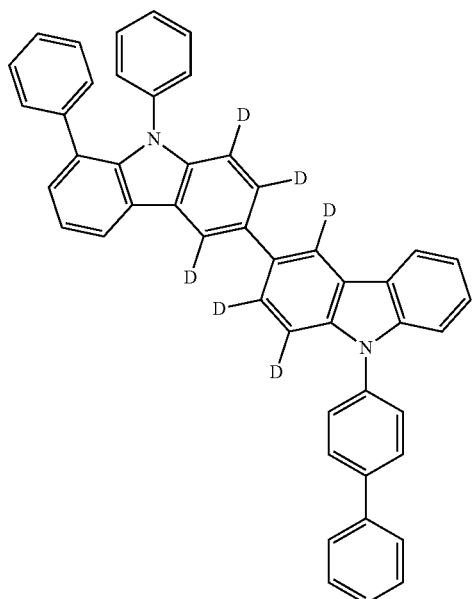
421

422
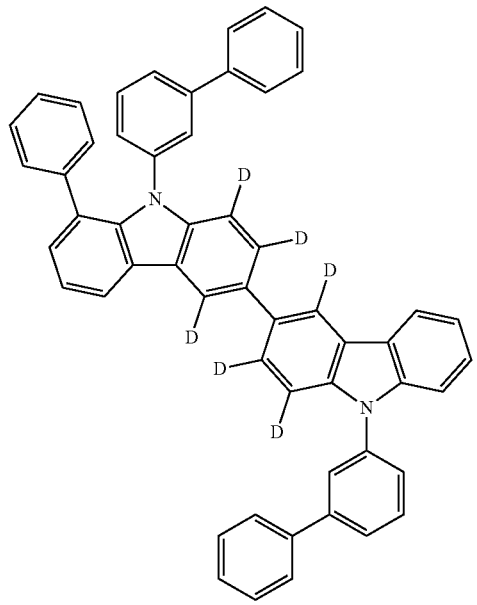
423
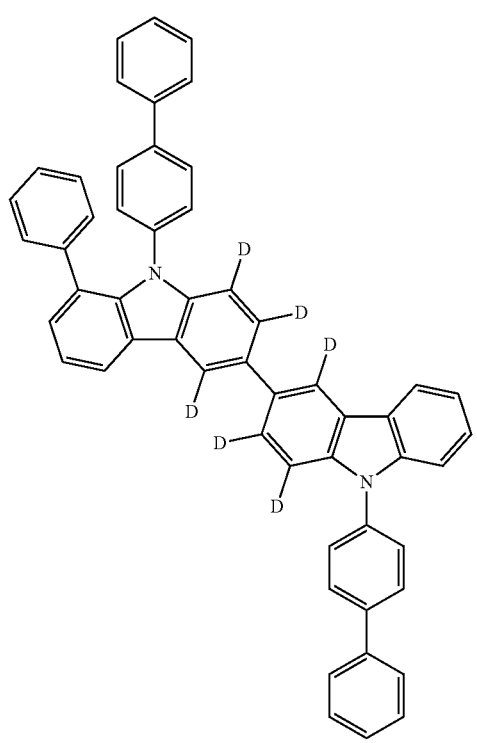
424
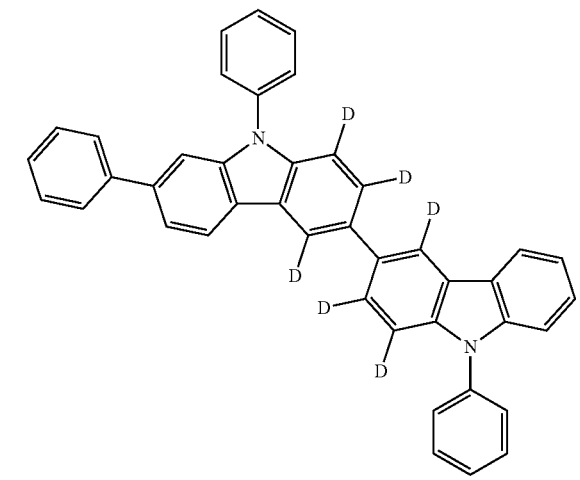
425
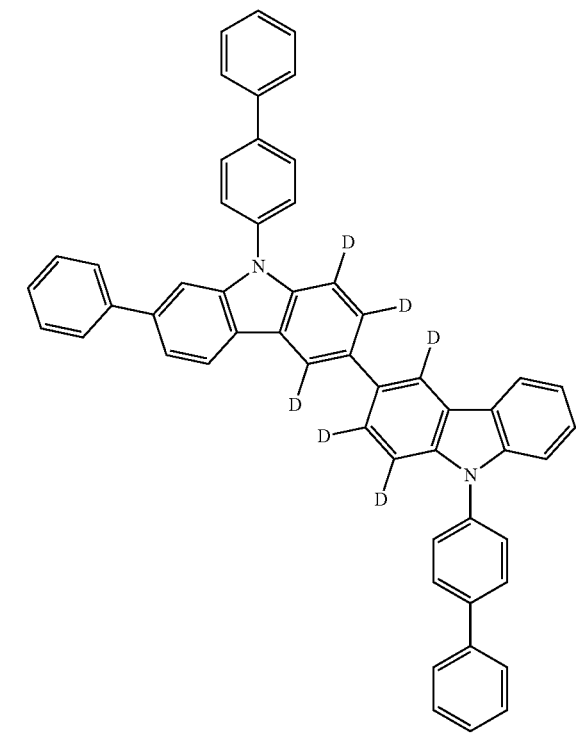

426
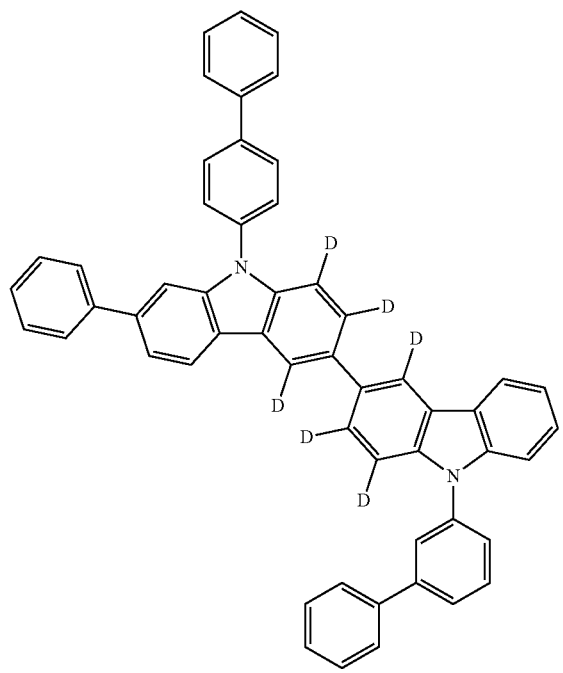
428
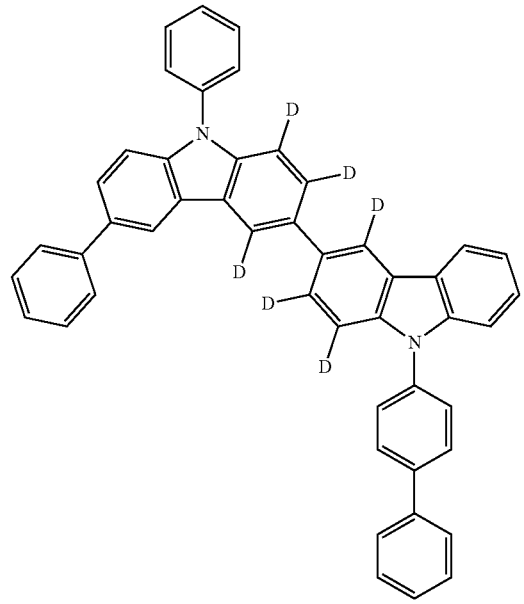
427
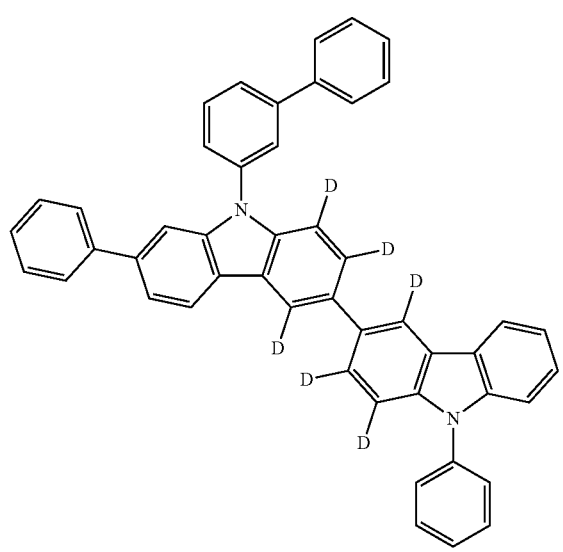
429
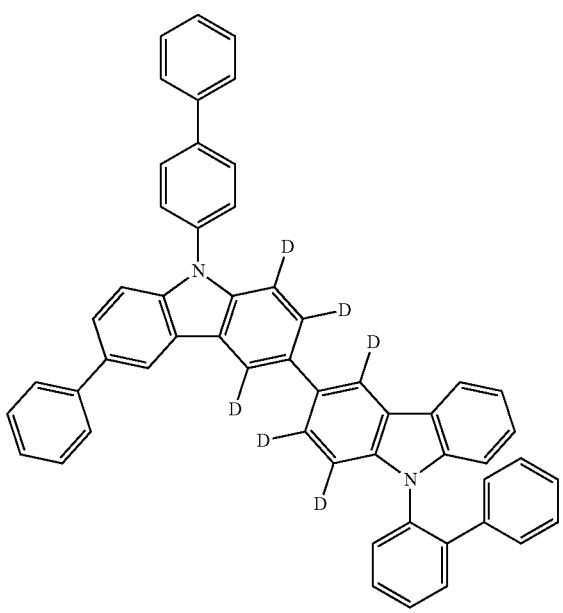

430
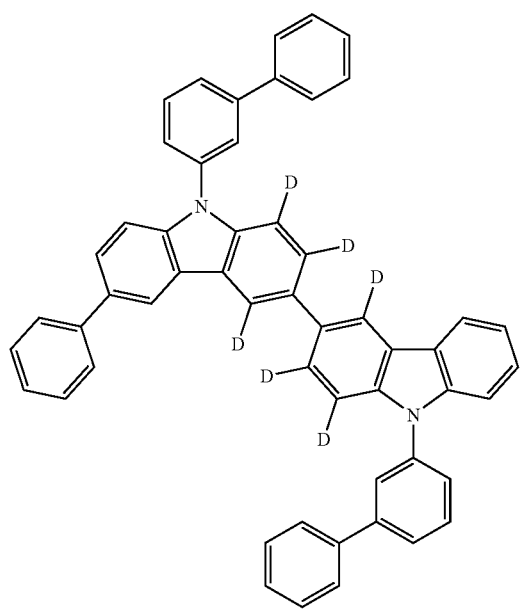
432
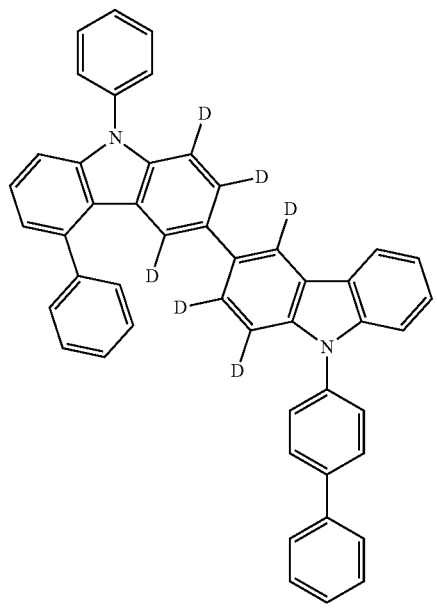
431
432

433
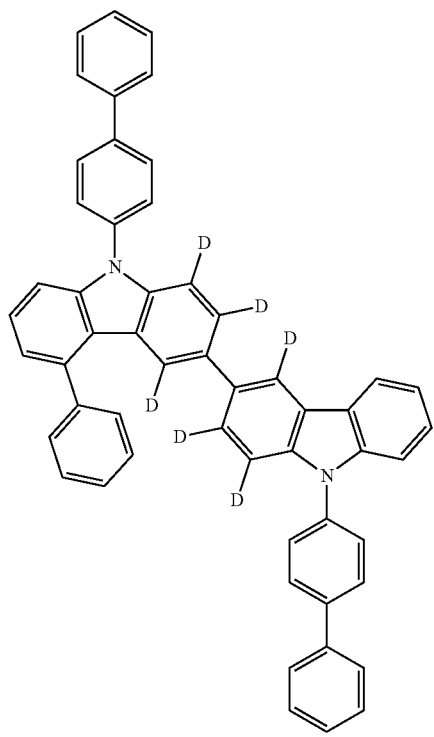
435
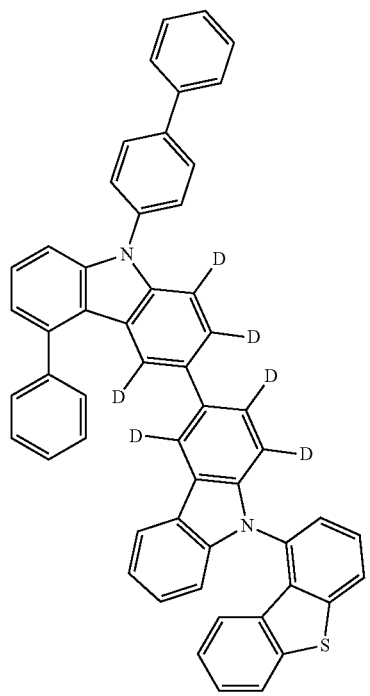
434
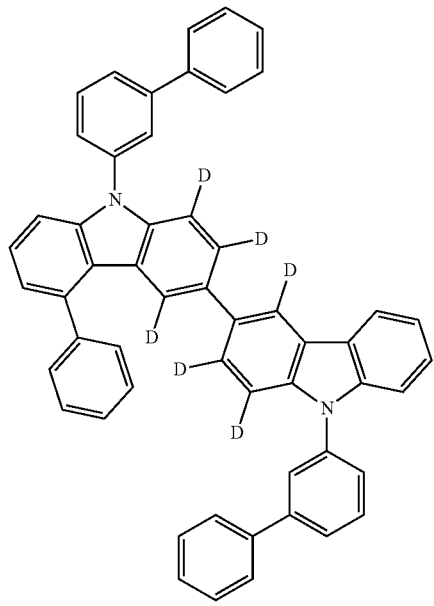
436
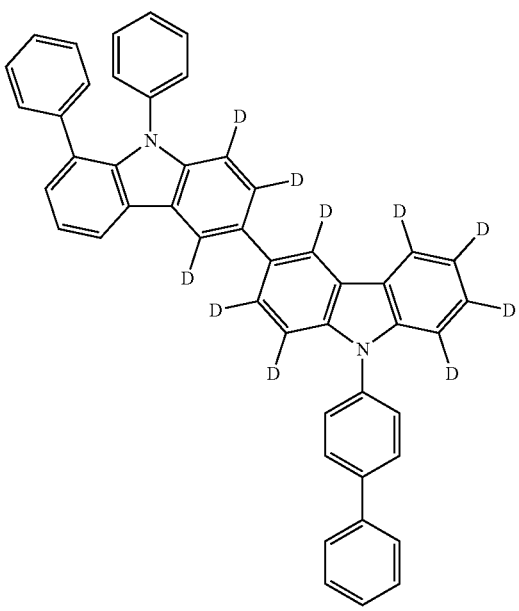

437
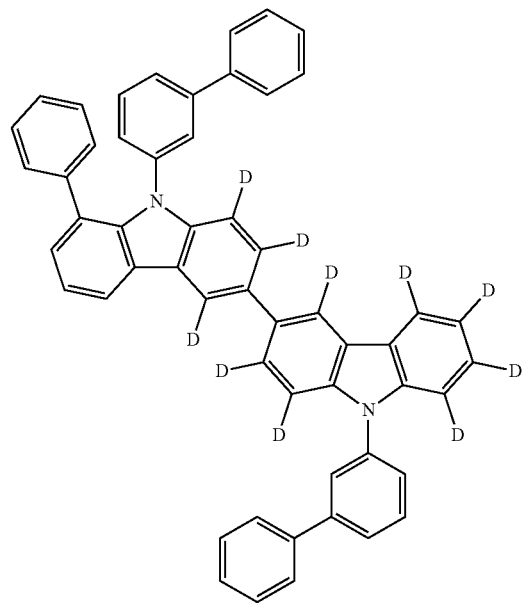
438
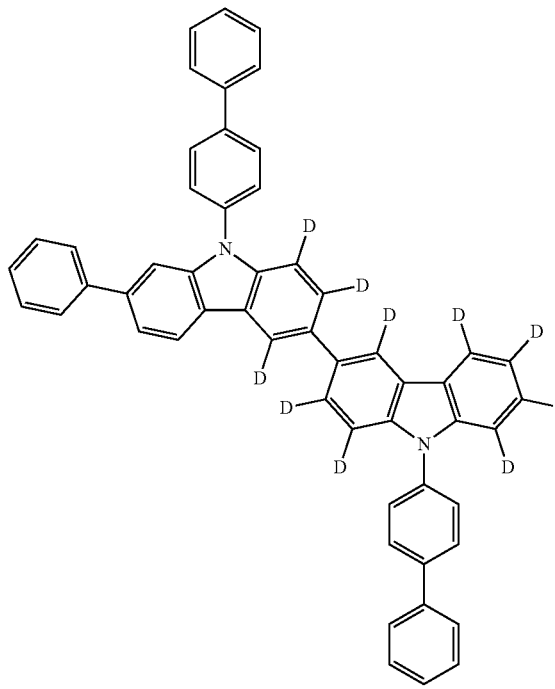
439
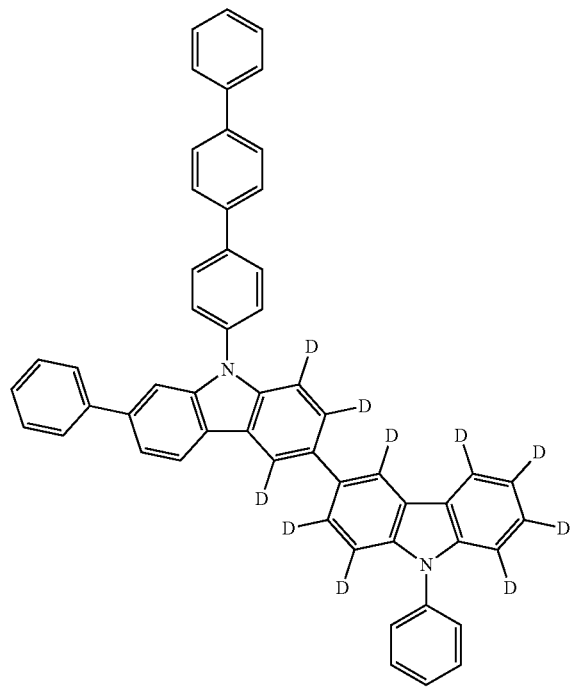
440
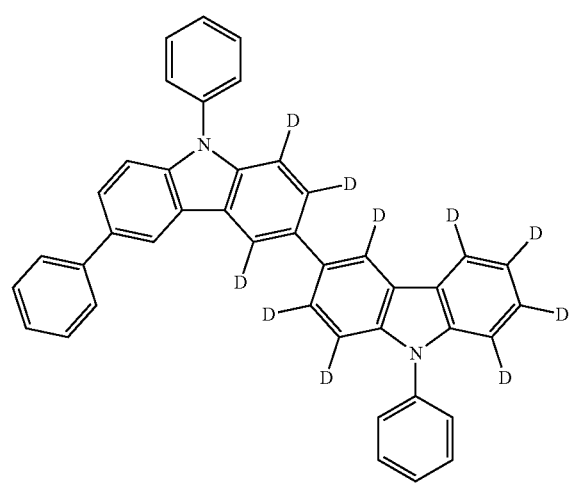

440
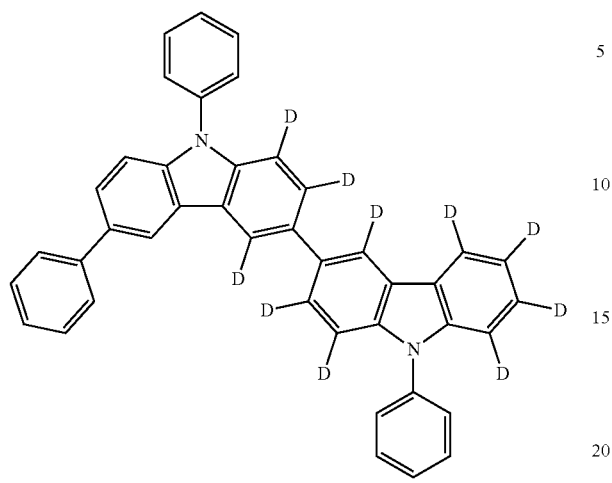
441
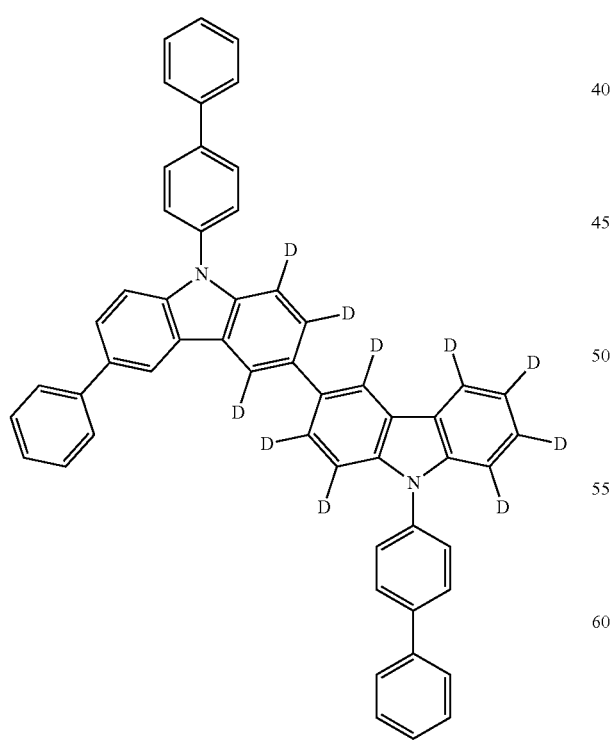
442
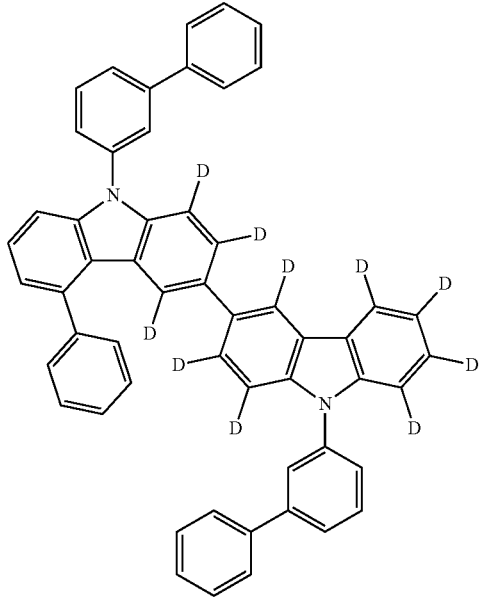
442
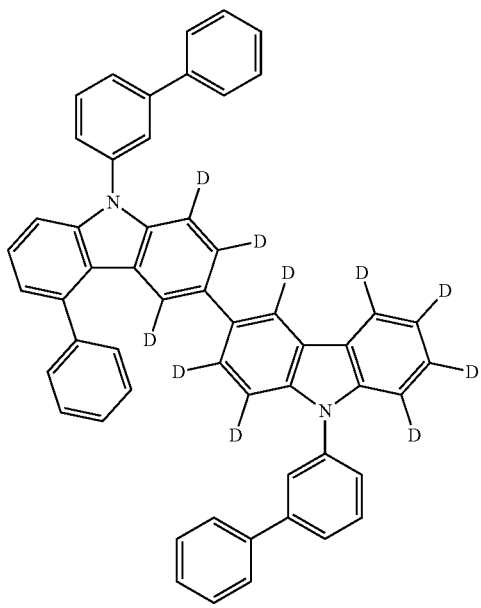

669
-continued
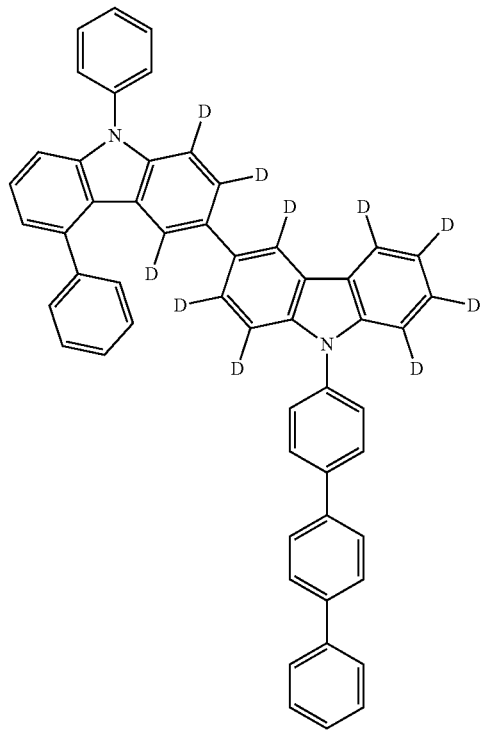
443
670
-continued
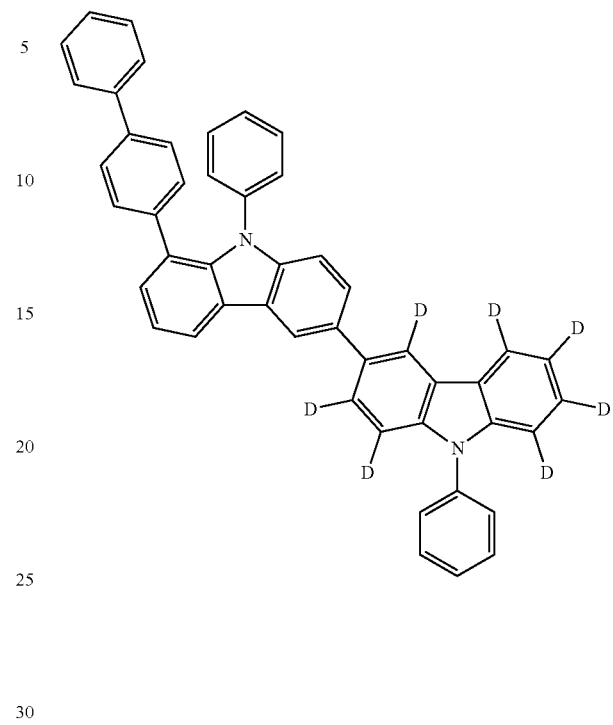
445
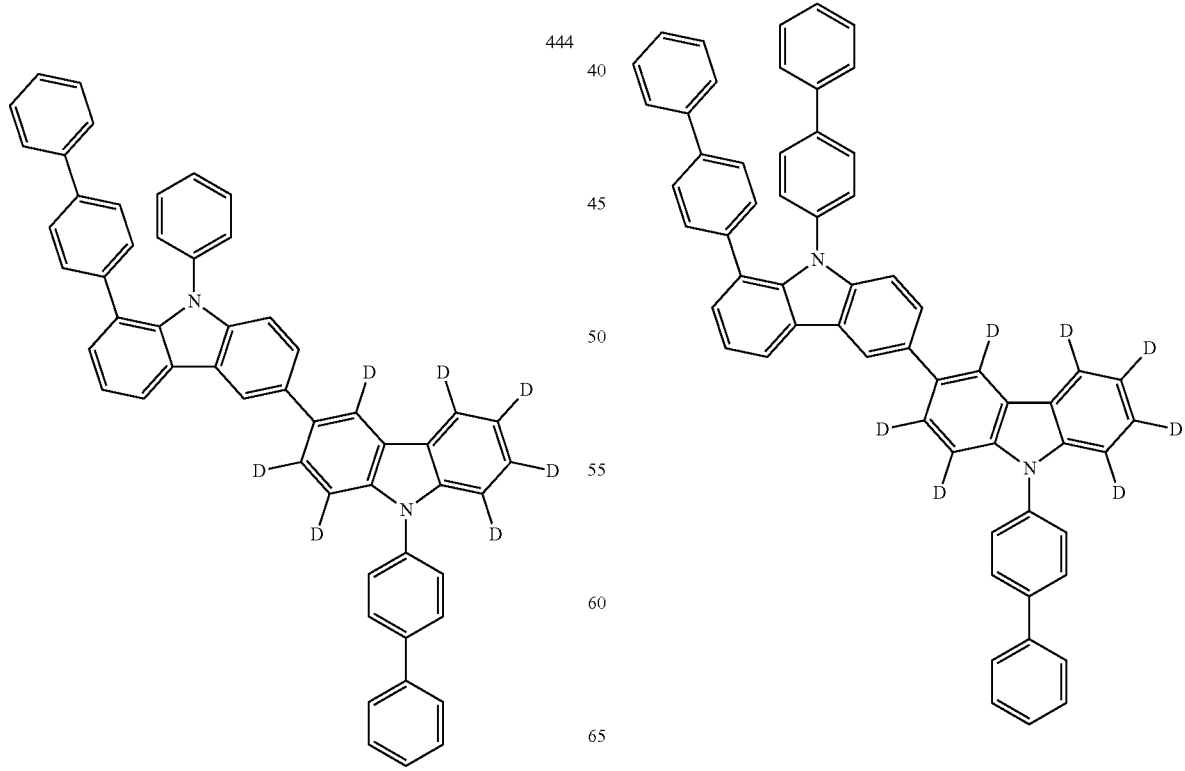
444
446

671
-continued
447
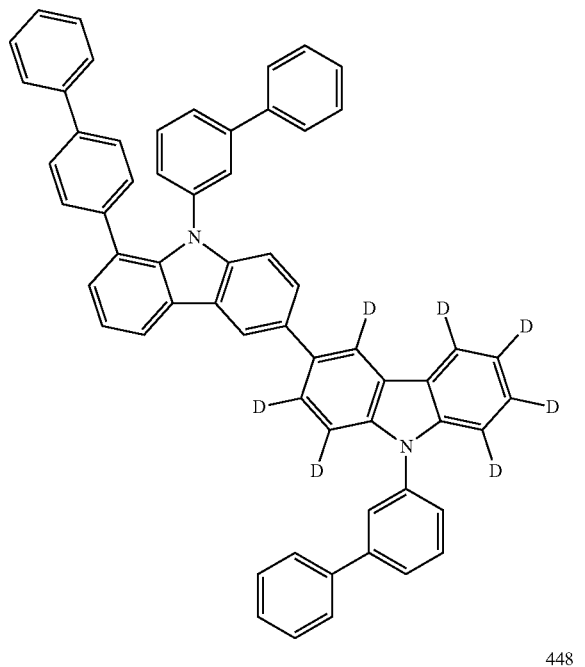
448
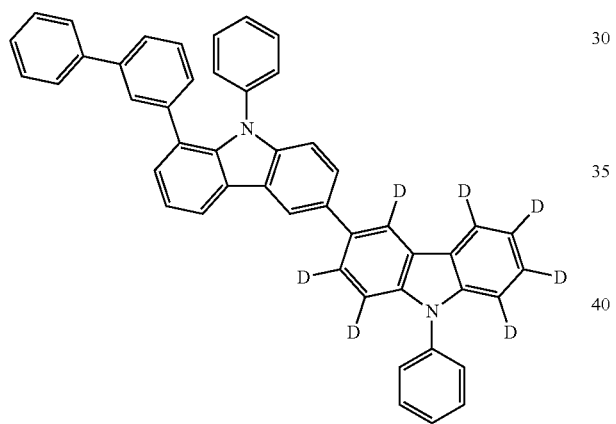
449
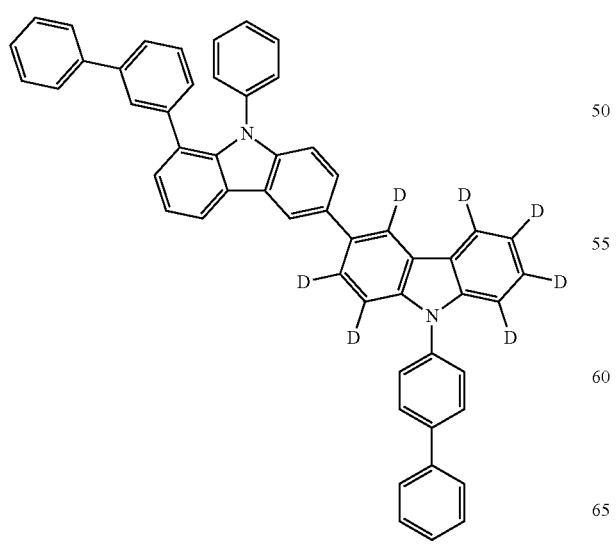
672
-continued
450
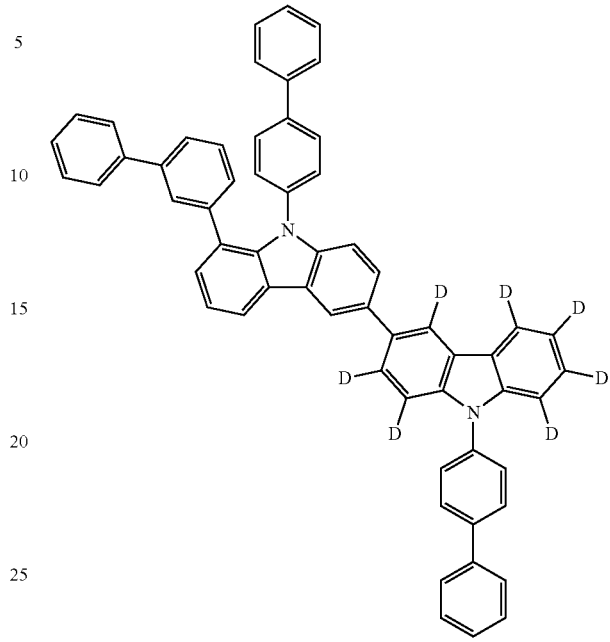
451

451
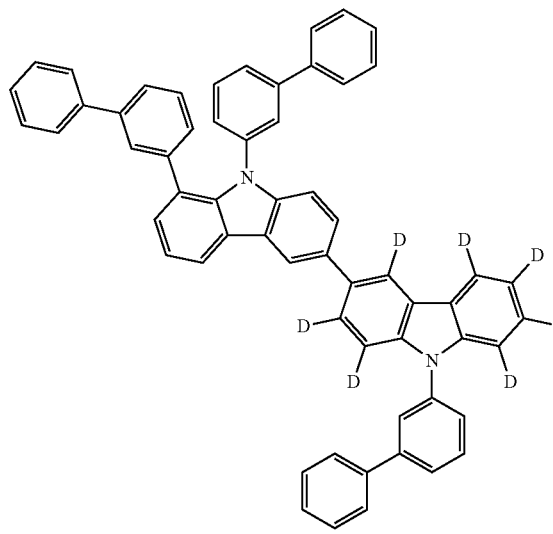
452
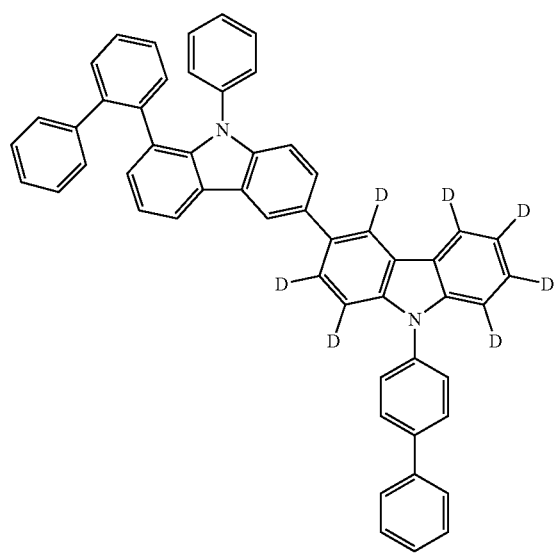
453
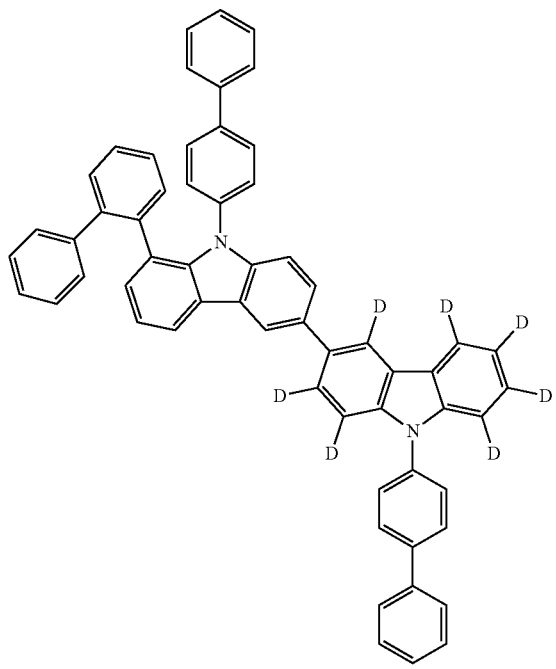
456
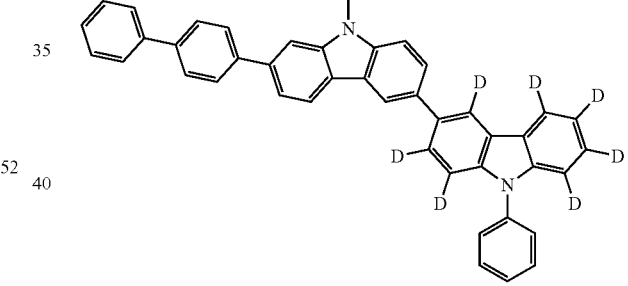
457
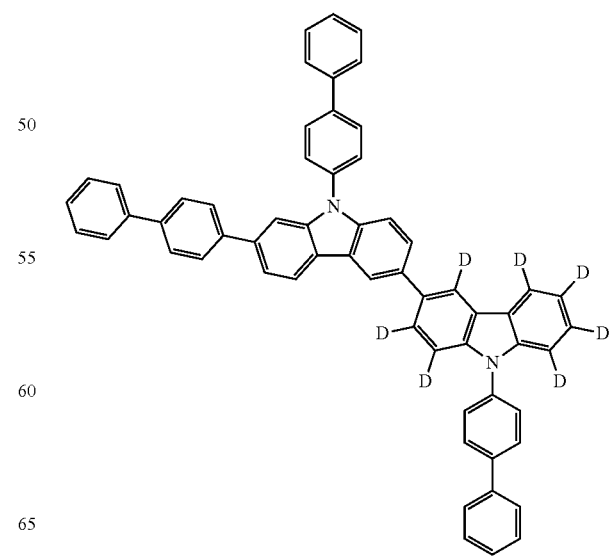

458
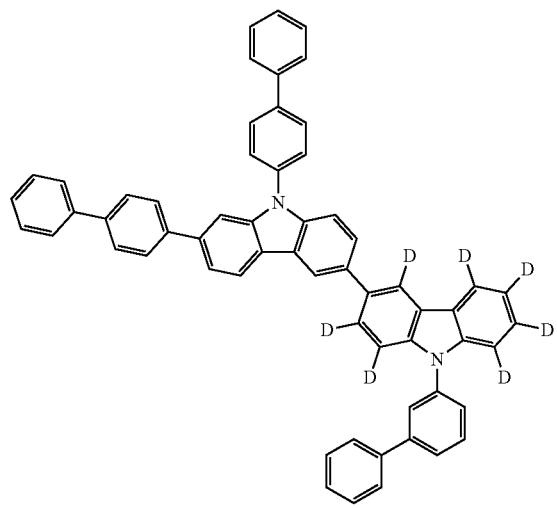
459
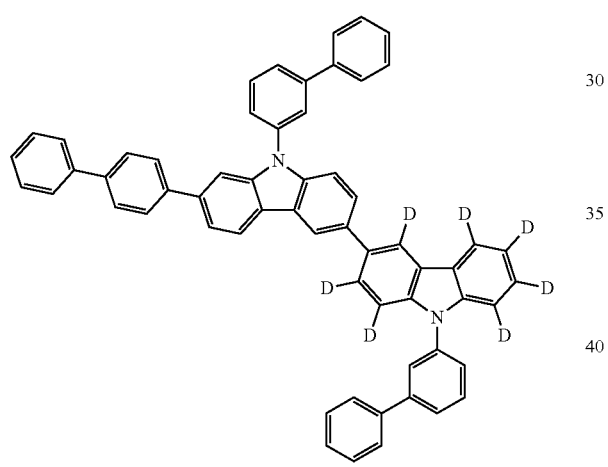
460
461
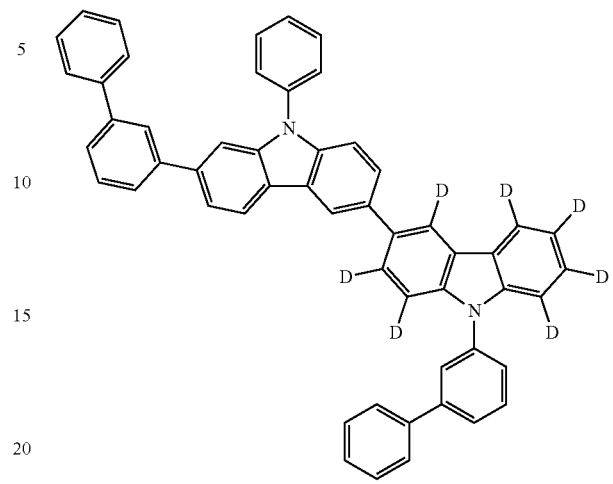
462
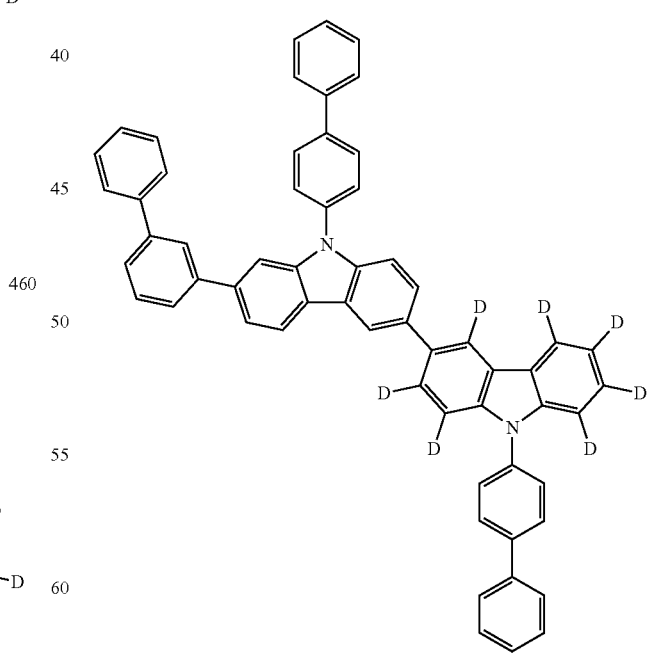

463
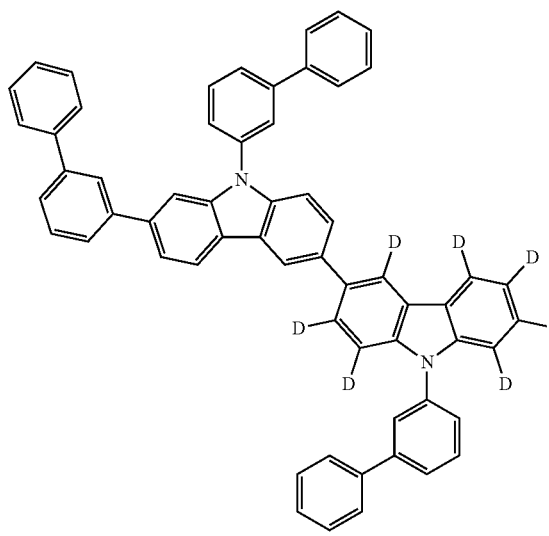
464
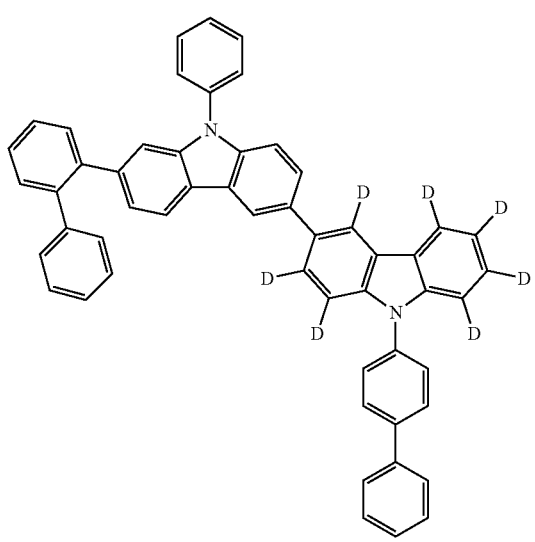
465
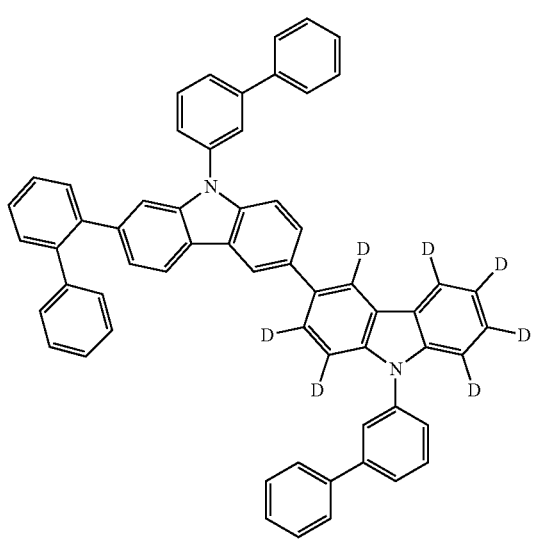
468
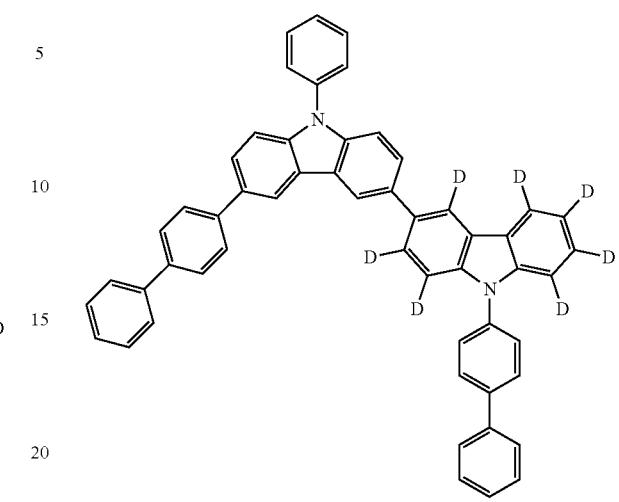
469
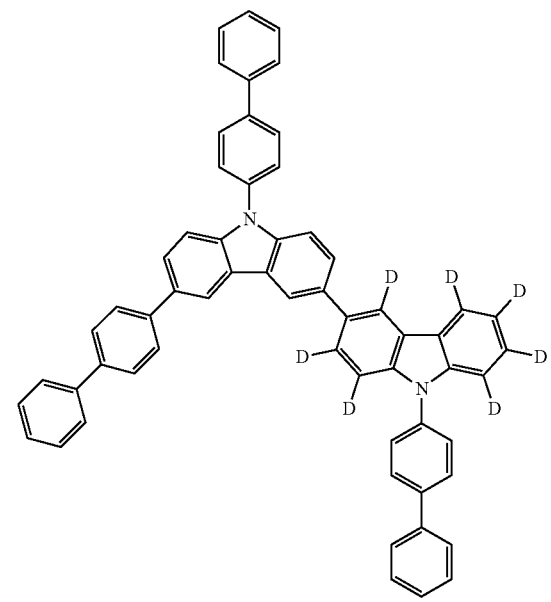
470
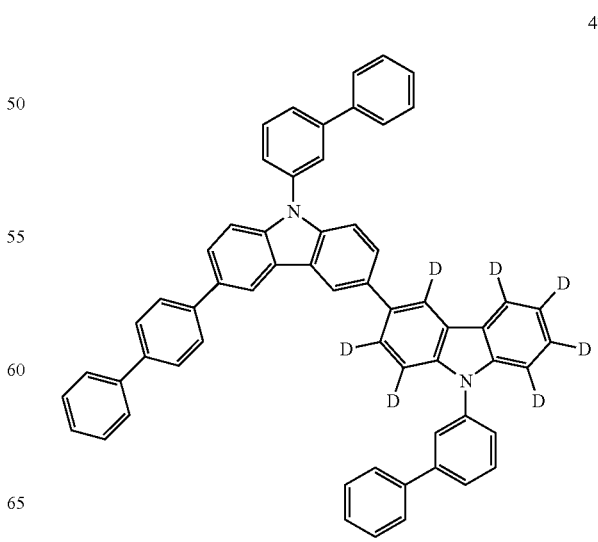

471
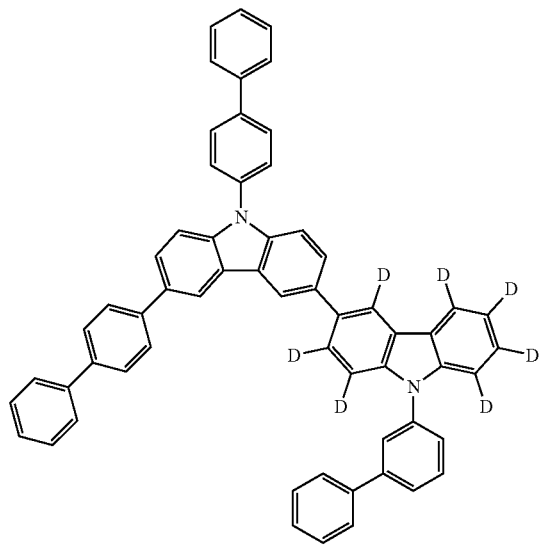
472
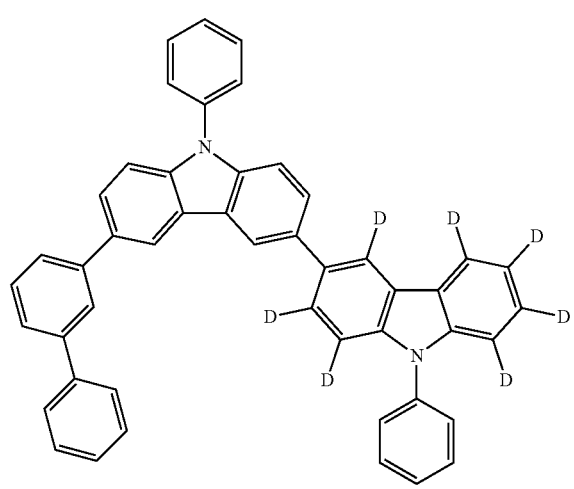
473
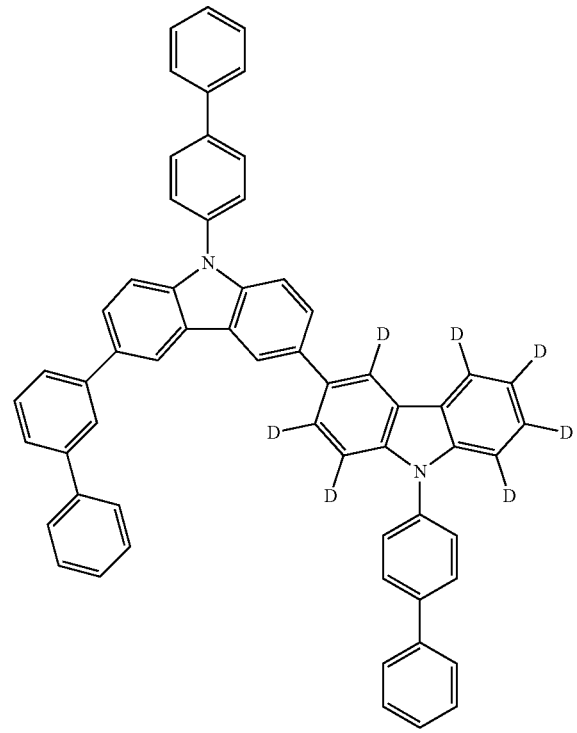
474
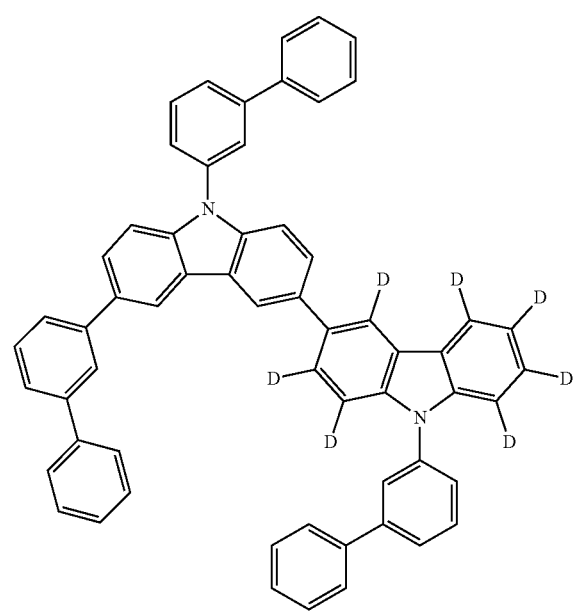

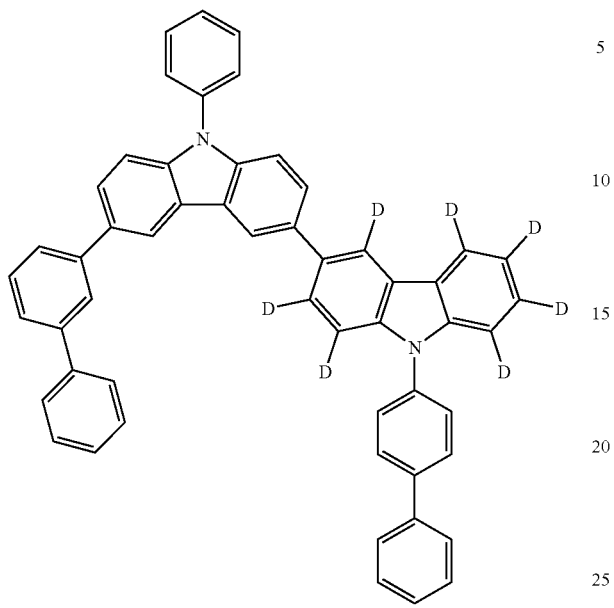
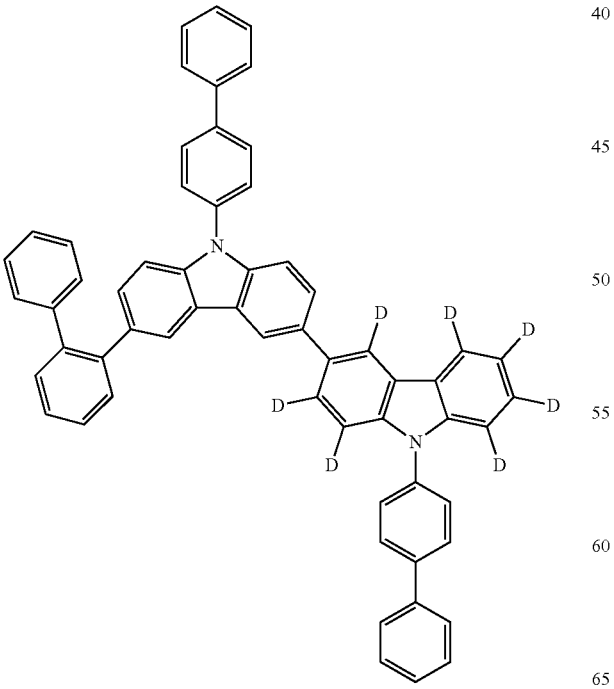

683
-continued
481
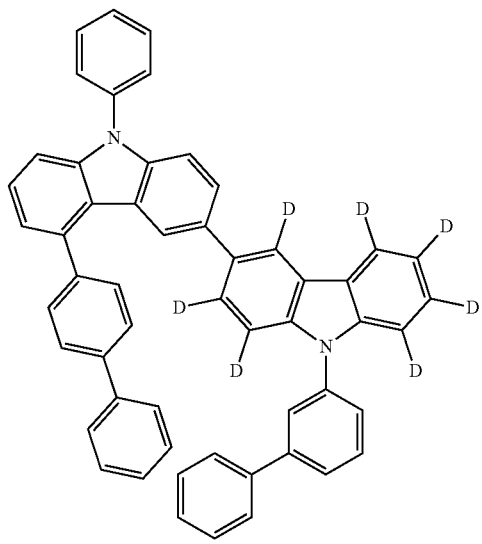
482
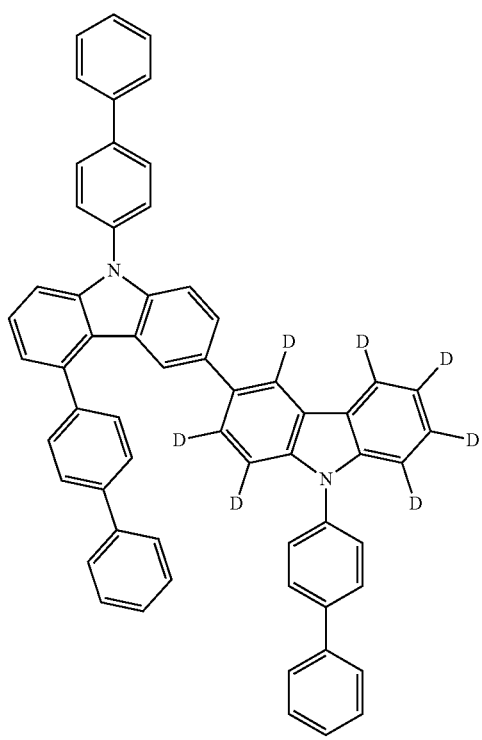
684
-continued
483
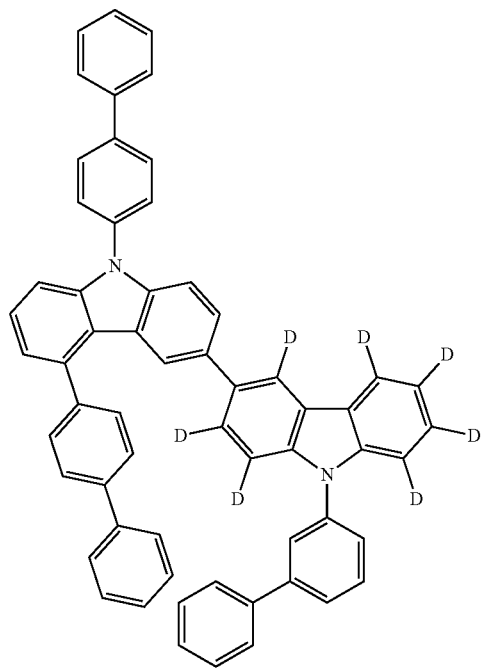
484
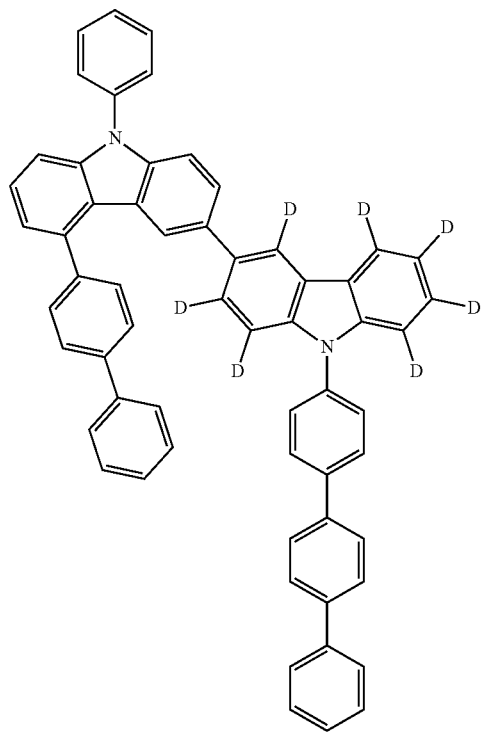

685
-continued
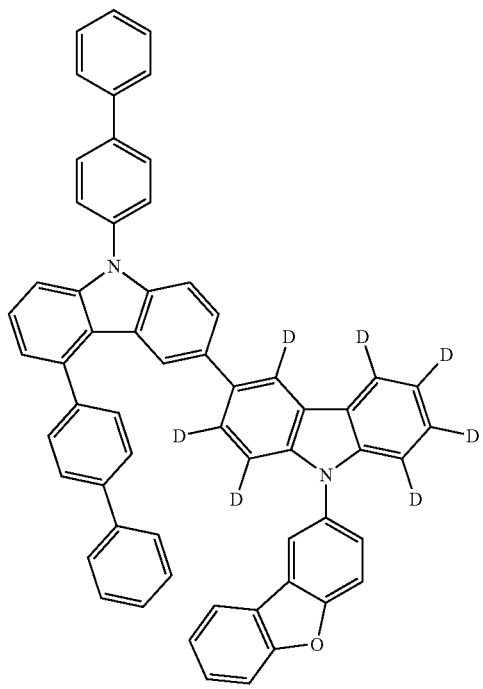
485
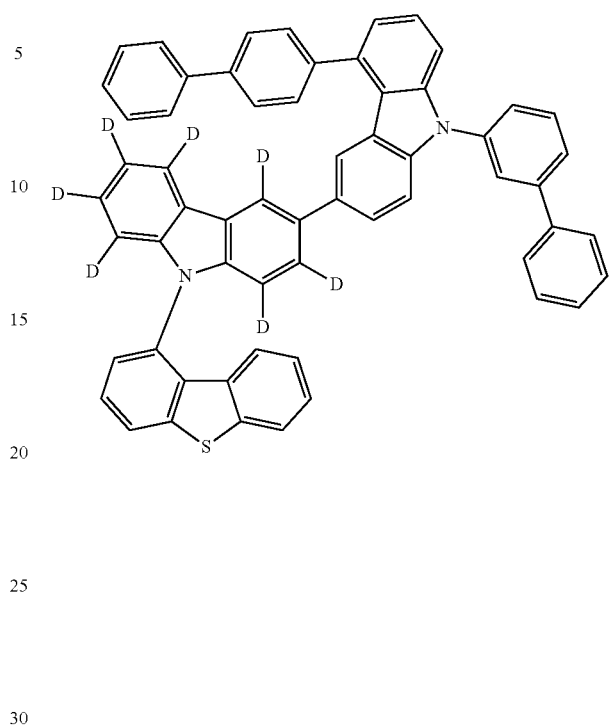
686
-continued
487
486
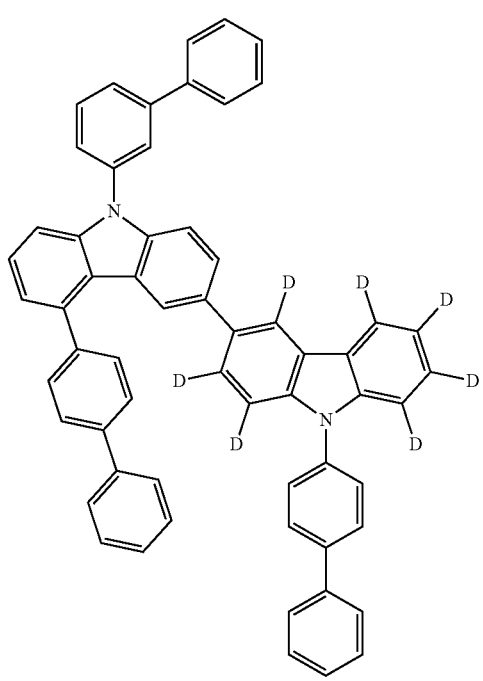
488
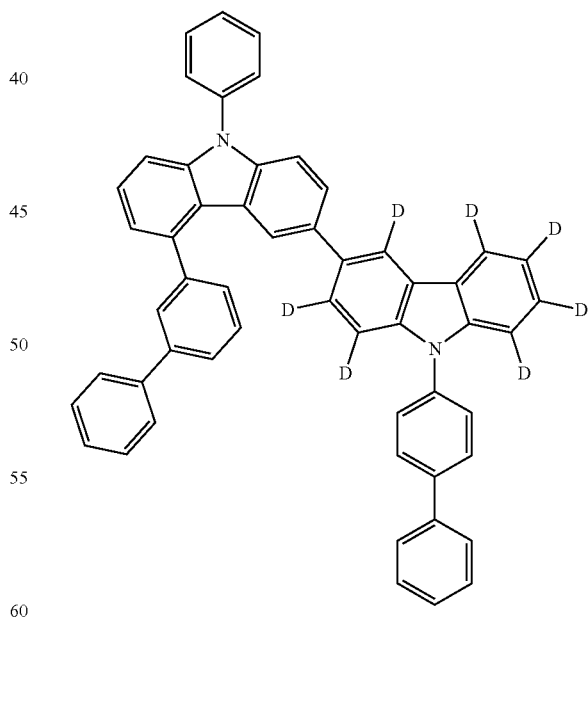

489
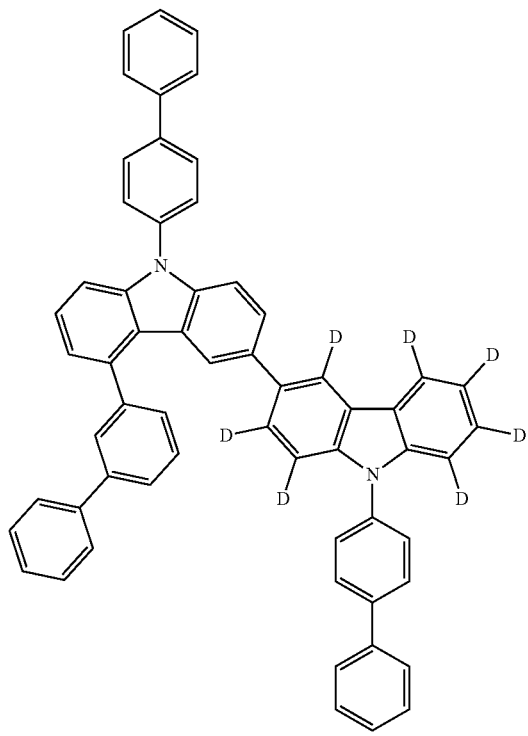
491
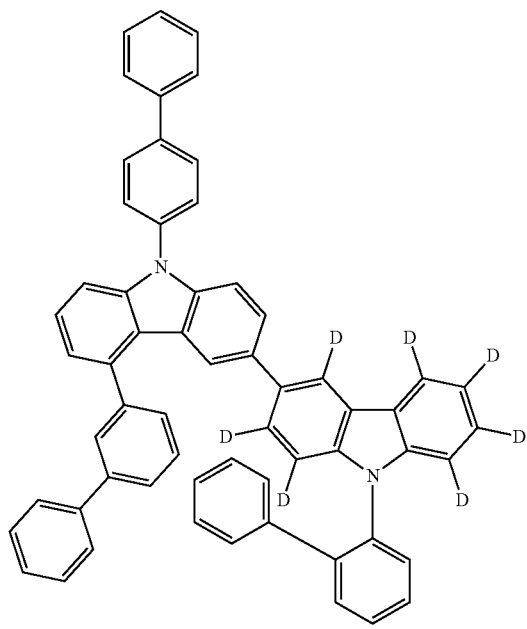
490
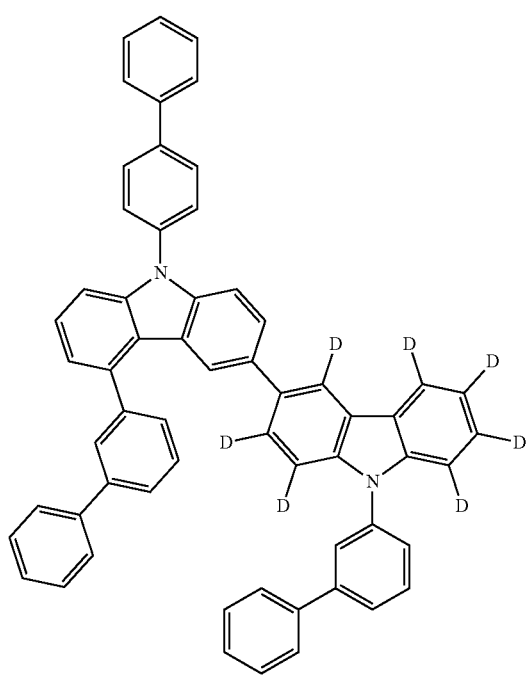
492
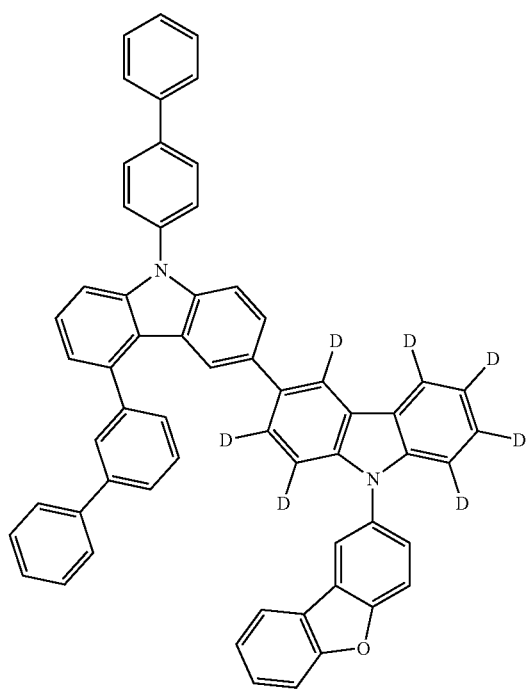

493
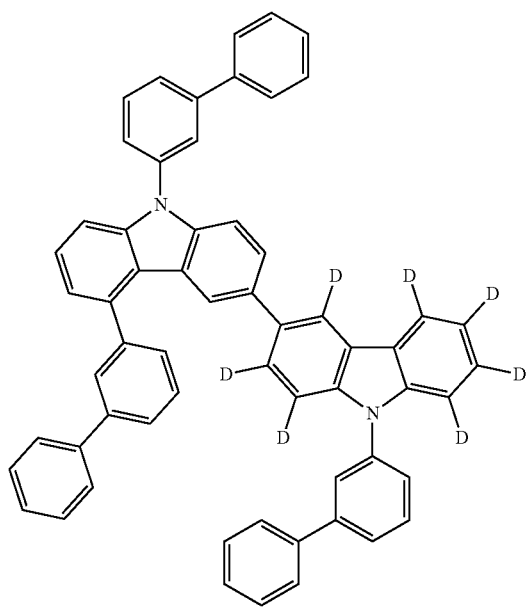
494
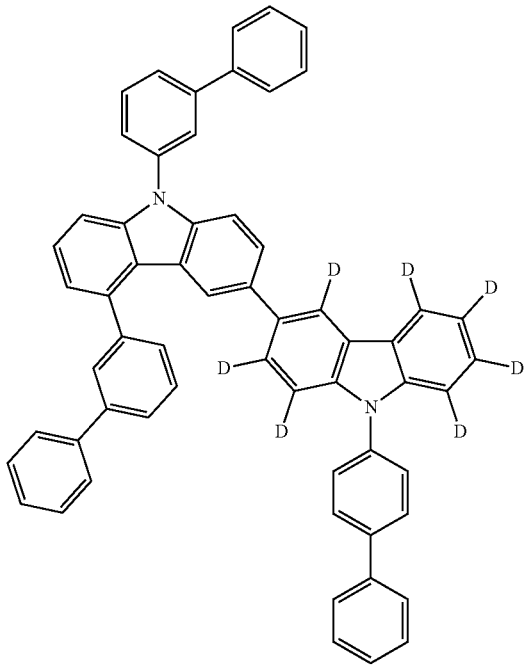
493
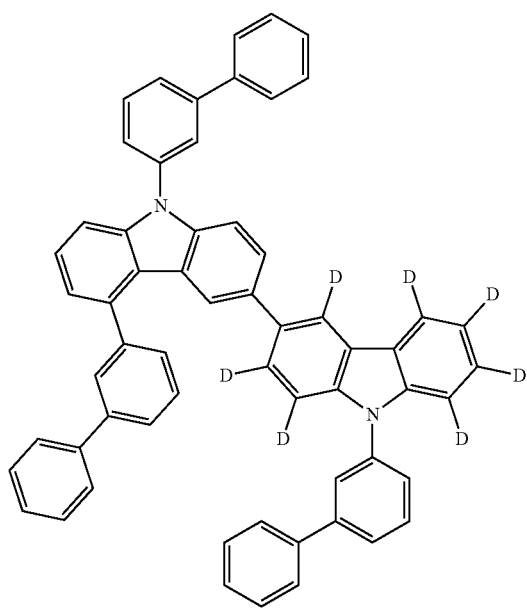
495
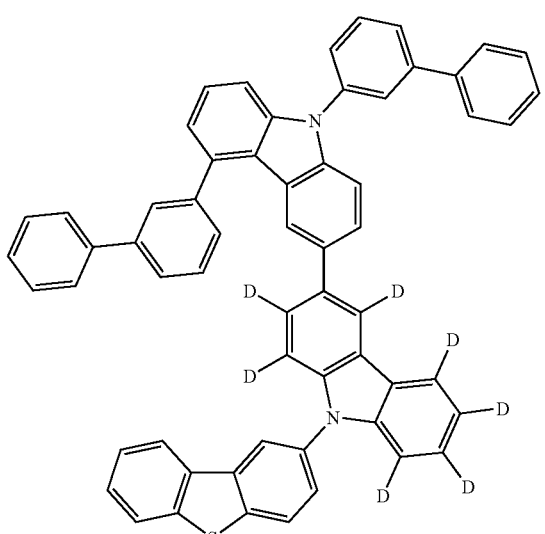

691
-continued
496
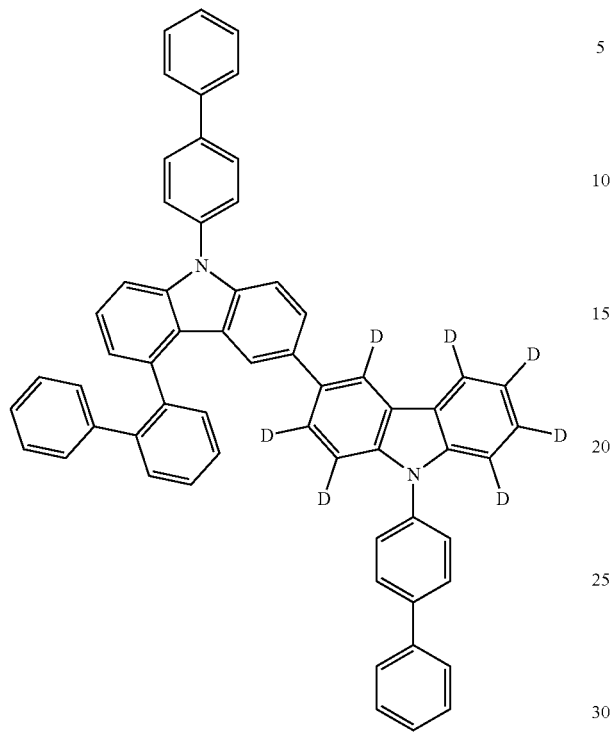
497
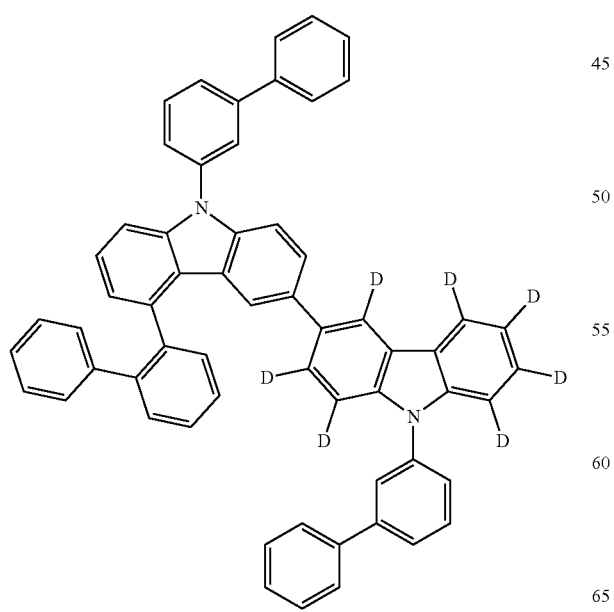
692
-continued
500
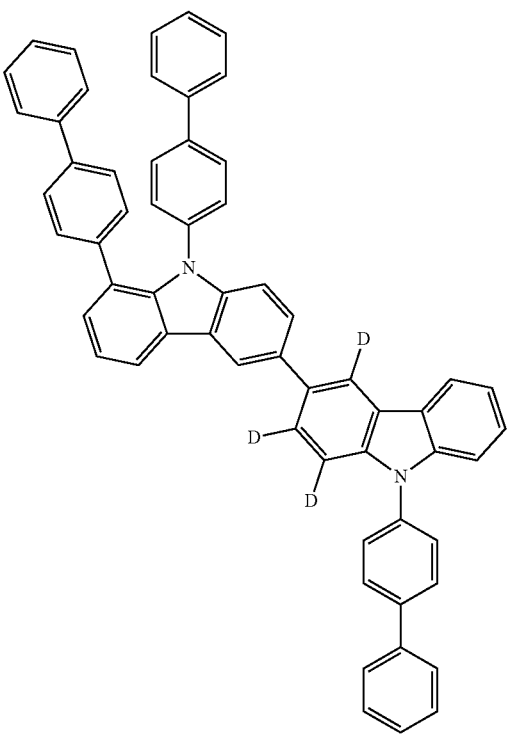
501
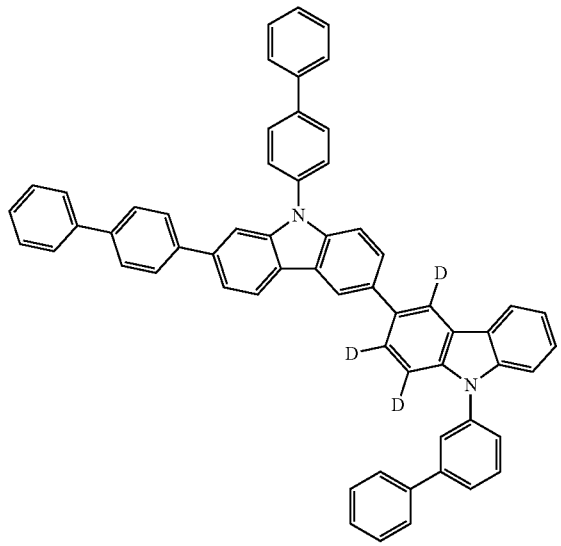

693
-continued
502
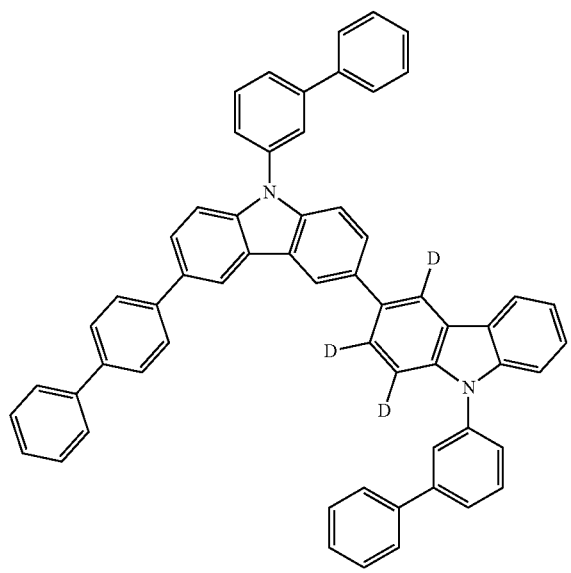
503
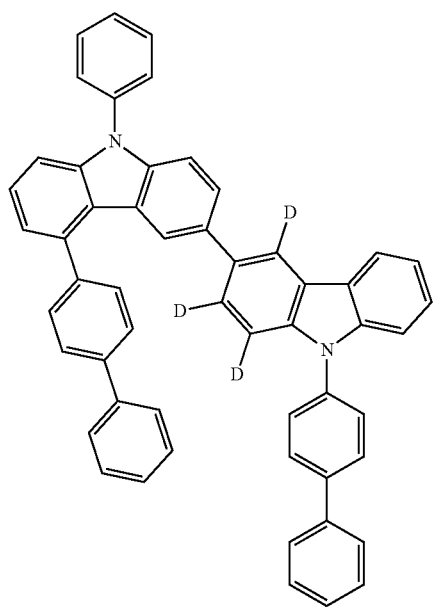
694
-continued
504
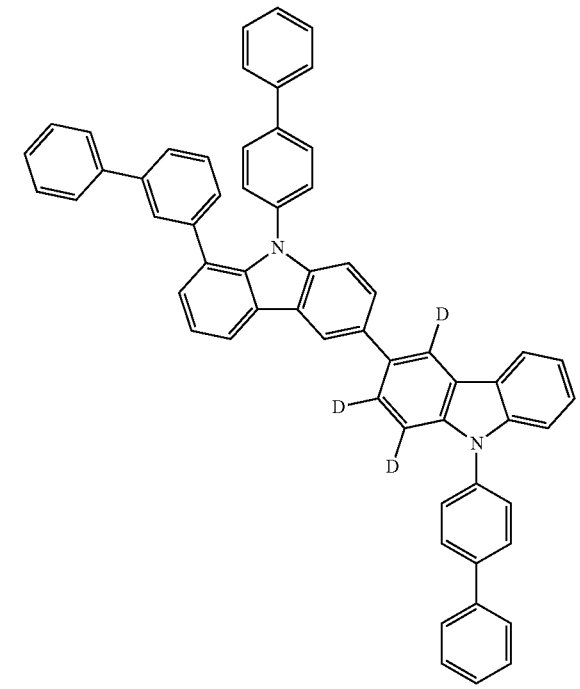
505
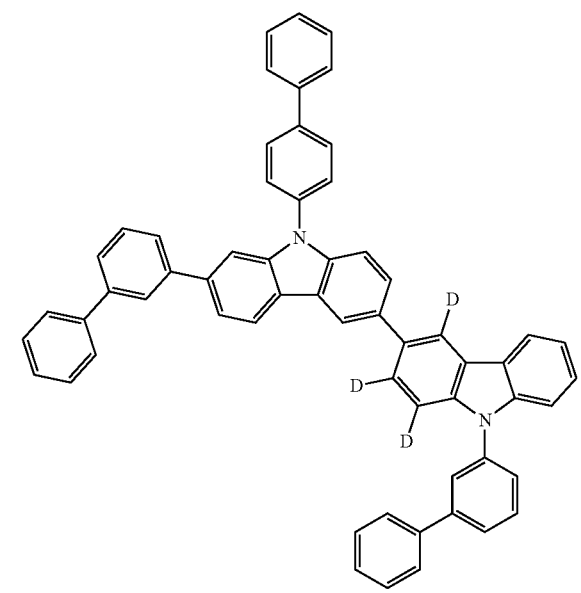

505
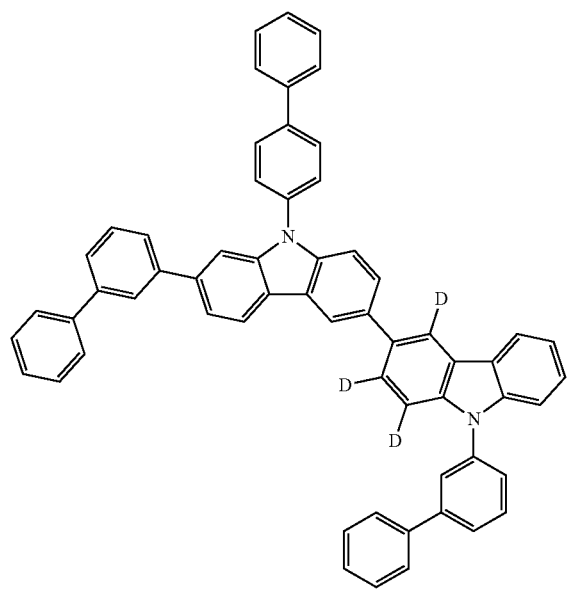
506
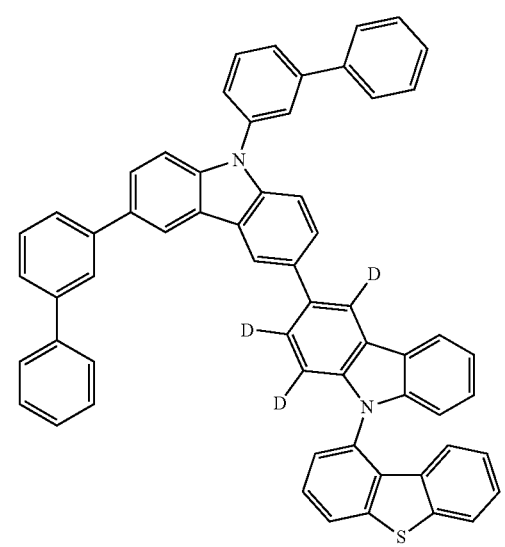
507
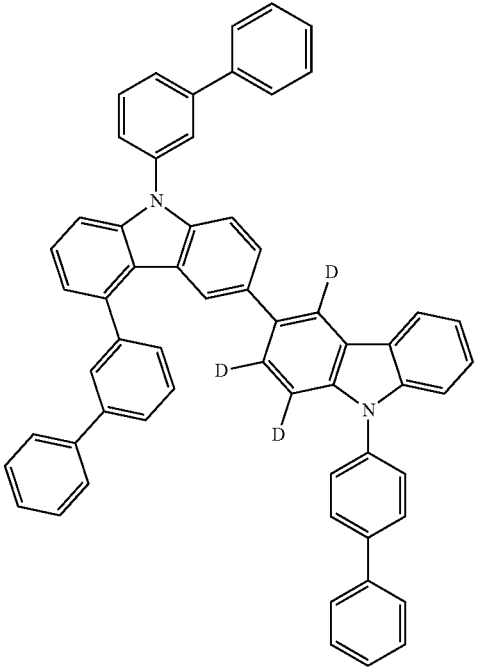
508
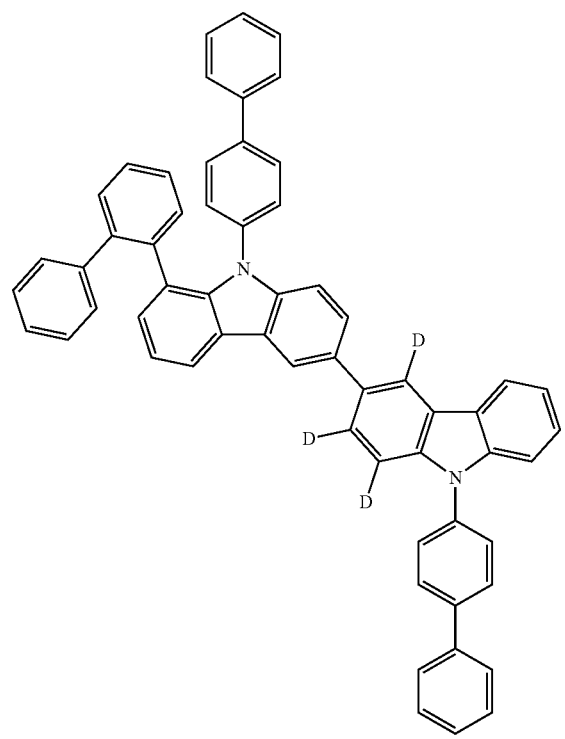

509
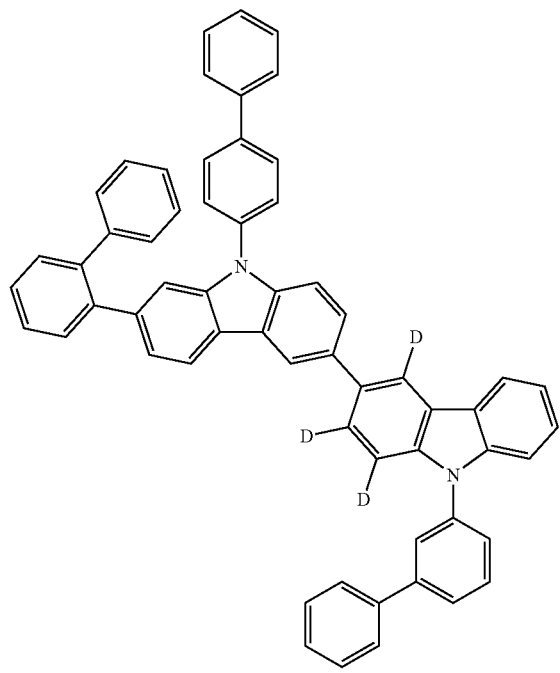
510
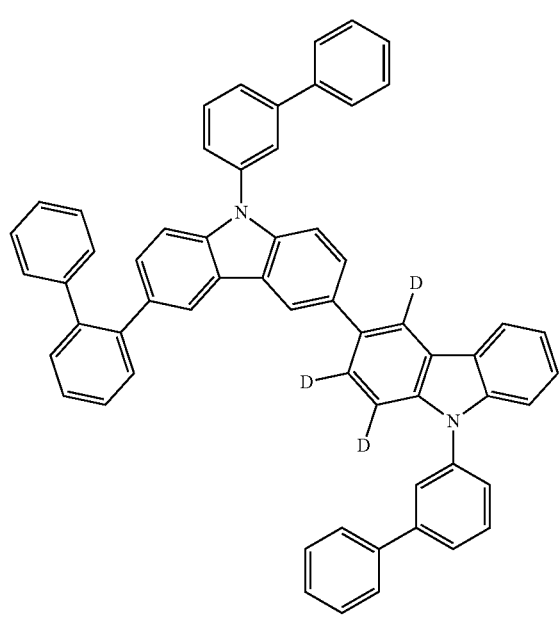
511
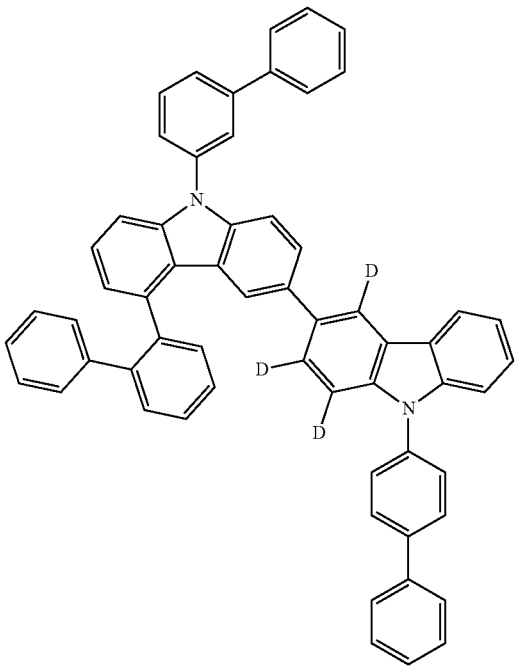
516
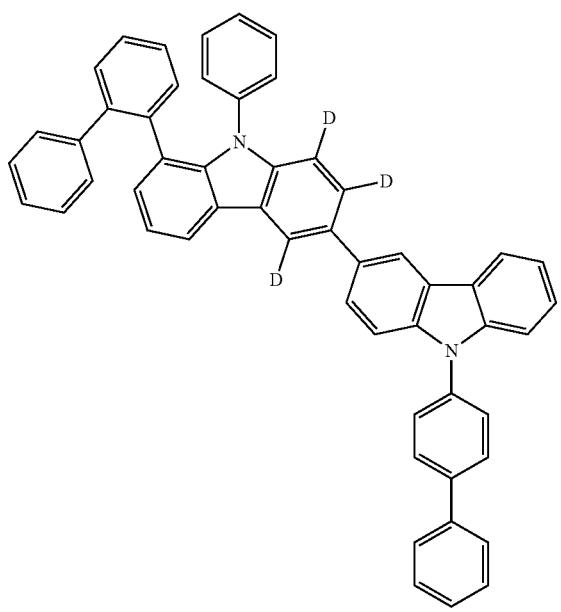

517
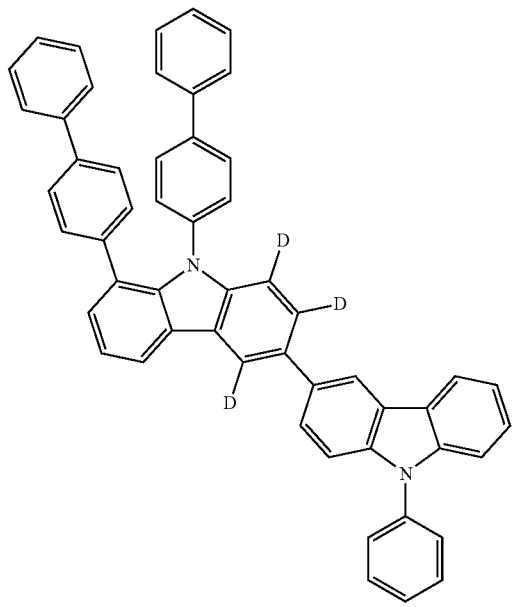
518
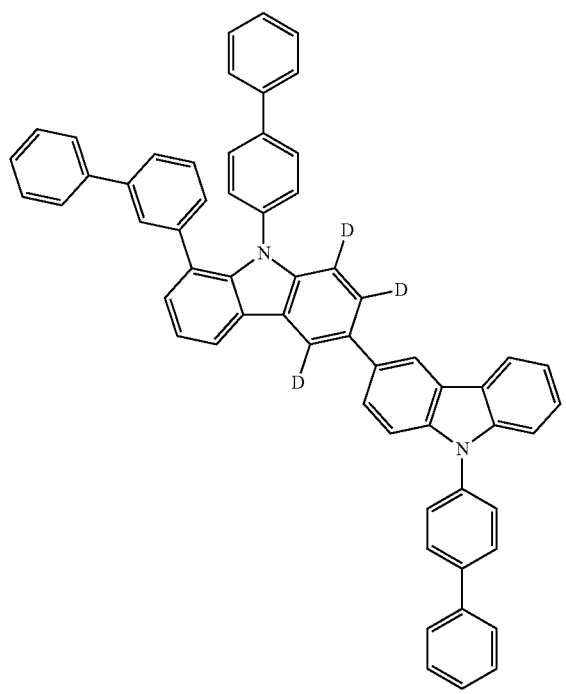
521
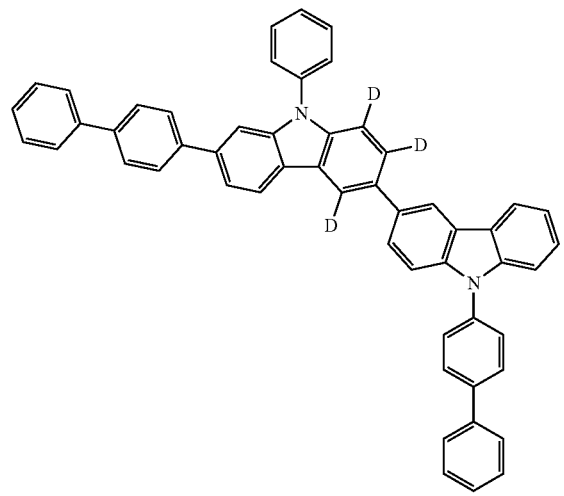
522
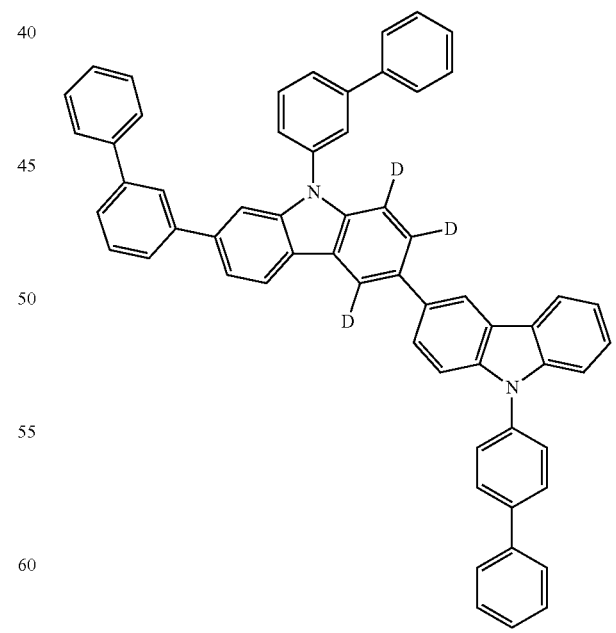

701
-continued
523
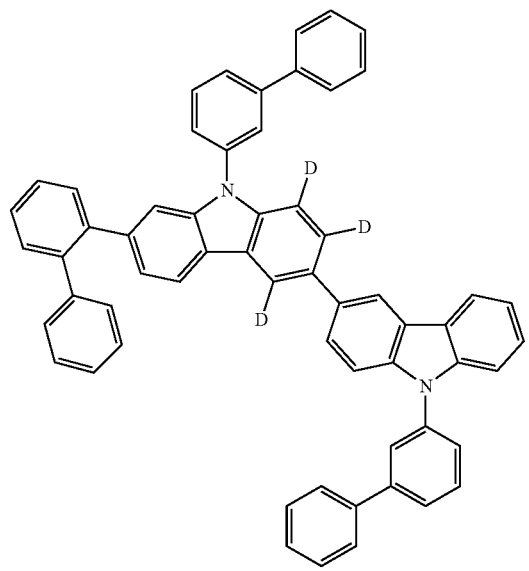
524
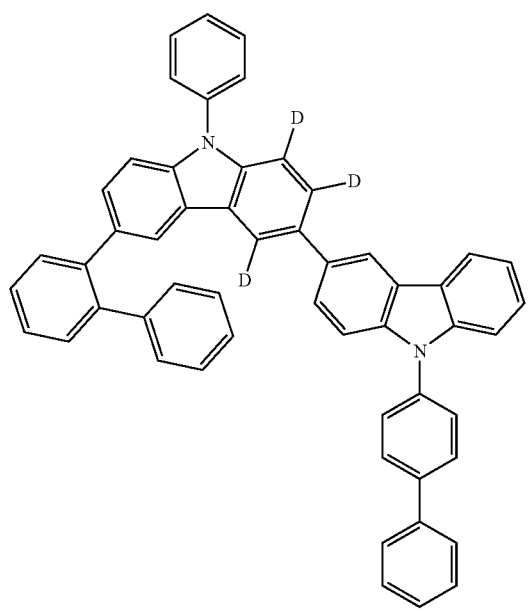
702
-continued
525
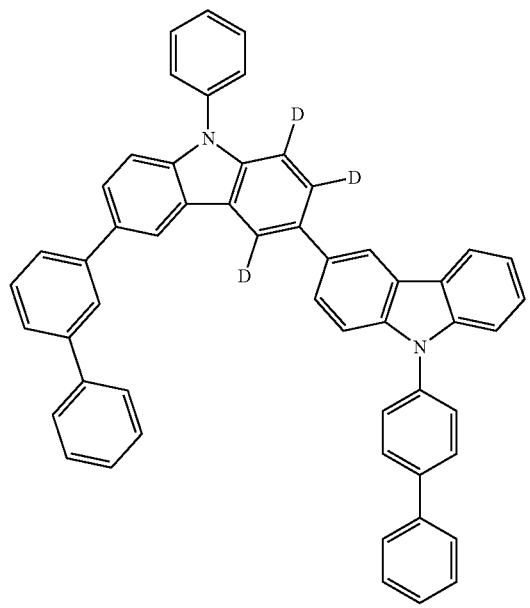
526

529
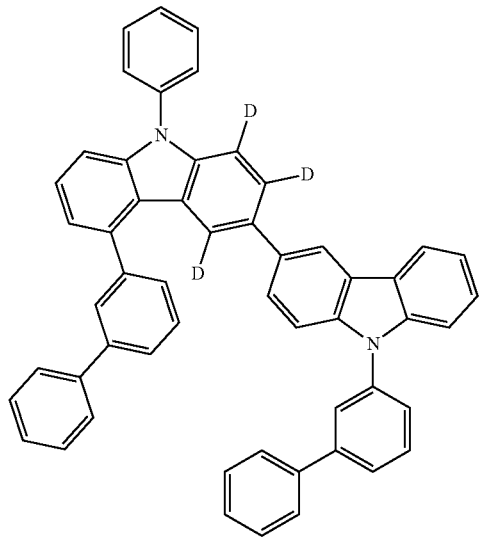
530
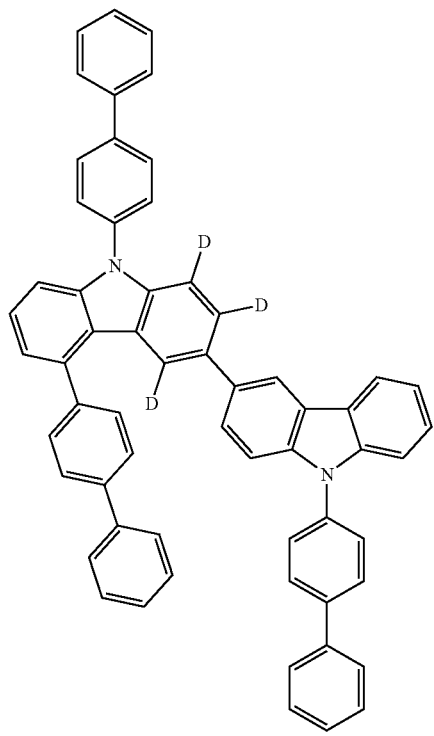
531
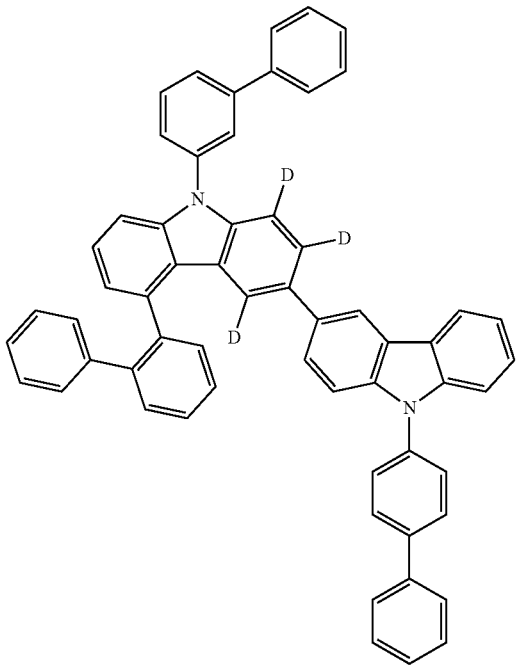
532
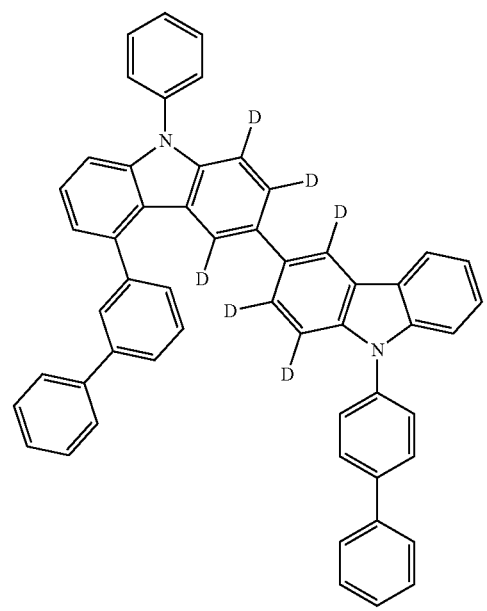

705
-continued
533
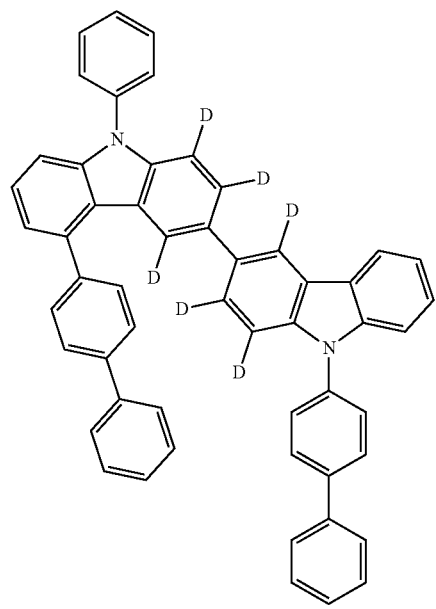
534
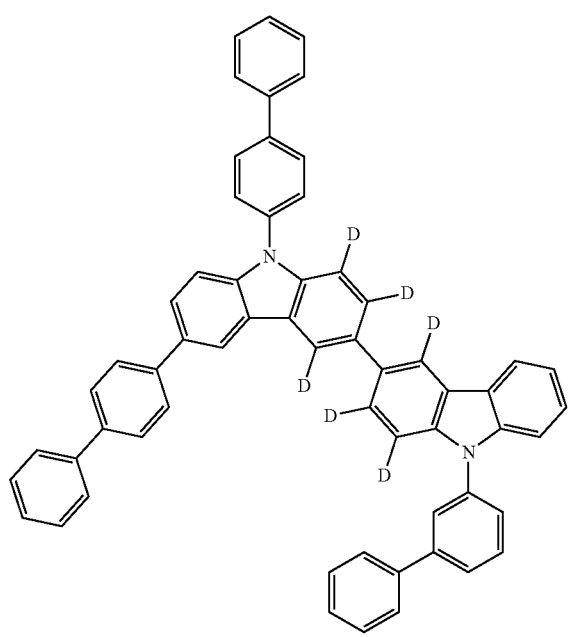
706
-continued
535
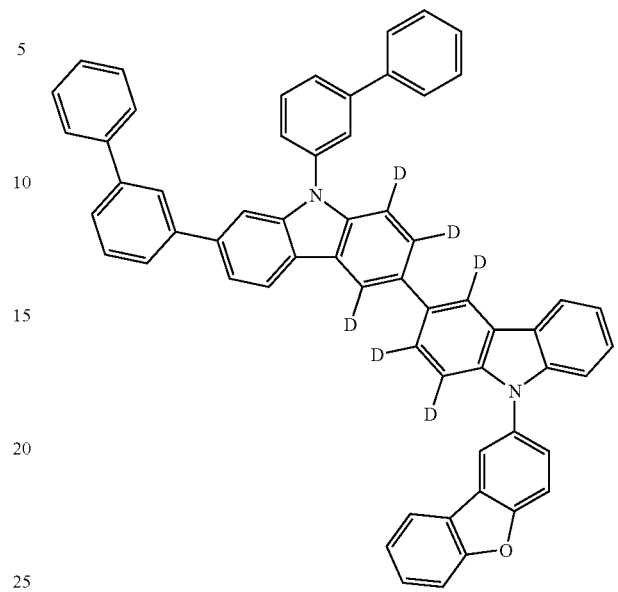
538
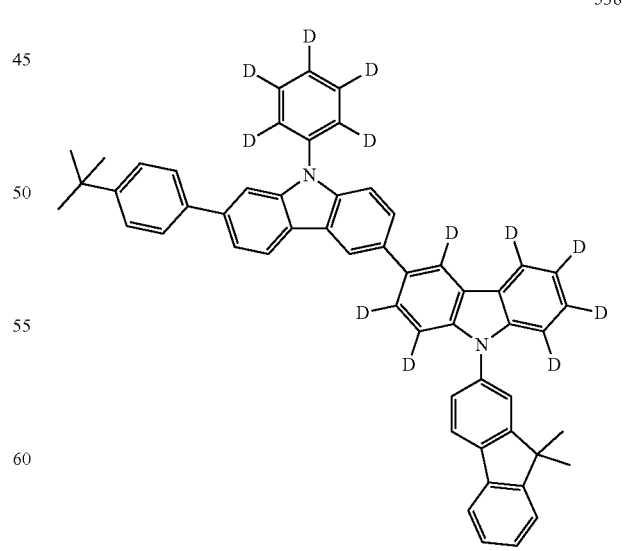

707
-continued
539
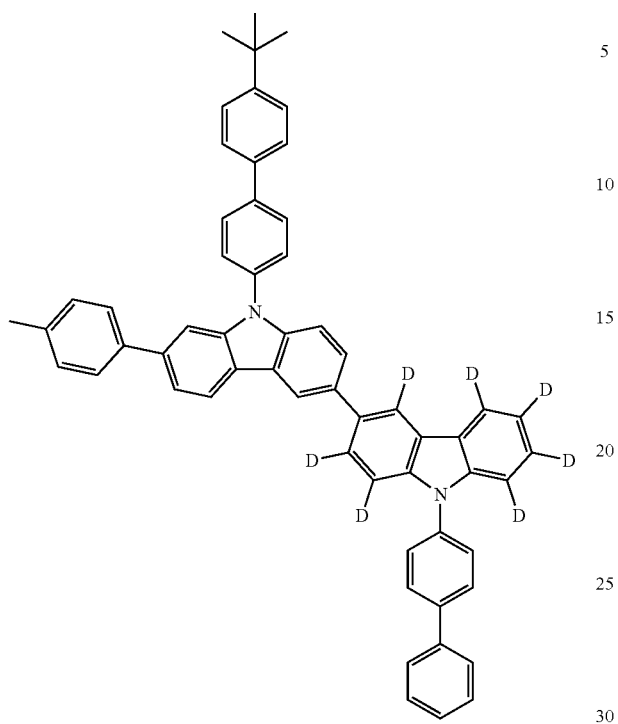
540
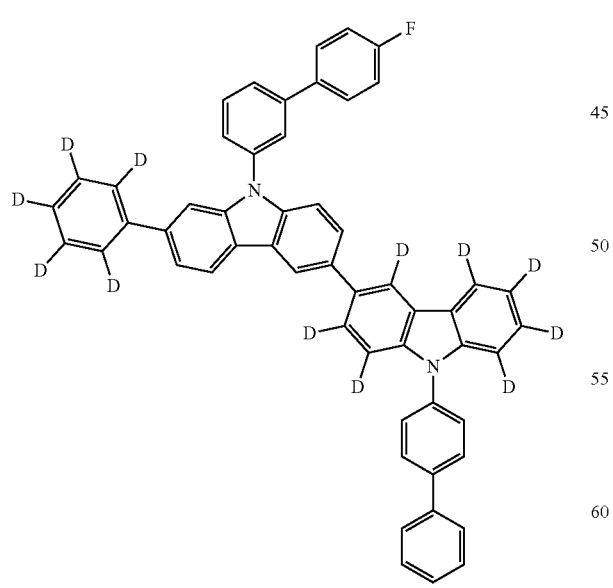
708
-continued
541
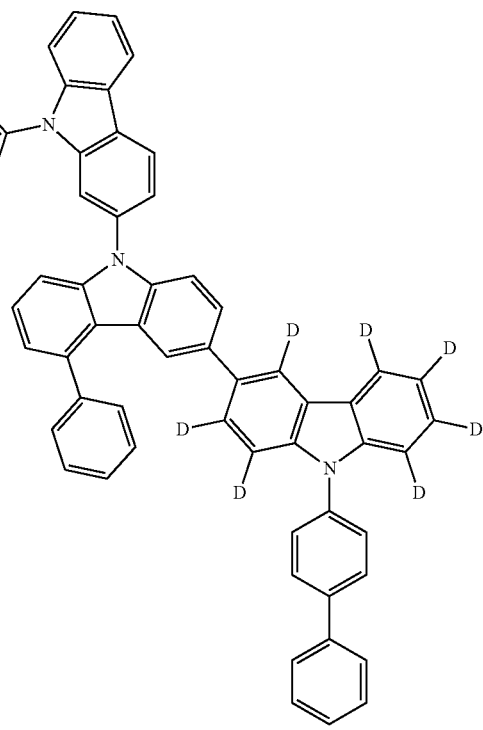
543
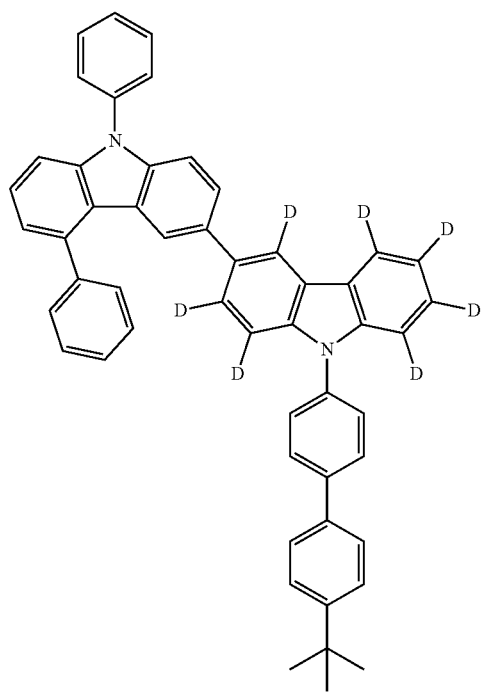 [SMILES: [2H]c1c([2H])c([2H])c2c(c1[2H])c1c([2H])c(-c3ccc4c(c3)c3c(-c5ccccc5)cccc3n4-c3ccccc3)c([2H])c([2H])c1n2-c1ccc(-c2ccc(C#N)cc2)cc1]

709
-continued
544
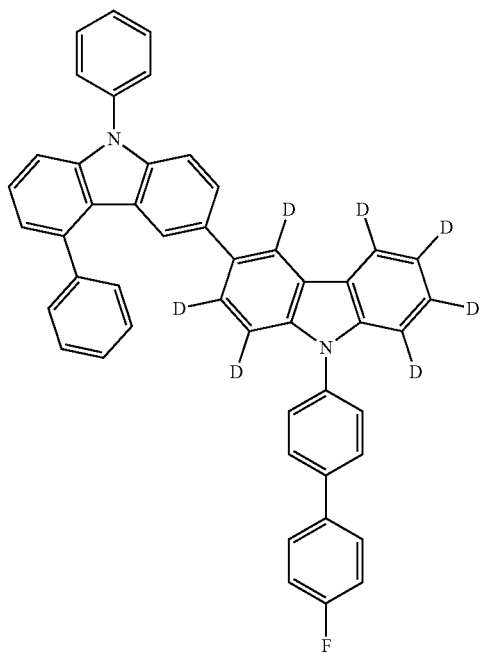
545
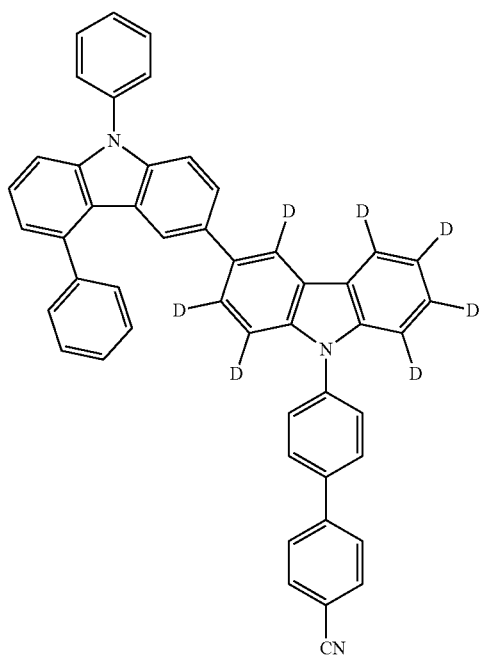
710
-continued
546
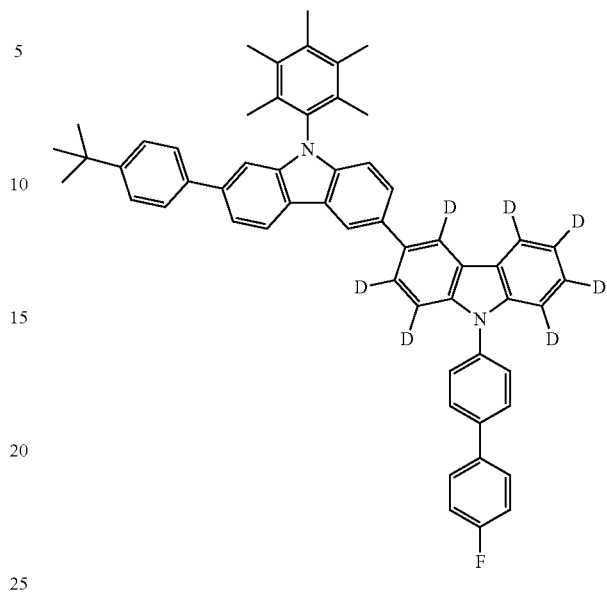
546
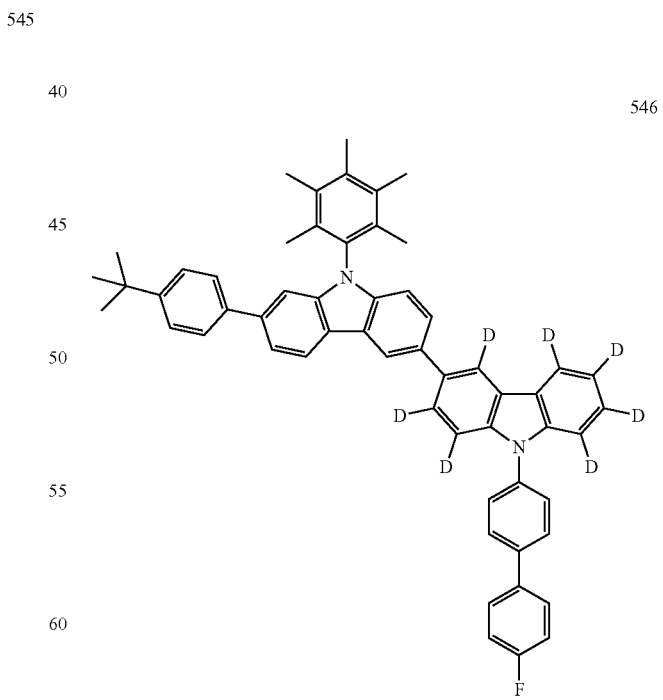

547
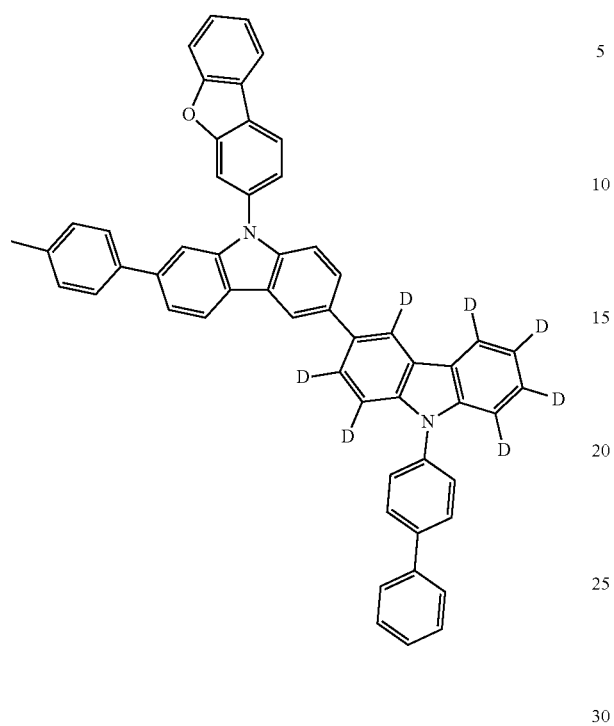
549
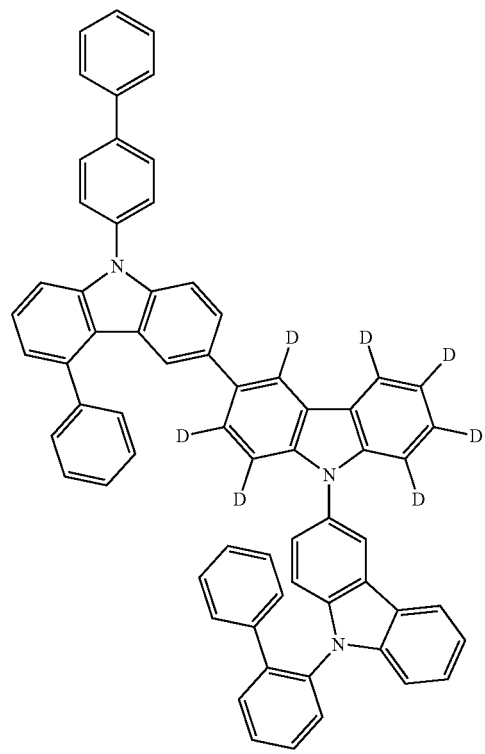
548
550
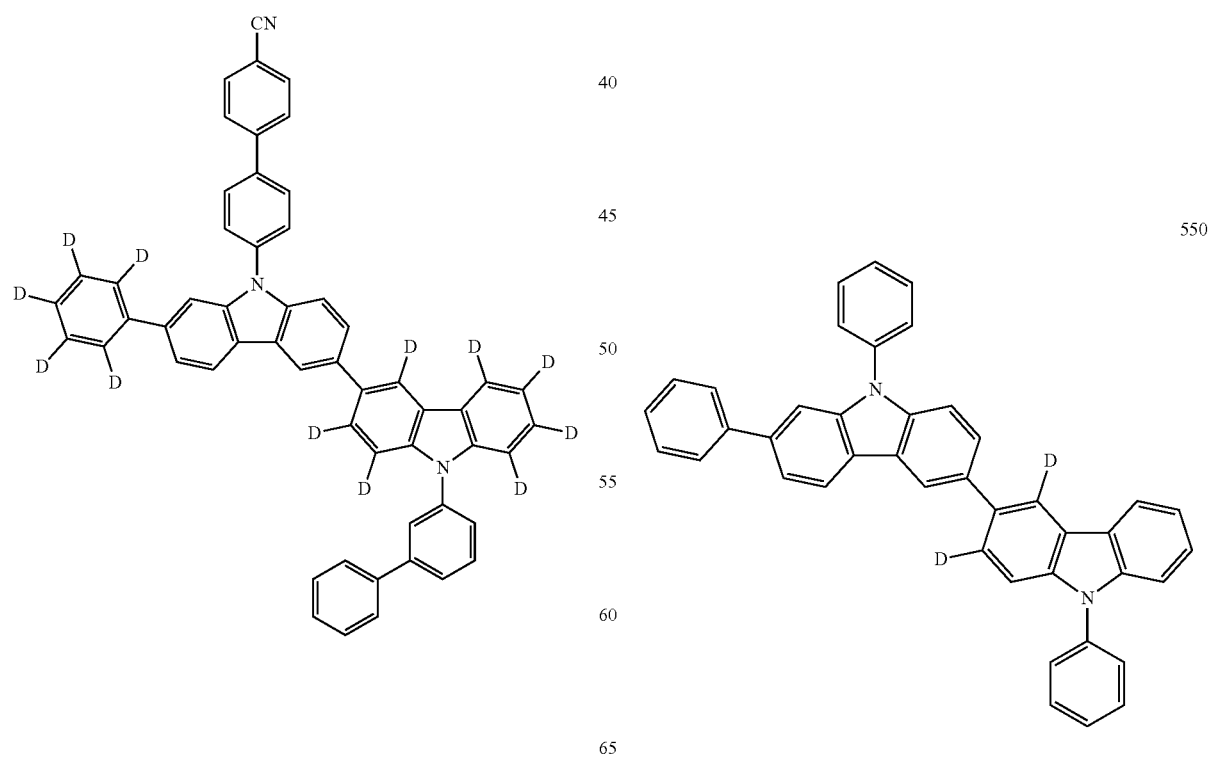

-continued
551
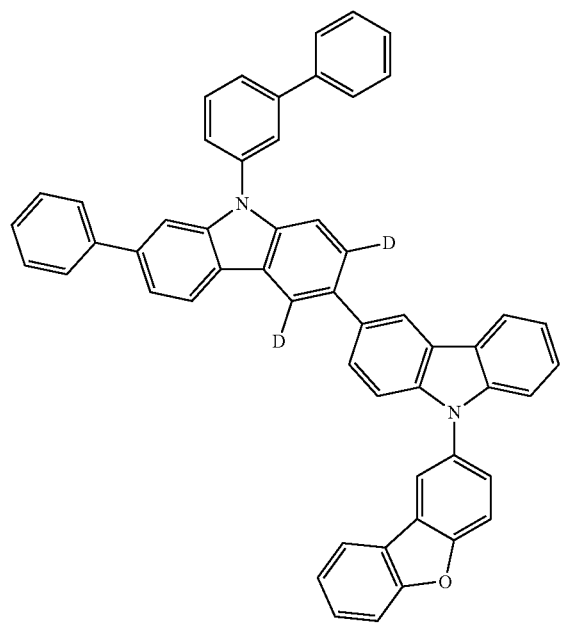
552
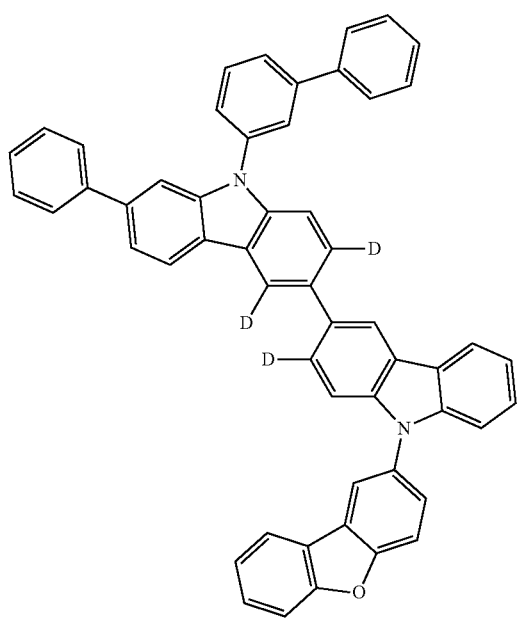
-continued
553
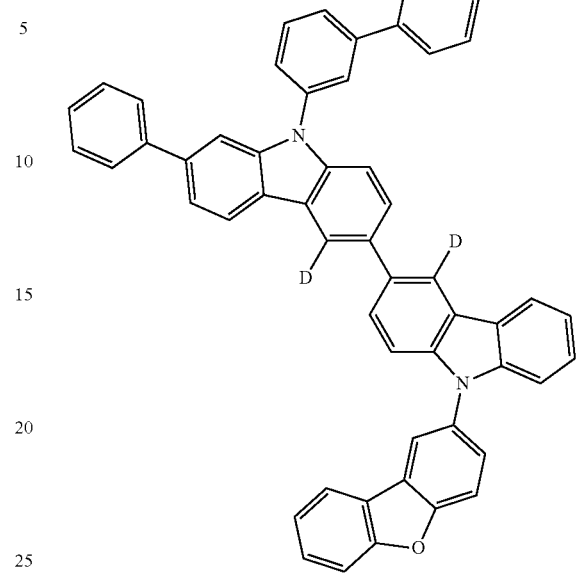
554
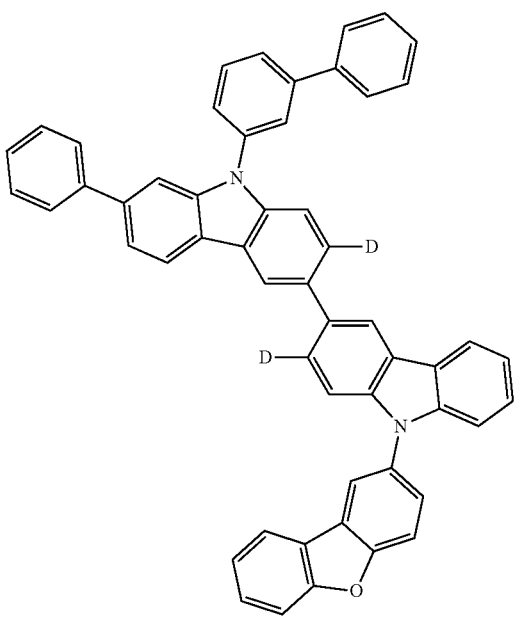

-continued
555
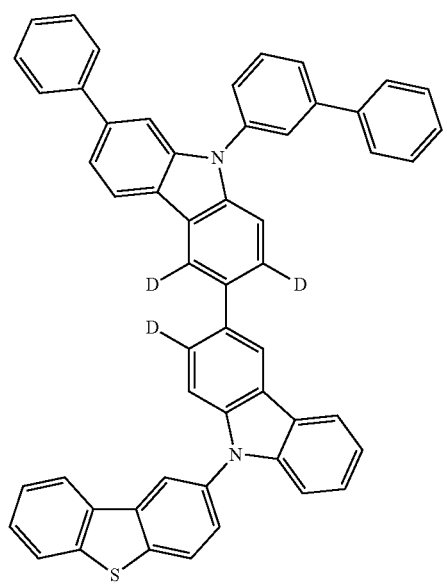
556
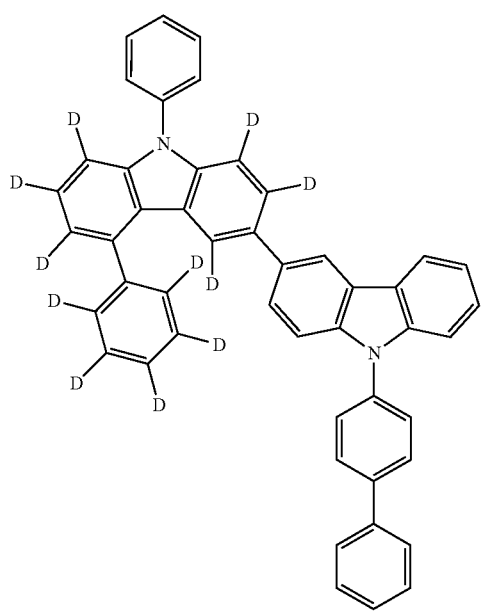
-continued
557
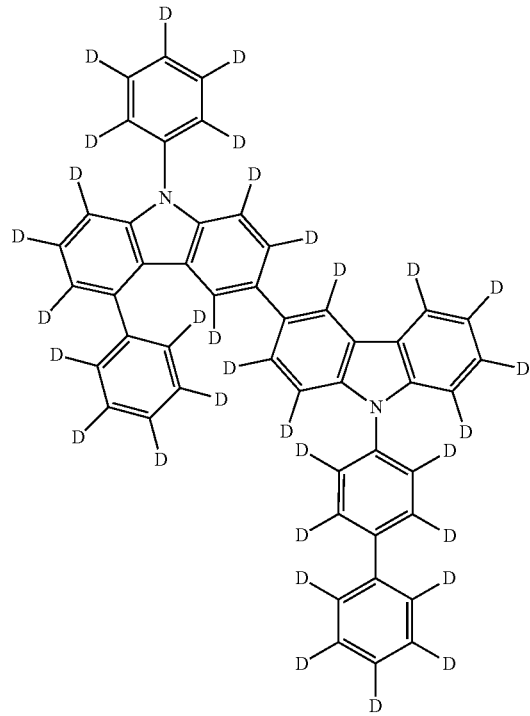
558
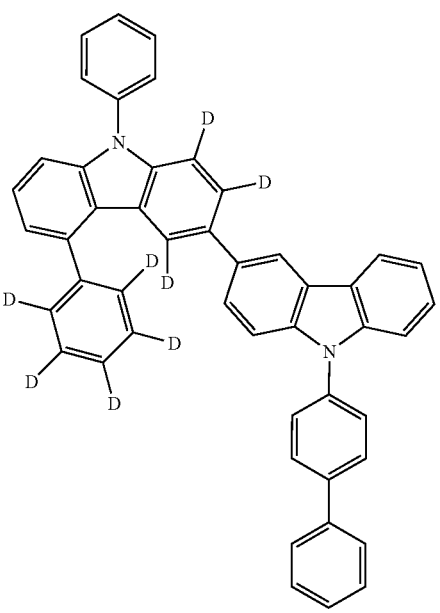

717
-continued
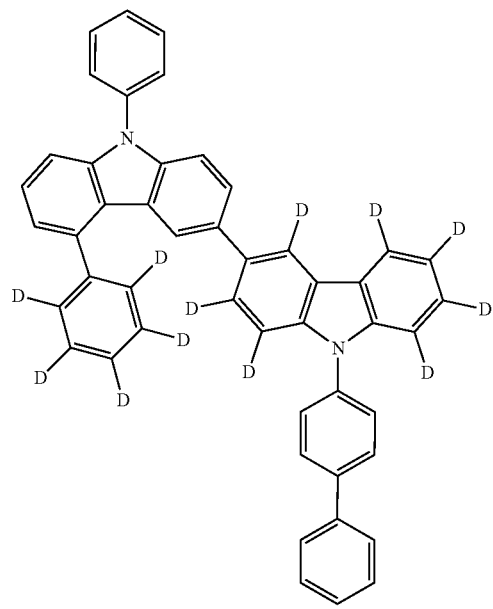
559
718
-continued
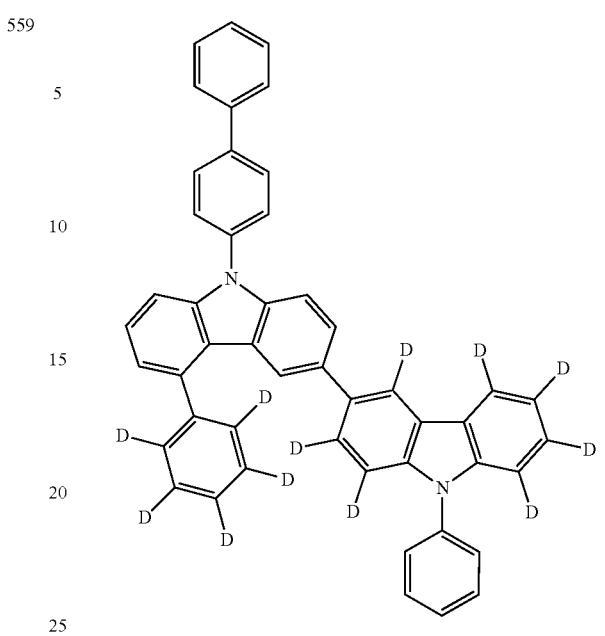
601
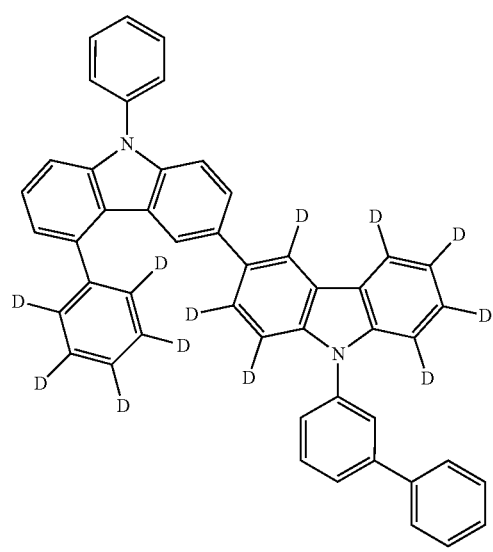
600
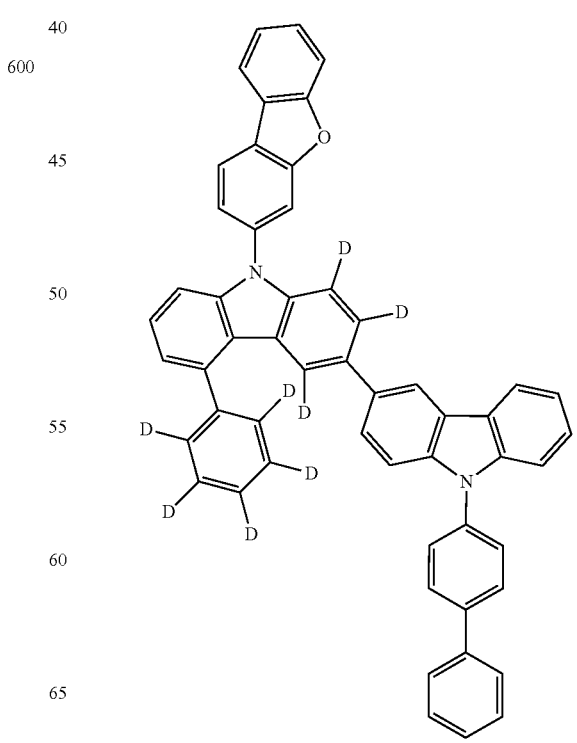
602

719
-continued
603
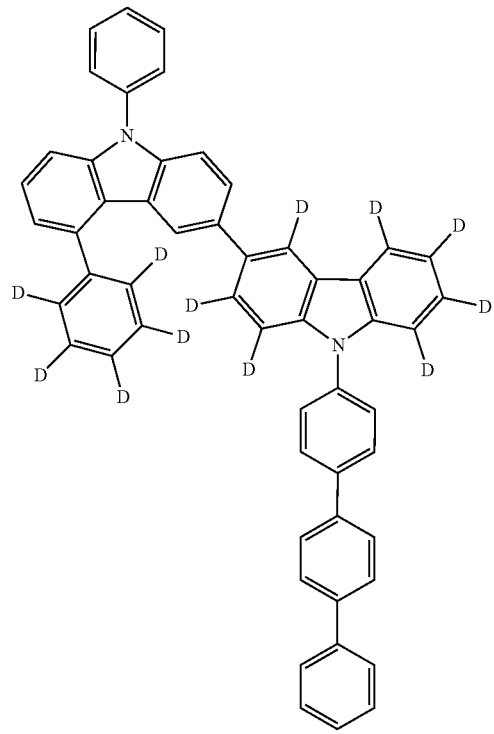
720
-continued
605
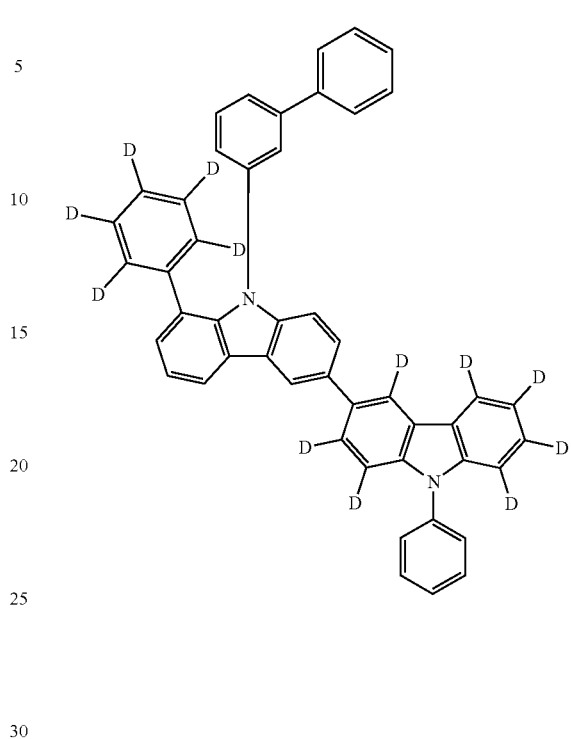
604
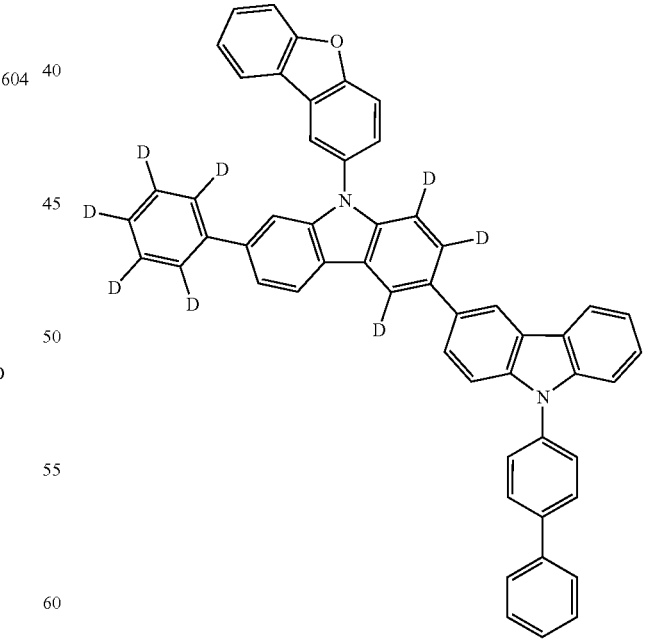
606

721
-continued
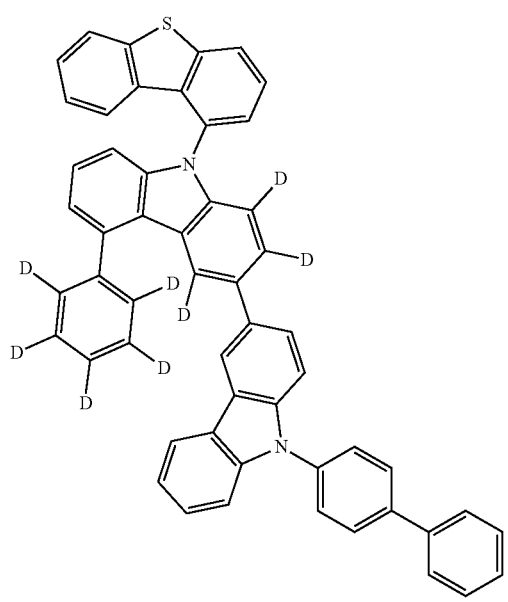
607
722
-continued
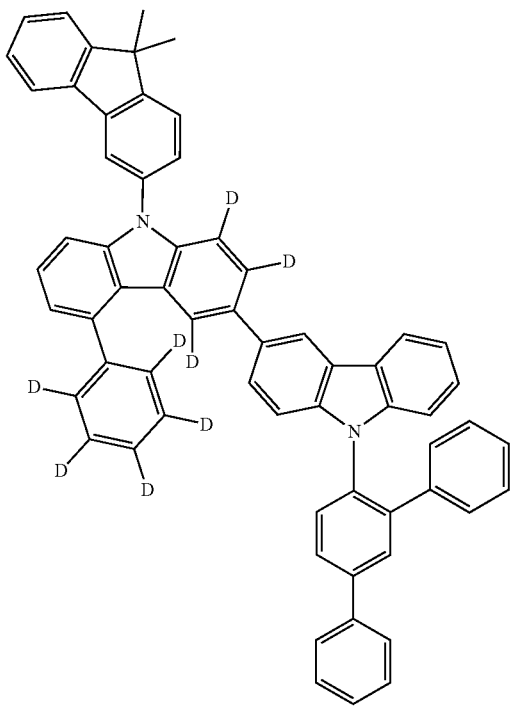
608
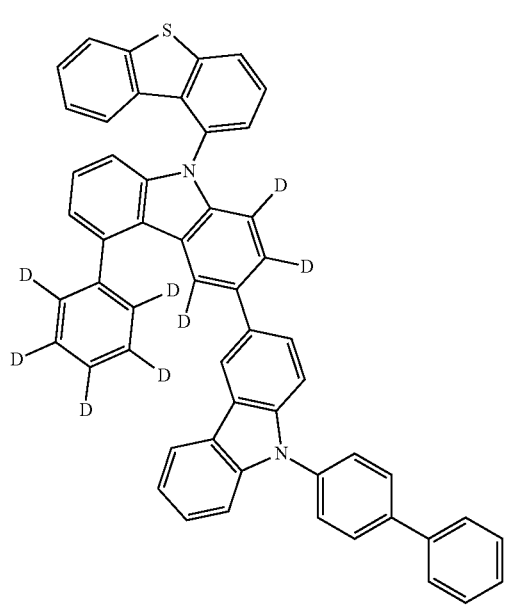
607
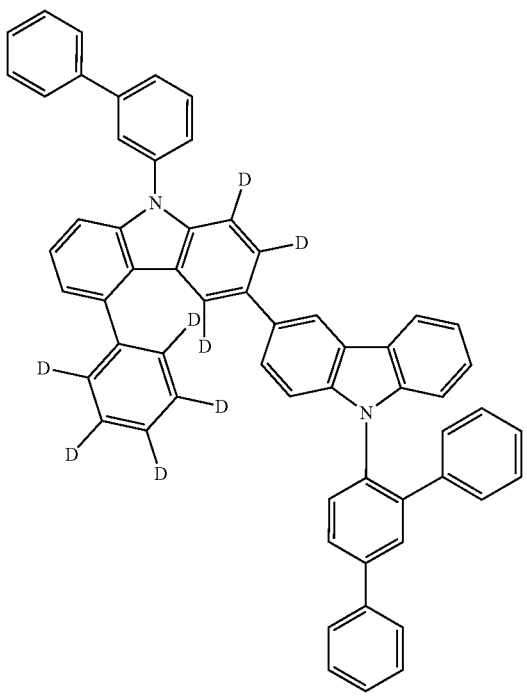
609

-continued

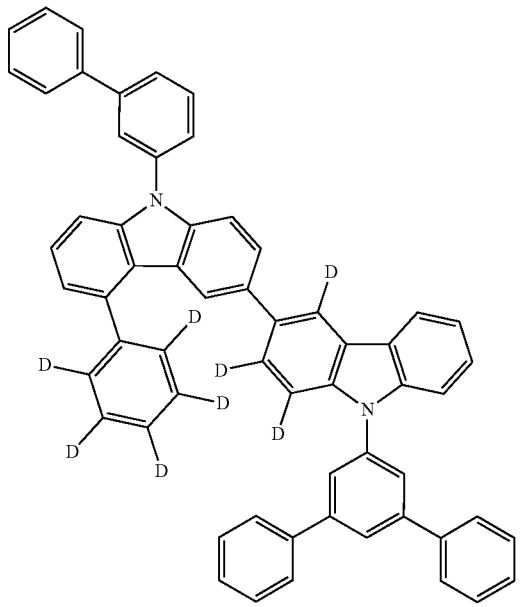

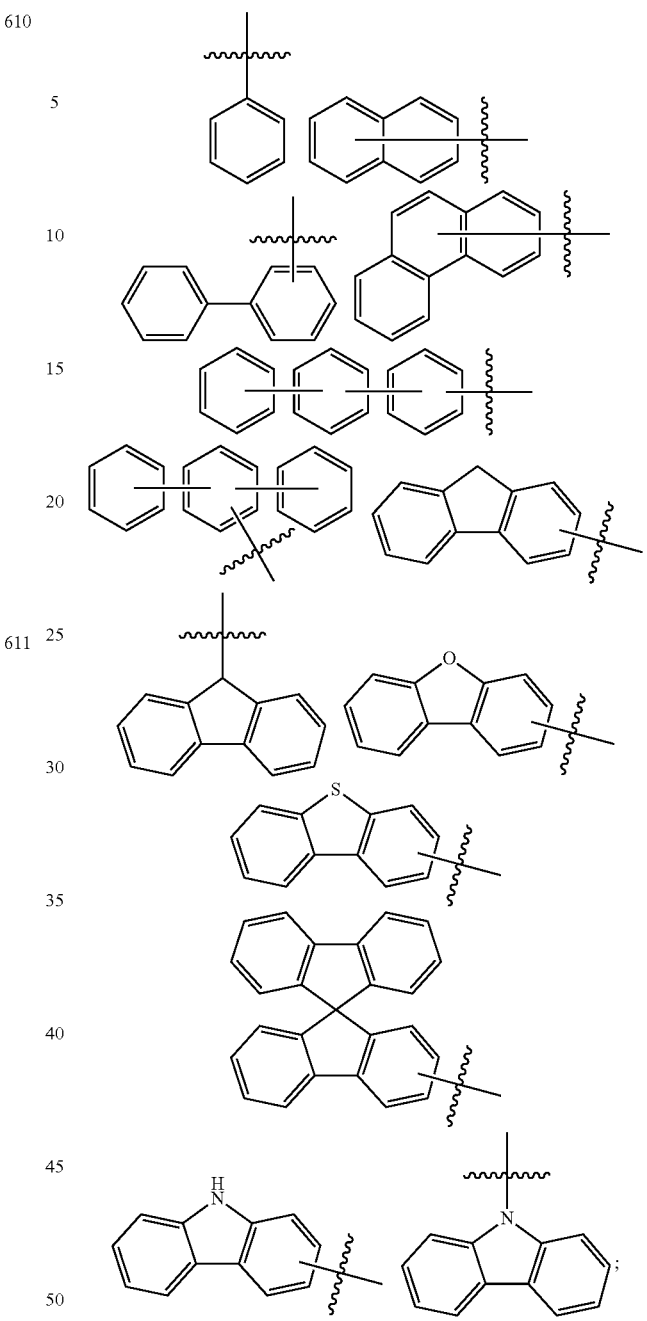

7. An organic electroluminescent device, comprising an anode and a cathode which are oppositely disposed, and a functional layer disposed between the anode and the cathode; wherein
the functional layer comprises the organic compound according to claim 1.

8. An electronic apparatus, comprising the organic electroluminescent device according to claim 7.

9. The organic compound according to claim 2, wherein $Ar_1$ and $Ar_2$ are respectively and independently selected from a substituted or unsubstituted group W, wherein the unsubstituted group W is selected from the group consisting of:

wherein represents a chemical bond; the substituted group W contains one or more substituents selected from deuterium, fluorine, cyano, methyl, ethyl, n-propyl, isopropyl, tert-butyl, phenyl, and naphthyl; and when the substituted group W contains a plurality of substituents, the substituents are the same or different.

10. The organic compound according to claim 2, wherein $R_1$, $R_2$ and $R_3$ are all deuterium, or $R_4$, $R_5$ and $R_6$ are all deuterium.

11. The organic compound according to claim 2, wherein $R_4$, $R_5$, $R_6$, $R_7$, $R_8$, $R_9$ and $R_{10}$ are all deuterium.

12. The organic electroluminescent device according to claim 7, wherein the functional layer comprises an organic light-emitting layer.

13. The organic electroluminescent device according to claim 7, wherein the organic electroluminescent device is a green organic electroluminescent device.

14. An organic electroluminescent device, comprising an anode and a cathode which are oppositely disposed, and a functional layer disposed between the anode and the cathode; wherein
   the functional layer comprises the organic compound according to claim 2.

15. The organic electroluminescent device according to claim 14, wherein the functional layer comprises an organic light-emitting layer.

16. The organic electroluminescent device according to claim 14, wherein the organic electroluminescent device is a green organic electroluminescent device.

17. An electronic apparatus, comprising the organic electroluminescent device according to claim 14.

* * * * *

UNITED STATES PATENT AND TRADEMARK OFFICE
CERTIFICATE OF CORRECTION

PATENT NO.        : 11,963,444 B2
APPLICATION NO.   : 18/024148
DATED             : April 16, 2024
INVENTOR(S)       : Tiantian Ma et al.

It is certified that error appears in the above-identified patent and that said Letters Patent is hereby corrected as shown below:

On the Title Page

Add item (30):
-- Oct. 28, 2021 (CN) 202111260690.0
Dec. 07, 2021 (CN) 202111488233.7 --

Signed and Sealed this
Twentieth Day of August, 2024

Katherine Kelly Vidal
*Director of the United States Patent and Trademark Office*